US009550999B2

(12) United States Patent
Dauner et al.

(10) Patent No.: US 9,550,999 B2
(45) Date of Patent: *Jan. 24, 2017

(54) RECOMBINANT HOST CELLS COMPRISING PHOSPHOKETOLASES

(71) Applicant: BUTAMAX ADVANCED BIOFUELS LLC, Wilmington, DE (US)

(72) Inventors: Michael Dauner, Claymont, DE (US); Lori Ann Maggio-Hall, Wilmington, DE (US); Jean-Francois Tomb, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/335,734

(22) Filed: Jul. 18, 2014

(65) Prior Publication Data

US 2014/0349349 A1 Nov. 27, 2014

Related U.S. Application Data

(63) Continuation of application No. 13/161,168, filed on Jun. 15, 2011, now Pat. No. 8,871,488.

(60) Provisional application No. 61/356,379, filed on Jun. 18, 2010.

(51) Int. Cl.
*C12N 1/20* (2006.01)
*C12N 1/00* (2006.01)
*C12N 9/00* (2006.01)
*C12N 15/00* (2006.01)
*C12P 7/16* (2006.01)
*C07H 21/04* (2006.01)
*C12N 15/81* (2006.01)
*C12N 9/02* (2006.01)
*C12N 9/10* (2006.01)
*C12N 9/88* (2006.01)
*C12N 15/52* (2006.01)
*C12N 15/74* (2006.01)
*C12P 7/18* (2006.01)
*C12P 7/26* (2006.01)
*C12P 7/46* (2006.01)
*C12P 7/56* (2006.01)
*C12P 13/06* (2006.01)
*C12P 13/08* (2006.01)

(52) U.S. Cl.
CPC ............ *C12N 15/81* (2013.01); *C12N 9/0008* (2013.01); *C12N 9/1029* (2013.01); *C12N 9/88* (2013.01); *C12N 15/52* (2013.01); *C12N 15/74* (2013.01); *C12P 7/16* (2013.01); *C12P 7/18* (2013.01); *C12P 7/26* (2013.01); *C12P 7/46* (2013.01); *C12P 7/56* (2013.01); *C12P 13/06* (2013.01); *C12P 13/08* (2013.01); *C12Y 102/07001* (2013.01); *C12Y 114/15003* (2013.01); *C12Y 118/01001* (2013.01); *C12Y 118/01002* (2013.01); *C12Y 203/01008* (2013.01); *C12Y 203/01054* (2013.01); *C12Y 401/01001* (2013.01); *C12Y 401/02009* (2013.01); *Y02E 50/10* (2013.01); *Y02P 20/52* (2015.11)

(58) Field of Classification Search
None
See application file for complete search history.

(56) References Cited

U.S. PATENT DOCUMENTS

| 7,405,068 | B2 | 7/2008 | van Maris et al. |
| 7,851,188 | B2 | 12/2010 | Donaldson et al. |
| 7,910,342 | B2 | 3/2011 | Liao et al. |
| 7,932,063 | B2 | 4/2011 | Dunson et al. |
| 8,530,210 | B2 | 9/2013 | Sun et al. |
| 8,871,488 | B2 * | 10/2014 | Dauner et al. ............ 435/252.3 |
| 2005/0059136 | A1 | 3/2005 | van Maris et al. |
| 2006/0040365 | A1 | 2/2006 | Kozlov et al. |
| 2007/0031950 | A1 | 2/2007 | Winkler |
| 2007/0190629 | A1 | 8/2007 | Wahlbom et al. |
| 2007/0259410 | A1 | 11/2007 | Donaldson et al. |
| 2007/0292927 | A1 | 12/2007 | Donaldson et al. |
| 2009/0155870 | A1 | 6/2009 | Donaldson et al. |
| 2009/0163376 | A1 | 6/2009 | Li et al. |
| 2009/0171129 | A1 | 7/2009 | Evanko et al. |
| 2009/0269823 | A1 | 10/2009 | Bramucci et al. |
| 2009/0305363 | A1 | 12/2009 | Anthony |
| 2010/0081154 | A1 | 4/2010 | Flint et al. |
| 2010/0120105 | A1 | 5/2010 | Anthony et al. |

(Continued)

FOREIGN PATENT DOCUMENTS

| WO | 03078643 | 9/2003 |
| WO | 2007050671 A2 | 5/2007 |

(Continued)

OTHER PUBLICATIONS

Akada et al., "PCR-mediated seamless gene deletion and marker recycling in *Saccharomyces cerevisiae*", Yeast, 2006 pp. 399-405, vol. 23.

(Continued)

*Primary Examiner* — Iqbal H Chowdhury

(57) ABSTRACT

The present invention is related to recombinant host cells comprising: (i) at least one deletion, mutation, and/or substitution in an endogenous gene encoding a polypeptide that converts pyruvate to acetaldehyde, acetyl-phosphate, or acetyl-CoA; and (ii) a heterologous polynucleotide encoding a polypeptide having phosphoketolase activity. The present invention is also related to recombinant host cells further comprising (iii) a heterologous polynucleotide encoding a polypeptide having phosphotransacetylase activity.

22 Claims, 8 Drawing Sheets

(56) References Cited

U.S. PATENT DOCUMENTS

| | | |
|---|---|---|
| 2010/0197519 A1 | 8/2010 | Li et al. |
| 2011/0124060 A1 | 5/2011 | Anthony et al. |
| 2013/0252296 A1 | 9/2013 | Maggio-Hall |

FOREIGN PATENT DOCUMENTS

| | | |
|---|---|---|
| WO | 2007086608 | 8/2007 |
| WO | 2009013159 A2 | 1/2009 |
| WO | 2009046370 A2 | 4/2009 |
| WO | 2010151832 A1 | 12/2010 |
| WO | 2011041415 A1 | 4/2011 |

OTHER PUBLICATIONS

Albert et al., "Site-specific integration of DNA into wild-type and mutant lox sites placed in the plant genome", The Plant Journal, 1995, pp. 649-659, vol. 7, No. 4.

Altschul et al., "Basic Local Alignment Search Tool", Journal of Molecular Biology, 1990, pp. 403-410, vol. 215.

Bellion et al., "Microb. Growth C1 Compd.", [Int. Symp.], 7th (1993), pp. 415-432, Editor(s): Murrell, J. Collin; Kelly, Don P. Publisher: Intercept, Andover, UK.

Bianchi et al., "The 'petite-negative' yeast kluyveromyces lactis has a single gene expressing pyruvate decarboxylase activity", Molecular Microbiology, 1996, pp. 27-36, vol. 19(1).

Boeke et al., "A positive selection for mutants lacking orotidine-5'-phosphate decarboxylase activity in yeast: 5-fluoro-orotic acid resistance", Molecular General Genetics, 1984, pp. 345-346, vol. 197.

Carlini et al., "Guerbet condensation of methanol with n-propanol to isobutyl alcohol over heterogeneous copper chromite/Mg-Al mixed oxides catalysts", J. Mol. Catal. A: Chem., 2004, pp. 215-220, vol. 220.

Chang et al., "BRENDA, AMENDA and FRENDA the enzyme information system: new content and tools in 2009", Nucleic Acids Research, 2009, pp. D588-D593, vol. 37.

Chinen et al., "Innovative metabolic pathway design for efficient l-glutamate production by suppressing CO2 emission", Journal of Bioscience and Bioengineering, vol. 103, No. 3, Mar. 1, 2007, pp. 262-269.

Deshpande, "Ethanol Production from Cellulose by Coupled Saccharification/Fermentation using Saccharomyces cerevisiae and Cellulase Complex from Sclerotium rolfsii UV-8 Mutant", Applied Biochemistry and Biotechnology, 1992, pp. 227-234, vol. 36.

Durre, "New insights and novel developments in clostridial acetone/butanol/isopropanol fermentation", Appl. Microbiol. Biotechnol., 1998, pp. 639-648, vol. 49.

Evans et al., "Induction of xylulose-5-phosphate phosphoketolase in a variety of yeasts grown on D-xylose: the key to efficient xylose metabolism", Archives of Microbiology, 1984, pp. 48-52, vol. 139.

Finn et al., "The Pfam protein families database", Nucleic Acids Research, 2008, pp. D281-D288, vol. 36.

Flikweert et al., "Pyruvate decarboxylase: an indispensable enzyme for growth of Saccharomyces cerevisiae on glucose", Yeast, 1996, pp. 247-257, vol. 12.

Flikweert et al., "Growth requirements of pyruvate-decarboxylase-negative Saccharomyces cerevisiae", FEMS Microbiology Letters, 1999, pp. 73-79, vol. 174.

Goldberg, I. et al., "Organic acids: old metabolites, new themes", Journal of Chemical Technology and Biotechnology, 2006, pp. 1601-1611, vol. 81.

Goldberg, M. et al., "[90] Phosphoketolase", Methods in Enzymology, 1966, pp. 515-520, vol. 9.

Groot et al., "Technologies for Butanol Recovery Integrated with Fermentations", Process Chemistry, 1992, pp. 61-75, vol. 27.

Guo et al., "Pervaporation study on the dehydration of aqueous butanol solutions: a comparison of flux vs. permeance, separation factor vs. selectivity", Journal of Membrane Science, 2004, pp. 199-210, vol. 245.

Heath et al., "Pentose Fermentation by Lactobacillus Plantarum", The Journal of Biological Chemistry, 1958, pp. 1009-1029, vol. 231.

Higgins et al., "Fast and sensitive multiple sequence alignments on a microcomputer", CABIOS Communications, 1989, pp. 151-153. vol. 5, No. 2.

Higgins et al., "CLUSTAL V: improved software for multiple sequence alignment", CABIOS, 1992, vol. 8, No. 2 pp. 189-191.

Hohmann, "Characterisation of PDC2, a gene necessary for high level expression of pyruvate decarboxylase structural genes in Saccharomyces cerevisiae", Mol. Gen. Genet., 1993, vol. 241, pp. 657-666.

Horton et al., "Engineering hybrid genes without the use of restriction enzymes: gene splicing by overlap extension", Gene, 1989, pp. 61-68, vol. 77.

Ishida et al., "Efficient production of L-lactic acid by metabolically engineered Saccharomyces cerevisiae with a genome-integrated L-lactate dehydrogenase gene", Applied and Environmental Microbiology, vol. 71, No. 4, Apr. 2005, pp. 1964-1970.

Krogh et al., "Hidden Markov Models in Computational Biology", Journal of Molecular Biology, 1994, pp. 1501-1531, vol. 235.

Langley et al., "Biochemical Genetics of the a-Keto Acid Dehydrogenase Complexes of Escherichia coli, K12: Isolation and Biochemical Properties of Deletion Mutants", Journal of General Microbiology, 1977, pp. 263-276, vol. 99.

Li et al., "Clustering of highly homologous sequences to reduce the size of large protein databases", Bioinformatics, 2001, pp. 282-283, vol. 17, No. 3.

Ma et al., "Plasmid construction by homologous recombination in yeast", Gene, 1987, pp. 201-216, vol. 58.

Methods in Yeast Genetics, 2005, Cold Spring Harbor Laboratory Press, Cold Spring Harbor, NY, pp. 201-202.

Mnaimneh et al., "Exploration of essential gene functions via titratable promoter alleles", Cell, 2004, pp. 31-44, vol. 118.

Nakamura et al., "Codon usage tabulated from international DNA sequence databases: status for the year 2000", Nucleic Acids Research, 2000, vol. 28, No., p. 292.

Nevoigt et al., "Engineering of promoter replacement cassettes for tine-tuning of gene expression in Saccharomyces cerevisiae", Applied and Environmental Microbiology, Aug. 2006, vol. 72, No. 8, pp. 5266-5273.

Nystrom et al., "Reduction of organic compounds by lithium aluminum hydride", J. Am. Chem. Soc., 1947, vol. 69, p. 1198.

Panagiotou et al., "Induction of Xylulosse-5-phosphate Phosphoketolase in Aspergillus Nidulans: the Key for Efficient Production of the Acetyl-coa Precursor Molecule", Internet Citation, Apr. 2006, p. 203, XP002477270.

Pearson, Comput. Methods Genome Res., [Proc. Int. Symp.] (1994), Meeting Date 1992, 111 20. Editor(s): Suhai, Sandor. Plenum: New York, NY.

Posthuma et al., "Expression of the Xylulose 5-Phospohate Phosphoketolase Gene, xpkA, from Lactobacillus pentosus MD363 Is Induced by Sugars That Are Fermented via the Phosphoketolase Pathway and Is Repressed by Glucose Mediated by CcpA and the Mannose Phosphoenolpyruvate Phosphotransferase System", Applied and Environmental Microbiology, Feb. 2002, pp. 831-837, vol. 68, No. 2.

Rado et al. "Phosphotransacetylase From Bacillus Subtilis: Purification and Physiological Studies", Biochimica et Biophysica Acta, 1973, pp. 114-125, vol. 321.

Romanos et al., "Direct selection of stabilised yeast URA3 transformants with 5-fluorouracil", Nucleic Acids Research, 1991, pp. 187, vol. 19, No. 1.

Saitou et al., "The Neighbor-joining Method: A New Method for Reconstructing Phylogenetic Trees", Molecular Biology Evolution, 1987, pp. 406-425, vol. 4, No. 4.

Sambrook, J., Fritsch, E. F. and Maniatis, T. Molecular Cloning: A Laboratory Manual, 2nd ed., Cold Spring Harbor Laboratory: Cold Spring Harbor, NY, 1989, particularly 9.50-9.51, 11.7-11.8 and Table 11.1.

Sauer, "Functional Expression of the cre-lox Site-Specific Recombination System in the Yeast Saccharomyces cerevisiae", Molecular and Cellular Biology, Jun. 1987, pp. 2087-2096, vol. 7, No. 6.

(56) References Cited

OTHER PUBLICATIONS

Schure et al., "Pyruvate decarboxylase catalyzes decarboxylation of branched-chain 2-oxo acids but is not essential for fusel alcohol production by *Saccharomyces cerevisiae*", Applied Environ Microbiol (1988) 64: 1303-1307.

Senecoff, et al., "DNA Recognition by the FLP Recominase of the Yeast 2 u Plasmid", Journal of Molecular Biology, 1988, pp. 405-421, vol. 201.

Sonderegger et al., "Metabolic Engineering of a Phosphoketolase Pathway for Pentose Catabolism in *Saccharomyces cerevisiae*", Applied and Environmental Microbiology, May 2004, pp. 2892-2897, vol. 70, No. 5.

Sulter et al., "Proliferation and metabolic significance of peroxisomes in candida boidinii during growth on D-alanine or oleic acid as the sole carbon source", Arch. Microbiol., 1990, pp. 485-489, vol. 153, No. 9.

Tamura et al., "MEGA4: Molecular Evolutionary Genetics Analysis (MEGA)" Software Version 4.0, Molecular Biology and Evolution, 2007, pp. 1596-1599, vol. 24.

Ullmann's Encyclopedia of Industrial Chemistry, 6th edition, 2003, Wiley-VCH Verlag GmbH and Co., Weinheim, Germany, vol. 5, pp. 716-719.

Thompson et al., "The CLUSTAL_X windows interface; flexible strategies for multiple sequence alignment aided by quality analysis tools", Nucleic Acids Research, 1997, pp. 4876-4882, vol. 25, No. 24.

van Maris et al., "Directed Evolution of Pyruvate Decarboxylase-Negative *Saccharomyces cerevisiae*, Yielding a C2-Independent, Glucose-Tolerant, and Pyruvate-Hyperproducing Yeast", Applied and Environmental Microbiology, Jan. 2004, pp. 159-166, vol. 70, No. 1.

van Maris et al., "Overproduction of Threonine Aldolase Circumvents the Biosynthetic Role of Pyruvate Decarboxylase in Glucose-Limited Chemostat Cultures of *Saccharomyces cervisiae*", Applied and Envirnomental Microbiology, Apr. 2003, pp. 2094-2099, vol. 69, No. 4.

Voloch et al., "Fermentation Derived 2,3-Butanediol," in Comprehensive Biotechnology, Pergamon Press Ltd., England, 1986, pp. 933-947,vol. 2, Section 3.

Wach et al., "New heterologous modules for classical or PCR-based gene disruptions in *Saccharomyces cerevisiae*", Yeast, 1994, pp. 1793-1808, vol. 10.

Waterhouse et al., "Jalview Version 2—a multiple sequence alignment editor and analysis workbench", Bioinformatics, 2009, pp. 1189-1191, vol. 25, No. 9.

Yu et al., "Double-joint PCR: a PCR-based molecular tool for gene manipulations in filamentous fungi", Fungal Genetics and Biology, 2004, pp. 973-981, vol. 41.

Zelle et al., "Malic Acid Production by *Saccharomyces cerevisiae*: Engineering of Pyruvate Carboxylation, Oxaloacetate Reduction, and Malate Export", Applied and Environmental Microbiology, May 2008, pp. 2766-2777, vol. 74, No. 9.

International Search Report and Written Opinion of corresponding PCT/US2011/040608 mailed Oct. 21, 2011.

* cited by examiner

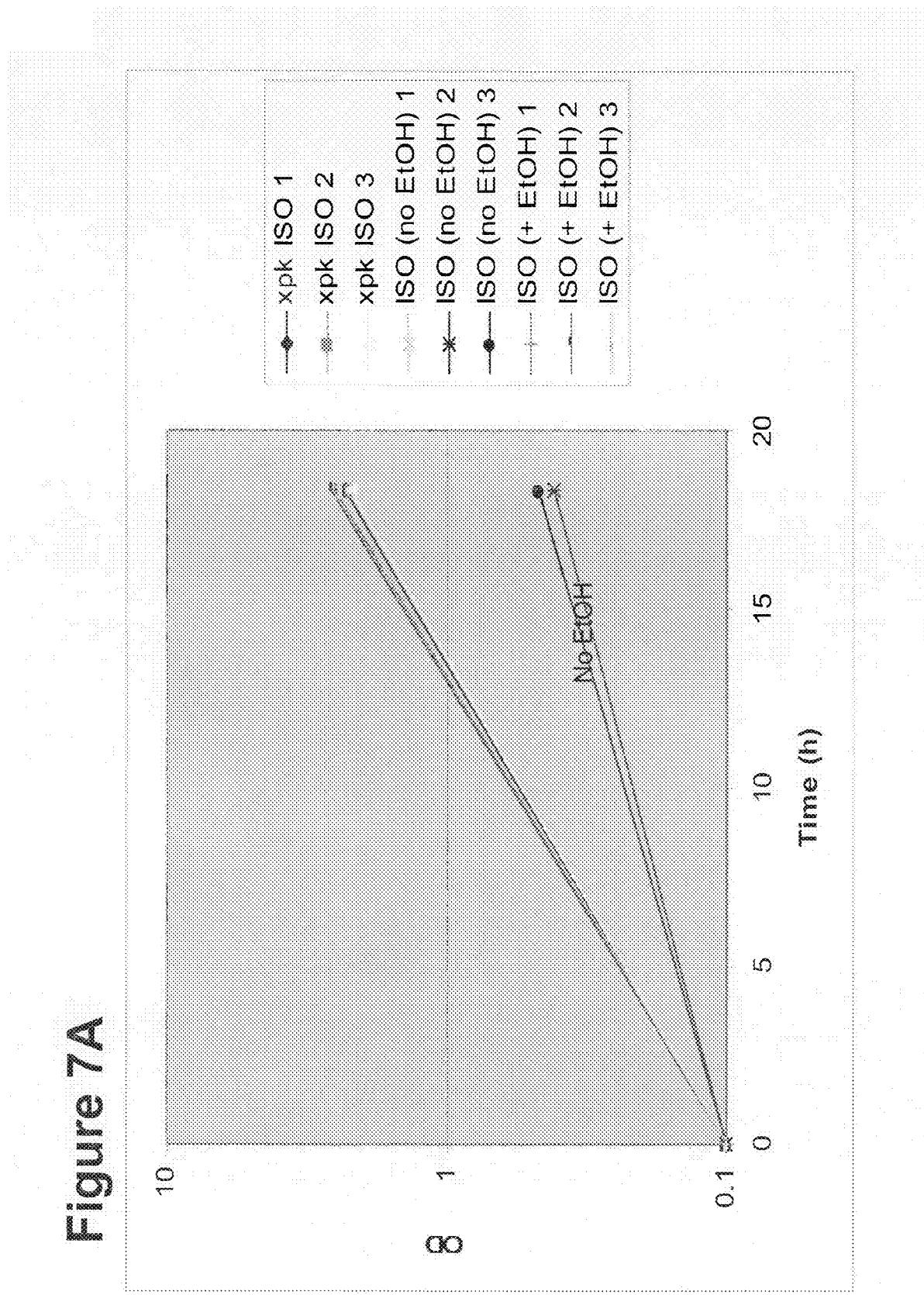

RECOMBINANT HOST CELLS COMPRISING PHOSPHOKETOLASES

CROSS-REFERENCE TO RELATED APPLICATIONS

This application is a continuation of and claims the benefit of U.S. application Ser. No. 13/161,168, filed on Jun. 15, 2011, which is related to and claims the benefit of priority of U.S. Provisional Patent Application No. 61/356,379, filed on Jun. 18, 2010. Each of the referenced applications is herein incorporated by reference.

FIELD OF THE INVENTION

The invention relates generally to the field of industrial microbiology. The invention relates to recombinant host cells comprising (i) a modification in an endogenous gene encoding a polypeptide that converts pyruvate to acetyl-CoA, acetaldehyde or acetyl-phosphate and (ii) a heterologous polynucleotide encoding a polypeptide having phosphoketolase activity. The invention also relates to recombinant host cells comprising (i) a modification in an endogenous gene encoding a polypeptide having pyruvate decarboxylase (PDC) activity, or a modification in an endogenous polypeptide having PDC activity, and (ii) a heterologous polynucleotide encoding a polypeptide having phosphoketolase activity. The invention also relates to recombinant host cells further comprising (iii) a heterologous polynucleotide encoding a polypeptide having phosphotransacetylase activity. Additionally, the invention relates to methods of making and using such recombinant host cells including, for example, methods of increasing cell growth, methods of reducing or eliminating the requirement of an exogenous carbon substrate for cell growth, methods of increasing glucose consumption and methods of increasing the production of a product of a pyruvate-utilizing pathway.

BACKGROUND OF THE INVENTION

Global demand for liquid transportation fuel is projected to strain the ability to meet certain environmentally driven goals, for example, the conservation of oil reserves and limitation of green house gas emissions. Such demand has driven the development of technology which allows utilization of renewable resources to mitigate the depletion of oil reserves and to minimize green house gas emissions.

Butanol is an important industrial chemical, useful as a fuel additive, as a feedstock chemical in the plastics industry, and as a food grade extractant in the food and flavor industry. Each year 10 to 12 billion pounds of butanol are produced by petrochemical means and the need for this commodity chemical will likely increase in the future.

Methods for the chemical synthesis of isobutanol are known, such as oxo synthesis, catalytic hydrogenation of carbon monoxide (Ullmann's Encyclopedia of Industrial Chemistry, 6th edition, 2003, Wiley-VCH Verlag GmbH and Co., Weinheim, Germany, Vol. 5, pp. 716-719) and Guerbet condensation of methanol with n-propanol (Carlini et al., *J. Molec. Catal. A: Chem.* 220:215-220, 2004). These processes use starting materials derived from petrochemicals, are generally expensive, and are not environmentally friendly. The production of isobutanol from plant-derived raw materials would minimize green house gas emissions and would represent an advance in the art.

2-Butanone, also referred to as methyl ethyl ketone (MEK) is a widely used solvent and is the most important commercially produced ketone, after acetone. It is used as a solvent for paints, resins, and adhesives, as well as a selective extractant, activator of oxidative reactions, and it can be chemically converted to 2-butanol by reacting with hydrogen in the presence of a catalyst (Nystrom, R. F. and Brown, W. G. (*J. Am. Chem. Soc.* (1947) 69:1198). 2,3-butanediol can be used in the chemical synthesis of butene and butadiene, important industrial chemicals currently obtained from cracked petroleum, and esters of 2,3-butanediol may be used as plasticizers (Voloch et al., "Fermentation Derived 2,3-butanediol," in Comprehensive Biotechnology, Pergamon Press Ltd., England Vol. 2, Section 3:933-947 (1986)).

Microorganisms can be engineered for the expression of biosynthetic pathways that initiate with cellular pyruvate to produce, for example, 2,3-butanediol, 2-butanone, 2-butanol and isobutanol. U.S. Pat. No. 7,851,188 discloses the engineering of recombinant microorganisms for production of isobutanol. U.S. Patent Application Publication Nos. US 20070259410 A1 and US 20070292927 A1 disclose the engineering of recombinant microorganisms for production of 2-butanone or 2-butanol. Multiple pathways are disclosed for biosynthesis of isobutanol and 2-butanol, all of which initiate with cellular pyruvate. Butanediol is an intermediate in the 2-butanol pathway disclosed in U.S. Patent Application Publication No. US 20070292927 A1.

The disruption of the enzyme pyruvate decarboxylase (PDC) in recombinant host cells engineered to express a pyruvate-utilizing biosynthetic pathway has been used to increase the availability of pyruvate for product formation via the biosynthetic pathway. For example, U.S. Application Publication No. US 20070031950 A1 discloses a yeast strain with a disruption of one or more pyruvate decarboxylase genes (a PDC knock-out or PDC-KO) and expression of a D-lactate dehydrogenase gene, which is used for production of D-lactic acid. U.S. Application Publication No. US 20050059136 A1 discloses glucose tolerant two-carbon source-independent (GCSI) yeast strains with no PDC activity, which may have an exogenous lactate dehydrogenase gene. Nevoigt and Stahl (*Yeast* 12:1331-1337 (1996)) describe the impact of reduced PDC and increased NAD-dependent glycerol-3-phosphate dehydrogenase iii *Saccharomyces cerevisiae* on glycerol yield. U.S. Application Publication No. 20090305363 A1 discloses increased conversion of pyruvate to acetolactate by engineering yeast for expression of a cytosol-localized acetolactate synthase and substantial elimination of PDC activity.

While PDC-KO recombinant host cells can be used to produce the products of pyruvate-utilizing biosynthetic pathways, PDC-KO recombinant host cells require exogenous carbon substrate supplementation (e.g., ethanol or acetate) for their growth (Flikweert et al. 1999. FEMS Microbiol. Lett. 174(1):73-79 "Growth requirements of pyruvate-decarboxylase-negative *Saccharomyces cerevisiae*"). A similar auxotrophy is observed in *Escherichia coli* strains carrying a mutation of one or more genes encoding pyruvate dehydrogenase (Langley and Guest, 1977, J. Gen, Microbiol. 99:263-276).

In commercial applications, addition of exogenous carbon substrate in addition to the substrate converted to a desired product can lead, to increased costs. There remains a need in the art for recombinant host cells with reduced or eliminated need for exogenous carbon substrate supplementation.

BRIEF SUMMARY OF THE INVENTION

One aspect of the invention relates to a recombinant host cell comprising (i) least one deletion, mutation, and/or substitution in an endogenous gene encoding a polypeptide that converts pyruvate to acetaldehyde, acetyl-phosphate, or acetyl-CoA; and ii) a heterologous polynucleotide encoding a polypeptide having phosphoketolase activity. Another aspect of the invention relates to such a recombinant host cell further comprising (iii) a heterologous polynucleotide encoding a polypeptide having phosphotransacetylase activity. In embodiments, the polypeptide that converts pyruvate to acetaldehyde, acetyl-phosphate, or acetyl-CoA is pyruvate decarboxylase, pyruvate-formate lyase, pyruvate dehydrogenase, pyruvate oxidase, or pyruvate:ferredoxin oxidoreductase.

One aspect of the invention relates to a recombinant host cell comprising (i) a modification in an endogenous gene encoding a polypeptide having pyruvate decarboxylase activity or in an endogenous polypeptide having pyruvate decarboxylase activity; and (ii) a heterologous polynucleotide encoding a polypeptide having phosphoketolase activity. Another aspect of the invention relates to such a recombinant host cell further comprising (iii) a heterologous polynucleotide encoding a polypeptide having phosphotransacetylase activity.

One aspect of the invention relates to a recombinant host cell comprising (i) at least one deletion, mutation, and/or substitution in an endogenous gene encoding a polypeptide having pyruvate decarboxylase activity; and (ii) a heterologous polynucleotide encoding a polypeptide having phosphoketolase activity. Another aspect of the invention relates to a recombinant host cell further comprising: (iii) a heterologous polynucleotide encoding a polypeptide having phosphotransacetylase activity. Another aspect of invention relates to a reduced or eliminated requirement of such cells for an exogenous two-carbon substrate for its growth in culture compared to a recombinant eukaryotic host cell comprising (i) and not (ii) or (iii). Another aspect of the invention relates to the growth of such host cells in culture media that is not supplemented with an exogenous two-carbon substrate, for example, at a growth rate substantially equivalent to, or greater than, the growth rate of a host cell comprising (i) and not (ii) or (iii) in culture media supplemented with an exogenous two-carbon substrate.

In one aspect of the invention, the recombinant host cell is a member of the genera *Clostridium*, *Zymomonas*, *Escherichia*, *Salmonella*, *Serratia*, *Erwinia*, *Klebsiella*, *Shigella*, *Rhodococcus*, *Pseudomonas*, *Bacillus*, *Lactobacillus*, *Enterococcus*, *Alcaligenes*, *Klebsiella*, *Paenibacillus*, *Arthrobacter*, *Corynebacterium*, *Brevibacterium*, *Schizosaccharomyces*, *Kluyveromyces*, *Yarrowia*, *Pichia*, *Candida*, *Hansenula*, or *Saccharomyces*. In another aspect of the invention, the recombinant host cell is *S. cerevisiae*

In another aspect of the invention, the recombinant host cell expresses a pyruvate-utilizing biosynthetic pathway including, for example, a biosynthetic pathway for a product such as 2,3-butanediol, isobutanol, 2-butanol, 2-butanone, valine, leucine, alanine, lactic acid, malic acid, fumaric acid, succinic acid, or isoamyl alcohol. Another aspect of the invention relates to expression of an isobutanol biosynthetic pathway in the recombinant host cell comprising at least one DNA molecule encoding a polypeptide that catalyzes a substrate to product conversion selected from the group consisting of (i) pyruvate to acetolactate; (ii) acetolactate to 2,3-dihydroxyisovalerate; (iii) 2,3-dihydroxyisovalerate to 2-ketoisovalerate; (iv) 2-ketoisovalerate to isobutyraldehyde; and (v) isobutyraldehyde to isobutanol. Another aspect of the invention relates to expression of a 2-butanone biosynthetic pathway in the recombinant host cell comprising at least one DNA molecule encoding a polypeptide that catalyzes a substrate to product conversion selected from the group consisting of (i) pyruvate to acetolactate; (ii) acetolactate to acetoin; (iii) acetoin to 2,3-butanediol; and (iv) 2,3-butanediol to 2-butanone.

Another aspect of the invention relates to expression of a 2-butanol biosynthetic pathway in the recombinant host cell comprising at least one DNA molecule encoding a polypeptide that catalyzes a substrate to product conversion selected from the group consisting of (i) pyruvate to acetolactate; (ii) acetolactate to acetoin; (iii) acetoin to 2,3-butanediol; (iv) 2,3-butanediol to 2-butanone; and (v) 2-butanone to 2-butanol.

One aspect of the invention relates to methods for the production of a product selected from the group consisting of 2,3-butanediol, isobutanol, 2-butanol, 2-butanone, valine, leucine, alanine, lactic acid, malic acid, fumaric acid, succinic acid and isoamyl alcohol comprising growing the recombinant host cells described herein under conditions wherein the product is produced and optionally recovering the product. Another aspect of the invention relates to methods of producing a recombinant host cell comprising transforming a host cell comprising at least one deletion, mutation, and/or substitution in an endogenous gene encoding a polypeptide having pyruvate decarboxylase activity with (i) a heterologous polynucleotide encoding a polypeptide having phosphoketolase activity; and optionally (ii) a heterologous polynucleotide encoding a polypeptide having phosphotransacetylase activity.

Another aspect of the invention relates to methods of improving the growth of a recombinant host cell comprising at least one deletion, mutation or substitution in an endogenous gene encoding a polypeptide having pyruvate decarboxylase activity, comprising (i) transforming the recombinant host cell with a heterologous polynucleotide encoding a polypeptide having phosphoketolase activity; and optionally (ii) transforming the recombinant host cell with a heterologous polynucleotide encoding a polypeptide having phosphotransacetylase activity. In embodiments, the methods further comprise growing the recombinant host cell in media containing limited carbon substrate.

Another aspect of the invention relates to methods of reducing the requirement for an exogenous two-carbon substrate for the growth of a recombinant host cell comprising at least one deletion, mutation or substitution in an endogenous gene encoding a polypeptide having pyruvate decarboxylase activity, comprising (i) transforming the host cell with a heterologous polynucleotide encoding, a polypeptide having, phosphoketolase activity; and optionally (ii) transforming the host cell with a heterologous polynucleotide encoding a polypeptide having phosphotransacetylase activity.

Another aspect of the invention relates to methods of eliminating the requirement for an exogenous two-carbon substrate for the growth of a recombinant host cell comprising at least one deletion, mutation or substitution in an endogenous gene encoding a polypeptide having pyruvate decarboxylase activity, comprising (i) transforming the host cell with a heterologous polynucleotide encoding a polypeptide having phosphoketolase activity; and optionally (ii) transforming the host cell with a heterologous polynucleotide encoding a polypeptide having phosphotransacetylase activity.

Still another aspect of the invention relates to methods for increasing the activity of the phosphoketolase pathway in a recombinant host cell comprising (i) providing a recombinant host cell of the invention; and (ii) growing the recombinant host cell under conditions whereby the activity of the phosphoketolase pathway in the recombinant host cell is increased.

In another aspect, the recombinant host cells comprise a phosphoketolase that matches the Profile HMM given in Table 6 with an E value of less than 7.5E-242. In another aspect, the phosphoketolase has at least about 40% identity to at least one of SEQ ID NO 355, 379, 381, 388, 481, 486, 468, or 504. In another aspect, the phosphoketolase has at least about 90% identity to at least one of SEQ ID NO: 355, 379, 381, 388, 481, 486, 468, or 504. In another aspect, the phosphoketolase matches the Profile HMMs given in Tables 6, 7, 8, and 9 with E values of less than 7.5E-242, 1.1E-124, 2.1E-49, 7.8E-37, respectively. In another aspect, the recombinant host cells further comprise a phosphotransacetylase which matches the Profile HMM given in Table 14 with an E value of less than 5E-34. In another aspect, the phosphotransacetylase has at least about 40% identity to SEQ ID NO: 1475, 1472, 1453, 1422, 1277, 1275, 1206, 1200, 1159, or 1129. In another aspect, the phosphotransacetylase has at least about 90% identity to SEQ ID NO: 1475, 1472, 1453, 1422, 1277, 1275, 1206, 1200, 1159, or 1129

BRIEF DESCRIPTION OF THE DRAWINGS/FIGURES AND INCORPORATION OF SEQUENCE LISTING AND TABLES

The various embodiments of the invention can be more fully understood from the detailed description, the figures, and the accompanying sequence descriptions, which form a part of this application.

Figure 4:
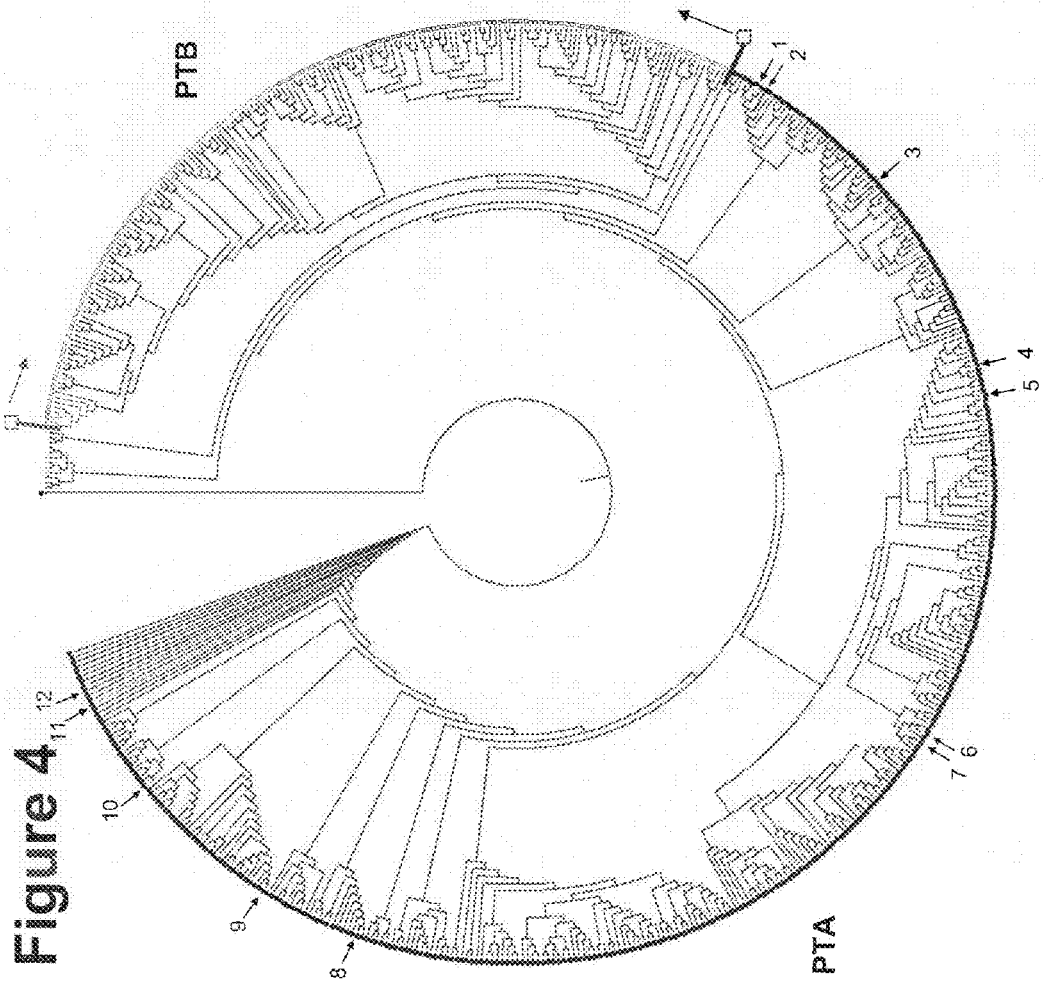
Figure 5:

FIG. 4 depicts a phylogenetic tree of phosphate acetyltransferase (PTA) and phosphate butyryltransferase (PTB) sequences. Multiple sequence alignment was performed with Clustal X using default parameters. Phylogenetic tree was deduced using neighbor-joining method and drawn with Mega 4 software. Marked sequences are as follows: (#, Species, GI#) 1, *S. enterica*, 56412650; 2, *E. coli* K12, 88192043; 3, *V. parvula*, 227371784; 4, *C. kluyveri*, 153954015; 5, *C. Acetobutylicum*, 15895019; 6, *C. thermocellum*, 196254011; 7, *M. thermophila*, 88192043; 8, *S. pyogenes*, 48425286; 9, *B. subtilis*, 58176784; 10, *L. fermentum*, 227514417; 11, *L. plantarum*, 28377658; 12, *L. sanfranciscensis*, 11862872;

FIG. 5 is a plasmid map of pRS426::GPD-xpk1+ADH-eutD map which is described herein.

Figure 6:
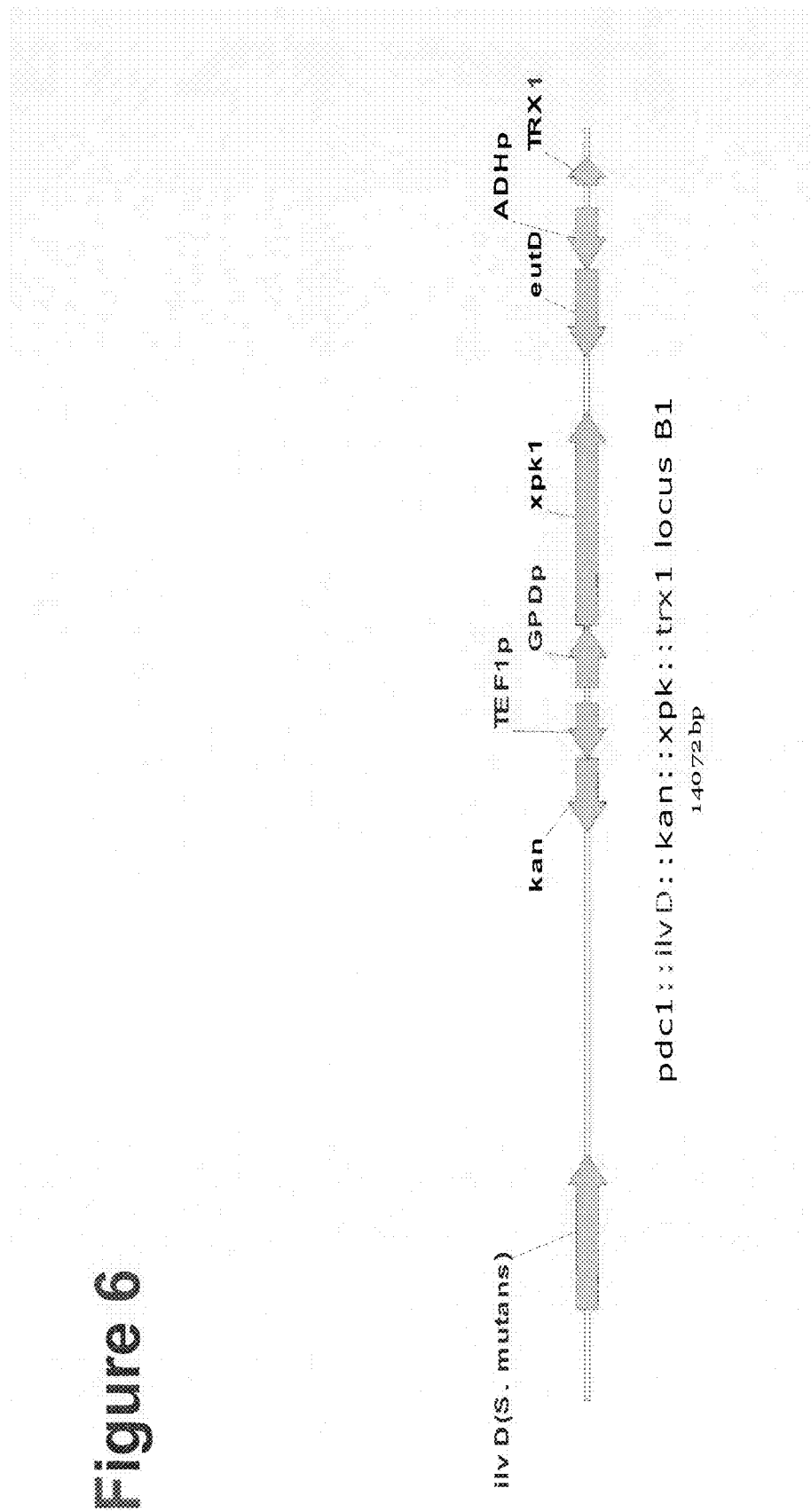

FIG. 6 depicts the Δpdc1::ilvD(Sm) locus of BP913 after integration of a phosphoketolase pathway vector (described herein).

FIG. 7A shows the growth of an isobutanol-producing strain in the absence (no ETOH) and presence (+ETOH) of EtOH and the absence and presence of the phosphoketolase pathway (xpk). ISO1, ISO2 and ISO3 refer to replicates.

Figure 7B:
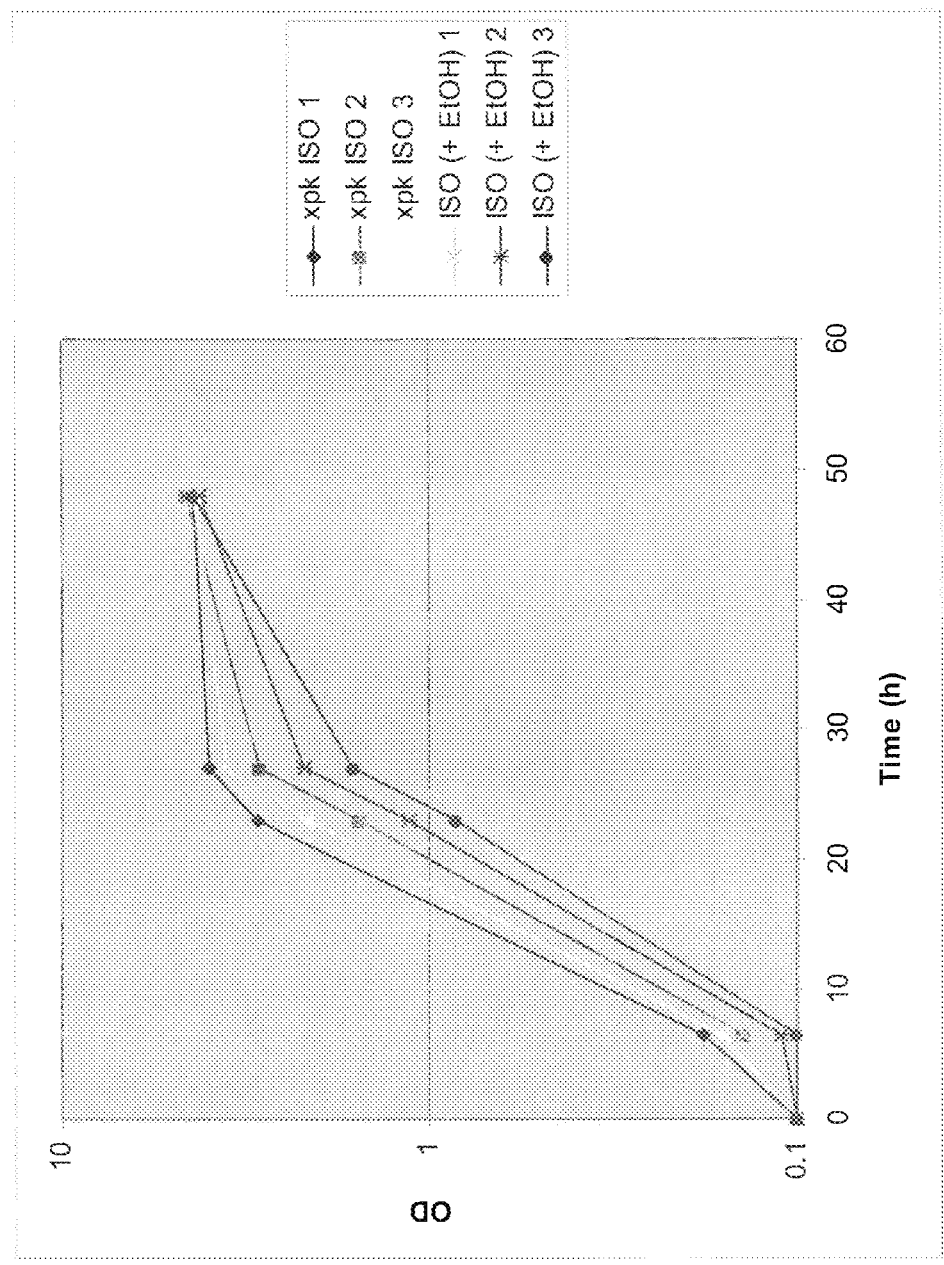

FIG. 7B shows the growth of a second subculture of strains from FIG. 7A.

Tables 6, 7, 8, 9, and 14 are tables of the Profile HMMs described herein. Table 6, 7, 8, and 14 are submitted herewith electronically and are incorporated herein by reference.

The invention can be more fully understood from the following detailed description and the accompanying sequence descriptions which form a part of this application.

The sequence listing provided herewith is herein incorporated by reference and conforms with 37 C.F.R. 1.821-1.825 ("Requirements for Patent Applications Containing Nucleotide Sequences and/or Amino Acid Sequence Disclosures—the Sequence Rules") and is consistent with World Intellectual Property Organization (WIPO) Standard ST.25 (2009) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822. The content of the electronically submitted sequence listing Name: 20110615_CL4871USNA_SeqList.txt; Size: 6.67 MB; and Date of Creation/Modification: Jun. 9, 2011/Jun. 15, 2011 is incorporated herein by reference in its entirety.

SEQ ID NOs: 1-20 are sequences of PDC target gene coding regions and proteins.

SEQ ID NOs: 21-638 are phosphoketolase target gene coding regions and proteins.

SEQ ID NOs: 762-1885 are phosphotransacetylase target gene coding regions and proteins.

SEQ ID NOs: 1893-1897 are hybrid promoter sequences.

SEQ ID NOs: 639-642, 644-654, 656-660, 662-701-714, 725-726, 729-740, 742-748, and 750-761 are primers.

SEQ ID NO: 643 is the vector pRS426::GPD-xpk1+ADH1-eutD.

SEQ ID NO: 655 is the TEF1p-kan-TEF1t gene.

SEQ ID NO: 661 is vector pLA54.

SEQ ID NO: 715 is vector pRS423::pGAL1-cre.

SEQ ID NO: 716 is the vector pLH468-sadB.

SEQ ID NOs: 717 and 718 are the amino acid and nucleic acid sequences for sadB from *Achromobacter xylosoxidans*.

SEQ ID NO: 719 is the kivD coding region from *L. lactis*.

SEQ ID NO: 720 is the plasmid pRS425::GPM-sadB.

SEQ ID NO: 721 is the GPM promoter.

SEQ ID NO: 722 is the ADH1 terminator.

SEQ ID NO: 723 is the GPM-sadB-ADHt segment.

SEQ ID NO: 724 is the pUC19-URA3 plasmid.

SEQ ID NO: 741 is the ilvD-FBA1t segment.

SEQ ID NO 749 is URA3r2 template DNA.

SEQ ID NO: 1886 is the ilvD coding region from *S. mutans*.

SEQ ID NO: 1888 is vector 011468.

SEQ ID NO: 1898 is pUC19-URA3::pdc1::GPD-xpk1+ADH1-eutD.

SEQ ID NOs: 1899-1906 are the sequences of modified *S. cerevisiae* loci.

SEQ ID NO: 1907 is the sequence of pLH702.

SEQ ID NO: 1908 is the sequence of pYZ067DkivDDhADH

SEQ ID NO: 1909 is the amino acid sequence of ALD6.

SEQ ID NO: 1910 is the amino acid sequence of K9D3.

SEQ ID NO: 1911 is the amino acid sequence of K9G9.

SEQ ID NO: 1912 is the amino acid sequence of YMR226c.

SEQ ID NOs: 1913 and 1914 are the nucleic acid and amino acid sequences of AFT1.

SEQ ID NOs: 1915 and 1916 are the nucleic acid and amino acid sequences of AFT2.

SEQ ID NOs: 1917 and 1918 are the nucleic acid and amino acid sequences of FRA2.

SEQ ID NOs. 1919 and 1920 are the nucleic acid and amino acid sequences of GRx3.

SEQ ID NOs: 1921 and 1922 are the nucleic acid and amino acid sequences of CCC1.

SEQ ID NO: 1923 is the amino acid sequence of an alcohol dehydrogenase from *Beijerinkia indica*.

DETAILED DESCRIPTION OF THE INVENTION

Applicants have solved the stated problem by reducing or eliminating the need for providing two substrates, one of which is converted to a desired product, the other fully or partly into acetyl-CoA by recombinant host cells requiring such supplementation for growth comprising the expression of enzymes of the phosphoketolase pathway in such cells. One such enzyme, phosphoketolase (Enzyme Commission Number EC 4.1.2.9), catalyzes the conversion of xylulose 5-phosphate into glyceraldehyde 3-phosphate and acetyl-phosphate (Heath et al., *J. Biol. Chem.* 231: 1009-29; 1958). Another such enzyme is phosphotransacetylase (Enzyme Commission Number EC 2.3.1.8) which converts acetyl-phosphate into acetyl-CoA.

Applicants have provided PDC-KO recombinant host cells comprising a heterologous polynucleotide encoding a polypeptide having phosphoketolase activity, and optionally a heterologous polynucleotide encoding a polypeptide having phosphotransacetylase activity. Such cells exhibit a reduced or eliminated requirement for exogenous two-carbon substrate supplementation for their growth compared to PDC-KO cells. Applicants have also provided methods of making and using such recombinant host cells including, for example, methods of increasing cell growth, methods of reducing or eliminating the requirement of an exogenous two-carbon substrate for cell growth, methods of increasing glucose consumption and methods of increasing the production of a product of a pyruvate-utilizing pathway.

Unless defined otherwise, all technical and scientific terms used herein have the same meaning as commonly understood by one of ordinary skill in the art to which this invention belongs. In case of conflict, the present application including the definitions will control. Unless otherwise required, by context, singular terms shall include pluralities and plural terms shall include the, singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

In order to further define this invention, the following terms, abbreviations and definitions are provided.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or use, solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "butanol" as used herein, refers to 2-butanol, 1-butanol, isobutanol, or mixtures thereof.

The term "pyruvate-utilizing biosynthetic pathway" refers to an enzyme pathway to produce a biosynthetic product from pyruvate.

The term "isobutanol biosynthetic pathway" refers to an enzyme pathway to produce isobutanol from pyruvate.

The term "2-butanol biosynthetic pathway" refers to an enzyme pathway to produce 2-butanol from pyruvate.

The term "2-butanone biosynthetic pathway" refers to an enzyme pathway to produce 2-butanone from pyruvate.

The terms "pdc-," "PDC knock-out," or "PDC-KO" as used herein refer to a cell that has a genetic modification to inactivate or reduce expression of at least one gene encoding pyruvate decarboxylase (PDC) so that the cell substantially or completely lacks pyruvate decarboxylase enzyme activity. If the cell has more than one expressed (active) PDC gene, then each of the active PDC genes may be inactivated or have minimal expression thereby producing a pdc-cell.

The term "carbon substrate" refers to a carbon source capable of being metabolized by the recombinant host cells disclosed herein. Non-limiting examples of carbon substrates are provided herein and include, but are not limited to, monosaccharides, oligosaccharides, polysaccharides, ethanol, lactate, succinate, glycerol, carbon dioxide, methanol, glucose, fructose, sucrose, xylose, arabinose, dextrose, or mixtures thereof.

The term "exogenous two-carbon substrate" refers to the carbon source provided to be metabolized into acetyl-CoA by a host cell that lacks the ability to convert pyruvic acid into acetyl-CoA. The term is used to distinguish from the carbon substrate which is converted into a pyruvate-derived product by a pyruvate-utilizing biosynthetic pathway, herein also referred to as the "pathway substrate" which includes, for example, glucose.

The term "polynucleotide" is intended to encompass a singular nucleic acid as well as plural nucleic acids, and refers to a nucleic acid molecule or construct, e.g., messenger RNA (mRNA) or plasmid DNA (pDNA). A polynucleotide can contain the nucleotide sequence of the full-length cDNA sequence, or a fragment thereof, including the untranslated 5' and 3' sequences and the coding sequences. The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. "Polynucleotide" embraces chemically, enzymatically, or metabolically modified forms.

A polynucleotide sequence may be referred to as "isolated," in which it has been removed from its native environment. For example, a heterologous polynucleotide encoding a polypeptide or polypeptide fragment having dihydroxy-acid dehydratase activity contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA may be comprised of one or more segments of cDNA, genomic DNA or synthetic DNA.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Endogenous gene" refers to a native gene in its natural location in the genome of an organism. A "heterologous gene" refers to a gene not normally found in the host organism, but that is introduced into the host organism by gene transfer. "Heterologous gene" includes a native coding region, or portion thereof, that is reintroduced into the source organism in a form that is different from the corresponding native gene. For example, a heterologous gene may include a native coding region that is a portion of a chimeric gene including non-native regulatory regions that is reintroduced into the native host. Foreign genes can comprise native genes inserted into a non-native organism, or chimeric genes.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. A polypeptide may be derived from a natural biological source or produced by recombinant technology, but is not necessarily translated from a designated nucleic acid sequence. It may be generated in any manner, including by chemical synthesis.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

As used herein, the term "valiant" refers to a polypeptide differing from a specifically recited polypeptide of the invention by amino acid insertions, deletions, mutations, and substitutions, created using, e.g., recombinant DNA techniques, such as mutagenesis. Guidance in determining which amino acid residues may be replaced, added, or deleted without abolishing activities of interest, may be found by comparing the sequence of the particular polypeptide with that of homologous polypeptides, e.g., yeast or bacterial, and minimizing the number of amino acid sequence changes made in regions of high homology (conserved regions) or by replacing amino acids with consensus sequences.

Alternatively, recombinant polynucleotide variants encoding these same or similar polypeptides may be synthesized or selected by making use of the "redundancy" in the genetic code. Various codon substitutions, such as silent changes which produce various restriction sites, may be introduced to optimize cloning into a plasmid or viral vector for expression. Mutations in the polynucleotide sequence may be reflected in the polypeptide or domains of other peptides added to the polypeptide to modify the properties of any part of the polypeptide.

Amino acid "substitutions" may be the result of replacing one amino acid with another amino acid having similar structural and/or chemical properties, i.e., conservative amino acid replacements, or they may be the result of replacing, one amino acid with an amino acid having different structural and/or chemical properties, i.e., non-conservative amino acid replacements. "Conservative" amino acid substitutions may be made on the basis of similarity in polarity, charge, solubility, hydrophobicity, hydrophilicity, or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and, histidine; and negatively charged (acidic) amino acids include aspartic acid and glutamic acid. Alternatively, "non-conservative" amino acid substitutions may be made by selecting the differences in polarity, charge, solubility, hydrophobicity, hydrophilicity, or the amphipathic nature of any of these amino acids. "Insertions" or "deletions" may be within the range of variation as structurally or functionally tolerated by the recombinant proteins. The variation allowed may be experimentally determined by systematically making insertions, deletions, or substitutions of amino acids in a polypeptide molecule using recombinant DNA techniques and assaying the resulting recombinant variants for activity.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths may have identical promoter activity. For example, it will be understood that "FBA1 promoter" can be used to refer to a fragment derived from the promoter region of the FBA1 gene.

The term "terminator" as used herein refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence. It is recognized that since in most cases the exact boundaries of regulatory sequences have not been completely defined, DNA fragments of different lengths may have identical terminator activity. For example, it will be understood that "CYC1 terminator" can be used to refer to a fragment derived from the terminator region of the CYC1 gene.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression," as used herein, refers to the transcription and stable accumulation of sense (mRNA) or antisense RNA derived from the nucleic acid fragment of the invention. Expression may also refer to translation of mRNA into a polypeptide.

The term "overexpression," as used herein, refers to expression that is higher than endogenous expression of the same or related gene. A heterologous gene is overexpressed if its expression is higher than that of a comparable endogenous gene.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| T | C | A | G |
|---|---|---|---|
| T TTT Phe (F) | TCT Ser (S) | TAT Tyr (Y) | TGT Cys (C) |
| TTC " | TCC " | TAC " | TGC |

TABLE 1-continued

The Standard Genetic Code

|   | T | C | A | G |
|---|---|---|---|---|
|   | TTA Leu (L) | TCA " | TAA Stop | TGA Stop |
|   | TTG " | TCG " | TAG Stop | TGG Trp (W) |
| C | CTT Leu (L) | CCT Pro (P) | CAT His (H) | CGT Arg (R) |
|   | CTC " | CCC " | CAC " | CGC " |
|   | CTA " | CCA " | CAA Gln (Q) | CGA " |
|   | CTG " | CCG " | CAG " | CGG " |
| A | ATT Ile (I) | ACT Thr (T) | AAT Asn (N) | AGT Ser (S) |
|   | ATC " | ACC " | AAC " | AGC " |
|   | ATA " | ACA " | AAA Lys (K) | AGA Arg (R) |
|   | ATG Met (M) | ACG " | AAG " | AGG " |
| G | GTT Val (V) | GCT Ala (A) | GAT Asp (D) | GGT Gly (G) |
|   | GTC " | GCC " | GAC " | GGC " |
|   | GTA " | GCA " | GAA Glu (E) | GGA " |
|   | GTG " | GCG " | GAG " | GGG " |

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at http://www.kazusa.or.jp/codon/ (visited Mar. 20, 2008), and these tables can be adapted in a number of ways. See Nakamura, Y., et al. *Nucl. Acids Res.* 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. Table 2 has been adapted so that frequencies are calculated for each amino acid, rather than for all 64 codons.

TABLE 2

Codon Usage Table for *Saccharomyces cerevisiae* Genes

| Amino Acid | Codon | Number | Frequency per thousand |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |

TABLE 2-continued

Codon Usage Table for *Saccharomyces cerevisiae* Genes

| Amino Acid | Codon | Number | Frequency per thousand |
|---|---|---|---|
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtransation function in the VectorNTI Suite, available from InforMax, Inc., Bethesda, Md., and the "backtranslate" function in the GCG-Wisconsin Package, available from Accelrys, Inc., San Diego, Calif. In addition, various resources are publicly available to codon-optimize coding region sequences, e.g., the "backtranslation" function at http://www.entelechon.com/bioinformatics/backtranslation.php?lang=eng (visited Apr. 15, 2008) and the "backtranseq" function available at http://bioinfo.pbi.nrc.ca:8090/EMBOSS/index.html (visited Jul. 9, 2002). Constructing a rudimentary algorithm to assign, codons based on a given frequency can also easily be accomplished with basic mathematical functions by one of ordinary skill in the art.

Codon-optimized coding regions can be designed by various methods known to those skilled in the art including software packages such as "synthetic gene designer" (http://phenotype.biosci.umbc.edu/codon/sal/index.php).

A polynucleotide or nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboraton Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tin) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence, of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.*, 215:403-410 (199.3)). In general, a sequence often or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The team "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY-10. Default parameters for pairwise alignments and calculation of percent identity of protein sequences using the Clustal method are KTUPLE=1, GAP PENALTY-3, WINDOW-5 and DIAGONALS SAVED=5. For nucleic acids these parameters are KTUPLE=2, GAP PENALTY=5, WINDOW=4 and DIAGONAS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, such as from other species, wherein such polypeptides have the same or similar function or activity. Useful examples of percent identities include, but are not limited to: 55%, 60%, 65%, 70%, 75%, 80%, 85%, 90%, or 95%, or any integer percentage from 55% to 100% may be useful in describing the present invention, such as 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res., [Proc. Int. Symp.]* (1994), Meeting Date 1992, 111-20. Editor(s): Suhai, Samlor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y.

(1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M, et al., *Current Protocols in Molecular Biology*, published by Greene Publishing Assoc. and Wiley-Interscience (1987). Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.). Other molecular tools and techniques are known in the art and include splicing by overlapping extension polymerase chain reaction (PCR) (Yu, et al. (2004) Fungal Genet. Biol. 41:973-981), positive selection for mutations at the URA3 locus of *Saccharomyces cerevisiae* (Boeke, J. D. et al. (1984) Mol. Gen. Genet. 197, 345-346; M A Romanos, et al. Nucleic Acids Res. 1991 Jan. 11; 19(1): 187), the cre-lox site-specific recombination system as well as mutant lox sites and FLP substrate mutations (Sauer, B. (1987) Mol Cell Biol 7: 2087-2096; Senecoff, et al. (1988) Journal of Molecular Biology, Volume 201, Issue 2, Pages 405-421; Albert, et al, (1995) The Plant Journal. Volume 7, Issue 4, pages 649-659), "seamless" gene deletion (Akada, et al. (2006) Yeast; 23(5):399-405), and gap repair methodology (Ma et al., *Genetics* 58:201-216; i. 981). Applicants have discovered that activation of the phosphoketolase pathway in a recombinant host cell comprising a modification in an endogenous gene encoding a polypeptide having pyruvate decarboxylase activity or a modification in an endogenous polypeptide having pyruvate decarboxylase activity, reduces or eliminates the need for an exogenous carbon substrate for the growth of such a cell. In embodiments, the recombinant host cells comprise (i) at least one deletion, mutation and/or substitution in an endogenous gene encoding a polypeptide having pyruvate decarboxylase activity); (ii) a heterologous polynucleotide encoding a polypeptide having phosphoketolase activity; and optionally (iii) a heterologous polynucleotide encoding a polypeptide having phosphotransacetylase activity.

The genetic manipulations of the host cells described herein can be performed using standard genetic techniques and screening and can be made in any host cell that is suitable to genetic manipulation (*Methods in Yeast Genetic's*, 2005, Cold Spring Harbor Laboratory Press Cold Spring Harbor, N.Y., pp. 201-202). In embodiments, the recombinant host cells disclosed herein can be any bacteria, yeast or fungi host useful for genetic modification and recombinant gene expression. In other embodiments a recombinant host cell can be a member of the genera *Clostridium, Zymomonas, Eseherichia, Salmonella, Serratia, Erwinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizoaccharomyces, Kluyveromyces, Yarrowia, Pichia, Candida, Hansenula, Issatchenkia, saccharomyces*. In other embodiments, the host cell can be *Saccharomyces cerevisiae, Schizosaccharomyces pombe, Kluyveromyces lactic, Kluyveromyces thermotolerans, Kluyveromyces marxianus, Candida glabrata, Candida albicans, Pichia stipitis, Yarrowia lipolytica, E. coli*, or *L. plantarum*. In still other embodiments, the host cell is a yeast host cell. In some embodiments, the host cell is a member of the genera *Saccharomyces*. In some embodiments, the host cell is Kluyveromyces *Candida glabrata* or *Schizosaccharomyces pombe*. In some embodiments, the host cell is *Saccharomyces cerevisiae. S. cerevisiae* yeast are known in the art and are available from a variety of sources, including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

Sources of Acetyl-CoA

Acetyl-CoA is a major cellular building block, required for the synthesis of fatty acids, sterols, and lysine. Pyruvate is often a major contributor to the acetyl-CoA pool. Pyruvate dehydrogenase catalyzes the direct conversion of pyruvate to acetyl-CoA (E.C. 1.2.4.1, E.C. 1.2.1.51) or acetate (E.C. 1.2.2.2) and is almost ubiquitous in nature. Other enzymes involved in conversion of pyruvate to acetyl-CoA, acetyl-phosphate or acetate include pyruvate-formate lyase (E.C. 2.3.1.54), pyruvate oxidase (E.C. 1.2.3.3, E.C. 1.2.3.6), pyruvate-ferredoxin oxidoreductase (E.C. 1.2.7.1), and pyruvate decarboxylase (E.C. 4.1.1.1). Genetic modifications made to a host cell to conserve the pyruvate pool for a product of interest may include those that restrict conversion to acetyl-CoA, leading to decreased growth in the absence of an exogenously supplied two-carbon substrate, a carbon substrate that can be readily converted to acetyl-CoA independent of pyruvate (e.g. ethanol or acetate). An example is the documented auxotrophy observed in pyruvate decarboxylase deficient *Saccharomyces cerevisiae* (Flikweert et al. 1999, supra). Another example is the documented auxotrophy observed in pyruvate dehydrogenase deficient *Escherichia coli* when grown aerobically on glucose (Langley and Guest, 1977, J. Gen. Microbial. 99:2630276).

Modification of Pyruvate Decarboxylase

In embodiments, the recombinant host cells disclosed herein comprise a modification in an endogenous polynucleotide encoding a polypeptide having pyruvate decarboxylase (PDC) or a modification in an endogenous polypeptide having PDC activity. In embodiments, the recombinant host cells disclosed herein can have a modification or disruption of one or more polynucleotides, genes or polypeptides encoding PDC. In embodiments, the recombinant host cell comprises at least one deletion, mutation, and/or substitution in one of more endogenous polynucleotides or genes encoding a polypeptide having PDC activity, or in one or more endogenous polypeptides having PDC activity. Such modifications, disruptions, deletions, mutations, and/or substitutions can result in PDC activity that is reduced or eliminated, resulting in a PDC knock-out (PDC-KO) phenotype.

In embodiments, the endogenous pyruvate decarboxylase activity of the recombinant host cells disclosed herein converts pyruvate to acetaldehyde, which can then be converted to ethanol or to acetyl-CoA via acetate.

In embodiments, the recombinant host cell is *Kluyveromyces lactis* containing one gene encoding pyruvate decarboxylase, *Candida glabrata* containing one gene encoding pyruvate decarboxylase, or *Schizosaccharomyces pombe* containing one gene encoding pyruvate decarboxylase.

In other embodiments, the recombinant host cell is *Saccharomyces cerevisiae* containing three isozymes of pyruvate decarboxylase encoded by the pdc1, pdc5, and pdc6 genes, as well as a pyruvate decarboxylase regulatory gene, pdc2. In a non-limiting example in *S. cerevisiae*, the pdc1 and pdc5 genes, or all three genes, are disrupted. In another non-limiting example in *S. cerevisiae*, pyruvate decarboxylase activity may be reduced by disrupting the pdc2 regulatory gene. In, another non-limiting example in *S. cerevisiae*, polynucleotides or genes encoding pyruvate decarboxylase proteins such as those having about 70% to about 75%, about 75% to about 80%, about 80% to about 85%, about 85% to about 90%, about 90% to about 95%, about 96%, about 97%, about 98%, or about 99% sequence identity to pdc1 or pdc5 can be disrupted.

In embodiments, the polypeptide having PDC activity or the polynucleotide or gene encoding a polypeptide having PDC activity is associated with Enzyme Commission Number EC 4.1.1.1. In other embodiments, a PDC gene of the recombinant host cells disclosed herein is not active under the fermentation conditions used, and therefore such a gene would not need to be modified or inactivated.

Examples of recombinant host cells with reduced pyruvate decarboxylase activity due to disruption of pyruvate decarboxylase encoding genes have been reported, such as for *Saccharomyces* in Flikweert et al. (*Yeast* (1996) 12:247-257), for *Kluyveromyces* in Bianchi et al. (*Mol. Microbiol.* (1996) 19(1):27-36), and disruption of the regulatory gene in Hohmann (*Mol. Gen. Genet.* (1993) 241:657-666). *Saccharomyces* strains having no pyruvate decarboxylase activity are available from the ATCC with Accession #200027 and #200028.

Examples of PDC polynucleotides, genes and polypeptides that can be targeted for modification or inactivation in the recombinant host cells disclosed herein include, but are not limited to, those of the following table.

TABLE 3

SEQ ID NOs of pyruvate decarboxylase (PDC) target gene coding regions and proteins.

| Description | SEQ ID NO: Nucleic acid | SEQ ID NO: Amino acid |
|---|---|---|
| PDC1 pyruvate decarboxylase from *Saccharomyces cerevisiae* | 1 | 2 |
| PDC5 pyruvate decarboxylase from *Saccharomyces cerevisiae* | 3 | 4 |
| PDC6 pyruvate decarboxylase from *Saccharomyces cerevisiae* | 5 | 6 |
| pyruvate decarboxylase from *Candida glabrata* | 7 | 8 |
| PDC1 pyruvate decarboxylase from *Pichia stipitis* | 9 | 10 |
| PDC2 pyruvate decarboxylase from *Pichia stipitis* | 11 | 12 |
| pyruvate decarboxylase from *Kluyveromyces lactis* | 13 | 14 |
| pyruvate decarboxylase from *Yarrowia lipolytica* | 15 | 16 |
| pyruvate decarboxylase from *Schizosaccharomyces pombe* | 17 | 18 |
| pyruvate decarboxylase from *Zygosaccharomyces rouxii* | 18 | 20 |

Other examples of PDC polynucleotides, genes and polypeptides that can be targeted for modification or inactivation in the recombinant host cells disclosed herein include, but are not limited to, PDC polynucleotides, genes and/or polypeptides having at least about 70% to about 75%, about 75% to about 80%, about 80% to about 85%, about 85% to about 90%, about 90% to about 95%, about 96%, about 97%, about 98%, or about 99% sequence identity to any one of the sequences of Table 3.

In embodiments, the sequences of other PDC polynucleotides, genes and/or polypeptides can be identified in the literature and in bioinformatics databases well known to the skilled person using sequences disclosed herein and available in the art. For example, such sequences can be identified through BLAST (as described above) searching of publicly available databases with known PDC encoding polynucleotide or polypeptide sequences. In such a method, identities can be based on the Clustal W method of alignment using the default parameters of GAP PENALTY=10, GAP LENGTH PENALTY=0.1, and Gonnet 250 series of protein weight matrix.

Additionally, the PDC polynucleotide or polypeptide sequences described herein or known the art can be used to identify other PDC homologs in nature. For example, each of the PDC encoding nucleic acid fragments described herein can be used to isolate genes encoding homologous proteins. Isolation of homologous genes using sequence-dependent protocols is well known in the art. Examples of sequence-dependent protocols include, but are not limited to (1) methods of nucleic acid hybridization; (2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker et al., *Proc. Natl. Acad. Sci. USA.,* 89:392 (1992)]; and (3) methods of library construction and screening by complementation.

In embodiments, PDC polynucleotides, genes and/or polypeptides related to the recombinant host cells described herein can be modified or disrupted. Many methods for genetic modification and disruption of target genes to reduce or eliminate expression are known to one of ordinary skill in the art and can be used to create the recombinant host cells described herein. Modifications that can be used include, but are not limited to, deletion of the entire gene or a portion of the gene encoding a PDC protein, inserting a DNA fragment into the encoding gene (in either the promoter or coding region) so that the protein is not expressed or expressed at lower levels, introducing a mutation into the coding region which adds a stop codon or frame shift such that a functional protein is not expressed, and introducing one or more mutations into the coding region to alter amino acids so that a non-functional or a less active protein is expressed. In other embodiments, expression of a target gene can be blocked by expression of an antisense RNA or an interfering RNA, and constructs can be introduced that result in, cosuppression. In other embodiments, the synthesis or stability of the transcript can be lessened by mutation. In embodiments, the efficiency by which a protein is translated from mRNA can be modulated by mutation. All of these methods can be readily practiced by one skilled in the art making use of the known or identified sequences encoding target proteins.

In other embodiments, DNA sequences surrounding a target PDC coding sequence are also useful in some modification procedures and are available, for example, for yeasts such as *Saccharomyces cerevisiae* in the complete genome sequence coordinated by Genome Project ID9518 of Genome Projects coordinated by NCBI (National Center for Biotechnology Information) with identifying GOPID #13838. An additional non-limiting example of yeast genomic sequences is that of *Candida albicans*, which is included in GPID #10771, #10701 and #16373, Other yeast genomic sequences can be readily found by one of skill in the art in publicly available databases.

In other embodiments, DNA sequences surrounding a target PDC coding sequence can be useful for modification methods using homologous recombination. In a non-limiting example of this method, PDC gene flanking sequences can be placed bounding a selectable marker gene to mediate homologous recombination whereby the marker gene replaces the PDC gene. In another non-limiting example, partial PDC gene sequences and PDC, gene flanking sequences bounding a selectable marker gene can be used to mediate homologous recombination whereby the marker gene replaces a portion of the target PDC, gene. In embodiments, the selectable marker can be bounded by site-specific recombination sites, so that following expression of the corresponding site-specific recombinase, the resistance gene is excised from the PDC gene without reactivating the latter. In embodiments, the site-specific recombination leaves behind a recombination site which disrupts expression of the PDC protein. In other embodiments, the homologous recombination vector can be constructed to also leave a deletion in the PDC gene following excision of the selectable marker, as is well known to one skilled in the art.

In other embodiments, deletions can be made to a PDC target gene using mitotic recombination as described in Wach et al. (*Yeast*, 10:1793-1808; 1994). Such a method can involve preparing a DNA fragment that contains a selectable marker between genomic regions that can be as short as 20 bp, and which bound a target DNA sequence. In other embodiments, this DNA fragment can be prepared by PCR amplification of the selectable marker gene using as primers oligonucleotides that hybridize to the ends of the marker gene and that include the genomic regions that can recombine with the yeast genome. In embodiments, the linear DNA fragment can be efficiently transformed into yeast and recombined into the genome resulting in gene replacement including with deletion of the target DNA sequence ((as described, for example, in *Methods in Enzymology*, Volume 194, Guide to Yeast Genetics and Molecular and Cell Biology (Part A. 2004, Christine Guthrie and Gerald R. Fink (Eds.), Elsevier Academic Press, San Diego, Calif.)).

Moreover, promoter replacement methods can be used to exchange the endogenous transcriptional control elements allowing another means to modulate expression such as described in Mnaimneh et al. ((2004) *Cell* 118(1):31-44).

In other embodiments, the PDC target gene encoded activity can be disrupted using random mutagenesis, which can then be followed by screening to identify strains with dependency on carbon substrates for growth. In this type of method, the DNA sequence of the target gene encoding region, or any other region of the genome affecting carbon substrate dependency for growth, need not be known. In embodiments, a screen for cells with reduced PDC activity and/or two-carbon substrate dependency, or other mutants having reduced PDC activity and a reduced or eliminated dependency for exogenous two-carbon substrate for growth, can be useful as recombinant host cells of the invention.

Methods for creating genetic mutations are common and well known in the art and can be applied to the exercise of creating mutants. Commonly used random genetic modification methods (reviewed in *Methods in Yeast Genetics*, 2005, Cold Spring Harbor Laboratory Press, Cold Spring Harbor, N.Y.) include spontaneous mutagenesis, mutagenesis caused by mutator genes, chemical mutagenesis, irradiation with UV or X-rays, or transposon mutagenesis.

Chemical mutagenesis of host cells can involve, but is not limited to, treatment with one of the following DNA mutagens: ethyl methanesulfonate (EMS), nitrous acid, diethyl sulfate, or N-methyl-N'-nitro-N-nitroso-guanidine (MNNG). Such methods of mutagenesis have been reviewed in Spencer et al., (Mutagenesis in Yeast, 1996, *Yeast Protocols: Methods in Cell and Molecular Biology*. Humana Press, Totowa, N.J.). In embodiments, chemical mutagenesis with EMS can be performed as described in *Methods in Yeast Genetics*, 2005, Cold Spring Harbor Laboratory Press, Cold Spring Harbor, N.Y. Irradiation with ultraviolet (UV) light or X-rays can also be used to produce random mutagenesis in yeast cells. The primary effect of mutagenesis by UV irradiation is the formation of pyrimidine dimers which disrupt the fidelity of DNA replication. Protocols for UV-mutagenesis of yeast can be found in Spencer et al. (Mutagenesis in Yeast, 1996, *Yeast Protocols: Methods in Cell and Molecular Biology*. Humana Press, Totowa, N.J.). In embodiments, the introduction of a mutator phenotype can also be used to generate random chromosomal mutations in host cells. In embodiments, common imitator phenotypes can be obtained through disruption of one or more of the following genes: PMS1, MAG1, RAD18 or RAD51. In other embodiments, restoration of the non-mutator phenotype can be obtained by insertion of the wildtype allele. In other embodiments, collections of modified cells produced from any of these or other known random mutagenesis processes may be screened for reduced or eliminated PDC activity.

Genomes have been completely sequenced and annotated and are publicly available for the following yeast strains: *Ashbya gossypii* ATCC 10895, *Candida glabrata* CBS138, *Kluyveromyces lactis* NRRL Y-1140, *Pichia stipitis* CBS 6054, *Saccharomyces cerevisiae* S288c, *Schizosaccharomyces pombe* 972h-, and *Yarrowia lipolytica* CLIB 122. Typically BLAST (described above) searching of publicly available databases with known PDC polynucleotide or polypeptide sequences, such as those provided herein, is used to identify PDC-encoding sequences of other host cells, such as yeast cells.

Accordingly, it is within the scope of the invention to provide pyruvate decarboxylase polynucleotides and polypeptides having at, least about 70% to about 75%, about 75% to about 80%, about 80% to about 85%, about 85% to about 90%, about 90% to about 95%, about 96%, about 97%, about 98%, or about 99% sequence identity to any of the PDC polypeptides or polypeptides disclosed herein (SEQ ID NOs: 1-20). Identities are based on the Clustal W method of alignment using the default parameters of GAP PENALTY=10, GAP LENGTH PENALTY=0.1, and Gonnet 250 series of protein weight matrix.

The modification of PDC in the host cells disclosed herein to reduce or eliminate PDC activity can be confirmed using methods known in the art. For example, PCR methods well known in the art can be used to confirm deletion of PDC. Other suitable methods will be known to those of skill in the art and include, but are not limited to lack of growth on yeast extract peptone-dextrose medium (YPD).

Introduction of the Phosphokeetolase Pathway

Applicants have found that expression of enzymes associated with the phosphoketolase pathway (e.g., phosphoketolase and/or phosphotransacetylase) results in a reduced or eliminated requirement for exogenous two-carbon substrate supplementation for growth of PDC-KO cells. Phosphoketolases and/or phosphotransacetylases identified as described herein, can be expressed in such cells using methods described herein.

Figure 1:
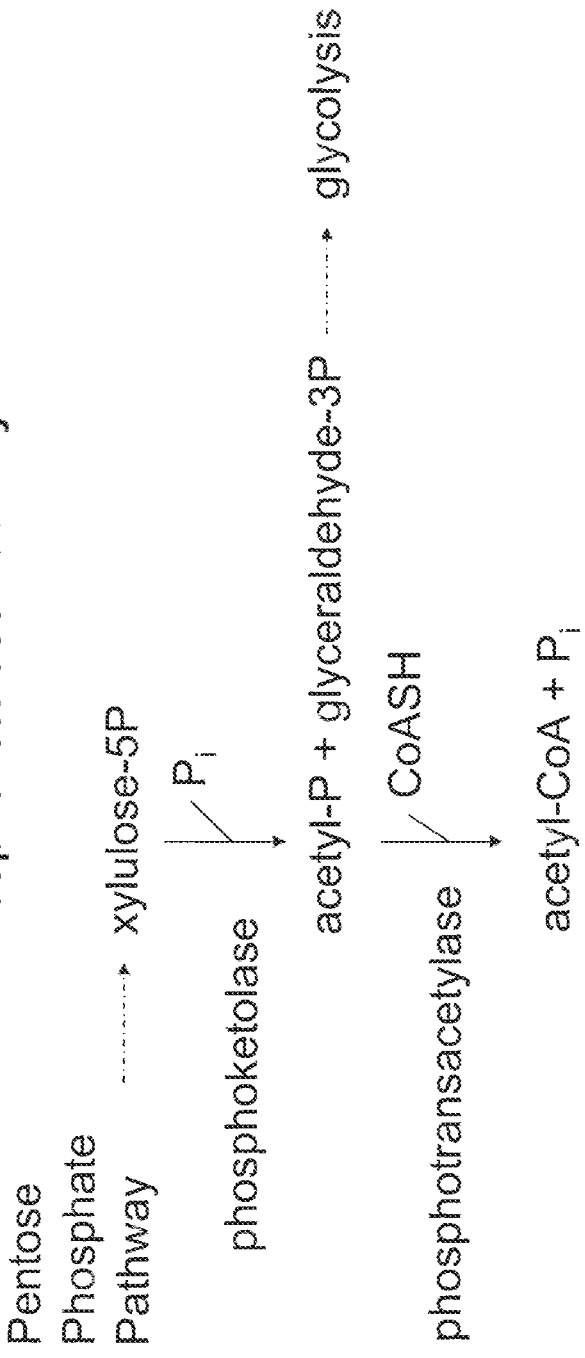
FIG. 1 depicts a schematic representation of the phosphoketolase pathway, including the phosphoketolase and phosphotransacetylase enzymes.

Enzymes of the phosphoketolase pathway include phosphoketolase and phosphotransacetylase (FIG. 1). Phosphoketolase (Enzyme Commission Number EC 4.1.2.9) catalyzes the conversion of xylulose. 5-phosphate into glyceraldehyde 3-phosphate and acetyl-phosphate (heath et al., *J. Biol. Chem.* 231: 1009-29; 1958). Phosphoketolase activity has been identified in several yeast strains growing with xylose as the sole carbon source but not in yeast strains grown with glucose (Evans and Ratledge; *Arch. Microbiol.*

139: 48-52; 1984). Inhibitors of phosphoketolase include, but are not limited to, erythrose 4-phosphate and glyceraldehyde 3-phosphate. Phosphotransacetylase (Enzyme Commission Number EC 2.3.1.8) converts acetyl-phosphate into acetyl-CoA.

In embodiments, the phosphoketolase pathway is activated in the recombinant host cells disclosed herein by engineering the cells to express polynucleotides and/or polypeptides encoding phosphoketolase and, optionally, phosphotransacetylase. In embodiments, the recombinant host cells disclosed herein comprise a heterologous polynucleotide encoding a polypeptide having phosphoketolase activity. In other embodiments, the recombinant host cells disclosed herein comprise a heterologous polynucleotide encoding, a polypeptide having phosphoketolase activity and a heterologous polynucleotide encoding a polypeptide having phosphotransacetylase activity. In other embodiments, the heterologous polynucleotide encoding a polypeptide having phosphoketolase activity is overexpressed, or expressed at a level that is higher than endogenous expression of the same or related endogenous gene, if any. In still other embodiments, the heterologous polynucleotide encoding a polypeptide having phosphotransacetylase activity is overexpressed, or expressed at a level that is higher than endogenous expression of the same or related endogenous gene, if any.

In embodiments, a polypeptide having phosphoketolase activity catalyzes the conversion of xylulose 5-phosphate into glyceraldehyde-3-phosphate and acetyl-phosphate and/or the conversion of fructose-6-phosphate into erythrose-4-phosphate and acetyl-phosphate. In embodiments, the activity of a polypeptide having phosphoketolase activity is inhibited by erythrose 4-phosphate and/or glyceraldehyde 3-phosphate. In other embodiments, a polypeptide having phosphotransacetylase activity catalyzes the conversion of acetyl-phosphate into acetyl-CoA.

Numerous examples of polynucleotides, genes and polypeptides encoding phosphoketolase activity are known in the art and can be used in the recombinant host cells disclosed herein. In embodiments, such a polynucleotide, gene and/or polypeptide can be the xylulose 5-phosphateketolase (XpkA) of *Lactobacillus pentosus* MD363 (Posthuma et al., *Appl. Environ Microbiol.* 68: 831-7; 2002). XpkA is the central enzyme of the phosphoketolase pathway (PKP) in lactic acid bacteria, and exhibits a specific activity of 4.455 µmol/min/mg (Posthuma et al., *Appl. Environ. Microbiol.* 68: 831-7; 2002). In other embodiments, such a polynucleotide, gene and/or polypeptide can be the phosphoketolase of *Leuconostoc mesenteroides* which exhibits a specific activity of 9.9 µmol/min/mg and is stable at pH above 4.5 (Goldberg et al., *Methods Enzymol.* 9: 515-520; 1966). This phosphoketolase exhibits a Km of 4.7 mM for D-xylulose 5-phosphate and a Km of 29 mM for fructose 6-phosphate (Goldberg et al., *Methods Enzymol.* 9: 515-520; 1966). In other embodiments, such a polynucleotide, gene and/or polypeptide can be the D-xylulose 5-phosphate/D-fructose 6-phosphate phosphoketolase gene xfp from *B. lactis*, as described, for example, in a pentose-metabolizing *S. cerevisiae* strain by Sonderegger et al. (*Appl. Environ. Microbiol.* 70: 2892-7; 2004).

In embodiments, a polynucleotide, gene and/or polypeptide encoding phosphoketolase corresponds to the Enzyme Commission Number EC 4.1.2.9.

In embodiments, host cells comprise a polypeptide having at least about 80%, at least about 85%, at least about 90%, or 100% identity to a polypeptide of Table 4 or an, active fragment thereof or a polynucleotide encoding such a polypeptide. In other embodiments, a polynucleotide, gene and/ or polypeptide encoding phosphoketolase can include, but is not limited to, a sequence provided in the following tables 4 or 5.

TABLE 4

| SEQ ID NOs of phosphoketolase target gene coding regions and proteins | | |
|---|---|---|
| Description | SEQ ID NO: Nucleic acid | SEQ ID NO: Amino acid | Amino Acid sequence |
| Xpk1 phosphoketolase from *Lactobacillus plantarum* | 172 | 481 | MTTDYSSPAYLQKVDKYWRAANYLSVGQLYLKDNPLLQRPL KASDVKVHPIGHWGTIAGQ NFIYAHLNRVINKYGLKMFYVEGPGHGGQVMVSNSYLDGTY TDIYPEITQDVEGMQKLFK QFSFPGGVASHAAPETPGSIHEGGELGYSISHGVGAILDNP DEIAAVVVGDGESETGPLA TSWQSTKFINPINDGAVLPILNLNGFKISNPTIFGRTSDAK IKEYFESMNWEPIFVEGDD PEKVHPALAKAMDEAVEKIKAIQKHARENNDATLPVWPMIV FRAPKGWTGPKSWDGDKIE GSFRAHQIPIPVDQNDMEHADALVDWLESYQPKELFNEDGS LKDDIKEIIPTGDSRMAAN PITNGGVDPKALNLPNFRDYAVDTSKEGANVKQDMIVWSDY LRDVIKKNPDNFRLFGPDE TMSNRLYGVFETTNRQWMEDIHPDSDQYEAPAGRVLDAQLS EHQAEGWLEGYVLTGRHGL FASYEAFLRVVDSMLTQHFKWLRKANELDWRKKYPSLNIIA ASTVFQQDHNGYTHQDPGA LTHLAEKKPEYIREYLPADANTLLAVGDVIFRSQEKINYVV TSKHPRQQWFSIEEAKQLV DNGLGIIDWASTDQGSEPDIVFAAAGTEPTLETLAAIQLLH DSFPEMKIRFVNVVDILKL RSPEKDPRGLSDAEFDHYFTKDKPVVFAFHGYEDLVRDIFF DRHNHNLYVHGYRENGDIT TPFDVRVMNQMDRFDLAKSAIAAQPAMENTGAAFVQSMDNM LAKHNAYIRDAGTDLPEVN DWQWKGLK |

TABLE 4-continued

SEQ ID NOs of phosphoketolase target gene coding regions and proteins

| Description | SEQ ID NO: Nucleic acid | SEQ ID NO: Amino acid | Amino Acid sequence |
|---|---|---|---|
| XpkA phospho-ketolase from *Lactobacillus pentosus* MD363 | 1890 | 1889 | MSTDYSSPAYLQKVDKYWRAANYLSVGQLYLKDNPLLQRPL KASDVKVHPIGHWGTIAGQ NFIYAHLNRVINKYGLKMFYVEGPGHGGQVMVSNSYLDGTY TDIYPEITQDVEGMQKLFK QFSFPGGVASHAAPETPGSIHEGGELGYSISHGVGAILDNP DEIAAVVVGDGESETGPLA TSWQSTKFINPINDGAVLPILNLNGFKISNPTIFGRTSDEK IKQYFESMNWEPIFVEGDD PEKVHPALAKAMDEAVEKIKAIQKNARENDDATLPVWPMIV FRAPKGWTGPKSWDGDKIE GSFRAHQIPIPVDQTDMEHADALVDWLESYQPKELFNEDGS LKDDIKEIIPTGDARMAAN PITNGGVDPKALNLPNFRDYAVDTSKHGANVKQDMIVWSDY LRDVIKKNPDNFRLFGPDE TMSNRLYGVFETTNRQWMEDIHPDSDQYEAPAGRVLDAQLS EHQAEGWLEGYVLTGRHGL FASYEAFLRVVDSMLTQHFKWLRKANELDWRKKYPSLNIIA ASTVFQQDHNGYTHQDPGA LTHLAEKKPEYIREYLPADANSLLAVGDVIFRSQEKINYVV TSKHPRQQWFSIEEAKQLV DNGLGIIDWASTDQGSEPDIVFAAAGTEPTLETLAAIQLLH DSFPDMKIRFVNVVDILKL RSPEKDPRGLSDAEFDHYFTKDKPVVFAFHGYEDLVRDIFF DRHNHNLHVHGYRENGDIT TPFDVRVMNQMDRFDLAKSAIAAQPAMENTGAAFVQDMDNM LAKHNAYIRDAGTDLPEVN DWQWKGLK |
| Xpf D-xylulose 5-phosphate/D-fructose 6-phosphate phospho-ketolase from *B. lactis* | 79 | 388 | MTNPVIGTPWQKLDRPVSEEAIEGMDKYWRVANYMSIGQIY LRSNPLMKEPFTRDDVKHR LVGHWGTTPGLNFLLAHINRLIADHQQNTVFIMGPGHGGPA GTAQSYIDGTYTEYYPNIT KDEAGLQKFFRQFSYPGGIPSHFAPETPGSIHEGGELGYAL SHAYGAIMDNPSLFVPCII GDGEAETGPLATGWQSNKLVNPRTDGIVLPILHLNGYKIAN PTILARISDEELHDFFRGM GYHPYEFVAGFDNEDHLSIHRRFAELFETIFDEICDIKAAA QTDDMTRPFYPMLIFRTPK GWTCPKFIDGKKTEGSWRAHQVPLASARDTEAHFEVLKGWM ESYKPEELFNADGSIKEDV TAFMPKGELRIGANPNANGGRIREDLKLPELDQYEITGVKE YGHGWGQVEAPRSLGAYCR DIIKNNPDSFRVFGPDETASNRLNATYEVTKKQWDNGYLSA LVDENMAVTGQVVEQLSEH QCEGFLEAYLLTGRHGIWSSYESFVHVIDSMLNQHAKWLEA TVREIPWRKPISSVNLLVS SHVWRQDHNGFSHQDPGVTSVLLNKTFNNDHVTNIYFATDA NMLLAIAEKCFKSTNKINA IFAGKQPAATWITLDEARAELEAGAAEWKWASNAKSNDEVQ VVLAAAGDVPTQEIMAASD ALNKMGIKFKVVNVVDLIKLQSSKENDEAMSDEDFADLFTA DKPVLFAYHSYAQDVRGLI YDRPNHDNFTVVGYKEQGSTTTPFDMVRVNDMDRYALQAKA LELIDADKYADKINELNEF RKTAFQFAVDNGYDIPEFTDWVYPDVKVDETSMLSATAATA GDNE |

In other embodiments, a polynucleotide, gene and/or polypeptide encoding phosphoketolase can have at least about 70% to about 75%, about 75% to about 80%, about 80% to about 85%, about 85% to about 90%, about 90% to about 95%, about 96%, about 97%, about 98%, or about 99% sequence identity to that of any one of the sequences of Table 4, wherein the polynucleotide, gene and/or polypeptide encodes a polypeptide having phosphoketolase activity.

In other embodiments, a polynucleotide, gene and/or polypeptide encoding phosphoketolase can be used to identify other phosphoketolase polynucleotide, gene and/or polypeptide sequences or to identify phosphoketolase homologs in other cells, as described above for PDC. Such phosphoketolase encoding sequences can be identified, for example, in, the literature and/or in bioinformatics databases well known to the skilled person. For example, the identification of phosphoketolase encoding sequences in other cell types using bioinformatics can be accomplished through BLAST (as described above) searching of publicly available databases with known phosphoketolase encoding DNA and polypeptide sequences, such as those provided herein. Identities are based on the Clustal W method of alignment using the default parameters of GAP PENALTY=10, GAP LENGTH PENALTY=0.1, and Gonnet 250 series of protein weight matrix.

Additional phosphoketolase target gene coding regions were identified using, diversity search, clustering, experimentally verified xylulose-5-phosphate/fructose-6-phosphate phosphoketolases and domain architecture. Briefly, a BLAST search with the experimentally verified sequences with an Evalue cut-off of 0.01 resulted in 595 sequence matches. Clustering with the CD-HIT program at 95% sequence identity and 90% length overlap reduced the number to 436. CD-HIT is a program for clustering large protein database at nigh sequence identity threshold. The program removes redundant sequences and gel erates a database of only the representatives. (Clustering of highly homologous sequences to reduce the size of large protein database, Weizhong Li, Lukasz Jaroszewski & Adam Godzik Bioinformatics, (2001) 17:282-283)

Xylulose-5-phosphate/fructose-6-phosphate phosphoketolases have three Pfam domains: XFP_N; XFP; XFP_C. Although each of these domains may be present in several domain architectures, e.g. XFP_N is found in eight architectures. The architecture of interest was determined to be XFP_N; XFP; XFP_C. The cumulative length of the three domains is 760 amino acids.

A structure/function characterization of the phosphoketolases was performed using the HMMER software package. The following information based on the HMMER software user guide gives some description of the way that the hmmbuild program prepares a Profile HMM. A Profile HMM is capable of modeling gapped alignments, e.g. including insertions and deletions, which lets the software describe a complete conserved domain (rather than just a small ungapped motif). Insertions and deletions are modeled using insertion (I) states and deletion (D) states. All columns that contain more than a certain fraction x of gap characters will be assigned as an insert column. By default, x is set to 0.5. Each match state has an I and a D state associated with it. HMMER calls a group of three states (M/D/I) at the same consensus position in the alignment a "node", These states are interconnected with arrows called state transition probabilities. M and I states are emitters, while D states are silent. The transitions are arranged so that at each node, either the M state is used (and a residue is aligned and scored) or the D state is, used (and no residue is aligned, resulting in a deletion-gap character, '-'). Insertions occur between nodes, and I states, have a self-transition, allowing one or more inserted residues to occur between consensus columns.

The scores of residues in a match state (i.e. match state emission scores), or in an insert state (i.e. insert state emission scores) are proportional to $Log\_2 (p\_x)/(null\_x)$. Where $p\_x$ is the probability of an amino acid residue, at a particular position in the alignment, according to the Profile HMM and $null\_x$ is the probability according to the Null model. The Null model is a simple one state probabilistic model with pre-calculated set of emission probabilities for each of the 20 amino acids derived from the distribution of amino acids in the SWISSPROT release 24. State transition scores are also calculated as log odds parameters and are propotional to $Log\_2 (t\_x)$. Where $t\_x$ is the probability of transiting to an emitter or non-emitter state.

Using a multiple sequence alignment of experimentally verified sequences containing the architecture of interest XFP_N; XFP; XFP_C, a profile Hidden Markov Model (HMM) was created for representing members of the xylulose-5-phosphate/fructose-6-phosphate phosphoketolases (XPK-XFP). As stated in the user guide, Profile HMMs are statistical models of multiple sequence alignments. They capture position-specific information about how conserved each column of the alignment is, and which amino acid residues are most likely to occur at each position. Thus HMMs have a formal probabilistic basis. Profile HMMs for a large number of protein families are publicly available in the PFAM database (Janelia Farm Research Campus, Ashburn, Va.), see ftp://ftp.sanger.ac.uk/pub/databases/Pfam/releases/Pfam24.0/.

Eight xylulose-5-phosphate/fructose-6-phosphate phosphoketolases sequences with experimentally verified function were identified in the BRENDA database:
1. CBF76492.1 from *Aspergillus nidulans* FGSC A4 (SEQ ID NO: 355)
2. AAR98787.1 from *Bifidobacterium longum* (SEQ ID NO: 379)
3. ZP_03646196.1 from *Bifidobacterium bifidum* NCIMB 41171 (SEQ ID NO: 381)
4. ZP_02962870.1 from *Bifidobacterium animalis* subsp. lactis HNO19 (SEQ ID NO: 388)
5. ZP_786060.1 from *Lactobacillus plantarum* WCFS1 (SEQ ID NO: 481)
6. ZP_03940142.1 from *Lactobacillus* brevis subsp. *gravesensis* ATCC 27305 (SEQ ID NO: 486)
7. ZP_03073172.1 from *Lactobacillus* reuteri 100-23 (SEQ ID NO 468)
8. YP_818922.1 from *Leuconostoc mesenteroides* subsp. *mesenteroides* ATCC 8293 (SEQ ID NO: 504)

The BRENDA database is a freely available information system containing biochemical and molecular information on all classified enzymes as well as software tools for querying the database and calculating molecular properties. The database covers information on classification and nomenclature, reaction and specificity, functional parameters, occurrence, enzyme structure and stability, mutants and enzyme engineering, preparation and isolation, the application of enzymes, and ligand-related data. (BRENDA, AMENDA and FRENDA the enzyme information system: new content and tools in 2009, Nucleic Acids Res. 2009 Jan; 37 (Database issue): D588-92. Epub 2008 Nov. 4. Chang A. Scheer M, Grote A, Schomburg I, Schomburg D.) The eight sequences were used to build a profile HMM which is provided herein as Table 6.

To further identify the proteins of interest, the 436 sequences were searched with tour profile HMMs: the generated XPK_XFP_HMM profile HMM provided in Table 6 as well as the three published profiles for the three domains XFP_N; XFP; XFP_C (PFAM DATABASE) described in Tables 7, 8, and 9, respectively. 309 protein sequences which lengths were between 650 amino acids and 900 amino acids, and contained the three domains were retained.

All 309 sequences are at least 40% identical to an experimentally verified phosphoketolase, with exception of 12 sequences that are within 35% identity distance. However, all 31.9 sequences have a highly significant match to all 4 profile HMMs. The least significant matches have Evalues of 7.5E-242, 1,1E-124, 2,1E-49, 7.8E-37 to XFP_XPK HMM, XFP_N, XFP, and XFP_C profile HMMs respectively. The 309 sequences are provided in Table 5, however, it is understood that any xylulose-5-phosphate/fructose-6-phosphate phosphoketolase identifiable by the method described may be expressed in host cells as described herein. Where accession information is given as "complement (NN_NNNNN.N:X . . . Y)", it should be understood to mean the reverse complement of nucleotides X to Y of the sequence with Accession number NN_NNNNNN.N. Where accession information is given as "join (NNNNNN.N: X . . . Y, NNNNNN.N:Z . . . Q)", it should be understood to mean the sequence resulting from joining nucleotides X to Y of NNNNNN.N to nucleotides Z to Q of NNNNNN.N.

TABLE 5

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 162147402 | complement (NC_010125.1: 1624982 . . . 1627414) | 21 | YP_001601863.1 | 330 | Gluconacetobacter diazotrophicus PAl 5 |
| 127512024 | complement (NC_009092.1: 1256548 . . . 1258914) | 22 | YP_001093221.1 | 331 | Shewanella loihica PV-4 |
| 119774052 | complement (NC_008700.1: 1105589 . . . 1107955) | 23 | YP_926792.1 | 332 | Shewanella amazonensis SB2B |
| 113971300 | NC_008321.1: 3541276 . . . 3543642 | 24 | YP_735093.1 | 333 | Shewanella sp. MR-4 |
| 126173290 | complement (NC_009052.1: 1204351 . . . 1206717) | 25 | YP_001049439.1 | 334 | Shewanella baltica OS155 |
| 163750647 | complement (NZ_ABIC01000018.1: 47875 . . . 50253) | 26 | ZP_02157884.1 | 335 | Shewanella benthica KT99 |
| 157374325 | complement (NC_009831.1: 1410491 . . . 1412857) | 27 | YP_001472925.1 | 336 | Shewanella sediminis HAW-EB3 |
| 170725643 | complement (NC_010506.1: 1624098 . . . 1626464) | 28 | YP_001759669.1 | 337 | Shewanella woodyi ATCC 51908 |
| 167623058 | complement (NC_010334.1: 1364332 . . . 1366698) | 29 | YP_001673352.1 | 338 | Shewanella halifaxensis HAW-EB4 |
| 91794082 | NC_007954.1: 3270590 . . . 3272956 | 30 | YP_563733.1 | 339 | Shewanella denitrificans OS217 |
| 254498997 | NZ_ACUL01000224.1: 8243 . . . 10492 | 31 | ZP_05111697.1 | 340 | Legionella drancourtii LLAP12 |
| 239607320 | join(EQ999973.1: 7995808 . . . 7995885, EQ999973.1: 7996059 . . . 7996116, EQ999973.1: 7996178 . . . 7996412, EQ999973.1: 7996486 . . . 7996638, EQ999973.1: 7996791 . . . 7997016, EQ999973.1: 7997082 . . . 7997548, EQ999973.1: 7997603 . . . 7997705, EQ999973.1: 7997779 . . . 7998604, EQ999973.1: 7998677 . . . 7998717) | 32 | EEQ84307.1 | 341 | Ajellomyces dermatitidis ER-3 |
| 261200667 | XM_002626688.1: 1 . . . 2034 | 33 | XP_002626734.1 | 342 | Ajellomyces dermatitidis SLH14081 |
| 154276328 | XM_001538959.1: 1 . . . 2421 | 34 | XP_001539009.1 | 343 | Ajellomyces capsulatus NAm1 |
| 225555843 | join(GG663374.1: 72330 . . . 72492, GG663374.1: 72695 . . . 72929, GG663374.1: 73005 . . . 73157, GG663374.1: 73216 . . . 74203, GG663374.1: 74274 . . . 75146) | 35 | EEH04133.1 | 344 | Ajellomyces capsulatus G186AR |
| 225681974 | join(DS544805.1: 2187102 . . . 2187264, DS544805.1: | 36 | EEH20258.1 | 345 | Paracoccidioides brasiliensis Pb03 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| | 2187353 ... 2187427, DS544805.1: 2187521 ... 2187755, DS544805.1: 2187839 ... 2187991, DS544805.1: 2188086 ... 2188395, DS544805.1: 2188462 ... 2189082, DS544805.1: 2189147 ... 2189263, DS544805.1: 2189358 ... 2189973, DS544805.1: 2190044 ... 2190084) | | | | |
| 226289140 | join(DS572750.1: 3105630 ... 3105792, DS572750.1: 3106049 ... 3106283, DS572750.1: 3106367 ... 3106519, DS572750.1: 3106614 ... 3106923, DS572750.1: 3107023 ... 3107610, DS572750.1: 3107675 ... 3108500, DS572750.1: 3108572 ... 3108612) | 37 | EEH44652.1 | 346 | *Paracoccidioides brasiliensis* Pb18 |
| 258564014 | XM_002582706.1: 1 ... 2421 | 38 | XP_002582752.1 | 347 | *Uncinocarpus reesii* 1704 |
| 240108203 | join(ACFW01000030.1: 1281918 ... 1282080, ACFW01000030.1: 1282133 ... 1282207, ACFW01000030.1: 1282266 ... 1282500, ACFW01000030.1: 1282551 ... 1282703, ACFW01000030.1: 1282757 ... 1283066, ACFW01000030.1: 1283132 ... 1283752, ACFW01000030.1: 1283828 ... 1284653, ACFW01000030.1: 1284726 ... 1284763) | 39 | EER26377.1 | 348 | *Coccidioides posadasii* C735 delta SOWgp |
| 238838423 | join(DS995701.1: 2675053 ... 2675215, DS995701.1: 2675278 ... 2675352, DS995701.1: 2675424 ... 2675658, DS995701.1: 2675745 ... 2675897, DS995701.1: 2675972 ... 2676281, DS995701.1: 2676341 ... 2676961, DS995701.1: 2677062 ... 2677836, DS995701.1: 2677864 ... 2677933, DS995701.1: 2677998 ... 2678013) | 40 | EEQ28085.1 | 349 | *Microsporum canis* CBS 113480 |
| 169770631 | XM_001819733.1: 1 ... 2457 | 41 | XP_001819785.1 | 350 | *Aspergillus oryzae* RIB40 |
| 145232813 | XM_001399743.1: 1 ... 2421 | 42 | XP_001399780.1 | 351 | *Aspergillus niger* |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 119491775 | XM_001263381.1: 1 . . . 2421 | 43 | XP_001263382.1 | 352 | *Neosartorya fischeri* NRRL 181 |
| 121705634 | XM_001271079.1: 1 . . . 2421 | 44 | XP_001271080.1 | 353 | *Aspergillus clavatus* NRRL 1 |
| 115396290 | XM_001213784.1: 1 . . . 2400 | 45 | XP_001213784.1 | 354 | *Aspergillus terreus* NIH2624 |
| 259482219 | join(BN001303.1: 576345 . . . 576507, BN001303.1: 576696 . . . 576930, BN001303.1: 576981 . . . 577133, BN001303.1: 577185 . . . 577494, BN001303.1: 577544 . . . 578161, BN001303.1: 578210 . . . 579035, BN001303.1: 579091 . . . 579128) | 46 | CBF76492.1 | 355 | *Aspergillus nidulans* FGSC A4 |
| 255942289 | XM_002561867.1: 1 . . . 2469 | 47 | XP_002561913.1 | 356 | *Penicillium chrysogenum* Wisconsin 54-1255 |
| 242784458 | XM_002480346.1: 69 . . . 2489 | 48 | XP_002480391.1 | 357 | *Talaromyces stipitatus* ATCC 10500 |
| 212527714 | XM_002143978.1: 139 . . . 2559 | 49 | XP_002144014.1 | 358 | *Penicillium marneffei* ATCC 18224 |
| 70999652 | XM_749450.1: 1 . . . 2145 | 50 | XP_754543.1 | 359 | *Aspergillus fumigatus* Af293 |
| 154314622 | XM_001556585.1: 1 . . . 2061 | 51 | XP_001556635.1 | 360 | *Botryotinia fuckeliana* B05.10 |
| 156053245 | XM_001592499.1: 1 . . . 2430 | 52 | XP_001592549.1 | 361 | *Sclerotinia sclerotiorum* 1980 |
| 46124351 | XM_386729.1: 1 . . . 2418 | 53 | XP_386729.1 | 362 | *Gibberella zeae* PH-1 |
| 256733824 | complement (join(GG698897.1: 220636 . . . 220670, GG698897.1: 220723 . . . 221650, GG698897.1: 221704 . . . 222510, GG698897.1: 222576 . . . 222732, GG698897.1: 222783 . . . 223020, GG698897.1: 223072 . . . 223146, GG698897.1: 223199 . . . 223361)) | 54 | EEU47171.1 | 363 | *Nectria haematococca* mpVI 77-13-4 |
| 261354209 | join(DS985216.1: 747889 . . . 748126, DS985216.1: 748174 . . . 748564, DS985216.1: 748620 . . . 748929, DS985216.1: 748985 . . . 749555, DS985216.1: 749607 . . . 749833, DS985216.1: 749946 . . . 750572) | 55 | EEY16637.1 | 364 | *Verticillium albo-atrum* VaMs. 102 |

TABLE 5-continued

SEQ ID NOs of xylulose-5-phosphate/fructose-6-phosphate
phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 85081035 | XM_951556.2: 215 . . . 2662 | 56 | XP_956649.1 | 365 | Neurospora crassa OR74A |
| 145609083 | XM_364271.2: 1 . . . 2442 | 57 | XP_364271.2 | 366 | Magnaporthe grisea 70-15 |
| 171679277 | XM_001904550.1: 1 . . . 2316 | 58 | XP_001904585.1 | 367 | Podospora anserine |
| 169859036 | XM_001836107.1: 1 . . . 2418 | 59 | XP_001836159.1 | 368 | Coprinopsis cinerea okayama7#130 |
| 19112755 | NM_001021872.1: 1 . . . 2478 | 60 | NP_595963.1 | 369 | Schizosaccharomyces pombe |
| 213405339 | XM_002173405.1: 1 . . . 2469 | 61 | XP_002173441.1 | 370 | Schizosaccharomyces japonicus yFS275 |
| 58267408 | XM_570860.1: 39 . . . 2594 | 62 | XP_570860.1 | 371 | Cryptococcus neoformans var. neoformans JEC21 |
| 71018661 | XM_754468.1: 1 . . . 2682 | 63 | XP_759561.1 | 372 | Ustilago maydis 521 |
| 254413307 | NZ_DS989851.1: 81897 . . . 84338 | 64 | ZP_05027078.1 | 373 | Microcoleus chthonoplastes PCC 7420 |
| 256377454 | NC_013093.1: 3941285 . . . 3943633 | 65 | YP_003101114.1 | 374 | Actinosynnema mirum DSM 43827 |
| 221195188 | NZ_ACFE01000002.1: 241103 . . . 243577 | 66 | ZP_03568244.1 | 375 | Atopobium rimae ATCC 49626 |
| 257785020 | complement (NC_013203.1: 1365893 . . . 1368364) | 67 | YP_003180237.1 | 376 | Atopobium parvulum DSM 20469 |
| 227516879 | complement (NZ_ACGK01000053.1: 213016 . . . 215490) | 68 | ZP_03946928.1 | 377 | Atopobium vaginae DSM 15829 |
| 210630184 | NZ_ABXJ01000012.1: 49466 . . . 51985 | 69 | ZP_03296299.1 | 378 | Collinsella stercoris DSM 13279 |
| 41056825 | AY518215.1: 989 . . . 3466 | 70 | AAR98787.1 | 379 | Bifidobacterium longum |
| 223467373 | NZ_ACCG01000015.1: 9765 . . . 12350 | 71 | ZP_03618909.1 | 380 | Bifidobacterium breve DSM 20213 |
| 224282874 | NZ_ABQP01000009.1: 218668 . . . 221073 | 72 | ZP_03646196.1 | 381 | Bifidobacterium bifidum NCIMB 41171 |
| 229817819 | complement (NZ_ABYS02000004.1: 901411 . . . 903888) | 73 | ZP_04448101.1 | 382 | Bifidobacterium angulatum DSM 20098 |
| 212716076 | complement (NZ_ABXY01000011.1: 578312 . . . 580789) | 74 | ZP_03324204.1 | 383 | Bifidobacterium catenulatum DSM 16992 |
| 41056831 | AY518218.1: 1430 . . . 3907 | 75 | AAR98790.1 | 384 | Bifidobacterium sp. CFAR 172 |
| 41056829 | AY518217.1: 951 . . . 3428 | 76 | AAR98789.1 | 385 | Bifidobacterium pullorum |
| 227507561 | NZ_ACGF01000124.1: 41655 . . . 44132 | 77 | ZP_03937610.1 | 386 | Gardnerella vaginalis ATCC 14019 |
| 261337317 | NZ_ABXB03000001.1: 154886 . . . 157366 | 78 | ZP_05965201.1 | 387 | Bifidobacterium gallicum DSM 20093 |
| 183601500 | complement (NZ_ABOT01000001.1: 194894 . . . 197371) | 79 | ZP_02962870.1 | 388 | Bifidobacterium animalis subsp. lactis HN019 |

TABLE 5-continued

SEQ ID NOs of xylulose-5-phosphate/fructose-6-phosphate
phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 41056827 | AY518216.1: 988 . . . 3465 | 80 | AAR98788.1 | 389 | *Bifidobacterium pseudolongum* subsp. *Globosum* |
| 227516469 | complement (NZ_ACGK01000047.1: 28634 . . . 31102) | 81 | ZP_03946518.1 | 390 | *Atopobium vaginae* DSM 15829 |
| 76556241 | AJ509177.1: 1 . . . 2625 | 82 | YP_001511171.1 | 391 | *Frankia* sp. EAN1pec |
| 158318663 | NC_009921.1: 8441355 . . . 8443790 | 83 | YP_713678.1 | 392 | *Frankia alni* ACN14a |
| 111222884 | complement (NC_008278.1: 3758441 . . . 3760909) | 84 | YP_002778395.1 | 393 | *Rhodococcus opacus* B4 |
| 226360617 | complement (NC_012522.1: 1273076 . . . 1275478) | 85 | YP_701466.1 | 394 | *Rhodococcus jostii* RHA1 |
| 111018494 | complement (NC_008268.1: 1575800 . . . 1578352) | 86 | ZP_04383880.1 | 395 | *Rhodococcus erythropolis* SK121 |
| 229490027 | NZ_ACNO01000014.1: 107516 . . . 109885 | 87 | YP_947598.1 | 396 | *Arthrobacter aurescens* TC1 |
| 119962524 | NC_008711.1: 2018415 . . . 2020796 | 88 | CAD48946.1 | 397 | *Propionibacterium freudenreichii* subsp. *Shermanii* |
| 28868876 | NC_004578.1: 1837381 . . . 1839888 | 89 | NP_791495.1 | 398 | *Pseudomonas syringae* pv. tomato str. DC3000 |
| 256425339 | NC_013132.1: 8027760 . . . 8030123 | 90 | YP_003125992.1 | 399 | *Chitinophaga pinensis* DSM 2588 |
| 161075783 | EU223897.1: 1 . . . 2430 | 91 | ABX56639.1 | 400 | *Verrucomicrobiae bacterium* V4 |
| 218246512 | complement (NC_011726.1: 1758431 . . . 1760839) | 92 | YP_002371883.1 | 401 | *Cyanothece* sp. PCC 8801 |
| 172055269 | NC_010547.1: 390265 . . . 392673 | 93 | YP_001806596.1 | 402 | *Cyanothece* sp. ATCC 51142 |
| 126659520 | complement (NZ_AAXW01000034.1: 5415 . . . 7823) | 94 | ZP_01730652.1 | 403 | *Cyanothece* sp. CCY0110 |
| 258380665 | complement (AM990467.1: 2704 . . . 5112) | 95 | CAQ48286.1 | 404 | *Planktothrix rubescens* NIVA-CYA 98 |
| 209527806 | NZ_ABYK01000067.1: 8063 . . . 10480 | 96 | ZP_03276298.1 | 405 | *Arthrospira maxima* CS-328 |
| 196258744 | NZ_ABVE01000007.1: 72906 . . . 75314 | 97 | ZP_03157277.1 | 406 | *Cyanothece* sp. PCC 7822 |
| 218440702 | complement (NC_011729.1: 4207741 . . . 4210149) | 98 | YP_002379031.1 | 407 | *Cyanothece* sp. PCC 7424 |
| 166366228 | complement (NC_010296.1: 3156762 . . . 3159182) | 99 | YP_001658501.1 | 408 | *Microcystis aeruginosa* NIES-843 |
| 119488765 | NZ_AAVU01000020.1: 110903 . . . 113317 | 100 | ZP_01621774.1 | 409 | *Lyngbya* sp. PCC 8106 |
| 17228976 | complement (NC_003272.1: 1746056 . . . 1748482) | 101 | NP_485524.1 | 410 | *Nostoc* sp. PCC 7120 |
| 254422632 | NZ_DS989904.1: 4613864 . . . 4616290 | 102 | ZP_05036350.1 | 411 | *Synechococcus* sp. PCC 7335 |
| 158333641 | NC_009925.1: 422232 . . . 424652 | 103 | YP_001514813.1 | 412 | *Acaryochloris marina* MBIC11017 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 254425820 | complement (NZ_DS989905.1: 71540 . . . 74017) | 104 | ZP_05039537.1 | 413 | *Synechococcus* sp. PCC 7335 |
| 170695087 | complement (NZ_ABLD01000020.1: 33972 . . . 36368) | 105 | ZP_02886235.1 | 414 | *Burkholderia graminis* C4D1M |
| 209515639 | complement (NZ_ABYL01000006.1: 33232 . . . 35628) | 106 | ZP_03264503.1 | 415 | *Burkholderia* sp. H160 |
| 87303015 | NZ_AANO01000008.1: 122233 . . . 124656 | 107 | ZP_01085819.1 | 416 | *Synechococcus* sp. WH 5701 |
| 254431900 | complement (NZ_DS990556.1: 2146872 . . . 2149313) | 108 | ZP_05045603.1 | 417 | *Cyanobium* sp. PCC 7001 |
| 88808134 | NZ_AAOK01000002.1: 342081 . . . 344516 | 109 | ZP_01123645.1 | 418 | *Synechococcus* sp. WH 7805 |
| 148238545 | complement (NC_009481.1: 226771 . . . 229206) | 110 | YP_001223932.1 | 419 | *Synechococcus* sp. WH 7803 |
| 87123187 | NZ_AANP01000001.1: 180603 . . . 183032 | 111 | ZP_01079038.1 | 420 | *Synechococcus* sp. RS9917 |
| 187919971 | complement (NC_010676.1: 1450148 . . . 1452541) | 112 | YP_001889002.1 | 421 | *Burkholderia phytofirmans* PsJN |
| 91778759 | complement (NC_007952.1: 1882080 . . . 1884473) | 113 | YP_553967.1 | 422 | *Burkholderia xenovorans* LB400 |
| 170690542 | NZ_ABLD01000001.1: 565487 . . . 567880 | 114 | ZP_02881709.1 | 423 | *Burkholderia graminis* C4D1M |
| 209521856 | NZ_ABYL01000194.1: 6778 . . . 9171 | 115 | ZP_03270532.1 | 424 | *Burkholderia* sp. H160 |
| 186474278 | complement (NC_010623.1: 2647064 . . . 2649448) | 116 | YP_001861620.1 | 425 | *Burkholderia phymatum* STM815 |
| 225873826 | complement (NC_012483.1: 2598033 . . . 2600420) | 117 | YP_002755285.1 | 426 | *Acidobacterium capsulatum* ATCC 51196 |
| 206602403 | DS995260.1: 236338 . . . 238704 | 118 | EDZ38884.1 | 427 | *Leptospirillum* sp. Group II '5-way CG |
| 251772639 | complement (GG693868.1: 86578 . . . 88956) | 119 | EES53204.1 | 428 | *Leptospirillum ferrodiazotrophum* |
| 56752022 | complement (NC_006576.1: 2156604 . . . 2158994) | 120 | YP_172723.1 | 429 | *Synechococcus elongatus* PCC 630 |
| 22298729 | complement (NC_004113.1: 1224195 . . . 1226633) | 121 | NP_681976.1 | 430 | *Thermosynechococcus elongatus* BP-1 |
| 53804073 | NC_002977.6: 1693459 . . . 1695894 | 122 | YP_114037.1 | 431 | *Methylococcus capsulatus* str. Bath |
| 220907266 | NC_011884.1: 1725657 . . . 1728098 | 123 | YP_002482577.1 | 432 | *Cyanothece* sp. PCC 7425 |
| 16332268 | NC_000911.1: 3500713 . . . 3503178 | 124 | NP_442996.1 | 433 | *Synechocystis* sp. PCC 6803 |
| 220907424 | complement (NC_011884.1: 1898702 . . . 1901167) | 125 | YP_002482735.1 | 434 | *Cyanothece* sp. PCC 7425 |
| 241777601 | complement (NZ_ACQQ01000020.1: 30393 . . . 32762) | 126 | ZP_04774866.1 | 435 | *Allochromatium vinosum* DSM 180 |
| 114778289 | NZ_AATS01000014.1: 23435 . . . 25801 | 127 | ZP_01453148.1 | 436 | *Mariprofundus ferrooxydans* PV-1 |
| 251827471 | complement (NZ_ACSD01000006.1: 39617 . . . 41986) | 128 | ZP_04830548.1 | 437 | *Gallionella ferruginea* ES-2 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 121712503 | XM_001273862.1: 1 . . . 2436 | 129 | XP_001273863.1 | 438 | *Aspergillus clavatu* NRRL 1 |
| 119473535 | XM_001258642.1: 1 . . . 2439 | 130 | XP_001258643.1 | 439 | *Neosartorya fischer* NRRL 181 |
| 169763560 | XM_001727628.1: 1 . . . 2433 | 131 | XP_001727680.1 | 440 | *Aspergillus oryzae* RIB40 |
| 145248115 | XM_001396269.1: 1 . . . 2448 | 132 | XP_001396306.1 | 441 | *Aspergillus niger* |
| 115400974 | XM_001216075.1: 1 . . . 2457 | 133 | XP_001216075.1 | 442 | *Aspergillus terreus* NIH2624 |
| 255952755 | XM_002567084.1: 1 . . . 2433 | 134 | XP_002567130.1 | 443 | *Penicillium chrysogenum* Wisconsin 54-1255 |
| 212527388 | XM_002143815.1: 98 . . . 2551 | 135 | XP_002143851.1 | 444 | *Penicillium marneffei* ATCC 18224 |
| 242783584 | XM_002480171.1: 1 . . . 2448 | 136 | XP_002480216.1 | 445 | *Talaromyces stipitatus* ATCC 10500 |
| 154321267 | XM_001559899.1: 1 . . . 2466 | 137 | XP_001559949.1 | 446 | *Botryotinia fuckeliana* B05.10 |
| 156054348 | XM_001593050.1: 1 . . . 2499 | 138 | XP_001593100.1 | 447 | *Sclerotinia sclerotiorum* 1980 |
| 189191706 | XM_001932157.1: 1 . . . 2469 | 139 | XP_001932192.1 | 448 | *Pyrenophora tritici-repentis* Pt-1C-BFP |
| 169600613 | XM_001793677.1: 1 . . . 2466 | 140 | XP_001793729.1 | 449 | *Phaeosphaeria nodorum* SN15 |
| 58260732 | XM_567776.1: 41 . . . 2545 | 141 | XP_567776.1 | 450 | *Cryptococcus neoformans* var. *neoformans* JEC21 |
| 46123901 | XM_386504.1: 1 . . . 2460 | 142 | XP_386504.1 | 451 | *Gibberella zeae* PH-1 |
| 256732917 | complement (join(GG698898.1: 321524 . . . 322233, GG698898.1: 322285 . . . 322489, GG698898.1: 322540 . . . 324081)) | 143 | EEU46265.1 | 452 | *Nectria haematococca* mpV 77-13-4 |
| 225729111 | FJ790496.1: 215 . . . 2677 | 144 | ACO24516.1 | 453 | *Metarhizium anisopliae* |
| 85094948 | XM_954892.2: 155 . . . 2638 | 145 | XP_959985.1 | 454 | *Neurospora crassa* OR74A |
| 171679479 | XM_001904651.1: 1 . . . 2517 | 146 | XP_001904686.1 | 455 | *Podospora anserine* |
| 198283820 | NC_011206.1: 1682860 . . . 1685307 | 147 | YP_002220141.1 | 456 | *Acidithiobacillus ferrooxidans* ATCC 53993 |
| 148243889 | NC_009468.1: 90683 . . . 93145 | 148 | YP_001220128.1 | 457 | *Acidiphilium cryptum* JF-5 |
| 157364435 | NC_009828.1: 1658895 . . . 1661258 | 149 | YP_001471202.1 | 458 | *Thermotoga lettingae* TMO |
| 217966781 | NC_011661.1: 369050 . . . 371428 | 150 | YP_002352287.1 | 459 | *Dictyoglomus turgidum* DSM 672 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 92109503 | complement (NC_007960.1: 14429 . . . 16810) | 151 | YP_571790.1 | 460 | Nitrobacter hamburgensis X14 |
| 87310270 | complement (NZ_AANZ01000017.1: 80191 . . . 82560) | 152 | ZP_01092401.1 | 461 | Blastopirellula marina DSM 3645 |
| 152995974 | NC_009654.1: 2214232 . . . 2216625 | 153 | YP_001340809.1 | 462 | Marinomonas sp. MWYL1 |
| 32473390 | NC_005027.1: 2520925 . . . 2523306 | 154 | NP_866384.1 | 463 | Rhodopirellula baltica SH 1 |
| 254495580 | complement (NZ_ACUL01000002.1: 21176 . . . 23557) | 155 | ZP_05108502.1 | 464 | Legionella drancourtii LLAP12 |
| 254380451 | NZ_DS570384.1: 88623 . . . 90992 | 156 | ZP_04995817.1 | 465 | Streptomyces sp. Mg1 |
| 227974767 | NZ_ACGW01000133.1: 1172 . . . 3235 | 157 | ZP_04023055.1 | 466 | Lactobacillus reuter SD2112 |
| 227530011 | NZ_ACGV01000134.1: 2320 . . . 4794 | 158 | ZP_03960060.1 | 467 | Lactobacillus vaginalis ATCC 49540 |
| 194467185 | complement (NZ_AAPZ02000001.1: 905298 . . . 907709) | 159 | ZP_03073172.1 | 468 | Lactobacillus reuter 100-23 |
| 256847586 | NZ_GG698803.1: 21616 . . . 24015 | 160 | ZP_05553031.1 | 469 | Lactobacillus coleohominis 101-4 CHN |
| 260662452 | complement (NZ_GG704700.1: 145244 . . . 147643) | 161 | ZP_05863347.1 | 470 | Lactobacillus fermentum 28-3-CHN |
| 227903484 | NZ_ACHN01000046.1: 59035 . . . 61452 | 162 | ZP_04021289.1 | 471 | Lactobacillus acidophilus ATCC 4796 |
| 227877116 | NZ_ACKR01000020.1: 11753 . . . 14191 | 163 | ZP_03995194.1 | 472 | Lactobacillus crispatus JV-V01 |
| 227893117 | NZ_ACGU01000035.1: 36787 . . . 39186 | 164 | ZP_04010922.1 | 473 | Lactobacillus ultunensis DSM 16047 |
| 256844475 | NZ_GG698762.1: 280846 . . . 283242 | 165 | ZP_05549961.1 | 474 | Lactobacillus crispatus 125-2-CHN |
| 227521312 | complement (NZ_ACGO01000008.1: 37191 . . . 39647) | 166 | ZP_03951361.1 | 475 | Lactobacillus gasseri JV-V03 |
| 259501613 | complement (NZ_ACLN01000019.1: 10173 . . . 12569) | 167 | ZP_05744515.1 | 476 | Lactobacillus iners DSM 13335 |
| 104773655 | NC_008054.1: 449229 . . . 451631 | 168 | YP_618635.1 | 477 | Lactobacillus delbrueckii subsp. bulgaricus ATCC 11842 |
| 227525868 | NZ_ACGQ01000037.1: 36941 . . . 39310 | 169 | ZP_03955917.1 | 478 | Lactobacillus jensenii JV-V16 |
| 227512366 | NZ_ACGH01000107.1: 31655 . . . 34045 | 170 | ZP_03942415.1 | 479 | Lactobacillus buchneri ATCC 11577 |
| 118587374 | complement (NZ_AAUV01000059.1: 59008 . . . 61416) | 171 | ZP_01544800.1 | 480 | Oenococcus oeni ATCC BAA-1163 |
| 28379168 | complement (NC_004567.1: 2362936 . . . 2365302) | 172 | NP_786060.1 | 481 | Lactobacillus plantarum WCFS1 |
| 21363093 | AJ309011.1: 181 . . . 2547 | 173 | Q937F6 | 482 | XPKA_LACPE |
| 81427904 | NC_007576.1: 286496 . . . 288859 | 174 | YP_394903.1 | 483 | Lactobacillus sakei subsp. sakei 23K |

TABLE 5-continued

SEQ ID NOs of xylulose-5-phosphate/fructose-6-phosphate
phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 116492156 | NC_008525.1: 398927 . . . 401290 | 175 | YP_803891.1 | 484 | *Pediococcus pentosaceus* ATCC 25745 |
| 259648565 | AP011548.1: 211570 . . . 213957 | 176 | BAI40727.1 | 485 | *Lactobacillus rhamnosus* GG |
| 227510093 | complement (NZ_ACGG01000115.1: 64541 . . . 66952) | 177 | ZP_03940142.1 | 486 | *Lactobacillus brevis* subsp. *gravesensis* ATCC 27305 |
| 227891468 | complement (NZ_ACGT01000007.1: 44265 . . . 46625) | 178 | ZP_04009273.1 | 487 | *Lactobacillus salivarius* ATCC 11741 |
| 227528594 | NZ_ACGS01000122.1: 352 . . . 2721 | 179 | ZP_03958643.1 | 488 | *Lactobacillus ruminis* ATCC 25644 |
| 229542373 | complement (NZ_AAWV02000001.1: 1384102 . . . 1386486) | 180 | ZP_04431433.1 | 489 | *Bacillus coagulans* 36D1 |
| 238021480 | complement (NZ_ACJW02000002.1: 913355 . . . 915730) | 181 | ZP_04601906.1 | 490 | *Kingella oralis* ATCC 51147 |
| 259046526 | NZ_ACKZ01000008.1: 36586 . . . 38955 | 182 | ZP_05736927.1 | 491 | *Granulicatella adiacens* ATCC 49175 |
| 157150221 | NC_009785.1: 333239 . . . 335623 | 183 | YP_001449631.1 | 492 | *Streptococcus gordonii* str. *Challis* substr. CH1 |
| 25011879 | complement (NC_004368.1: 1900754 . . . 1903132) | 184 | NP_736274.1 | 493 | *Streptococcus agalactiae* NEM316 |
| 229555065 | complement (NZ_ACCR01000006.1: 74043 . . . 76418) | 185 | ZP_04442854.1 | 494 | *Listeria grayi* DSM 20601 |
| 257866707 | NZ_GG670386.1: 478278 . . . 480644 | 186 | ZP_05646360.1 | 495 | *Enterococcus casseliflavus* EC30 |
| 257870669 | NZ_GG670289.1: 233512 . . . 235875 | 187 | ZP_05650322.1 | 496 | *Enterococcus gallinarum* EG2 |
| 257895654 | NZ_GG670306.1: 612981 . . . 615353 | 188 | ZP_05675307.1 | 497 | *Enterococcus faecium* Com12 |
| 238810139 | AP009608.1: 744956 . . . 747334 | 189 | BAH69929.1 | 498 | *Mycoplasma fermentans* PG18 |
| 193216764 | NC_011025.1: 384420 . . . 386801 | 190 | YP_002000006.1 | 499 | *Mycoplasma arthritidis* 158L3-1 |
| 148377390 | NC_009497.1: 136795 . . . 139182 | 191 | YP_001256266.1 | 500 | *Mycoplasma agalactiae* PG2 |
| 191639669 | NC_010999.1: 2885324 . . . 2887711 | 192 | YP_001988835.1 | 501 | *Lactobacillus casei* BL23 |
| 28379861 | NC_004567.1: 3169067 . . . 3171478 | 193 | NP_786753.1 | 502 | *Lactobacillus plantarum* WCFS1 |
| 227892171 | complement (NZ_ACGT01000037.1: 21330 . . . 23759) | 194 | ZP_04009976.1 | 503 | *Lactobacillus salivarius* ATCC 11741 |
| 116618551 | NC_008531.1: 1449343 . . . 1451709 | 195 | YP_818922.1 | 504 | *Leuconostoc mesenteroides* subsp. *mesenteroides* ATCC 8293 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 116333142 | NC_008497.1: 507704 . . . 510163 | 196 | YP_794669.1 | 505 | *Lactobacillus brevis* ATCC 367 |
| 241895257 | complement (NZ_ACKU01000007.1: 101374 . . . 103833) | 197 | ZP_04782553.1 | 506 | *Weissella paramesenteroides* ATCC 33313 |
| 170016535 | NC_010471.1: 181964 . . . 184417 | 198 | YP_001727454.1 | 507 | *Leuconostoc citreum* KM20 |
| 116619034 | complement (NC_008531.1: 1934181 . . . 1936622) | 199 | YP_819405.1 | 508 | *Leuconostoc mesenteroides* subsp. *mesenteroides* ATCC 8293 |
| 161702316 | EU255918.1: 18411 . . . 20879 | 200 | ABX75772.1 | 509 | *Lactococcus lactis* subsp. *Lactis* |
| 116491770 | complement (NC_008528.1: 1731509 . . . 1733962) | 201 | YP_811314.1 | 510 | *Oenococcus oeni* PSU-1 |
| 182419955 | complement (NZ_ABDT01000107.2: 13616 . . . 15991) | 202 | ZP_02951191.1 | 511 | *Clostridium butyricum* 5521 |
| 255523324 | complement (NZ_ACVI01000003.1: 55354 . . . 57747) | 203 | ZP_05390294.1 | 512 | *Clostridium carboxidivorans* P7 |
| 15894622 | NC_003030.1: 1482782 . . . 1485172 | 204 | NP_347971.1 | 513 | *Clostridium acetobutylicum* ATCC 824 |
| 226324778 | complement (NZ_ABVR01000041.1: 500857 . . . 503232) | 205 | ZP_03800296.1 | 514 | *Coprococcus comes* ATCC 27758 |
| 253580358 | NZ_GG696051.1: 158015 . . . 160390 | 206 | ZP_04857624.1 | 515 | *Ruminococcus* sp. 5_1_39B_FAA |
| 257413435 | NZ_ABYJ02000055.1: 10320 . . . 12779 | 207 | ZP_04743029.2 | 516 | *Roseburia intestinalis* L1-82 |
| 154500233 | complement (NZ_AAXG02000041.1: 34174 . . . 36609) | 208 | ZP_02038271.1 | 517 | *Bacteroides capillosus* ATCC 29799 |
| 219119570 | XM_002180506.1: 1 . . . 2508 | 209 | XP_002180542.1 | 518 | *Phaeodactylum tricornutum* CCAP 1055/1 |
| 91975971 | NC_007958.1: 1660408 . . . 1662762 | 210 | YP_568630.1 | 519 | *Rhodopseudomonas palustris* BisB5 |
| 86750966 | complement (NC_007778.1: 4411322 . . . 4413676) | 211 | YP_487462.1 | 520 | *Rhodopseudomonas palustris* HaA2 |
| 39934743 | NC_005296.1: 1858439 . . . 1860790 | 212 | NP_947019.1 | 521 | *Rhodopseudomonas palustris* CGA009 |
| 90425290 | complement (NC_007925.1: 4235875 . . . 4238229) | 213 | YP_533660.1 | 522 | *Rhodopseudomonas palustris* BisB18 |
| 121583071 | NC_008758.1: 65532 . . . 67904 | 214 | YP_973512.1 | 523 | *Polaromonas naphthalenivorans* CJ2 |
| 115376972 | complement (NZ_AAMD01000095.1: 4173 . . . 6533) | 215 | ZP_01464191.1 | 524 | *Stigmatella aurantiaca* DW4/3-1 |
| 148547676 | complement (NC_009512.1: 2807645 . . . 2810020) | 216 | YP_001267778.1 | 525 | *Pseudomonas putid* F1 |
| 116668711 | NC_008541.1: 145493 . . . 147928 | 217 | YP_829644.1 | 526 | *Arthrobacter* sp. FB24 |
| 220911083 | NC_011886.1: 321712 . . . 324174 | 218 | YP_002486392.1 | 527 | *Arthrobacter chlorophenolicus* A6 |

TABLE 5-continued

SEQ ID NOs of xylulose-5-phosphate/fructose-6-phosphate
phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 260517200 | complement (NZ_ABUN01000002.1: 92936 . . . 95461) | 219 | ZP_05816651.1 | 528 | Sanguibacter keddieii DSM 10542 |
| 229821527 | NC_012669.1: 3398743 . . . 3401217 | 220 | YP_002883053.1 | 529 | Beutenbergia cavernae DSM 12333 |
| 256832813 | NC_013174.1: 1712156 . . . 1714588 | 221 | YP_003161540.1 | 530 | Jonesia denitrificans DSM 20603 |
| 227428425 | complement (NZ_ABVC01000008.1: 152502 . . . 154988) | 222 | ZP_03911482.1 | 531 | Xylanimonas cellulosilytica DSM 15894 |
| 165929357 | AM182260.1: 1 . . . 2481 | 223 | CAJ57850.1 | 532 | Cellulomonas flavigena |
| 145223927 | NC_009338.1: 3525804 . . . 3528275 | 224 | YP_001134605.1 | 533 | Mycobacterium gilvum PYR-GCK |
| 120404048 | NC_008726.1: 3236585 . . . 3239083 | 225 | YP_953877.1 | 534 | Mycobacterium vanbaalenii PYR-1 |
| 257069356 | NC_013172.1: 2493744 . . . 2496215 | 226 | YP_003155611.1 | 535 | Brachybacterium faecium DSM 4810 |
| 256824167 | NC_013169.1: 273585 . . . 276047 | 227 | YP_003148127.1 | 536 | Kytococcus sedentarius DSM 20547 |
| 148271607 | NC_009480.1: 506602 . . . 509040 | 228 | YP_001221168.1 | 537 | Clavibacter michiganensis subsp. michiganensis NCPPB 382 |
| 145594129 | complement (NC_009380.1: 1798516 . . . 1800918) | 229 | YP_001158426.1 | 538 | Salinispora tropica CNB-440 |
| 159037167 | complement (NC_009953.1: 1767167 . . . 1769569) | 230 | YP_001536420.1 | 539 | Salinispora arenicola CNS-205 |
| 238063593 | complement (NZ_GG657738.1: 5405062 . . . 5407251) | 231 | ZP_04608302.1 | 540 | Micromonospora sp ATCC 39149 |
| 118469963 | NC_008596.1: 3674267 . . . 3676639 | 232 | YP_887914.1 | 541 | Mycobacterium smegmatis str. MC2 155 |
| 108799759 | NC_008146.1: 2939527 . . . 2941947 | 233 | YP_639956.1 | 542 | Mycobacterium sp. MCS |
| 240170498 | complement (NZ_ACBV01000039.1: 21 . . . 2423) | 234 | ZP_04749157.1 | 543 | Mycobacterium kansasii ATCC 12478 |
| 183982748 | complement (NC_010612.1: 3341817 . . . 3344219) | 235 | YP_001851039.1 | 544 | Mycobacterium marinum M |
| 41407671 | complement (NC_002944.2: 1726717 . . . 1729131) | 236 | NP_960507.1 | 545 | Mycobacterium avium subsp. paratuberculosis K-10 |
| 254819329 | NZ_ABIN01000047.1: 36474 . . . 38837 | 237 | ZP_05224330.1 | 546 | Mycobacterium intracellulare ATCC 13950 |
| 169629591 | complement (NC_010397.1: 2559451 . . . 2561871) | 238 | YP_001703240.1 | 547 | Mycobacterium abscessus |
| 84496279 | complement (NZ_AAMN01000002.1: 433314 . . . 435707) | 239 | ZP_00995133.1 | 548 | Janibacter sp. HTCC2649 |
| 72163369 | NC_007333.1: 3478272 . . . 3480650 | 240 | YP_291026.1 | 549 | Thermobifida fusca YX |
| 227984600 | complement (NZ_ABUZ01000013.1: 70531 . . . 72909) | 241 | ZP_04031845.1 | 550 | Thermomonospora curvata DSM 43183 |

TABLE 5-continued

SEQ ID NOs of xylulose-5-phosphate/fructose-6-phosphate
phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 229855558 | complement (NZ_ABUU01000106.1: 1385 . . . 3700) | 242 | ZP_04475514.1 | 551 | Streptosporangium roseum DSM 43021 |
| 229209207 | NZ_ABUI01000028.1: 55841 . . . 58189 | 243 | ZP_04335641.1 | 552 | Nocardiopsis dassonvillei subsp. dassonvillei DSM 43111 |
| 229862587 | NZ_ABUS01000001.1: 1911934 . . . 1914330 | 244 | ZP_04482201.1 | 553 | Stackebrandtia nassauensis DSM 44728 |
| 256376052 | NC_013093.1: 2125566 . . . 2127935 | 245 | YP_003099712.1 | 554 | Actinosynnema mirum DSM 43827 |
| 32141117 | complement (NC_003888.3: 656319 . . . 658772) | 246 | NP_733508.1 | 555 | Streptomyces coelicolor A3(2) |
| 117164830 | complement (AM238664.1: 846551 . . . 849055) | 247 | CAJ88379.1 | 556 | Streptomyces ambofaciens ATCC 23877 |
| 256811868 | complement (NZ_ACFA01000015.1: 3377 . . . 5761) | 248 | ZP_05536883.1 | 557 | Streptomyces griseoflavus Tu4000 |
| 254405496 | complement (NZ_DS570938.1: 43288 . . . 45726) | 249 | ZP_05020421.1 | 558 | Streptomyces sviceus ATCC 29083 |
| 260644540 | complement (FN554889.1: 480316 . . . 482694) | 250 | CBG67625.1 | 559 | Streptomyces scabiei 87.22 |
| 29827814 | complement (NC_003155.4: 1579336 . . . 1581717) | 251 | NP_822448.1 | 560 | Streptomyces avermitilis MA-4680 |
| 239932594 | NZ_ABYA01000503.1: 5217 . . . 7595 | 252 | ZP_04689547.1 | 561 | Streptomyces ghanaensis ATCC 14672 |
| 256800397 | complement (NZ_ACEZ01000048.1: 24916 . . . 27303) | 253 | ZP_05530021.1 | 562 | Streptomyces viridochromogenes DSM 40736 |
| 256774038 | complement (NZ_ACEX01000074.1: 46221 . . . 48614) | 254 | ZP_05512501.1 | 563 | Streptomyces hygroscopicus ATCC 53653 |
| 260452518 | NZ_ACZH01000001.1: 321972 . . . 324359 | 255 | ZP_05800927.1 | 564 | Streptomyces flavogriseus ATCC 33331 |
| 182440556 | NC_010572.1: 8084439 . . . 8086826 | 256 | YP_001828275.1 | 565 | Streptomyces griseus subsp. griseus NBRC 13350 |
| 239982969 | NZ_ABYC01000425.1: 13265 . . . 15646 | 257 | ZP_04705493.1 | 566 | Streptomyces albus J1074 |
| 254381599 | NZ_DS570386.1: 118817 . . . 121204 | 258 | ZP_04996963.1 | 567 | Streptomyces sp. Mg1 |
| 256674998 | NZ_ACEU01000020.1: 1507 . . . 3900 | 259 | ZP_05485309.1 | 568 | Streptomyces sp. SPB78 |
| 227377421 | NZ_ABUC01000002.1: 229225 . . . 231603 | 260 | ZP_03860882.1 | 569 | Kribbella flavida DSM 17836 |
| 54023297 | complement (NC_006361.1: 1487629 . . . 1490097) | 261 | YP_117539.1 | 570 | Nocardia farcinica IFM 10152 |
| 158313048 | NC_009921.1: 1426213 . . . 1428621 | 262 | YP_001505556.1 | 571 | Frankia sp. EAN1pec |
| 86742227 | complement (NC_007777.1: 4238578 . . . 4240986) | 263 | YP_482627.1 | 572 | Frankia sp. CcI3 |
| 256395329 | NC_013131.1: 7133131 . . . 7135533 | 264 | YP_003116893.1 | 573 | Catenulispora acidiphila DSM 44928 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 117927729 | NC_008578.1: 555555 . . . 557948 | 265 | YP_872280.1 | 574 | *Acidothermus cellulolyticus* 11B |
| 119717842 | complement (NC_008699.1: 3839565 . . . 3841961) | 266 | YP_924807.1 | 575 | *Nocardioides* sp. JS614 |
| 134098496 | NC_009142.1: 2098116 . . . 2100512 | 1267 | YP_001104157.1 | 576 | *Saccharopolyspora erythraea* NRRL 2338 |
| 209550756 | NC_011369.1: 3264963 . . . 3267347 | 268 | YP_002282673.1 | 577 | *Rhizobium leguminosarum* bv. *trifolii* WSM2304 |
| 241206160 | NC_012850.1: 3503904 . . . 3506288 | 269 | YPJ002977256.1 | 578 | *Rhizobium leguminosarum* bv. *trifolii* WSM1325 |
| 190893254 | NC_010994.1: 3714233 . . . 3716620 | 270 | YP_001979796.1 | 579 | *Rhizobium etli* CIAT 652 |
| 86359034 | NC_007761.1: 3623921 . . . 3626308 | 271 | YP_470926.1 | 580 | *Rhizobium etli* CF42 |
| 222081270 | complement (NC_011983.1: 490969 . . . 493383) | 272 | YP_002540633.1 | 581 | *Agrobacterium radiobacter* K84 |
| 254720555 | NZ_ACBQ01000064.1: 129340 . . . 131718 | 273 | ZP_05182366.1 | 582 | *Brucella* sp. 83/13 |
| 239835057 | complement (NZ_ACQA01000003.1: 10528 . . . 13017) | 274 | ZP_04683384.1 | 583 | *Ochrobactrum intermedium* LMG 3301 |
| 153012043 | NC_009671.1: 16319 . . . 18706 | 275 | YP_001373254.1 | 584 | *Ochrobactrum anthropi* ATCC 49188 |
| 146339061 | complement (NC_009445.1: 2141749 . . . 2144226) | 276 | YP_001204109.1 | 585 | *Bradyrhizobium* sp. ORS278 |
| 148253833 | complement (NC_009485.1: 2424642 . . . 2427059) | 277 | YP_001238418.1 | 586 | *Bradyrhizobium* sp. BTAi1 |
| 27377629 | complement (NC_004463.1: 2749734 . . . 2752139) | 278 | NP_769158.1 | 587 | *Bradyrhizobium japonicum* USDA 110 |
| 92117435 | complement (NC_007964.1: 2109162 . . . 2111570) | 279 | YP_577164.1 | 588 | *Nitrobacter hamburgensis* X14 |
| 240137143 | NC_012808.1: 407982 . . . 410417 | 280 | YP_002961612.1 | 589 | *Methylobacterium extorquens* AM1 |
| 110634584 | complement (NC_008254.1: 2388345 . . . 2390747) | 281 | YP_674792.1 | 590 | *Mesorhizobium* sp. BNC1 |
| 260467447 | NZ_ACZA01000051.1: 15952 . . . 18360 | 282 | ZP_05813617.1 | 591 | *Mesorhizobium opportunistum* WSM2075 |
| 75676138 | NC_007406.1: 2135469 . . . 2137856 | 283 | YP_318559.1 | 592 | *Nitrobacter winogradskyi* Nb-255 |
| 170749020 | complement (NC_010505.1: 2769888 . . . 2772470) | 284 | YP_001755280.1 | 593 | *Methylobacterium radiotolerans* JCM 2831 |
| 170746859 | complement (NC_010505.1: 465997 . . . 468552) | 285 | YP_001753119.1 | 594 | *Methylobacterium radiotolerans* JCM 2831 |
| 254558916 | NC_012988.1: 271224 . . . 273809 | 286 | YP_003066011.1 | 595 | *Methylobacterium extorquens* DM4 |
| 240140298 | NC_012808.1: 3931130 . . . 3933676 | 287 | YP_002964777.1 | 596 | *Methylobacterium extorquens* AM1 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 220925990 | NC_011894.1: 6291823 . . . 6294321 | 288 | YP_002501292.1 | 597 | *Methylobacterium nodulans* ORS 2060 |
| 220919962 | complement (NC_011892.1: 451339 . . . 453840) | 289 | YP_002495265.1 | 598 | *Methylobacterium nodulans* ORS 2060 |
| 170741732 | NC_010511.1: 3988668 . . . 3991166 | 290 | YP_001770387.1 | 599 | *Methylobacterium* sp. 4-46 |
| 239815802 | complement (NC_012791.1: 2971257 . . . 2973608) | 291 | YP_002944712.1 | 600 | *Variovorax paradoxus* S110 |
| 89069402 | NZ_AAOT01000017.1: 31124 . . . 33460 | 292 | ZP_01156757.1 | 601 | *Oceanicola granulosus* HTCC2516 |
| 119509641 | complement (NZ_AAVW01000007.1: 15878 . . . 18259) | 293 | ZP_01628787.1 | 602 | *Nodularia spumigena* CCY9414 |
| 186682350 | NC_010628.1: 2389837 . . . 2392218 | 294 | YP_001865546.1 | 603 | *Nostoc punctiforme* PCC 73102 |
| 75906719 | complement (NC_007413.1: 617971 . . . 620352) | 295 | YP_321015.1 | 604 | *Anabaena variabilis* ATCC 29413 |
| 225522346 | NZ_ACIR01000182.1: 624 . . . 2756 | 296 | ZP_03769140.1 | 605 | *Nostoc azollae'* 070 |
| 37520566 | NC_005125.1: 1065716 . . . 1068097 | 297 | NP_923943.1 | 606 | *Gloeobacter violaceus* PCC 7421 |
| 86608623 | NC_007776.1: 1182311 . . . 1184686 | 298 | YP_477385.1 | 607 | *Synechococcus* sp. JA-2-3B'a(2-13) |
| 150398192 | complement (NC_009636.1: 3144485 . . . 3146857) | 299 | YP_001328659.1 | 608 | *Sinorhizobium medicae* WSM419 |
| 116249832 | complement (NC_008380.1: 82152 . . . 84617) | 300 | YP_765670.1 | 609 | *Rhizobium leguminosarum* bv. *viciae* 3841 |
| 195970218 | complement (NC_003047.1: 123688 . . . 126141) | 301 | NP_384212.2 | 610 | *Sinorhizobium meliloti* 1021 |
| 171912985 | NZ_ABIZ01000001.1: 4370841 . . . 4373354 | 302 | ZP_02928455.1 | 611 | *Verrucomicrobium spinosum* DSM 4136 |
| 163849496 | complement (NC_010172.1: 46285 . . . 48720) | 303 | YP_001637539.1 | 612 | *Methylobacterium extorquens* PA1 |
| 85714839 | NZ_AAMY01000005.1: 72844 . . . 75210 | 304 | ZP_01045825.1 | 613 | *Nitrobacter* sp. Nb-311A |
| 168704325 | complement (NZ_ABGO01000323.1: 57 . . . 2462) | 305 | ZP_02736602.1 | 614 | *Gemmata obscuriglobus* UQM 2246 |
| 256829143 | complement (NC_013173.1: 1530488 . . . 1532881) | 306 | YP_003157871.1 | 615 | *Desulfomicrobium baculatum* DSM 4028 |
| 223939426 | complement (NZ_ABOX02000044.1: 41392 . . . 43863) | 307 | ZP_03631304.1 | 616 | bacterium Ellin514 |
| 237747078 | complement (NZ_GG658151.1: 2005797 . . . 2008190) | 308 | ZP_04577558.1 | 617 | *Oxalobacter formigenes* HOxBLS |
| 237749232 | complement (NZ_GG658170.1: 2042015 . . . 2044411) | 309 | ZP_04579712.1 | 618 | *Oxalobacter formigenes* OXCC13 |
| 116624013 | NC_008536.1: 6218168 . . . 6220537 | 310 | YP_826169.1 | 619 | *Solibacter usitatus* Ellin6076 |
| 194336959 | complement (NC_011060.1: 2004498 . . . 2006885) | 311 | YP_002018753.1 | 620 | *Pelodictyon phaeoclathratiforme* BU-1 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 194334425 | complement (NC_011059.1: 1762093 ... 1764489) | 312 | YP_002016285.1 | 621 | Prosthecochloris aestuarii DSM 271 |
| 189346840 | complement (NC_010803.1: 1427679 ... 1430054) | 313 | YP_001943369.1 | 622 | Chlorobium limicola DSM 245 |
| 21674344 | complement (NC_002932.3: 1423776 ... 1426289) | 314 | NP_662409.1 | 623 | Chlorobium tepidum TLS |
| 110597897 | complement (NZ_AASE01000009.1: 37756 ... 40179) | 315 | ZP_01386179.1 | 624 | Chlorobium ferrooxidans DSM 13031 |
| 78187379 | complement (NC_007512.1: 1709621 ... 1712050) | 316 | YP_375422.1 | 625 | Chlorobium luteolum DSM 273 |
| 71907690 | complement (NC_007298.1: 2220090 ... 2222456) | 317 | YP_285277.1 | 626 | Dechloromonas aromatica RCB |
| 74316849 | NC_007404.1: 876540 ... 878978 | 318 | YP_314589.1 | 627 | Thiobacillus denitrificans ATCC 25259 |
| 91775246 | complement (NC_007947.1: 935825 ... 938200) | 319 | YP_545002.1 | 628 | Methylobacillus flagellatus KT |
| 30250069 | NC_004757.1: 2318109 ... 2320481 | 320 | NP_842139.1 | 629 | Nitrosomonas europaea ATCC 19718 |
| 114332052 | NC_008344.1: 2209596 ... 2211971 | 321 | YP_748274.1 | 630 | Nitrosomonas eutrqpha C91 |
| 82702122 | NC_007614.1: 1152112 ... 1154535 | 322 | YP_411688.1 | 631 | Nitrosospira multiformis ATCC 25196 |
| 77166175 | NC_007484.1: 3082455 ... 3084869 | 323 | YP_344700.1 | 632 | Nitrosococcus oceani ATCC 1970 |
| 46445639 | complement (NC_005861.1: 5907 ... 8303) | 324 | YP_007004.1 | 633 | Candidatus Protochlamydia amoebophila UWE25 |
| 16263040 | complement (NC_003037.1: 591065 ... 593440) | 325 | NP_435833.1 | 634 | Sinorhizobium meliloti 1021 |
| 229532493 | NZ_ABUV01000006.1: 47234 ... 49585 | 326 | ZP_04421874.1 | 635 | Sulfurospirillum deleyianum DSM 6946 |
| 13475490 | NC_002678.2: 5384229 ... 5386652 | 327 | NP_107054.1 | 636 | Mesorhizobium loti MAFF303099 |
| 209885940 | complement (NC_011386.1: 2786353 ... 2788746) | 328 | YP_002289797.1 | 637 | Oligotropha carboxidovorans OM5 |
| 182679166 | NC_010581.1: 2524033 ... 2526420 | 329 | YP_001833312.1 | 638 | Beijerinckia indica subsp. indica ATCC 9039 |

Numerous examples of polynucleotides, genes and/or polypeptides encoding phosphotransacetylase are known in the art and can be used in relation to the recombinant host cells disclosed herein. In embodiments, the phosphotransacetylase can be EutD from *Lactobacillus plantarum*. In embodiments, the phosphotransacetylase can be the phosphotransacetylase from *Bacillus subtilis*. This phosphotransacetylase has a specific activity of 1371 mmol/min/mg and a Km 0.06 mM for acetyl-CoA (Rado and Hoch, *Biochim. Biophys. Acta.* 321: 114-25; 1973). In addition, the equilibrium constant (Keq) of this reaction was found to be 154±14 in favor of the formation of acetyl-CoA according to the following formula:

$$\frac{[\text{acetyl-CoA}][Pi]}{[\text{CoA}][\text{acetyl-}P]} = Keq$$

In embodiments, host cells comprise a polypeptide having at least about 80%, at least about 85%, at least about 90%, or at least about 99% identity to a polypeptide of Table 10 or an active fragment thereof or a polynucleotide encoding such a polypeptide. In embodiments, the phospolotransacetylase can be a polypeptide having at least about 80%, at least about 85%, at least about 90%, at least about 95%, or at least about 99% identity to SEQ ID NO: 1472 or an active fragment thereof. In other embodiments, a polynucleotide, gene and/or polypeptide encoding phosphotransacetylase can include, but is not limited to, a sequence provided in the following tables 10 or 12.

is a collection of multiple sequence alignments and profile hidden Markov models (HMMs). Each Pfam HMM represents a protein family or domain. By searching a protein sequence against the Pfam library of HMMs, it is possible to determine which domains it carries i.e. its domain architecture. (The Pfam protein families database: R. D. Finn, J. Tate, J. Mistry, P. C. Coggill, J. S. Sammut, H. R. Hotz, G. Ceric, K. Forslund, S. R. Eddy, E. L. Sonnhammer and A. Bateman Nucleic Acids Research (2008) Database Issue 36:D281-D288)

Twelve of the experimentally verified proteins only contained the PTA_PTB domain. Two sequences, from *R.*

TABLE 10

SEQ ID NOs of phosphotransacetylase target gene coding regions and proteins.

| Description | SEQ ID NO: Nucleic acid | SEQ ID NO: Amino acid | Amino acid sequence |
|---|---|---|---|
| EutD phospho-trans-acetylase from *Lactobacillus plantarum* | 1111 | 1472 | MDLFESLAQKITGKDQTIVFPEGTEPRIVGAAARLAADGLVKPIVLGATDKVQAVANDLN ADLTGVQVLDPATYPAEDKQAMLDALVERRKGKNTPEQAAKMLEDENYFGTMLVYMGKAD GMVSGAIHPTGDTVRPALQIIKTKPGSHRISGAFIMQKGEERYVFADCAINIDPDADTLA EIATQSAATAKVFDIDPKVAMLSFSTKGSAKGEMVTKVQEATAKAQAAEPELAIDGELQF DAAFVEKVGLQKAPGSKVAGHANVFVFPELQSGNIGYKIAQRFGHFEAVGPVLQGLNKPV SDLSRGCSEEDVYKVAIITAAQGLA |
| Phospho-trans-acetylase from *Bacillus subtilis* | 1061 | 1422 | MADLFSTVQEKVAGKDVKIVFPEGLDERILEAVSKLAGNKVLNPIVIGNENEIQAKAKEL NLTLGGVKIYDPHTYEGMEDLVQAFVERRKGKATEEQARKALLDENYFGTMLVYKGLADG LVSGAAHSTADTVRPALQIIKTKEGVKKTSGVFIMARGEEQYVFADCAINIAPDSQDLAE IAIESANTAKMFDIEPRVAMLSFSTKGSAKSDETEKVADAVKIAKEKAPELTLDGEFQFD AAFVPSVAEKKAPDSEIKGDANVFVFPSLEAGNIGYKIAQRLGNFEAVGPILQGLNMPVN DLSRGCNAEDVYNLALITAAQAL |

Additional suitable phosphotransacetylase target gene coding regions and proteins were identified by diversity searching and clustering. A blast search of the non redundant GenBank protein database (NR) was performed with the *L. plantarum* EutD protein as a query sequence. A blast cut-off (Evalue) of 0.01 was applied. This search resulted in 2124 sequence matches. Redundancy reduction was achieved by clustering proteins with the CD-HIT program with parameters set at 95% sequence identity and 90% length overlap. The longest seed sequence, representative of each cluster, is retained for further analysis. Clustering reduced the number of protein sequences to 1336. Further clean-up of the sequences by removing sequences <280 amino acids and sequences >795 amino acids resulted in 1231 seqs.

The Brenda database was queried for experimentally verified phosphate acetyltransferases. Thirteen were found in the following organisms: *S. enterica, E. coli* K12, *V. Parvula, C. Kluyveri, C. Acetobutylicum, C. Thermocellum, M thermophila, S. pyogenes, B. subtilis, L. fermentum, L. plantarum, L. sanfranciscensis, B subtilis, L. fermentum, L. plantarum, L. sanfranciscensis, R. palustris, E. coli.*

Experimentally verified phosphate acetyltransferases (EC 2.3.1.8) belong to the PTA_PTB pfam family. However, the PTA_PTB domain is present in 13 distinct architectures (http://pfam.janelia.org/family/PF01515, Pfam database version 24). The motivation for investigating the domain architecture is to determine which of the proteins, that were identified by BLAST search, are likely to be phosphate acetyltransferases.

Experimentally verified sequences extracted from the BRENDA database as well as sequences retained after the CD-HIT clustering and clean-up, were searched against the Pfam database to determine their domain architecture. Pfam

*palustris* and *E. coli*, contained two domains PTA_PTB and DRTGG, a domain of unknown function. Therefore, from the CD-HIT clustering results, proteins that contained either the PTA_PTB domain only (Group 1: 549 sequences) or a combination of PTA_PTB+DRTGG domains (Group 2: 201 sequences) were chosen.

Furthermore, the PTA_PTB domain, as the name indicates, is actually not specific to phosphate acetyltransferases. The domain is also a signature for phosphate butyryltransferases (EC 2.3.1.19) methods to distinguish between the two subfamilies: acetyltransferases and butyryltransferases were employed and are as follows:

To further characterize the relationship among the sequences, multiple sequence alignment MSA), phylogenetic analysis. profile HMMs and GroupSim analysis were performed, For this set of analyses, the phosphate acetyltransferases are split in two groups. Group 1 contains phosphate acetyltransferases with the PTA_PTB domain only, while Group 2 contains phosphate acetyltransferases with PTA_PTB+DRTGG. The motivation here is to generate groups with similar lengths.

Clustal X, version 2.0 was used for sequence alignments with default parameters. (Thompson JD, et al. The CLUSTAL_X windows interface: flexible strategies for multiple sequence alignment aided by quality analysis tools. *Nucleic Acids Res.* (1997) 25:4876-4882.)

Alignment results were utilized to compute % sequence identities to a reference sequence. If the sequence from *L. plantarum* is taken as a reference, % IDs range from as low as 10.5% to 75.6% for the closest sequence. Alignment results also provided the basis for re-constructing phylogenetic trees. The Neighbor Joining method, available in the Jalview package version 2.3, was used to produce the trees, and computed trees were visualized in MEGA 4 (Tamura, Dudley, Nei, and Kumar 2007). The Neighbor Joining method is a method for re-constructing phylogenetic trees, and computing the lengths of the branches of this tree. In each stage, the two nearest nodes of the tree (the term "nearest nodes" will be defined in the following paragraphs) are chosen and defined as neighbors in our tree. This is done recursively until all of the nodes are paired together. "The neighbor-joining method: a new method for reconstructing phylogenetic trees. Mol Biol Evol. 1987 July; 4(4):406-25. Saitou N, Nei M." Jalview Version 2 is a system for interactive editing, analysis and annotation of multiple sequence alignments (Waterhouse, A. M., Procter, J. B., Martin, D. M. A, Clamp, M. and Barton, G. J. (2009) "Jalview Version 2—a multiple sequence alignment editor and analysis workbench" *Bioinformatics* 25 (9) 1189-1191). The MEGA software provides tools for exploring, discovering, and analyzing DNA and protein sequences from an evolutionary perspective. MEGA4 enables the integration of sequence acquisition with evolutionary analysis. It contains an array of input data and multiple results explorers for visual representation; the handling and editing of sequence data, sequence alignments, inferred phylogenetic trees; and estimated evolutionary distances. The results explorers allow users to browse, edit, summarize, export, and generate publication-quality captions for their results. MEGA 4 also includes distance matrix and phylogeny explorers as well as advanced graphical modules for the visual representation of input data and output results (Tamura K, Dudley J, Nei M & Kumar S (2007) MEGA4: Molecular Evolutionary Genetics Analysis (MEGA) software version 4.0. Molecular Biology and Evolution 24:1596-1599).

Taken together, % IDs and the generated tree (FIG. 4) indicated that potential phosphate acetyltransferases (PTA_PTB domain only) are divided in two major subfamilies. Subfamily 1 from 10.5% ID to ~20% ID (176 sequences) and Subfamily 2 from ~20% ID to 75.6% ID (361 sequences). The third Subfamily, of 12 sequences, has % ID ranging from 17% ID to 25% ID with respect to the *L. plantarum* sequence.

Based on experimentally verified sequences contained within each of the Subfamilies, Subfamily 1 and Subfamily 2 were determined to represent phosphate butyryltransferases (PTB) and phosphate acetylytransferases (PTA) respectively.

Discrimination between Subfamily 1 members and Subfamily 2 members was also performed by GroupSim analysis (Capra and Singh (2008) Bioinformatics 24: 1473-1480). The GroupSim method identifies amino acid residues that determine a protein's functional specificity. In a multiple sequence alignment (MSA) of a protein family whose sequences are, divided into multiple Subfamilies, amino acid residues that distinguish between the functional Subfamilies of sequences can be identified. The method takes a multiple sequence alignment (MSA) and known specificity groupings as input, and assigns a score to each amino acid position in the MSA. Higher scores indicate a greater likelihood that an amino acid position is a specificity determining position (SDP).

GroupSim analysis performed on the MSA of 537 sequences (divided into Subfamily 1 and Subfamily 2 by the phylogenetic analysis, above) identified highly discriminating positions. Listed in Table 11 are positions (Pos) having scores greater than to 0.7, where, a perfect score of 1.0 would indicate that all proteins within the Subfamily have the listed amino acid in the specified position and between Subfamilies the amino acid would always be different. The "Pattern" columns give the amino acid(s) in single letter code. Numbers between parentheses indicate frequency of occurrence of each amino acid at the particular position. The amino acid position number in column 1 is for the PTA protein sequence from *Lactobacillus plantarum*, the representative protein of group 2 with a GI#28377658 (SEQ ID NO: 1472).

TABLE 11

Highly discriminating amino acid positions for Subfamily 1 (PTB) and Subfamily 2 (PTA) from GroupSim analysis.

| Pos | Score | Pattern PTB | Pattern PTA |
|---|---|---|---|
| 212 | 0.980314 | Group 1: E(173), D(2), L(1) | Group 2: S(360), N(1) |
| 305 | 0.87236 | Group 1: L(152), V(11), M(5), I(5), F(3) | Group 2: D(360), Q(1) |
| 242 | 0.831201 | Group 1: A(142), D(15), S(13), G(4), T(2) | Group 2: Q(361) |
| 208 | 0.776954 | Group 1: L(130), I(35), V(11) | Group 2: S(355), A(6) |
| 125 | 0.705868 | Group 1: K(175), R(1) | Group 2: S(215), A(85), G(41), C(14), N(4), T(2) |

An alternative structure/function characterization of the PTA and PTB subfamilies of enzymes was performed using the HMMER software package (the theory behind profile HMMs is described in R. Durbin, S. Eddy, A. Krogh, and G. Mitchison, Biological sequence analysis: probabilistic models of proteins and nucleic acids, Cambridge University Press, 1998; Krogh et al., 1994; J. Mol. Biol. 235:1501-1531), following the user guide which is available from HMMER (Janelia Farm Research Campus, Ashburn, Va.).

Using a multiple sequence alignment of the experimentally verified sequences (containing the PTA_PTB domain only) in Subfamily 2, a profile Hidden Markov Model (HMM) was created for representing Subfamily 2 members. The sequences were:
1. BAB19267.1 from *Lactobacillus sanfranciscensis* (SEQ ID NO: 1475)
2. NP_784550.1 from *Lactobacillus plantarum* WCFS1 (SEQ ID NO: 1472)
3. ZP_03944466.1 from *Lactobacillus* fermentum ATCC 14931 (SEQ ID NO: 1453)
4. NP_391646.1 from *Bacillus subtilis* subsp. *subtilis* str. 168 (SEQ ID NO: 1422)
5. AAA72041.1 from *Methanosarcina thermophila* (SEQ ID NO: 1277)
6. ZP_03152606.1 from *Clostridium thermocellum* DSM 4150 (SEQ ID NO: 1275)
7. NP_348368.1 from *Clostridium acetobutylicum* ATCC 824 (SEQ ID NO: 1206)
8. YP 001394780.1 from *Clostridium kluyveri* DSM 555 (SEQ ID NO: 1200)
9. ZP_03855267.1 from *Veillonella parvula* DSM 2008 (SEQ ID NO: 1159)
10. YP_149725.1 from *Salmonella enterica* subsp. enterica serovar Paratyphi A str. ATCC 9150 (SEQ ID NO: 1129)

The Profile HMM was built as follows: The 10 seed sequences (sequences representing experimentally verified function) that are in Subfamily 2 were aligned using Clustal X (interface to Clustal W) with default parameters. The hmmbuild program was run on each set of the aligned sequences using default parameters. hmmbuild reads the multiple sequence alignment file, builds a new Profile HMM, and saves the Profile HMM to file. Using this program an un-calibrated profile was generated from the multiple alignment for each set of subunit sequences described above.

The Profile HMM was read using hrnmcalibrate which scores a large number of synthesized random sequences with the Profile (the default number of synthetic sequences used is 5,000), fits an extreme value distribution (EVD) to the histogram of those scores, and re-saves the HMM file now including the EVD parameters. These EVD parameters (µ and λ) are used to calculate the E-values of bit scores when the profile is searched against a protein sequence database. hmmcalibrate writes two parameters into the HMM file on a line labeled "EVD": these parameters are the μ (location) and λ (scale) parameters of an extreme value distribution (EVD) that best fits a histogram of scores calculated on randomly generated sequences of about the same length and residue composition as SWISS-PROT. This calibration was done once for the Profile HMM.

The calibrated pofile HMM for the Subfamily 2 set is provided as Table 14. The Profile HMM table gives the probability of each amino acid occurring at each position in the amino acid sequence. The amino acids are represented by the one letter code. The first line for each position reports the match emission scores: probability for each amino acid to be in that state (highest score is highlighted). The second line reports the insert emission scores, and the third line reports on state transition scores: M→M, M→I, M→D; I→M, I→I; D→M, D→D; B→M; M→E. Table 14 shows that in the Subfamily 2 profile HMM, methionine has a 3792 ans 4481 probability of being in the first two positions.

The Subfamily 2 profile HMM was evaluated using, hmmsearch, with the Z parameter set to one billion, for the ability to discriminate Subfamily 1 members from those of Subfamily 2. The hmmsearch program takes the hmm file for the Subfamily 2 profile HMM and all the sequences from both Subfamilies and assigns an E-value score to each sequence. This E-value score is a measure of fit to the Profile HMM, with a lower score being a better fit. The Profile HMM distinguished Subfamily 2 members from Subfamily 1 members and there was a large margin of E-value difference between the worst scoring Subfamily 2 member (5e-34) and the best scoring Subfamily 1 member (4.3e-07). This analysis shows that the Profile HMM prepared for Subfamily 2 phosphate acetyltransferases (PTA) distinguishes PTA sequences from phosphate butyryltransferase PTB protein sequences.

Based on these analyses, 361 phosphate acetyltransferase sequences (PTA_PTB domain only) were identified and are provided in Table 12a.

TABLE 12a

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 255994631 | complement (NZ_ACON01000003.1: 407639 . . . 408607) | 762 | ZP_05427766.1 | 1123 | Eubacterium saphenum ATCC 49989 |
| 223935781 | NZ_ABOX02000007.1: 10458 . . . 11600 | 763 | ZP_03627696.1 | 1124 | bacterium Ellin514 |
| 196232920 | NZ_ABVL01000018.1: 134406 . . . 135449 | 764 | ZP_03131770.1 | 1125 | Chthoniobacter flavus Ellin428 |
| 187735919 | NC_010655.1: 1714393 . . . 1715484 | 765 | YP_001878031.1 | 1126 | Akkermansia muciniphila ATCC BAA-835 |
| 237732443 | complement (NZ_GG657366.1: 2437071 . . . 2438087) | 766 | ZP_04562924.1 | 1127 | Citrobacter sp. 30_2 |
| 157144617 | NC_009792.1: 326993 . . . 328009 | 767 | YP_001451936.1 | 1128 | Citrobacter koseri ATCC BAA-895 |
| 56412650 | NC_006511.1: 473496 . . . 474512 | 768 | YP_149725.1 | 1129 | Salmonella enterica subsp. enterica serovar Paratyphi A str. ATCC 9150 |
| 161502384 | NC_010067.1: 425125 . . . 426141 | 769 | YP_001569496.1 | 1130 | Salmonella enterica subsp. arizonae serovar 62:z4, z23:-- |
| 16130383 | complement (NC_000913.2: 2570511 . . . 571527) | 770 | NP_416953.1 | 1131 | Escherichia coli str. K-12 substr. MG1655 |
| 238895918 | complement (NC_012731.1: 3863205 . . . 3864221) | 771 | YP_002920654.1 | 1132 | Klebsiella pneumoniae NTUH-K2044 |
| 238794182 | complement (NZ_AALF02000025.1: 17041 . . . 18039) | 772 | ZP_04637797.1 | 1133 | Yersinia intermedia ATCC 29909 |
| 90414632 | complement (NZ_AAPH01000046.1: 12550 . . . 13527) | 773 | ZP_01222604.1 | 1134 | Photobacterium profundum 3TCK |
| 163749608 | complement (NZ_ABIC01000008.1: 73942 . . . 74913) | 774 | ZP_02156855.1 | 1135 | Shewanella benthica KT99 |
| 120554157 | NC_008740.1: 1389827 . . . 1390810 | 775 | YP_958508.1 | 1136 | Marinobacter aquaeolei VT8 |
| 51246887 | complement (NC_006138.1: 3433697 . . . 3434677) | 776 | YP_066771.1 | 1137 | Desulfotalea psychrophila LSv54 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 226362753 | complement (NC_012522.1: 3613049 . . . 3614074) | 777 | YP_002780531.1 | 1138 | *Rhodococcus opacus* B4 |
| 111020534 | complement (NC_008268.1: 3751557 . . . 3752585) | 778 | YP_703506.1 | 1139 | *Rhodococcus jostii* RHA1 |
| 256669010 | NZ_ACEV01000044.1: 80096 . . . 81085 | 779 | ZP_05479963.1 | 1140 | *Streptomyces* sp. AA4 |
| 226227292 | complement (NC_012489.1: 2203452 . . . 2204474) | 780 | YP_002761398.1 | 1141 | *Gemmatimonas aurantiaca* T-27 |
| 239627158 | complement (NZ_DS990260.1: 924717 . . . 925736) | 781 | ZP_04670189.1 | 1142 | *Clostridiales bacterium* 1_7_47FAA |
| 256753163 | complement (NZ_ACXX01000001.1: 167634 . . . 168635) | 782 | ZP_05493958.1 | 1143 | *Clostridium papyrosolvens* DSM 2782 |
| 257063834 | NC_013165.1: 1278820 . . 1279818 | 783 | YP_003143506.1 | 1144 | *Slackia heliotrinireducens* DSM 20476 |
| 254477436 | NZ_DS999054.1: 3384063 . . . 3384914 | 784 | ZP_05090822.1 | 1145 | *Ruegeria* sp. R11 |
| 126732220 | complement (NZ_AAYA01000016.1: 68052 . . . 68996) | 785 | ZP_01748021.1 | 1146 | *Sagittula stellata* E-37 |
| 19704507 | complement (NC_003454.1: 1833702 . . . 1834715) | 786 | NP_604069.1 | 1147 | *Fusobacterium nucleatum* subsp. *nucleatum* ATCC 25586 |
| 260494604 | NZ_GG704456.1: 222376 . . . 223389 | 787 | ZP_05814734.1 | 1148 | *Fusobacterium* sp. 3_1_33 |
| 262067001 | complement (NZ_ACJY01000064.1: 9865 . . . 10869) | 788 | ZP_06026613.1 | 1149 | *Fusobacterium periodonticum* ATCC 33693 |
| 257452333 | complement (NZ_ACDD01000037.1: 1250 . . . 2263) | 789 | ZP_05617632.1 | 1150 | *Fusobacterium* sp. 3_1_5R |
| 257463639 | NZ_ACDG01000104.1: 17109 . . . 18122 | 790 | ZP_05628030.1 | 1151 | *Fusobacterium* sp. D12 |
| 253583748 | complement (NZ_GG696122.1: 645905 . . . 646912) | 791 | ZP_04860946.1 | 1152 | *Fusobacterium varium* ATCC 27725 |
| 237736963 | NZ_GG657909.1: 489336 . . . 490343 | 792 | ZP_04567444.1 | 1153 | *Fusobacterium mortiferum* ATCC 9817 |
| 157736754 | complement (NC_009850.1: 500921 . . . 501916) | 793 | YP_001489437.1 | 1154 | *Arcobacter butzleri* RM4018 |
| 257125122 | NC_013192.1: 327731 . . . 328735 | 794 | YP_003163236.1 | 1155 | *Leptotrichia buccalis* C-1013-b |
| 260891157 | NZ_ACVB02000026.1: 170989 . . . 171993 | 795 | ZP_05902420.1 | 1156 | *Leptotrichia hofstadii* F0254 |
| 262037878 | complement (NZ_ADAD01000064.1: 9188 . . . 10195) | 796 | ZP_06011308.1 | 1157 | *Leptotrichia goodfellowii* F0264 |
| 229859891 | NZ_ABUT01000004.1: 63190 . . . 64215 | 797 | ZP_04479548.1 | 1158 | *Streptobacillus moniliformis* DSM 12112 |
| 227371784 | NZ_ABVB01000002.1: 260421 . . . 261419 | 798 | ZP_03855267.1 | 1159 | *Veillonella parvula* DSM 2008 |
| 227498373 | complement (NZ_ACGB01000001.1: 109630 . . . 110643) | 799 | ZP_03928523.1 | 1160 | *Acidaminococcus* sp. D21 |
| 42525561 | NC_002967.9: 48816 . . . 49823 | 800 | NP_970659.1 | 1161 | *Treponema denticola* ATCC 35405 |
| 257456313 | NZ_ACYH01000011.1: 210840 . . . 211847 | 801 | ZP_05621510.1 | 1162 | *Treponema vincentii* ATCC 35580 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 15639088 | NC_000919.1: 102879 ... 103889 | 802 | NP_218534.1 | 1163 | *Treponema pallidum* subsp. *pallidum* str. Nichols |
| 228000316 | complement (NZ_ABTG01000001.1: 1179041 ... 1180048) | 803 | ZP_04047318.1 | 1164 | *Brachyspira murdochii* DSM 12563 |
| 225619252 | NC_012225.1: 340269 ... 341276 | 804 | YP_002720478.1 | 1165 | *Brachyspira hyodysenteriae* WA1 |
| 218960931 | complement (NS_000195.1: 716420 ... 717424) | 805 | YP_001740706.1 | 1166 | *Candidatus Cloacamonas acidaminovorans* |
| 239878221 | complement (join(GG681098.1: 49679 ... 49966, GG681098.1: 50017 ... 50325, GG681098.1: 50380 ... 50442, GG681098.1: 50494 ... 50605, GG681098.1: 50656 ... 50780, GG681098.1: 50826 ... 50908, GG681098.1: 50958 ... 51039)) | 806 | EER05013.1 | 1167 | *Perkinsus marinus* ATCC 50983 |
| 119953373 | NC_008710.1: 614125 ... 615171 | 807 | YP_945582.1 | 1168 | *Borrelia turicatae* 91E135 |
| 187918450 | NC_010673.1: 616784 ... 617842 | 808 | YP_001884013.1 | 1169 | *Borrelia hermsii* DAH |
| 203284493 | NC_011229.1: 622676 ... 623746 | 809 | YP_002222233.1 | 1170 | *Borrelia duttonii* Ly |
| 224534734 | complement (NZ_ABKB02000009.1: 27640 ... 28677) | 810 | ZP_03675306.1 | 1171 | *Borrelia spielmanii* A14S |
| 216263399 | NZ_ABCU02000001.1: 172066 ... 173103 | 811 | ZP_03435394.1 | 1172 | *Borrelia afzelii* ACA-1 |
| 219685198 | NZ_ABPZ02000001.1: 172004 ... 173041 | 812 | ZP_03540018.1 | 1173 | *Borrelia garinii* Far04 |
| 224532296 | NZ_ABCY02000001.1: 609419 ... 610456 | 813 | ZP_03672928.1 | 1174 | *Borrelia valaisiana* VS116 |
| 15594934 | NC_001318.1: 608020 ... 609078 | 814 | NP_212723.1 | 1175 | *Borrelia burgdorferi* B31 |
| 189485346 | NS_000191.1: 518918 ... 519919 | 815 | YP_001956287.1 | 1176 | uncultured Termite group 1 bacterium phylotype Rs-D17 |
| 42560817 | NC_005364.2: 308545 ... 309513 | 816 | NP_975268.1 | 1177 | *Mycoplasma mycoides* subsp. *mycoides* SC str. PG1 |
| 83319483 | NC_007633.1: 277239 ... 278207 | 817 | YP_424216.1 | 1178 | *Mycoplasma capricolum* subsp. *capricolum* ATCC 27343 |
| 50364858 | NC_006055.1: 58892 ... 59860 | 818 | YP_053283.1 | 1179 | *Mesoplasma florum* L1 |
| 110005214 | complement (AM285317.1: 14153 ... 15130) | 819 | CAK99540.1 | 1180 | *Spiroplasma citri* |
| 12045155 | complement (NC_000908.2: 368733 ... 369695) | 820 | NP_072966.1 | 1181 | *Mycoplasma genitalium* G37 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 13508167 | complement (NC_000912.1: 515605 ... 516567) | 821 | NP_110116.1 | 1182 | *Mycoplasma pneumoniae* M129 |
| 31544825 | complement (NC_004829.1: 851083 ... 852075) | 822 | NP_853403.1 | 1183 | *Mycoplasma gallisepticum* R |
| 26553955 | complement (NC_004432.1: 640803 ... 641777) | 823 | NP_757889.1 | 1184 | *Mycoplasma penetrans* HF-2 |
| 54020554 | complement (NC_006360.1: 638554 ... 639507) | 824 | YP_116016.1 | 1185 | *Mycoplasma hyopneumoniae* 232 |
| 240047219 | NC_012806.1: 88435 ... 89406 | 825 | YP_002960607.1 | 1186 | *Mycoplasma conjunctivae* |
| 148377406 | NC_009497.1: 159649 ... 160605 | 826 | YP_001256282.1 | 1187 | *Mycoplasma agalactiae* PG2 |
| 238809713 | complement (AP009608.1: 242111 ... 243064) | 827 | BAH69503.1 | 1188 | *Mycoplasma fermentans* PG18 |
| 71894663 | complement (NC_007294.1: 757812 ... 758771) | 828 | YP_278771.1 | 1189 | *Mycoplasma synoviae* 53 |
| 15828708 | NC_002771.1: 274992 ... 275948 | 829 | NP_326068.1 | 1190 | *Mycoplasma pulmonis* UAB CTIP |
| 47459003 | NC_006908.1: 230100 ... 231068 | 830 | YP_015865.1 | 1191 | *Mycoplasma mobile* 163K |
| 148377754 | NC_009497.1: 572993 ... 573967 | 831 | YP_001256630.1 | 1192 | *Mycoplasma agalactiae* PG2 |
| 116515056 | NC_008513.1: 131608 ... 132594 | 832 | YP_802685.1 | 1193 | *Buchnera aphidicola* str. Cc (*Cinara cedri*) |
| 187934490 | NC_010674.1: 1263289 ... 1264287 | 833 | YP_001885432.1 | 1194 | *Clostridium botulinum* B str. Eklund 17B |
| 150016048 | NC_009617.1: 1384403 ... 1385404 | 834 | YP_001308302.1 | 1195 | *Clostridium beijerinckii* NCIMB 8052 |
| 254519224 | complement (NZ_EQ999773.1: 2015491 ... 2016492) | 835 | ZP_05131280.1 | 1196 | *Clostridium* sp. 7_2_43FAA |
| 182417251 | NZ_ABDT01000035.2: 9769 ... 10770 | 836 | ZP_02948604.1 | 1197 | *Clostridium butyricum* 5521 |
| 18310707 | complement (NC_003366.1: 2001712 ... 2002719) | 837 | NP_562641.1 | 1198 | *Clostridium perfringens* str. 13 |
| 255524273 | complement (NZ_ACVI01000014.1: 63543 ... 64547) | 838 | ZP_05391232.1 | 1199 | *Clostridium carboxidivorans* P7 |
| 153954015 | NC_009706.1: 1428554 ... 1429555 | 839 | YP_001394780.1 | 1200 | *Clostridium kluyveri* DSM 555 |
| 187778946 | NZ_ABKW02000004.1: 733017 ... 734015 | 840 | ZP_02995419.1 | 1201 | *Clostridium sporogenes* ATCC 15579 |
| 28210926 | NC_004557.1: 1326340 ... 1327359 | 841 | NP_781870.1 | 1202 | *Clostridium tetani* E88 |
| 253681395 | NZ_ACSJ01000007.1: 344343 ... 345338 | 842 | ZP_04862192.1 | 1203 | *Clostridium botulinum* D str. 1873 |
| 118444574 | complement (NC_008593.1: 1416375 ... 1417373) | 843 | YP_878298.1 | 1204 | *Clostridium novyi* NT |
| 242260238 | NZ_ACPD01000011.1: 83320 ... 84318 | 844 | ZP_04804960.1 | 1205 | *Clostridium cellulovorans* 743B |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 15895019 | NC_003030.1: 1890289 . . . 1891290 | 845 | NP_348368.1 | 1206 | *Clostridium acetobutylicum* ATCC 824 |
| 169247670 | EU313773.1: 40 . . . 1026 | 846 | ACA51668.1 | 1207 | *Thermoanaerobacterium saccharolyticum* |
| 255257449 | NZ_ACVG01000034.1: 8635 . . . 9621 | 847 | ZP_05336886.1 | 1208 | *Thermoanaerobacterium thermosaccharolyticum* DSM 571 |
| 20807926 | complement (NC_003869.1: 1451520 . . . 1452515) | 848 | NP_623097.1 | 1209 | *Thermoanaerobacter tengcongensis* MB4 |
| 167040369 | complement (NC_010320.1: 1738259 . . . 1739257) | 849 | YP_001663354.1 | 1210 | *Thermoanaerobacter* sp. X514 |
| 220931863 | NC_011899.1: 1110901 . . . 1111899 | 850 | YP_002508771.1 | 1211 | *Halothermothrix orenii* H 168 |
| 258514457 | complement (NC_013216.1: 1194895 . . . 1195899) | 851 | YP_003190679.1 | 1212 | *Desulfotomaculum acetoxidans* DSM 771 |
| 188586231 | complement (NC_010718.1: 1692944 . . . 1693942) | 852 | YP_001917776.1 | 1213 | *Natranaerobius thermophilus* JW/NM-WN-LF |
| 78044760 | complement (NC_007503.1: 1302969 . . . 1303973) | 853 | YP_360288.1 | 1214 | *Carboxydothermus hydrogenoformans* Z-2901 |
| 262295620 | complement (GG705150.1: 648642 . . . 649655) | 854 | EEY83551.1 | 1215 | *Bacteroides* sp. 2_1_33B |
| 154494088 | complement (NZ_AAXE02000107.1: 241237 . . . 242250) | 855 | ZP_02033408.1 | 1216 | *Parabacteroides merdae* ATCC 43184 |
| 34540818 | complement (NC_002950.2: 1149763 . . . 1150773) | 856 | NP_905297.1 | 1217 | *Porphyromonas gingivalis* W83 |
| 228471187 | complement (NZ_ACLR01000214.1: 23231 . . . 24238) | 857 | ZP_04056000.1 | 1218 | *Porphyromonas uenonis* 60-3 |
| 229496164 | NZ_ACNN01000020.1: 205218 . . . 206225 | 858 | ZP_04389884.1 | 1219 | *Porphyromonas endodontalis* ATCC 35406 |
| 160887812 | complement (NZ_AAYH02000031.1: 6367 . . . 7386) | 859 | ZP_02068815.1 | 1220 | *Bacteroides uniformis* ATCC 8492 |
| 218131945 | NZ_ABVO01000052.1: 25694 . . . 26710 | 860 | ZP_03460749.1 | 1221 | *Bacteroides eggerthii* DSM 20697 |
| 224536405 | complement (NZ_ACCH01000118.1: 1796 . . . 2812) | 861 | ZP_03676944.1 | 1222 | *Bacteroides cellulosilyticus* DSM 14838 |
| 53711769 | NC_006347.1: 557297 . . . 558316 | 862 | YP_097761.1 | 1223 | *Bacteroides fragilis* YCH46 |
| 237715344 | complement (NZ_EQ973249.1: 217217 . . . 218236) | 863 | ZP_04545825.1 | 1224 | *Bacteroides* sp. D1 |
| 224025178 | NZ_ACBW01000140.1: 3350 . . . 4369 | 864 | ZP_03643544.1 | 1225 | *Bacteroides coprophilus* DSM 18228 |
| 198274546 | NZ_ABQC02000011.1: 44269 . . . 45279 | 865 | ZP_03207078.1 | 1226 | *Bacteroides plebeius* DSM 17135 |
| 150003111 | NC_009614.1: 740818 . . . 741831 | 866 | YP_001297855.1 | 1227 | *Bacteroides vulgatus* ATCC 8482 |
| 258649233 | complement (NZ_ACIJ02000031.1: 14596 . . . 15612) | 867 | ZP_05736702.1 | 1228 | *Prevotella tannerae* ATCC 51259 |
| 261881160 | NZ_ACKS01000109.1: 4227 . . . 5276 | 868 | ZP_06007587.1 | 1229 | *Prevotella bergensis* DSM 17361 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 260593477 | NZ_ACVA01000073.1: 31053 ... 32099 | 869 | ZP_05858935.1 | 1230 | Prevotella veroralis F0319 |
| 260910323 | complement (NZ_ACZS01000043.1: 34220 ... 35257) | 870 | ZP_05916997.1 | 1231 | Prevotella sp. oral taxon 472 str. F0295 |
| 212550465 | complement (NC_011565.1: 126538 ... 127539) | 871 | YP_002308782.1 | 1232 | Candidatus Azobacteroides pseudotrichonymphae genomovar. CFP2 |
| 114566305 | NC_008346.1: 872558 ... 873550 | 872 | YP_753459.1 | 1233 | Syntrophomonas wolfei subsp. wolfei str. Goettingen |
| 139437229 | NZ_AAVN02000001.1: 368246 ... 369226 | 873 | ZP_01771389.1 | 1234 | Collinsella aerofaciens ATCC 25986 |
| 210631306 | complement (NZ_ABXJ01000041.1: 3328 ... 4308) | 874 | ZP_03296849.1 | 1235 | Collinsella stercoris DSM 13279 |
| 229814970 | complement (NZ_ABXH02000002.1: 65772 ... 66770) | 875 | ZP_04445308.1 | 1236 | Collinsella intestinalis DSM 13280 |
| 221194458 | complement (NZ_ACFE01000001.1: 86128 ... 87273) | 876 | ZP_03567515.1 | 1237 | Atopobium rimae ATCC 49626 |
| 257784450 | complement (NC_013203.1: 723329 ... 724309) | 877 | YP_003179667.1 | 1238 | Atopobium parvulum DSM 20469 |
| 227516084 | complement (NZ_ACGK01000007.1: 63717 ... 64691) | 878 | ZP_03946133.1 | 1239 | Atopobium vaginae DSM 15829 |
| 227872296 | NZ_ACKX01000061.1: 10209 ... 11261 | 879 | ZP_03990654.1 | 1240 | Oribacterium sinus F0268 |
| 229824780 | NZ_ACIN02000002.1: 126870 ... 127931 | 880 | ZP_04450849.1 | 1241 | Abiotrophia defectiva ATCC 49176 |
| 260443831 | NZ_ACIQ01000073.1: 32192 ... 33196 | 881 | ZP_05797601.1 | 1242 | Oribacterium sp. oral taxon 078 str. F0262 |
| 225176688 | complement (NZ_ACFX01000006.1: 113088 ... 114089) | 882 | ZP_03730247.1 | 1243 | Clostridium sp. M62/1 |
| 253578981 | complement (NZ_GG696046.1: 364564 ... 365595) | 883 | ZP_04856252.1 | 1244 | Ruminococcus sp. 5_1_39BFAA |
| 153813664 | NZ_AAVO02000036.1: 4823 ... 5992 | 884 | ZP_01966332.1 | 1245 | Ruminococcus obeum ATCC 29174 |
| 255281061 | complement (NZ_ACCL02000005.1: 162813 ... 163811) | 885 | ZP_05345616.1 | 1246 | Bryantella formatexigens DSM 14469 |
| 225571965 | NZ_ACBZ01000008.1: 1408 ... 2442 | 886 | ZP_03780829.1 | 1247 | Blautia hydrogenotrophica DSM 10507 |
| 210612569 | NZ_ABWO01000095.2: 3132 ... 4127 | 887 | ZP_03289360.1 | 1248 | Clostridium nexile DSM 1787 |
| 154505354 | complement (NZ_AAYG02000022.1: 50151 ... 51146) | 888 | ZP_02042092.1 | 1249 | Ruminococcus gnavus ATCC 29149 |
| 197303064 | NZ_ABOU02000039.1: 71843 ... 72838 | 889 | ZP_03168112.1 | 1250 | Ruminococcus lactaris ATCC 29176 |
| 153816169 | complement (NZ_AAVP02000015.1: 36559 ... 37554) | 890 | ZP_01968837.1 | 1251 | Ruminococcus torques ATCC 27756 |
| 167758299 | complement (NZ_ABFY02000009.1: 238358 ... 239380) | 891 | ZP_02430426.1 | 1252 | Clostridium scindens ATCC 35704 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 225570721 | NZ_ABYI02000032.1: 3477 . . . 4499 | 892 | ZP_03779744.1 | 1253 | *Clostridium hylemonae* DSM 15053 |
| 166031766 | NZ_AAXA02000013.1: 54410 . . . 55414 | 893 | ZP_02234595.1 | 1254 | *Dorea formicigenerans* ATCC 27755 |
| 153853264 | complement (NZ_AAXB02000002.1: 216862 . . . 217857) | 894 | ZP_01994673.1 | 1255 | *Dorea longicatena* DSM 13814 |
| 160879474 | NC_010001.1: 1657582 . . . 1658577 | 895 | YP_01558442.1 | 1256 | *Clostridium phytofermentans* ISDg |
| 239624054 | complement (NZ_DS990263.1: 658578 . . . 659573) | 896 | ZP_04667085.1 | 1257 | *Clostridiales bacterium* 1_7_47FAA |
| 160938034 | complement (NZ_ABCC02000027.1: 52316 . . . 53311) | 897 | ZP_02085391.1 | 1258 | *Clostridium bolteae* ATCC BAA-613 |
| 260437037 | complement (NZ_ABWN01000017.1: 33488 . . . 34483) | 898 | ZP_05790853.1 | 1259 | *Butyrivibrio crossotus* DSM 2876 |
| 154483586 | complement (NZ_AAVL02000033.1: 74910 . . . 75941) | 899 | ZP_02026034.1 | 1260 | *Eubacterium ventriosum* ATCC 27560 |
| 238916996 | complement (NC_012778.1: 1076225 . . . 1077220) | 900 | YP_002930513.1 | 1261 | *Eubacterium eligens* ATCC 27750 |
| 242309058 | NZ_DS990446.1: 108718 . . . 109737 | 901 | ZP_04808213.1 | 1262 | *Helicobacter pullorum* MIT 98-5489 |
| 224418114 | complement (NZ_ABQS01000024.1: 18744 . . . 19745) | 902 | ZP_03656120.1 | 1263 | *Helicobacter canadensis* MIT 98-5491 |
| 237752737 | NZ_GG661974.1: 463241 . . . 464236 | 903 | ZP_04583217.1 | 1264 | *Helicobacter winghamensis* ATCC BAA-430 |
| 32266808 | complement (NC_004917.1: 1266998 . . . 1267993) | 904 | NP_860840.1 | 1265 | *Helicobacter hepaticus* ATCC 51449 |
| 224436915 | complement (NZ_ABQT01000013.1: 10506 . . . 11522) | 905 | ZP_03657896.1 | 1266 | *Helicobacter cinaedi* CCUG 18818 |
| 167745652 | complement (NZ_ABAX03000002.1: 101957 . . . 102961) | 906 | ZP_02417779.1 | 1267 | *Anaerostipes caccae* DSM 14662 |
| 167765558 | complement (NZ_ABGC03000004.1: 50807 . . . 51820) | 907 | ZP_02437622.1 | 1268 | *Clostridium* sp. SS2/1 |
| 163814038 | NZ_ABEY02000003.1: 15727 . . . 16794 | 908 | ZP_02205430.1 | 1269 | *Coprococcus eutactus* ATCC 27759 |
| 168334441 | complement (NZ_ABEQ01000029.2: 21420 . . . 22418) | 909 | ZP_02692616.1 | 1270 | *Epulopiscium* sp. 'N.t. morphotype B' |
| 257791476 | NC_013204.1: 2035882 . . . 2036880 | 910 | YP_003182082.1 | 1271 | *Eggerthella lenta* DSM 2243 |
| 256827068 | complement (NC_013170.1: 735166 . . . 736167) | 911 | YP_003151027.1 | 1272 | *Cryptobacterium curtum* DSM 15641 |
| 257063929 | complement (NC_013165.1: 1407526 . . . 1408521) | 912 | YP_003143601.1 | 1273 | *Slackia heliotrinireducens* DSM 20476 |
| 256757417 | complement (NZ_ACXX01000078.1: 7706 . . . 8701) | 913 | ZP_05498135.1 | 1274 | *Clostridium papyrosolvens* DSM 2782 |
| 196254011 | NZ_ABVG01000076.1: 9016 . . . 10092 | 914 | ZP_03152606.1 | 1275 | *Clostridium thermocellum* JW20 |
| 146297046 | complement (NC_009437.1: 2185773 . . . 2186804) | 915 | YP_001180817.1 | 1276 | *Caldicellulosiruptor saccharolyticus* DSM 8903 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 349833 | L23147.1: 207 . . . 1208 | 916 | AAA72041.1 | 1277 | *Methanosarcina thermophila* |
| 20092407 | complement (NC_003552.1: 4448053 . . . 4449054) | 917 | NP_618482.1 | 1278 | *Methanosarcina acetivorans* C2A |
| 73669327 | complement (NC_007355.1: 2275987 . . . 2276988) | 918 | YP_305342.1 | 1279 | *Methanosarcina barkeri* str. Fusaro |
| 163734840 | NZ_ABIG01000010.1: 132890 . . . 133867 | 919 | ZP_02142278.1 | 1280 | *Roseobacter litoralis* Och 149 |
| 110678177 | complement (NC_008209.1: 803709 . . . 804707) | 920 | YP_681184.1 | 1281 | *Roseobacter denitrificans* OCh 114 |
| 159044374 | complement (NC_009952.1: 1904769 . . . 1905794) | 921 | YP_001533168.1 | 1282 | *Dinoroseobacter shibae* DFL 12 |
| 254512869 | NZ_DS999532.1: 435221 . . . 436255 | 922 | ZP_05124935.1 | 1283 | *Rhodobacteraceae bacterium* KLH11 |
| 260432366 | complement (NZ_GG704596.1: 1443685 . . . 1444707) | 923 | ZP_05786337.1 | 1284 | *Silicibacter lacuscaerulensis* ITI-1157 |
| 150376990 | NC_009620.1: 1371590 . . . 1372624 | 924 | YP_001313586.1 | 1285 | *Sinorhizobium medicae* WSM419 |
| 16264720 | NC_003078.1: 1058537 . . . 1059529 | 925 | NP_437512.1 | 1286 | *Sinorhizobium meliloti* 1021 |
| 239833801 | complement (NZ_ACQA01000002.1: 595918 . . . 596886) | 926 | ZP_04682129.1 | 1287 | *Ochrobactrum intermedium* LMG 3301 |
| 153010822 | complement (NC_00968.1: 862920 . . . 863897) | 927 | YP_001372036.1 | 1288 | *Ochrobactrum anthropi* ATCC 49188 |
| 187919084 | complement (NC_010676.1: 423371 . . . 424405) | 928 | YP_001888115.1 | 1289 | *Burkholderia phytofirmans* PsJN |
| 91779405 | NC_007952.1: 2605754 . . . 2606791 | 929 | YP_554613.1 | 1290 | *Burkholderia xenovorans* LB400 |
| 186470979 | NC_010625.1: 763673 . . . 764704 | 930 | YP_001862297.1 | 1291 | *Burkholderia phymatum* STM815 |
| 73537607 | complement (NC_007348.1: 372720 . . . 373757) | 931 | YP_297974.1 | 1292 | *Ralstonia eutropha* JMP134 |
| 194292312 | NC_010530.1: 1692071 . . . 1693105 | 932 | YP_002008219.1 | 1293 | *Cupriavidus taiwanensis* |
| 161521061 | NC_010086.1: 1600765 . . . 1601856 | 933 | YP_001584488.1 | 1294 | *Burkholderia multivorans* ATCC 17616 |
| 206563034 | complement (NC_011001.1: 1288493 . . . 1289527) | 934 | YP_002233797.1 | 1295 | *Burkholderia cenocepacia* J2315 |
| 90412230 | complement (NZ_AAPH01000013.1: 616 . . . 1653) | 935 | ZP_01220235.1 | 1296 | *Photobacterium profundum* 3TCK |
| 224825256 | complement (NZ_ACIS01000005.1: 7593 . . . 8612) | 936 | ZP_03698361.1 | 1297 | *Lutiella nitroferrum* 2002 |
| 148973982 | complement (NZ_AAZW01000001.1: 115872 . . . 116945) | 937 | ZP_01811515.1 | 1298 | *Vibrionales bacterium* SWAT-3 |
| 84385317 | complement (NZ_AAMR01000001.1: 227808 . . . 228881) | 938 | ZP_00988349.1 | 1299 | *Vibrio splendidus* 12B01 |
| 149187938 | NZ_ABCH01000003.1: 163877 . . . 164926 | 939 | ZP_01866234.1 | 1300 | *Vibrio shilonii* AK1 |
| 260776268 | complement (NZ_ACZN01000015.1: 316917 . . . 317966) | 940 | ZP_05885163.1 | 1301 | *Vibrio coralliilyticus* ATCC BAA-450 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 45862014 | AY498613.1: 8897 . . . 9853 | 941 | AAS78789.1 | 1302 | *Paracoccus denitrificans* |
| 77404622 | NC_007488.1: 38175 . . . 39173 | 942 | YP_345196.1 | 1303 | *Rhodobacter sphaeroides* 2.4.1 |
| 23630309 | AY134843.1: 2180 . . . 3148 | 943 | AAN08490.1 | 1304 | *Castellaniella defragrans* |
| 83952615 | NZ_AALY01000004.1: 6833 . . . 7819 | 944 | ZP_00961345.1 | 1305 | *Roseovarius nubinhibens* ISM |
| 56698382 | complement (NC_003911.11: 3772593 . . . 3773606) | 945 | YP_168755.1 | 1306 | *Ruegeria pomeroyi* DSS-3 |
| 149912659 | NZ_ABCR01000001.1: 262172 . . . 263161 | 946 | ZP_01901193.1 | 1307 | *Roseobacter* sp. AzwK-3b |
| 126736835 | complement (NZ_AAYC01000001.1: 23010 . . . 24029) | 947 | ZP_01752570.1 | 1308 | *Roseobacter* sp. SK209-2-6 |
| 163732628 | complement (NZ_ABIG01000003.1: 152433 . . . 153374) | 948 | ZP_02140073.1 | 1309 | *Roseobacter litoralis* Och 149 |
| 89055338 | NC_007802.1: 2864232 . . . 2865239 | 949 | YP_510789.1 | 1310 | *Jannaschia* sp. CCS1 |
| 254459737 | NZ_DS995276.1: 713420 . . . 714472 | 950 | ZP_05073153.1 | 1311 | *Rhodobacterales bacterium* HTCC2083 |
| 116620211 | NC_008536.1: 1336713 . . . 1337708 | 951 | YP_822367.1 | 1312 | *Candidatus Solibacter usitatus* Ellin6076 |
| 95930364 | NZ_AAEW02000012.1: 74280 . . . 75281 | 952 | ZP_01313101.1 | 1313 | *Desulfuromonas acetoxidans* DSM 684 |
| 77920135 | NC_007498.2: 2984046 . . . 2985047 | 953 | YP_357950.1 | 1314 | *Pelobacter carbinolicus* DSM 2380 |
| 222054722 | complement (NC_011979.1: 1793784 . . . 1794785) | 954 | YP_002537084.1 | 1315 | *Geobacter* sp. FRC-32 |
| 148265418 | NC_009483.1: 3992460 . . . 2993461 | 955 | YP_001232124.1 | 1316 | *Geobacter uraniireducens* Rf4 |
| 39997800 | NC_002939.4: 2984470 . . . 2985471 | 956 | NP_953751.1 | 1317 | *Geobacter sulfurreducens* PCA |
| 78222253 | complement (NC_007517.1: 1150703 . . . 1151704) | 957 | YP_384000.1 | 1318 | *Geobacter metallireducens* GS-15 |
| 118579718 | complement (NC_008609.1: 1359173 . . . 1360177) | 958 | YP_900968.1 | 1319 | *Pelobacter propionicus* DSM 2379 |
| 189424275 | complement (NC_010814.1: 1256052 . . . 1257053) | 959 | YP_001951452.1 | 1320 | *Geobacter lovleyi* SZ |
| 255059775 | NZ_ACPJ01000030.1: 50425 . . . 51426 | 960 | ZP_05311922.1 | 1321 | *Geobacter* sp. M18 |
| 253700569 | complement (NC_012918.1: 2257017 . . . 2258018) | 961 | YP_003021758.1 | 1322 | *Geobacter* sp. M21 |
| 77920440 | complement (NC_007498.2: 3332135 . . . 3333136) | 962 | YP_358255.1 | 1323 | *Pelobacter carbinolicus* DSM 2380 |
| 227423754 | NZ_ABTN01000011.1: 41883 . . . 42872 | 963 | ZP_03906856.1 | 1324 | *Denitrovibrio acetiphilus* DSM 12809 |
| 193215894 | NC_011026.1: 2629909 . . . 2630916 | 964 | YP_001997093.1 | 1325 | *Chloroherpeton thalassium* ATCC 35110 |
| 150386298 | complement (NZ_ABDE01000122.1: 6609 . . . 7619) | 965 | ZP_01924858.1 | 1326 | *Victivallis vadensis* ATCC BAA-548 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 217034411 | NZ_ABSX01000018.1: 29972 ... 31570 | 966 | ZP_03439825.1 | 1327 | *Helicobacter pylori* 98-10 |
| 254779508 | complement (NC_012973.1: 876982 ... 878538) | 967 | YP_003057614.1 | 1328 | *Helicobacter pylori* B38 |
| 188527730 | complement (NC_010698.2: 936737 ... 938293) | 968 | YP_001910417.1 | 1329 | *Helicobacter pylori* Shi470 |
| 15611908 | complement (NC_000921.1: 920263 ... 921822) | 969 | NP_223559.1 | 1330 | *Helicobacter pylori* J99 |
| 109947805 | complement (NC_008229.1: 1105678 ... 1107201) | 970 | YP_665033.1 | 1331 | *Helicobacter acinonychis* str. Sheeba |
| 148926656 | NZ_AASY01000008.1: 52243 ... 53778 | 971 | ZP_01810337.1 | 1332 | *Campylobacter jejuni* subsp. *jejuni* CG8486 |
| 57167700 | complement (NZ_AAFL01000001.1: 232544 ... 234046) | 972 | ZP_00366840.1 | 1333 | *Campylobacter coli* RM2228 |
| 57242590 | complement (NZ_AAFJ01000004.1: 6136 ... 7638) | 973 | ZP_00370527.1 | 1334 | *Campylobacter upsaliensis* RM3195 |
| 222823645 | NC_012039.1: 612447 ... 613916 | 974 | YP_002575219.1 | 1335 | *Campylobacter lari* RM2100 |
| 154148075 | complement (NC_009714.1: 1098161 ... 1099597) | 975 | YP_001406718.1 | 1336 | *Campylobacter hominis* ATCC BAA-381 |
| 257459711 | NZ_ACYG01000019.1: 245785 ... 247383 | 976 | ZP_05624820.1 | 1337 | *Campylobacter gracilis* RM3268 |
| 118475502 | complement (NC_008599.1: 824533 ... 825927) | 977 | YP_891988.1 | 1338 | *Campylobacter fetus* subsp. *fetus* 82-40 |
| 157164211 | NC_009802.1: 1056736 ... 1058103 | 978 | YP_001466901.1 | 1339 | *Campylobacter concisus* 13826 |
| 154173700 | complement (NC_009715.1: 947742 ... 949112) | 979 | YP_001408221.1 | 1340 | *Campylobacter curvus* 525.92 |
| 255322202 | NZ_ACVQ01000017.1: 43696 ... 45081 | 980 | ZP_05363348.1 | 1341 | *Campylobacter showae* RM3277 |
| 225351910 | NZ_ABXX02000003.1: 117844 ... 119514 | 981 | ZP_03742933.1 | 1342 | *Bifidobacterium pseudocatenulatum* DSM 20438 |
| 171743080 | complement (NZ_ABIX02000002.1: 2348529 ... 2350229) | 982 | ZP_02918887.1 | 1343 | *Bifidobacterium dentium* ATCC 27678 |
| 154487476 | complement (NZ_AAX1302000028.1: 209751 ... 211442) | 983 | ZP_02028883.1 | 1344 | *Bifidobacterium adolescentis* L2-32 |
| 229817818 | complement (NZ_ABYS02000004.1: 899528 ... 901234) | 984 | ZP_04448100.1 | 1345 | *Bifidobacterium angulatum* DSM 20098 |
| 223467350 | complement (NZ_ACCG01000014.1: 93417 ... 95159) | 985 | ZP_03618886.1 | 1346 | *Bifidobacterium breve* DSM 20213 |
| 227546035 | NZ_ACHI01000009.1: 13043 ... 14755 | 986 | ZP_03976084.1 | 1347 | *Bifidobacterium longum* subsp. *infantis* ATCC 55813 |
| 213692597 | NC_011593.1: 1898224 ... 1899936 | 987 | YP_002323183.1 | 1348 | *Bifidobacterium longum* subsp. *infantis* ATCC 15697 |
| 224282865 | complement (NZ_ABQP01000009.1: 208984 ... 210654) | 988 | ZP_03646187.1 | 1349 | *Bifidobacterium bifidum* NCIMB 41171 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 227507562 | NZ_ACGF01000124.1: 44384 ... 46048 | 989 | ZP_03937611.1 | 1350 | *Gardnerella vaginalis* ATCC 14019 |
| 183601499 | complement (NZ_ABOT01000001.1: 192971 ... 194653) | 990 | ZP_02962869.1 | 1351 | *Bifidobacterium animalis* subsp. *lactis* HN019 |
| 261337301 | complement (NZ_ABXB03000001.1: 137782 ... 139455) | 991 | ZP_05965185.1 | 1352 | *Bifidobacterium gallicum* DSM 20093 |
| 154507766 | NZ_AAYI02000004.1: 231567 ... 233045 | 992 | ZP_02043408.1 | 1353 | *Actinomyces odontolyticus* ATCC 17982 |
| 227494860 | complement (NZ_ACFG01000030.1: 86700 ... 88295) | 993 | ZP_03925176.1 | 1354 | *Actinomyces coleocanis* DSM 15436 |
| 19553946 | complement (NC_003450.3: 2936506 ... 2937891) | 994 | NP_601948.1 | 1355 | *Corynebacterium glutamicum* ATCC 13032 |
| 25029147 | complement (NC_004369.1: 2758982 ... 2760496) | 995 | NP_739201.1 | 1356 | *Corynebacterium efficiens* YS-314 |
| 38234612 | complement (NC_002935.2: 2103677 ... 2105128) | 996 | NP_940379.1 | 1357 | *Corynebacterium diphtheriae* NCTC 13129 |
| 252124104 | complement (NZ_ACSH01000003.1: 61905 ... 63305) | 997 | ZP_04835255.1 | 1358 | *Corynebacterium matruchotii* ATCC 14266 |
| 227489285 | NZ_ABYP01000094.1: 61648 ... 63048 | 998 | ZP_03919601.1 | 1359 | *Corynebacterium glucuronolyticum* ATCC 51867 |
| 258561950 | NZ_ACLJ01000070.1: 13162 ... 14523 | 999 | ZP_05708623.1 | 1360 | *Corynebacterium genitalium* ATCC 33030 |
| 227547861 | NZ_ACHJ01000017.1: 9541 ... 10899 | 1000 | ZP_03977910.1 | 1361 | *Corynebacterium lipophiloflavum* DSM 44291 |
| 227502015 | NZ_ACGD01000004.1: 82938 ... 84305 | 1001 | ZP_03932064.1 | 1362 | *Corynebacterium accolens* ATCC 49725 |
| 255325798 | NZ_ACVP01000037.1: 5746 ... 7107 | 1002 | ZP_05366890.1 | 1363 | *Corynebacterium tuberculostearicum* SK141 |
| 227505901 | NZ_ACGE01000122.1: 37468 ... 38826 | 1003 | ZP_03935950.1 | 1364 | *Corynebacterium striatum* ATCC 6940 |
| 227834110 | complement (NC_012590.1: 2492850 ... 2494214) | 1004 | YP_002835817.1 | 1365 | *Corynebacterum aurimucosum* ATCC 700975 |
| 68535315 | NC_007164.1: 307337 ... 308848 | 1005 | YP_250020.1 | 1366 | *Corynebacterium jeikeium* K411 |
| 172041418 | complement (NC_010545.1: 2018026 ... 2019369) | 1006 | YP_001801132.1 | 1367 | *Corynebacterium urealyticum* DSM 7109 |
| 237786249 | complement (NC_012704.1: 1975731 ... 1977287) | 1007 | YP_002906954.1 | 1368 | *Corynebacterium kroppenstedtii* DSM 44385 |
| 213965099 | complement (NZ_ABZU01000003.1: 128017 ... 129543) | 1008 | ZP_03393297.1 | 1369 | *Corynebacterium amycolatum* SK46 |
| 225075788 | complement (NZ_ACEN01000020.1: 5387 ... 6889) | 1009 | ZP_03718987.1 | 1370 | *Neisseria flavescens* NRL30031/H210 |
| 255067101 | NZ_ACKO02000012.1: 64851 ... 66353 | 1010 | ZP_05318956.1 | 1371 | *Neisseria sicca* ATCC 29256 |
| 161869564 | complement (NC_010120.1: 603202 ... 604836) | 1011 | YP_001598731.1 | 1372 | *Neisseria meningitidis* 053442 |
| 238022551 | NZ_ACJW02000003.1: 751672 ... 753150 | 1012 | ZP_04602977.1 | 1373 | *Kingella oralis* ATCC 51147 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 83592714 | complement (NC_007643.1: 1625036 . . . 1626802) | 1013 | YP_426466.1 | 1374 | *Rhodospirillum rubrum* ATCC 11170 |
| 32490929 | complement (NC_004344.2: 212680 . . . 214818) | 1014 | NP_871183.1 | 1375 | *Wigglesworthia glossinidia* endosymbiont of *Glossina brevipalpis* |
| 27904667 | NC_004545.1: 186377 . . . 188524 | 1015 | NP_777793.1 | 1376 | *Buchnera aphidicola* str. Bp (*Baizongia pistaciae*) |
| 261415723 | complement (NC_013410.1: 1639393 . . . 1640796) | 1016 | YP_003249406.1 | 1377 | *Fibrobacter succinogenes* subsp. *succinogenes* S85 |
| 219556226 | NZ_ABQH01000061.1: <3 . . . 1196 | 1017 | ZP_03535302.1 | 1378 | *Mycobacterium tuberculosis* T17 |
| 228471665 | complement (NZ_ACLQ01000003.1: 154599 . . . 155657) | 1018 | ZP_04056438.1 | 1379 | *Capnocytophaga gingivalis* ATCC 33624 |
| 256370675 | NC_013123.1: 116952 . . . 117950 | 1019 | YP_003108500.1 | 1380 | *Candidatus Sulcia muelleri* SMDSEM |
| 6685772 | X89084.1: 1009 . . . 199 | 1020 | P77844 | 1381 | *Corynebacterium glutamicum* |
| 227876041 | NZ_ACKW01000045.1: 33898 . . . 34887 | 1021 | ZP_03994160.1 | 1382 | *Mobiluncus mulieris* ATCC 35243 |
| 227492324 | NZ_ACCQ01000004.1: 214416 . . . 215417 | 1022 | ZP_03922640.1 | 1383 | *Mobiluncus curtisii* ATCC 43063 |
| 225027017 | NZ_ACEP01000064.1: 10650 . . . 11609 | 1023 | ZP_03716209.1 | 1384 | *Eubacterium halli* DSM 3353 |
| 225028951 | complement (NZ_ACEP01000172.1: 22364 . . . 23416) | 1024 | ZP_03718143.1 | 1385 | *Eubacterium hallii* DSM 3353 |
| 257438679 | complement (NZ_ACOP02000029.1: 99 . . . 1124) | 1025 | ZP_05614434.1 | 1386 | *Faecalibacterium prausnitzii* A2-165 |
| 154496156 | complement (NZ_AAXG02000004.1: 103391 . . . 104380) | 1026 | ZP_02034852.1 | 1387 | *Bacteroides capillosus* ATCC 29799 |
| 225376322 | NZ_ACFY01000086.1: 6940 . . . 7992 | 1027 | ZP_03753543.1 | 1388 | *Roseburia inulinivorans* DSM 16841 |
| 257414121 | complement (NZ_ABYJ02000202.1: 41125 . . . 42165) | 1028 | ZP_04745275.2 | 1389 | *Roseburia intestinalis* L1-82 |
| 238923816 | NC_012781.1: 1324280 . . . 1325263 | 1029 | YP_002937332.1 | 1390 | *Eubacterium rectale* ATCC 33656 |
| 160893459 | NZ_AAYW02000007.1: 63870 . . . 64919 | 1030 | ZP_02074244.1 | 1391 | *Clostridium* sp. L2-50 |
| 229829305 | complement (NZ_ACIP02000002.1: 495313 . . . 496299) | 1031 | ZP_04455374.1 | 1392 | *Shuttleworthia satelles* DSM 14600 |
| 218282181 | complement (NZ_ABYT01000061.1: 45 . . . 1016) | 1032 | ZP_03488480.1 | 1393 | *Eubacterium biforme* DSM 3989 |
| 160916120 | complement (NZ_ABAW02000025.1: 71684 . . . 72694) | 1033 | ZP_02078327.1 | 1394 | *Eubacterium dolichum* DSM 3991 |
| 160915347 | NZ_ABAW02000020.1: 14646 . . . 15638 | 1034 | ZP_02077559.1 | 1395 | *Eubacterium dolichum* DSM 3991 |
| 212697404 | NZ_ABXA01000047.1: 41715 . . . 42701 | 1035 | ZP_03305532.1 | 1396 | *Anaerococcus hydrogenalis* DSM 7454 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 256545936 | complement (NZ_ACXU01000022.1: 22101 . . . 23087) | 1036 | ZP_05473291.1 | 1397 | *Anaerococcus vaginalis* ATCC 51170 |
| 227501001 | NZ_ACGC01000115.1: 23122 . . . 24108 | 1037 | ZP_03931050.1 | 1398 | *Anaerococcus tetradius* ATCC 35098 |
| 257067207 | complement (NC_013171.1: 1868769 . . . 1869752) | 1038 | YP_003153463.1 | 1399 | *Anaerococcus prevotii* DSM 20548 |
| 227485732 | complement (NZ_ABYO01000196.1: 43814 . . . 44833) | 1039 | ZP_03916048.1 | 1400 | *Anaerococcus lactolyticus* ATCC 51172 |
| 19746077 | NC_003485.1: 903788 . . . 904783 | 1040 | NP_607213.1 | 1401 | *Streptococcus pyogenes* MGAS8232 |
| 13622266 | AE004092.1: 923921 . . . 924916 | 1041 | AAK34003.1 | 1402 | *Streptococcus pyogenes* M1 GAS |
| 222153008 | NC_012004.1: 834034 . . . 835026 | 1042 | YP_002562185.1 | 1403 | *Streptococcus uberis* 0140J |
| 225868503 | NC_012470.1: 1034662 . . . 1035663 | 1043 | YP_002744451.1 | 1404 | *Streptococcus equi* subsp. *Zooepidemicus* |
| 254997415 | AP010655.1: 1031526 . . . 1032521 | 1044 | BAH88016.1 | 1405 | *Streptococcus mutans* NN2025 |
| 171779341 | NZ_ABJK02000020.1: 38474 . . . 39472 | 1045 | ZP_02920305.1 | 1406 | *Streptococcus infantarius* subsp. *infantarius* ATCC BAA-102 |
| 76787123 | complement (NC_007432.1: 1155758 . . . 1156750) | 1046 | YP_329798.1 | 1407 | *Streptococcus agalactiae* A909 |
| 228477151 | complement (NZ_ACLO01000062.1: 54543 . . . 55526) | 1047 | ZP_04061789.1 | 1408 | *Streptococcus salivarius* SK126 |
| 55821439 | complement (NC_006448.1: 1286014 . . . 1286997) | 1048 | YP_139881.1 | 1409 | *Streptococcus thermophilus* LMG 18311 |
| 237650772 | NZ_ABZC01000093.1: 10653 . . . 11627 | 1049 | ZP_04525024.1 | 1410 | *Streptococcus pneumoniae* CCRI 1974 |
| 262282806 | complement (NZ_GG7049411.1: 11119 . . . 12096) | 1050 | ZP_06060573.1 | 1411 | *Streptococcus* sp. 2_1_36FAA |
| 146318711 | complement (NC_009442.1: 1032399 . . . 1033379) | 1051 | YP_001198423.1 | 1412 | *Streptococcus suis* 05ZYH33 |
| 42518809 | NC_005362.1: 788505 . . . 789482 | 1052 | NP_964739.1 | 1413 | *Lactobacillus johnsonii* NCC 533 |
| 58337025 | NC_006814.3: 698578 . . . 699567 | 1053 | YP_193610.1 | 1414 | *Lactobacillus acidophilus* NCFM |
| 227893214 | NZ_ACGU01000037.1: 27358 . . . 28347 | 1054 | ZP_04011019.1 | 1415 | *Lactobacillus ultunensis* DSM 16047 |
| 227877224 | NZ_ACKR01000025.1: 14947 . . . 15936 | 1055 | ZP_03995297.1 | 1416 | *Lactobacillus crispatus* JV-V01 |
| 260102516 | NZ_ACLM01000112.1: 6924 . . . 7913 | 1056 | ZP_05752753.1 | 1417 | *Lactobacillus helveticus* DSM 20075 |
| 227525975 | NZ_ACGQ01000041.1: 59881 . . . 60858 | 1057 | ZP_03956024.1 | 1418 | *Lactobacillus jensenii* JV-V16 |
| 228854857 | complement (NZ_ACOY01000013.1: 251390 . . . 252367) | 1058 | ZP_04645187.1 | 1419 | *Lactobacillus jensenii* 269-3 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 104773739 | NC_008054.1: 547017 . . . 548006 | 1059 | YP_618719.1 | 1420 | *Lactobacillus delbrueckii* subsp. *bulgaricus* ATCC 11842 |
| 259501464 | NZ_ACLN01000013.1: 15438 . . . 16418 | 1060 | ZP_05744366.1 | 1421 | *Lactobacillus iners* DSM 13335 |
| 16080818 | complement (NC_000964.3: 3865355 . . . 3866326) | 1061 | NP_391646.1 | 1422 | *Bacillus subtilis* subsp. *subtilis* str. 168 |
| 154687884 | complement (NC_009725.1: 3590964 . . . 3591935) | 1062 | YP_001423045.1 | 1423 | *Bacillus amyloliquefaciens* FZB42 |
| 52082282 | complement (NC_006270.3: 3821313 . . . 3822284) | 1063 | YP_081073.1 | 1424 | *Bacillus licheniformis* ATCC 14580 |
| 194016487 | complement (NZ.ABRX01000004.1: 144981 . . . 145952) | 1064 | ZP_03055101.1 | 1425 | *Bacillus pumilus* ATCC 7061 |
| 212640578 | complement (NC_011567.1: 2748264 . . . 2749247) | 1065 | YP_002317098.1 | 1426 | *Anoxybacillus flavithermus* WK1 |
| 239828646 | complement (NC_012793.1: 3393094 . . . 3394068) | 1066 | YP_002951270.1 | 1427 | *Geobacillus* sp. WCH70 |
| 138896990 | complement (NC_009328.1: 3468960 . . . 3469934) | 1067 | YP_001127443.1 | 1428 | *Geobacillus thermodenitrificans* NG80-2 |
| 56421950 | complement (NC_006510.1: 3456185 . . . 3457165) | 1068 | YP_149268.1 | 1429 | *Geobacillus kaustophilus* HTA426 |
| 149182788 | NZ_ABCF01000043.1: 11583 . . . 12554 | 1069 | ZP_01861251.1 | 1430 | *Bacillus* sp. SG-1 |
| 205375387 | NZ_ABFU01000065.2: 12128 . . . 13099 | 1070 | ZP_03228176.1 | 1431 | *Bacillus coahuilensis* m4-4 |
| 89101108 | complement (NZ_AAOX01000058.1: 10738 . . . 11715) | 1071 | ZP_01173945.1 | 1432 | *Bacillus* sp. NRRL B-14911 |
| 23100477 | complement (NC_004193.1: 3134492 . . . 3135466) | 1072 | NP_693944.1 | 1433 | *Oceanobacillus iheyensis* HTE831 |
| 229187615 | complement (NZ_ACLU01000117.1: 31676 . . . 32647) | 1073 | ZP_04314753.1 | 1434 | *Bacillus cereus* BGSC 6E1 |
| 46908338 | complement (NC_002973.6: 2171357 . . . 2172334) | 1074 | YP_014727.1 | 1435 | *Listeria monocytogenes* str. 4b F2365 |
| 229555968 | NZ_ACCR01000020.1: 18426 . . . 19403 | 1075 | ZP_04443757.1 | 1436 | *Listeria grayi* DSM 20601 |
| 15616385 | complement (NC_002570.2: 3947889 . . . 3948881) | 1076 | NP_244690.1 | 1437 | *Bacillus halodurans* C-125 |
| 56965668 | complement (NC_006582.1: 4069370 . . . 4070365) | 1077 | YP_177402.1 | 1438 | *Bacillus clausii* KSM-K16 |
| 229917170 | complement (NC_012673.1: 1410227 . . . 1411216) | 1078 | YP_002885816.1 | 1439 | *Exiguobacterium* sp. AT1b |
| 172056261 | NC_010556.1: 233988 . . . 234974 | 1079 | YP_001812721.1 | 1440 | *Exiguobacterium sibiricum* 255-15 |
| 163762281 | NZ_ABHZ01000002.1: 94480 . . . 95457 | 1080 | ZP_02169346.1 | 1441 | *Bacillus selenitireducens* MLS10 |
| 242372812 | NZ_ACJB01000048.1: 8122 . . . 9111 | 1081 | ZP_04818386.1 | 1442 | *Staphylococcus epidermidis* M23864: W1 |
| 223042925 | complement (NZ_ACFR01000002.1: 330954 . . . 331943) | 1082 | ZP_03612973.1 | 1443 | *Staphylococcus capitis* SK14 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 239636796 | complement (NZ_ACPZ01000027.:1 569915 . . . 570904) | 1083 | ZP_04677798.1 | 1444 | *Staphylococcus warneri* L37603 |
| 27467277 | NC_004461.1: 356818 . . . 357807 | 1084 | NP_763914.1 | 1445 | *Staphylococcus epidermidis* ATCC 12228 |
| 258422775 | NZ_ACKI01000006.1: 980 . . . 1966 | 1085 | ZP_05685678.1 | 1446 | *Staphylococcus aureus* A9635 |
| 70727403 | complement (NC_007168.1: 2403280 . . . 2404269) | 1086 | YP_254319.1 | 1447 | *Staphylococcus haemolyticus* JCSC1435 |
| 228475091 | NZ_ACLP01000011.1: 16037 . . . 17026 | 1087 | ZP_04059818.1 | 1448 | *Staphylococcus hominis* SK119 |
| 150011041 | EF456699.1: 1 . . . 987 | 1088 | ABR57177.1 | 1449 | *Staphylococcus xylosus* |
| 73663433 | complement (NC_007356.1: 2190871 . . . 2191857) | 1089 | YP_302214.1 | 1450 | *Staphylococcus saprophyticus* subsp. *saprophyticus* ATCC 15305 |
| 224475734 | NC_012121.1: 250258 . . . 251247 | 1090 | YP_002633340.1 | 1451 | *Staphylococcus carnosus* subsp. *carnosus* TM300 |
| 222152076 | complement (NC_011999.1: 1968130 . . . 1969119) | 1091 | YP_002561236.1 | 1452 | *Macrococcus caseolyticus* JCSC5402 |
| 227514417 | NZ_ACGI01000058.1: 71225 . . . 72199 | 1092 | ZP_03944466.1 | 1453 | *Lactobacillus fermentum* ATCC 14931 |
| 256848058 | complement (NZ_GG698804.1: 125094 . . . 126059) | 1093 | ZP_05553502.1 | 1454 | *Lactobacillus coleohominis* 101-4-CHN |
| 227529580 | NZ_ACGV01000117.1: 1634 . . . 2608 | 1094 | ZP_03959629.1 | 1455 | *Lactobacillus vaginalis* ATCC 49540 |
| 148543634 | NC_009513.1: 451991 . . . 452965 | 1095 | YP_001271004.1 | 1456 | *Lactobacillus reuteri* DSM 20016 |
| 259502766 | NZ_ACLL01000024.1: 18101 . . . 19072 | 1096 | ZP_05745668.1 | 1457 | *Lactobacillus antri* DSM 16041 |
| 116618560 | complement (NC_008531.1: 1461235 . . . 1462215) | 1097 | YP_818931.1 | 1458 | *Leuconostoc mesenteroides* subsp. *mesenteroides* ATCC 8293 |
| 170016912 | NC_010471.1: 577967 . . . 578959 | 1098 | YP_001727831.1 | 1459 | *Leuconostoc citreum* KM20 |
| 241894748 | complement (NZ_ACKU01000002.1: 15496 . . . 16476) | 1099 | ZP_04782044.1 | 1460 | *Weissella paramesenteroides* ATCC 33313 |
| 118587037 | NZ_AAUV01000054.1: 44038 . . . 45132 | 1100 | ZP_01544468.1 | 1461 | *Oenococcus oeni* ATCC BAA-1163 |
| 259046893 | complement (NZ_ACKZ01000012.:1 86436 . . . 87425) | 1101 | ZP_05737294.1 | 1462 | *Granulicatella adiacens* ATCC 49175 |
| 260584167 | complement (NZ_GG703805.1: 786281 . . . 787264) | 1102 | ZP_05851915.1 | 1463 | *Granulicatella elegans* ATCC 700633 |
| 163789527 | complement (NZ_ABHH01000002.1: 8081 . . . 9061) | 1103 | ZP_02183965.1 | 1464 | *Carnobacterium* sp. AT7 |
| 257870102 | NZ_GG670288.1: 145742 . . . 146725 | 1104 | ZP_05649755.1 | 1465 | *Enterococcus gallinarum* EG2 |
| 227517869 | NZ_ACGL01000051.1: 2376 . . . 3401 | 1105 | ZP_03947918.1 | 1466 | *Enterococcus faecalis* TX0104 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 227552175 | complement (NZ.ACHL01000118.1: 1216 . . . 2232) | 1106 | ZP_03982224.1 | 1467 | *Enterococcus faecium* TX1330 |
| 81428954 | complement (NC_007576.1: 1313600 . . . 1314586) | 1107 | YP_395954.1 | 1468 | *Lactobacillus sakei* subsp. *sakei* 23K |
| 229823693 | NZ_ACIL02000007.1: 6499 . . . 7482 | 1108 | ZP_04449762.1 | 1469 | *Catonella morbi* ATCC 51271 |
| 125623617 | NC_009004.1: 752099 . . . 753079 | 1109 | YP_001032100.1 | 1470 | *Lactococcus lactis* subsp. *cremoris* MG1363 |
| 116494500 | NC_008526.1: 981403 . . . 982380 | 1110 | YP_806234.1 | 1471 | *Lactobacillus casei* ATCC 334 |
| 28377658 | NC_004567.1: 748192 . . . 749169 | 1111 | NP_784550.1 | 1472 | *Lactobacillus plantarum* WCFS1 |
| 116333321 | NC_008497.1: 702374 . . . 703348 | 1112 | YP_794848.1 | 1473 | *Lactobacillus brevis* ATCC 367 |
| 227524782 | complement (NZ_ACGP01000192.1: 2135 . . . 3112) | 1113 | ZP_03954831.1 | 1474 | *Lactobacillus hilgardii* ATCC 8290 |
| 11862872 | AB035800.1: 1006 . . . 1992 | 1114 | BAB19267.1 | 1475 | *Lactobacillus sanfranciscensis* |
| 227528239 | NZ_ACGS01000093.1: 64718 . . . 65695 | 1115 | ZP_03958288.1 | 1476 | *Lactobacillus ruminis* ATCC 25644 |
| 90962126 | complement (NC_007929.1: 1183945 . . . 1184922) | 1116 | YP_536042.1 | 1477 | *Lactobacillus salivarius* UCC118 |
| 259504733 | NZ_ACLK01000016.1: 55937 . . . 56917 | 1117 | ZP_05747635.1 | 1478 | *Erysipelothrix rhusiopathiae* ATCC 19414 |
| 116492140 | NC_008525.1: 385259 . . . 386230 | 1118 | YP_803875.1 | 1479 | *Pediococcus pentosaceus* ATCC 25745 |
| 160946581 | NZ_ABEE02000016.1: 72101 . . . 73072 | 1119 | ZP_02093784.1 | 1480 | *Parvimonas micra* ATCC 33270 |
| 169825312 | complement (NC_010376.1: 1782855 . . . 1783826) | 1120 | YP_001692923.1 | 1481 | *Finegoldia magna* ATCC 29328 |
| 229542439 | NZ_AAWV02000001.1: 1452854 . . . 1453825 | 1121 | ZP_04431499.1 | 1482 | *Bacillus coagulans* 36D1 |
| 241888505 | NZ_ACDZ02000004.1: 11622 . . . 12602 | 1122 | ZP_04775813.1 | 1483 | *Gemella haemolysans* ATCC 10379 |

In addition, 201 phosphate acetyltransferase sequences that are characterized by two domains (DRTGG and PTA_PTB) are provided in Table 12b. MSA and phylogenetic analysis were performed as described above. Percent identity with respect to experimentally verified (or human curated) sequences is equal to or larger than 40, except for 4 sequences derived from plant organisms. Furthermore, hmmer search of the 201 sequences against the profile HMM of subfamily 2 (Table 14), clearly indicates that all Group 2 sequences belong to the PTA subfamily (least significant Evalue is 4.1e-93).

TABLE 12b

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 152964825 | complement (NC_009664.2: 1430885 . . . 1432984) | 1484 | YP_001360609.1 | 1685 | *Kineococcus radiotolerans* SRS30216 |
| 88800302 | complement (NZ_AAOE01000024.1: 59450 . . . 61609) | 1485 | ZP_01115869.1 | 1686 | *Reinekea blandensis* MED297 |
| 254786809 | complement (NC_012997.1: 3139764 . . . 3141917) | 1486 | YP_003074238.1 | 1687 | *Teredinibacter turnerae* T7901 |
| 120554060 | complement (NC_008740.1: 1283732 . . . 1285885) | 1487 | YP_958411.1 | 1688 | *Marinobacter aquaeolei* VT8 |
| 83647145 | NC_007645.1: 4579211 . . . 4581358 | 1488 | YP_435580.1 | 1689 | *Hahella chejuensis* KCTC 2396 |
| 146308660 | NC_009439.1: 4021959 . . . 4024052 | 1489 | YP_001189125.1 | 1690 | *Pseudomonas mendocina* ymp |
| 116048757 | NC_008463.1: 4740071 . . . 4742185 | 1490 | YP_792443.1 | 1691 | *Pseudomonas aeruginosa* UCBPP-PA14 |
| 28868382 | complement (NC_004578.1: 1283902 . . . 1285992) | 1491 | NP_791001.1 | 1692 | *Pseudomonas syringae* pv. tomato str. DC3000 |
| 70728320 | complement (NC_004129.6: 1081214 . . . 1083313) | 1492 | YP_258069.1 | 1693 | *Pseudomonas fluorescens* Pf-5 |
| 104780139 | complement (NC_008027.1: 952666 . . . 954756) | 1493 | YP_606637.1 | 1694 | *Pseudomonas entomophila* L48 |
| 226945506 | complement (NC_012560.1: 3530138 . . . 3532276) | 1494 | YP_002800579.1 | 1695 | *Azotobacter vinelandii* DJ |
| 146281510 | complement (NC_009434.1: 1238536 . . . 1240632) | 1495 | YP_001171663.1 | 1696 | *Pseudomonas stutzeri* A1501 |
| 30248315 | complement (NC_004757.1: 326321 . . . 328408) | 1496 | NP_840385.1 | 1697 | *Nitrosomonas europaea* ATCC 19718 |
| 226946148 | NC_012560.1: 4145609 . . . 4147684 | 1497 | YP_002801221.1 | 1698 | *Azotobacter vinelandii* DJ |
| 226357371 | NC_012526.1: 2779899 . . . 2782016 | 1498 | YP_002787111.1 | 1699 | *Deinococcus deserti* VCD115 |
| 94984159 | complement (NC_008025.1: 46701 . . . 48812) | 1499 | YP_603523.1 | 1700 | *Deinococcus geothermalis* DSM 11300 |
| 15805114 | complement (NC_001263.1: 69707 . . . 71875) | 1500 | NP_293799.1 | 1701 | *Deinococcus radiodurans* R1 |
| 89899079 | complement (NC_007908.1: 264127 . . . 266178) | 1501 | YP_521550.1 | 1702 | *Rhodoferax ferrireducens* T118 |
| 90422592 | NC_007925.1: 1181422 . . . 1183572 | 1502 | YP_530962.1 | 1703 | *Rhodopseudomonas palustris* BisB18 |
| 90423512 | NC_007925.1: 2183340 . . . 2185475 | 1503 | YP_531882.1 | 1704 | *Rhodopseudomonas palustris* BisB18 |
| 115525859 | NC_008435.1: 4320999 . . . 4323140 | 1504 | YP_782770.1 | 1705 | *Rhodopseudomonas palustris* BisA53 |
| 167574473 | complement (NZ_ABBG01000507.1: 7891 . . . 9969) | 1505 | ZP_02367347.1 | 1706 | *Burkholderia oklahomensis* C6786 |
| 83594327 | complement (NC_007643.1: 3449832 . . . 3451943) | 1506 | YP_428079.1 | 1707 | *Rhodospirillum rubrum* ATCC 11170 |
| 90422165 | NC_007925.1: 696325 . . . 698388 | 1507 | YP_530535.1 | 1708 | *Rhodopseudomonas palustris* BisB18 |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 34496985 | complement (NC_005085.1: 1636285 ... 1638366) | 1508 | NP_901200.1 | 1709 | *Chromobacterium violaceum* ATCC 12472 |
| 224825239 | complement (NZ_ACIS01000004.1: 398128 ... 400215) | 1509 | ZP_03698345.1 | 1710 | *Lutiella nitroferrum* 2002 |
| 148652157 | complement (NC_009524.1: 415573 ... 417720) | 1510 | YP_001279250.1 | 1711 | *Psychrobacter* sp. PRwf-1 |
| 93005047 | complement (NC_007969.1: 257926 ... 260082) | 1511 | YP_579484.1 | 1712 | *Psychrobacter cryohalolentis* K5 |
| 257453691 | NZ_ACYI01000010.1: 16653 ... 18797 | 1512 | ZP_05618978.1 | 1713 | *Enhydrobacter aerosaccus* SK60 |
| 255321153 | NZ_ACVR01000080.1: 44385 ... 46529 | 1513 | ZP_05362319.1 | 1714 | *Acinetobacter radioresistens* SK82 |
| 50083778 | complement (NC_005966.1: 527524 ... 529686) | 1514 | YP_045288.1 | 1715 | *Acinetobacter* sp. ADP1 |
| 260549093 | NZ_GG704496.1: 86045 ... 88189 | 1515 | ZP_05823314.1 | 1716 | *Acinetobacter* sp. RUH2624 |
| 226953952 | complement (NZ_ABYN01000201.1: 23157 ... 25289) | 1516 | ZP_03824416.1 | 1717 | *Acinetobacter* sp. ATCC 27244 |
| 153005955 | NC_009675.1: 3624676 ... 3626811 | 1517 | YP_001380280.1 | 1718 | *Anaeromyxobacter* sp. Fw109-5 |
| 86159318 | complement (NC_007760.1: 3267950 ... 3270094) | 1518 | YP_466103.1 | 1719 | *Anaeromyxobacter dehalogenans* 2CP-C |
| 52425053 | complement (NC_006300.1: 977458 ... 979596) | 1519 | YP_088190.1 | 1720 | *Mannheimia succiniciproducens* MBEL55E |
| 152979320 | NC_009655.1: 1823344 ... 1825485 | 1520 | YP_001344949.1 | 1721 | *Actinobacillus succinogenes* 130Z |
| 251792685 | NC_012913.1: 968721 ... 970856 | 1521 | YP_003007411.1 | 1722 | *Aggregatibacter aphrophilus* NJ8700 |
| 145633066 | NZ_AAZF01000004.1: 73469 ... 75604 | 1522 | ZP_01788798.1 | 1723 | *Haemophilus influenzae* 3655 |
| 113460945 | complement (NC_008309.1: 873911 ... 876049) | 1523 | YP_719012.1 | 1724 | *Haemophilus somnus* 129PT |
| 15602570 | NC_002663.1: 821181 ... 823319 | 1524 | NP_245642.1 | 1725 | *Pasteurella multocida* subsp. *multocida* str. Pm70 |
| 260913970 | complement (NZ_ACZR01000013.1: 172766 ... 174904) | 1525 | ZP_05920444.1 | 1726 | *Pasteurella dagmatis* ATCC 43325 |
| 53729159 | complement (NZ_AACK01000004.1: 12180 ... 14318) | 1526 | ZP_00133992.2 | 1727 | *Actinobacillus pleuropneumoniae* serovar 1 str. 4074 |
| 240949203 | NZ_ACQL01000097.1: 15931 ... 18069 | 1527 | ZP_04753547.1 | 1728 | *Actinobacillus minor* NM305 |
| 33152520 | NC_002940.2: 1192390 ... 1194528 | 1528 | NP_873873.1 | 1729 | *Haemophilus ducreyi* 35000HP |
| 254362832 | NZ_DS264681.1: 4949 ... 7084 | 1529 | ZP_04978908.1 | 1730 | *Mannheimia haemolytica* PHL213 |
| 219870647 | NC_011852.1: 435431 ... 437566 | 1530 | YP_002475022.1 | 1731 | *Haemophilus parasuis* SH0165 |
| 258637834 | NZ_ACYJ01000022.1: 41620 ... 43764 | 1531 | ZP_05730581.1 | 1732 | *Pantoea* sp. At-9b |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 188533336 | complement (NC_010694.1: 1324250 . . . 1326379) | 1532 | YP_001907133.1 | 1733 | *Erwinia tasmaniensis* Et1/99 |
| 85059585 | NC_007712.1: 2759501 . . . 2761645 | 1533 | YP_455287.1 | 1734 | *Sodalis glossinidius* str. 'morsitans' |
| 258631105 | complement (NZ_ACYK01000004.1: 104546 . . . 106687) | 1534 | ZP_05723922.1 | 1735 | *Dickeya dadantii* Ech586 |
| 261820783 | complement (NC_013421.1: 1606509 . . . 1608647) | 1535 | YP_003258889.1 | 1736 | *Pectobacterium wasabiae* WPP163 |
| 242239978 | NC_012880.1: 3004583 . . . 3006724 | 1536 | YP_002988159.1 | 1737 | *Dickeya dadantii* Ech703 |
| 22125515 | complement (NC_004088.1: 1788905 . . . 1791058) | 1537 | NP_668938.1 | 1738 | *Yersinia pestis* KIM 10 |
| 157371554 | NC_009832.1: 3673293 . . . 3675482 | 1538 | YP_001479543.1 | 1739 | *Serratia proteamaculans* 568 |
| 238920583 | NC_012779.1: 2589897 . . . 2592035 | 1539 | YP_002934098.1 | 1740 | *Edwardsiella ictaluri* 93-146 |
| 197285630 | NC_010554.1: 1898593 . . . 1900737 | 1540 | YP_002151502.1 | 1741 | *Proteus mirabilis* HI4320 |
| 37526984 | NC_005126.1: 3612456 . . . 3614597 | 1541 | NP_930328.1 | 1742 | *Photorhabdus luminescens* subsp. *laumondii* TTO1 |
| 238895817 | NC_012731.1: 3763302 . . . 3765449 | 1542 | YP_002920553.1 | 1743 | *Klebsiella pneumoniae* NTUH-K2044 |
| 146312483 | NC_009436.1: 3080629 . . . 3082770 | 1543 | YP_001177557.1 | 1744 | *Enterobacter* sp. 638 |
| 260598715 | NC_013282.1: 3057676 . . . 3059814 | 1544 | YP_003211286.1 | 1745 | *Cronobacter turicensis* |
| 601935 | D21123.1: 77 . . . 2218 | 1545 | BAA04663.1 | 1746 | *Escherichia coli* |
| 238898722 | complement (NC_012751.1: 1494526 . . . 1496655) | 1546 | YP_002924403.1 | 1747 | *Candidatus Hamiltonella defensa* 5AT (*Acyrthosiphon pisum*) |
| 227114079 | NZ_ABVX01000029.1: 23117 . . . 25261 | 1547 | ZP_03827735.1 | 1748 | *Pectobacterium carotovorum* subsp. *brasiliensis* PBR1692 |
| 89072717 | complement (NZ_AAOU01000004.1: 98074 . . . 100221) | 1548 | ZP_01159282.1 | 1749 | *Photobacterium* sp. SKA34 |
| 54309953 | NC_006370.1: 3245262 . . . 3247418 | 1549 | YP_130973.1 | 1750 | *Photobacterium profundum* SS9 |
| 262274670 | NZ_ADAQ01000011.1: 496361 . . . 498520 | 1550 | ZP_06052481.1 | 1751 | *Grimontia hollisae* CIP 101886 |
| 260768101 | complement (NZ_ACZP01000013.1: 239301 . . . 241427) | 1551 | ZP_05877035.1 | 1752 | *Vibrio furnissii* CIP 102972 |
| 260773044 | николNZ_ACZO01000006.1: 1066216 . . . 1068360 | 1552 | ZP_05881960.1 | 1753 | *Vibrio metschnikovii* CIP 69.14 |
| 163802859 | complement (NZ_ABGR01000013.1: 61871 . . . 64036) | 1553 | ZP_02196748.1 | 1754 | *Vibrio* sp. AND4 |
| 37680318 | NC_005139.1: 2144915 . . . 2147059 | 1554 | NP_934927.1 | 1755 | *Vibrio vulnificus* YJ016 |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 149188151 | complement (NZ_ABCH01000004.1: 163878 . . . 166022) | 1555 | ZP_01866446.1 | 1756 | *Vibrio shilonii* AK1 |
| 218708991 | complement (NC_011753.1: 1031606 . . . 1033810) | 1556 | YP_002416612.1 | 1757 | *Vibrio splendidus* LGP32 |
| 209695557 | NC_011312.1: 2262635 . . . 2264806 | 1557 | YP_002263486.1 | 1758 | *Aliivibrio salmonicida* LFI1238 |
| 229525709 | complement (NZ_ACHV01000001.1: 2574339 . . . 2576483) | 1558 | ZP_04415114.1 | 1759 | *Vibrio cholerae* bv. *albensis* VL426 |
| 145300284 | NC_009348.1: 3681431 . . . 3683584 | 1559 | YP_001143125.1 | 1760 | *Aeromonas salmonicida* subsp. *salmonicida* A449 |
| 237807651 | complement (NC_012691.1: 958413 . . . 960569) | 1560 | YP_002892091.1 | 1761 | *Tolumonas auensis* DSM 9187 |
| 90407162 | complement (NZ_AAPG01000006.1: 41954 . . . 44116) | 1561 | ZP_01215350.1 | 1762 | *Psychromonas* sp. CNPT3 |
| 119946918 | NC_008709.1: 4084304 . . . 4086466 | 1562 | YP_944598.1 | 1763 | *Psychromonas ingrahamii* 37 |
| 157374843 | complement (NC_009831.1: 2041698 . . . 2043839) | 1563 | YP_001473443.1 | 1764 | *Shewanella sediminis* HAW-EB3 |
| 170727231 | NC_010506.1: 3531467 . . . 3533608 | 1564 | YP_001761257.1 | 1765 | *Shewanella woodyi* ATCC 51908 |
| 127513322 | NC_009092.1: 2807561 . . . 2809699 | 1565 | YP_001094519.1 | 1766 | *Shewanella loihica* PV-4 |
| 167624517 | NC_010334.1: 3149368 . . . 3151515 | 1566 | YP_001674811.1 | 1767 | *Shewanella halifaxensis* HAW-EB4 |
| 117919999 | complement (NC_008577.1: 1806421 . . . 180857 | 1567 | YP_869191.1 | 1768 | *Shewanella* sp. ANA-3 |
| 119774631 | complement (NC_008700.1: 1807689 . . . 1809827) | 1568 | YP_927371.1 | 1769 | *Shewanella amazonensis* SB2B |
| 114563647 | NC_008345.1: 2956515 . . . 2958662 | 1569 | YP_751160.1 | 1770 | *Shewanella frigidimarina* NCIMB 400 |
| 91793762 | NC_007954.1: 2868611 . . . 2870791 | 1570 | YP_563413.1 | 1771 | *Shewanella denitrificans* OS217 |
| 157376672 | NC_009831.1: 4313346 . . . 4315484 | 1571 | YP_001475272.1 | 1772 | *Shewanella sediminis* HAW-EB3 |
| 167624655 | complement (NC_010334.1: 3320048 . . . 3322198) | 1572 | YP_001674949.1 | 1773 | *Shewanella halifaxensis* HAW-EB4 |
| 239996136 | complement (NZ_ABQB01000564.1: 6079 . . . 8301) | 1573 | ZP_04716660.1 | 1774 | *Alteromonas macleodii* ATCC 27126 |
| 109898905 | NC_008228.1: 3144369 . . . 3146513 | 1574 | YP_662160.1 | 1775 | *Pseudoalteromonas atlantica* T6c |
| 119469286 | NZ_AAVS01000006.1: 30053 . . . 32206 | 1575 | ZP_01612225.1 | 1776 | *Alteromonadales bacterium* TW-7 |
| 88860001 | complement (NZ_AAOH01000005.1: 230650 . . . 232797) | 1576 | ZP_01134640.1 | 1777 | *Pseudoalteromonas tunicata* D2 |
| 71282469 | NC_003910.7: 3309465 . . . 3311585 | 1577 | YP_269873.1 | 1778 | *Colwellia psychrerythraea* 34H |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 152996332 | NC_009654.1: 2608121 . . . 2610220 | 1578 | YP_001341167.1 | 1779 | *Marinomonas* sp. MWYL1 |
| 87121463 | NZ_AANE01000011.1: 112021 . . . 114096 | 1579 | ZP_01077352.1 | 1780 | *Marinomonas* sp. MED121 |
| 146328905 | NC_009446.1: 489780 . . . 491837 | 1580 | YP_001209362.1 | 1781 | *Dichelobacter nodosus* VCS1703A |
| 258544959 | NZ_ACKY01000059.1: 4448 . . . 6562 | 1581 | ZP_05705193.1 | 1782 | *Cardiobacterium hominis* ATCC 15826 |
| 262104765 | complement (DS028152.1: 677306 . . . 679621) | 1582 | EEY62817.1 | 1783 | *Phytophthora infestans* T30-4 |
| 262104764 | complement (DS028152.1: 674496 . . . 676781) | 1583 | EEY62816.1 | 1784 | *Phytophthora infestans* T30-4 |
| 159472743 | XM_001694452.1: 258 . . . 2636 | 1584 | XP_001694504.1 | 1785 | *Chlamydomonas reinhardtii* |
| 168000833 | XM_001753068.1: 1 . . . 2367 | 1585 | XP_001753120.1 | 1786 | *Physcomitrella patens* subsp. *Patens* |
| 172038009 | complement (NC_010546.1: 3214848 . . . 3216944) | 1586 | YP_001804510.1 | 1787 | *Cyanothece* sp. ATCC 51142 |
| 126658068 | NZ_AAXW01000014.1: 79066 . . . 81162 | 1587 | ZP_01729220.1 | 1788 | *Cyanothece* sp. CCY0110 |
| 257060449 | NC_013161.1: 2659296 . . . 2661419 | 1588 | YP_003138337.1 | 1789 | *Cyanothece* sp. PCC 8802 |
| 218441705 | complement (NC_011729.1: 5341705 . . . 5343810) | 1589 | YP_002380034.1 | 1790 | *Cyanothece* sp. PCC 7424 |
| 166368837 | NC_010296.1: 5646854 . . . 5648950 | 1590 | YP_001661110.1 | 1791 | *Microcystis aeruginosa* NIES-843 |
| 220909840 | NC_011884.1: 4551169 . . . 4553265 | 1591 | YP_002485151.1 | 1792 | *Cyanothece* sp. PCC 7425 |
| 16330299 | NC_000911.1: 1250442 . . . 1252535 | 1592 | NP_441027.1 | 1793 | *Synechocystis* sp. PCC 6803 |
| 86142732 | NZ_AANC01000005.1: 209172 . . . 211268 | 1593 | ZP_01061171.1 | 1794 | *Leeuwenhoekiella blandensis* MED217 |
| 146301271 | complement (NC_009441.1: 4208789 . . . 4210882) | 1594 | YP_001195862.1 | 1795 | *Flavobacterium johnsoniae* UW101 |
| 260061847 | NC_013222.1: 1408358 . . . 1410454 | 1595 | YP_003194927.1 | 1796 | *Robiginitalea biformata* HTCC2501 |
| 88713711 | complement (NZ_AAOC01000008.1: 22821 . . . 24917) | 1596 | ZP_01107792.1 | 1797 | *Flavobacteriales bacterium* HTCC2170 |
| 86133149 | complement (NZ_CH902588.1: 146636 . . . 148729) | 1597 | ZP_01051731.1 | 1798 | *Polaribacter* sp. MED152 |
| 88803680 | NZ_AAOG01000005.1: 54861 . . . 56951 | 1598 | ZP_01119204.1 | 1799 | *Polaribacter irgensii* 23-P |
| 213962668 | NZ_ABZV01000006.1: 103363 . . . 105438 | 1599 | ZP_03390929.1 | 1800 | *Capnocytophaga sputigena* ATCC 33612 |
| 256820698 | complement (NC_013162.1: 2243972 . . . 2246047) | 1600 | YP_003141977.1 | 1801 | *Capnocytophaga ochracea* DSM 7271 |
| 46581432 | NC_002937.3: 3152216 . . . 3154330 | 1601 | YP_012240.1 | 1802 | *Desulfovibrio vulgaris* str. Hildenborough |
| 218886955 | NC_011769.1: 2286534 . . . 2288648 | 1602 | YP_002436276.1 | 1803 | *Desulfovibrio vulgaris* str. 'Miyazaki F' |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 78358281 | NC_007519.1: 3235663 . . . 3237822 | 1603 | YP_389730.1 | 1804 | *Desulfovibrio desulfuricans* subsp. *desulfuricans* str. G20 |
| 242280036 | complement (NC_012881.1: 2812652 . . . 2814769) | 1604 | YP_002992165.1 | 1805 | *Desulfovibrio salexigens* DSM 2638 |
| 258405159 | complement (NC_013223.1: 1218708 . . . 1220816) | 1605 | YP_003197901.1 | 1806 | *Desulfohalobium retbaense* DSM 5692 |
| 256828849 | NC_013173.1: 1143375 . . . 1145477 | 1606 | YP_003157577.1 | 1807 | *Desulfomicrobium baculatum* DSM 4028 |
| 225198782 | complement (NZ_ACJN01000010.1: 60728 . . . 62824) | 1607 | ZP_03737911.1 | 1808 | *Desulfonatronospira thiodismutans* ASO3-1 |
| 242278203 | NC_012881.1: 802309 . . . 804414 | 1608 | YP_002990332.1 | 1809 | *Desulfovibrio salexigens* DSM 2638 |
| 212704109 | complement (NZ_ABXU01000065.1: 34368 . . . 36470) | 1609 | ZP_03312237.1 | 1810 | *Desulfovibrio piger* ATCC 29098 |
| 220903578 | complement (NC_011883.1: 357004 . . . 359112) | 1610 | YP_002478890.1 | 1811 | *Desulfovibrio desulfuricans* subsp. *desulfuricans* str. ATCC 27774 |
| 51244410 | NC_006138.1: 608983 . . . 611115 | 1611 | YP_064294.1 | 1812 | *Desulfotalea psychrophila* LSv54 |
| 94986723 | NC_008011.1: 347892 . . . 350012 | 1612 | YP_594656.1 | 1813 | *Lawsonia intracellularis* PHE/MN1-00 |
| 119488858 | complement (NZ_AAVU01000021.1: 33384 . . . 35414) | 1613 | ZP_01621820.1 | 1814 | *Lyngbya* sp. PCC 8106 |
| 209524350 | NZ_ABYK01000010.1: 35808 . . . 37916 | 1614 | ZP_03272899.1 | 1815 | *Arthrospira maxima* CS-328 |
| 116748909 | NC_008554.1: 1826816 . . . 1828915 | 1615 | YP_845596.1 | 1816 | *Syntrophobacter fumaroxidans* MPOB |
| 241776655 | NZ_ACQQ01000008.1: 86078 . . . 88198 | 1616 | ZP_04773932.1 | 1817 | *Allochromatium vinosum* DSM 180 |
| 32476008 | NC_005027.1: 5198833 . . . 5200932 | 1617 | NP_869002.1 | 1818 | *Rhodopirellula baltica* SH 1 |
| 78776256 | NC_007575.1: 60204 . . . 62282 | 1618 | YP_392571.1 | 1819 | *Sulfurimonas denitrificans* DSM 1251 |
| 254458291 | complement (NZ_DS995288.1: 173480 . . . 175561) | 1619 | ZP_05071717.1 | 1820 | *Campylobacterales bacterium* GD 1 |
| 229532518 | NZ_ABUV01000006.1: 73569 . . . 75677 | 1620 | ZP_04421899.1 | 1821 | *Sulfurospirillum deleyianum* DSM 6946 |
| 152993574 | NC_009663.1: 2069625 . . . 2071724 | 1621 | YP_001359295.1 | 1822 | *Sulfurovum* sp. NBC37-1 |
| 120401715 | NC_008726.1: 740616 . . . 742694 | 1622 | YP_951544.1 | 1823 | *Mycobacterium vanbaalenii* PYR-1 |
| 145220810 | complement (NC_009338.1: 189392 . . . 191515) | 1623 | YP_001131488.1 | 1824 | *Mycobacterium gilvum* PYR-GCK |
| 108797517 | NC_008146.1: 594117 . . . 596231 | 1624 | YP_637714.1 | 1825 | *Mycobacterium* sp. MCS |
| 118473540 | NC_008596.1: 867578 . . . 869656 | 1625 | YP_885188.1 | 1826 | *Mycobacterium smegmatis* str. MC2 155 |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 169631304 | complement (NC_010397.1: 4294451 . . . 4296532) | 1626 | YP_001704953.1 | 1827 | *Mycobacterium abscessus* |
| 240168870 | NZ_ACBV01000011.1: 33884 . . . 35974 | 1627 | ZP_04747529.1 | 1828 | *Mycobacterium kansasii* ATCC 12478 |
| 183980733 | NC_010612.1: 853987 . . . 856071 | 1628 | YP_001849024.1 | 1829 | *Mycobacterium marinum* M |
| 15607549 | NC_000962.2: 491786 . . . 493858 | 1629 | NP_214922.1 | 1830 | *Mycobacterium tuberculosis* H37Rv |
| 41409983 | NC_002944.2: 4345845 . . . 4347932 | 1630 | NP_962819.1 | 1831 | *Mycobacterium avium* subsp. *paratuberculosis* K-10 |
| 254818871 | complement (NZ_ABIN01000026.1: 2280 . . . 4439) | 1631 | ZP_05223872.1 | 1832 | *Mycobacterium intracellulare* ATCC 13950 |
| 226304961 | NC_012490.1: 1605870 . . . 1607948 | 1632 | YP_002764919.1 | 1833 | *Rhodococcus erythropolis* PR4 |
| 111019190 | complement (NC_008268.1: 2308925 . . . 2311045) | 1633 | YP_702162.1 | 1834 | *Rhodococcus jostii* RHA1 |
| 54027320 | complement (NC_006361.1: 5652808 . . . 5654895) | 1634 | YP_121562.1 | 1835 | *Nocardia farcinica* IFM 10152 |
| 227978095 | NZ_ABVA01000001.1: 785441 . . . 787570 | 1635 | ZP_04025361.1 | 1836 | *Tsukamurella paurometabola* DSM 20162 |
| 262204223 | complement (NC_013441.1: 4704088 . . . 4706208) | 1636 | YP_003275431.1 | 1837 | *Gordonia bronchialis* DSM 43247 |
| 256831883 | complement (NC_013174.1: 683848 . . . 685947) | 1637 | YP_003160610.1 | 1838 | *Jonesia denitrificans* DSM 20603 |
| 260517199 | complement (NZ_ABUN01000002.1: 90744 . . . 92939) | 1638 | ZP_05816650.1 | 1839 | *Sanguibacter keddieii* DSM 10542 |
| 229243856 | complement (NZ_ABTJ01000131.1: 4381 . . . 6468) | 1639 | ZP_04368027.1 | 1840 | *Cellulomonas flavigena* DSM 20109 |
| 229821528 | NC_012669.1: 3401218 . . . 3403323 | 1640 | YP_002883054.1 | 1841 | *Beutenbergia cavernae* DSM 12333 |
| 227428424 | complement (NZ_ABVC01000008.1: 150308 . . . 152407) | 1641 | ZP_03911481.1 | 1842 | *Xylanimonas cellulosilytica* DSM 15894 |
| 119717178 | complement (NC_008699.1: 3139954 . . . 3142044) | 1642 | YP_924143.1 | 1843 | *Nocardioides* sp. JS614 |
| 227381337 | complement (NZ_ABUC01000011.1: 233655 . . . 235784) | 1643 | ZP_03864789.1 | 1844 | *Kribbella flavida* DSM 17836 |
| 88856399 | NZ_AAOB01000010.1: 2970 . . . 5138 | 1644 | ZP_01131057.1 | 1845 | marine actinobacterium PHSC20C1 |
| 170780609 | NC_010407.1: 179995 . . . 182112 | 1645 | YP_001708941.1 | 1846 | *Clavibacter michiganensis* subsp. *Sepedonicus* |
| 50954174 | NC_006087.1: 335128 . . . 337257 | 1646 | YP_061462.1 | 1847 | *Leifsonia xyli* subsp. *xyli* str. CTCB07 |
| 114331961 | complement (NC_008344.1: 2107910 . . . 2110039) | 1647 | YP_748183.1 | 1848 | *Nitrosomonas eutropha* C91 |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 256395328 | complement (NC_013131.1: 7130890 . . . 7133034) | 1648 | YP_003116892.1 | 1849 | *Catenulispora acidiphila* DSM 44928 |
| 258650827 | NC_013235.1: 639398 . . . 641491 | 1649 | YP_003199983.1 | 1850 | *Nakamurella multipartita* DSM 44233 |
| 257068066 | complement (NC_013172.1: 995592 . . . 997667) | 1650 | YP_003154321.1 | 1851 | *Brachybacterium faecium* DSM 4810 |
| 227497260 | complement (NZ_ACFH01000109.1: 3054 . . . 5108) | 1651 | ZP_03927492.1 | 1852 | *Actinomyces urogenitalis* DSM 15434 |
| 256824971 | NC_013169.1: 1149994 . . . 1152081 | 1652 | YP_003148931.1 | 1853 | *Kytococcus sedentarius* DSM 20547 |
| 260455562 | NZ_ACZH01000022.1: 9845 . . . 11917 | 1653 | ZP_05803950.1 | 1854 | *Streptomyces flavogriseus* ATCC 33331 |
| 182435904 | NC_010572.1: 2506931 . . . 2509012 | 1654 | YP_001823623.1 | 1855 | *Streptomyces griseus* subsp. *griseus* NBRC 13350 |
| 254387454 | NZ_DS570624.1: 26512 . . . 28596 | 1655 | ZP_05002693.1 | 1856 | *Streptomyces clavuligerus* ATCC 27064 |
| 254400535 | NZ_DS570905.1: 178100 . . . 180199 | 1656 | ZP_05015493.1 | 1857 | *Streptomyces sviceus* ATCC 29083 |
| 256813645 | NZ_ACFA01000303.1: 9482 . . . 11584 | 1657 | ZP_05538660.1 | 1858 | *Streptomyces griseoflavus* Tu4000 |
| 239928836 | NZ_ABYA01000185.1: 2180 . . . 4282 | 1658 | ZP_04685789.1 | 1859 | *Streptomyces ghanaensis* ATCC 14672 |
| 256804684 | complement (NZ_ACEZ01000169.1: 8822 . . . 10924) | 1659 | ZP_05534308.1 | 1860 | *Streptomyces viridochromogenes* DSM 40736 |
| 256785123 | NZ_ACEY01000098.1: 97187 . . . 99280 | 1660 | ZP_05523554.1 | 1861 | *Streptomyces lividans* TK24 |
| 29829365 | NC_003155.4: 3467325 . . . 3469415 | 1661 | NP_823999.1 | 1862 | *Streptomyces avermitilis* MA-4680 |
| 260646824 | FN554889.1: 3224239 . . . 3226344 | 1662 | CBG69921.1 | 1863 | *Streptomyces scabiei* 87.22 |
| 239982381 | complement (NZ_ABYC01000362.1: 40088 . . . 42163) | 1663 | ZP_04704905.1 | 1864 | *Streptomyces albus* J1074 |
| 254382385 | complement (NZ_DS570390.1: 111950 . . . 114034) | 1664 | ZP_04997745.1 | 1865 | *Streptomyces* sp. Mg1 |
| 256769973 | complement (NZ_ACEW01000403.1: 16454 . . . 18541) | 1665 | ZP_05509147.1 | 1866 | *Streptomyces* sp. C |
| 256776255 | NZ_ACEX01000277.1: 2545 . . . 4641 | 1666 | ZP_05514718.1 | 1867 | *Streptomyces hygroscopicus* ATCC 53653 |
| 254378850 | NZ_DS570550.1: 40417 . . . 42507 | 1667 | ZP_04994290.1 | 1868 | *Streptomyces* sp. SPB74 |
| 229854086 | complement (NZ_ABUU01000066.1: 39364 . . . 41415) | 1668 | ZP_04474082.1 | 1869 | *Streptosporangium roseum* DSM 43021 |
| 145596204 | NC_009380.1: 4234932 . . . 4237007 | 1669 | YP_001160501.1 | 1870 | *Salinispora tropica* CNB-440 |
| 159039600 | NC_009953.1: 4631907 . . . 4633976 | 1670 | YP_001538853.1 | 1871 | *Salinispora arenicola* CNS-205 |
| 238060866 | NZ_GG657738.1: 2330097 . . . 2332163 | 1671 | ZP_04605575.1 | 1872 | *Micromonospora* sp. ATCC 39149 |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 116671783 | complement (NC_008541.1: 3648900 . . . 3651011) | 1672 | YP_832716.1 | 1873 | Arthrobacter sp. FB24 |
| 148807608 | complement (EF6018801: 72 . . . 2150) | 1673 | ABR13603.1 | 1874 | Arthrobacter oxydans |
| 239916738 | complement (NC_012803.1: 190981 . . . 193056) | 1674 | YP_002956296.1 | 1875 | Micrococcus luteus NCTC 2665 |
| 255326162 | NZ_ACVO01000004.1: 127571 . . . 129661 | 1675 | ZP_05367249.1 | 1876 | Rothia mucilaginosa ATCC 25296 |
| 184199797 | complement (NC_010617.1: 164688 . . . 166781) | 1676 | YP_001854004.1 | 1877 | Kocuria rhizophila DC2201 |
| 254368446 | NZ_DS264133.1: 69966 . . . 72062 | 1677 | ZP_04984463.1 | 1878 | Francisella tularensis subsp. holarctica FSC022 |
| 167626922 | complement (NC_010336.1: 741506 . . . 743602) | 1678 | YP_001677422.1 | 1879 | Francisella philomiragia subsp. philomiragia ATCC 25017 |
| 94676965 | NC_007984.1: 392877 . . . 395012 | 1679 | YP_588827.1 | 1880 | Baumannia cicadellinicola str. Hc (Homalodisca coagulata) |
| P57273 | BA000003.2: 189582 . . . 191708 | 1680 | NP_240007.1 | 1881 | Buchnera aphidicola str. APS (Acyrthosiphon pisum) |
| 254444018 | NZ_DS990592.1: 1298899 . . . 1201010 | 1681 | ZP_05057494.1 | 1882 | Verrucomicrobiae bacterium DG1235 |
| 171914782 | NZ_ABIZ01000001.1: 6593044 . . . 6595128 | 1682 | ZP_02930252.1 | 1883 | Verrucomicrobium spinosum DSM4136 |
| 114777389 | NZ_AATS01000006.1: 50467 . . . 52602 | 1683 | ZP_01452386.1 | 1884 | Mariprofundus ferrooxydans PV-1 |
| 94500866 | NZ_AAQH01000011.1: 33324 . . . 35456 | 1684 | ZP_01307392.1 | 1885 | Bermanella marisrubri |

In other embodiments, a polynucleotide, gene and/or polypeptide encoding phosphotransacetylase can have at least about 70% to about 75%, about 80% to about 85%, about 85% to about 90%, about 90% to about 95%, about 96%, about 97%, about 98%, or about 99% sequence identity to any one of the sequences of Tables 10 or 12a or 12b, wherein the polynucleotide, gene and/or polypeptide encodes a polypeptide having phosphotransacetylase activity.

In embodiments, a polynucleotide, gene and/or polypeptide encoding phosphotransacetylase corresponds to the Enzyme Commission Number EC 2.3.1.8.

In other embodiments, the phosphotransacetylase polynucleotide, gene and/or polypeptide sequences described herein or those recited in the art can be used to identify phosphotransacetylase sequences or phosphotransacetylase homologs in other cells, as described above for PDC.

Methods for gene expression in recombinant host cells, including, but not limited to, yeast cells are known in the art (see, for example, Methods in Enzymology, Volume 194, Guide to Yeast Genetics and Molecular and Cell Biology (Part A, 2004, Christine Guthrie and Gerald R. Fink (Eds.), Elsevier Academic Press, San Diego, Calif.). In embodiments, the coding region for the phosphoketolase and/or phosphotransacetylase genes to be expressed can be codon optimized for the target host cell, as well known to one skilled in the art. Expression of genes in recombinant host cells, including but not limited to yeast cells, can require a promoter operably linked to a coding region of interest, and a transcriptional terminator. A number of promoters can be used in constructing expression cassettes for genes, including, but not limited to, the following constitutive promoters suitable for use in yeast: FBA1, TDH3 (GPD), ADH1, and GPM1; and the following inducible promoters suitable for use in yeast: GAL1, GAL10 and CUP1. Other yeast promoters include hybrid promoters UAS(PGK1)-FBA1p (SEQ ID NO: 1893), UAS(PGK1)-ENO2p (SEQ ID NO: 1894), UAS(FBA1)-PDC1p (SEQ ID NO: 1895), UAS(PGK1)-PDC1p (SEQ II) NO: 1896), and UAS(PGK)-OLE1p (SEQ ID NO: 1897). Suitable transcriptional terminators that can be used in a chimeric gene construct for expression include, but are not limited to, FBA1t, TDH3t, GPM1t. ERG10t, GAL1t, CYC1t, and ADH1t.

Recombinant polynucleotides are typically cloned for expression using the coding sequence as part of a chimeric gene used for transformation, which includes a promoter operably linked to the coding sequence as well as a ribosome binding site and a termination control region. The coding region may be from the host cell for transformation and combined with regulatory sequences that are not native to the natural gene encoding phosphoketolase and/or phosphotransacetylase. Alternatively, the coding region may be from another host cell.

Vectors useful for the transformation of a variety of host cells are common and described in the literature. Typically the vector contains a selectable marker and sequences allowing autonomous replication or chromosomal integration in the desired host. In addition, suitable vectors can comprise a promoter region which harbors transcriptional initiation controls and a transcriptional termination control region, between which a coding region DNA fragment may be inserted, to provide expression of the inserted coding region. Both control regions can be derived from genes homologous to the transformed host cell, although it is to be understood that such control regions can also be derived from genes that are not native to the specific species chosen as a production host.

In embodiments, suitable promoters, transcriptional terminators, and phosphoketolase and/or phosphotransacetylase coding regions can be cloned into E. coli-yeast shuttle vectors, and transformed into yeast cells. Such vectors allow strain propagation in both E. coli and yeast strains, and can contain a selectable marker and sequences allowing autonomous replication or chromosomal integration in the desired host. Typically used plasmids in yeast include, but are not limited to, shuttle vectors pRS423, pRS424, pRS425, and pRS426 (American Type Culture Collection, Rockville, Md.), which contain an E. coli replication origin (e.g., pMB1), a yeast 2-micron origin of replication, and a marker for nutritional selection. The selection markers for these four vectors are 141S3 (vector pRS423), TRP1 (vector pRS424), LEU2 (vector pRS425) and URA3 (vector pRS426).

In embodiments, construction of expression vectors with a chimeric gene encoding the described phosphoketolases and/or phosphotransacetylases can be performed by the gap repair recombination method in yeast. In embodiments, a yeast vector DNA is digested (e.g., in its multiple cloning site) to create a "gap" in its sequence. A number of insert DNAs of interest are generated that contain an approximately 21 by sequence at both the 5' and the 3' ends that sequentially overlap with each other, and with the 5' and 3' terminus of the vector DNA. For example, to construct a yeast expression vector for "Gene X," a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 by overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an E. coli strain, e.g. TOP10, followed by mini preps and restriction mapping to further verify the plasmid construct. Finally the construct can be verified by sequence analysis.

Like the gap repair technique, integration into the yeast genome also takes advantage of the homologous recombination system in yeast. In embodiments, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The FCR product is then transformed into yeast and plated on medium containing the appropriate compound mixtures that allow selection for the integrated auxotrophic marker. For example, to integrate "Gene X" into chromosomal location "Y", the promoter-coding region X-terminator construct is PCR amplified from a plasmid DNA construct and joined to an, autotrophic marker (such as URA3) by either SOE PCR or by common restriction digests and cloning. The full cassette, containing the promoter-coding regionX-terminator-URA3 region, is PCR amplified with primer sequences that contain 40-70 by of homology to the legions 5' and 3' of location "Y" on the yeast chromosome. The PCR product is transformed into yeast and selected on growth media lacking, uracil. Transformants can be verified either by colony PCR or by direct sequencing of chromosomal DNA.

The presence of phosphoketolase and phosphotransacetylase activity in the recombinant host cells disclosed herein can be, confirmed using routine methods known in the art. In a non-limiting example, and as described in the Examples herein, transformants can be screened by PCR using primers for the phosphoketolase and phosphotransacetylase genes. In embodiments, and as described in the Examples herein, transformants can be screened by PCR with primers N1039 and N1040 (SEQ ID NOs: 639 and 640) to confirm integration of the xpk1 gene, and primers N1041 and N1042 (SEQ ID NOs: 641 and 642) can be used to confirm integration of the eutD gene. In another non-limiting example, and as described in the Examples herein, transformants can be, screened for integration of phosphoketolase constructs and/or phosphotransacetylase constructs at the Δpdc1::ilvD(Sm) locus by the loss of ilvD(Sm) in the host cells.

In another non-limiting example, and as described in the examples herein, phosphoketolase activity can be assayed by expressing phosphoketolase identifiable by the methods disclosed herein in a recombinant host cell disclosed herein that lacks endogenous phosphoketolase activity. If phosphoketolase activity is present, such cells exhibit a reduced or eliminated requirement for exogenous two-carbon substrate supplementation for growth in culture.

In another non-limiting example, and as described in the examples herein, phosphoketolase and phosphotransacetylase activity can be assayed by expressing phosphoketolase and phosphotransacetylase activity identifiable by the methods disclosed herein in a recombinant host cell disclosed herein that lacks endogenous phosphoketolase and phosphotransacetylase activity. If phosphoketolase activity and phosphoketolase activity are present, such cells exhibit a reduced or eliminated requirement for exogenous two-carbon substrate supplementation for growth in culture.

In another non-limiting example, phosphoketolase, and/or phosphotransacetylase activity can be confirmed by more indirect methods, such as by assaying for a downstream product in a pathway requiring phosphoketolase activity. For example, a polypeptide having phosphoketolase activity can catalyze the conversion of xylulose-5-phosphate into glyceraldehyde-3-phosphate and acetyl-phosphate and/or the conversion of fructose-6-phosphate into erythrose-4-phosphate and acetyl-phosphate. Also, a polypeptide having phosphotransacetylase activity can catalyze the conversion of acetyl-phosphate into acetyl-CoA.

Suitable Pathway Carbon Substrates and Exogenous Two-Carbon Substrate Supplementation PDC-KO cells fail to grow in glucose-containing media (e.g., 2% glucose), but PDC-KO cells carrying a functional butanediol biosynthetic pathway have been shown to grow on glucose supplemented with exogenous two-carbon substrates such as ethanol (see for example, US Patent Application Publication No. 20090305363, herein incorporated by reference). In embodiments, the host cells disclosed herein can be grown in fermentation media which contains a suitable pathway carbon substrate and two-substrate supplement, including combinations of suitable pathway carbon substrates with C2-substrate supplement. Non-limiting examples of suitable pathway carbon substrates include, but are not limited to, monosaccharides such as fructose, oligosaccharides such as lactose maltose, galactose, or sucrose, polysaccharides such as starch or cellulose or mixtures thereof and unpurified mixtures from renewable feedstocks such as cheese whey permeate, cornsteep liquor, sugar beet molasses, and barley malt, including any combinations thereof. In other embodiments, the suitable pathway carbon substrates can include lactate, glycerol, or combinations thereof.

In embodiments, a suitable carbon substrate can be a one-carbon substrate such as carbon dioxide, or methanol for which metabolic conversion into key biochemical intermediates has been demonstrated, or combinations thereof. In other embodiments related to methylotrophic organisms, the carbon substrate can be carbon containing compounds such as methylamine, glucosamine and a variety of amino acids for metabolic activity. In a non-limiting example, methylotrophic yeasts are known to utilize the carbon from methylamine to form trehalose or glycerol (Bellion et al., *Microb. Growth C1 Compd.*, [Int. Symp.], 7th (1993), 415-32, Editor(s): Murrell, J. Collin; Kelly Don P. Publisher: Intercept, Andover, UK). In another non-limiting example, various species of *Candida* can metabolize alanine (Sulter et al., *Arch. Microbiol.* 153:485-489 (1990)). Hence it is contemplated that the source of carbon utilized in the present invention can encompass a wide variety of carbon containing substrates and will only be limited by the choice of organism.

In other embodiments. the suitable pathway carbon substrate can be glucose, fructose. and sucrose, or mixtures of these with five-ca hon (C5) sugars such as xylose and/or arabinose for yeasts cells modified to use C5 sugars. In embodiments. sucrose can be derived from renewable sugar sources such as sugar cane, sugar beets, cassava; sweet sorghum and mixtures thereof. In other embodiment. glucose and dextrose can derived from renewable grain sources through saccharification of starch based feedstocks including grains such as corn, wheat, rye, barley, oats. and mixtures thereof. In embodiments, the pathway carbon substrates can be derived from renewable cellulosic or lignocellulosic biomass through processes of pretreatment and saccharification, as described, for example, in U.S. Patent Application Publication No. US 20070031918 A1, which is herein incorporated by reference.

As used herein, "biomass" refers to any cellulosic or lignocellulosic material and includes, but is not limited to, materials comprising cellulose, and optionally further comprising hemicellulose, lignin, starch, oligosaccharides and/or monosaccharides. In embodiments, biomass can also comprise additional components, such as protein and/or lipid. In other embodiments, biomass can be derived from a single source, or biomass can comprise a mixture derived from more than one source; for example, biomass can comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Other non-limiting examples of biomass include, but are not limited to, corn grain, corn cobs, crop residues such as corn husks, corn stover, grasses, wheat, wheat straw, barley, barley straw. hay, rice straw, switchgrass, waste paper, sugar cane bagasse. sorghum, soy, components obtained from milling of grains, trees, branches, roots, leaves, wood chips, sawdust, shrubs and bushes, vegetables, fruits, flowers, animal manure and mixtures thereof.

The recombinant host cells described herein can be cultured using standard laboratory techniques known in the art (see, e.g. *Methods in Yeast Genetics*, 2005, Cold Spring Harbor Laboratory Press, Cold Spring harbor, NY, pp. 201-202). In embodiments related to media supplemented with exogenous two-carbon substrates, and as described in, the Examples, recombinant host cells can be grown in synthetic complete medium supplemented with one or more exogenous two-carbon substrates as described herein at a concentration of about 0.01%, about 0.05%, about 0.1%, about 0.5%, about 1.0%, about 1.5%, about 1.5% or about 2% (v/v) of the media. In embodiments, the recombinant host cells can be grown in synthetic complete culture without uracil or histidine, supplemented with 0.5% (v/v) ethanol. In embodiments related to growth in media that is not supplemented with exogenous two-carbon substrates, the recombinant host cells described herein can be first grown in culture medium comprising an exogenous two carbon substrate and then diluted (e.g., starting OD=0.1, ml medium in a 125 ml vented flask) into media that is not supplemented with exogenous two-carbon substrate.

The growth of the recombinant, host cells described herein can be measured by methods known in the art (see, e.g., *Methods in Yeast Genetics*, 2005, Cold Spring Harbor Laboratory Press, Cold Spring Harbor, N.Y., pp. 201-202). In a non-limiting example, the growth of the recombinant host cells described herein can be determined by measuring the optical density (OD) of cell cultures over time. For example, the OD at 600 nm for a yeast culture is proportional to yeast cell number. In another non-limiting example, the growth of the recombinant host cells described herein can be determined by counting viable cells in a sample of the culture over time.

Applicants have provided cells that have a reduced or eliminated requirement for two-carbon substrate supplementation for growth. In embodiments, such cells comprise (i) a deletion, mutation, and/or substitution in an endogenous gene encoding, a polypeptide that converts pyruvate to acetaldehyde, acetyl-phosphate or acetyl-CoA that results in a requirement for exogenous two-carbon substrate supplementation for optimal growth; (ii) a heterologous polynucleotide encoding a polypeptide having phosphoketolase activity; and optionally (iii) a heterologous polynucleotide encoding a polypeptide having phosphotransacetylase activity. In embodiments, such cells comprise (i) a modification in an endogenous polypeptide having PDC activity which results in reduced or eliminated PDC activity; (ii) a heterologous polynucleotide encoding a polypeptide having phosphoketolase activity; and optionally (iii) a heterologous polynucleotide encoding a polypeptide having phosphotransacetylase activity. As such, Applicants have also provided methods of improving the growth of a recombinant host cell comprising at least one modification in an endogenous polypeptide that converts pyruvate to acetaldehyde, acetyl-phosphate or acetyl-CoA that results in a requirement for exogenous two-carbon substrate supplementation for optimal growth comprising transforming the host cell with a heterologous polynucleotide encoding a polypeptide having phosphoketolase activity. Applicants have also provided methods of improving the growth of a recombinant host cell comprising at least one, modification in an endogenous polypeptide having pyruvate decarboxylase activity (e.g., having at least one deletion, mutation or substitution in an endogenous gene encoding a polypeptide having PDC activity that results in reduced or eliminated PDC activity) comprising transforming the host cell with a heterologous polynucleotide encoding a polypeptide having phosphoketolase activity. In other embodiments, the method further comprises transforming, a recombinant host cell described herein with a heterologous polynucleotide encoding a polypeptide having phosphotransacetylase activity.

Applicants have also provided methods of reducing or eliminating the requirement for an exogenous two-carbon substrate for the growth of a recombinant host cell comprising at least one modification in an endogenous activity that converts pyruvate to acetaldehyde, acetyl-phosphate or acetyl-CoA that results in a requirement for exogenous two-carbon substrate supplementation for optimal growth comprising transforming the host cell with a heterologous polynucleotide encoding a polypeptide having phosphoketolase activity comprising, transforming the recombinant host cell with a heterologous polynucleotide encoding a polypeptide having phosphoketolase activity. In other embodiments, the method further comprises transforming the recombinant host cell with a heterologous polynucleotide encoding a polypeptide having phosphotransacetylase activity.

Applicants have also provided methods of reducing the requirement for an exogenous two-carbon substrate for the growth of a recombinant host cell comprising at least one modification in an endogenous polypeptide having. PDC activity (e.g., having at least one deletion, mutation or substitution in an endogenous gene encoding a polypeptide having pyruvate decarboxylase activity) comprising transforming the recombinant host cell with a heterologous polynucleotide encoding a polypeptide having phosphoketolase activity. In other embodiments, the method further comprises transforming the recombinant host cell with a heterologous polynucleotide encoding a polypeptide having phosphotransacetylase activity.

In addition, Applicants have provided methods of eliminating the requirement for an exogenous two-carbon substrate for the growth of a recombinant host cell comprising at least one modification in an endogenous polypeptide having PDC activity (e.g., having at least one deletion, mutation or substitution in an endogenous gene encoding a polypeptide having PDC activity that results in reduced or eliminated PDC activity) comprising transforming the recombinant host cell with a heterologous polynucleotide encoding a polypeptide having phosphoketolase activity. In other embodiments, the method further comprises transforming the recombinant host cell with a heterologous polynucleotide encoding a polypeptide having phosphotransacetylase activity.

In embodiments, a reduced requirement for exogenous two-carbon substrate supplementation can be a growth rate of the recombinant host cells described herein in media that is not supplemented, with an exogenous two-carbon substrate that is the same or substantially equivalent to the growth rate of a recombinant host cell comprising a modification in an endogenous activity that converts pyruvate to acetaldehyde, acetyl-phosphate or acetyl-CoA grown in media that is supplemented with an exogenous two-carbon substrate. In embodiments, such a growth rate can be at least about 70%, at least about 75%, at least about 80%, at least about 85%, at least about 90%, at least about 95%, at least about 96%, at least about 97%, at least about 98%, or at least about 99% of the growth rate of a recombinant host cell comprising a modification in an endogenous activity that converts pyruvate to acetaldehyde, acetyl-phosphate or acetyl-CoA grown in media that is supplemented with an exogenous two-carbon substrate.

In embodiments, a reduced requirement for exogenous two-carbon substrate supplementation can be a growth rate of the recombinant host cells described herein in media that is not supplemented with an exogenous two-carbon substrate that is the same or substantially equivalent to the growth rate of a recombinant host cell comprising a modification in an endogenous PDC activity grown in media that is supplemented with an exogenous two-carbon substrate. In embodiments, such a growth rate can be at least about 70%, at least about 75%, at least about 80%, at least about 85%, at least about 90%, at least about 95%, at least about 96%, at least about 97%, at least about 98%, or at least about 99% of the growth rate of a recombinant host cell comprising a modification in an endogenous PDC activity grown in media that is supplemented with an exogenous two-carbon substrate.

In other embodiments, the recombinant host cells described herein have a growth rate in media that is not supplemented with an exogenous two-carbon substrate that is greater than the growth rate of a recombinant host cell comprising a modification in an endogenous activity that converts pyruvate to acetaldehyde, acetyl-phosphate or acetyl-CoA in media that is not supplemented with an exogenous two-carbon substrate.

In other embodiments, the recombinant host cells described herein have a growth rate in media that is not supplemented with an exogenous two-carbon substrate that is greater than the growth rate of a recombinant host cell comprising a modification in an endogenous PDC activity in media that is not supplemented with an exogenous two-carbon substrate.

In other embodiments, the recombinant host cells described herein can have an increased glucose consumption compared to a recombinant host cell comprising a modification in an endogenous polypeptide that converts pyruvate to acetaldehyde, acetyl-phosphate or acetyl-CoA.

In other embodiments, the recombinant host cells described herein can have an increased glucose consumption compared to a recombinant host cell comprising a modification in an endogenous polypeptide having PDC activity (e.g., at least one deletion, mutation, and/or substitution in an endogenous gene encoding a polypeptide having PDC activity that reduces or eliminates PDC activity).

Glucose consumption of the recombinant host cells described herein can be measured by methods known in the art (see, e.g., *Methods in Yeast Genetics,* 2005, Cold Spring Harbor Laboratory Press, Cold Spring Harbor, N.Y., pp. 201-202). In a non-limiting example, glucose consumption can be measured by quantitating the amount of glucose in culture media by HPLC or with a YSI Biochemistry Analyzer (YSI, Inc., Yellow Springs, Ohio).

In other embodiments, methods of producing a recombinant host cell are provided comprising transforming a recombinant host cell comprising a modification in an endogenous polynucleotide, gene or polypeptide encoding pyruvate decarboxylase (e.g., at least one deletion, mutation, and/or substitution in an endogenous gene encoding a polypeptide having pyruvate decarboxylase activity) with a heterologous polynucleotide encoding a polypeptide having phosphoketolase activity. In other embodiments, the method further comprises transforming the recombinant host cell with a heterologous polynucleotide encoding a polypeptide having phosphotransacetylase activity.

In other embodiments, methods for the conversion of xylulose 5-phosphate or fructose 6-phosphate into acetyl-phosphate are provided comprising (i) providing a recombinant host cell as described herein, or combinations thereof; and (ii) growing the recombinant host cell under conditions wherein xylulose 5-phosphate or fructose-6-phosphate is converted into acetyl-phosphate. In other embodiments, methods for the conversion of xylulose 5-phosphate or fructose-6-phosphate into acetyl-CoA are provided comprising (i) providing a recombinant rose cell as described herein, or combinations thereof; and (ii) growing the recombinant host cell under conditions where xylulose 5-phosphate or fructose-6-phosphate is converted into acetyl-CoA.

In other embodiments, methods for the conversion of acetyl-phosphate to, acetyl-CoA are provided comprising (i) providing a recombinant host cell as described herein, or combinations thereof; and (ii) growing the recombinant host cell under conditions where acetyl-phosphate is converted into acetyl-CoA. In other embodiments, methods for increasing the specific activity of a heterologous polypeptide having phosphoketolase activity in a recombinant host cell are provided comprising (i) providing a recombinant host cell as described herein, or combinations thereof; and (ii) growing the recombinant host cell under conditions wherein the heterologous polypeptide having phosphoketolase activity is expressed in functional form having a specific activity greater than the same recombinant host cell lacking the heterologous polypeptide having phosphoketolase activity.

In other embodiments, methods for increasing the specific activity of a heterologous polypeptide having phosphotransacetylase activity in a recombinant host cell are provided comprising (i) providing a recombinant host cell described herein, or combinations thereof; and (ii) growing the recombinant host cell under conditions whereby the heterologous polypeptide having phosphotransacetylase activity is expressed in functional form having a specific activity greater than the same recombinant host cell lacking a heterologous polypeptide having phosphotransacetylase activity.

In still other embodiments, methods for increasing the activity of the phosphoketolase pathway in a recombinant host cell are provided comprising (i) providing a recombinant host cell as described herein, or combinations thereof; and (ii) growing the host cell under conditions whereby the activity of the phosphoketolase pathway in the host cell is increased.

Threonine aldolase (E.C. number 4.1.2.5) catalyzes cleavage of threonine to produce glycine and acetaldehyde. Plasmid-based overexpression of a gene encoding this enzyme in *S. cerevisiae* PDC-KO strains was shown to eliminate the requirement for exogenous C2 supplementation (van Maris et al, Appl Environ Microbiol. 2003 April; 69(4):2094-9). In embodiments, recombinant host cells comprise (i) a deletion, mutation, and/or substitution in an endogenous gene encoding a polypeptide that converts pyruvate to acetaldehyde, acetyl-phosphate or acetyl-CoA that results in a requirement for exogenous two-carbon substrate supplementation for optimal growth; and (ii) heterologous polynucleotide encoding a polypeptide having threonine aldolase activity.

Engineered Biosynthetic Pathways Using Pyruvate

In embodiments, the recombinant host cells described herein can be engineered to have a biosynthetic pathway for production of a product from pyruvate. A product from such a pyruvate-utilizing biosynthetic pathway includes, but is not limited to, 2,3-butanediol, isobutanol, 2-butanol, 2-butanone, valine, leucine, alanine, lactic acid, malic acid, fumaric acid, succinic acid and isoamyl alcohol. The features of any pyruvate-utilizing biosynthetic pathway may be engineered in the recombinant host cells described herein in any order. Any product made using a biosynthetic pathway that has, pyruvate as the initial substrate can be produced with greater effectiveness in a recombinant host cell disclosed herein having a, modification in an endogenous polypeptide that converts pyruvate to acetaldehyde, acetyl-phosphate or acetyl-CoA (such as pyruvate decarboxylase, pyruvate formate lyase, pyruvate dehydrogenase, pyruvate oxidase, or pyruvate:ferredoxin oxioreductase) and having heterologous phosphoketolase and/or phosphotransacetylase activity, compared to a recombinant host cell having a modification in an endogenous polypeptide that converts pyruvate to acetaldehyde, acetyl-phosphate or acetyl-CoA (such as pyruvate decarboxylase, pyruvate formate lyase, pyruvate dehydrogenase, pyruvate oxidase, or pyruvate:ferredoxin oxioreductase). Any product made using a biosynthetic pathway that has pyruvate as the initial substrate can be produced with greater effectiveness in a recombinant host cell disclosed herein having a modification in an endogenous polypeptide having PDC activity that reduces or eliminates PDC activity and having heterologous phosphoketolase and/or phosphotransacetylase activity, compared to a recombinant host cell having a modification in an endogenous polypeptide having PDC activity that reduces or eliminates PDC activity.

The biosynthetic pathway of the recombinant host cells described herein can be any pathway that utilizes pyruvate and produces a desired product. The pathway genes may include endogenous genes and/or heterologous genes. Typically at least one gene in the biosynthetic pathway is a heterologous gene. Suitable biosynthetic pathways for production of butanol are known in the art, and certain suitable pathways are described herein. In some embodiments, the butanol biosynthetic pathway comprises, at least one gene that is heterologous to the host cell. In some embodiments, the butanol biosynthetic pathway comprises more than one gene that is heterologous to the host cell. In some embodiments, the butanol biosynthetic pathway comprises heterologous genes encoding polypeptides corresponding to every step of a biosynthetic pathway.

Genes and polypeptides that can be used for substrate to product conversions described herein as well as methods of identifying such, genes and polypeptides, are described herein and/or in the art, for example, for isobutanol, in the Examples and in U.S. Pat. No. 7,851,188. Ketol-acid reductoisomerase (KARI) enzymes are described in U.S. Patent Appl. Pub. Nos. 20080261230 A1, 20090163376 A1, 20100197519 A1, and PCT Appl. Pub. No. WO/2011/04.1415. Examples of KARIs disclosed therein are those from *Lactococcus lactis*, *Vibrio cholera*, *Pseudomonas aeruginosa* PAO1, and *Pseudomonas fluorescens* PF5 mutants. KARIs include Anaerostipes caccae KARI variants "K9G9" and "K9D3" (SEQ ID NOs: 1911 and 1910, respectively). US Appl. Pub. No. 20100081154 A1, and U.S. Pat. No. 7,851,188 describe dihydroxyacid dehydratases (DHADs), including a DHAD from *Streptococcus mutans*. U.S. Patent Appl. Publ. No. 20090269823 A1 describes SadB, an alcohol dehydrogenase (ADH) from *Achromobacter xylosoxidans*. Alcohol dehydrogenases also include horse liver ADH and *Beijerinkia indica* ADH (protein SEQ ID NO: 1923).

An example of a biosynthetic pathway for producing 2,3-butanediol can be engineered in the recombinant host cells described herein, as described in U.S. Patent Application No. 20090305363, which is herein incorporated by reference. The 2,3-butanediol pathway is a portion of the 2-butanol biosynthetic pathway that is disclosed in U.S. Patent Application Publication No. US 20070292927 A1, which is herein incorporated by reference. Such pathway steps include, but are not limited to, conversion of pyruvate to acetolactate by acetolactate synthase, conversion of acetolactate to acetoin by acetolactate decarboxylase, and conversion of acetoin to 2,3-butanediol by butanediol dehydrogenase. The skilled person will appreciate that polypeptides having the activity of such pathway steps can be isolated from a variety of sources can be used in the recombinant host cells described herein.

In addition, examples of biosynthetic pathways for production of 2-butanone or 2-butanol that can be engineered in the recombinant host cells described herein are disclosed in U.S. Patent Application Publication Nos. US 20070292927 A1 and US 20070259410 A1, which are herein incorporated by reference. The pathway in U.S. Patent Application Publication No. US 20070292927 A1 is the same as described for butanediol production with the addition of the following steps:
  2,3-butanediol to 2-butanone as catalyzed for example by diol dehydratase or glycerol dehydratase; and
  2-butanone to 2-butanol as catalyzed for example by butanol dehydrogenase.

Described in U.S. Patent Application Publication No. US 20090155870 A1, which is herein incorporated by reference, is the construction of chimeric genes and genetic engineering of yeast for 2-butanol production using the U.S. Patent Application Publication No. US 20070292927 A1 disclosed biosynthetic pathway. Further description for gene construction and expression related to these pathways can be found, for example, in International Publication No. WO 2009046370 (e.g., butanediol dehydratases); and U.S. Patent Application Publication No. US 20090269823 A1 (e.g., butanol dehydrogenase) and U.S. Patent Application Publication No. US 20070259410 A1 which are herein incorporated by reference. The skilled person will appreciate that polypeptides having the activity of such pathway steps can be isolated from a variety of sources can be used in the recombinant host cells described herein.

Biosynthetic pathways for the production of isobutanol that may be used include those described in U.S. Pat. No. 7,851,188 and PCT Publication WO 2007050671, incorporated herein by reference. One isobutanol biosynthetic pathway comprises the following substrate to product conversions:
  pyruvate to acetolactate, which may be catalyzed, for example, by acetolactate synthase;
  acetolactate to 2,3-dihydroxyisovalerate, which may be catalyzed, for example, by acetohydroxy acid reductoisomerase;
  2,3-dihydroxyisovalerate to α-ketoisovalerate, which may be catalyzed, for example, by acetohydroxy acid dehydratase;
  α-ketoisovalerate to isobutyraldehyde, which may be catalyzed, for example, by a branched-chain keto acid decarboxylase; and
  isobutyraldehyde to isobutanol, which may be catalyzed, for example, by a branched-chain alcohol dehydrogenase. In some embodiments, the isobutanol biosynthetic pathway comprises at least one gene, at least two genes, at least three genes, or at least four genes that is/are heterologous to the yeast cell. In embodiments, each substrate to product conversion of an isobutanol biosynthetic pathway in a recombinant host cell is catalyzed by a heterologous polypeptide. In embodiments, the polypeptide catalyzing the substrate to product conversions of acetolactate to 2,3-dihydroxyisovalerate and/or the polypeptide catalyzing the substrate to product conversion of isobutyraldehyde to isobutanol are capable of utilizing NADH as a cofactor.

An example of a biosynthetic pathway for production of valine that can be engineered in the recombinant host cells described herein includes the steps of acetolactate conversion to 2,3-dihydroxy-isovalerate by acetohydroxyacid reductoisomerase (ILV5), conversion of 2,3-dihydroxy-isovalerate to 2-keto-isovalerate by dihydroxy-acid dehydratase (ILV3), and conversion of 2-keto-isovalerate to valine by branched-chain, amino acid transaminase (BAT2) and branched-chain amino acid aminotransferase (BAT1). Biosynthesis of leucine includes the same steps to 2-keto-isovalerate, followed by conversion of 2-keto-isovalerate to alpha-isopropylmalate by alpha-isopropylmalate synthase (LEU9. LEU4), conversion of alpha-isopropylmalate to beta-isopropylmalate by isopropylmalate isomerase (LEU1), conversion of beta-isopropylmalate to alpha-ketoisocaproate by beta-IPM dehydrogenase (LEU2), and finally conversion of alpha-ketoisocaproate to leucine by branched-chain amino acid transaminase (BAT2) and branched-chain amino acid aminotransferase (BAT1). It is desired for production of valine or leucine to overexpress at least one of the enzymes in these described pathways.

An example of a biosynthetic pathway for production of isoamyl alcohol that can be engineered in the recombinant host cells described herein includes the steps of leucine conversion to alpha-ketoisocaproate by branched-chain amino acid transaminase (BAT2) and branched-chain amino acid aminotransferase (BAT1), conversion of alpha-ketoisocaproate to 3-methylbutanal by ketoisocaproate decarboxylase (THI3) or decarboxylase ARO10, and finally conversion of 3-methylbutanal to isoamyl alcohol by an alcohol dehydrogenase such as ADH1 or SFA1. Production of isoamyl alcohol benefits from increased production of leucine or the alpha-ketoisocaproate intermediate by overexpression of one or more enzymes in biosynthetic pathways for these chemicals. In addition, one or both enzymes for the final two steps can be overexpressed.

An example of a biosynthetic pathway for production of lactic acid that can be engineered in the recombinant host cells described herein includes pyruvate conversion to lactic acid by lactate dehydrogenase. Engineering yeast for lactic acid production using lactate dehydrogenase, known as EC 1.1.1.27, is well known in the art such as in Ishida et al. (*Appl. Environ. Microbiol.* 71:1964-70 (2005)).

An example of a biosynthetic pathway for production of alanine that can be engineered in the recombinant host cells described herein includes pyruvate conversion to alanine by aminotransferase.

An example of a biosynthetic pathway for production of malate that can be engineered in the recombinant host cells described herein includes pyruvate conversion to oxaloacetate by pyruvate carboxylase, and conversion of oxaloacetate to malate by malate dehydrogenase as described in Zelle et al. (*Applied and Environmental Microbiology* 74:2766-77 (2008)). In addition, a malate transporter can be expressed.

An example of a biosynthetic pathway for production of fumarate that can be engineered in the recombinant host cells described herein includes pyruvate conversion to oxaloacetate by pyruvate carboxylase, and conversion of oxaloacetate to malate by malate dehydrogenase as described in Zelle et al. (*Applied and Environmental Microbiology* 74:2766-77 (2008)). In addition, a fumarase and a fumarate transporter can be expressed. Favorable production conditions and engineering of fungi for fumarate production is well known in the art, described e.g. by Goldberg et al. (*Journal of Chemical Technology and Biotechnology* 81:1601-1611 (2006)).

An example of a biosynthetic pathway for production of succinate that can be engineered in the recombinant host cells described herein includes pyruvate conversion to oxaloacetate by pyruvate carboxylase, and conversion of oxaloacetate to malate by malate dehydrogenase as described in Zelle et al. (*Applied and Environmental Microbiology* 74:2766-77 (2008)). In addition, a fumarase, a succinate dehydrogenase and a succinate transporter can be expressed.

The skilled person will appreciate that polypeptides having activities of the above-mentioned biosynthetic pathways can be isolated from a variety of sources can be used in the recombinant host cells described herein.

It will be appreciated that host cells comprising a butanol biosynthetic pathway such as an isobutanol biosynthetic pathway as provided herein may further comprise one or more additional modifications. U.S. Appl. Pub. No. 20090305363 (incorporated by reference) discloses increased conversion of pyruvate to acetolactate by engineering yeast for expression of a cytosol-localized acetolactate synthase and substantial elimination of pyruvate decarboxylase activity. Modifications to reduce glycerol-3-phosphate dehydrogenase activity and/or disruption in at least one gene encoding a polypeptide having pyruvate decarboxylase activity or a disruption in at least one gene encoding a regulatory element controlling pyruvate decarboxylase gene expression as described in U.S. Patent Appl. Pub. No. 20090305363 (incorporated herein by reference), modifications to a host cell that provide for increased carbon flux through an Entner-Doudoroff Pathway or reducing equivalents balance as described in U.S. Patent Appl. Pub. No. 20100120105 (incorporated herein by reference). Other modifications include integration of at least one polynucleotide encoding a polypeptide that catalyzes a step in a pyruvate-utilizing biosynthetic pathway. Other modifications include at least one deletion, mutation, and/or substitution in an endogenous polynucleotide encoding a polypeptide having acetolactate reductase activity. In embodiments, the polypeptide having acetolactate reductase activity is YMR226C (SEQ ID NO: 1912) of *Saccharomyces cerevisae* or a homolog thereof. Additional modifications include a deletion, mutation, and/or substitution in an endogenous polynucleotide encoding a polypeptide having aldehyde dehydrogenase and/or aldehyde oxidase activity. In embodiments, the polypeptide having aldehyde dehydrogenase activity is ALD6 (SEQ ID NO: 1909) from *Saccharomyces cerevisiae* or a homolog thereof. A genetic modification which has the effect of reducing glucose repression wherein the yeast production host cell is pdc—is described in U.S. Appl. Publication No. 20110124060, incorporated herein by reference.

Recombinant host cells may further comprise (a) at least one heterologous polynucleotide encoding a polypeptide having dihydroxy-acid dehydratase activity; and (b)(i) at least one deletion, mutation, and/or substitution in an endogenous gene encoding a polypeptide affecting Fe-S cluster biosynthesis; and/or (ii) at least one heterologous polynucleotide encoding a polypeptide affecting Fe-S cluster biosynthesis. In embodiments, the polypeptide affecting Fe-S cluster biosynthesis is encoded by AFT1 (nucleic acid SEQ ID NO: 1913, amino acid SEQ ID NO: 1914), AFT2 (SEQ ID NOs: 1915 and 1916), FRA2 (SEQ ID NOs: 1917 and 1918), GRx3(SEQ ID NOs: 1919 and 1920), or CCC1 (SEQ ID NOs: 1921 and 1922). In embodiments, the polypeptide affecting Fe-S cluster biosynthesis is constitutive mutant AFT1 L99A, AFT1 L102A, AFT1 C291F, or AFT1 C293F.

Fermentation Media

The recombinant host cells disclosed herein can be grown in fermentation media for production of a product utilizing pyruvate. For maximal production of some products, such as 2,3-butanediol, isobutanol, 2-butanone, or 2-butanol, the recombinant host cells disclosed herein used as production hosts preferably have enhanced tolerance to the produced chemical, and have a high rate of carbohydrate utilization. These characteristics can be conferred by mutagenesis and selection, genetic engineering, or can be natural.

Fermentation media for production of the products disclosed herein may contain glucose. Additional carbon substrates for product production pathways can include but are not limited to those described above. It is contemplated that the source of carbon utilized can encompass a wide variety of carbon containing substrates and will only be limited by the choice of organism.

In addition to an appropriate carbon source, fermentation media can contain suitable minerals, salts, cofactors, buffers and other components, known to those skilled in the art, suitable for the growth of the cultures and promotion of the enzymatic pathway necessary for production of the desired product.

Culture Conditions

10192 Typically cells are grown at a temperature in the range of about 20° C. to about 37° C. in, an appropriate medium. Suitable growth media for the recombinant host cells described herein are common commercially prepared media such as broth that includes yeast nitrogen base, ammonium sulfate, and dextrose as the carbon/energy source) or YPD Medium, a blend of peptone, yeast extract, and dextrose in optimal proportions for growing most *Saccharomyces cerevisiae* strains. Other defined or synthetic growth media may also be used and the appropriate medium for growth of the particular microorganism will be known by one skilled in the art of microbiology or fermentation science.

Suitable pH ranges for the fermentation are between pH 3.0 to pH 7.5, where pH 4.5 to pH 6.5 is preferred as the initial condition.

Fermentations can be performed under aerobic or anaerobic conditions, where anaerobic or microaerobic conditions are preferred.

The amount of product in the fermentation medium can be determined using a number of methods known in the art, for example, high performance liquid chromatography (HPLC) or gas chromatography (GC).

Industrial Batch and Continuous Fermentations

A batch method of fermentation can be used with the recombinant host cells described herein. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system, change constantly up to the time the fermentation is stopped. Within batch cultures cells progress through a static lag phase to a high growth log phase and finally to a stationary phase where growth rate is diminished or halted. If untreated, cells in the stationary phase will eventually die. Cells in log phase generally are responsible for the bulk of production of end product or intermediate.

A Fed-Batch system can also be used with the recombinant host cells described herein. A Fed-Batch system is similar to a typical batch system with the exception that the carbon source substrate is added in increments as the fermentation progresses. Fed-Batch systems are useful when catabolite repression (e.g. glucose repression) is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Although a batch mode can be performed, it is also contemplated that continuous fermentation methods could also be performed with the recombinant host cells described herein. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to vary. In other systems a number of factors affecting growth can be altered continuously while the cell concentration, measured by media turbidity, is kept constant. Continuous systems strive to maintain steady state growth, conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention can be practiced using either batch, fed-batch or continuous processes and that any known mode of fermentation would be suitable. Additionally, it is contemplated that cells can be immobilized on a substrate as whole cell catalysts and subjected to fermentation conditions for production.

Product Isolation from Fermentation Medium

Products can be isolated from the fermentation medium by methods known to one skilled in the art. For example, bioproduced isobutanol may be isolated from the fermentation medium using methods known in the art for ABE fermentations (see, e.g., Dune, Appl. Microbiol. Biotechnol. 49:639-648 (1998), Groot et al., Process. Biochem. 27:61-75 (1992), and references therein). For example, solids may be removed from the fermentation medium by centrifugation, filtration, decantation, or the like. Then, the isobutanol may be isolated from the fermentation medium using methods such as distillation, azeotropic distillation, liquid-liquid extraction, adsorption, gas stripping, membrane evaporation, pervaporation or vacuum flash fermentation (see e.g., U.S. Pub. No. 20090171129 A1, and International Pub. No. WO2010/151832 A1, both incorporated herein by reference in their entirety).

Because butanol forms a low boiling point, azeotropic mixture with, water, distillation can be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see, e.g., Doherty and Malone, Conceptual Design of Distillation Systems, McGraw Hill, N.Y., 2001).

The butanol-water mixture forms a heterogeneous azeotrope so that distillation may be used in combination with decantation to isolate and purify the isobutanol. In this method, the isobutanol containing fermentation broth is distilled to near the azeotropic composition. Then, the azeotropic mixture is condensed, and the isobutanol is separated from the fermentation medium by decantation. The decanted aqueous phase may be returned to the first distillation column as reflux. The isobutanol-rich decanted organic phase may be further purified by distillation in a second distillation column.

The butanol can also be isolated from the fermentation medium using liquid-liquid extraction in combination with distillation. In this method, the isobutanol is extracted from the fermentation broth using liquid-liquid extraction with a suitable solvent. The isobutanol-containing organic phase is then distilled to separate the butanol from the solvent.

Distillation in combination with adsorption can also be used to isolate isobutanol from the fermentation medium. In this method, the fermentation broth containing the isobutanol is distilled to near the azeotropic composition and then the remaining water is removed by use of an adsorbent. such as molecular sieves (Aden et al., Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, June 2002).

Additionally, distillation in combination with pervaporation may be used to isolate and purify the isobutanol from the fermentation medium. In this method, the fermentation broth containing the isobutanol is distilled to near the azeotropic composition, and then the remaining water is removed by pervaporation through a hydrophilic membrane (Guo et al., J. Membr. Sci. 245, 199-210 (2004)).

In situ product removal (ISPR) (also referred to as extractive fermentation) can be used to remove butanol (or other fermentative alcohol) from the fermentation vessel as it is produced, thereby allowing the microorganism to produce butanol at high yields. One method for ISPR for removing fermentative alcohol that has been described in the art is liquid-liquid extraction. In, general, with regard to butanol fermentation, for example, the fermentation medium, which includes the microorganism, is contacted with an organic extractant at a time before the butanol concentration reaches a toxic level. The organic extractant and, the fermentation medium form a biphasic mixture. The butanol partitions into the organic extractant phase, decreasing the concentration in the aqueous phase containing the microorganism, thereby limiting the exposure of the microorganism to the inhibitory butanol.

Liquid-liquid extraction can be performed, for example, according to the processes described in U.S. Patent Appl.

Pub. No. 20090305370, the disclosure of which is hereby incorporated in its entirety. U.S. Patent Appl. Pub. No. 20090305370 describes methods for producing and recovering butanol from a fermentation broth using liquid-liquid extraction, the methods comprising the step of contacting the fermentation broth with a water immiscible extractant to form a two-phase mixture comprising an aqueous phase and an organic phase. Typically, the extractant can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof. The extractant(s) for ISPR can be non-alcohol extractants. The ISPR extractant can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof.

In some embodiments, the alcohol can be esterfied by contacting the alcohol in a fermentation medium with an organic acid (e.g., fatty acids) and a catalyst (e.g. enzyme such as a lipase) capable of esterifying the alcohol with the organic acid. In such embodiments, the organic acid can serve as an ISPR extractant into which the alcohol esters partition. The organic acid can be supplied to the fermentation vessel and/or derived from the biomass supplying fermentable carbon fed to the fermentation vessel. Lipids present in the feedstock can be catalytically hydrolyzed to organic acid, and the same catalyst (e.g., enzymes) can esterify the organic acid with the alcohol. The catalyst can be supplied to the feedstock prior to fermentation, or can be supplied to the fermentation vessel before or contemporaneously with the supplying of the feedstock. When the catalyst is supplied to the fermentation vessel, alcohol esters can be obtained by hydrolysis of the lipids into organic acid and substantially simultaneous esterification of the organic acid with butanol present in the fermentation vessel. Organic acid and/or native oil not derived from the feedstock can also be fed to the fermentation vessel, with the native oil being hydrolyzed into organic acid. Any organic acid not esterified with the alcohol can serve as part of the ISPR extractant. The extractant containing alcohol esters can be separated from the fermentation medium, and the alcohol can be recovered from the extractant. The extractant can be recycled to the fermentation vessel. Thus, in the case of butanol production, for example, the conversion of the butanol to an ester reduces the free butanol concentration in the fermentation medium, shielding the microorganism from the toxic effect of increasing butanol concentration. In addition, unfractionated grain can be used as feedstock without separation of lipids therein, since the lipids can be catalytically hydrolyzed to organic acid, thereby decreasing the rate of build-up of lipids in the ISPR extractant.

In situ product removal can be carried out in a batch mode or a continuous mode. In a continuous mode of in situ product removal, product is continually removed from the reactor. In a batchwise mode of in situ product removal, a volume of organic extractant is added to the fermentation vessel and the extractant is not removed during the process. For in situ product removal, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production according to some embodiments of the present invention, the organic acid extractant can contact the fermentation medium at a time before the butanol concentration reaches a toxic level, so as to esterify the butanol with the organic acid to produce butanol esters and consequently reduce the concentration of butanol in the fermentation vessel. The ester-containing organic phase can then be removed from the fermentation vessel (and separated from the fermentation broth which constitutes the aqueous phase) after a desired effective titer of the butanol esters is achieved. In some embodiments, the ester-containing organic phase is separated from the aqueous phase after fermentation of the available fermentable sugar in the fermentation vessel is substantially complete.

EXAMPLES

The meaning of abbreviations used is as follows: "min" means minute(s), "h" means hour(s), "sec" means second(s), "µl" means microliter(s), "ml" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "rpm" means revolutions per minute, "w/v" means weight/volume, "v/v" means volume/volume, "OD" means optical density, "bp" means base pair(s), and "PCR" means polymerase chain reaction.

General Methods:

Standard recombinant DNA and molecular cloning techniques used in the Examples are well known in the art and are described by Sambrook, J., Fritsch, E. F. and Mamatis, T., *Molecular Cloning: A Laboratory Manual*, Cold Spring Harbor Laboratory Press, Cold Spring Harbor, N.Y., 1989, by T. J. Sillavy, M. L. Bennan, and L. W. Enquist, *Experiments' with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987. Phusion® HF Master Mix (NEB Cat. No. F-531) and HotStarTaq® Master Mix (Qiagen Cat. No. 203443) were used for PCR in gene cloning and clone screening, respectively.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from Aldrich Chemicals (Milwaukee, Wis.), BD Diagnostic Systems (Sparks, Md.)), Life Technologies (Rockville, Md.), or Sigma Chemical Company (St. Louis, Mo.), unless otherwise specified.

HPLC

Analysis for fermentation by-product composition is well known to those skilled in the art. For example, one high performance liquid chromatography (HPLC) method utilizes a Shodex SH-1011 column with a Shodex SH-G guard column (both available from Waters Corporation, Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol retention time is 47.6 minutes. For butanediol, meso-butanediol eluted at 26.0 min and 2R,3R-butanediol eluted at 27.7 min.

Example 1

Construction of phosphoketolase/phosphotransacetylase expression cassette

The xpk1 and eutD genes (GenBank GI numbers 28379168 (SEQ ID NO: 172) and 28377658 (SEQ ID NO: 1111), respectively) were obtained from *Lactobacillus plantarum* (ATCC No. BAA-793) via polymerase chain reaction (PCR) using primers N1039 and N1040 (for xpk1) and N1041 and N1042 (for eutD). The primer sequences of N1039, N1040, N1041 and N1042 correspond to SEQ ID Nos. 639-642, respectively.

The xpk1 and eutD genes were fused to a DNA fragment containing opposing yeast terminator sequences (CYC and ADH terminators, obtained from PacI digestion of pRS423::CUP1-alsS+FBA-budA, described in U.S. Patent Application Publication No. 20090155870, herein incorporated by reference) by overlap PCR method (Yu et al., Fungal Genet. Biol. 41: 973-981; 2003). The resulting PCR product was cloned into an *E. coli-yeast* shuttle vector using gap repair methodology (Ma et al., Genetics 58:201-216; 1981). The shuttle vector was based on pRS426 (ATCC No. 77107) and contained both GPD (also known as TDH3) and ADH1 promoters. The resulting vector contained xpk1 under control of the GPD promoter and eutD under control of the ADH1 promoter in opposing orientation. The sequence of the resulting vector (pRS426::GPD-xpk1+ADH1-eutD) is provided as SEQ ID No: 643 (see FIG. 5 for a map of this vector).

Example 2

Construction of Phosphoketolase/Phosphotransacetylase Integration Vector

An expression cassette of the pRS426::GPD-xpk1+ADH1-eutD vector (GPD-xpk1+ADH1-eutD) was prepared by digestion with EcoRI and SacI restriction enzymes. The resulting cassette was ligated into the yeast integration vector pUC19-URA3-MCS which was also prepared by digestion with EcoRI and SacI restriction enzymes.

Vector pUC19-URA3MCS is pUC19-based and contains the sequence of the URA3 gene from *Saccaromyces cerevisiae* situated within a multiple cloning site (MCS). pUC19 (American Type Culture Collection, Manassas, Va.; ATCC#37254) contains the pMB 1 replicon and a gene coding for beta-lactamase for replication and selection in *Escherichia coli*. In addition to the coding sequence for LRA3, the sequences from upstream and downstream of this gone are included for expression of the URA3 gene in yeast. The vector can be used for cloning purposes and can be used as a yeast integration vector.

The DNA encompassing the URA3 coding region along with 250 bp upstream and 150 bp downstream of the URA3 coding region from *Saccaromyces* cerevisiae CEN.PK 113-7D (CBS 8340; Centraalbureau voor Schimmelcultures (CBS) Fungal Biodiversity Centre, Netherlands) genomic DNA was amplified with primers oBP438 (SEQ ID NO: 644), containing BamHI, AscI, PineI, and FseI restriction sites, and oBP439 (SEQ ID NO: 645), containing XbaI, PacI, and NotI restriction sites. Genomic DNA was prepared using a Gentra Puregene Yeast/Bact kit (Qiagen). The PCR product and, pUC19 were ligated with T4 DNA ligase after digestion with BamHI and XbaI to create vector pUC19-URA3MCS. The vector was confirmed by PCR and sequencing with primers oBP264 (SEQ ID NO:646) and oBP265 (SEQ ID NO:647).

The ligation reaction was transformed into *E. coli* Stb13 cells, according to the manufacturer's instructions (Invitrogen, Carlsbad, Calif., Cat. No. C7373). Transformants were screened by polymerase chain reaction (PCR) to detect the eutD gene using the primers N1041 and N1042 (SEQ ID NOs: 641 and 642, respectively). Positive clones for eutD gene expression detected by PCR were further confirmed for eutD gene incorporation by digestion of the vector with SacII restriction enzyme.

Two confirmed clones were selected and an integration targeting sequence was added to the clones as follows. PCR was used to amplify regions of the genome of *S. cerevisiae* strain BY4700 (ATCC No. 200866) both 5' and 3' of the PDC1 gene using the following primers: N1049 and N1050 (5') and N1047 and N1048 (3') (SEQ ID NOs: 648-651, respectively). Primer N1049 enables the 3' end of the 161-bp PDC1 3' sequence to be fused to the 5' end of the 237 bp PDC1 5' sequence via PCR. This pdc 1 3'-5'-fusion fragment (368 by in length) was cloned into the pCR11—Blunt TOPO vector according to the manufacturer's instructions (Invitrogen, Carlsbad, Calif., Cat. No. K2800).

Transformants were screened by PCR to detect the pdc1 3'-5'-fusion fragment using primers N1047 and N1050. The pdc1 3'-5'-fusion fragment was isolated from positive clones and released from the vector by digestion with EcoRI enzyme, and ligated into a pUC19-URA3::GPD-xpk1+ADH-eutD vector that had been linearized by digestion with EcoRI restriction enzyme to generate the "phosphoketolase pathway" vector. Additionally, the pdc1 3'-5'-fusion fragment was ligated with pUC19-URA3-MCS digested with EcoRI restriction enzyme to generate the control vector. Both ligation reactions were transformed into *E. coli* Stb13 cells according to the manufacturer's instructions (Invitrogen, Carlsbad, Calif., Cat. No. C7373). The resulting transformants were screened by PCR to detect the pdc1 3'-5'-fusion fragment using primers N1047 and N1050. Positive clones containing the pdc1 3'-5'-fusion fragment were identified and the vectors were digested with either NcoI restriction enzyme (control vector) or BsgI restriction enzyme (phosphoketolase pathway vector) to confirm cloning orientation. One control clone (=pUC19-URA3::pdc1) and one phosphoketolase pathway clone (=pUC19-URA3::pde1::GPD-xpk1+ADH1-eutD; SEQ ID NO: 1898) were selected for integration.

Example 3

Construction of Pyruvate Decarboxylase Knockout (PDC-KO) Yeast Strain Containing Phosphoketolase and Phosphotransacetylase Genes The control and phosphoketolase pathway vectors described in Example 2 were linearized with AflII restriction enzyme and transformed into strain BP913 (CEN.PK113-7D Δura3::loxP Δhis3 Δpdc6 Δpdc1::ilvD(Sm) Δpc-1c5::sadB)

to form control and phosphoketolase pathway strains. Strain BP913 is further described in Example 10.

Transformed cells were plated on synthetic complete medium without uracil containing ethanol as the sole carbon source (1% vol/vol) and screened by PCR using primers N238 and oBP264 (SEQ ID Nos. 652 and 646, respectively to confirm integration at the pdc1 locus. Integration at the Δpdc1::ilvD(Sm) locus resulted in the loss of ilvD(Sm).

Example 4

Figure 2:
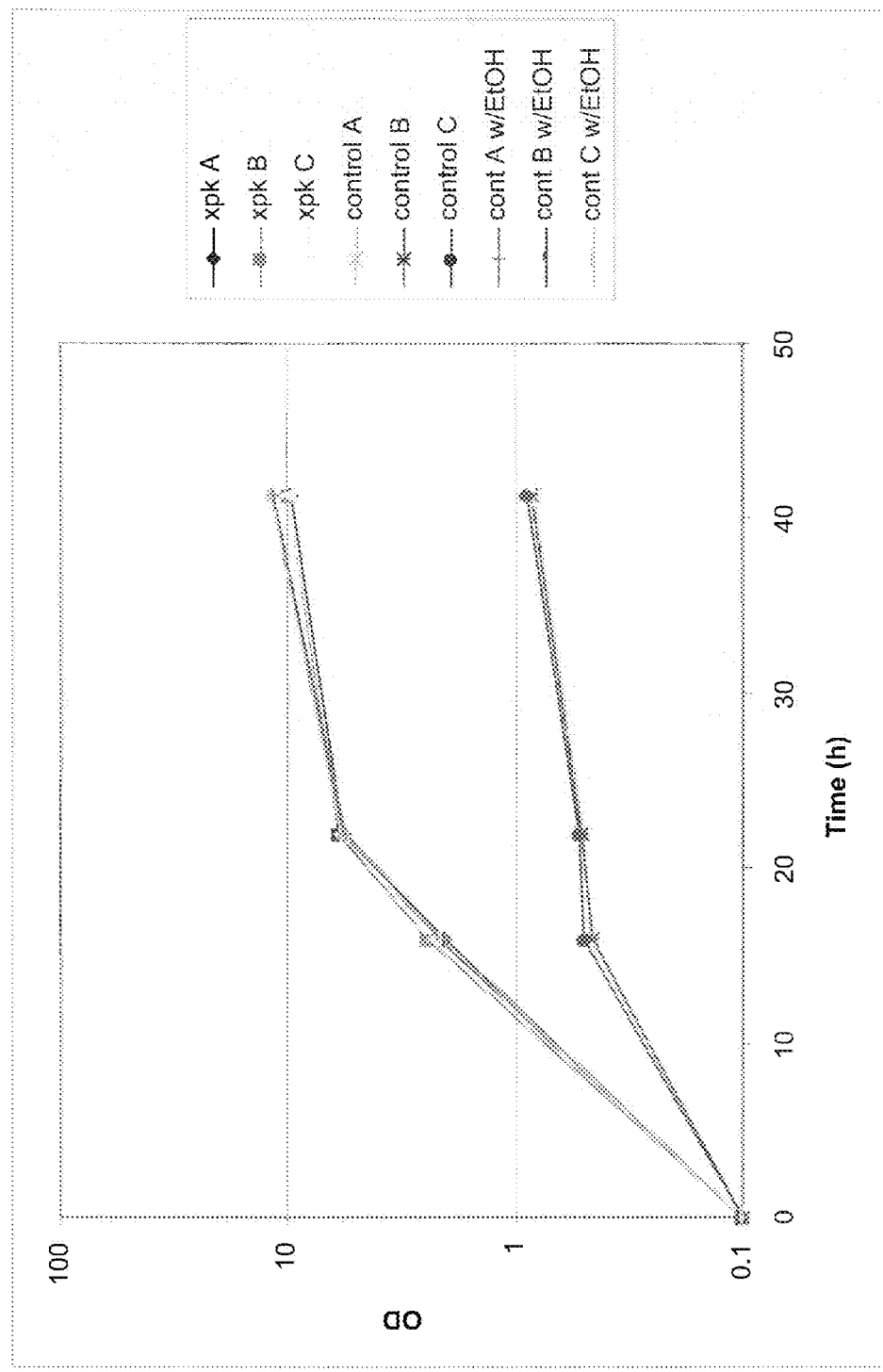
FIG. 2 depicts the growth of PDC-KO yeast strains expressing phosphoketolase and phosphotransacetylase without exogenous carbon substrate supplementation.

Introduction of Phosphoketolase and Phosphotransacetylase Allows Growth of PDC-KO Cells without Exogenous Two-Carbon Substrate Supplementation Pyruvate decarboxylase knockout (PDC-KO) yeast strains are unable to grow in media containing 2% glucose as the sole carbon source, but can grow in 2% glucose supplemented with ethanol as shown with a strain transformed with one or more plasmids encoding members of the butanediol pathway (described in U.S. Patent Application Publication No. 20090305363, herein incorporated by reference). To test whether the introduction of the phosphoketolase and phosphotransacetylase genes could support growth of PDC-KO cells, PDC-KO yeast were transformed with the phosphoketolase and phosphotransacetylase gene (as described in Example 3) and with the vector pRS423CUP1-alsS+F13A-budA (described in U.S. Patent Application Publication No. 20090155870, herein incorporated by reference) encoding members of the butanediol pathway. After cultivation in media containing 2% glucose (synthetic complete minus his and ura) supplemented with 0.05% v/v ethanol, cultures were diluted into the same media lacking ethanol (starting OD=0.1, 20 ml medium in a 125 ml vented flask). For comparison, a control PDC-KO strain without introduction of the phosphoketolase and phosphotransacetylase genes was also diluted into medium supplemented with ethanol (0.05% vol/vol). The optical density at 600 nm was measured during growth (results shown in FIG. 2 and Table 13).

TABLE 13

| Strain | Condition | | | |
| --- | --- | --- | --- | --- |
|  | 0 h OD | 16 h OD | 22 h OD | 41.3 h OD |
| xpk A | 0.1 | 2.07 | 5.63 | 9.64 |
| xpk B | 0.1 | 2.44 | 5.93 | 9.78 |
| xpkC | 0.1 | 2.26 | 5.83 | 9.96 |
| control A | 0.1 | 0.47 | 0.5 | 0.822 |
| control B | 0.1 | 0.45 | 0.51 | 0.849 |
| control C | 0.1 | 0.5 | 0.52 | 0.879 |
| cont A w/EtOH | 0.1 | 2.01 | 5.49 | 11.44 |
| cont B w/EtOH | 0.1 | 2.16 | 5.7 | 11.5 |
| cont C w/EtOH | 0.1 | 2.12 | 5.76 | 11.76 |

The growth of PDC-KO yeast transformed with phosphoketolase and phosphotransacetylase in media that was not supplemented with ethanol (xpkA-xpkC, representing n=3 results) was indistinguishable from the growth of PDC-KO yeast strains grown in media containing 2% glucose that was supplemented with ethanol (cont A-cont C w/EtOH, representing n=3 results). The average growth rate of the phosphoketolase- and phosphotransacetylase-transformed strains under these conditions was 0.19 h$^{-1}$, A growth rate of 0.23 h$^{-1}$ for the phosphoketolase- and phosphotransacetylase-transformed strains was observed upon culturing under the same conditions with higher aeration (data not shown). PDC-KO yeast strains grown in media containing 2% glucose that was not supplemented with ethanol showed some growth in the first 16 hours, but then grew at a rate of only 0.01 h$^{-1}$ (control A-control C, representing n=3 results).

Example 5

Construction of Pyruvate Decarboxylase Knockout (PDC-KO) Yeast Strains Containing Either Phosphoketolase or Phosphotransacetylase Genes The integration vector described above (pUC19-URA3::pdc1::GPD-xpk1+ADH1-eutD) was modified to eliminate either the xpk1 phosphoketolase gene or the eutD phosphotransacetylase gene. Specifically, to remove eutD, the integration vector was digested with the ClaI and SpeI restriction enzymes to remove a 0.6 kb region from the eutD coding sequence, forming the vector pUC19-URA3::pdc1::GPD-xpk1. To remove xpk1, the integration vector was digested with the SpeI and KpnI restriction enzymes to remove the 3.4 kb region from SpeI to KpnI, forming the vector pUC19-URA3::pdc1::ADH-eutD. The resulting vectors, were linearized with digestion with the AflII restriction enzyme and transformed into BP913/pRS423::CUP1-alsS+FBA-budA cells (described in Example 3). Transformed cells were screened by PCR to confirm integration at the pdc1 locus and cultured, as described above.

Example 6

Introduction of Phosphoketolase Allows Growth of PDC-KO Cells without Exogenous Two Carbon Substrate Supplementation To test whether the introduction of either the phosphoketolase or phosphotransacetylase genes could support the growth of PDC-KO cells, PDC-KO yeast were transformed with either the phosphoketolase or phosphotransacetylase genes (as described in Example 5) and with the vector pRS423::CUP1-alsS+FBA-budA encoding members of the butanediol pathway (as described in Example 4). After cultivation in media containing 2% glucose (synthetic complete minus his and ura) supplemented with 0.05% v/v ethanol, cultures were diluted into the same media lacking ethanol (starting OD=0.1, 20 ml medium in a 125 ml vented flask). For comparison, a PDC-KO strain without introduction of the phosphoketolase or phosphotransacetylase genes were grown under the same conditions. The optical density at 600 nm was measured during growth (results shown in FIG. 3 and Table 15).

TABLE 15

| Strain | 0 h OD | 24 h OD |
| --- | --- | --- |
| xpk1 + eutD | 0.1 | 7.48 |
| none (control) | 0.1 | 0.575 |
| eutD only | 0.1 | 0.338 |
| eutD only | 0.1 | 0.28 |
| xpk1 only | 0.1 | 6.74 |
| xpk1 only | 0.1 | 7.26 |

Figure 3:
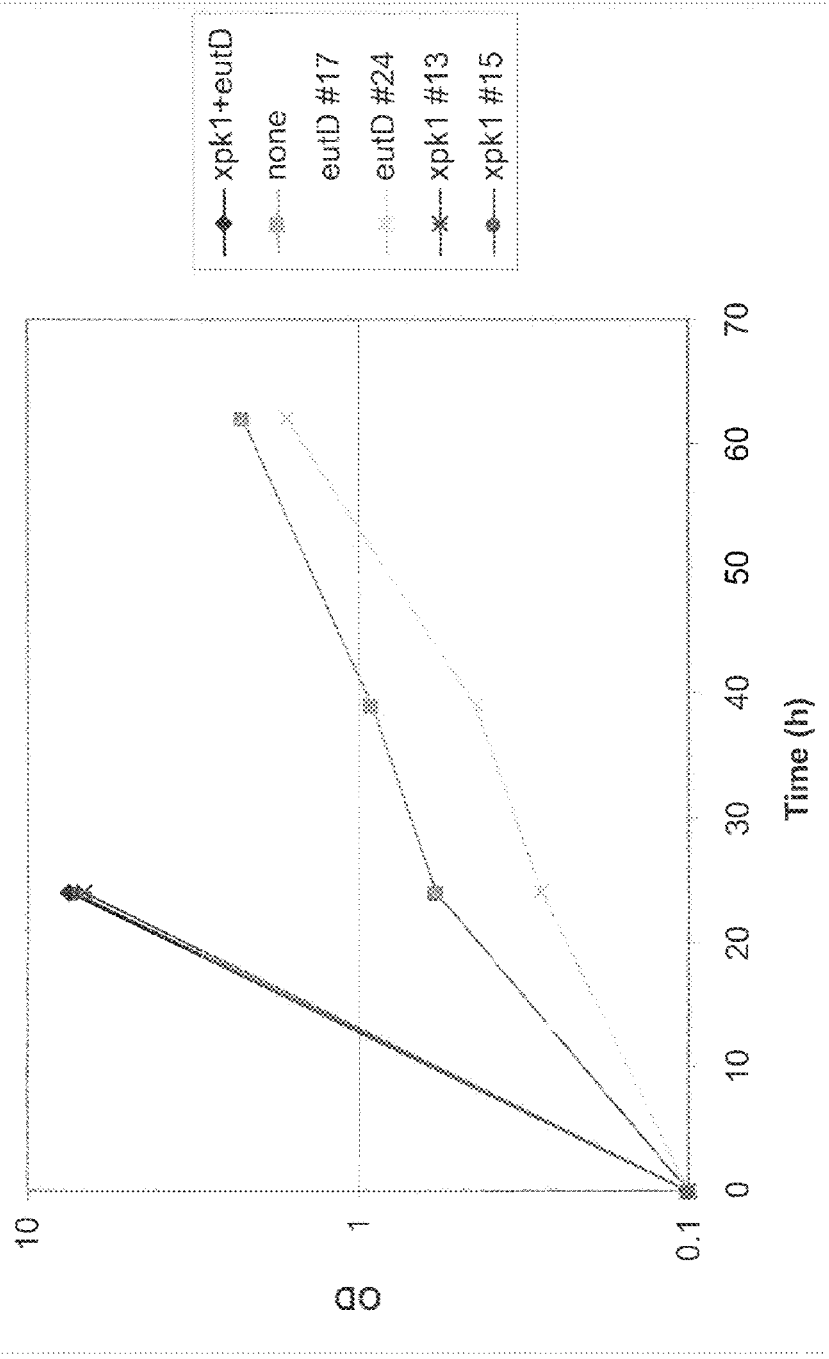
FIG. 3 depicts the growth of PDC-KO yeast strains expressing phosphoketolase and/or phosphotransacetylase in without exogenous carbon substrate supplementation.

The growth of PDC-KO yeast transformed with phosphoketolase in media that was not supplemented with exogenous carbon substrate (xpk1, FIG. 3) was indistinguishable from the growth of PDC-KO yeast transformed with phosphoketolase and phosphotransacetylase grown in media containing 2% glucose that was supplemented with ethanol (xpk1+eutD, FIG. 3). The growth of PDC-KO yeast transformed with phosphotransacetylase (eutD, FIG. 3) was not significantly improved compared to PDC-KO yeast strains in media that was not supplemented with exogenous two-carbon substrate (none, FIG. 3).

Example 7

Introduction of Phosphoketolase to PDC-KO Cells Increases Glucose Consumption and Butanediol Yield To test the effects of introduction of p iosphoketolase into PDC-KO cells on glucose consumption and butanediol yield, PDC-KO yeast ransformed with either (1) phosphoketolase and phosphotransacetylase (as described in Example 4) and the vector pRS423::CUP1-alsS+FBA-budA encoding members of the butanediol (BDO pathway (as described in Example 4 ) ("Xpk" in Table 16 below); or with (2) the vector pRS423::CUP1-alsS+FBA-budA encoding members of the butanediol pathway ("Control" in Table 6 below).

After cultivation in medium containing 2% glucose (synthetic complete minus histidine and uracil) supplemented with 0.05% ethanol, Xpk and Control cultures were diluted into medium without ethanol (starting OD=0.1, 20 ml, medium in a 125 ml vented flask). Glucose consumption and butanediol yield of Xpk and Control cultures were measured by HPLC analysis of culture media for amount of glucose and butanediol as shown in the Table below.

TABLE 16

Introduction of Phosphoketolase Increases Glucose Consumption and Butanediol Yield of PDC-KO Cells.

| Strains | Glucose consumed (mM) | Butanediol Molar Yield |
|---|---|---|
| Xpk (n = 3) | 73.9 ± 2.4 | 0.475 ± 0.001 |
| Control (n = 3) | 48.3 ± 0.6 | 0.359 ± 0.003 |

The glucose consumption of Xpk cells (n=3) was nearly twice the amount of glucose consumption of control strains (n=3). In addition, the butanediol molar yield of Xpk cells was increased compared to the butanediol molar yield of Control cells.

Example 8

Construction of an Additional Phosphoketolase Pathway Integration Vector

A phosphoketolase/phosphotransacetylase integration vector similar to the one described in Example 2 was constructed. In this case the xpk1 and eutD gene constricts were cloned so that they would be integrated immediately downstream of the Δpdc1::ilvD(Sm) locus of BP913. To do this, the intergenic region between ilvD(Sm) and TRX1 was amplified from BP913 genomic DNA using primers N1110 and N1111 (SEQ ID Nos. 653 and 654). This was cloned into pUC19-URA3-MCS at the PmeI site, as follows. The ilvD-TRX1 PCR product was phosphorylated with polynucleotide kinase (NEB Cat. No. MO201), the vector was prepared by digesting with PmeI and treating with calf intestinal phosphatase, the two fragments were ligated overnight and cloned into E. coli Stb13 cells. Clones were screened by PCR (using N1110 and N1111 primers) and then digested with BsgI to determine the orientation of the ilvD-TRX1 insertion. One clone from each orientation (pUC19-URA3::ilvD-TRX1 A and B was carried over to the next step: addition of the xpk1/eutD expression cassette. The xpk1/eutD expression cassette from pRS426::GPD-xpk1+ADH1-eutD was obtained by digestion with BglII and EcoRV. The 5' overhanging DNA was filled in using Klenow Fragment. pUC19-URA3::ilvD-TRX1 was linearized with AflII and the 5' overhanging DNA was filled in using Klenow fragment. This vector was then ligated with the prepared xpk1/eutD cassette. Ligation reactions were transformed into E. coli Stb13 cells. Clones were screened using primers for eutD (N1041 and N1042) and then digested with BamHI to determine orientation of the xpk1/eutD cassette relative to the ilvD-TRX1 DNA sequence.

The URA3 marker gene was then replaced with a geneticin resistance marker as follows. A chimeric geneticin resistance gene was constructed that contained the *Kluyveromyces lactis* TEF1 promoter and terminator (TEF1p-kan-TEF1t gene, provided as SEQ ID No. 655). This gene was maintained in a pUC19 vector (cloned at the SmaI site). The kan gene was isolated from pUC19 by first digesting with KpnI, removal of 3' overhanging DNA using Klenow Fragment (NEB, Cat. No. M212), digesting, with HincII and then gel purifying the 1.8 kb gene fragment (Zymoclean™ Gel DNA Recovery Kit, Cat. No. D4001, Zymo Research, Orange, Calif.). The URA3 marker was removed from pUC19-URA3::ilvD::GPD-xpk1+ADH1-eutD::TRX1 (paragraph above) using NsiI and NaeI (the 3' overhanging DNA from NsiI digestion was removed with Klenow fragment). The vector and kan gene were ligated overnight and transformed into E. coli Stb13 cells. Clones were screened by PCR using primers BK468 and either N1090 or N1113 (SEQ ID Nos. 656, 657, and 658, respectively)—positive PCR results indicate presence and orientation of kan gene. Clones in both orientations were digested with PmeI and transformed into BP913 with selection on yeast extract-peptone medium supplied with 1% (v/v) ethanol as carbon source and 200 μg/ml geneticin (G418). A single transformant was obtained, as confirmed by PCR (primers N886 and oBP264 for the 5' end N1090 and oBP512 for the 3' end, SEQ ID Nos.659, 646, 657, and 660, respectively). FIG. 6 depicts the locus after integration of the plasmid.

Example 9

Construction of an Isobutanol-Producing Strain Carrying the Phosphoketolase Pathway The strain described in Example 8 was transformed with 2 plasmids containing genes for an isobutanol pathway pYZ090 and pYZ067 (SEQ ID NOs: 1892 and 1891).

pYZ090 was constructed to contain a chimeric gene having the coding region of the alsS gene from *Bacillus subtilis* (nt position 457-2172) expressed from the yeast CUP1 promoter (nt 2-449) and followed by the CYC1 terminator (nt 2181-2430) for expression of ALS, and a chimeric gene having the coding region of the ilvC gene from *Lactococcus lactis* (nt 3634-4656) expressed from the yeast ILV5 promoter (2433-3626) and followed by the ILV5 terminator (nt 4682-5304) for expression of KARI. pYZ067 was constructed to contain the following chimeric genes: 1) the coding region of the ilvD gene from *S. mutans* UA159 with a C-terminal Lumio tag (nt 2260-3972) expressed from the yeast FBA1 promoter (nt 1661-2250) followed by the FBA1 terminator (nt 40005-4317) for expression of dihydroxy acid dehydratase, 2) the coding region for horse liver ADH (nt 4680-5807) expressed from the yeast GPM1 promoter (nt 5819-6575) followed by the ADH1 terminator (nt 4356-4671) for expression of alcohol dehydrogenase, and 3) the coding region of the kivD gene from *Lactococcus* lactis (nt 7175-8821) expressed from the yeast TDH3 promoter (nt 8830-9493) followed by the TDH3 terminator (nt 6582-7161) for expression of ketoisovalerate decarboxylase.

Transformants were obtained on synthetic complete medium lacking uracil and histidine with 1% (v/v) ethanol as carbon source and 100 µg/ml geneticin. Control strains (BP913) were also transformed with the same plasmids and plated without geneticin. A number of transformants were then patched to the same medium containing 2% glucose as carbon source and supplemented with 0.05% (v/v) ethanol. After 36 hours, patches were used to inoculate liquid medium (same composition as the plates). After 48 hours, ODs for both phosphoketolase pathway and control strains were similar (ca. 4-5 OD) and all were subcultured into medium lacking ethanol (i.e. no exogenous two-carbon substrate source). The phosphoketolase cultures grew without ethanol supplementation, similar to ethanol supplemented control strains. Results are shown in FIG. 7A (and Table 17A). These were subcultured again to confirm growth rates, and results are shown in FIG. 7B (and Table 17B). Phosphoketolase strains appeared to have a decreased lag phase compared to controls, but the exponential growth rates were not statistically different (average rate of $0.16h^{-1}$).

TABLE 17A

| Strain | Condition | |
|---|---|---|
| | 0 h OD | 18.3 h OD |
| xpk ISO 1 | 0.1 | 2.3 |
| xpk ISO 2 | 0.1 | 2.2 |
| xpk ISO 3 | 0.1 | 2.2 |
| ISO (no EtOH) 1 | 0.1 | 0.48 |
| ISO (no EtOH) 2 | 0.1 | 0.41 |
| ISO (no EtOH) 3 | 0.1 | 0.47 |
| ISO (+EtOH) 1 | 0.1 | 2.5 |
| ISO (+EtOH) 2 | 0.1 | 2.6 |
| ISO (+EtOH) 3 | 0.1 | 2.4 |

TABLE 17B

| Strain | Condition | | | | |
|---|---|---|---|---|---|
| | 0 h OD | 6.5 h OD | 23 h OD | 27 h OD | 48 h OD |
| xpk ISO 1 | 0.1 | 0.18 | 2.91 | 4 | 4.4 |
| xpk ISO 2 | 0.1 | 0.14 | 1.54 | 2.88 | 4.6 |
| xpk ISO 3 | 0.1 | 0.16 | 2.15 | 3.54 | 4.3 |
| ISO (+EtOH) 1 | 0.1 | 0.14 | 2.21 | 3.46 | 4.4 |
| ISO (+EtOH) 2 | 0.1 | 0.11 | 1.13 | 2.18 | 4.2 |
| ISO (+EtOH) 3 | 0.1 | 0.1 | 0.84 | 1.6 | 4.4 |

Example 10

Construction of *Saccharomyces cerevisiae* Strain BP913

The purpose of this example is to describe the construction of *Saccharomyces cerevisiae* strain BP913. The strain was derived from CEN.PK 113-7D (CBS 8340; Centraalbureau voor Schimmelcultures (CBS) Fungal Biodiversity Centre, Netherlands) and contains deletions of the following genes: URA3, HIS3, PDC1, PDC5, and PDC6.

Deletions, which completely removed the entire coding sequence, were created by homologous recombination with PCR fragments containing regions of homology upstream and downstream of the target gene and either a G418 resistance marker or URA3 gene for selection of transformants. The G418 resistance marker, flanked by loxP sites, was removed using Cre recombinase. The URA3 gene was removed by homologous recombination to create a scarless deletion.

In general, the PCR cassette for each scarless deletion was made by combining four fragments, A-B-U-C, by overlapping PCR. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene). Fragments A and C, each 500 bp long, corresponded to the 500 bp immediately upstream of the target gene (Fragment A) and the 3' 500 by of the target gene (Fragment C). Fragments A and C were used for integration of the cassette into the chromosome by homologous recombination. Fragment B (500 by long) corresponded to the 500 bp immediately downstream of the target gene and was used for excision of the URA3 marker and Fragment C from the chromosome by homologous recombination, as a direct repeat of the sequence corresponding to Fragment B was created upon integration of the cassette into the chromosome. Using the PCR product ABUC cassette, the URA3 marker was first integrated into and then excised from the chromosome by homologous recombination. The initial integration deleted the gene, excluding the 3' 500 bp. Upon excision, the 3' 500 bp region of the gene was also deleted. For integration of genes using this method, the gene to be integrated was included in the PCR cassette between fragments A and B. URA3 Deletion To delete the endogenous URA3 coding region, a ura3::loxP-kanMX-loxP cassette was PCR-amplified from pLA54 template DNA (SEQ ID NO: 661). pLA54 contains the *K. lactis* TEF1 promoter ar d kanMX marker, and is flanked by loxP sites to allow recombination with Cre recombinase and removal of the marker. PCR was done using Phusion DNA polymerase and primers BK505 and BK506 (SEQ ID NOs: 662 and 663). The URA3 portion of each primer was derived from the 5' region upstream of the URA3 promoter and 3' region downstream of the coding region such that integration of the loxP-kanMX-loxP marker resulted in replacement of the URA3 coding region. The PCR product was transformed into CEN.PK 113-7D using standard genetic techniques (Methods in Yeast Genetics, 2005, Cold Spring Harbor Laboratory Press, Cold Spring Harbor, N.Y., pp. 201-202) and transformants were selected on YPD containing G418 (100 µg/ml) at 30 C. Transformants were screened to verify correct integration by PCR using primers LA468 and LA492 (SEQ ID NOs: 664 and 665) and designated CEN.PK 113-7D Δura3::kanMX.

HIS3 Deletion

The four fragments for the PCR cassette for the scarless HIS3 deletion were amplified using Phusion High Fidelity PCR Master Mix (New England BioLabs) and CEN.PK 113-7D genomic DNA as template, prepared with a Centra Puregene Yeast/Bact kit (Qiagen; Valencia, Calif.). HIS3 Fragment A was amplified with primer oBP452 (SEQ ID NO: 666) and primer oBP453 (SEQ ID NO: 667), containing a 5' tail with homology to the 5' end of HIS3 Fragment B. HIS3 Fragmeht B was amplified with primer oBP454 (SEQ ID NO: 668), containing a 5' tail with homology to the 3' end of HIS3 Fragment A, and primer oBP455 (SEQ ID NO: 669), containing a 5' tail with homology to the 5' end of HIS3 Fragment U. HIS3 Fragment U was amplified with primer oBP456 (SEQ ID NO: 670), containing a 5' tail with homology to the 3' end of HIS3 Fragment B, and primer oBP457 (SEQ ID NO: 671), containing a 5' tail with homology to the 5' end of HIS3 Fragment C. HIS3 Fragment C was amplified with primer oBP458 (SEQ ID NO: 672), containing a 5' tail with homology to the 3' end of HIS3 Fragment U, and primer oBP459 (SEQ ID NO: 673). PCR products were purified with a PCR Purification kit (Qiagen, Valencia, Calif.). HIS3 Fragment AB was created by overlapping PCR by mixing HIS3 Fragment A and HIS3 Fragment B and amplifying with primers oBP452 (SEQ ID NO: 666) and oBP455 (SEQ ID NO: 669). HIS3 Fragment UC was created by overlapping PCR by mixing HIS3 Fragment U and HIS3 Fragment C and amplifying with primers oBP456 (SEQ ID NO: 670) and oBP459 (SEQ ID NO: 673). The resulting PCR products were purified on an agarose gel followed by a Gel Extraction kit (Qiagen, Valencia, Calif.). The HIS3 ABUC cassette was created by overlapping PCR by mixing HIS3 Fragment AB and HIS3 Fragment UC and amplifying with primers oBP452 (SEQ ID NO: 666) and oBP459 (SEQ ID NO: 673). The PCR product was purified with a PCR Purification kit (Qiagen, Valencia, Calif.).

Competent cells of CEN.PK 113-7D) Δura3::kanMX were made and transformed with the HIS3 ABUC PCR cassette using a Frozen-EZ Yeast Transformation II kit (Zymo Research, Orange, Calif.). Transformation mixtures were plated on synthetic complete media lacking uracil supplemented with 2% glucose at 30 C. Transformants with a his knockout were screened for by PCR with primers oBP460 (SEQ ID NO: 674) and oBP461 (SEQ ID NO: 671) using genomic DNA prepared with a Gentra Puregene Yeast/Bact kit (Qiagen). A correct transformant was selected as strain CEN.PK 113-7D Δura3::kanMX Δhis3::URA3.

KanMX Marker Removal from the Δura3 Site and URA3 Marker Removal from the Δhis3 Site The KanMX marker was removed by transforming CEN.PK 113-7D Δura3::kanMX Δhis3::URA3 with pRS423::PGAL1-cre (SEQ ID NO: 715) using a Frozen-EZ Yeast Transformation II kit (Zymo Research, Orange, Calif.) and plating on synthetic complete medium lacking histidine and uracil supplemented with 2% glucose at 30 C. Transformants were grown in YP supplemented with 1% galactose at 30 C for ~6 hours to induce the Cre recombinase and KanMX marker excision and plated onto YPD (2% glucose) plates at 30 C for recovery. An isolate was grown overnight in YPD and plated on synthetic complete medium containing 5-fluoro-orotic acid (0.1%) at 30 C to select for isolates that lost the URA3 marker. 5-FOA resistant isolates were grown in and plated on YPD for removal of the pRS423::PGAL1-cre plasmid. Isolates were checked for loss of the KanMX marker, URA3 marker, and pRS423::PGAL1-cre plasmid by assaying, growth on YPD+G418 plates, synthetic complete medium lacking uracil plates, and synthetic complete medium lacking histidine plates. A correct isolate that was sensitive to G418 and auxotrophic for uracil and histidine was selected as strain CEN.PK 113-7D Δura3::loxP Δhis3 and designated as BP857. The deletions and marker removal were confirmed by PCR and sequencing with primers oBP450 (SEQ ID NO: 676) and oBP451 (SEQ ID NO: 677) for Δura3 and primers oBP460 (SEQ ID NO: 674) and oBP461 (SEQ ID NO: 675) for Δhis3 using genomic DNA prepared with a Gentra Puregene Yeast/Bact kit (Qiagen, Valencia, Calif.).

PDC6 Deletion

The four fragments for the PCR cassette for the starless PDC6 deletion were amplified using Phusion High Fidelity PCR Master Mix (New England BioLabs, Ipswich, Mass.) and CEN.PK 113-7D genomic DNA as template, prepared with a Gentra Puregene Yeast/Bact kit (Qiagen). PDC6 Fragment A was amplified with primer oBP440 (SEQ ID NO: 670) and primer oBP441 (SEQ ID NO: 679), containing a 5' tail with homology to the 5' end of PDC6 Fragment B. PDC6 Fragment B was amplified with primer oBP442 (SEQ ID NO: 680), containing a 5' tail with homology to the 3' end of PDC6 Fragment A, and primer oBP443 (SEQ ID NO: 681), containing, a 5' tail with homology to the 5' end of PDC6 Fragment U. PDC6 Fragment U was amplified with primer oBP444 (SEQ ID NO: 682), containing a 5' tail with homology to the 3' end of PDC6 Fragment B, and primer oBP445 (SEQ ID NO: 683), containing a 5' tail with homology to the 5' end of PDC6 Fragment C. PDC6 Fragment C was amplified with primer oBP446 (SEQ ID NO: 684), containing a 5' tail with homology to the 3' end of PDC6 Fragment U, and primer oBP447 (SEQ ID NO: 685). PCR products were purified with, a PCR Purification kit (Qiagen). PDC6 Fragment AB was created by overlapping PCR by mixing PDC6 Fragment A and PDC6 Fragment B and amplifying with primers oBP440 (SEQ ID NO: 678) and oBP443 (SEQ ID NO: 681). PDC6 Fragment UC was created by overlapping PCR by mixing PDC6 Fragment U and PDC6 Fragment C and amplifying with primers oBP444 (SEQ ID NO: 682) and oBP447 (SEQ ID NO: 685). The resulting PCR products were purified on an agarose gel followed by a Gel Extraction kit (Qiagen). The PDC6 ABUC cassette was created by overlapping PCR by mixing PDC6 Fragment AB and PDC6 Fragment UC and amplifying with primers oBP440 (SEQ ID NO: 678) and oBP447 (SEQ ID NO 685). The PCR product was purified with a PCR Purification kit (Qiagen).

Competent cells of CEN.PK 113-7D Δura3::loxP Δhis3 were made and transformed with the PDC6 ABUC PCR cassette using a Frozen-EZ Yeast Transformation II kit (Zymo Research), Transformation mixtures were plated on synthetic complete media lacking uracil supplemented with 2% glucose at 30 C. Transformants with a pdc6 knockout were screened for by PCR with primers oBP448 (SEQ ID NO 686) and oBP449 (SEQ ID NO; 687) using genomic DNA prepared with a Gentra Puregene Yeast/Bact kit (Qiagen). A correct transformant was selected as strain CEN.PK 113-7D Δura3::loxP Δhis3 Δpdc6::URA3.

CEN.PK 113-7D Δura3::loxP Δhis3 Δpdc6::URA3 was grown overnight in YPD and plated on synthetic complete medium containing 5-fluoro-orotic acid (0,1%) at 30 C to select for isolates that lost the URA3 marker. The deletion and marker removal were confirmed by PCR and sequencing with primers oBP448 (SEQ ID NO: 686) and oBP449 (SEQ ID NO 687) using genomic DNA prepared with a Gentra Puregene Yeast/Bact kit (Qiagen). The absence of the PDC6 gene from the isolate was demonstrated by a negative PCR result using primers specific for the coding sequence of PDC6, oBP554 (SEQ ID NO 688) and oBP555 (SEQ ID NO 689). The correct isolate was selected as strain CEN.PK 113-7D Δura3::loxP Δhis3 Δpdc6 and designated as BP891.

PDC1 Deletion ilvDSm Integration

The PDC1 gene was deleted and replaced with the ilvD coding region from *Streptococcus mutans* ATCC #700610 (SEQ ID NO: 1886). The A fragment followed by the ilvD coding region from *Streptococcus mutans* for the PCR cassette for the PDC1 deletion-ilvDSm integration was amplified using Phusion High Fidelity PCR Master Mix (New England BioLabs) and NYLA83 genomic DNA as template (construction of strain NYLA83 is described in U.S. Application Pub. No. 20110124060 A1, incorporated herein by reference), prepared with a Gentra Puregene Yeast/Bact kit (Qiagen). PDC1 Fragment A-ilvDSm was amplified with primer oBP513 (SEQ ID NO: 690) and primer oBP515 (SEQ ID NO: 691), containing a 5' tail with homology to the 5' end of PDC1 Fragment B. The B, U, and C fragments for the PCR cassette for the PDC1 deletion-ilvDSm integration were amplified using Phusion High Fidelity PCR Master Mix (New England BioLabs) and CEN.PK 113-7D genomic DNA as template, prepared with a Gentra Puregene Yeast/Bact kit (Qiagen). PDC1 Fragment B was amplified with primer oBP516 (SEQ ID NO: 692), containing a 5' tail with homology to the 3' end of PDC1 Fragment A-ilvDSm, and primer oBP517 (SEQ ID NO: 693), containing a 5' tail with homology to the 5' end of PDC1 Fragment U. PDC1 Fragment U was amplified with primer oBP518 (SEQ ID NO: 694), containing a 5' tail with homology to the 3' end of PDC1 Fragment B, and primer oBP519 (SEQ ID NO: 695), containing a 5' tail with homology to the 5' end of PDC1 Fragment C. PDC1 Fragment C was amplified with primer oBP520 (SEQ ID NO: 696), containing a 5' tail with homology to the 3' end of PDC1 Fragment U, and primer oBP521 (SEQ ID NO: 697). PCR products were purified with a PCR Purification kit (Qiagen). PDC1 Fragment A-ilvDSm-B was created by overlapping PCR by mixing PDC1 Fragment A-ilvDSrn and PDC1 Fragment B and amplifying with primers oBP513 (SEQ ID NO: 690) and oBP517 (SEQ ID NO: 693). PDC Fragment UC was created by overlapping PCR by mixing PDC1 Fragment U and PDC1 Fragment C and amplifying with primers oBP518 (SEQ ID NO: 694) and oBP521 (SEQ ID NO: 697). The resulting PCR products were purified on an agarose gel followed by a Gel Extraction kit (Qiagen). The PDC 1 A-ilvDSm-BUC cassette was created by overlapping PCR by mixing PDC 1 Fragment A-ilvDSm-B and PDC1 Fragment UC and amplifying with primers oBP513 (SEQ ID NO 690) and oBP521 (SEQ ID NO: 697). The PCR product was purified with a PCR Purification kit (Qiagen).

Competent cells of CEN.PK 113-7D Δura3::loxP Δhis3 Δpdc6 were made and transformed with the PDC1 A-ilvDSm-BUC PCR cassette using a Frozen-EZ Yeast Transformation II kit (Zymo Research). Transformation mixtures were plated on synthetic complete media lacking uracil supplemented with 2% glucose at 30 C. Transformants with a pdc1 knockout ilvDSm integration were screened for by PCR with primers oBP511 (SEQ ID NO: 698) and oBP512 (SEQ ID NO: 699) using genomic DNA prepared with a Gentra Puregene Yeast/Bact kit (Qiagen). The absence of the PDC1 gene from the isolate was demonstrated by a negative PCR result using primers specific for the coding sequence of PDC1, oBP550 (SEQ ID NO: 700) and oBP551 (SEQ ID NO: 701). A correct transformant was selected as strain CEN.PK 113-7D Δura3::loxP Δhis3 Δpdc6 Δpdc 1::ilvDSm-URA3.

CEN.PK 113-7D Δura3::loxP Δhis3 Δpdc6 Δpdc1::ilvDSm-URA3 was grown overnight in YPD and plated on synthetic complete medium containing 5-fluoro-orotic acid (0.1%) at 30 C to select for isolates that lost the URA3 marker. The deletion of PDC1, integration of ilvDSm, and marker removal were confirmed by PCR and sequencing with primers oBP511 (SEQ ID NO: 698) and oBP512 (SEQ ID NO: 699) using genomic DNA prepared with a Gentra Puregene Yeast/Bact kit (Qiagen). The correct isolate was selected as strain CEN.PK 113-7D Δura3::loxP Δhis3 Δpdc6 Δpdc1::ilvDSm and designated as BP907.

PDC5 Deletion sadB Integration

The PDC5 gene was deleted and replaced with the sadB coding region from *Achromobacter* xylosoxidans. A segment of the PCR cassette for the PDC5 deletion-sadB integration was first cloned into plasmid pUC19-URA3MCS (described in Example 2). The coding sequence of sadB (SEQ ID NO: 718) and PDC5 Fragment B were cloned into pUC19-URA3MCS to create the sadB-BU portion of the PDC5 A-sadB-BUC PCR cassette. The coding sequence of sadB was amplified using pLH468-sadB (SEQ ID NO: 716) as template with primer oBP530 (SEQ ID NO: 702), containing an AscI restriction site, and primer oBP531 (SEQ ID NO: 703), containing a 5' tail with homology to the 5' end of PDC5 Fragment B. PDC5 Fragment B was amplified from CEN.PK 113-7D genomic DNA with primer oBP532 (SEQ ID NO: 704), containing a 5' tail with homology to the 3' end of sadB, and primer oBP533 (SEQ ID NO: 705), containing a PmeI restriction site PCR products were purified with a PCR Purification kit (Qiagen). sadB-PDC5 Fragment B was created by overlapping PCR by mixing the sadB and PDC5 Fragment B PCR products and amplifying with primers oBP530 (SEQ ID NO: 702) and oBP533 (SEQ ID NO 705). The resulting PCR product was digested with AscI and PmeI and ligated with T4 DNA ligase into the corresponding sites of pUC19-URA3MCS after digestion with the appropriate enzymes. The resulting plasmid was used as a template for amplification of sadB-Fragment B-Fragment U using primers oBP536 (SEQ ID NO: 706) and oBP546 (SEQ ID NO: 707), containing a 5' tail with homology to the 5' end of PDC5 Fragment C. PDC5 Fragment C was amplified from CEN.PK 113-7D genomic DNA with primer oBP547 (SEQ ID NO: 708), containing a 5' tail with homology to the 3' end of PDC5 sadB-Fragment B-Fragment U, and primer oBP539 (SEQ ID NO: 709). PCR products were purified with a PCR Purification kit (Qiagen). PDC5 sadB-Fragment B-Fragment U-Fragment C was created by overlapping PCR by mixing PDC5 sadB-Fragment B-Fragment U and PDC5 Fragment C and amplifying with primers oBP536 (SEQ ID NO: 706) and oBP539 (SEQ II) NO: 709). The resulting PCR product was purified on an agarose gel followed by a Gel Extraction kit (Qiagen). The PDC5 A-sadB-BUC cassette was created by amplifying PDC5 sadB-Fragment B-Fragment U-Fragment C with primers oBP542 (SEQ ID NO: 710) containing a 5' tail with homology to the 50 nucleotides immediately upstream of the native PDC5 coding sequence, and oBP539 (SEQ ID NO: 709). The PCR product was purified with a PCR Purification kit (Qiagen).

Competent cells of CEN.PK 113-7D Δura3::loxP Δhis3 Δpdc6 Δpdc1::ilvDSm were made and transformed with the PDC5 A-sadB-13UC PCR cassette using a Frozen-EZ Yeast Transformation II kit (Zymo Research). Transformation mixtures were plated on synthetic complete media lacking uracil supplemented with 1% ethanol (no glucose) at 30 C. Transformants with a pdc5 knockout sadB integration were screened for by PCR with primers oBP540 (SEQ ID NO: 711) and oBP541 (SEQ ID NO: 712) using genomic DNA prepared with a Gentra Puregene Yeast/Bact kit (Qiagen). The absence of the PDC5 gene from the isolate was demonstrated by a negative PCR result using primers specific for the coding sequence of PDC5, oBP552 (SEQ ID NO: 713) and oBP553 (SEQ ID NO: 714). A correct transformant was selected as strain CEN.PK 113-7D Δura3::loxP Δhis3 Δpdc6 Δpdc1::ilvDSrn Δpdc5::sadB-URA3.

CEN.PK 113-7D Δura3::loxP Δhis3 Δpdc6 Δpdc1::ilvDSm Δpdc5::sadB-URA3 was grown overnight in YPE (1% ethanol) and plated on synthetic complete medium supplemented with ethanol (no glucose) and containing 5-fluoro-orotic acid (0.1%) at 30 C to select for isolates that lost the URA3 marker. The deletion, of PDC5, integration of sadB, and marker removal were confirmed by PCR with primers oBP540 (SEQ ID NO 711) and oBP541 (SEQ ID NO: 712) using genomic DNA prepared with a Gentra Puregene Yeast/Bact kit (Qiagen). The correct isolate was selected as strain CEN.PK 113-7D Δura3::loxP Δhis3 Δpdc6 Δpdc1::ilvDSm Δpdc5::sadB and designated as BP913.

Example 11

Construction of Strain NYLA83

This example describes insertion-inactivation of endogenous PDC1 and PDC6 genes of S. cerevisiae. PDC1, PDC5, and PDC6 genes encode the three major isozymes of pyruvate decarboxylase. The resulting strain was used as described in Example 10.
Construction of pRS425::GPM-sadB A DNA fragment encoding a butanol dehydrogenase (SEQ ID NO: 717) from *Achromobacter xylosoxidans* (disclosed in US Patent Application Publication No. US20090269823) was cloned. The coding region of this gene called sadB for secondary alcohol dehydrogenase (SEQ ID NO: 718) was amplified using standard conditions from *A. xylosoxidans* genomic DNA, prepared using a Gentra Puregene kit (Gentra Systems, Inc., Minneapolis, Minn.; catalog number D-5500A) following the recommended protocol for gram negative organisms using forward and reverse primers N473 and N469 (SEQ ID NOs:725 and 726), respectively. The PCR product was TOPO-Blunt cloned into pCR4 BLUNT (Invitrogen) to produce pCR4Blunt::sadB, which was transformed into *E. coli* Mach-1 cells. Plasmid was subsequently isolated from four clones, and the sequence verified.

The sadB coding region was PCR amplified from pCR4Blunt::sadB. PCR primers contained additional 5' sequences that would overlap with the yeast GPM 1 promoter and the ADH1 terminator (N583 and N584, provided as SEQ ID NOs:727 and 728). The PCR product was then cloned using "gap repair" methodology in *Saccharomyces cerevisiae* (Ma et al. ibid) as follows. The yeast-*E. coli* shuttle vector pRS425::GPM::kivD::ADH which contains the GPM1 promoter (SEQ ID NO:721), kivD coding region from *Lactococcus lactis* (SEQ D NO:719), and ADH1 terminator (SEQ ID NO:722) (described in U.S. Pat. No. 7,851,188, Example 17) was digested with BbvCI and PacI restriction enzymes to release the kivD coding region. Approximately 1 μg of the remaining vector fragment was transformed into *S. cerevisiae* strain 13Y4741 along, with 1 mg of sadB PCR product. Transformants were selected on synthetic complete medium lacking leucine. The proper recombination event, generating pRS425::GPM-sadB, was confirmed by PCR using primers N142 and N459 (SEQ ID NOs:729 and 730).
Construction of pdc6::P$_{GPM1}$-sadB Integration Cassette and PDC6 Deletion:

A pdc6:: P$_{GPM1}$-sadB-ADH/t-URA3r integration cassette was made by joining the GPM-sadB-ADHt segment (SEQ ID NO:723) from pRS425::GPM-sadB (SEQ ID NO: 720) to the URA3r gene from pUC19-URA3r. pUC19-URA3r (SEQ ID NO:724) contains the URA3 marker from pRS426 (ATCC #77107) flanked by 75 by homologous repeat sequences to allow homologous recombination in vivo and removal of the URA3 marker. The two DNA segments were joined by SOE PCR (as described by Horton et al. (1989) Gene 77:61-68) using as template pRS425::GPM-sadB and pUC19-URA3r plasmid DNAs, with Phusion DNA polymerase (New England Biolabs Inc., Beverly, Mass.; catalog no. F-5405) and primers 114117-11A through 114117-11D (SEQ ID NOs:731, 732, 733 and 734), and 114117-13A and 114117-13B (SEQ ID NOs:735 and 736).

The outer primers for the SOE PCR (114117-13A and 114117-13B) contained 5' and 3' ~50 by regions homologous to regions upstream and downstream of the PDC6 promoter and terminator, respectively. The completed cassette PCR fragment was transformed into BY4700 (ATCC #200866) and transformants were maintained on synthetic complete media lacking uracil and supplemented with 2% glucose at 30° C. using standard genetic techniques (*Methods in Yeast Genetics*, 2005, Cold Spring Harbor Laboratory Press, Cold Spring Harbor, N.Y., pp. 201-202). Transformants were screened by PCR using primers 112590-34G and 112590-34H (SEQ ID NOs:737 and 738), and 112590-34F and 112590-49E (SEQ ID NOs: 739 and 740) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain has the genotype: BY4700pdc6::P$_{Gpm1}$-sadB-ADH1t.
Construction of pdc1::P$_{PDC1}$-ilvD Integration Cassette and PDC1 Deletion:

A pdch:: P$_{PDC1}$-ilvD-FBA1t-URA3r integration cassette was made by joining the ilvD-FBA1t segment (SEQ ID NO:741) from pLH468 (SEQ ID NO: 1888) to the URA3r gene from pUC19-URA3r by SOE FCR (as described by Horton et al. (1989) Gene 77:61-68) using as template pLH468 and pUC19-UR.\3r plasmid DNAs, with Phusion DNA polymerase (New England Biolabs Inc., Beverly, Mass.; catalog no. F-540S) and primers 114117-27A through 114117-27D (SEQ ID NOs:742, 743, 744 and 745).

The outer primers for the SOE PCR (114117-27A and 114117-27D) contained 5' and 3' ~50 by regions homologous to regions downstream of the PDC1 promoter and downstream of the PDC1 coding sequence. The completed cassette PCR fragment was transformed into BY4700 pdc6:: P$_{GPM1}$-sadB-ADH1t and transformants were maintained on synthetic complete media lacking uracil and supplemented with 2% glucose at 30° C. using standard, genetic techniques (Methods in Yeast Genetics, 2005, Cold Spring Harbor Laboratory Press, Cold Spring Harbor, N.Y., pp. 201-202). Transformants were screened by PCR using primers 114117-36D and 135 (SEQ ID NOs 746 and 747), and primers 112590-49E and 112590-30F (SEQ ID NOs 740 and 748) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-UR \ media to verify the absence of growth. The resulting identified strain "NYLA67" has the genotype: BY4700 pdc6:: P$_{GPM1}$-sadB-ADH1t pdc1::_ P$_{PDC}$1-ilvD-FBA1t.
HIS3 Deletion To delete the endogenous HIS3 coding region, a his 3:URA3r2 cassette was PCR-amplified from URA3r2 template DNA (SEQ ID NO: 749). URA3r2 contains the URA3 marker from pRS426 (ATCC #77107) flanked by 500 by homologous repeat sequences to allow homologous recombination in vivo and removal of the URA3 marker. PCR was done using Phusion DNA polymerase and primers 114117-

45A and 114117-45B (SEQ ID NOs:750 and 751) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (Methods in Yeast Genetics, 2005, Cold Spring Harbor Laboratory Press, Cold Spring Harbor, N.Y., pp. 201-202) and transformants were selected on synthetic complete media lacking, uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies, from the 5-FOA plates onto SD-URA. media to verify the absence of growth. The resulting identified strain, called NYLA73, has the genotype: BY4700 pdc6 . . . $P_{GPM1}$/sadB-ADH1t ppc1:: $P_{PDC1}$-ilvD-FBA1t Δhis3.

Construction of pdc5::kanMX Integration Cassette and PDC5 Deletion:

A pdc5::kanMX4 cassette was PCR-amplified from strain YLR134W chromosomal DNA (ATCC No. 4034091) using Phusion DNA polymetase and primers PDC5::KanMXF and PDC5.:KanMXR (SEQ ID NOs:752 and 753) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (Methods in *Yeast Genetics,* 2005, Cold Spring Harbor Laboratory Press, Cold Spring Harbor, N.Y., pp. 201-202) and transformants were selected on YP media supplemented with 1% ethanol and geneticin (200 μg/ml) at 30° C. Transformants were screened by PCR to verify correct integration at the PDC locus with replacement of the PDC5 coding region using primers PDC5kofor and N175 (SEQ ID NOs: 754 and 755). The identified correct transformants have the genotype: BY4700 pdc 6:: $P_{GPM1}$-sadB-ADH1t pdc 1::$P_{PDC1}$-ilvD-FBA1t Δhis3 pdc5::kanMX4. The strain was named NYLA74.

Deletion of HXK2 (hexokinase II):

A hxk2::URA3r cassette was PCR-amplified from URA3r2 template (described above) using Phusion DNA polymerase and primers 384 and 385 (SEQ ID NOs:756 and 757) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NOs:758 and 759). The URA3r2 marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth, and by PCR to verify correct marker removal using primers N946 and N947 (SEQ ID NOs:760 and 761). The resulting identified strain named NYLA83 has the genotype: BY4700 pdc6:: $P_{GPM1}$-sadB-ADH1t pdc1:: $P_{PDC1}$-ilvD-FBA1t Δhis3 Δhxk2.

Example 12

Construction of *Saccharomyces cerevisiae* Strain PNY2257

Strain PNY2242 was constructed in several steps from BP913 (described above). First, the native GPD2 gene on Chromsome XV was deleted. The coding region was deleted using CRE-lox mediated marker removal (methodology described above), so the resulting locus contains one loxP site. The sequence of the modified locus is provided as SEQ ID NO 1899 (Upstream region=nt 1-500; loxP site=nt 531-564; Downstream region=nt 616-1115). Second, the native FRA2 gene on Chromosome VII was deleted. Elimination of FRA2 was a scarless deletion of only the coding region. The sequence of the modified locus is provided as SEQ ID NO 1900 (Upstream region=nt 1-501; Downstream region=nt 526-1025). Next, the ADH1 gene on Chromosome XV was deleted along with insertion of a chimeric gene comprised of the UAS(PGK1)—FBA1 promoter and the kivD coding region. The native ADH1 terminator was used to complete the gene. The sequence of the modified locus is provided as SEQ ID No. 1901 (Upstream region=nt 1-500; UAS(PGK1) FBA promoter=nt 509-1233; kivD coding region=nt 1242-2888; Downstream region (includes terminator)=nt 2889-3388). Next, a chimeric gene comprised of the FBA1 promoter, the alsS coding region and the CYC1 terminator was integrated into Chromosome XII, upstream of the TRX1 gene. The sequence of the modified locus is provided as SEQ ID No. 1902(Upstream region=nt 1-154; FBA1 promoter=nt 155-802; alsS CDS=nt 810-2525; CYC1 terminator=nt 2534-2788; Downstream region=nt 2790-3015). Next, two copies of a gene encoding, horse liver alcohol dehydrogenase were integrated into Chromsomes VII and XVI. On Chromosome VII, a chimeric gene comprised of the PDC1 promoter, the hADH coding region and the ADH 1 terminator were placed into the fra2Δlocus (the original deletion of FRA2 is described above). The sequence of the modified locus is provided as SEQ ID No. 1903 (Upstream region=nt 1-300; PDC1 promoter=nt 309-1178; hADH coding region=nt 1179-2306; ADH1 terminator=nt 2315-2630; Downstream region=nt 2639-2900). On Chromosome XVI, a chimeric gene comprised of the PDC5 promoter, the hADH coding region and the ADH1 terminator were integrated in, the region formerly occupied by the long term repeat element YPRCdelta15. The sequence of the modified locus is provided as SEQ ID No. 1904 (Upstream region=nt 1-150; PDC5 promoter=nt 159-696; hADH coding region=nt 697-1824; ADH1 terminator=nt 1833-2148: Downstream region=nt 2157-2656). Then the native genes YMR226c and ALD6 were deleted. Elimination of YMR226c was a scarless deletion of only the coding region. The sequence of the modified locus is provided as SEQ ID No. 1905 (Upstream region=nt 1-250; Downstream region=nt 251-451). The ALD6 coding region plus 700 by of upstream sequence were deleted using CRE-lox mediated marker removal, so the resulting locus contains one loxP site. The sequence of the modified locus is provided as SEQ ID No. 1906(Upstream region=nt 1-500; loxP site=nt 551-

584; Downstream region=nt 678-1128). The geneticin-selectable phosphoketolase expression vector described in Example 8 was transformed into the strain and confirmed as described above (the locus is depicted in FIG. 6). Finally, plasmids were introduced into the strain for expression of KARI (pLH702, plasmid SEQ ID. No. 1907) and DHAD (pYZ067DkivDDhADH, SEQ ID. No. 1908), resulting in the strain named PNY2257. A control strain containing all of the elements above except for the phosphoketolase pathway construct is called PNY2242.

Growth rates were assessed as described in previous examples. Over a 24 hour period, PNY2257 displayed growth rates without ethanol or other two-carbon supplement similar to those growth rates observed for PNY2242 with supplementation.

TABLE 6

```
HMMER2.0 [2.2g]
NAME  XFP_XPK_exp_seqs
LENG  845
ALPH  Amino
RF    no
CS    no
MAP   yes
COM   /app/public/hmmer/current/bin/hmmbuild XFP_XPK_HMM XFP_XPK_exp_seqs.aln
COM   /app/public/hmmer/current/bin/hmmcalibrate - mean 800 XFP_XPK_HMM
NSEQ  8
DATE  Fri Dec 4 15:29:49 2009
CKSUM 6589
XT    -8455 -4 -1000 -1000 -8455 -4 -8455 -4
NULT  -4 -8455
NULE  595 -1558 85 338 -294 453 -1158 197 249 902 -1085 -142 -21 -313 45 531 201 384 -1998 -644
EVD   -614.573792 0.077043
```

| HMM | A (m->m) | C (m->i) | D (m->d) | E (i->m) | F (i->i) | G (d->m) | H (d->d) | I (b->m) | K (m->e) | L | M | N | P | Q | R | S | T | V | W | Y | |
|---|---|---|---|---|---|---|---|---|---|---|---|---|---|---|---|---|---|---|---|---|---|
|   | -476 | * | -1831 | | | | | | | | | | | | | | | | | | |
| 1(M) | -579 | -646 | -1823 | -1279 | -241 | -1949 | -816 | 340 | -991 | 1145 | 2778 | -1234 | 1286 | -828 | -1131 | -1025 | -537 | 205 | -1033 | -696 | 11 |
| —    | -149 | -500 | -500  | 43    | -381 | 399   | 106  | -626 | 210  | -466 | -720 | 275   | 394  | 45   | 96    | 359   | 117  | -369 | -294  | -249 | |
| —    | -25  | -6428 | -7470 | -894 | -1115 | -701 | -1378 | -476 | * | | | | | | | | | | | | |
| 2(W) | -424 | -1143 | -649  | -112  | -1118 | -1430 | -73  | -944 | 1343 | -1091 | -364 | -285  | 1428 | 217  | 174   | -480  | -363 | -730 | 3083  | -756 | 12 |
| —    | -149 | -500 | 233   | 43    | -381 | 399   | 106  | -626 | 210  | -466 | -720 | 275   | 394  | 45   | 96    | 359   | 117  | -369 | -294  | -249 | |
| —    | -25  | -6428 | -7470 | -894 | -1115 | -701 | -1378 | * | * | | | | | | | | | | | | |
| 3(Q) | -411 | -1812 | 202   | 1278  | -2120 | 997  | 53   | -1844 | 1011 | -1806 | -940 | 170   | -1370 | 1483 | 39    | -277  | -358 | -1435 | -1985 | -1327 | 13 |
| —    | -149 | -500 | 233   | 43    | -381 | 399   | 106  | -626 | 210  | -466 | -720 | 275   | 394  | 45   | 96    | 359   | 117  | -369 | -294  | -249 | |
| —    | -25  | -6428 | -7470 | -894 | -1115 | -701 | -1378 | * | * | | | | | | | | | | | | |
| 4(M) | -554 | -1770 | -500  | 1294  | -2084 | -1496 | -45 | -1741 | 1490 | -1726 | 2375 | -163  | -1571 | 384  | 1179  | -467  | -467 | -1393 | -1906 | -1358 | 14 |
| —    | -149 | -500 | 233   | 43    | -381 | 399   | 106  | -626 | 210  | -466 | -720 | 275   | 394  | 45   | 96    | 359   | 117  | -369 | -294  | -249 | |
| —    | -19  | -6836 | -7878 | -894 | -1115 | -701 | -1378 | * | * | | | | | | | | | | | | |
| 5(V) | 582  | -614 | -1167 | 546   | -657  | -1623 | -419 | -47  | -453 | 583   | 188  | -696  | -1707 | -324 | -741  | -630  | 773  | 1221 | -1069 | -649 | 15 |
| —    | -149 | -500 | 233   | 43    | -381 | 399   | 106  | -626 | 210  | -466 | -720 | 275   | 394  | 45   | 96    | 359   | 117  | -369 | -294  | -249 | |
| —    | -19  | -6836 | -7878 | -894 | -1115 | -701 | -1378 | * | * | | | | | | | | | | | | |
| 6(M) | -388 | -632 | 233   | -716  | -648  | -1697 | -471 | 1170 | -550 | -499  | 1779 | 218   | -1768 | -407 | -821  | -698  | 1278 | 799  | -1059 | -646 | 16 |
| —    | -149 | -500 | 233   | 43    | -381 | 399   | 106  | -626 | 210  | -466 | -720 | 275   | 394  | 45   | 96    | 359   | 117  | -369 | -294  | -249 | |
| —    | -17  | -7025 | -8067 | -894 | -1115 | -701 | -1378 | * | * | | | | | | | | | | | | |
| 7(D) | 54   | -2137 | 2020  | 1380  | -2436 | -1385 | -196 | -2201 | 126  | -2144 | -1250 | 1219 | -1583 | 239  | 702   | -471  | -581 | -1750 | -2320 | -1600 | 17 |
| —    | -149 | -500 | 233   | 43    | -381 | 399   | 106  | -626 | 210  | -466 | -720 | 275   | 394  | 45   | 96    | 359   | 117  | -369 | -294  | -249 | |
| —    | -17  | -7025 | -8067 | -894 | -1115 | -701 | -1378 | * | * | | | | | | | | | | | | |
| 8(Y) | -508 | -822 | -1280 | -702  | -673  | -1748 | -430 | 832  | -332 | -675  | -3   | -776  | 809  | -344 | 1190  | -762  | -446 | -274 | -1076 | 2458 | 18 |
| —    | -149 | -500 | 233   | 43    | -381 | 399   | 106  | -626 | 210  | -466 | -720 | 275   | 394  | 45   | 96    | 359   | 117  | -369 | -294  | -249 | |
| —    | -17  | -7025 | -8067 | -894 | -1115 | -701 | -1378 | * | * | | | | | | | | | | | | |
| 9(D) | -469 | -1542 | 1605  | 42    | -1969 | -1375 | -320 | -1627 | -36 | -1747 | -919 | -219  | 1080 | 65   | -522  | 1153  | -479 | 670  | -2048 | -1444 | 19 |
| —    | -149 | -500 | 233   | 43    | -381 | 399   | 106  | -626 | 210  | -466 | -720 | 275   | 394  | 45   | 96    | 359   | 117  | -369 | -294  | -249 | |
| —    | -17  | -7025 | -8067 | -894 | -1115 | -701 | -1378 | * | * | | | | | | | | | | | | |
| 10(S) | -586 | -1385 | -736 | -829  | -2829 | -1309 | -1317 | -2735 | -1241 | -2859 | -2047 | 1835 | -1910 | -1051 | -1602 | 2833 | -881 | -1997 | -2969 | -2410 | 20 |
| —    | -149 | -500 | 233   | 43    | -381 | 399   | 106  | -626 | 210  | -466 | -720 | 275   | 394  | 45   | 96    | 359   | 117  | -369 | -294  | -249 | |
| —    | -17  | -7025 | -8067 | -894 | -1115 | -701 | -1378 | * | * | | | | | | | | | | | | |

TABLE 6-continued

| | | | | | | | | | | | | | | | | | | |
|---|---|---|---|---|---|---|---|---|---|---|---|---|---|---|---|---|---|---|
| 11(P) | −526 | −1890 | −212 | 1174 | −2213 | −1420 | −120 | −1928 | 1548 | −1905 | −1024 | −80 | 1551 | 317 | −111 | −415 | 763 | −1521 | −2093 | −1450 | 21 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −17 | −7025 | −8067 | −894 | −1115 | −701 | −1378 | * | | | | | | | | | | | | | |
| 12(D) | 1339 | −2192 | 1728 | 1307 | −2485 | −1401 | −248 | −2248 | 996 | −2199 | −1317 | −28 | −1622 | 180 | −495 | −529 | −648 | −1804 | −2382 | −1658 | 22 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −17 | −7025 | −8067 | −894 | −1115 | −701 | −1378 | * | | | | | | | | | | | | | |
| 13(Y) | 984 | −983 | −1421 | −1092 | −837 | −1586 | −819 | −1015 | −973 | −1266 | −608 | −1029 | 1341 | −855 | −1218 | −770 | −660 | −790 | −1317 | 3268 | 23 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −17 | −7025 | −8067 | −894 | −1115 | −701 | −1378 | * | | | | | | | | | | | | | |
| 14(L) | −877 | −775 | −2589 | −1991 | 1160 | −2382 | −1170 | 1029 | 960 | 1849 | 533 | −1790 | −2366 | −1386 | −1652 | −1454 | −810 | 77 | −1124 | −783 | 24 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −17 | −7025 | −8067 | −894 | −1115 | −701 | −1378 | * | | | | | | | | | | | | | |
| 15(N) | −730 | −2232 | 123 | 1772 | −2530 | −1420 | −275 | −2293 | 34 | −2239 | −1364 | 1865 | 1127 | 1325 | −496 | −569 | −693 | −1850 | −2418 | −1697 | 25 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −17 | −7025 | −8067 | −894 | −1115 | −701 | −1378 | * | | | | | | | | | | | | | |
| 16(S) | −406 | −1619 | −309 | 191 | −1903 | 406 | −102 | −1593 | 986 | −317 | −789 | 1064 | −1504 | 317 | −181 | 1301 | −358 | −1237 | −1903 | −1286 | 26 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −17 | −7025 | −8067 | −894 | −1115 | −701 | −1378 | * | | | | | | | | | | | | | |
| 17(M) | −675 | −566 | −2528 | −1928 | −364 | −2184 | 2126 | 218 | −1592 | 743 | 2772 | −1654 | −2210 | −1313 | −1560 | −1256 | −614 | 1711 | −990 | −635 | 27 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 18(D) | −749 | −1575 | 2786 | −299 | −2062 | −1566 | −768 | −1153 | −635 | −1769 | −1097 | −535 | −1902 | −450 | −1112 | −799 | 731 | 1070 | −2328 | −1751 | 28 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 19(K) | 1232 | −1674 | −736 | −295 | −2360 | −1534 | −473 | −2014 | 2326 | −2058 | −1228 | −486 | 1165 | −74 | −221 | −634 | −677 | −1596 | −2264 | −1735 | 29 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 20(Y) | −2075 | −2643 | 1686 | −985 | −266 | −2358 | −869 | −2644 | −1801 | −2467 | −2120 | −1177 | −2732 | −1384 | −2229 | −1931 | −2114 | −2488 | −905 | 4141 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 21(W) | −2473 | −2122 | −3795 | −3534 | 136 | −3469 | −1296 | −944 | −2887 | 1176 | −449 | −2889 | −3469 | −2568 | −2708 | −2895 | −2429 | −1317 | 5419 | 316 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 22(R) | −1335 | −1772 | −2246 | −1513 | −2127 | −2222 | −955 | −1242 | 35 | −1675 | −1197 | −1424 | −2426 | −659 | 3303 | −1507 | −1331 | 1211 | −2220 | −1868 | 32 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 23(A) | 1948 | −1167 | −891 | 1114 | −1539 | −1605 | −710 | −688 | −551 | −1278 | −608 | −703 | −1861 | −451 | −928 | −724 | −609 | 1295 | −1870 | −1386 | 33 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 24(A) | 2275 | −1339 | −993 | −558 | −2142 | −1451 | −682 | −1733 | 1352 | −1909 | −1113 | −663 | −1785 | −334 | −564 | −587 | 928 | −1336 | −2220 | −1732 | 34 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 25(N) | −1216 | −1775 | −1072 | −1034 | −1473 | −1967 | −1153 | −1429 | −1009 | 767 | −1165 | 3461 | −2339 | −1043 | −1259 | −1335 | −1316 | −1331 | −1982 | −1273 | 35 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 26(Y) | −2131 | −1808 | −3471 | −3249 | 538 | −3299 | −814 | 1516 | −2817 | −864 | −742 | −2495 | −3305 | −2356 | −2649 | −2520 | −2091 | −784 | −205 | 4093 | 36 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 27(L) | −2321 | −1872 | −4652 | −4075 | −539 | −4266 | −3092 | 2178 | −3803 | 2345 | 2067 | −3915 | −3747 | −2978 | −3487 | −3494 | −2215 | −175 | −2130 | −2157 | 37 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |

TABLE 6-continued

| | | | | | | | | | | | | | | | | | | |
|---|---|---|---|---|---|---|---|---|---|---|---|---|---|---|---|---|---|---|
| 28(S) | −482 | −1136 | −1858 | −1915 | −3072 | −1315 | −1996 | −2905 | −2045 | −3106 | −2272 | −1475 | 1651 | −1840 | −2205 | 3016 | −873 | −2011 | −3242 | −2908 | 38 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 29(V) | 845 | −1090 | −3817 | −3373 | −1522 | −3377 | −2794 | 2147 | −3161 | −649 | −421 | −3056 | −3362 | −2955 | −3177 | −2598 | −1419 | 2690 | −2606 | −2197 | 39 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 30(G) | −1283 | −2067 | −837 | −965 | −3177 | 3042 | −1462 | −3119 | −1171 | −3141 | −2429 | −1111 | −2331 | 2005 | −1448 | −1320 | −1499 | −2538 | −3099 | −2665 | 40 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 31(Q) | −974 | −2142 | −780 | −270 | −2589 | −1791 | −328 | −2217 | 1581 | −2142 | −1329 | −487 | −1903 | 3083 | 262 | −876 | 671 | −1860 | −2250 | −1764 | 41 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 32(L) | −1375 | −1127 | −3503 | −2949 | −697 | −3071 | −2054 | 1887 | −2629 | 2035 | 342 | −2656 | −2990 | −2251 | −2534 | −2214 | 1157 | 428 | −1759 | −1511 | 42 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 33(Y) | −1937 | −2273 | −1926 | −1563 | −232 | −2608 | −650 | −2164 | 1538 | −2035 | −1599 | −1501 | −2740 | −960 | −541 | −1929 | −1851 | −2048 | −794 | 4044 | 43 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 34(L) | −2871 | −2457 | −4231 | −4103 | −1033 | −3803 | −3165 | −541 | −3734 | 3130 | −31 | −3935 | −3797 | −3286 | −3484 | −3713 | −2869 | −1136 | −2394 | −2220 | 44 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 35(K) | −565 | −1769 | −542 | 1150 | −2042 | −1544 | −133 | −1707 | 1529 | −200 | 1362 | −220 | −1622 | 291 | 1492 | −490 | −487 | −1367 | −1948 | −1377 | 45 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 36(D) | −733 | −2199 | 2095 | 230 | −2550 | 256 | −327 | −2314 | 1307 | −2269 | −1390 | −100 | −1681 | 97 | −574 | 1114 | −708 | −1861 | −2454 | −1735 | 46 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 37(N) | −1190 | −2662 | 1381 | 127 | −3153 | −1520 | −768 | −2990 | −757 | −2945 | −2156 | 3138 | −1961 | −405 | −1416 | 1061 | −1253 | −2479 | −3137 | −2313 | 47 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 38(P) | −1777 | −2801 | 1868 | −561 | −3633 | −1918 | −1524 | −3634 | −1721 | −3620 | −2978 | −881 | 3543 | −1257 | −2350 | −1648 | −1944 | −3091 | −3510 | −2972 | 48 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 39(C) | −1617 | 2940 | −3806 | −3389 | −788 | −2963 | −2369 | −4 | −2967 | 2637 | 197 | −2927 | −3094 | −2569 | −2799 | −2284 | −1672 | −278 | −1950 | −1680 | 49 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 40(M) | −1138 | −1232 | 1092 | −1546 | −625 | −2468 | −1290 | −56 | −1453 | 1974 | 2682 | −1610 | −2481 | −1228 | −1655 | −1558 | −1079 | −283 | −1540 | −1223 | 50 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 41(H) | −30 | 439 | 11 | 363 | −394 | −739 | 699 | −414 | 463 | −757 | 501 | 286 | −577 | 639 | 165 | −23 | 111 | −312 | 697 | −25 | 51 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 42(K) | 784 | −2190 | −977 | −302 | −2645 | −1847 | −256 | −2259 | 2452 | −2136 | −1309 | −504 | −1900 | 1339 | 1312 | −874 | −863 | −1897 | −2202 | −1742 | 52 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 43(E) | −648 | −1915 | −516 | 1778 | −2222 | −1578 | −162 | −1899 | 439 | 163 | −1023 | −238 | −1667 | 1297 | 1557 | −552 | −568 | −1536 | −2057 | −1482 | 53 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 44(P) | −1091 | −2157 | −710 | −354 | −2472 | −1828 | 2409 | −2236 | 1296 | −2195 | −1418 | −568 | 2737 | −72 | 88 | −1007 | −1021 | −1903 | −2268 | −1751 | 54 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |

TABLE 6-continued

| | | | | | | | | | | | | | | | | | | | |
|---|---|---|---|---|---|---|---|---|---|---|---|---|---|---|---|---|---|---|---|
| 45(L) | −1149 −149 −16 | −1110 −500 −7108 | −2516 233 −8150 | −1945 43 −894 | 1939 −381 −1115 | −2543 399 −701 | −1114 106 −1378 | −128 −626 * | 1051 210 * | 1953 −466 | 309 −720 | −1805 275 | −2527 394 | −1346 45 | −1480 96 | −1629 359 | −1078 117 | −306 −369 | −1080 −294 | −509 −249 | 55 |
| 46(T) | −695 −149 −16 | −1464 −500 −7108 | −884 233 −8150 | −358 43 −894 | −1467 −381 −1115 | −1703 399 −701 | −361 106 −1378 | −1272 −626 * | 1547 210 * | −1430 −466 | −690 −720 | −543 275 | −1822 394 | −57 45 | −149 96 | −739 359 | 2166 117 | −1045 −369 | −1654 −294 | 1676 −249 | 56 |
| 47(R) | 1626 −149 −16 | −2138 −500 −7108 | −1332 233 −8150 | −620 43 −894 | −2693 −381 −1115 | −1985 399 −701 | −403 106 −1378 | −2249 −626 * | 1356 210 * | −2167 −466 | −1392 −720 | −747 275 | −2067 394 | 11 45 | 2526 96 | −1100 359 | −1051 117 | −1929 −369 | −2243 −294 | −1870 −249 | 57 |
| 48(E) | 378 −149 −16 | −1941 −500 −7108 | 703 233 −8150 | 1824 43 −894 | −2252 −381 −1115 | −1386 399 −701 | −100 106 −1378 | −2000 −626 * | 289 210 * | −1956 −466 | −1046 −720 | −24 275 | −1516 394 | 349 45 | 1172 96 | 476 359 | −427 117 | −1561 −369 | −2134 −294 | −1447 −249 | 58 |
| 49(D) | 923 −149 −16 | −2559 −500 −7108 | 2894 233 −8150 | 160 43 −894 | −2929 −381 −1115 | −1519 399 −701 | −635 106 −1378 | −2712 −626 * | −524 210 * | −2688 −466 | −1882 −720 | −189 275 | −1895 394 | 1449 45 | −1131 96 | −904 359 | −1111 117 | −2258 −369 | −2898 −294 | −2120 −249 | 59 |
| 50(V) | 1091 −149 −16 | −1040 −500 −7108 | −3230 233 −8150 | −3029 43 −894 | −1839 −381 −1115 | −2191 399 −701 | −2521 106 −1378 | 453 −626 * | −2807 210 * | −1107 −466 | −816 −720 | −2387 275 | −2674 394 | −2598 45 | −2801 96 | −1506 359 | −1141 117 | −2258 −369 | −2726 −294 | −2349 −249 | 60 |
| 51(K) | 1016 −149 −16 | −1925 −500 −7108 | −1252 233 −8150 | −838 43 −894 | −2825 −381 −1115 | −1834 399 −701 | −758 106 −1378 | −2369 −626 * | 3094 210 * | −2408 −466 | −1667 −720 | −917 275 | −2126 394 | −380 45 | −14 96 | −1094 359 | −1125 117 | −1973 −369 | −2524 −294 | −2145 −249 | 61 |
| 52(H) | −477 −149 −16 | −400 −500 −7108 | −2258 233 −8150 | −1664 43 −894 | 1050 −381 −1115 | −1948 399 −701 | 2313 106 −1378 | 1043 −626 * | −1367 210 * | −239 −466 | 404 −720 | −1388 275 | 365 394 | −1083 45 | −1355 96 | −1008 359 | −417 117 | 3085 −369 | −715 −294 | 1744 −249 | 62 |
| 53(H) | −1023 −149 −16 | −1918 −500 −7108 | −1234 233 −8150 | −509 43 −894 | −2208 −381 −1115 | −1943 399 −701 | 3152 106 −1378 | 947 −626 * | 1315 210 * | −1817 −466 | −1055 −720 | −662 275 | −1981 394 | 64 45 | 1825 96 | −993 359 | −895 117 | −1542 −369 | −1997 −294 | −1584 −249 | 63 |
| 54(P) | 1113 −149 −16 | −913 −500 −7108 | −1858 233 −8150 | −1496 43 −894 | −1358 −381 −1115 | −1604 399 −701 | −1238 106 −1378 | −756 −626 * | −1296 210 * | 958 −466 | −503 −720 | −1306 275 | 2592 394 | −1174 45 | −1479 96 | −817 359 | −686 117 | −602 −369 | −1858 −294 | −1474 −249 | 64 |
| 55(I) | 846 −149 −16 | −1093 −500 −7108 | −3818 233 −8150 | −3374 43 −894 | −1512 −381 −1115 | −3374 399 −701 | −2792 106 −1378 | 2798 −626 * | −3161 210 * | −633 −466 | −411 −720 | −3056 275 | −3360 394 | −2951 45 | −3174 96 | −2596 359 | −1422 117 | 2077 −369 | −2600 −294 | −2195 −249 | 65 |
| 56(G) | −2594 −149 −16 | −2690 −500 −7108 | −3304 233 −8150 | −3623 43 −894 | −4328 −381 −1115 | 3747 399 −701 | −3462 106 −1378 | −4761 −626 * | −3953 210 * | −4671 −466 | −4212 −720 | −3320 275 | −3352 394 | −3748 45 | −3779 96 | −2839 359 | −2981 117 | −4004 −369 | −3668 −294 | −4222 −249 | 66 |
| 57(H) | −3205 −149 −16 | −3079 −500 −7108 | −2723 233 −8150 | −2890 43 −894 | −2110 −381 −1115 | −3046 399 −701 | 5295 106 −1378 | −4135 −626 * | −2617 210 * | −3813 −466 | −3561 −720 | −2886 275 | −3482 394 | −2833 45 | −2620 96 | −3291 359 | −3356 117 | −3895 −369 | −2397 −294 | −1681 −249 | 67 |
| 58(W) | −4114 −149 −16 | −3274 −500 −7108 | −4214 233 −8150 | −4453 43 −894 | −1722 −381 −1115 | −3496 399 −701 | −2681 106 −1378 | −4109 −626 * | −4149 210 * | −3619 −466 | −3615 −720 | −4044 275 | −3885 394 | −4032 45 | −3816 96 | −4355 359 | −4248 117 | −4133 −369 | 6191 −294 | −1474 −249 | 68 |
| 59(G) | −2594 −149 −16 | −2690 −500 −7108 | −3304 233 −8150 | −3623 43 −894 | −4328 −381 −1115 | 3747 399 −701 | −3462 106 −1378 | −4761 −626 * | −3953 210 * | −4671 −466 | −4212 −720 | −3320 275 | −3352 394 | −3748 45 | −3779 96 | −2839 359 | −2981 117 | −4004 −369 | −3668 −294 | −4222 −249 | 69 |
| 60(T) | −1213 −149 −16 | −1674 −500 −7108 | −2755 233 −8150 | −2906 43 −894 | −3163 −381 −1115 | −1922 399 −701 | −2659 106 −1378 | −2698 −626 * | −2788 210 * | −3105 −466 | −2612 −720 | −2311 275 | −2600 394 | −2708 45 | −2753 96 | −2839 359 | 3819 117 | −2197 −369 | −3286 −294 | −3156 −249 | 70 |
| 61(C) | −859 −149 −16 | 2735 −500 −7108 | −3125 233 −8150 | −2633 43 −894 | −1043 −381 −1115 | −2353 399 −701 | −1765 106 −1378 | 2619 −626 * | −2314 210 * | −561 −466 | −137 −720 | −2173 275 | −2560 394 | −2046 45 | −2258 96 | −1540 359 | 1442 117 | 680 −369 | −1746 −294 | −1384 −249 | 71 |

TABLE 6-continued

| | | | | | | | | | | | | | | | | | | | |
|---|---|---|---|---|---|---|---|---|---|---|---|---|---|---|---|---|---|---|---|
| 62(P) | 1490 | -891 | -2212 | -1956 | -2077 | -1371 | -1689 | -1274 | -1796 | -1861 | -1203 | -1479 | 2954 | -1611 | -1936 | -653 | -684 | 816 | -2478 | -2131 | 72 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 63(G) | -382 | -1055 | -1768 | -1819 | -3131 | 2891 | -1951 | -2904 | -2042 | -3099 | -2224 | -1384 | 1043 | -1771 | -2236 | 1022 | -775 | -1958 | -3301 | -2980 | 73 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 64(Q) | -1532 | -1831 | -1845 | -1487 | -1032 | -2520 | -1248 | -707 | -794 | 1863 | -184 | -1573 | -2625 | 2991 | -924 | -1768 | -1488 | -990 | -1859 | -1397 | 74 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 65(N) | -1040 | -1491 | -1193 | -1126 | -1577 | -1932 | -1248 | 1438 | -1138 | -1433 | -1011 | 3384 | -2307 | -1120 | -1396 | -1256 | -1150 | -579 | -2101 | -1473 | 75 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 66(F) | -2629 | -2152 | -4261 | -4009 | 3717 | -3972 | -1470 | -438 | -3655 | 1364 | 94 | -3253 | -3712 | -2829 | -3311 | -3250 | -2543 | -971 | -709 | 261 | 76 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 67(I) | -1794 | -1354 | -4306 | -3856 | -1267 | -3968 | -3273 | 2808 | -3666 | 1262 | -89 | -3607 | -3721 | -3300 | -3605 | -3222 | -1758 | 1880 | -2695 | -2428 | 77 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 68(Y) | -1692 | -1412 | -3458 | -3020 | 258 | -3136 | -1081 | 1186 | -2630 | 646 | -31 | -2459 | -3064 | -2167 | -2476 | -2272 | -1624 | -329 | -544 | 3829 | 78 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 69(A) | 2378 | -934 | -2147 | -1885 | -2779 | 826 | -1775 | -2485 | -1781 | -2703 | -1842 | -1381 | -1860 | -1577 | -1989 | 1353 | 1040 | -1689 | -2983 | -2654 | 79 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 70(H) | -3205 | -3079 | -2723 | -2890 | -2110 | -3046 | 5295 | -4135 | -2617 | -3813 | -3561 | -2886 | -3482 | -2833 | -2620 | -3291 | -3356 | -3895 | -2397 | -1681 | 80 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 71(L) | -2379 | -1915 | -4669 | -4151 | -621 | -4360 | -3248 | 1934 | -3862 | 2632 | 553 | -4017 | -3845 | -3099 | -3585 | -3641 | -2289 | -24 | -2250 | -2225 | 81 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 72(N) | -2171 | -2655 | -1458 | -1748 | -3334 | -2364 | -2267 | -3943 | -2365 | -3936 | -3437 | 4205 | -2932 | -2205 | -2608 | -2224 | -2439 | -3392 | -3253 | -2909 | 82 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 73(R) | -1929 | -2343 | -2336 | -1600 | -825 | -2607 | -677 | -2317 | 45 | -2153 | -1653 | -1506 | -2681 | -679 | 3382 | -1922 | -1792 | -2176 | -1232 | 2267 | 83 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 74(V) | 503 | -701 | -3099 | -2506 | 1199 | -2516 | -1425 | 486 | -2168 | 1370 | 379 | -2113 | -2515 | -1800 | -2039 | -1621 | -848 | 2021 | -1247 | -916 | 84 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 75(I) | -2091 | -1746 | -3971 | -3840 | -1676 | -3532 | -3289 | 3684 | -3581 | -659 | -693 | -3562 | -3674 | -3445 | -3521 | -3194 | -2146 | 449 | -2877 | -2493 | 85 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 76(K) | 1051 | -1939 | -439 | -69 | -2445 | -1557 | -349 | -2132 | 2202 | -2116 | -1268 | 1786 | -1753 | 70 | -141 | -646 | -704 | -1719 | -2284 | -1701 | 86 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 77(K) | -1384 | -2800 | 1892 | -69 | -3174 | -1733 | -742 | -2966 | 2973 | -2873 | -2105 | -400 | -2087 | -365 | -775 | -1179 | -1372 | -2535 | -2949 | -2288 | 87 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| 78(Y) | -2118 | -2084 | -2592 | -2218 | 1983 | -3049 | 2937 | -1851 | -1966 | -1662 | -1339 | -1862 | -3049 | 1795 | -2085 | -2125 | -2036 | -1809 | 122 | 3287 | 88 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |

TABLE 6-continued

```
Label  | Col1   Col2   Col3   Col4   Col5   Col6   Col7   Col8   | Col9   Col10  Col11  Col12  Col13  Col14  Col15  Col16  Col17  Col18  Col19  Col20  | Idx
79(N)  | -1107  -2701  1326    223  -2992   1724   -586  -2799   |  -472  -2733  -1910   2292  -1876   1179  -1098   -894  -1109  -2331  -2923  -2116 |  89
       |  -149   -500   233     43   -381    399    106   -626   |   210   -466   -720    275    394     45     96    359    117   -369   -294   -249
       |   -16  -7108  -8150   -894  -1115   -701  -1378     *
80(L)  | -1690  -1806  -2247  -1903   -837  -2782  -1536   -464  | -1204   2489     81  -1939  -2835   1986  -1289  -2052  -1642   -850  -1841  -1451 |  90
       |  -149   -500   233     43   -381    399    106   -626   |   210   -466   -720    275    394     45     96    359    117   -369   -294   -249
       |   -16  -7108  -8150   -894  -1115   -701  -1378     *
81(D)  | -1292  -2956   2598   202  -3213  -1558   -693  -3045   |   851  -2958  -2170   2502  -1967   -318  -1262  -1043  -1304  -2569  -3134  -2291 |  91
       |  -149   -500   233     43   -381    399    106   -626   |   210   -466   -720    275    394     45     96    359    117   -369   -294   -249
       |   -16  -7108  -8150   -894  -1115   -701  -1378     *
82(M)  |  -866  -1094  -2548  -2220  -1176  -1993  -1696   -374  | -1810   -470   4232  -1867  -2385  -1729  -1855  -1260   1587   -400  -1960  -1618 |  92
       |  -149   -500   233     43   -381    399    106   -626   |   210   -466   -720    275    394     45     96    359    117   -369   -294   -249
       |   -16  -7108  -8150   -894  -1115   -701  -1378     *
83(F)  | -1725  -1400  -3934  -3394   2962  -3436  -2055    325  | -3076   1369    437  -3005  -3243  -2505  -2863  -2595  -1653   1644  -1488   -995 |  93
       |  -149   -500   233     43   -381    399    106   -626   |   210   -466   -720    275    394     45     96    359    117   -369   -294   -249
       |   -16  -7108  -8150   -894  -1115   -701  -1378     *
84(Y)  | -2852  -2251  -3961  -3935   2281  -3735   -476    168  | -3538  -1379  -1299  -2630  -3641  -2627  -3134  -2925  -2756  -1840    233   4154 |  94
       |  -149   -500   233     43   -381    399    106   -626   |   210   -466   -720    275    394     45     96    359    117   -369   -294   -249
       |   -16  -7108  -8150   -894  -1115   -701  -1378     *
85(I)  | -1759  -1305  -4328  -3965  -1743  -4047  -3735   3086  | -3833   -588   -522  -3726  -3872  -3681  -3903  -3364  -1752   2354  -3250  -2813 |  95
       |  -149   -500   233     43   -381    399    106   -626   |   210   -466   -720    275    394     45     96    359    117   -369   -294   -249
       |   -16  -7108  -8150   -894  -1115   -701  -1378     *
86(M)  |  -700  -1108  -1144   2046  -1106  -1894   -710   -177  |  -572   -648   2421   -857  -1997   -497   -908   -934   -657   1171  -1602  -1155 |  96
       |  -149   -500   233     43   -381    399    106   -626   |   210   -466   -720    275    394     45     96    359    117   -369   -294   -249
       |   -16  -7108  -8150   -894  -1115   -701  -1378     *
87(G)  | -2594  -2690  -3304  -3623  -4328   3747  -3462  -4761  | -3953  -4671  -4212  -3320  -3352  -3748  -3779  -2839  -2981  -4004  -3668  -4222 |  97
       |  -149   -500   233     43   -381    399    106   -626   |   210   -466   -720    275    394     45     96    359    117   -369   -294   -249
       |   -16  -7108  -8150   -894  -1115   -701  -1378     *
88(P)  |  -526  -1169  -1848  -1957  -3095  -1343  -2052  -2946  | -2123  -3152  -2333  -1513   3407  -1917  -2261   1632   -922  -2053  -3267  -2938 |  98
       |  -149   -500   233     43   -381    399    106   -626   |   210   -466   -720    275    394     45     96    359    117   -369   -294   -249
       |   -16  -7108  -8150   -894  -1115   -701  -1378     *
89(G)  | -2594  -2690  -3304  -3623  -4328   3747  -3462  -4761  | -3953  -4671  -4212  -3320  -3352  -3748  -3779  -2839  -2981  -4004  -3668  -4222 |  99
       |  -149   -500   233     43   -381    399    106   -626   |   210   -466   -720    275    394     45     96    359    117   -369   -294   -249
       |   -16  -7108  -8150   -894  -1115   -701  -1378     *
90(H)  | -3205  -3079  -2723  -2890  -2110  -3046   5295  -4135  | -2617  -3813  -3561  -2886  -3482  -2833  -2620  -3291  -3356  -3895  -2397  -1681 | 100
       |  -149   -500   233     43   -381    399    106   -626   |   210   -466   -720    275    394     45     96    359    117   -369   -294   -249
       |   -16  -7108  -8150   -894  -1115   -701  -1378     *
91(G)  | -2594  -2690  -3304  -3623  -4328   3747  -3462  -4761  | -3953  -4671  -4212  -3320  -3352  -3748  -3779  -2839  -2981  -4004  -3668  -4222 | 101
       |  -149   -500   233     43   -381    399    106   -626   |   210   -466   -720    275    394     45     96    359    117   -369   -294   -249
       |   -16  -7108  -8150   -894  -1115   -701  -1378     *
92(H)  |   -30    439    11    363   -394   -739    699   -414   |   463   -757    501    286   -577    639    165    -23    111   -312    697    -25 | 102
       |  -149   -500   233     43   -381    399    106   -626   |   210   -466   -720    275    394     45     96    359    117   -369   -294   -249
       |   -16  -7108  -8150   -894  -1115   -701  -1378     *
93(G)  |  1432  -1081  -2340  -2519  -3309   3113  -2408  -3041  | -2687  -3327  -2482  -1740  -2062  -2353  -2689   -702   -903  -2058  -3476  -3301 | 103
       |  -149   -500   233     43   -381    399    106   -626   |   210   -466   -720    275    394     45     96    359    117   -369   -294   -249
       |   -16  -7108  -8150   -894  -1115   -701  -1378     *
94(Q)  | -1326  -2187   -825   -789  -2878  -1884  -1131  -2784  |  -631  -2752  -2063   -977   2646   3194   -881  -1313  -1428  -2357  -2787  -2310 | 104
       |  -149   -500   233     43   -381    399    106   -626   |   210   -466   -720    275    394     45     96    359    117   -369   -294   -249
       |   -16  -7108  -8150   -894  -1115   -701  -1378     *
95(V)  |  1470   -815  -2475  -2234  -1874   1135  -1780   -892  | -2064  -1657  -1016  -1624  -2020  -1814  -2121   -717   -687   2477  -2329  -1999 | 105
       |  -149   -500   233     43   -381    399    106   -626   |   210   -466   -720    275    394     45     96    359    117   -369   -294   -249
       |   -16  -7108  -8150   -894  -1115   -701  -1378     *
```

TABLE 6-continued

| | | | | | | | | | | | | | | | | | | |
|---|---|---|---|---|---|---|---|---|---|---|---|---|---|---|---|---|---|---|
| 96(M) | -883 -149 -16 | -899 -500 -7108 | -2454 233 -8150 | -1951 43 -894 | -595 -381 -1115 | 991 399 -701 | -1285 106 -1378 | -31 -626 * | -1626 210 * | 1077 -466 | 3599 -720 | -1754 275 | -2362 394 | -1420 45 | -1669 96 | -1376 359 | -878 117 | -131 -369 | -1359 -294 | -1024 -249 | 106 |
| 97(V) | -1205 -149 -16 | -914 -500 -7108 | -3493 233 -8150 | -2955 43 -894 | -1023 -381 -1115 | -3025 399 -701 | -2085 106 -1378 | 1649 -626 * | -2672 210 * | 917 -466 | -32 -720 | -2617 275 | -2982 394 | -2375 45 | -2606 96 | -2169 359 | 1373 117 | 2267 -369 | -1903 -294 | -1552 -249 | 107 |
| 98(S) | 1719 -149 -16 | -1145 -500 -7108 | -1296 233 -8150 | -1130 43 -894 | -2738 -381 -1115 | -1260 399 -701 | -1357 106 -1378 | -2461 -626 * | -1234 210 * | -2624 -466 | -1769 -720 | 1171 275 | -1844 394 | -1070 45 | 1576 96 | 2383 359 | -686 117 | -1744 -369 | -2874 -294 | -2423 -249 | 108 |
| 99(N) | -809 -149 -16 | -2086 -500 -7108 | -98 233 -8150 | 33 43 -894 | -2593 -381 -1115 | -1494 399 -701 | -488 106 -1378 | -2361 -626 * | -147 210 * | -2346 -466 | -1503 -720 | 2681 275 | -1787 394 | 1970 45 | -607 96 | 984 359 | -825 117 | -1908 -369 | -2521 -294 | -1851 -249 | 109 |
| 100(S) | 878 -149 -16 | -890 -500 -7108 | -1818 233 -8150 | -1458 43 -894 | -1679 -381 -1115 | -1418 399 -701 | -1269 106 -1378 | -1166 -626 * | -1293 210 * | 665 -466 | -837 -720 | -1224 275 | -1904 394 | -1156 45 | -1509 96 | 2469 359 | -610 117 | -869 -369 | -2068 -294 | -1669 -249 | 110 |
| 101(Y) | -3588 -149 -16 | -2709 -500 -7108 | -4120 233 -8150 | -4323 43 -894 | 1034 -381 -1115 | -3994 399 -701 | -419 106 -1378 | -2613 -626 * | -3834 210 * | -2031 -466 | -2055 -720 | -2741 275 | -3905 394 | -2826 45 | -3349 96 | -3280 359 | -3472 117 | -2736 -369 | 3673 -294 | 4312 -249 | 111 |
| 102(L) | -2496 -149 -16 | -2027 -500 -7108 | -4721 233 -8150 | -4202 43 -894 | -560 -381 -1115 | -4432 399 -701 | -3262 106 -1378 | 1210 -626 * | -3887 210 * | 2852 -466 | 611 -720 | -251 275 | -3876 394 | -3086 45 | -3587 96 | -3729 359 | -2397 117 | -232 -369 | -2211 -294 | -2201 -249 | 112 |
| 103(D) | -1791 -149 -16 | -3663 -500 -7108 | 3414 233 -8150 | 1659 43 -894 | -3853 -381 -1115 | -1647 399 -701 | -1043 106 -1378 | -3807 -626 * | -1343 210 * | -3679 -466 | -3054 -720 | -3320 275 | -2201 394 | -725 45 | -2227 96 | -1438 359 | -1872 117 | -3282 -369 | -3836 -294 | -2831 -249 | 113 |
| 104(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -3953 210 * | -4671 -466 | -4212 -720 | -3320 275 | -3352 394 | -3748 45 | -3779 96 | -2839 359 | -2981 117 | -4004 -369 | -3668 -294 | -4222 -249 | 114 |
| 105(S) | -342 -149 -16 | -976 -500 -7108 | -2177 233 -8150 | -2128 43 -894 | -2921 -381 -1115 | -1229 399 -701 | -2008 106 -1378 | -2606 -626 * | -2073 210 * | -2888 -466 | -2058 -720 | -1512 275 | -1936 394 | -1871 45 | -2189 96 | 2669 359 | 2327 117 | -1779 -369 | -3151 -294 | -2842 -249 | 115 |
| 106(Y) | -2652 -149 -16 | -2206 -500 -7108 | -3673 233 -8150 | -3556 43 -894 | 726 -381 -1115 | -3580 399 -701 | -692 106 -1378 | -1359 -626 * | -3066 210 * | 982 -466 | -936 -720 | -2620 275 | -3538 394 | -2500 45 | -2832 96 | -2837 359 | -2587 117 | -1595 -369 | -24 -294 | 4185 -249 | 116 |
| 107(T) | -502 -149 -16 | -1110 -500 -7108 | -2201 233 -8150 | -2282 43 -894 | -3095 -381 -1115 | 1340 399 -701 | -2204 106 -1378 | -2779 -626 * | -2341 210 * | -3075 -466 | -2268 -720 | -1660 275 | -2066 394 | -2111 45 | -2412 96 | -729 359 | 3346 117 | -1945 -369 | -3276 -294 | -3043 -249 | 117 |
| 108(E) | -1163 -149 -16 | -2811 -500 -7108 | 1893 233 -8150 | 2460 43 -894 | -3072 -381 -1115 | -1535 399 -701 | -594 106 -1378 | -2884 -626 * | 1337 210 * | -2797 -466 | -1978 -720 | -140 275 | -1898 394 | -203 45 | -1072 96 | -933 359 | -1159 117 | -2412 -369 | -2972 -294 | -2157 -249 | 118 |
| 109(I) | 561 -149 -16 | -338 -500 -7108 | -2506 233 -8150 | -1896 43 -894 | 1485 -381 -1115 | -1980 399 -701 | -829 106 -1378 | 1917 -626 * | -1557 210 * | -155 -466 | 470 -720 | -1524 275 | -2033 394 | -1236 45 | -1465 96 | -1055 359 | 777 117 | 309 -369 | -776 -294 | 1058 -249 | 119 |
| 110(Y) | -3611 -149 -16 | -2705 -500 -7108 | -4166 233 -8150 | -4409 43 -894 | 2531 -381 -1115 | -4042 399 -701 | -397 106 -1378 | -2533 -626 * | -3989 210 * | -1938 -466 | -1983 -720 | -2747 275 | -3929 394 | -2851 45 | -3444 96 | -3294 359 | -3491 117 | -2684 -369 | 345 -294 | 4289 -249 | 120 |
| 111(P) | -2931 -149 -16 | -2878 -500 -7108 | -3420 233 -8150 | -3706 43 -894 | -4181 -381 -1115 | -2925 399 -701 | -3468 106 -1378 | -4621 -626 * | -3859 210 * | -4490 -466 | -4165 -720 | -3491 275 | -4225 394 | -3781 45 | -3695 96 | -3182 359 | -3279 117 | -4087 -369 | -3594 -294 | -4064 -249 | 121 |
| 112(E) | -785 -149 -16 | -2281 -500 -7108 | -2 233 -8150 | 1960 43 -894 | -2596 -381 -1115 | -1496 399 -701 | -297 106 -1378 | -2348 -626 * | 660 210 * | -2275 -466 | -1399 -720 | 1934 275 | -1705 394 | 1721 45 | -381 96 | -626 359 | -738 117 | -1906 -369 | -2432 -294 | -1737 -249 | 122 |

TABLE 6-continued

| | | | | | | | | | | | | | | | | | |
|---|---|---|---|---|---|---|---|---|---|---|---|---|---|---|---|---|---|
| 113(I) | -1722 -149 -16 | -1438 -500 -7108 | -3424 233 -8150 | -3080 43 -894 | 131 -381 -1115 | -3150 399 -701 | -1169 106 -1378 | 2917 -626 * | -2681 210 * | -503 -466 | -344 -720 | -2513 275 | -3144 394 | -2305 45 | -2554 96 | -2347 359 | -1683 117 | -39 -369 | -645 -294 | 2880 -249 | 123 |
| 114(T) | -1213 -149 -16 | -1674 -500 -7108 | -2755 233 -8150 | -2906 43 -894 | -3163 -381 -1115 | -1922 399 -701 | -2659 106 -1378 | -2698 -626 * | -2788 210 * | -3105 -466 | -2612 -720 | -2311 275 | -2600 394 | -2708 45 | -2753 96 | -1463 359 | 3819 117 | -2197 -369 | -3286 -294 | -3156 -249 | 124 |
| 115(Q | -1609 -149 -16 | -2594 -500 -7108 | -1354 233 -8150 | -790 43 -894 | -3182 -381 -1115 | -2213 399 -701 | -519 106 -1378 | -2737 -626 * | 2527 210 * | -2514 -466 | -1787 -720 | -903 275 | -2297 394 | 3031 45 | 525 96 | -1483 359 | -1437 117 | -2432 -369 | -2460 -294 | -2150 -249 | 125 |
| 116(D | -2784 -149 -16 | -3432 -500 -7108 | 4016 233 -8150 | -1200 43 -894 | -4140 -381 -1115 | -2466 399 -701 | -2197 106 -1378 | -4505 -626 * | -2621 210 * | -4365 -466 | -3956 -720 | -1551 275 | -3014 394 | -2039 45 | -3232 96 | -2593 359 | -2938 117 | -4046 -369 | -3710 -294 | -3552 -249 | 126 |
| 117(E) | -495 -149 -16 | -1766 -500 -7108 | -320 233 -8150 | 2020 43 -894 | -2044 -381 -1115 | -1449 399 -701 | -133 106 -1378 | -1708 -626 * | 1298 210 * | -1759 -466 | -898 -720 | -124 275 | -1562 394 | 295 45 | -155 96 | -410 359 | 632 117 | 108 -369 | -1998 -294 | -1374 -249 | 127 |
| 118(E) | 1485 -149 -16 | -2051 -500 -7108 | -202 233 -8150 | 1709 43 -894 | -2406 -381 -1115 | -1511 399 -701 | -270 106 -1378 | -2112 -626 * | 1557 210 * | -2089 -466 | -1228 -720 | -183 275 | -1688 394 | 156 45 | -234 96 | -586 359 | -657 117 | -1706 -369 | -2272 -294 | -1633 -249 | 128 |
| 119(G | -2594 -149 -16 | -2690 -500 -7108 | -3304 233 -8150 | -3623 43 -894 | -4328 -381 -1115 | 3747 399 -701 | -3462 106 -1378 | -4761 -626 * | -3953 210 * | -4671 -466 | -4212 -720 | -3320 275 | -3352 394 | -3748 45 | -3779 96 | -2839 359 | -2981 117 | -4004 -369 | -3668 -294 | -4222 -249 | 129 |
| 120(M | -2568 -149 -16 | -2113 -500 -7108 | -4714 233 -8150 | -4154 43 -894 | -462 -381 -1115 | -4418 399 -701 | -3155 106 -1378 | 99 -626 * | -3799 210 * | 2469 -466 | 3538 -720 | -4062 275 | -3833 394 | -2972 45 | -3479 96 | -3691 359 | -2450 117 | -587 -369 | -2108 -294 | -2139 -249 | 130 |
| 121(Q | 447 -149 -16 | -1907 -500 -7108 | -448 233 -8150 | -115 43 -894 | -2176 -381 -1115 | -1605 399 -701 | 2296 106 -1378 | -1980 -626 * | 143 210 * | -2000 -466 | -1194 -720 | -367 275 | -1799 394 | 3046 45 | -194 96 | -715 359 | -752 117 | -1626 -369 | -2150 -294 | -1543 -249 | 131 |
| 122K | -1448 -149 -16 | -2495 -500 -7108 | -1440 233 -8150 | -709 43 -894 | -3095 -381 -1115 | -2161 399 -701 | -406 106 -1378 | -2616 -626 * | 2874 210 * | -2399 -466 | -1636 -720 | 1544 275 | -2197 394 | 22 45 | 1483 96 | -1326 359 | -1270 117 | -2295 -369 | -2364 -294 | -2043 -249 | 132 |
| 123(L) | -2430 -149 -16 | -1987 -500 -7108 | -4659 233 -8150 | -4071 43 -894 | 2109 -381 -1115 | -4260 399 -701 | -2828 106 -1378 | 67 -626 * | -3779 210 * | 2463 -466 | 2382 -720 | -3869 275 | -3717 394 | -2880 45 | -3418 96 | -3473 359 | -2306 117 | -623 -369 | -1874 -294 | -1724 -249 | 133 |
| 124(F | -2144 -149 -16 | -1762 -500 -7108 | -4034 233 -8150 | -3706 43 -894 | 3638 -381 -1115 | -3656 399 -701 | -1587 106 -1378 | 1655 -626 * | -3381 210 * | 102 -466 | 23 -720 | -3073 275 | -3507 394 | -2734 45 | -3134 96 | -2896 359 | -2093 117 | -241 -369 | -906 -294 | 16 -249 | 134 |
| 125(K | -1297 -149 -16 | -2351 -500 -7108 | -1405 233 -8150 | -643 43 -894 | -2938 -381 -1115 | -2076 399 -701 | -377 106 -1378 | -2482 -626 * | 2603 210 * | -2306 -466 | -1527 -720 | -768 275 | -2120 394 | 51 45 | 1973 96 | 899 359 | -1147 117 | -2149 -369 | -2307 -294 | -1957 -249 | 135 |
| 126(Q | -753 -149 -16 | -1991 -500 -7108 | -692 233 -8150 | -91 43 -894 | -2345 -381 -1115 | -1670 399 -701 | 1700 106 -1378 | -2009 -626 * | 519 210 * | -1957 -466 | -1111 -720 | -334 275 | -1745 394 | 2315 45 | 1728 96 | -656 359 | 1061 117 | -1645 -369 | -2095 -294 | -1558 -249 | 136 |
| 127(F | -3342 -149 -16 | -2776 -500 -7108 | -4026 233 -8150 | -4232 43 -894 | 4354 -381 -1115 | -3545 399 -701 | -1431 106 -1378 | -2315 -626 * | -4038 210 * | -1801 -466 | -1900 -720 | -3299 275 | -3780 394 | -3350 45 | -3645 96 | -3490 359 | -3420 117 | -2566 -369 | -739 -294 | 349 -249 | 137 |
| 128(S | -897 -149 -16 | -1462 -500 -7108 | -2333 233 -8150 | -2543 43 -894 | -3185 -381 -1115 | -1640 399 -701 | -2474 106 -1378 | -3294 -626 * | -2686 210 * | -3497 -466 | -2780 -720 | -1973 275 | -2360 394 | -2483 45 | -2703 96 | 3465 359 | -1316 117 | -2413 -369 | -3310 -294 | -3025 -249 | 138 |
| 129(F | -1908 -149 -16 | -1643 -500 -7108 | -3261 233 -8150 | -2963 43 -894 | 3263 -381 -1115 | -3050 399 -701 | -509 106 -1378 | -1219 -626 * | -2636 210 * | -1197 -466 | -851 -720 | -2199 275 | -3071 394 | -2085 45 | -2476 96 | -2189 359 | 1297 117 | -1211 -369 | 77 -294 | 2811 -249 | 139 |

TABLE 6-continued

| | | | | | | | | | | | | | | | | | | |
|---|---|---|---|---|---|---|---|---|---|---|---|---|---|---|---|---|---|---|
| 130(P) | −540 −149 −16 | −1180 −500 −7108 | −1850 233 −8150 | −1974 43 −894 | −3103 −381 −1115 | −1352 399 −701 | −2072 106 −1378 | −2962 −626 * | −2149 210 * | −3170 −466 | −2355 −720 | −1527 275 | 3509 394 | −1943 45 | −2279 96 | 1382 359 | −938 117 | −2068 −369 | −3276 −294 | −2949 −249 | 140 |
| 131(G) | 1432 −149 −16 | −1081 −500 −7108 | −2340 233 −8150 | −2519 43 −894 | −3309 −381 −1115 | 3113 399 −701 | −2408 106 −1378 | −3041 −626 * | −2687 210 * | −3327 −466 | −2482 −720 | −1740 275 | −2062 394 | −2353 45 | −2689 96 | −702 359 | −903 117 | −2058 −369 | −3476 −294 | −3301 −249 | 141 |
| 132(G) | −2594 −149 −16 | −2690 −500 −7108 | −3304 233 −8150 | −3623 43 −894 | −4328 −381 −1115 | 3747 399 −701 | −3462 106 −1378 | −4761 −626 * | −3953 210 * | −4671 −466 | −4212 −720 | −3320 275 | −3352 394 | −3748 45 | −3779 96 | −2839 359 | −2981 117 | −4004 −369 | −3668 −294 | −4222 −249 | 142 |
| 133(V) | −1322 −149 −16 | −992 −500 −7108 | −3697 233 −8150 | −3181 43 −894 | −1158 −381 −1115 | −3230 399 −701 | −2353 106 −1378 | 2069 −626 * | −2914 210 * | 914 −466 | −126 −720 | −2840 275 | −3160 394 | −2624 45 | −2849 96 | −2396 359 | 641 117 | 2352 −369 | −2122 −294 | −1765 −249 | 143 |
| 134(P) | 2498 −149 −16 | −1088 −500 −7108 | −2250 233 −8150 | −2290 43 −894 | −3023 −381 −1115 | −1338 399 −701 | −2177 106 −1378 | −2668 −626 * | −2306 210 * | −2970 −466 | −2190 −720 | −1656 275 | 2760 394 | −2080 45 | −2382 96 | −710 359 | −882 117 | −1878 −369 | −3231 −294 | −2984 −249 | 144 |
| 135(S) | −897 −149 −16 | −1462 −500 −7108 | −2333 233 −8150 | −2543 43 −894 | −3185 −381 −1115 | −1640 399 −701 | −2474 106 −1378 | −3294 −626 * | −2686 210 * | −3497 −466 | −2780 −720 | −1973 275 | −2360 394 | −2483 45 | −2703 96 | 3465 359 | −1316 117 | −2413 −369 | −3310 −294 | −3025 −249 | 145 |
| 136(H) | −3205 −149 −16 | −3079 −500 −7108 | −2723 233 −8150 | −2890 43 −894 | −2110 −381 −1115 | −3046 399 −701 | 5295 106 −1378 | −4135 −626 * | −2617 210 * | −3813 −466 | −3561 −720 | −2886 275 | −3482 394 | −2833 45 | −2620 96 | −3291 359 | −3356 117 | −3895 −369 | −2397 −294 | −1681 −249 | 146 |
| 137(A) | 1947 −149 −16 | −745 −500 −7108 | −2823 233 −8150 | −2285 43 −894 | 1846 −381 −1115 | −2348 399 −701 | −1328 106 −1378 | 1572 −626 * | −1988 210 * | −154 −466 | 207 −720 | −1942 275 | −2439 394 | −1677 45 | −1944 96 | −1473 359 | −836 117 | 359 −369 | −1231 −294 | −781 −249 | 147 |
| 138(A) | 2029 −149 −16 | −2389 −500 −7108 | 1954 233 −8150 | 92 43 −894 | −2936 −381 −1115 | −1492 399 −701 | −703 106 −1378 | −2716 −626 * | −623 210 * | −2715 −466 | −1906 −720 | 1712 275 | −1898 394 | −331 45 | −1237 96 | −881 359 | −1089 117 | −2229 −369 | −2931 −294 | −2168 −249 | 148 |
| 139(P) | 1935 −149 −16 | −1116 −500 −7108 | −2232 233 −8150 | −2301 43 −894 | −3058 −381 −1115 | −1358 399 −701 | −2206 106 −1378 | −2705 −626 * | −2336 210 * | −3009 −466 | −2238 −720 | −1674 275 | 3272 394 | −2114 45 | −2406 96 | −739 359 | −914 117 | −1913 −369 | −3260 −294 | −3019 −249 | 149 |
| 140(E) | −1349 −149 −16 | −2706 −500 −7108 | −162 233 −8150 | 2827 43 −894 | −3109 −381 −1115 | −1785 399 −701 | −624 106 −1378 | −2820 −626 * | 1799 210 * | −2704 −466 | −1931 −720 | −437 275 | −2073 394 | −230 45 | −334 96 | −1160 359 | −1298 117 | −2421 −369 | −2774 −294 | −2189 −249 | 150 |
| 141(T) | −645 −149 −16 | −1000 −500 −7108 | −2671 233 −8150 | −2474 43 −894 | −1925 −381 −1115 | −1699 399 −701 | −2057 106 −1378 | −385 −626 * | −2200 210 * | −1416 −466 | −1020 −720 | −1885 275 | −2274 394 | −2057 45 | −2247 96 | −1011 359 | 3256 117 | 1160 −369 | −2570 −294 | −2205 −249 | 151 |
| 142(P) | −2931 −149 −16 | −2878 −500 −7108 | −3420 233 −8150 | −3706 43 −894 | −4181 −381 −1115 | −2925 399 −701 | −3468 106 −1378 | −4621 −626 * | −3859 210 * | −4490 −466 | −4165 −720 | −3491 275 | 4225 394 | −3781 45 | −3695 96 | −3182 359 | −3279 117 | −4087 −369 | −3594 −294 | −4064 −249 | 152 |
| 143(H) | −30 −149 −16 | 439 −500 −7108 | 11 233 −8150 | 363 43 −894 | −394 −381 −1115 | −739 399 −701 | 699 106 −1378 | −414 −626 * | 463 210 * | −757 −466 | 501 −720 | 286 275 | −577 394 | 639 45 | 165 96 | −23 359 | 111 117 | −312 −369 | 697 −294 | −25 −249 | 153 |
| 144(G) | −2594 −149 −16 | −2690 −500 −7108 | −3304 233 −8150 | −3623 43 −894 | −4328 −381 −1115 | 3747 399 −701 | −3462 106 −1378 | −4761 −626 * | −3953 210 * | −4671 −466 | −4212 −720 | −3320 275 | −3352 394 | −3748 45 | −3779 96 | −2839 359 | −2981 117 | −4004 −369 | −3668 −294 | −4222 −249 | 154 |
| 145(S) | 1426 −149 −16 | −949 −500 −7108 | −2380 233 −8150 | −2419 43 −894 | −3107 −381 −1115 | −1201 399 −701 | −2226 106 −1378 | −2819 −626 * | −2411 210 * | −3105 −466 | −2246 −720 | −1618 275 | −1944 394 | −2131 45 | −2456 96 | −2839 359 | −742 117 | −1874 −369 | −3336 −294 | −3080 −249 | 155 |
| 146(I) | −2091 −149 −16 | −1746 −500 −7108 | −3971 233 −8150 | −3840 43 −894 | −1676 −381 −1115 | −3532 399 −701 | −3289 106 −1378 | 3684 −626 * | −3581 210 * | −659 −466 | −693 −720 | −3562 275 | −3674 394 | −3445 45 | −3521 96 | −3194 359 | −2146 117 | 449 −369 | −2877 −294 | −2493 −249 | 156 |

TABLE 6-continued

| | | | | | | | | | | | | | | | | | | | |
|---|---|---|---|---|---|---|---|---|---|---|---|---|---|---|---|---|---|---|---|
| 147(H) | -3205 -149 -16 | -3079 -500 -7108 | -2723 233 -8150 | -2890 43 -894 | -2110 -381 -1115 | -3046 399 -701 | 5295 106 -1378 | -4135 -626 * | -2617 210 * | -3813 -466 | -3561 -720 | -2886 275 | -3482 394 | -2833 45 | -2620 96 | -3291 359 | -3356 117 | -3895 -369 | -2397 -294 | -1681 -249 | 157 |
| 148(E) | -2641 -149 -16 | -3308 -500 -7108 | -896 233 -8150 | 3732 43 -894 | -3966 -381 -1115 | -2458 399 -701 | -2043 106 -1378 | -4105 -626 * | -2128 210 * | -4016 -466 | -3555 -720 | -1531 275 | -2959 394 | -1842 45 | -2560 96 | -2479 359 | -2750 117 | -3722 -369 | -3563 -294 | -3385 -249 | 158 |
| 149(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -3953 210 * | -4671 -466 | -4212 -720 | -3320 275 | -3352 394 | -3748 45 | -3779 96 | -2839 359 | -2981 117 | -4004 -369 | -3668 -294 | -4222 -249 | 159 |
| 150(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -3953 210 * | -4671 -466 | -4212 -720 | -3320 275 | -3352 394 | -3748 45 | -3779 96 | -2839 359 | -2981 117 | -4004 -369 | -3668 -294 | -4222 -249 | 160 |
| 151(E) | 669 -149 -16 | -2323 -500 -7108 | -22 233 -8150 | 3133 43 -894 | -3044 -381 -1115 | -1600 399 -701 | -954 106 -1378 | -2706 -626 * | -853 210 * | -2824 -466 | -2095 -720 | -473 275 | -2059 394 | -614 45 | -1376 96 | -1068 359 | -1279 117 | -2254 -369 | -3056 -294 | -2376 -249 | 161 |
| 152(L) | -2871 -149 -16 | -2457 -500 -7108 | -4231 233 -8150 | -4103 43 -894 | -1033 -381 -1115 | -3803 399 -701 | -3165 106 -1378 | -541 -626 * | -3734 210 * | 3130 -466 | -31 -720 | -3935 275 | -3797 394 | -3286 45 | -3484 96 | -3713 359 | -2869 117 | -1136 -369 | -2394 -294 | -2220 -249 | 162 |
| 153(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -3953 210 * | -4671 -466 | -4212 -720 | -3320 275 | -3352 394 | -3748 45 | -3779 96 | -2839 359 | -2981 117 | -4004 -369 | -3668 -294 | -4222 -249 | 163 |
| 154(Y) | -3482 -149 -16 | -2868 -500 -7108 | -3701 233 -8150 | -3919 43 -894 | 238 -381 -1115 | -3552 399 -701 | -1112 106 -1378 | -3000 -626 * | -3638 210 * | -2516 -466 | -2526 -720 | -3027 275 | -3772 394 | -3101 45 | -3341 96 | -3418 359 | -3527 117 | -3071 -369 | 441 -294 | 4711 -249 | 164 |
| 155(S) | 2313 -149 -16 | -937 -500 -7108 | -2414 233 -8150 | -2419 43 -894 | -3070 -381 -1115 | -1197 399 -701 | -2205 106 -1378 | -2774 -626 * | -2385 210 * | -3059 -466 | -2200 -720 | -1614 275 | -1936 394 | -2106 45 | -2436 96 | 2518 359 | -728 117 | -1846 -369 | -3302 -294 | -3046 -249 | 165 |
| 156(L) | -2364 -149 -16 | -1901 -500 -7108 | -4660 233 -8150 | -4144 43 -894 | -630 -381 -1115 | -4349 399 -701 | -3246 106 -1378 | 2015 -626 * | -3856 210 * | 2597 -466 | 544 -720 | -4006 275 | -3841 394 | -3101 45 | -3583 96 | -3629 359 | -2275 117 | 2 -369 | -2255 -294 | -2227 -249 | 166 |
| 157(S) | -643 -149 -16 | -1153 -500 -7108 | -1942 233 -8150 | -1769 43 -894 | -1726 -381 -1115 | -1574 399 -701 | -1553 106 -1378 | -1424 -626 * | -1560 210 * | 381 -466 | -1167 -720 | -1475 275 | -2124 394 | -1504 45 | -1711 96 | 2968 359 | -911 117 | -1168 -369 | -2234 -294 | -1683 -249 | 167 |
| 158(H) | -1208 -149 -16 | -1519 -500 -7108 | -1818 233 -8150 | -1600 43 -894 | -796 -381 -1115 | -2137 399 -701 | 4436 106 -1378 | -1042 -626 * | -1134 210 * | -1422 -466 | -996 -720 | -1514 275 | -2459 394 | -1277 45 | -1260 96 | -1442 359 | -1296 117 | 1290 -369 | -1367 -294 | -527 -249 | 168 |
| 159(G) | 1625 -149 -16 | -934 -500 -7108 | -2312 233 -8150 | -2287 43 -894 | -3120 -381 -1115 | 2515 399 -701 | -2142 106 -1378 | -2866 -626 * | -2304 210 * | -3096 -466 | -2206 -720 | -1553 275 | -1910 394 | -2010 45 | -2401 96 | 1405 359 | -705 117 | -1884 -369 | -3324 -294 | -3069 -249 | 169 |
| 160(Y) | 553 -149 -16 | -516 -500 -7108 | -2670 233 -8150 | -2093 43 -894 | 1648 -381 -1115 | -2153 399 -701 | -831 106 -1378 | 125 -626 * | -1753 210 * | -275 -466 | 301 -720 | -1673 275 | -2204 394 | -1407 45 | -1649 96 | -1238 359 | -604 117 | 1878 -369 | -648 -294 | 2121 -249 | 170 |
| 161(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -3953 210 * | -4671 -466 | -4212 -720 | -3320 275 | -3352 394 | -3748 45 | -3779 96 | -2839 359 | -2981 117 | -4004 -369 | -3668 -294 | -4222 -249 | 171 |
| 162(A) | 3438 -149 -16 | -1472 -500 -7108 | -2846 233 -8150 | -3040 43 -894 | -3287 -381 -1115 | -1726 399 -701 | -2735 106 -1378 | -2840 -626 * | -3028 210 * | -3257 -466 | -2662 -720 | -2236 275 | -2447 394 | -2798 45 | -2944 96 | -1216 359 | -1387 117 | -2183 -369 | -3405 -294 | -3320 -249 | 172 |
| 163(I) | -1759 -149 -16 | -1304 -500 -7108 | -4329 233 -8150 | -3967 43 -894 | -1748 -381 -1115 | -4050 399 -701 | -3739 106 -1378 | 3054 -626 * | -3836 210 * | -593 -466 | -525 -720 | -3728 275 | -3874 394 | -3686 45 | -3907 96 | -3367 359 | -1751 117 | 2401 -369 | -3255 -294 | -2817 -249 | 173 |

TABLE 6-continued

| | | | | | | | | | | | | | | | | | | |
|---|---|---|---|---|---|---|---|---|---|---|---|---|---|---|---|---|---|---|
| 164(M | -2389 | -1957 | -4609 | -4018 | 1345 | -4211 | -2821 | 78 | -3724 | 2123 | 3673 | -3822 | -3688 | -2852 | -3378 | -3418 | -2267 | -598 | -1888 | -1767 | 174 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 165(D | -2784 | -3432 | 4016 | -1200 | -4140 | -2466 | -2197 | -4505 | -2621 | -4365 | -3956 | -1551 | -3014 | -2039 | -3232 | -2593 | -2938 | -4046 | -3710 | -3552 | 175 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 166(N | -2171 | -2655 | -1458 | -1748 | -3334 | -2364 | -2267 | -3943 | -2365 | -3936 | -3437 | 4205 | -2932 | -2205 | -2608 | -2224 | -2439 | -3392 | -3253 | -2909 | 176 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 167(P | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | -3594 | -4064 | 177 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 168(D | -1220 | -2896 | 2608 | 1191 | -3149 | -1530 | -651 | -2978 | -602 | -2895 | -2089 | 1257 | -1925 | -269 | -1273 | 1237 | -1229 | -2498 | -3083 | -2233 | 178 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 169(L | -1037 | -975 | -2376 | 275 | -735 | -2518 | -1412 | 367 | -1669 | 2017 | 219 | -1835 | -2540 | -1484 | -1766 | -1625 | -988 | 1640 | -1541 | -1207 | 179 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 170(I | -1918 | -1539 | -4076 | -3666 | 2083 | -3676 | -2142 | 3117 | -3379 | 145 | 94 | -3221 | -3504 | -2843 | -3198 | -2911 | -1872 | 334 | -1508 | -773 | 180 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 171(V | 2267 | -970 | -2988 | -2782 | -1867 | -1873 | -2265 | 74 | -2556 | -1277 | -903 | -2107 | -2419 | -2332 | -2560 | -1182 | -982 | 2421 | -2604 | -2249 | 181 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 172(A | 2401 | -935 | -2092 | -1865 | -2596 | -1235 | -1739 | -2211 | -1758 | -2497 | -1687 | -1386 | 1817 | -1571 | -1946 | -528 | 1549 | -1545 | -2846 | -2512 | 182 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 173(C | 152 | 3737 | -3346 | -3008 | -1521 | -2075 | -2187 | 405 | -2700 | -983 | -575 | -2269 | -2516 | -2413 | -2614 | -1349 | -959 | 2580 | -2260 | -1908 | 183 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 174(V | -1189 | -1030 | -2667 | 1142 | -1294 | -2870 | -1904 | 1998 | -2055 | -599 | -276 | -2175 | -2880 | -1914 | -2228 | -1998 | -1157 | 2462 | -2134 | -1721 | 184 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 175(V | -1753 | -1297 | -4327 | -3965 | -1769 | -4049 | -3747 | 2530 | -3837 | -621 | -545 | -3725 | -3875 | -3695 | -3913 | -3366 | -1745 | 2911 | -3274 | -2827 | 185 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 176(G | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 186 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 177(D | -2784 | -3432 | 4016 | -1200 | -4140 | -2466 | -2197 | -4505 | -2621 | -4365 | -3956 | -1551 | -3014 | -2039 | -3232 | -2593 | -2938 | -4046 | -3710 | -3552 | 187 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 178(G | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 188 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 179(E | -2641 | -3308 | -896 | 3732 | -3966 | -2458 | -2043 | -4105 | -2128 | -4016 | -3555 | -1531 | -2959 | -1842 | -2560 | -2479 | -2750 | -3722 | -3563 | -3385 | 189 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 180(A | 3124 | -934 | -2490 | -2562 | -3082 | -1203 | -2297 | -2766 | -2535 | -3081 | -2234 | -1670 | -1954 | -2236 | -2534 | 920 | -746 | -1844 | -3332 | -3091 | 190 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |

TABLE 6-continued

| | | | | | | | | | | | | | | | | | | | |
|---|---|---|---|---|---|---|---|---|---|---|---|---|---|---|---|---|---|---|---|
| 181(E) | −2641 −149 −16 | −3308 −500 −7108 | −896 233 −8150 | 3732 43 −894 | −3966 −381 −1115 | −2458 399 −701 | −2043 106 −1378 | −4105 −626 * | −2128 210 * | −4016 −466 | −3555 −720 | −1531 275 | −2959 394 | −1842 45 | −2560 96 | −2479 359 | −2750 117 | −3722 −369 | −3563 −294 | −3385 −249 | 191 |
| 182(T) | −1213 −149 −16 | −1674 −500 −7108 | −2755 233 −8150 | −2906 43 −894 | −3163 −381 −1115 | −1922 399 −701 | −2659 106 −1378 | −2698 −626 * | −2788 210 * | −3105 −466 | −2612 −720 | −2311 275 | −2600 394 | −2708 45 | −2753 96 | −1463 359 | 3819 117 | −2197 −369 | −3286 −294 | −3156 −249 | 192 |
| 183(G) | 1080 −149 −16 | −1108 −500 −7108 | −2311 233 −8150 | −2509 43 −894 | −3336 −381 −1115 | 3223 399 −701 | −2424 106 −1378 | −3074 −626 * | −2706 210 * | −3361 −466 | −2521 −720 | −1751 275 | −2082 394 | −2372 45 | −2708 96 | −729 359 | −932 117 | −2089 −369 | −3493 −294 | −3324 −249 | 193 |
| 184(P) | −2931 −149 −16 | −2878 −500 −7108 | −3420 233 −8150 | −3706 43 −894 | −4181 −381 −1115 | −2925 399 −701 | −3468 106 −1378 | −4621 −626 * | −3859 210 * | −4490 −466 | −4165 −720 | −3491 275 | 4225 394 | −3781 45 | −3695 96 | −3182 359 | −3279 117 | −4087 −369 | −3594 −294 | −4064 −249 | 194 |
| 185(L) | −1369 −149 −16 | −1384 −500 −7108 | −3092 233 −8150 | −2737 43 −894 | −825 −381 −1115 | −2649 399 −701 | −2073 106 −1378 | −44 −626 * | −2334 210 * | 2571 −466 | 187 −720 | −2437 275 | −2847 394 | −2125 45 | −2306 96 | −1915 359 | 1278 117 | −290 −369 | −1941 −294 | −1678 −249 | 195 |
| 186(A) | 2912 −149 −16 | −1000 −500 −7108 | −2422 233 −8150 | −2157 43 −894 | −1636 −381 −1115 | −1634 399 −701 | −1753 106 −1378 | −816 −626 * | −1876 210 * | −1128 −466 | 1988 −720 | −1694 275 | −2169 394 | −1741 45 | −1956 96 | −923 359 | −861 117 | −675 −369 | −2256 −294 | −1899 −249 | 196 |
| 187(T) | 973 −149 −16 | −953 −500 −7108 | −2483 233 −8150 | −2484 43 −894 | −2838 −381 −1115 | −1268 399 −701 | −2195 106 −1378 | −2209 −626 * | −2352 210 * | −2704 −466 | −1971 −720 | −1675 275 | −1991 394 | −2131 45 | −2373 96 | −617 359 | 3427 117 | −1554 −369 | −3148 −294 | −2888 −249 | 197 |
| 188(S) | −437 −149 −16 | −1083 −500 −7108 | −2006 233 −8150 | −2144 43 −894 | −3262 −381 −1115 | 1583 399 −701 | −2197 106 −1378 | −3097 −626 * | −2380 210 * | −3307 −466 | −2434 −720 | −1562 275 | −2008 394 | −2077 45 | −2485 96 | 2965 359 | −857 117 | −2074 −369 | −3426 −294 | −3160 −249 | 198 |
| 189(W) | −4114 −149 −16 | −3274 −500 −7108 | −4214 233 −8150 | −4453 43 −894 | −1722 −381 −1115 | −3496 399 −701 | −2681 106 −1378 | −4109 −626 * | −4149 210 * | −3619 −466 | −3615 −720 | −4044 275 | −3885 394 | −4032 45 | −3816 96 | −4355 359 | −4248 117 | −4133 −369 | 6191 −294 | 569 −249 | 199 |
| 190(H) | −1323 −149 −16 | −1832 −500 −7108 | −1402 233 −8150 | −994 43 −894 | 2149 −381 −1115 | −2268 399 −701 | 3183 106 −1378 | −1595 −626 * | −684 210 * | −1541 −466 | −1023 −720 | −1062 275 | −2358 394 | 2478 45 | −951 96 | −1335 359 | −1257 117 | −1461 −369 | −476 −294 | 569 −249 | 200 |
| 191(S) | 1326 −149 −16 | −873 −500 −7108 | −2274 233 −8150 | −2002 43 −894 | −2263 −381 −1115 | −1287 399 −701 | −1735 106 −1378 | −1644 −626 * | −1844 210 * | −2124 −466 | −1388 −720 | −1463 275 | −1915 394 | −1637 45 | −1990 96 | 2623 359 | −646 117 | 880 −369 | −2605 −294 | −2269 −249 | 201 |
| 192(N) | −573 −149 −16 | −1630 −500 −7108 | 864 233 −8150 | 62 43 −894 | −1860 −381 −1115 | −1478 399 −701 | −310 106 −1378 | 843 −626 * | −39 210 * | −1634 −466 | −837 −720 | 2440 275 | −1658 394 | 65 45 | −526 96 | −537 359 | 638 117 | −1154 −369 | −1980 −294 | −1380 −249 | 202 |
| 193(K) | −1324 −149 −16 | −1987 −500 −7108 | −1657 233 −8150 | −1059 43 −894 | −2437 −381 −1115 | −2134 399 −701 | −750 106 −1378 | −1568 −626 * | 3217 210 * | −1940 −466 | −1374 −720 | −1107 275 | −2304 394 | −391 45 | 150 96 | −1379 359 | −1277 117 | 548 −369 | −2320 −294 | −1952 −249 | 203 |
| 194(H) | −30 −149 −16 | 439 −500 −7108 | 11 233 −8150 | 363 43 −894 | −394 −381 −1115 | −739 399 −701 | 699 106 −1378 | −414 −626 * | 463 210 * | −757 −466 | 501 −720 | 286 275 | −577 394 | 639 45 | 165 96 | −23 359 | 111 117 | −312 −369 | 697 −294 | −25 −249 | 204 |
| 195(F) | −2721 −149 −16 | −2160 −500 −7108 | −3990 233 −8150 | −3906 43 −894 | 3360 −381 −1115 | −3716 399 −701 | −572 106 −1378 | −1433 −626 * | −3510 210 * | 1177 −466 | −922 −720 | −2674 275 | −3597 394 | −2614 45 | −3108 96 | −2899 359 | −2622 117 | −1671 −369 | 137 −294 | 2722 −249 | 205 |
| 196(I) | −1769 −149 −16 | −1321 −500 −7108 | −4308 233 −8150 | −3881 43 −894 | −1430 −381 −1115 | −3998 399 −701 | −3403 106 −1378 | 2941 −626 * | −3713 210 * | 744 −466 | −240 −720 | −3637 275 | −3769 394 | −3419 45 | −3696 96 | −3267 359 | −1740 117 | 2073 −369 | −2864 −294 | −2543 −249 | 206 |
| 197(N) | −1660 −149 −16 | −3287 −500 −7108 | 1909 233 −8150 | 69 43 −894 | −3610 −381 −1115 | −1646 399 −701 | −1046 106 −1378 | −3616 −626 * | −1275 210 * | −3528 −466 | −2867 −720 | 3539 275 | −2186 394 | −731 45 | −2069 96 | −1373 359 | −1757 117 | −3086 −369 | −3624 −294 | −2697 −249 | 207 |

TABLE 6-continued

| | | | | | | | | | | | | | | | | | | | |
|---|---|---|---|---|---|---|---|---|---|---|---|---|---|---|---|---|---|---|---|
| 198(P) | −2931 | −2878 | −3420 | −3706 | −4181 | −2925 | −3468 | −4621 | −3859 | −4490 | −4165 | −3491 | 4225 | −3781 | −3695 | −3182 | −3279 | −4087 | −3594 | −4064 | 208 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 199(R | 780 | −954 | −1042 | −463 | −1021 | −1681 | −388 | 1232 | 838 | −838 | −132 | −612 | −1756 | −173 | 1322 | −665 | −418 | 574 | −1339 | −893 | 209 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 200(N | −622 | −2053 | −110 | 1285 | −2366 | −1450 | −199 | −2102 | 1009 | −2062 | −1176 | 2124 | −1614 | 238 | −276 | −491 | 1247 | −1677 | −2241 | −1566 | 210 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 201(D | −1369 | −2674 | 3374 | −58 | −3453 | −1571 | −1095 | −3380 | −1289 | −3368 | −2659 | −394 | −2124 | −784 | −2016 | 1149 | −1529 | −2785 | −3505 | −2662 | 211 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 202(G | −2594 | −2690 | −3304 | −3623 | −4328 | 3747 | −3462 | −4761 | −3953 | −4671 | −4212 | −3320 | −3352 | −3748 | −3779 | −2839 | −2981 | −4004 | −3668 | −4222 | 212 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 203(A | 2246 | −790 | −2416 | −1988 | −1270 | −1821 | −1490 | 1726 | −1755 | −905 | −386 | −1651 | −2194 | −1557 | −1854 | −1027 | 949 | 146 | −1839 | −1474 | 213 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 204(V | −1771 | −1603 | −3750 | −3689 | −2037 | −3050 | −3231 | 403 | −3479 | −1154 | −1076 | −3246 | −3399 | −3383 | −3437 | −2628 | −1917 | 3536 | −3074 | −2677 | 214 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 205(L) | −2871 | −2457 | −4231 | −4103 | −1033 | −3803 | −3165 | −541 | −3734 | 3130 | −31 | −3935 | −3797 | −3286 | −3484 | −3713 | −2869 | −1136 | −2394 | −2220 | 215 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 206(P) | −2931 | −2878 | −3420 | −3706 | −4181 | −2925 | −3468 | −4621 | −3859 | −4490 | −4165 | −3491 | 4225 | −3781 | −3695 | −3182 | −3279 | −4087 | −3594 | −4064 | 216 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 207(I) | −2091 | −1746 | −3971 | −3840 | −1676 | −3532 | −3289 | 3684 | −3581 | −659 | −693 | −3562 | −3674 | −3445 | −3521 | −3194 | −2146 | 449 | −2877 | −2493 | 217 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 208(L) | −2475 | −2006 | −4716 | −4195 | −570 | −4423 | −3262 | 1353 | −3887 | 2819 | 603 | −4084 | −3871 | −3089 | −3590 | −3715 | −2377 | −194 | −2218 | −2208 | 218 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 209(H | −1047 | −2367 | −130 | −12 | −2443 | −1653 | 3422 | −2425 | 11 | −2366 | −1567 | 2352 | −1902 | 1348 | −351 | −897 | −1003 | −2040 | −2389 | −1693 | 219 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 210(L) | −1968 | −1597 | −4244 | −3772 | −812 | −3841 | −2955 | 582 | −3473 | 2391 | 322 | −3529 | −3600 | −2960 | −3315 | −3097 | −1926 | 2070 | −2269 | −2100 | 220 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 211(N | −2171 | −2655 | −1458 | −1748 | −3334 | −2364 | −2267 | −3943 | −2365 | −3936 | −3437 | 4205 | −2932 | −2205 | −2608 | −2224 | −2439 | −3392 | −3253 | −2909 | 221 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 212(G | −2594 | −2690 | −3304 | −3623 | −4328 | 3747 | −3462 | −4761 | −3953 | −4671 | −4212 | −3320 | −3352 | −3748 | −3779 | −2839 | −2981 | −4004 | −3668 | −4222 | 222 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 213(F) | −3581 | −2688 | −4165 | −4401 | 3865 | −4034 | −401 | −2491 | −3981 | −1903 | −1944 | −2746 | −3921 | −2847 | −3438 | −3284 | −3462 | −2647 | −3001 | 3054 | 223 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 214K | −2620 | −2961 | −2461 | −2046 | −3743 | −2791 | −1570 | −3603 | 3784 | −3387 | −2839 | −2048 | −3039 | −1260 | −465 | −2604 | −2536 | −3331 | 341 | −2988 | 224 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | | | | | | | | | | | | | |

TABLE 6-continued

| | | | | | | | | | | | | | | | | | | | |
|---|---|---|---|---|---|---|---|---|---|---|---|---|---|---|---|---|---|---|---|
| 215(I) | −2091 | −1746 | −3971 | −3840 | −1676 | −3532 | −3289 | 3684 | −3581 | −659 | −693 | −3562 | −3674 | −3445 | −3521 | −3194 | −2146 | 449 | −2877 | −2493 | 225 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 216(A) | 2478 | −935 | −2423 | −2429 | −3066 | −1197 | −2208 | −2769 | −2392 | −3055 | −2196 | −1617 | −1936 | −2112 | −2440 | 2351 | −728 | −1843 | −3300 | −3045 | 226 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 217(N) | −1558 | −3098 | 310 | 1592 | −3431 | −1657 | −945 | −3340 | −959 | −3271 | −2572 | 3495 | −2146 | −611 | −1578 | −1301 | −1621 | −2860 | −3383 | −2547 | 227 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 218(P) | −1664 | −2231 | −2030 | −1695 | −3192 | −2240 | −1444 | −3029 | −556 | −2975 | −2319 | −1668 | 3549 | −1149 | 1833 | −1745 | −1774 | −2613 | −2848 | −2650 | 228 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 219(T) | −1213 | −1674 | −2755 | −2906 | −3163 | −1922 | −2659 | −2698 | −2788 | −3105 | −2612 | −2311 | −2600 | −2708 | −2753 | −1463 | 3819 | −2197 | −3286 | −3156 | 229 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 220(I) | −1764 | −1326 | −4294 | −3932 | −1658 | −3987 | −3644 | 3354 | −3776 | −498 | −454 | −3684 | −3833 | −3599 | −3826 | −3303 | −1760 | 1799 | −3153 | −2738 | 230 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 221(F) | −2604 | −2127 | −4552 | −4135 | 2542 | −4236 | −2203 | −115 | −3820 | 2542 | 500 | −3692 | −3785 | −2927 | −3457 | −3508 | −2493 | −769 | −1337 | −643 | 231 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 222(S) | 846 | −947 | −2243 | −2217 | −3137 | 1905 | −2112 | −2888 | −2254 | −3112 | −2218 | −1528 | −1909 | −1968 | −2369 | 2545 | −708 | −1899 | −3331 | −3067 | 232 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 223(R) | −1454 | 3144 | −2763 | −2070 | −2728 | −2193 | −1414 | −2383 | −460 | −2518 | −1907 | −1827 | −2567 | −1160 | 3510 | −1626 | −1582 | −2068 | −2596 | −2366 | 233 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 224(M) | −434 | −912 | −967 | 653 | −960 | −1640 | −368 | 1179 | 682 | −787 | 2592 | −569 | −1718 | −161 | −575 | −617 | 633 | −341 | −1294 | −841 | 234 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 225(S) | −1102 | −2199 | 1764 | −235 | −3206 | −1518 | −1117 | −3089 | −1203 | −3129 | −2368 | −513 | −2060 | −804 | −1816 | 2841 | −1292 | −2470 | −3271 | −2541 | 235 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 226(D) | −1724 | −3448 | 3411 | 103 | −3726 | −1642 | −1058 | −3734 | −1342 | −3628 | −2991 | 1884 | −2196 | −745 | −2191 | −1408 | −1822 | −3197 | −3743 | −2768 | 236 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 227(E) | 391 | −2060 | −303 | 2460 | −2453 | −1565 | −312 | −2145 | 213 | −2119 | −1272 | −258 | −1745 | 110 | 1394 | −657 | −720 | −1747 | −2290 | −1683 | 237 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 228(E) | −843 | −2213 | −113 | 2617 | −2562 | −1553 | −357 | −2268 | 1012 | −2237 | −1392 | −212 | −1769 | 60 | −324 | −706 | 776 | −1863 | −2412 | −1764 | 238 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 229(L) | −2324 | −1864 | −4634 | −4121 | −657 | −4319 | −3239 | 2224 | −3838 | 2493 | 517 | −3975 | −3830 | −3106 | −3578 | −3596 | −2239 | 73 | −2272 | −2231 | 239 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 230(H) | −505 | −1236 | −775 | −228 | −1373 | −1593 | −1058 | −963 | 872 | −1178 | −425 | −432 | −1693 | 14 | −290 | −578 | 1743 | 825 | −1578 | −1083 | 240 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |
| 231(C) | −561 | 2259 | 1449 | 1476 | −2294 | −1417 | −164 | −2034 | 1472 | −2003 | −1111 | −57 | −1572 | 275 | −300 | −433 | −510 | −1609 | −2194 | −1510 | 241 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −16 | −7108 | −8150 | −894 | −1115 | −701 | −1378 | * |  |  |  |  |  |  |  |  |  |  |  |  |  |

TABLE 6-continued

| | | | | | | | | | | | | | | | | | | |
|---|---|---|---|---|---|---|---|---|---|---|---|---|---|---|---|---|---|---|
| 232(Y) | -2882 -149 -16 | -2267 -500 -7108 | -4018 233 -8150 | -3995 -894 | 2580 -381 -1115 | -3778 399 -701 | -511 106 -1378 | -1658 -626 * | -3593 210 * | 923 -466 | -1152 -720 | -2675 275 | -3663 394 | -2654 45 | -3169 96 | -2969 359 | -2779 117 | -1865 -369 | 205 -294 | 3751 -249 | 242 |
| 233(F) | -3342 -149 -16 | -2776 -500 -7108 | -4026 233 -8150 | -4232 43 -894 | 4354 -381 -1115 | -3545 399 -701 | -1431 106 -1378 | -2315 -626 * | -4038 210 * | -1801 -466 | -1900 -720 | -3299 275 | -3780 394 | -3350 45 | -3645 96 | -3490 359 | -3420 117 | -2566 -369 | -739 -294 | 349 -249 | 243 |
| 234(H) | -559 -149 -16 | -1906 -500 -7108 | -319 233 -8150 | 1741 43 -894 | -2211 -381 -1115 | -1478 399 -701 | 2491 106 -1378 | -1923 -626 * | 355 210 * | -1899 -466 | -1021 -720 | -132 275 | -1591 394 | 303 45 | 791 96 | -452 359 | 1019 117 | -1527 -369 | -2083 -294 | -1454 -249 | 244 |
| 235(G) | -456 -149 -16 | -1098 -500 -7108 | -1993 233 -8150 | -2173 43 -894 | -3296 -381 -1115 | 2968 399 -701 | -2244 106 -1378 | -3141 -626 * | -2461 210 * | -3355 -466 | -2485 -720 | -1583 275 | -2025 394 | -2139 45 | -2549 96 | 1723 359 | -881 117 | -2104 -369 | -3461 -294 | -3203 -249 | 245 |
| 236(M) | -1532 -149 -16 | -1301 -500 -7108 | -3405 233 -8150 | -2864 43 -894 | -57 -381 -1115 | -3050 399 -701 | -1438 106 -1378 | -56 -626 * | -2477 210 * | 1096 -466 | 3967 -720 | -2484 275 | -2939 394 | -2042 45 | -2342 96 | -2169 359 | -1455 117 | -370 -369 | -989 -294 | 2079 -249 | 246 |
| 237(G) | -1038 -149 -16 | -1765 -500 -7108 | -926 233 -8150 | -1191 43 -894 | -3372 -381 -1115 | 3233 399 -701 | -1826 106 -1378 | -3379 -626 * | -1926 210 * | -3481 -466 | -2725 -720 | 1285 275 | -2271 394 | -1628 45 | -2264 96 | -1145 359 | -1377 117 | -2554 -369 | -3401 -294 | -2980 -249 | 247 |
| 238(W) | -3553 -149 -16 | -2695 -500 -7108 | -4100 233 -8150 | -4288 43 -894 | 1022 -381 -1115 | -3972 399 -701 | -428 106 -1378 | -2592 -626 * | -3792 210 * | -2021 -466 | -2038 -720 | -2737 275 | -3890 394 | -2815 45 | -3323 96 | -3265 359 | -3440 117 | -2712 -369 | 4944 -294 | 3677 -249 | 248 |
| 239(H) | -693 -149 -16 | -2112 -500 -7108 | -279 233 -8150 | 1837 43 -894 | -2456 -381 -1115 | -1534 399 -701 | 2434 106 -1378 | -2176 -626 * | 1108 210 * | -2098 -466 | -1217 -720 | -167 275 | -1666 394 | 1691 45 | -39 96 | -560 359 | -624 117 | -1753 -369 | -2235 -294 | -1604 -249 | 249 |
| 240(P) | -853 -149 -16 | -1252 -500 -7108 | -2460 233 -8150 | -2393 43 -894 | -2139 -381 -1115 | -1784 399 -701 | -2109 106 -1378 | -974 -626 * | -2210 210 * | -1748 -466 | -1364 -720 | -1924 275 | 3453 394 | -2108 45 | -2271 96 | -1167 359 | -1152 117 | 1448 -369 | -2678 -294 | -2307 -249 | 250 |
| 241(Y) | -812 -149 -16 | -1365 -500 -7108 | -1241 233 -8150 | -1255 -894 | -4 -381 -1115 | -1806 399 -701 | -48 106 -1378 | -1150 -626 * | 314 210 * | -1157 -466 | -604 -720 | -702 275 | -1897 394 | -107 45 | 2106 96 | -965 359 | -822 117 | -1011 -369 | -491 -294 | 2916 -249 | 251 |
| 242(Y) | -906 -149 -27 | -6323 -500 -7108 | -7365 233 -8150 | -688 43 -894 | -381 -1115 | -292 399 -701 | -2448 106 -1378 | -626 * | -528 210 * | -626 -466 | 43 -720 | -777 275 | -1822 394 | -410 45 | -817 96 | -751 359 | 649 117 | -143 -369 | -1165 -294 | 1945 -249 | 252 |
| 243(F) | -476 -149 -16 | -775 -500 -7108 | -1198 233 -8150 | 1077 43 -894 | -755 -381 -1115 | -1738 399 -701 | -505 106 -1378 | 1586 -626 * | 463 210 * | -626 -466 | -206 -720 | -2800 275 | -3287 394 | -2604 45 | -2951 96 | -2505 359 | -1863 117 | 1480 -369 | -853 -294 | 99 -249 | 253 |
| 244(V) | -1857 -149 -16 | -1592 -500 -7108 | -3755 233 -8150 | -3460 43 -894 | 3638 -381 -1115 | -3255 399 -701 | -1454 106 -1378 | -16 -626 * | -3144 210 * | -214 -466 | -819 -720 | -1390 275 | -2525 394 | -1332 45 | -1696 96 | -1574 359 | -1248 117 | 2962 -369 | -2384 -294 | -1907 -249 | 254 |
| 245(H) | -1203 -149 -16 | -1434 -500 -7108 | -1278 233 -8150 | 1166 43 -894 | -1756 -381 -1115 | -2236 399 -701 | -1499 106 -1378 | 75 -626 * | -1412 210 * | -1192 -466 | 501 -720 | 286 275 | -577 394 | 639 45 | 165 96 | -23 359 | 111 117 | -312 -369 | 697 -294 | -25 -249 | 255 |
| | -30 -149 -16 | 439 -500 -7108 | 11 233 -8150 | 363 43 -894 | -394 -381 -1115 | -739 399 -701 | 699 106 -1378 | 414 -626 * | 463 210 * | -757 -466 | | | | | | | | | | | |
| 246(E) | 1028 -149 -16 | -2230 -500 -7108 | 1464 233 -8150 | 1545 43 -894 | -2560 -381 -1115 | -1444 399 -701 | -343 106 -1378 | -2324 -626 * | -77 210 * | -2285 -466 | -1411 -720 | -93 275 | -1690 394 | 78 45 | -635 96 | 1220 359 | -730 117 | -1876 -369 | -2478 -294 | -1750 -249 | 256 |
| 247(G) | 802 -149 -16 | -892 -500 -7108 | -1664 233 -8150 | -1291 43 -894 | -1774 -381 -1115 | 2148 399 -701 | -1181 106 -1378 | -1363 -626 * | -1177 210 * | 617 -466 | -906 -720 | -1109 275 | -1839 394 | -1027 45 | -1436 96 | 836 359 | -560 117 | -1000 -369 | -2098 -294 | -1700 -249 | 257 |
| 248(F) | -737 -149 -16 | -1710 -500 -7108 | 1482 233 -8150 | 1223 43 -894 | 2205 -381 -1115 | -1628 399 -701 | -301 106 -1378 | -1513 -626 * | -202 210 * | -1603 -466 | -865 -720 | -339 275 | -1790 394 | -72 45 | -681 96 | -695 359 | -688 117 | -1259 -369 | -1410 -294 | 1271 -249 | 258 |

TABLE 6-continued

| | | | | | | | | | | | | | | | | |
|---|---|---|---|---|---|---|---|---|---|---|---|---|---|---|---|---|
| 249(D) | -1662 -149 -16 | -3241 -500 -7108 | 3494 233 -8150 | 12 43 -894 | -3550 -381 -1115 | -1708 399 -701 | -991 106 -1378 | -3449 -626 * | 907 210 * | -3360 -466 | -2675 -720 | -360 275 | -2197 394 | -658 45 | -1631 96 | -1384 359 | -1715 117 | -2975 -369 | -3451 -294 | -2636 -249 | 259 |
| 250(K) | 374 -149 -16 | -1824 -500 -7108 | 783 233 -8150 | 927 43 -894 | -2121 -381 -1115 | -1368 399 -701 | -40 106 -1378 | 525 -626 * | 1057 210 * | -1830 -466 | -920 -720 | 824 275 | 249 394 | 411 45 | -141 96 | -290 359 | -342 117 | -1433 -369 | -2020 -294 | -1349 -249 | 260 |
| 251(E) | 424 -149 -16 | -2247 -500 -7108 | 1450 233 -8150 | 1906 43 -894 | -2557 -381 -1115 | 209 399 -701 | -314 106 -1378 | -2325 -626 * | -37 210 * | -2276 -466 | -1395 -720 | -75 275 | 659 394 | 111 45 | -595 96 | -584 359 | -710 117 | -1874 -369 | -2461 -294 | -1729 -249 | 261 |
| 252(D) | -1129 -149 -570 | -2752 -500 -7108 | 2889 233 -1648 | 513 43 -894 | -3030 -381 -1115 | -1216 399 -701 | -532 106 -1378 | -2959 -626 * | -669 212 * | -2896 -466 | -2188 -721 | 2229 275 | -1714 394 | -198 45 | -1413 96 | -860 359 | -1196 117 | -2465 -370 | -3041 -295 | -2140 -248 | 262 |
| 253(H) | -696 -149 -25 | -961 -500 -6457 | -1261 233 -7499 | -873 43 -894 | -178 -381 -1115 | -1785 399 -701 | 3652 105 -1008 | 1381 -626 * | -427 210 * | -516 -466 | -92 -720 | -889 275 | -1934 394 | -521 45 | -602 96 | -945 359 | -673 117 | -203 -369 | -756 -294 | 22 -249 | 273 |
| 254(M) | -1561 -149 -25 | -1309 -500 -6457 | -3310 233 -7499 | -2786 43 -894 | -99 -381 -1115 | -1666 399 -701 | -546 106 -1378 | 569 -626 * | -2364 210 * | 1604 -466 | 3948 -720 | -2656 275 | -2936 394 | -1983 45 | -2284 96 | -2361 359 | -1493 117 | 116 -369 | -1472 -294 | -1272 -249 | 274 |
| 255(K) | -475 -149 -25 | -1891 -500 -6457 | -137 233 -7499 | 1054 43 -894 | -2221 -381 -1115 | -1359 399 -777 | -30 106 -1263 | -1946 -626 * | 1632 210 * | -1890 -466 | -999 -720 | 2 275 | -1483 394 | 1488 45 | 30 96 | 1135 359 | -411 117 | -1523 -369 | -2049 -294 | -1403 -249 | 275 |
| 256(V) | -1531 -149 -19 | -1105 -500 -6850 | -4020 233 -7893 | -3576 43 -894 | -1227 -381 -1115 | -3695 399 -1215 | -3034 106 -813 | 2323 -626 * | -3387 210 * | 793 -466 | -62 -720 | -3320 275 | -3500 394 | -3101 45 | -3368 96 | -2941 359 | -1501 117 | 2608 -369 | -2576 -294 | -2243 -249 | 276 |
| 257(H) | -1244 -149 -19 | -2186 -500 -6850 | -246 233 -7893 | -319 43 -894 | -1501 -381 -1115 | -1694 399 -1215 | 4400 106 -813 | -2492 -626 * | -417 210 * | -2436 -466 | -1795 -720 | 1396 275 | -2075 394 | -501 45 | -711 96 | -1152 359 | -1294 117 | -2140 -369 | -1842 -294 | -960 -249 | 277 |
| 258(R) | -675 -149 -19 | -1969 -500 -6850 | -242 233 -7893 | 1673 43 -894 | -2340 -381 -1115 | -1479 399 -701 | -164 106 -813 | -2032 -626 * | 420 210 * | -1985 -466 | -1141 -720 | -153 275 | -1738 394 | 261 45 | 1760 96 | -560 359 | -613 117 | -1643 -369 | -2136 -294 | -1550 -249 | 278 |
| 259(E) | 377 -149 -19 | -1835 -500 -6850 | 1113 233 -7893 | 1421 43 -894 | -2128 -381 -1115 | -1382 399 -453 | -69 106 -1893 | -1857 -626 * | 329 210 * | -1840 -466 | -939 -720 | -29 275 | -1493 394 | 377 45 | 1329 96 | -322 359 | -374 117 | 19 -369 | -2039 -294 | -1371 -249 | 279 |
| 260(M) | -2315 -149 -16 | -1899 -500 -7108 | -4526 233 -8150 | -3941 43 -894 | 2102 -381 -1115 | -4105 399 -701 | -2681 106 -1378 | 70 -626 * | -3638 210 * | 1954 -466 | 1509 -720 | -3704 275 | -3629 394 | -2798 45 | -3304 96 | -3301 359 | -2198 117 | -582 -369 | -1802 -294 | -1604 -249 | 280 |
| 261(A) | 2818 -149 -16 | -1372 -500 -7108 | -1321 233 -8150 | -1214 43 -894 | -2015 -381 -1115 | -1557 399 -701 | 2623 106 -1378 | -2096 -626 * | -1108 210 * | -2284 -466 | -1581 -720 | -1154 275 | -2074 394 | -1121 45 | -1340 96 | -881 359 | -964 117 | -1649 -369 | -2321 -294 | -1711 -249 | 281 |
| 262(K) | -793 -149 -16 | -2177 -500 -7108 | -220 233 -8150 | 1469 43 -894 | -2548 -381 -1115 | -1561 399 -701 | -289 106 -1378 | -2263 -626 * | 2325 210 * | -2196 -466 | -1334 -720 | -214 275 | -1738 394 | 141 45 | -150 96 | 898 359 | -737 117 | -1844 -369 | -2341 -294 | -1711 -249 | 282 |
| 263(A) | 1931 -149 -16 | -776 -500 -7108 | -2058 233 -8150 | -1612 43 -894 | -1165 -381 -1115 | -1647 399 -701 | -1206 106 -1378 | -433 -626 * | -1382 210 * | 945 -466 | -310 -720 | -1370 275 | -2014 394 | -1216 45 | -1530 96 | -832 359 | 1640 117 | -293 -369 | -1672 -294 | -1305 -249 | 283 |
| 264(M) | -1519 -149 -16 | -1247 -500 -7108 | -3637 233 -8150 | -3077 43 -894 | 1725 -381 -1115 | -3081 399 -701 | -1493 106 -1378 | -37 -626 * | -2718 210 * | 1089 -466 | 3901 -720 | -2600 275 | -2950 394 | -2153 45 | -2487 96 | -2201 359 | -1437 117 | -379 -369 | 1806 -294 | -356 -249 | 284 |
| 265(D) | -1378 -149 -16 | -3094 -500 -7108 | 2801 233 -8150 | 1763 43 -894 | -3349 -381 -1115 | -1556 399 -701 | -771 106 -1378 | -3202 -626 * | -821 210 * | -3114 -466 | -2349 -720 | -164 275 | -2006 394 | -409 45 | -1544 96 | 1050 359 | -1411 117 | -2709 -369 | -3307 -294 | -2411 -249 | 285 |

TABLE 6-continued

| | | | | | | | | | | | | | | | | |
|---|---|---|---|---|---|---|---|---|---|---|---|---|---|---|---|---|
| 266(W) | -426 -149 -16 | -1591 -500 -7108 | -384 233 -8150 | 832 43 -894 | -1812 -381 -1115 | -1435 399 -701 | -111 106 -1378 | -1488 -626 * | 966 210 * | -1565 -466 | -720 -720 | -131 275 | -1532 394 | 300 45 | -184 96 | 757 359 | 1423 117 | -1162 -369 | 2539 -294 | -1242 -249 | 286 |
| 267(V) | 1401 -149 -16 | -623 -500 -7108 | -2516 233 -8150 | -1981 43 -894 | -808 -381 -1115 | -2086 399 -701 | -1255 106 -1378 | 1461 -626 * | -1718 210 * | -518 -466 | 36 -720 | -1694 275 | -2253 394 | -1472 45 | -1752 96 | 293 359 | -658 117 | 1939 -369 | -1375 -294 | -1008 -249 | 287 |
| 268(W) | -857 -149 -16 | -644 -500 -7108 | -3104 233 -8150 | -2515 43 -894 | 1895 -381 -1115 | -2435 399 -701 | -1142 106 -1378 | 1168 -626 * | -2142 210 * | -39 -466 | 357 -720 | -2021 275 | -2440 394 | -1737 45 | -1961 96 | -1534 359 | -797 117 | 2161 -369 | 2512 -294 | -335 -249 | 288 |
| 269(E) | -1213 -149 -16 | -2845 -500 -7108 | 1928 233 -8150 | 2618 43 -894 | -3115 -381 -1115 | -1534 399 -701 | -660 106 -1378 | -2926 -626 * | -607 210 * | -2864 -466 | -2064 -720 | -150 275 | -1929 394 | -281 45 | -1267 96 | -980 359 | 833 117 | -2457 -369 | -3061 -294 | -2225 -249 | 289 |
| 270(E) | -1357 -149 -16 | -2719 -500 -7108 | -146 233 -8150 | 2868 43 -894 | -3119 -381 -1115 | -1782 399 -701 | -634 106 -1378 | -2833 -626 * | 1719 210 * | -2718 -466 | -1948 -720 | -434 275 | -2077 394 | -242 45 | -361 96 | -1166 359 | -1309 117 | -2433 -369 | -2790 -294 | -2201 -249 | 290 |
| 271(I) | -2091 -149 -16 | -1746 -500 -7108 | -3971 233 -8150 | -3840 43 -894 | -1676 -381 -1115 | -3532 399 -701 | -3289 106 -1378 | 3684 -626 * | -3581 210 * | -659 -466 | -693 -720 | -3562 275 | -3674 394 | -3445 45 | -3521 96 | -3194 359 | -2146 117 | 449 -369 | -2877 -294 | -2493 -249 | 291 |
| 272(C) | -1095 -149 -16 | 2832 -500 -7108 | -1254 233 -8150 | -506 43 -894 | -2502 -381 -1115 | -1969 399 -701 | 1775 106 -1378 | -2085 -626 * | 2238 210 * | -2024 -466 | -1241 -720 | -660 275 | -2004 394 | 96 45 | 1706 96 | -1025 359 | -959 117 | -1790 -369 | -2126 -294 | -1723 -249 | 292 |
| 273(D) | 1682 -149 -16 | -2499 -500 -7108 | 2383 233 -8150 | 115 43 -894 | -3011 -381 -1115 | -1503 399 -701 | -717 106 -1378 | -2803 -626 * | -660 210 * | -2789 -466 | -1985 -720 | 1727 275 | -1918 394 | -347 45 | -1292 96 | -922 359 | -1145 117 | -2313 -369 | -2999 -294 | -2214 -249 | 293 |
| 274(I) | -2091 -149 -16 | -1746 -500 -7108 | -3971 233 -8150 | -3840 43 -894 | -1676 -381 -1115 | -3532 399 -701 | -3289 106 -1378 | 3684 -626 * | -3581 210 * | -659 -466 | -693 -720 | -3562 275 | -3674 394 | -3445 45 | -3521 96 | -3194 359 | -2146 117 | 449 -369 | -2877 -294 | -2493 -249 | 294 |
| 275(Q) | -1627 -149 -16 | -2584 -500 -7108 | -1823 233 -8150 | -913 43 -894 | -3248 -381 -1115 | -2312 399 -701 | -430 106 -1378 | -2707 -626 * | 1993 210 * | -2449 -466 | -1710 -720 | -969 275 | -2306 394 | 3139 45 | 1660 96 | -1504 359 | -1407 117 | -2413 -369 | -2377 -294 | -2126 -249 | 295 |
| 276(K) | 949 -149 -16 | -2020 -500 -7108 | -181 233 -8150 | 1024 43 -894 | -2347 -381 -1115 | -1460 399 -701 | -176 106 -1378 | -2077 -626 * | 2067 210 * | -2031 -466 | -1143 -720 | 996 275 | -1606 394 | 264 45 | -187 96 | -477 359 | -547 117 | -1653 -369 | -2203 -294 | -1543 -249 | 296 |
| 277(H) | 1280 -149 -16 | -1815 -500 -7108 | -274 233 -8150 | 261 43 -894 | -2114 -381 -1115 | -1392 399 -701 | 1493 106 -1378 | -1840 -626 * | 1076 210 * | -1818 -466 | -916 -720 | 946 275 | -1489 394 | 1230 45 | -102 96 | -316 359 | 245 117 | -1427 -369 | -2010 -294 | -1354 -249 | 297 |
| 278(A) | 3438 -149 -16 | -1472 -500 -7108 | -2846 233 -8150 | -3040 43 -894 | -3287 -381 -1115 | -1726 399 -701 | -2735 106 -1378 | -2840 -626 * | -3028 210 * | -3257 -466 | -2662 -720 | -2236 275 | -2447 394 | -2798 45 | -2944 96 | -1216 359 | -1387 117 | -2183 -369 | -3405 -294 | -3320 -249 | 298 |
| 279(R) | -836 -149 -16 | -1922 -500 -7108 | -846 233 -8150 | -238 43 -894 | -2255 -381 -1115 | -1752 399 -701 | -261 106 -1378 | -1878 -626 * | 494 210 * | -1879 -466 | -1072 -720 | 484 275 | -1828 394 | 1594 45 | 2601 96 | -770 359 | -741 117 | 369 -369 | -2053 -294 | -1564 -249 | 299 |
| 280(E) | -531 -149 -16 | -1917 -500 -7108 | -152 233 -8150 | 1776 43 -894 | -2240 -381 -1115 | -1412 399 -701 | -166 106 -1378 | -1971 -626 * | 212 210 * | -1955 -466 | -1067 -720 | -76 275 | -1565 394 | 1351 45 | -287 96 | 854 359 | 1223 117 | -1553 -369 | -2155 -294 | -1485 -249 | 300 |
| 281(N) | -756 -149 -1243 | -2277 -500 -7108 | 1639 233 -8150 | 264 43 -894 | -2584 -381 -1115 | 735 399 -701 | -320 106 -1378 | -2357 -626 * | -45 210 * | -2301 -466 | -1420 -720 | 1764 275 | -1681 394 | 1399 45 | -604 96 | 499 359 | -725 117 | -1902 -369 | -2482 -294 | -1746 -249 | 301 |
| 282(T) | 391 -149 -36 | -254 -500 -5902 | -749 233 -6944 | -541 43 -894 | -1519 -381 -1115 | -523 399 -701 -2014 | -582 106 -1378 -410 | -1080 -626 * | -464 210 * | -1400 -466 | -646 -720 | -345 275 | -1090 394 | -368 45 | -718 96 | 1584 359 | 1914 117 | -580 -369 | -1775 -294 | -1351 -249 | 302 |

TABLE 6-continued

| | | | | | | | | | | | | | | | | | | |
|---|---|---|---|---|---|---|---|---|---|---|---|---|---|---|---|---|---|---|
| 283(N) | 1419 | −678 | −16 | 71 | −1606 | −696 | −281 | −1227 | −86 | −1488 | −735 | 2022 | −1167 | 9 | −450 | 17 | −79 | −791 | −1790 | −1251 | 303 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −36 | −5902 | −6944 | −894 | −1115 | −655 | −1455 | * | * | | | | | | | | | | | | |
| 284(N) | −690 | −2252 | 1313 | 1338 | −2538 | −1300 | −208 | −2319 | 1491 | −2250 | −1381 | 1988 | −1564 | 211 | −512 | −509 | −660 | −1861 | −2424 | −1672 | 304 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −20 | −6788 | −7830 | −894 | −1115 | −421 | −1984 | * | * | | | | | | | | | | | | |
| 285(D) | −1304 | −3019 | 2680 | 1285 | −3255 | −1544 | −705 | −3097 | −703 | −3006 | −2219 | 1388 | 1348 | −331 | −1399 | −1044 | −1321 | −2611 | −3195 | −2320 | 305 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 286(H) | −30 | 439 | 11 | 363 | −394 | −739 | 699 | −414 | 463 | −757 | 501 | 286 | −577 | 639 | 165 | −23 | 111 | −312 | 697 | −25 | 306 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 287(M) | 1003 | −593 | 321 | −1362 | −615 | −2007 | −849 | 1868 | −1149 | −373 | 2071 | −1286 | −2064 | −949 | −1296 | −1049 | −514 | 769 | −1128 | −747 | 307 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 288(M) | −426 | −945 | −995 | −468 | −1082 | −1580 | 1667 | −681 | −299 | −938 | 2081 | −605 | −1724 | −229 | −641 | 445 | 2054 | −498 | −1403 | −940 | 308 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 289(R) | −1619 | −2365 | −2075 | −1064 | −2835 | −2363 | −469 | −2305 | 1823 | 763 | −1488 | −1073 | −2345 | −67 | 2817 | −1563 | −1402 | −2096 | −2243 | −1997 | 309 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 290(P) | −2931 | −2878 | −3420 | −3706 | −4181 | −2925 | −3468 | −4621 | −3859 | −4490 | −4165 | −3491 | 4225 | −3781 | −3695 | −3182 | −3279 | −4087 | −3594 | −4064 | 310 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 291(Q) | −802 | −740 | −2393 | −1814 | 1799 | −2272 | −1035 | 123 | −1529 | 790 | 401 | −1638 | −2287 | 2034 | −1573 | −1335 | −740 | 1456 | −1046 | −619 | 311 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 292(W) | −3500 | −2678 | −4063 | −4226 | 995 | −3934 | −449 | −2563 | −3717 | −2009 | −2016 | −2732 | −3866 | −2798 | −3276 | −3242 | −3394 | −2681 | 5405 | 3043 | 312 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 293(P) | −2931 | −2878 | −3420 | −3706 | −4181 | −2925 | −3468 | −4621 | −3859 | −4490 | −4165 | −3491 | 4225 | −3781 | −3695 | −3182 | −3279 | −4087 | −3594 | −4064 | 313 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 294(M) | −2406 | −2296 | −3638 | −3594 | −1525 | −3105 | −2824 | −1047 | −3121 | −596 | 5043 | −3293 | −3425 | −3046 | −2996 | −2911 | −2552 | −1398 | −2513 | −2207 | 314 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 295(I) | −2034 | −1595 | −4395 | −3950 | −974 | −4099 | −3249 | 3261 | −3681 | 1202 | 174 | −3748 | −3784 | −3212 | −3556 | −3388 | −1988 | 627 | −2497 | −2285 | 315 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 296(I) | −1757 | −1299 | −4333 | −3971 | −1766 | −4057 | −3755 | 2831 | −3844 | −614 | −541 | −3733 | −3880 | −3700 | −3920 | −3375 | −1749 | 2665 | −3275 | −2830 | 316 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 297(F) | −2590 | −2117 | −4458 | −4084 | 3096 | −4144 | −1957 | −191 | −3757 | 2203 | 405 | −3544 | −3752 | −2887 | −3401 | −3410 | −2485 | −812 | −1135 | −337 | 317 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 298(R) | −2957 | −3022 | −3318 | −2735 | −3796 | −2998 | −1968 | −3912 | −846 | −3631 | −3157 | −2611 | −3280 | −1724 | 4056 | −3026 | −2913 | −3650 | −3096 | −3185 | 318 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |
| 299(T) | 2050 | −905 | −2305 | −2099 | −2720 | −1206 | −1895 | −2371 | −1974 | −2648 | −1815 | −1479 | −1888 | −1753 | −2118 | 1016 | 2546 | −1624 | −2968 | −2665 | 319 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | * | | | | | | | | | | | | |

TABLE 6-continued

| Label | C1 | C2 | C3 | C4 | C5 | C6 | C7 | C8 | C9 | C10 | C11 | C12 | C13 | C14 | C15 | C16 | C17 | C18 | C19 | C20 | ID |
|---|---|---|---|---|---|---|---|---|---|---|---|---|---|---|---|---|---|---|---|---|---|
| 300(P) | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | -3594 | -4064 | 320 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 301(K) | -2620 | -2961 | -2461 | -2046 | -3743 | -2791 | -1570 | -3603 | 3784 | -3387 | -2839 | -2048 | -3039 | -1260 | -465 | -2604 | -2536 | -3331 | -3001 | -2988 | 321 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 302(G) | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 322 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 303(W) | -4114 | -3274 | -4214 | -4453 | -1722 | -3496 | -2681 | -4109 | -4149 | -3619 | -3615 | -4044 | -3885 | -4032 | -3816 | -4355 | -4248 | -4133 | 6191 | -1329 | 323 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 304(T) | -353 | -974 | -2215 | -2202 | -2896 | -1238 | -2053 | -2560 | -2141 | -2867 | -2052 | -1547 | -1951 | -1940 | -2229 | 1380 | 3291 | -1759 | -3143 | -2840 | 324 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 305(C) | -845 | 3595 | -3279 | -3420 | -3342 | 3140 | -2815 | -3103 | -3232 | -3426 | -2671 | -2300 | -2379 | -2934 | -3057 | -1107 | -1278 | -2270 | -3401 | -3393 | 325 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 306(P) | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | -3594 | -4064 | 326 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 307(K) | -2620 | -2961 | -2461 | -2046 | -3743 | -2791 | -1570 | -3603 | 3784 | -3387 | -2839 | -2048 | -3039 | -1260 | -465 | -2604 | -2536 | -3331 | -3001 | -2988 | 327 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 308(M) | -402 | -813 | -1034 | 898 | 582 | -1639 | -381 | -420 | -330 | -698 | 1526 | -611 | -1715 | -218 | -668 | 337 | 1310 | -272 | -1195 | 1104 | 328 |
| | -149 | -500 | 234 | 43 | -381 | 399 | 106 | -626 | 210 | -466 | -720 | 275 | 394 | 45 | 96 | 359 | 117 | -369 | -294 | -249 | |
| — | -176 | -7108 | -8150 | -310 | -2369 | -701 | -1378 | * | * | | | | | | | | | | | | |
| 309(W) | -1600 | -3166 | -3759 | -3181 | -295 | -3243 | -1874 | 1788 | -2803 | 1756 | 538 | -2802 | -3074 | -2285 | -2600 | -2379 | -1521 | -139 | 4106 | -936 | 330 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 310(D) | -1718 | -3250 | 3403 | -27 | -3066 | -1736 | 2667 | -3486 | -1211 | -3381 | -2732 | -400 | -2240 | -752 | -1917 | -1439 | -1784 | -3023 | -3204 | -2299 | 331 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 311(G) | -1708 | -2667 | 1499 | -644 | -3784 | 3218 | -1636 | -3799 | -1910 | -3782 | -3127 | -941 | -2466 | -1384 | -2554 | -1618 | -1929 | -3151 | -3633 | -3136 | 332 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 312(K) | -708 | -2195 | 956 | 221 | -2514 | -1474 | -242 | -2264 | 2240 | -2194 | -1308 | 1084 | -1658 | 1697 | -314 | -557 | -656 | -1821 | -2352 | -1662 | 333 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 313(P) | -762 | -1504 | -940 | -454 | 1424 | -1749 | -441 | -1317 | 1946 | -1439 | -747 | -629 | 1988 | -176 | -300 | -813 | -723 | -1105 | -1603 | -967 | 334 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 314(I) | -1232 | -1121 | -3291 | -2953 | -1431 | -2753 | -2412 | 3122 | -2652 | -599 | -404 | -2590 | -2982 | -2506 | -2674 | -2020 | 1485 | 773 | -2421 | -2034 | 335 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 315(E) | -2641 | -3308 | -896 | 3732 | -3966 | -2458 | -2043 | -4105 | -2128 | -4016 | -3555 | -1531 | -2959 | -1842 | -2560 | -2479 | -2750 | -3722 | -3563 | -3385 | 336 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 316(G) | -1046 | -1820 | -755 | -1003 | -3341 | 2933 | -1683 | -3325 | -1756 | -3410 | -2651 | 2259 | -2235 | -1456 | -2142 | -1125 | -1359 | -2537 | -3369 | -2897 | 337 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |

TABLE 6-continued

| | | | | | | | | | | | | | | | | | | | | |
|---|---|---|---|---|---|---|---|---|---|---|---|---|---|---|---|---|---|---|---|---|
| 317(S) | -897 -149 -16 | -1462 -500 -7108 | -2333 233 -8150 | -2543 -894 | -3185 -381 -1115 | -1640 399 -701 | -2474 106 -1378 | -3294 -626 * | -2686 210 * | -3497 -466 | -2780 -720 | -1973 275 | -2360 394 | -2483 45 | -2703 96 | 3465 359 | -1316 117 | -2413 -369 | -3310 -294 | -3025 -249 | 338 |
| 318(W) | -3425 -149 -16 | -2618 -500 -7108 | -4155 233 -8150 | -4330 43 -894 | 3859 -381 -1115 | -3949 399 -701 | -484 106 -1378 | -2303 -626 * | -3894 210 * | -1728 -466 | -1759 -720 | -2779 275 | -3865 394 | -2847 45 | -3389 96 | -3247 359 | -3323 117 | -2490 -369 | -3919 -294 | 1426 -249 | 339 |
| 319(R) | -1940 -149 -16 | -2623 -500 -7108 | -2163 233 -8150 | -1317 43 -894 | -2718 -381 -1115 | -2498 399 -701 | 2633 106 -1378 | -2821 -626 * | 557 210 * | -2576 -466 | -1920 -720 | -1294 275 | -2549 394 | -305 45 | 3406 96 | -1859 359 | -1734 117 | -2575 -369 | -2279 -294 | -1885 -249 | 340 |
| 320(A) | 2865 -149 -16 | -932 -500 -7108 | -2456 233 -8150 | -2481 43 -894 | -3066 -381 -1115 | -1198 399 -701 | -2239 106 -1378 | -2763 -626 * | -2443 210 * | -3058 -466 | -2203 -720 | -1637 275 | -1941 394 | -2156 45 | -2474 96 | 1737 359 | -732 117 | -1840 -369 | -3307 -294 | -3058 -249 | 341 |
| 321(H) | -3205 -149 -16 | -3079 -500 -7108 | -2723 233 -8150 | -2890 43 -894 | -2110 -381 -1115 | -3046 399 -701 | 5295 106 -1378 | -4135 -626 * | -2617 210 * | -3813 -466 | -3561 -720 | -2886 275 | -3482 394 | -2833 45 | -2620 96 | -3291 359 | -3356 117 | -3895 -369 | -2397 -294 | -1681 -249 | 342 |
| 322(Q) | -2562 -149 -16 | -2904 -500 -7108 | -1886 233 -8150 | -1971 43 -894 | -3251 -381 -1115 | -2661 399 -701 | -2079 106 -1378 | -3690 -626 * | -1565 210 * | -3469 -466 | -3081 -720 | -2107 275 | -3091 394 | 4371 45 | -1665 96 | -2585 359 | -2674 117 | -3411 -369 | -3077 -294 | -2821 -249 | 343 |
| 323(I) | -1757 -149 -16 | -1300 -500 -7108 | -4333 233 -8150 | -3971 43 -894 | -1764 -381 -1115 | -4057 399 -701 | -3754 106 -1378 | 2871 -626 * | -3843 210 * | -611 -466 | -539 -720 | -3733 275 | -3880 394 | -3699 45 | -3919 96 | -3375 359 | -1749 117 | 2625 -369 | -3273 -294 | -2829 -249 | 344 |
| 324(P) | -2931 -149 -16 | -2878 -500 -7108 | -3420 233 -8150 | -3706 43 -894 | -4181 -381 -1115 | -2925 399 -701 | -3468 106 -1378 | -4621 -626 * | -3859 210 * | -4490 -466 | -4165 -720 | -3491 275 | 4225 394 | -3781 45 | -3695 96 | -3182 359 | -3279 117 | -4087 -369 | -3594 -294 | -4064 -249 | 345 |
| 325(I) | -1899 -149 -16 | -1466 -500 -7108 | -4358 233 -8150 | -3871 43 -894 | -1002 -381 -1115 | -3993 399 -701 | -3149 106 -1378 | 2479 -626 * | -3652 210 * | -3469 -466 | 170 -720 | -3634 275 | -3690 394 | -3153 45 | -3516 96 | -3233 359 | -1847 117 | 1460 -369 | -2466 -294 | -2295 -249 | 346 |
| 326(P) | 1615 -149 -16 | -1136 -500 -7108 | -2222 233 -8150 | -2310 43 -894 | -3082 -381 -1115 | -1373 399 -701 | -2227 106 -1378 | -2731 -626 * | -2358 210 * | -3036 -466 | -2272 -720 | -1689 275 | 3445 394 | -2139 45 | -2424 96 | -761 359 | -938 117 | -1937 -369 | -3279 -294 | -3042 -249 | 347 |
| 327(V) | 776 -149 -16 | -978 -500 -7108 | -1248 233 -8150 | -821 43 -894 | -1609 -381 -1115 | -1418 399 -701 | -840 106 -1378 | -1138 -626 * | -733 210 * | -1453 -466 | -710 -720 | 1478 275 | -1781 394 | -614 45 | -1074 96 | 1249 359 | -508 117 | 1777 -369 | -1905 -294 | -1460 -249 | 348 |
| 328(D) | 1973 -149 -16 | -1793 -500 -7108 | 2321 233 -8150 | -222 43 -894 | -2801 -381 -1115 | -1401 399 -701 | -864 106 -1378 | -2543 -626 * | -758 210 * | -2614 -466 | -1785 -720 | -457 275 | -1858 394 | -510 45 | -1294 96 | 684 359 | -896 117 | -1978 -369 | -2851 -294 | -2198 -249 | 349 |
| 329(Q) | -1008 -149 -16 | -2231 -500 -7108 | -986 233 -8150 | -310 43 -894 | -2701 -381 -1115 | -1861 399 -701 | -258 106 -1378 | -2315 -626 * | 1642 210 * | -2173 -466 | -1344 -720 | -511 275 | -1911 394 | 2494 45 | 1827 96 | 403 359 | -883 117 | -1946 -369 | -2224 -294 | -1767 -249 | 350 |
| 330(D) | -1037 -149 -16 | -2659 -500 -7108 | -2253 233 -8150 | 1117 43 -894 | -2928 -381 -1115 | -1504 399 -701 | -509 106 -1378 | -2731 -626 * | 1324 210 * | -2651 -466 | -1807 -720 | 1958 275 | -1830 394 | -106 45 | -940 96 | -826 359 | -1023 117 | -2261 -369 | -2827 -294 | -2032 -249 | 351 |
| 331(H) | -935 -149 -16 | -2308 -500 -7108 | 2421 233 -8150 | 146 43 -894 | -2574 -381 -1115 | -1508 399 -701 | 2726 106 -1378 | -2388 -626 * | -331 210 * | -2395 -466 | -1577 -720 | -187 275 | -1822 394 | -135 45 | -890 96 | -787 359 | 1407 117 | -1976 -369 | -2588 -294 | -1852 -249 | 352 |
| 332(M) | -650 -149 -16 | -1996 -500 -7108 | 1349 233 -8150 | 1466 43 -894 | -2242 -381 -1115 | -1448 399 -701 | -264 106 -1378 | -1958 -626 * | 34 210 * | -1982 -466 | 2809 -720 | -101 275 | 597 394 | 150 45 | -493 96 | -533 359 | -608 117 | -1580 -369 | -2227 -294 | -1552 -249 | 353 |
| 333(E) | 1263 -149 -16 | -2196 -500 -7108 | -74 233 -8150 | 2930 43 -894 | -2933 -381 -1115 | -1571 399 -701 | -907 106 -1378 | -2588 -626 * | -778 210 * | -2712 -466 | -1962 -720 | -469 275 | -2014 394 | -562 45 | -1290 96 | -991 359 | -1179 117 | -2137 -369 | -2954 -294 | -2290 -249 | 354 |

TABLE 6-continued

| | | | | | | | | | | | | | | | | | | |
|---|---|---|---|---|---|---|---|---|---|---|---|---|---|---|---|---|---|---|
| 334(H) — — | -1082 -149 -16 | -2079 -500 -7108 | -440 233 -8150 | 1291 43 -894 | -845 -381 -1115 | -1821 399 -701 | 3880 106 -1378 | -1961 -626 * | -281 210 * | -1944 -466 | -1264 -720 | -509 275 | -2017 394 | -267 45 | -666 96 | -989 359 | -1031 117 | -1699 -369 | -1298 -294 | 1603 -249 | 355 |
| 335(F) — — | 1005 -149 -16 | -431 -500 -7108 | -2207 233 -8150 | -1610 43 -894 | 1664 -381 -1115 | -1966 399 -701 | -799 106 -1378 | 1077 -626 * | 332 210 * | 809 -466 | 427 -720 | -1386 275 | -2016 394 | -1061 45 | -1337 96 | -1023 359 | -432 117 | 229 -369 | -879 -294 | -519 -249 | 356 |
| 336(H) — — | -30 -149 -16 | 439 -500 -7108 | 11 233 -8150 | 363 43 -894 | -394 -381 -1115 | -739 399 -701 | 699 106 -1378 | -414 -626 * | 463 210 * | -757 -466 | 501 -720 | 286 275 | -577 394 | 639 45 | 165 96 | -23 359 | 111 117 | -312 -369 | 697 -294 | -25 -249 | 357 |
| 337(D) — — | -996 -149 -16 | -2602 -500 -7108 | 2234 233 -8150 | 1640 43 -894 | -2872 -381 -1115 | -1493 399 -701 | 484 106 -1378 | -2671 -626 * | -308 210 * | -2598 -466 | -1748 -720 | -104 275 | 783 394 | 1779 45 | -913 96 | -792 359 | -980 117 | -2205 -369 | -2778 -294 | -1990 -249 | 358 |
| 338(A) — — | 1659 -149 -16 | -679 -500 -7108 | -1813 233 -8150 | -1259 43 -894 | -745 -381 -1115 | -1962 399 -701 | -855 106 -1378 | 1055 -626 * | -1039 210 * | -483 -466 | 101 -720 | -1222 275 | -2054 394 | 1021 45 | -1227 96 | -1014 359 | -543 117 | 1478 -369 | -1248 -294 | -857 -249 | 359 |
| 339(L) — — | -2871 -149 -16 | -2457 -500 -7108 | -4231 233 -8150 | -4103 43 -894 | -1033 -381 -1115 | -3803 399 -701 | -3165 106 -1378 | -541 -626 * | -3734 210 * | 3130 -466 | -31 -720 | -3935 275 | -3797 394 | -3286 45 | -3484 96 | -3713 359 | -2869 117 | -1136 -369 | -2394 -294 | -2220 -249 | 360 |
| 340(V) — — | -891 -149 -16 | -1677 -500 -7108 | -1034 233 -8150 | -464 43 -894 | -1912 -381 -1115 | -1849 399 -701 | -400 106 -1378 | -1350 -626 * | 1652 210 * | -1575 -466 | -859 -720 | -635 275 | -1938 394 | 1706 45 | 124 96 | -916 359 | -803 117 | 2029 -369 | -1916 -294 | -1472 -249 | 361 |
| 341(D) — — | -869 -149 -16 | -2445 -500 -7108 | 2202 233 -8150 | 1077 43 -894 | -2729 -381 -1115 | 120 399 -701 | -389 106 -1378 | -2516 -626 * | 1310 210 * | -2445 -466 | -1574 -720 | 1245 275 | -1739 394 | 29 45 | -730 96 | -684 359 | -841 117 | -2053 -369 | -2620 -294 | -1858 -249 | 362 |
| 342(W) — — | -4114 -149 -16 | -3274 -500 -7108 | -4214 233 -8150 | -4453 43 -894 | -1722 -381 -1115 | -3496 399 -701 | -2681 106 -1378 | -4109 -626 * | -4149 210 * | -3619 -466 | -3615 -720 | -4044 275 | -3885 394 | -4032 45 | -3816 96 | -4355 359 | -4248 117 | -4133 -369 | 6191 -294 | -1329 -249 | 363 |
| 343(L) — — | -2642 -149 -16 | -2168 -500 -7108 | -4788 233 -8150 | -4235 43 -894 | -465 -381 -1115 | -4513 399 -701 | -3241 106 -1378 | 96 -626 * | -3878 210 * | 2891 -466 | 2122 -720 | -4166 275 | -3888 394 | -3023 45 | -3544 96 | -3807 359 | -2521 117 | -607 -369 | -2140 -294 | -2183 -249 | 364 |
| 344(E) — — | -588 -149 -16 | -2030 -500 -7108 | -204 233 -8150 | 1763 43 -894 | -2360 -381 -1115 | -1459 399 -701 | -147 106 -1378 | -2094 -626 * | 1522 210 * | -2032 -466 | -1135 -720 | -95 275 | -1592 394 | 1372 45 | -129 96 | 847 359 | -526 117 | -1661 -369 | -2190 -294 | -1529 -249 | 365 |
| 345(S) — — | -897 -149 -16 | -1462 -500 -7108 | -2333 233 -8150 | -2543 43 -894 | -3185 -381 -1115 | -1640 399 -701 | -2474 106 -1378 | -3294 -626 * | -2686 210 * | -3497 -466 | -2780 -720 | -1973 275 | -2360 394 | -2483 45 | -2703 96 | 3465 359 | -1316 117 | -2413 -369 | -3310 -294 | -3025 -249 | 366 |
| 346(Y) — — | -3482 -149 -16 | -2868 -500 -7108 | -3701 233 -8150 | -3919 43 -894 | 238 -381 -1115 | -3552 399 -701 | -1112 106 -1378 | -3000 -626 * | -3638 210 * | -2516 -466 | -2526 -720 | -3027 275 | -3772 394 | -3101 45 | -3341 96 | -3418 359 | -3527 117 | -3071 -369 | -441 -294 | 4711 -249 | 367 |
| 347(K) — — | -1779 -149 -16 | -2672 -500 -7108 | -1588 233 -8150 | -963 43 -894 | -3316 -381 -1115 | -2329 399 -701 | -561 106 -1378 | -2833 -626 * | 3294 210 * | -2578 -466 | -1879 -720 | -1030 275 | -2399 394 | 1424 45 | 589 96 | -1653 359 | -1579 117 | -2550 -369 | -2489 -294 | -2237 -249 | 368 |
| 348(P) — — | -2931 -149 -16 | -2878 -500 -7108 | -3420 233 -8150 | -3706 43 -894 | -4181 -381 -1115 | -2925 399 -701 | -3468 106 -1378 | -4621 -626 * | -3859 210 * | -4490 -466 | -4165 -720 | -3491 275 | 4225 394 | -3781 45 | -3695 96 | -3182 359 | -3279 117 | -4087 -369 | -3594 -294 | -4064 -249 | 369 |
| 349(E) — — | -1283 -149 -16 | -2980 -500 -7108 | 2293 233 -8150 | 2465 43 -894 | -3222 -381 -1115 | -1551 399 -701 | -680 106 -1378 | -3054 -626 * | 846 210 * | -2961 -466 | -2167 -720 | -151 275 | -1956 394 | -302 45 | -1278 96 | -1029 359 | -1292 117 | -2574 -369 | -3140 -294 | -2287 -249 | 370 |
| 350(E) — — | -2641 -149 -16 | -3308 -500 -7108 | -896 233 -8150 | 3732 43 -894 | -3966 -381 -1115 | -2458 399 -701 | -2043 106 -1378 | -4105 -626 * | -2128 210 * | -4016 -466 | -3555 -720 | -1531 275 | -2959 394 | -1842 45 | -2560 96 | -2479 359 | -2750 117 | -3722 -369 | -3563 -294 | -3385 -249 | 371 |

TABLE 6-continued

| | | | | | | | | | | | | | | | | | | | | |
|---|---|---|---|---|---|---|---|---|---|---|---|---|---|---|---|---|---|---|---|---|
| 351(L) | -2871 / -149 / -16 | -2457 / -500 / -7108 | -4231 / 233 / -8150 | -4103 / 43 / -894 | -1033 / -381 / -1115 | -3803 / 399 / -701 | -3165 / 106 / -1378 | -541 / -626 / * | -3734 / 210 / * | 3130 / -466 | -31 / -720 | -3935 / 275 | -3797 / 394 | -3286 / 45 | -3484 / 96 | -3713 / 359 | -2869 / 117 | -1136 / -369 | -2394 / -294 | -2220 / -249 | 372 |
| 352(F) | -3342 / -149 / -16 | -2776 / -500 / -7108 | -4026 / 233 / -8150 | -4232 / 43 / -894 | 4354 / -381 / -1115 | -3545 / 399 / -701 | -1431 / 106 / -1378 | -2315 / -626 / * | -4038 / 210 / * | -1801 / -466 | -1900 / -720 | -3299 / 275 | -3780 / 394 | -3350 / 45 | -3645 / 96 | -3490 / 359 | -3420 / 117 | -2566 / -369 | -739 / -294 | 349 / -249 | 373 |
| 353(D) | -1170 / -149 / -16 | -2662 / -500 / -7108 | 2768 / 233 / -8150 | 152 / 43 / -894 | -3076 / -381 / -1115 | -1523 / 399 / -701 | -716 / 106 / -1378 | -2882 / -626 / * | -677 / 210 / * | -2851 / -466 | -2058 / -720 | 1883 / 275 | -1940 / 394 | -347 / 45 | -1326 / 96 | -973 / 359 | 1251 / 117 | -2402 / -369 | -3056 / -294 | -2245 / -249 | 374 |
| 354(E) | 1031 / -149 / -16 | -2152 / -500 / -7108 | -91 / 233 / -8150 | 2416 / 43 / -894 | -2507 / -381 / -1115 | -1517 / 399 / -701 | -346 / 106 / -1378 | -2220 / -626 / * | 982 / 210 / * | -2201 / -466 | -1350 / -720 | -188 / 275 | -1736 / 394 | 71 / 45 | -388 / 96 | -657 / 359 | -752 / 117 | -1810 / -369 | -2390 / -294 | -1731 / -249 | 375 |
| 355(N) | -1247 / -149 / -16 | -2802 / -500 / -7108 | 2354 / 233 / -8150 | 164 / 43 / -894 | -3217 / -381 / -1115 | -1531 / 399 / -701 | -760 / 106 / -1378 | -3060 / -626 / * | -767 / 210 / * | -2997 / -466 | -2213 / -720 | 2573 / 275 | -1971 / 394 | -395 / 45 | -1447 / 96 | 1055 / 359 | -1298 / 117 | -2553 / -369 | -3188 / -294 | -2339 / -249 | 376 |
| 356(G) | -2594 / -149 / -16 | -2690 / -500 / -7108 | -3304 / 233 / -8150 | -3623 / 43 / -894 | -4328 / -381 / -1115 | 3747 / 399 / -701 | -3462 / 106 / -1378 | -4761 / -626 / * | -3953 / 210 / * | -4671 / -466 | -4212 / -720 | -3320 / 275 | -3352 / 394 | -3748 / 45 | -3779 / 96 | -2839 / 359 | -2981 / 117 | -4004 / -369 | -3668 / -294 | -4222 / -249 | 377 |
| 357(H) | 969 / -149 / -16 | -1896 / -500 / -7108 | 1173 / 233 / -8150 | 279 / 43 / -894 | -2199 / -381 / -1115 | -1387 / 399 / -701 | 1573 / 106 / -1378 | -1938 / -626 / * | 276 / 210 / * | -1912 / -466 | -1011 / -720 | -34 / 275 | -1518 / 394 | 1339 / 45 | -236 / 96 | 939 / 359 | -421 / 117 | -1513 / -369 | -2105 / -294 | -1426 / -249 | 378 |
| 358(V) | -1097 / -149 / -16 | -861 / -500 / -7108 | -3273 / 233 / -8150 | -2702 / 43 / -894 | -715 / -381 / -1115 | -2790 / 399 / -701 | -1749 / 106 / -1378 | 1319 / -626 / * | -2390 / 210 / * | 1604 / -466 | 246 / -720 | -2365 / 275 | 510 / 394 | -2047 / 45 | -2299 / 96 | -1909 / 359 | -1047 / 117 | 2041 / -369 | -1564 / -294 | -1253 / -249 | 379 |
| 359(K) | -627 / -149 / -16 | -934 / -500 / -7108 | -1396 / 233 / -8150 | -826 / 43 / -894 | -1049 / -381 / -1115 | -1906 / 399 / -701 | -680 / 106 / -1378 | 1291 / -626 / * | 2041 / 210 / * | -745 / -466 | -142 / -720 | -930 / 275 | -1983 / 394 | -512 / 45 | -793 / 96 | -921 / 359 | 762 / 117 | 912 / -369 | -1475 / -294 | -1045 / -249 | 380 |
| 360(D) | 417 / -149 / -16 | -2242 / -500 / -7108 | 2268 / 233 / -8150 | 951 / 43 / -894 | -2534 / -381 / -1115 | -1439 / 399 / -701 | -289 / 106 / -1378 | -2301 / -626 / * | 2 / 210 / * | -2249 / -466 | -1365 / -720 | -64 / 275 | 475 / 394 | 1392 / 45 | -551 / 96 | -566 / 359 | -688 / 117 | -1853 / -369 | -2431 / -294 | -1702 / -249 | 381 |
| 361(D) | -756 / -149 / -16 | -2213 / -500 / -7108 | 2042 / 233 / -8150 | 1784 / 43 / -894 | -2484 / -381 / -1115 | -1455 / 399 / -701 | -327 / 106 / -1378 | -2233 / -626 / * | -59 / 210 / * | -287 / -466 | -1351 / -720 | -90 / 275 | -1688 / 394 | 90 / 45 | -612 / 96 | 609 / 359 | -722 / 117 | -1813 / -369 | -2423 / -294 | -1705 / -249 | 382 |
| 362(I) | -1758 / -149 / -16 | -1302 / -500 / -7108 | -4331 / 233 / -8150 | -3969 / 43 / -894 | -1754 / -381 / -1115 | -4053 / 399 / -701 | -3745 / 106 / -1378 | 3003 / -626 / * | -3839 / 210 / * | -600 / -466 | -530 / -720 | -3730 / 275 | -3876 / 394 | -3691 / 45 | -3912 / 96 | -3370 / 359 | -1751 / 117 | 2469 / -369 | -3262 / -294 | -2822 / -249 | 383 |
| 363(K) | -489 / -149 / -16 | -1736 / -500 / -7108 | -399 / 233 / -8150 | 869 / 43 / -894 | -1996 / -381 / -1115 | -1468 / 399 / -701 | -108 / 106 / -1378 | -1679 / -626 / * | 1463 / 210 / * | 680 / -466 | -849 / -720 | -140 / 275 | -1560 / 394 | 1326 / 45 | -65 / 96 | -410 / 359 | 492 / 117 | -1326 / -369 | -1942 / -294 | -1336 / -249 | 384 |
| 364(E) | 1607 / -149 / -16 | -1738 / -500 / -7108 | -268 / 233 / -8150 | 2001 / 43 / -894 | -2459 / -381 / -1115 | -1405 / 399 / -701 | -567 / 106 / -1378 | -2171 / -626 / * | -308 / 210 / * | -2231 / -466 | -1384 / -720 | -339 / 275 | -1737 / 394 | -179 / 45 | -802 / 96 | 1027 / 359 | -695 / 117 | -1699 / -369 | -2473 / -294 | -1839 / -249 | 385 |
| 365(I) | -521 / -149 / -16 | -410 / -500 / -7108 | -2443 / 233 / -8150 | -1845 / 43 / -894 | 1682 / -381 / -1115 | -2040 / 399 / -701 | -909 / 106 / -1378 | 1831 / -626 / * | -1536 / 210 / * | -217 / -466 | 389 / -720 | 581 / 275 | -2091 / 394 | -1245 / 45 | -1495 / 96 | -1112 / 359 | 673 / 117 | 1143 / -369 | -913 / -294 | -551 / -249 | 386 |
| 366(M) | -1028 / -149 / -16 | -781 / -500 / -7108 | -3313 / 233 / -8150 | -2728 / 43 / -894 | -655 / -381 / -1115 | -2725 / 399 / -701 | -1667 / 106 / -1378 | 2105 / -626 / * | -2396 / 210 / * | 791 / -466 | 2636 / -720 | -2332 / 275 | -2694 / 394 | -2027 / 45 | -2260 / 96 | -1840 / 359 | 662 / 117 | 1307 / -369 | -1459 / -294 | -1146 / -249 | 387 |
| 367(P) | -2931 / -149 / -16 | -2878 / -500 / -7108 | -3420 / 233 / -8150 | -3706 / 43 / -894 | -4181 / -381 / -1115 | -2925 / 399 / -701 | -3468 / 106 / -1378 | -4621 / -626 / * | -3859 / 210 / * | -4490 / -466 | -4165 / -720 | -3491 / 275 | 4225 / 394 | -3781 / 45 | -3695 / 96 | -3182 / 359 | -3279 / 117 | -4087 / -369 | -3594 / -294 | -4064 / -249 | 388 |

TABLE 6-continued

| | | | | | | | | | | | | | | | | | | |
|---|---|---|---|---|---|---|---|---|---|---|---|---|---|---|---|---|---|---|
| 368(K) | -420 -149 -16 | -1711 -500 -7108 | -319 233 -8150 | 889 43 -894 | -1985 -381 -1115 | -1406 399 -701 | -81 106 -1378 | -1683 -626 * | 1799 210 * | -1711 -466 | -835 -720 | -80 275 | -1506 394 | 351 45 | -148 96 | 802 359 | 593 117 | 66 -369 | -1944 -294 | -1311 -249 | 389 |
| 369(G) | -1210 -149 -16 | -2695 -500 -7108 | 1728 233 -8150 | 114 43 -894 | -3097 -381 -1115 | 2436 399 -701 | -713 106 -1378 | -2899 -626 * | 1005 210 * | -2848 -466 | -2055 -720 | -236 275 | -1965 394 | -340 45 | -1178 96 | -1009 359 | -1238 117 | -2429 -369 | -3026 -294 | -2250 -249 | 390 |
| 370(D) | -1173 -149 -16 | -2847 -500 -7108 | 2185 233 -8150 | 2156 43 -894 | -3091 -381 -1115 | -1523 399 -701 | 1843 106 -1378 | -2917 -626 * | -527 210 * | -2832 -466 | -2014 -720 | 1280 275 | -1899 394 | -221 45 | -1180 96 | -937 359 | -1174 117 | -2440 -369 | -3014 -294 | -2176 -249 | 391 |
| 371(K) | -733 -149 -16 | -1639 -500 -7108 | -900 233 -8150 | -275 43 -894 | -1870 -381 -1115 | -1727 399 -701 | -272 106 -1378 | -1476 -626 * | 1449 210 * | 1052 -466 | -793 -720 | -476 275 | -1798 394 | 105 45 | 1100 96 | 1022 359 | -645 117 | -1222 -369 | -1849 -294 | -1373 -249 | 392 |
| 372(R) | -2124 -149 -16 | -2788 -500 -7108 | -2710 233 -8150 | -1449 43 -894 | -3624 -381 -1115 | -2637 399 -701 | -576 106 -1378 | -2974 -626 * | 1929 210 * | -2640 -466 | -1977 -720 | -1344 275 | -2596 394 | -161 45 | 3417 96 | -2010 359 | -1819 117 | -2745 -369 | -2479 -294 | -2379 -249 | 393 |
| 373(M) | -2186 -149 -16 | -1770 -500 -7108 | -4484 233 -8150 | -3908 43 -894 | -547 -381 -1115 | -4083 399 -701 | -2924 106 -1378 | 1892 -626 * | -3619 210 * | 1562 -466 | 3822 -720 | -3715 275 | -3642 394 | -2876 45 | -3343 96 | -3290 359 | -2088 117 | -106 -369 | -2072 -294 | -2052 -249 | 394 |
| 374(A) | 2525 -149 -16 | -1036 -500 -7108 | -2401 233 -8150 | -2529 43 -894 | -3239 -381 -1115 | 2375 399 -701 | -2366 106 -1378 | -2958 -626 * | -2629 210 * | -3244 -466 | -2393 -720 | -1719 275 | -2028 394 | -2303 45 | -2639 96 | -657 359 | -852 117 | -1993 -369 | -3425 -294 | -3237 -249 | 395 |
| 375(M) | 1980 -149 -16 | -959 -500 -7108 | -1279 233 -8150 | -892 43 -894 | -1385 -381 -1115 | -1524 399 -701 | -842 106 -1378 | -905 -626 * | -763 210 * | -1211 -466 | 2928 -720 | 1065 275 | -1852 394 | -673 45 | -1053 96 | -675 359 | -559 117 | -683 -369 | -1743 -294 | -1304 -249 | 396 |
| 376(N) | -1426 -149 -19 | -2353 -500 -6850 | -948 233 -8150 | -735 43 -894 | -2920 -381 -1115 | -1991 399 -701 | -796 106 -1378 | -2769 -626 * | 68 210 * | -2666 -466 | -1942 -720 | 3441 275 | -2268 394 | -432 45 | 1742 96 | -1361 359 | -1415 117 | -2383 -369 | -2592 -294 | -2147 -249 | 397 |
| 377(P) | -566 -149 -16 | -1202 -500 -7108 | -1850 233 -8150 | -1997 43 -894 | -3117 -381 -1115 | -1371 399 -701 | -2101 106 -1378 | -2989 -626 * | -2185 210 * | -3198 -466 | -2391 -720 | -1549 275 | 3625 394 | -1982 45 | -2305 96 | 1013 359 | -967 117 | -2094 -369 | -3288 -294 | -2963 -249 | 398 |
| 378(I) | -820 -149 -16 | -759 -500 -7108 | -2582 233 -8150 | -1810 43 -894 | -939 -381 -1115 | -2345 399 -701 | -1389 106 -1378 | 2404 -626 * | -1595 210 * | -425 -466 | -18 -720 | 1689 275 | -2430 394 | -1447 45 | -1742 96 | -1465 359 | -804 117 | 1594 -369 | -1641 -294 | -1225 -249 | 399 |
| 379(T) | 1785 -149 -19 | -6850 -500 -6850 | -2281 233 -7893 | -1994 43 -894 | -2428 -381 -1115 | -1215 399 -701 | -813 -1893 | -1811 -626 * | -1860 210 * | -2282 -466 | -1548 -720 | -1351 275 | -1750 394 | -1665 45 | -1956 96 | -390 359 | 2954 117 | -1225 -369 | -2740 -294 | -2439 -249 | 400 |
| 380(N) | -1558 -149 -19 | -3098 -500 -6850 | -2107 233 -7893 | 1592 43 -894 | -3431 -381 -1115 | -1657 399 -701 | -1767 106 -1378 | -3340 -626 * | -959 210 * | -3271 -466 | -2572 -720 | 3495 275 | -2146 394 | -611 45 | -1578 96 | -1301 359 | -1621 117 | -2860 -369 | -3383 -294 | -2547 -249 | 401 |
| 381(G) | 2030 -149 -16 | -1051 -500 -7108 | -2376 233 -8150 | -2525 43 -894 | -3268 -381 -1115 | 2820 399 -701 | -2382 106 -1378 | -2992 -626 * | -2652 210 * | -3277 -466 | -2428 -720 | -1726 275 | -2039 394 | -2322 45 | -2659 96 | -672 359 | -869 117 | -2018 -369 | -3447 -294 | -3263 -249 | 402 |
| 382(G) | -1587 -149 -16 | -1953 -500 -7108 | -2017 233 -8150 | -2080 43 -894 | -898 -381 -1115 | 3122 399 -701 | -1483 106 -1378 | -2565 -626 * | -2178 210 * | -2576 -466 | -2101 -720 | -1908 275 | -2727 394 | -2015 45 | -2307 96 | -1743 359 | -1817 117 | -2251 -369 | -1457 -294 | 2463 -249 | 403 |
| 383(K) | -585 -149 -195 | -1070 -500 -7108 | -1140 233 -3069 | -510 43 -894 | -1174 -381 -1115 | -1742 399 -701 | -358 106 -1378 | 751 -626 * | 1799 210 * | -916 -466 | -239 -720 | -641 275 | -1802 394 | -103 45 | 873 96 | -754 359 | -507 117 | 1342 -369 | -1431 -294 | -1005 -249 | 404 |
| 384(I) | -732 -149 -16 | -1273 -500 -6931 | 1962 233 -7973 | -516 43 -894 | -1501 -381 -1115 | -1754 399 -701 | -770 106 -1760 | 1970 -626 * | -673 210 * | -1163 -466 | -572 -720 | -718 275 | -1976 394 | -522 45 | -1082 96 | -902 359 | 1162 117 | -263 -369 | -1908 -294 | -1404 -249 | 405 |

TABLE 6-continued

| | | | | | | | | | | | | | | | | | | | |
|---|---|---|---|---|---|---|---|---|---|---|---|---|---|---|---|---|---|---|---|
| 385(H) | -542 | -1652 | -558 | 18 | -1880 | -1542 | 2080 | 339 | 360 | -1605 | -778 | -241 | 1147 | 1217 | 1461 | -492 | -468 | -1229 | -1864 | -1303 | 406 |
| | -149 | -500 | 233 | 43 | -381 | -381 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 386K | -682 | -1971 | -580 | 740 | -2315 | -1607 | -158 | -1989 | 2284 | 162 | -1077 | 529 | -1686 | 280 | 734 | -578 | -595 | -1611 | -2087 | -1523 | 407 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 387(H) | -30 | 439 | 11 | 363 | -394 | -739 | 699 | -414 | 463 | -757 | 501 | 286 | -577 | 639 | 165 | -23 | 111 | -312 | 697 | -25 | 408 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 388(P) | 415 | -2181 | 1668 | 189 | -2543 | -1458 | -400 | -2293 | -146 | -2281 | -1425 | -138 | 2240 | 1274 | -694 | -643 | -769 | -1860 | -2492 | -1780 | 409 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 389(L) | -1646 | -1694 | -2904 | -2680 | -1050 | -2701 | -2138 | -547 | -2336 | 2673 | -123 | -2479 | 1513 | -2198 | -2336 | -2107 | -1735 | -860 | -2077 | -1777 | 410 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 390(D | -430 | -1571 | 1536 | 153 | -1777 | -1435 | -129 | 307 | 1131 | -1533 | -700 | 889 | -1538 | 275 | -255 | -380 | -371 | 598 | -1838 | -1235 | 411 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 391(L) | -2871 | -2457 | -4231 | -4103 | -1033 | -3803 | -3165 | -541 | -3734 | 3130 | -31 | -3935 | -3797 | -3286 | -3484 | -3713 | -2869 | -1136 | -2394 | -2220 | 412 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 392(P) | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | -3594 | -4064 | 413 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 393(D | -123 | -3021 | 2652 | 1083 | -3262 | -1545 | -715 | -3102 | -722 | -3016 | -2232 | 2288 | -1970 | -344 | -1422 | -1053 | -1333 | -2618 | -3208 | -2331 | 414 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 394(W | -1183 | -940 | -3255 | -2753 | 1534 | -2632 | -772 | 1086 | -2365 | 1132 | 71 | -2086 | -2628 | -1856 | -2132 | -1737 | -1115 | -336 | 3856 | 1849 | 415 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 395(R | -1025 | -2540 | 1775 | 1142 | -2847 | -1561 | -472 | -2610 | -136 | -2532 | -1695 | -183 | -1846 | -64 | 2638 | -837 | -993 | -2170 | -2686 | -1970 | 416 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 396(D | -1284 | -2963 | 2433 | 216 | -3207 | -1549 | -693 | -3050 | -653 | -2963 | -2174 | 2058 | -1961 | 2341 | -1315 | -1034 | -1299 | -2571 | -3142 | -2286 | 417 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 397(Y | -3621 | -2707 | -4176 | -4424 | 2970 | -4050 | -394 | -2539 | -4003 | -1942 | -1987 | -2749 | -3933 | -2855 | -3451 | -3299 | -3499 | -2690 | 349 | 4083 | 418 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 398(C | 1443 | 2403 | -1117 | 1144 | -997 | -1629 | -520 | -480 | -452 | 234 | -131 | -706 | -1773 | -348 | -779 | -656 | -418 | -324 | -1362 | -922 | 419 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 399(V | -1742 | -1294 | -4287 | -3868 | -1507 | -3983 | -3425 | 2151 | -3706 | 586 | -316 | -3621 | -3770 | -3449 | -3709 | -3254 | -1716 | 2871 | -2925 | -2571 | 420 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 400(D | -730 | -2244 | 2028 | 1115 | -2543 | -1450 | -283 | -2307 | 1800 | -2248 | -1364 | -74 | -1665 | 147 | -498 | -571 | 502 | -1859 | -2424 | -1702 | 421 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 401(N | -410 | -1793 | -248 | 958 | -2083 | -143 | -54 | -1808 | 1270 | -1797 | -898 | 1557 | -1482 | 391 | -146 | -306 | 586 | 53 | -2000 | -1340 | 422 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |

TABLE 6-continued

| | | | | | | | | | | | | | | | | | | | |
|---|---|---|---|---|---|---|---|---|---|---|---|---|---|---|---|---|---|---|---|
| 402(Q) | -430 -149 -16 | -1511 -500 -7108 | -419 233 -8150 | 58 43 -894 | -1825 -381 -1115 | 563 399 -701 | -219 106 -1378 | -1494 -626 * | 116 210 * | -1597 -466 | -764 -720 | 1033 275 | -1570 394 | 1217 45 | -353 96 | 1025 359 | -404 117 | 892 -369 | -1898 -294 | -1308 -249 | 423 |
| 403(K) | 42 -149 -16 | -2025 -500 -7108 | 1238 233 -8150 | 279 43 -894 | -2338 -381 -1115 | -1408 399 -701 | -138 106 -1378 | -2090 -626 * | 1948 210 * | -2034 -466 | -1127 -720 | 1026 275 | -1554 394 | 1361 45 | -253 96 | -410 359 | -491 117 | -1645 -369 | -2204 -294 | -1512 -249 | 424 |
| 404(E) | -625 -149 -1300 | -2031 -500 -7108 | -279 233 -769 | 1765 43 -894 | -2367 -381 -1115 | -1499 399 -701 | -161 106 -1378 | -2087 -626 * | 353 210 * | -2026 -466 | -1140 -720 | -139 275 | 1309 394 | 1668 45 | 922 96 | -500 359 | -559 117 | -1667 -369 | -2180 -294 | -1544 -249 | 425 |
| 405(Y) | -1580 -149 -38 | -1211 -500 -5845 | -2445 233 -6888 | -2254 43 -894 | 2497 -381 -1115 | -2497 399 -701 | 449 106 -1636 | -742 -626 * | -1944 210 * | -476 -466 | -322 -720 | -1430 275 | -2471 394 | -1343 45 | -1796 96 | -1668 359 | -1507 117 | -820 -369 | 1088 -294 | 3543 -249 | 426 |
| 406(G) | -1371 -149 -19 | -2394 -500 -6850 | 1717 233 -7893 | -285 43 -894 | -3391 -381 -1115 | 3003 399 -1215 | -1248 106 -813 | -3345 -626 * | -1454 210 * | -3349 -466 | -2666 -720 | -589 275 | -2148 394 | -975 45 | -2092 96 | -1270 359 | -1563 117 | -2745 -369 | -3295 -294 | -2730 -249 | 427 |
| 407(H) | 1177 -149 -19 | -1467 -500 -6850 | -267 233 -7893 | 124 43 -894 | -1912 -381 -1115 | -1286 399 -1215 | 2549 106 -813 | -1618 -626 * | 132 210 * | -1695 -466 | -852 -720 | 1230 275 | -1499 394 | 193 45 | -333 96 | 681 359 | -372 117 | -1236 -369 | -1957 -294 | -1349 -249 | 428 |
| 408(N) | -352 -149 -19 | -1085 -500 -6850 | -738 233 -7893 | -561 43 -894 | -1975 -381 -1115 | 1933 399 -1215 | -822 106 -813 | -1555 -626 * | -672 210 * | -1841 -466 | -1078 -720 | 2120 275 | -1685 394 | -547 45 | -1041 96 | -473 359 | -532 117 | 758 -369 | -2198 -294 | -1695 -249 | 429 |
| 409(W) | -725 -149 | -6850 -500 | -1371 233 | -894 43 | -381 -1115 | -1215 399 | -813 106 | -626 * | -210 * | -1073 -466 | -478 -720 | -390 275 | -1652 394 | -90 45 | -302 96 | -705 359 | -607 117 | -812 -369 | 4240 -294 | -180 -249 | 430 |
| | -643 -149 -348 | -1210 -500 -6155 | -455 233 -2320 | 1427 43 -894 | -532 -381 -1115 | -1453 399 -701 | -184 106 -457 | -970 -626 * | -26 210 * | | | | | | | | | | | | |
| 410(G) | -461 -149 -38 | -838 -500 -5845 | -976 233 -6888 | -1119 43 -894 | -2120 -381 -1115 | -1881 399 -701 | -1219 106 -1636 | -2101 -626 * | -1326 210 * | -2273 -466 | -1700 -720 | -986 275 | -1505 394 | -1212 45 | -1430 96 | -653 359 | -781 117 | -1558 -369 | -1923 -294 | -1928 -249 | 431 |
| 411(Q) | -389 -149 -19 | -1056 -500 -6850 | -645 233 -7893 | 768 43 -894 | -1124 -381 -1115 | 3148 399 -560 | -222 106 -1636 | -612 -626 * | 34 210 * | 219 -466 | -187 -720 | -343 275 | -1598 394 | 1815 45 | -346 96 | -489 359 | -329 117 | 1199 -369 | -1410 -294 | -918 -249 | 432 |
| 412(F) | 523 -149 -16 | -749 -500 -7108 | -1182 233 -8150 | -612 43 -894 | 1262 -381 -1115 | -1508 399 -701 | -436 106 -1893 | -327 -626 * | 1202 210 * | 257 -466 | 75 -720 | -713 275 | -1761 394 | -315 45 | 572 96 | -681 359 | -361 117 | 558 -369 | -1146 -294 | -721 -249 | 433 |
| 413(Q) | -838 -149 -16 | -2270 -500 -7108 | 27 233 -8150 | 1546 43 -894 | -2609 -381 -1115 | -1690 399 -701 | -383 106 -1378 | -2361 -626 * | -43 210 * | -2318 -466 | -1463 -720 | -158 275 | -1752 394 | 2803 45 | -531 96 | 937 359 | -810 117 | -1929 -369 | -2497 -294 | -1800 -249 | 434 |
| 414(D) | 2081 -149 -16 | -2191 -500 -7108 | 2846 233 -8150 | -271 43 -894 | -3192 -381 -1115 | 1503 -1547 399 -701 | -1150 106 -1378 | -2913 -626 * | -1247 210 * | -3052 -466 | -2319 -720 | -548 275 | -2085 394 | -840 45 | -1860 96 | -1066 359 | -1314 117 | -2364 -369 | -3266 -294 | -2572 -249 | 435 |
| 415(M) | 746 -149 -16 | -729 -500 -7108 | -1725 233 -8150 | -1241 43 -894 | -1091 -381 -1115 | -1556 399 -701 | -930 106 -1378 | -594 -626 * | -1043 210 * | -922 -466 | 3667 -720 | -1111 275 | 404 394 | -891 45 | -1250 96 | -698 359 | 914 117 | -410 -369 | -1509 -294 | -1123 -249 | 436 |
| 416(I) | -556 -149 -16 | -796 -500 -7108 | -1468 233 -8150 | -861 43 -894 | -813 -381 -1115 | -1848 399 -701 | -559 106 -1378 | 1435 -626 * | 1067 210 * | 271 -466 | 42 -720 | -912 275 | -1905 394 | -460 45 | 1342 96 | -865 359 | -488 117 | 747 -369 | -1213 -294 | -814 -249 | 437 |
| 417(E) | 738 -149 -16 | -1306 -500 -7108 | -528 233 -8150 | 1243 43 -894 | -1448 -381 -1115 | -1471 399 -701 | -165 106 -1378 | -1079 -626 * | 130 210 * | -90 -466 | -452 -720 | -231 275 | -1559 394 | 192 45 | 330 96 | 328 359 | 268 117 | 267 -369 | -1616 -294 | -1069 -249 | 438 |
| 418(W) | -1686 -149 -16 | -1388 -500 -7108 | -3865 233 -8150 | -3280 43 -894 | -313 -381 -1115 | -3346 399 -701 | -1998 106 -1378 | 1605 -626 * | -2910 210 * | 2183 -466 | 589 -720 | -2918 275 | -3142 394 | -2351 45 | -2689 96 | -2486 359 | -1602 117 | -216 -369 | 3506 -294 | -1080 -249 | 439 |

TABLE 6-continued

| | | | | | | | | | | | | | | | | | | | | | |
|---|---|---|---|---|---|---|---|---|---|---|---|---|---|---|---|---|---|---|---|---|---|
| 419(G) | -497 | -1132 | -1973 | -2195 | -3328 | 3237 | -2289 | -3194 | -2532 | -3410 | -2549 | -1611 | -2057 | -2201 | -2603 | 897 | -926 | -2151 | -3487 | -3237 | 440 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 420(K) | 632 | -1777 | 1362 | 250 | -2087 | -1381 | -86 | -1807 | 1431 | -1808 | -914 | -51 | -1497 | 355 | -193 | 817 | -369 | -425 | -2019 | -1362 | 441 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 421(Y) | -3621 | -2707 | -4176 | -4424 | 2953 | -4049 | -394 | -2539 | -4002 | -1942 | -1987 | -2749 | -3933 | -2854 | -3451 | -3299 | -3499 | -2690 | 349 | 4093 | 442 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 422(C) | -642 | 1771 | -2908 | -2287 | 1063 | -2214 | -1093 | 1477 | -1913 | 1497 | 494 | -1833 | -2239 | -1538 | -1745 | -1304 | 765 | 369 | -942 | -612 | 443 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 423(R) | -1005 | -2443 | 1533 | 92 | -2784 | -1584 | -463 | -2543 | -1913 | -2471 | -1639 | 1177 | -1853 | -56 | 2770 | -836 | -972 | -2113 | -2612 | -1931 | 444 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 424(D) | -1148 | -2724 | 2898 | 174 | -3006 | -1564 | -566 | -2796 | 951 | -2711 | -1895 | -178 | -1903 | 1815 | -851 | -933 | -1132 | -2344 | -2872 | -2108 | 445 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 425(V) | -1646 | -1230 | -4148 | -3696 | -1391 | -3782 | -3103 | 2535 | -3497 | -323 | 1927 | -3416 | -3609 | -3214 | -3466 | -3018 | -1616 | 2552 | -2681 | -2340 | 446 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 426(I) | 401 | -900 | -3283 | -2756 | 1640 | -2752 | -1735 | 2834 | -2451 | -121 | 132 | -2375 | -2775 | -2110 | -2360 | -1897 | -1085 | 615 | -1519 | -1079 | 447 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 427(K) | -834 | -1941 | -615 | 845 | -2257 | -1704 | -312 | -1778 | 2586 | -1890 | -1101 | -402 | -1823 | 95 | 65 | -764 | -756 | 788 | -2124 | -1599 | 448 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 428(N) | -857 | -1859 | -733 | -254 | -2082 | -1745 | -340 | -1726 | 1897 | 679 | -1022 | 2134 | -1861 | 45 | 77 | -813 | -778 | -1455 | -2024 | -1510 | 449 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 429(N) | -2171 | -2655 | -1458 | -1748 | -3334 | -2364 | -2267 | -3943 | -2365 | -3936 | -3437 | 4205 | -2932 | -2205 | -2608 | -2224 | -2439 | -3392 | -3253 | -2909 | 450 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 430(P) | -1140 | -1553 | -2272 | -2156 | -1935 | -1979 | -1912 | -1526 | -1824 | -1503 | -981 | -1897 | 3724 | -1871 | -1917 | -1397 | -1391 | -1428 | -2485 | -2072 | 451 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 431(H) | -464 | -1881 | 1234 | 255 | -2190 | -1407 | 2368 | -1921 | 1008 | -1884 | 1339 | -50 | -1513 | 375 | 482 | -349 | 1263 | -1498 | -2063 | -1403 | 452 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 432(N) | -761 | -2121 | 1175 | 150 | -2581 | -1441 | -443 | -2337 | -205 | -2327 | -1467 | 2649 | -1731 | -36 | -757 | 420 | 1163 | -1879 | -2535 | -1825 | 453 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 433(F) | -1857 | -1592 | -3755 | -3460 | 3638 | -3255 | -1454 | -16 | -3144 | -214 | -206 | -2800 | -3287 | -2604 | -2951 | -2505 | -1863 | 1480 | -853 | 99 | 454 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 434(R) | -2957 | -3022 | -3318 | -2735 | -3796 | -2998 | -1968 | -3912 | -846 | -3631 | -3157 | -2611 | -3280 | -1724 | 4056 | -3026 | -2913 | -3650 | -3096 | -3185 | 455 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |
| 435(L) | -886 | -722 | -2913 | -2339 | -608 | 1022 | -1423 | 1356 | -2029 | 1682 | 294 | -2025 | -2497 | -1718 | -1972 | -1579 | -842 | 1130 | -1337 | -1008 | 456 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | | |
| — | | | | | | | | | | | | | | | | | | | | | |

TABLE 6-continued

| | | | | | | | | | | | | | | | | | | | |
|---|---|---|---|---|---|---|---|---|---|---|---|---|---|---|---|---|---|---|---|
| 436(F) | -3342 | -2776 | -4026 | -4232 | 4354 | -3545 | -1431 | -2315 | -4038 | -1801 | -1900 | -3299 | -3780 | -3350 | -3645 | -3490 | -3420 | -2566 | -739 | 349 | 457 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 437(G) | -468 | -1108 | -1987 | -2183 | -3307 | 3093 | -2261 | -3159 | -2489 | -3374 | -2507 | -1593 | -2035 | -2163 | -2570 | 1410 | -895 | -2119 | -3471 | -3217 | 458 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 438(H) | -30 | 439 | 11 | 363 | -394 | -739 | 699 | -414 | 463 | -757 | 501 | 286 | -577 | 639 | 165 | -23 | 111 | -312 | 697 | -25 | 459 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 439(P) | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | -3594 | -4064 | 460 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 440(D) | -2784 | -3432 | 4016 | -1200 | -4140 | -2466 | -2197 | -4505 | -2621 | -4365 | -3956 | -1551 | -3014 | -2039 | -3232 | -2593 | -2938 | -4046 | -3710 | -3552 | 461 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 441(E) | -2641 | -3308 | -896 | 3732 | -3966 | -2458 | -2043 | -4105 | -2128 | -4016 | -3555 | -1531 | -2959 | -1842 | -2560 | -2479 | -2750 | -3722 | -3563 | -3385 | 462 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 442(T) | -439 | -840 | -1804 | -1403 | -1361 | -1523 | -1133 | -816 | -1185 | 681 | -536 | -1214 | -1931 | -1069 | -1378 | 642 | 2718 | -603 | -1788 | -1389 | 463 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 443(A) | 1657 | -1594 | -404 | 1150 | -1818 | -1465 | -154 | -1471 | 969 | -1566 | 1309 | -173 | -1572 | 248 | -202 | -422 | -412 | -1160 | -1861 | -1272 | 464 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 444(S) | -897 | -1462 | -2333 | -2543 | -3185 | -1640 | -2474 | -3294 | -2686 | -3497 | -2780 | -1973 | -2360 | -2483 | -2703 | 3465 | -1316 | -2413 | -3310 | -3025 | 465 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 445(N) | -2171 | -2655 | -1458 | -1748 | -3334 | -2364 | -2267 | -3943 | -2365 | -3936 | -3437 | 4205 | -2932 | -2205 | -2608 | -2224 | -2439 | -3392 | -3253 | -2909 | 466 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 446(R) | -1905 | -2715 | -2334 | -1200 | -3487 | -2506 | -485 | -2858 | 1904 | -2546 | -1846 | -1167 | -2464 | 1439 | 3148 | -1780 | -1627 | -2602 | -2423 | -2263 | 467 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 447(L) | -2639 | -2158 | -4642 | -4194 | 1586 | -4340 | -2490 | -51 | -3890 | 2827 | 573 | -3860 | -3832 | -2979 | -3524 | -3629 | -2524 | -732 | -1565 | -1006 | 468 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 448(Q) | -549 | -1725 | -324 | 98 | -1793 | -1481 | -198 | -1668 | 163 | -1723 | -892 | 839 | -1618 | 2328 | -290 | 843 | -499 | -1331 | -1882 | 1794 | 469 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 449(A) | 2109 | -2374 | 1307 | 1077 | -2738 | 326 | -514 | -2505 | -344 | -2485 | -1647 | -151 | -1804 | -118 | -934 | -766 | -932 | -2058 | -2698 | -1950 | 470 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 450(A) | 1280 | -376 | -2219 | -1624 | 1011 | -1905 | -779 | 1073 | -1336 | -235 | 411 | -1368 | -1975 | -1065 | -1339 | 339 | 580 | 955 | -851 | -492 | 471 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 451(F) | -2619 | -2089 | -3969 | -3846 | 3011 | -3673 | -612 | -1304 | -3453 | 1530 | -788 | -2671 | -3552 | -2584 | -3066 | -2851 | -2522 | -1556 | -1882 | 2879 | 472 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 452(E) | 400 | -2342 | 1163 | 2306 | -2664 | -1461 | -401 | -2438 | -168 | -2392 | -1527 | -102 | -1735 | 14 | -743 | 947 | -818 | -1984 | -2583 | -1837 | 473 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |

TABLE 6-continued

| | | | | | | | | | | | | | | | | | | |
|---|---|---|---|---|---|---|---|---|---|---|---|---|---|---|---|---|---|---|
| 453(H) | -424 -149 -16 | -834 -500 -7108 | -1231 233 -8150 | -741 43 -894 | -1039 -381 -1115 | 183 399 -701 | 2171 106 -1378 | -588 -626 * | -582 210 * | -902 -466 | -199 -720 | -797 275 | -1793 394 | -479 45 | -878 96 | -660 359 | 1442 117 | 1664 -369 | -1404 -294 | -972 -249 | 474 |
| 454(T) | -825 -149 -16 | -1543 -500 -7108 | -1050 233 -8150 | -931 43 -894 | -2411 -381 -1115 | -1607 399 -701 | -1105 106 -1378 | -2069 -626 * | -661 210 * | -2229 -466 | -1555 -720 | -978 275 | -2065 394 | 1333 45 | -881 96 | -930 359 | 3234 117 | -1676 -369 | -2544 -294 | -2072 -249 | 475 |
| 455(N) | -948 -149 -16 | -2217 -500 -7108 | -192 233 -8150 | -59 43 -894 | -2753 -381 -1115 | 871 399 -701 | -516 106 -1378 | -2480 -626 * | 1579 210 * | -2431 -466 | -1604 -720 | 2747 275 | -1874 394 | -115 45 | -403 96 | -831 359 | -947 117 | -2039 -369 | -2574 -294 | -1954 -249 | 476 |
| 456(R) | -2118 -149 -16 | -2789 -500 -7108 | -2710 233 -8150 | -1441 43 -894 | -3626 -381 -1115 | -2635 399 -701 | -569 106 -1378 | -2972 -626 * | 2088 210 * | -2636 -466 | -1971 -720 | -1337 275 | -2591 394 | -153 45 | 3343 96 | -2003 359 | -1811 117 | -2743 -369 | -2476 -294 | -2375 -249 | 477 |
| 457(Q) | -2077 -149 -276 | -2533 -500 -7108 | -2582 233 -8150 | -1467 43 -894 | -2808 -381 -1115 | -2285 399 -701 | -1598 106 -1378 | -3134 -626 * | -1059 210 * | -2958 -466 | -2537 -720 | -1616 275 | -2694 394 | 4251 45 | -1184 96 | -2087 359 | -2168 117 | -2871 -369 | -2703 -294 | -2369 -249 | 478 |
| 458(W) | -3599 -149 -19 | -2878 -500 -6850 | -3805 233 -7893 | -3989 43 -894 | -1220 -381 -1115 | -3156 399 -1215 | -2211 106 -813 | -3491 -626 * | -3618 210 * | -3057 -466 | -3027 -720 | -3568 275 | -3532 394 | -3525 45 | -3338 96 | -3829 359 | -3720 117 | -3529 -369 | 6135 -294 | -830 -249 | 479 |
| 459(M) | -718 -149 -19 | -1070 -500 -6850 | 1476 233 -7893 | -726 43 -894 | -732 -381 -1115 | -1903 399 -1215 | -713 106 -813 | -152 -626 * | -681 210 * | 774 -466 | 3189 -720 | -882 275 | -1991 394 | -541 45 | -1003 96 | -968 359 | -669 117 | -221 -369 | -1408 -294 | -983 -249 | 480 |
| 460(E) | 598 -149 -19 | -1592 -500 -6850 | -123 233 -7893 | 1874 43 -894 | -1828 -381 -1115 | -1337 399 -1215 | -104 106 -813 | -1490 -626 * | 228 210 * | -43 -466 | -755 -720 | 967 275 | -1490 394 | 296 45 | -254 96 | -355 359 | -375 117 | -1164 -369 | -1876 -294 | -1258 -249 | 481 |
| 461(P) | -556 -149 -1043 | -1744 -500 -6850 | 1230 233 -7893 | 129 43 -894 | -2482 -381 -1115 | 1292 399 -1215 | -454 106 -813 | -2234 -626 * | -252 210 * | -2255 -466 | -1403 -720 | -147 275 | 1758 394 | -66 45 | -790 96 | 781 359 | -633 117 | -1727 -369 | -2476 -294 | -1801 -249 | 482 |
| 462(Y) | -1345 -149 -38 | -1235 -500 -5845 | -1689 233 -6888 | -1605 43 -894 | 1266 -381 -1115 | -1964 399 -560 | 117 106 -1636 | -925 -626 * | -1303 210 * | -775 -466 | -592 -720 | -1236 275 | -2169 394 | -1119 45 | -1309 96 | -1450 359 | -1367 117 | -939 -369 | 590 -294 | 3938 -249 | 483 |
| 463(I) | -1578 -149 -19 | -1151 -500 -6850 | 4046 233 -7893 | -3597 43 -894 | -1151 -381 -1115 | -3733 399 -453 | -3046 106 -1893 | 3001 -626 * | -3402 210 * | 771 -466 | 18 -720 | -3355 275 | -3517 394 | -3085 45 | -3372 96 | -2981 359 | -1545 117 | 1808 -369 | -2540 -294 | -2237 -249 | 484 |
| 464(H) | -620 -149 -19 | -1972 -500 -6850 | -273 233 -7893 | 140 43 -894 | -2293 -381 -1115 | -1493 399 -701 | 2910 106 -1378 | -2020 -626 * | 1123 210 * | -1988 -466 | -1114 -720 | 1414 275 | -1632 394 | 244 45 | -127 96 | 1037 359 | -563 117 | -1615 -369 | -2160 -294 | -1523 -249 | 485 |
| 465(E) | 290 -149 -16 | -1861 -500 -7108 | 861 233 -8150 | 1446 43 -894 | 981 -381 -1115 | -1390 399 -701 | -101 106 -1378 | -1871 -626 * | 273 210 * | -1861 -466 | -968 -720 | 953 275 | 303 394 | 339 45 | -239 96 | -355 359 | -411 117 | -1463 -369 | -2069 -294 | -1398 -249 | 486 |
| 466(P) | -546 -149 -16 | -1977 -500 -7108 | 862 233 -8150 | 1025 43 -894 | -2262 -381 -1115 | -1409 399 -701 | -155 106 -1378 | -2002 -626 * | 204 210 * | -546 -466 | -1086 -720 | -48 275 | 1748 394 | 1636 45 | -313 96 | -420 359 | -495 117 | -1582 -369 | -2175 -294 | -1489 -249 | 487 |
| 467(W) | -477 -149 -16 | -661 -500 -7108 | -1479 233 -8150 | -920 43 -894 | -458 -381 -1115 | -1795 399 -701 | -520 106 -1378 | -227 -626 * | -729 210 * | -529 -466 | 143 -720 | 1513 275 | -1868 394 | -571 45 | -958 96 | 304 359 | -420 117 | 1257 -369 | 2766 -294 | 1177 -249 | 488 |
| 468(D) | -2784 -149 -16 | -3432 -500 -7108 | 4016 233 -8150 | -1200 43 -894 | -4140 -381 -1115 | -2466 399 -701 | -2197 106 -1378 | -4505 -626 * | -2621 210 * | -4365 -466 | -3956 -720 | -1551 275 | -3014 394 | -2039 45 | -3232 96 | -2593 359 | -2938 117 | -4046 -369 | -3710 -294 | -3552 -249 | 489 |
| 469(Q) | -1336 -149 -16 | -2814 -500 -7108 | 130 233 -8150 | 2632 43 -894 | -3112 -381 -1115 | -1670 399 -701 | -702 106 -1378 | -2921 -626 * | -403 210 * | -2830 -466 | -2067 -720 | -313 275 | -2037 394 | 2655 45 | -853 96 | -1120 359 | -1328 117 | -2494 -369 | -2954 -294 | -2238 -249 | 490 |

TABLE 6-continued

| | | | | | | | | | | | | | | | | | | | | |
|---|---|---|---|---|---|---|---|---|---|---|---|---|---|---|---|---|---|---|---|---|
| 470(W) | -1164 / -149 / -16 | -1540 / -500 / -7108 | 661 / 233 / -8150 | -1080 / 43 / -894 | 2483 / -381 / -1115 | -2257 / 399 / -701 | 1994 / 106 / -1378 | -1245 / -626 / * | -947 / 210 / * | -1304 / -466 | -742 / -720 | 745 / 275 | -2310 / 394 | -770 / 45 | -1263 / 96 | -1253 / 359 | -1097 / 117 | -1115 / -369 | 2555 / -294 | 1863 / -249 | 491 |
| 471(M) | -459 / -149 / -16 | -840 / -500 / -7108 | -1110 / 233 / -8150 | 504 / 43 / -894 | -907 / -381 / -1115 | -1674 / 399 / -701 | -501 / 106 / -1378 | -397 / -626 / * | -456 / 210 / * | -727 / -466 | 3234 / -720 | -715 / 275 | -1788 / 394 | -352 / 45 | -771 / 96 | 770 / 359 | -419 / 117 | 680 / -369 | -1288 / -294 | -853 / -249 | 492 |
| 472(H) | 1702 / -149 / -16 | -1846 / -500 / -7108 | -317 / 233 / -8150 | 119 / 43 / -894 | -2155 / -381 / -1115 | -1480 / 399 / -701 | 1717 / 106 / -1378 | -1860 / -626 / * | 1008 / 210 / * | -1870 / -466 | -1009 / -720 | 1392 / 275 | -1616 / 394 | 236 / 45 | -157 / 96 | -482 / 359 | -520 / 117 | -1482 / -369 | -2080 / -294 | -1459 / -249 | 493 |
| 473(P) | 1735 / -149 / -16 | -849 / -500 / -7108 | -2213 / 233 / -8150 | -1898 / 43 / -894 | -1800 / -381 / -1115 | -1446 / 399 / -701 | -1575 / 106 / -1378 | -902 / -626 / * | -1724 / 210 / * | -1568 / -466 | -933 / -720 | -1474 / 275 | 2335 / 394 | -1533 / 45 | -1863 / 96 | -706 / 359 | -666 / 117 | 1535 / -369 | -2237 / -294 | -1882 / -249 | 494 |
| 474(K) | 373 / -149 / -16 | -1864 / -500 / -7108 | 703 / 233 / -8150 | 990 / 43 / -894 | -2179 / -381 / -1115 | -1360 / 399 / -701 | -29 / 106 / -1378 | -1928 / -626 / * | 1276 / 210 / * | -1877 / -466 | -955 / -720 | 4 / 275 | -1460 / 394 | 1260 / 45 | -124 / 96 | 542 / 359 | 486 / 117 | -1483 / -369 | -2049 / -294 | -1367 / -249 | 495 |
| 475(G) | -2594 / -149 / -16 | -2690 / -500 / -7108 | -3304 / 233 / -8150 | -3623 / 43 / -894 | -4328 / -381 / -1115 | 3747 / 399 / -701 | -3462 / 106 / -1378 | -4761 / -626 / * | -3953 / 210 / * | -4671 / -466 | -4212 / -720 | -3320 / 275 | -3352 / 394 | -3748 / 45 | -3779 / 96 | -2839 / 359 | -2981 / 117 | -4004 / -369 | -3668 / -294 | -4222 / -249 | 496 |
| 476(R) | -1165 / -149 / -16 | -2238 / -500 / -7108 | -1063 / 233 / -8150 | -503 / 43 / -894 | -2794 / -381 / -1115 | 820 / 399 / -701 | -418 / 106 / -1378 | -2401 / -626 / * | 526 / 210 / * | -2281 / -466 | -1492 / -720 | -670 / 275 | -2047 / 394 | 2040 / 45 | 2681 / 96 | -1075 / 359 | -1064 / 117 | -2048 / -369 | -2328 / -294 | -1916 / -249 | 497 |
| 477(V) | -823 / -149 / -16 | -660 / -500 / -7108 | -2789 / 233 / -8150 | -2196 / 43 / -894 | -638 / -381 / -1115 | -2422 / 399 / -701 | -1317 / 106 / -1378 | 1842 / -626 / * | -1836 / 210 / * | -191 / -466 | 1866 / -720 | -1913 / 275 | -2436 / 394 | -1596 / 45 | 1039 / 96 | -1512 / 359 | -768 / 117 | 2028 / -369 | -1296 / -294 | -949 / -249 | 498 |
| 478(V) | -1748 / -149 / -16 | -1297 / -500 / -7108 | -4301 / 233 / -8150 | -3885 / 43 / -894 | -1515 / -381 / -1115 | -3999 / 399 / -701 | -3451 / 106 / -1378 | 2579 / -626 / * | -3726 / 210 / * | 585 / -466 | -321 / -720 | -3638 / 275 | -3782 / 394 | -3470 / 45 | -3730 / 96 | -3273 / 359 | -1722 / 117 | 2581 / -369 | -2943 / -294 | -2589 / -249 | 499 |
| 479(D) | -1067 / -149 / -16 | -2475 / -500 / -7108 | 2632 / 233 / -8150 | 1644 / 43 / -894 | -2683 / -381 / -1115 | -1544 / 399 / -701 | -584 / 106 / -1378 | 1013 / -626 / * | -469 / 210 / * | -2422 / -466 | -1654 / -720 | -180 / 275 | -1882 / 394 | -209 / 45 | -1071 / 96 | -894 / 359 | -1059 / 117 | -1933 / -369 | -2725 / -294 | -1977 / -249 | 500 |
| 480(S) | 717 / -149 / -340 | -1527 / -500 / -7108 | -107 / 233 / -8150 | 1500 / 43 / -894 | -2213 / -381 / -1115 | -1229 / 399 / -701 | -377 / 106 / -1378 | -1911 / -626 / * | -112 / 210 / * | -1988 / -466 | -1149 / -720 | -164 / 275 | -1554 / 394 | 7 / 45 | -597 / 96 | 1919 / 359 | -503 / 117 | -1461 / -369 | -2242 / -294 | -1620 / -249 | 501 |
| 481(Q) | -20 / -149 / -16 | -6788 / -500 / -7830 | -1563 / 233 / -8150 | -1026 / 43 / -894 | -923 / -381 / -1115 | 421 / 399 / -701 | -1984 / 106 / -1378 | -178 / -626 / * | -669 / 210 / * | -369 / -466 | 1897 / -720 | -1109 / 275 | -2120 / 394 | 2919 / 45 | -906 / 96 | -1087 / 359 | -746 / 117 | 1186 / -369 | -1510 / -294 | -1104 / -249 | 502 |
| 482(L) | -790 / -149 / -16 | -1076 / -500 / -7108 | -4231 / 233 / -8150 | -4103 / 43 / -894 | -1033 / -381 / -1115 | -2037 / 399 / -701 | -834 / 106 / -1378 | -541 / -626 / * | -3734 / 210 / * | 3130 / -466 | -31 / -720 | -3935 / 275 | -3797 / 394 | -3286 / 45 | -3484 / 96 | -3713 / 359 | -2869 / 117 | -1136 / -369 | -2394 / -294 | -2220 / -249 | 503 |
| 483(S) | -2871 / -149 / -16 | -2457 / -500 / -7108 | 2632 / 233 / -8150 | -2543 / 43 / -894 | -3185 / -381 / -1115 | -3803 / 399 / -701 | -3165 / 106 / -1378 | -3294 / -626 / * | -2686 / 210 / * | -3497 / -466 | -2780 / -720 | -1973 / 275 | -2360 / 394 | -2483 / 45 | -2703 / 96 | 3465 / 359 | -1316 / 117 | -2413 / -369 | -3310 / -294 | -3025 / -249 | 504 |
| 484(E) | -897 / -149 / -16 | -1462 / -500 / -7108 | -2333 / 233 / -8150 | -2543 / 43 / -894 | -3185 / -381 / -1115 | -1640 / 399 / -701 | -2474 / 106 / -1378 | -3294 / -626 / * | -2686 / 210 / * | -3497 / -466 | -2780 / -720 | -1531 / 275 | -2959 / 394 | -1842 / 45 | -2560 / 96 | -2479 / 359 | -2750 / 117 | -3722 / -369 | -3563 / -294 | -3385 / -249 | 505 |
| 485(H) | -3205 / -149 / -16 | -3079 / -500 / -7108 | -2723 / 233 / -8150 | -2890 / 43 / -894 | -3966 / -381 / -1115 | -2458 / 399 / -701 | -2043 / 106 / -1378 | -4105 / -626 / * | -2128 / 210 / * | -4016 / -466 | -3555 / -720 | -2886 / 275 | -3482 / 394 | -2833 / 45 | -2620 / 96 | -3291 / 359 | -3356 / 117 | -3895 / -369 | -2397 / -294 | -1681 / -249 | 506 |
| 486(Q) | -1064 / -149 / -16 | -1426 / -500 / -7108 | -1517 / 233 / -8150 | -1022 / 43 / -894 | -242 / -381 / -1115 | -2170 / 399 / -701 | -535 / 106 / -1378 | -884 / -626 / * | -583 / 210 / * | 715 / -466 | -396 / -720 | -1085 / 275 | -2235 / 394 | -3051 / 45 | -804 / 96 | -1225 / 359 | -994 / 117 | -864 / -369 | -835 / -294 | 1693 / -249 | 507 |

TABLE 6-continued

| | | | | | | | | | | | | | | | | | | |
|---|---|---|---|---|---|---|---|---|---|---|---|---|---|---|---|---|---|---|
| 487(C) | 1096 -149 -16 | 3020 -500 -7108 | 1354 233 -8150 | -606 43 -894 | -1109 -381 -1115 | -1571 399 -701 | -566 106 -1378 | -613 -626 * | -497 210 * | -939 -466 | 1724 -720 | -707 275 | -1762 394 | -380 45 | -838 96 | -622 359 | -428 117 | -433 -369 | -1460 -294 | -1015 -249 | 508 |
| 488(E) | -1401 -149 -16 | -2897 -500 -7108 | 169 233 -8150 | 3007 43 -894 | -3185 -381 -1115 | -1677 399 -701 | -753 106 -1378 | -3009 -626 * | -498 210 * | -2916 -466 | -2170 -720 | -319 275 | -2069 394 | 1880 45 | -966 96 | -1173 359 | -1402 117 | -2580 -369 | -3040 -294 | -2307 -249 | 509 |
| 489(H) | -30 -149 -16 | 439 -500 -7108 | 11 233 -8150 | 363 43 -894 | -394 -381 -1115 | -739 399 -701 | 699 106 -1378 | -414 -626 * | 463 210 * | -757 -466 | 501 -720 | 286 275 | -577 394 | 639 45 | 165 96 | -23 359 | 111 117 | -312 -369 | 697 -294 | -25 -249 | 510 |
| 490(G) | -2594 -149 -16 | -2690 -500 -7108 | -3304 233 -8150 | -3623 -894 | -4328 -381 -1115 | 3747 399 -701 | -3462 106 -1378 | -4761 -626 * | -3953 210 * | -4671 -466 | -4212 -720 | -3320 275 | -3352 394 | -3748 45 | -3779 96 | -2839 359 | -2981 117 | -4004 -369 | -3668 -294 | -4222 -249 | 511 |
| 491(W) | -2172 -149 -16 | -1773 -500 -7108 | -3771 233 -8150 | -3493 43 -894 | 3388 -381 -1115 | -3396 399 -701 | -717 106 -1378 | -939 -626 * | -3099 210 * | -528 -466 | 2179 -720 | -2555 275 | -3307 394 | -2387 45 | -2796 96 | -2550 359 | -2089 117 | -1165 -369 | 3733 -294 | 1010 -249 | 512 |
| 492(L) | -2620 -149 -16 | -2150 -500 -7108 | -4778 233 -8150 | -4218 43 -894 | -461 -381 -1115 | -4493 399 -701 | -3219 106 -1378 | 96 -626 * | -3870 210 * | 2765 -466 | 2758 -720 | -4143 275 | -3872 394 | -3009 45 | -3534 96 | -3777 359 | -2498 117 | -607 -369 | -2129 -294 | -2177 -249 | 513 |
| 493(E) | -1401 -149 -16 | -2897 -500 -7108 | 169 233 -8150 | 3007 43 -894 | -3185 -381 -1115 | -1677 399 -701 | -753 106 -1378 | -3009 -626 * | -498 210 * | -2916 -466 | -2170 -720 | -319 275 | -2069 394 | 1880 45 | -966 96 | -1173 359 | -1402 117 | -2580 -369 | -3040 -294 | -2307 -249 | 514 |
| 494(G) | 2172 -149 -16 | -1046 -500 -7108 | -2384 233 -8150 | -2525 43 -894 | -3259 -381 -1115 | 2719 399 -701 | -2377 106 -1378 | -2982 -626 * | -2644 210 * | -3267 -466 | -2417 -720 | -1723 275 | -2035 394 | -2315 45 | -2652 96 | -666 359 | -864 117 | -2010 -369 | -3440 -294 | -3255 -249 | 515 |
| 495(Y) | -3482 -149 -16 | -2868 -500 -7108 | -3701 233 -8150 | -3919 43 -894 | 238 -381 -1115 | -3552 399 -701 | -1112 106 -1378 | -3000 -626 * | -3638 210 * | -2516 -466 | -2526 -720 | -3027 275 | -3772 394 | -3101 45 | -3341 96 | -3418 359 | -3527 117 | -3071 -369 | -441 -294 | 4711 -249 | 516 |
| 496(T) | -971 -149 -16 | -915 -500 -7108 | -2809 233 -8150 | -2296 43 -894 | -857 -381 -1115 | -2442 399 -701 | -1626 106 -1378 | 433 -626 * | -1998 210 * | 1151 -466 | 92 -720 | -2043 275 | -2569 394 | -1769 45 | -2033 96 | -1592 359 | 2524 117 | 1200 -369 | -1666 -294 | -1332 -249 | 517 |
| 497(L) | -2871 -149 -16 | -2457 -500 -7108 | 4231 233 -8150 | -4103 43 -894 | -1033 -381 -1115 | -3803 399 -701 | -3165 106 -1378 | -541 -626 * | -3734 210 * | 3130 -466 | -31 -720 | -3935 275 | -3797 394 | -3286 45 | -3484 96 | -3713 359 | -2869 117 | -1136 -369 | -2394 -294 | -2220 -249 | 518 |
| 498(T) | -1213 -149 -16 | -1674 -500 -7108 | -2755 233 -8150 | -2906 43 -894 | -3163 -381 -1115 | -1922 399 -701 | -2659 106 -1378 | -2698 -626 * | -2788 210 * | -3105 -466 | -2612 -720 | -2311 275 | -2600 394 | -2708 45 | -2753 96 | -1463 359 | 3819 117 | -2197 -369 | -3286 -294 | -3156 -249 | 519 |
| 499(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -3953 210 * | -4671 -466 | -4212 -720 | -3320 275 | -3352 394 | -3748 45 | -3779 96 | -2839 359 | -2981 117 | -4004 -369 | -3668 -294 | -4222 -249 | 520 |
| 500(R) | -2957 -149 -16 | -3022 -500 -7108 | -3318 233 -8150 | -2735 43 -894 | -3796 -381 -1115 | -2998 399 -701 | -1968 106 -1378 | -3912 -626 * | -846 210 * | -3631 -466 | -3157 -720 | -2611 275 | -3280 394 | -1724 45 | 4056 96 | -3026 359 | -2913 117 | -3650 -369 | -3096 -294 | -3185 -249 | 521 |
| 501(H) | -999 -149 -16 | -1647 -500 -7108 | -1206 233 -8150 | -1105 43 -894 | -1780 -381 -1115 | -1755 399 -701 | 4476 106 -1378 | -2154 -626 * | -805 210 * | -2276 -466 | -1630 -720 | -1129 275 | -2202 394 | -979 45 | -999 96 | -1106 359 | 1428 117 | -1786 -369 | -2106 -294 | -1395 -249 | 522 |
| 502(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -3953 210 * | -4671 -466 | -4212 -720 | -3320 275 | -3352 394 | -3748 45 | -3779 96 | -2839 359 | -2981 117 | -4004 -369 | -3668 -294 | -4222 -249 | 523 |
| 503(I) | -1567 -149 -16 | -1223 -500 -7108 | -3950 233 -8150 | -3399 43 -894 | 2055 -381 -1115 | -3419 399 -701 | -2370 106 -1378 | 2527 -626 * | -3104 210 * | 944 -466 | 309 -720 | -3048 275 | -3245 394 | -2620 45 | -2927 96 | -2582 359 | -1507 117 | 1309 -369 | -1899 -294 | -1632 -249 | 524 |

TABLE 6-continued

| | | | | | | | | | | | | | | | | | | | |
|---|---|---|---|---|---|---|---|---|---|---|---|---|---|---|---|---|---|---|---|
| 504(W) | −3425 | −2618 | −4155 | −4330 | 3859 | −3949 | −484 | −2303 | −3894 | −1728 | −1759 | −2779 | −3865 | −2847 | −3389 | −3247 | −3323 | −2490 | 3919 | 1426 | 525 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 505(A | 2014 | −983 | −1788 | −1434 | −2527 | −1231 | −1430 | −2209 | −1330 | −2413 | −1572 | −1164 | 1491 | −1179 | −1621 | 1494 | 990 | −1548 | −2719 | −2324 | 526 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 506(S) | −352 | −985 | −2207 | −2221 | −3013 | −1228 | −2099 | −2715 | −2192 | −3001 | −2167 | −1553 | −1952 | −1978 | −2279 | 3131 | 1106 | −1840 | −3241 | −2944 | 527 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 507(Y) | −3482 | −2868 | −3701 | −3919 | 238 | −3552 | −1112 | −3000 | −3638 | −2516 | −2526 | −3027 | −3772 | −3101 | −3341 | −3418 | −3527 | −3071 | −441 | 4711 | 528 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 508(E) | −2641 | −3308 | −896 | 3732 | −3966 | −2458 | −2043 | −4105 | −2128 | −4016 | −3555 | −1531 | −2959 | −1842 | −2560 | −2479 | −2750 | −3722 | −3563 | −3385 | 529 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 509(S) | 1981 | −864 | −2260 | −1969 | −2205 | −1291 | −1697 | −1605 | −1808 | −2070 | −1333 | −1448 | −1910 | −1601 | −1958 | 2200 | −636 | 877 | −2550 | −2211 | 530 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 510(F) | −3342 | −2776 | −4026 | −4232 | 4354 | −3545 | −1431 | −2315 | −4038 | −1801 | −1900 | −3299 | −3780 | −3350 | −3645 | −3490 | −3420 | −2566 | −739 | 349 | 531 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 511(V | −929 | −722 | −3094 | −2519 | −671 | 72 | −1536 | 1450 | −2197 | 1669 | 235 | −2159 | −2584 | −1873 | −2107 | −1688 | −882 | 1742 | −1406 | −1072 | 532 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 512(R | −1152 | −2148 | −1103 | −556 | −2568 | 841 | 2681 | −2297 | 448 | −2220 | −1446 | −714 | −2063 | −63 | 2686 | −1086 | −1067 | −1962 | −2250 | −1802 | 533 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 513(V | −1261 | −1032 | −2990 | 401 | −1324 | −3032 | −2128 | 1904 | −2354 | −591 | −293 | −2430 | −3023 | −2199 | −2472 | −2185 | −1232 | 2780 | −2221 | −1813 | 534 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 514(V | −1755 | −1298 | −4332 | −3970 | −1769 | −4057 | −3755 | 2730 | −3843 | −618 | −544 | −3732 | −3880 | −3701 | −3920 | −3374 | −1748 | 2759 | −3277 | −2831 | 535 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 515(D | −1718 | −3250 | 3403 | −27 | −3066 | −1736 | 2667 | −3486 | −1211 | −3381 | −2732 | −400 | −2240 | −752 | −1917 | −1439 | −1784 | −3023 | −3204 | −2299 | 536 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 516(S) | −635 | −1657 | 1163 | −252 | −2614 | −1382 | −780 | −2338 | −601 | −2421 | −1582 | −466 | −1801 | −415 | −1101 | 2397 | 1307 | −1804 | −2665 | −2044 | 537 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 517(M | −2406 | −2296 | −3638 | −3594 | −1525 | −3105 | −2824 | −1047 | −3121 | −596 | 5043 | −3293 | −3425 | −3046 | −2996 | −2911 | −2552 | −1398 | −2513 | −2207 | 538 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 518(M | −2437 | −1975 | −4738 | −4148 | −487 | −4369 | −3139 | 1386 | −3872 | 2524 | 2731 | −4019 | −3789 | −2984 | −3525 | −3603 | −2318 | −374 | −2113 | −2174 | 539 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 519(T) | −504 | −959 | −1413 | −1049 | −1473 | −1580 | −994 | −629 | −943 | −1256 | −601 | 1702 | −1931 | −837 | −1224 | −750 | 1993 | 1780 | −1865 | −1432 | 540 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |
| 520(Q | −2562 | −2904 | −1886 | −1971 | −3251 | −2661 | −2079 | −3690 | −1565 | −3469 | −3081 | −2107 | −3091 | 4371 | −1665 | −2585 | −2674 | −3411 | −3077 | −2821 | 541 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7108 | −8150 | −894 | −1115 | −701 | −1378 | * | | | | | | | | | | | | |

TABLE 6-continued

| | | | | | | | | | | | | | | | | | | |
|---|---|---|---|---|---|---|---|---|---|---|---|---|---|---|---|---|---|---|
| 521(H) | −2992 −149 −16 | −2589 −500 −7108 | −3064 233 −8150 | −3043 43 −894 | 863 −381 −1115 | −3512 399 −701 | 4371 106 −1378 | −2521 −626 * | −2584 210 * | −2051 −466 | −1961 −720 | −2327 275 | −3545 394 | −2255 45 | −2492 96 | −2815 359 | −2919 117 | −2563 −369 | 158 −294 | 3265 −249 | 542 |
| 522(F) | 1777 −149 −16 | −758 −500 −7108 | −2605 233 −8150 | −2069 43 −894 | 2426 −381 −1115 | −2201 399 −701 | −1138 106 −1378 | 17 −626 * | −1776 210 * | −51 −466 | 1943 −720 | −1762 275 | −2314 394 | −1474 45 | −1762 96 | −1320 359 | −786 117 | −23 −369 | −1063 −294 | −575 −249 | 543 |
| 523(K) | −2620 −149 −16 | −2961 −500 −7108 | −2461 233 −8150 | −2046 43 −894 | −3743 −381 −1115 | −2791 399 −701 | −1570 106 −1378 | −3603 −626 * | 3784 210 * | −3387 −466 | −2839 −720 | −2048 275 | −3039 394 | −1260 45 | −465 96 | −2604 359 | −2536 117 | −3331 −369 | −3001 −294 | −2988 −249 | 544 |
| 524(W) | −3358 −149 −16 | −2599 −500 −7108 | −4116 233 −8150 | −4259 43 −894 | 2442 −381 −1115 | −3892 399 −701 | −536 106 −1378 | −2247 −626 * | −3821 210 * | −1683 −466 | −1712 −720 | −2792 275 | −3835 394 | −2843 45 | −3352 96 | −3227 359 | −3271 117 | −2441 −369 | 5485 −294 | 1363 −249 | 545 |
| 525(L) | 841 −149 −16 | −1175 −500 −7108 | −3469 233 −8150 | −2926 43 −894 | −668 −381 −1115 | −3037 399 −701 | −2058 106 −1378 | 1328 −626 * | −2615 210 * | 2287 −466 | 379 −720 | −2642 275 | −2978 394 | −2226 45 | −2526 96 | −2188 359 | −1355 117 | 301 −369 | −1760 −294 | −1526 −249 | 546 |
| 526(R) | −837 −149 −16 | −2176 −500 −7108 | −602 233 −8150 | 1392 43 −894 | −2587 −381 −1115 | −1688 399 −701 | −216 106 −1378 | −2257 −626 * | 1534 210 * | −2141 −466 | −1281 −720 | 1107 275 | −1779 394 | 227 45 | −2109 96 | −709 359 | −741 117 | −1854 −369 | −2229 −294 | −1683 −249 | 547 |
| 527(M | 888 −149 −16 | −1677 −500 −7108 | −357 233 −8150 | 850 43 −894 | −1922 −381 −1115 | −1428 399 −701 | 1639 106 −1378 | −1611 −626 * | 1435 210 * | −1654 −466 | 1807 −720 | −103 275 | −1521 394 | 338 45 | −129 96 | −358 359 | −369 117 | −1259 −369 | −1902 −294 | −1285 −249 | 548 |
| 528(A | 2576 −149 −16 | −902 −500 −7108 | −2349 233 −8150 | −2158 43 −894 | −2756 −381 −1115 | −1202 399 −701 | −1937 106 −1378 | −2410 −626 * | −2031 210 * | −2688 −466 | −1852 −720 | −1502 275 | −1892 394 | −1801 45 | −2162 96 | −1376 359 | 1811 117 | −1644 −369 | −3004 −294 | −2709 −249 | 549 |
| 529(K | −583 −149 −16 | −1746 −500 −7108 | −490 233 −8150 | 34 43 −894 | −1989 −381 −1115 | −1543 399 −701 | 1732 106 −1378 | −1666 −626 * | 1763 210 * | −1714 −466 | −880 −720 | 1553 275 | −1641 394 | 238 45 | −31 96 | −516 359 | −513 117 | 875 −369 | −1945 −294 | −1367 −249 | 550 |
| 530(R | −1300 −149 −16 | −1572 −500 −7108 | 724 233 −8150 | 108 43 −894 | −1851 −381 −1115 | −1418 399 −701 | −201 106 −1378 | −1534 −626 * | 126 210 * | −1626 −466 | −789 −720 | −169 275 | 1640 394 | 198 45 | −358 96 | 575 359 | −413 117 | −1199 −369 | −1916 −294 | 922 −249 | 551 |
| 531(E | 787 −149 −16 | −1387 −500 −7108 | −1141 233 −8150 | −641 43 −894 | −1786 −381 −1115 | −1421 399 −701 | −246 106 −1378 | −1638 −626 * | 712 210 * | −1598 −466 | −1052 −720 | −657 275 | −1663 394 | 43 45 | 3215 96 | −962 359 | −890 117 | −1418 −369 | −1542 −294 | −1280 −249 | 552 |
| 532(I) | −4114 −149 −16 | −3274 −500 −7108 | −4214 233 −8150 | −4453 43 −894 | −1722 −381 −1115 | −3496 399 −701 | −2681 106 −1378 | −4109 −626 * | −4149 210 * | −3619 −466 | −3615 −720 | −4044 275 | −3885 394 | −4032 45 | −3816 96 | −4355 359 | −4248 117 | −4133 −369 | 6191 −294 | −1329 −249 | 553 |
| 533(P) | −915 −149 −16 | −5845 −500 −7108 | −6888 233 −8150 | −38 43 −894 | −3749 −381 −1115 | −238 399 −701 | −2716 106 −1378 | −3679 −626 * | −1227 210 * | −3559 −466 | −2898 −720 | −238 275 | −2166 394 | −662 45 | −2065 96 | −1376 359 | −1779 117 | −3163 −369 | −3720 −294 | −2744 −249 | 554 |
| 534(W | −1710 −149 −16 | −3547 −500 −7108 | 2209 233 −8150 | 3007 43 −894 | −3749 −381 −1115 | −1634 399 −701 | −990 106 −1378 | −3679 −626 * | −1499 210 * | 1009 −466 | 366 −720 | −1553 275 | −2152 394 | 765 45 | −1506 96 | −1178 359 | 1103 117 | 1145 −369 | −1019 −294 | −667 −249 | 555 |
| 535(R | −599 −149 −16 | −507 −500 −7108 | −2385 233 −8150 | −1791 43 −894 | −457 −381 −1115 | −2112 399 −701 | −969 106 −1378 | 1604 −626 * | −1499 210 * | 1009 −466 | −789 −720 | −169 275 | 1640 394 | 198 45 | −358 96 | 575 359 | −413 117 | 1145 −369 | −1916 −294 | 922 −249 | 555 |
| 536(H | −1940 −149 −16 | −2623 −500 −7108 | −2163 233 −8150 | −1317 43 −894 | −2718 −381 −1115 | −2498 399 −701 | 2633 106 −1378 | −2821 −626 * | 557 210 * | −2576 −466 | −1920 −720 | −1294 275 | −2549 394 | −305 45 | 3406 96 | −1859 359 | −1734 117 | −2575 −369 | −2279 −294 | −1885 −249 | 556 |
| 537(D | −1345 −149 −16 | −2440 −500 −7108 | −1207 233 −8150 | −576 43 −894 | −2915 −381 −1115 | −2072 399 −701 | 3063 106 −1378 | −2527 −626 * | 2588 210 * | −2343 −466 | −1569 −720 | −727 275 | −2129 394 | 1381 45 | 532 96 | −1222 359 | −1187 117 | −2200 −369 | −2324 −294 | −1939 −249 | 557 |
| — | −695 −149 −16 | −2182 −500 −7108 | 1890 233 −8150 | 241 43 −894 | −2491 −381 −1115 | −1456 399 −701 | −249 106 −1378 | −2246 −626 * | 1496 210 * | −2187 −466 | −1300 −720 | −85 275 | 1264 394 | 1306 45 | −385 96 | −545 359 | −648 117 | −1804 −369 | −2357 −294 | −1656 −249 | 558 |

TABLE 6-continued

| | | | | | | | | | | | | | | | | | | | | |
|---|---|---|---|---|---|---|---|---|---|---|---|---|---|---|---|---|---|---|---|---|
| 538(Y) | −1138 −149 −16 | −876 −500 −7108 | −3345 233 −8150 | −2810 43 −894 | −645 −381 −1115 | −2852 399 −701 | −1674 106 −1378 | 1928 −626 * | −2488 210 * | −317 −466 | 10 −720 | −2411 275 | −2835 394 | −2166 45 | −2393 96 | −1984 359 | −1094 117 | 2117 −369 | −1423 −294 | 2681 −249 | 559 |
| 539(P) | 1031 −149 −16 | −974 −500 −7108 | −2031 233 −8150 | −1918 43 −894 | −2925 −381 −1115 | −1207 399 −701 | −1878 106 −1378 | −2641 −626 * | −1913 210 * | −2865 −466 | −2004 −720 | −1407 275 | 2879 394 | −1695 45 | −2096 96 | 1838 359 | −694 117 | −1790 −369 | −3123 −294 | −2802 −249 | 560 |
| 540(H) | −30 −149 −16 | 439 −500 −7108 | 11 233 −8150 | 363 43 −894 | −394 −381 −1115 | −739 399 −701 | 699 106 −1378 | −414 −626 * | 463 210 * | −757 −466 | 501 −720 | 286 275 | −577 394 | 639 45 | 165 96 | −23 359 | 111 117 | −312 −369 | 697 −294 | −25 −249 | 561 |
| 541(S) | 1737 −149 −16 | −944 −500 −7108 | −2392 233 −8150 | −2415 43 −894 | −3092 −381 −1115 | −1199 399 −701 | −2214 106 −1378 | −2801 −626 * | −2395 210 * | −3086 −466 | −2226 −720 | −1614 275 | −1940 394 | −2116 45 | −2445 96 | 2898 359 | −735 117 | −1863 −369 | −3322 −294 | −3065 −249 | 562 |
| 542(M) | −1968 −149 −16 | −1576 −500 −7108 | −4331 233 −8150 | −3761 43 −894 | −611 −381 −1115 | −3859 399 −701 | −2765 106 −1378 | 1741 −626 * | −3480 210 * | 2227 −466 | 2250 −720 | −3502 275 | −3515 394 | −2812 45 | −3229 96 | −3049 359 | −1885 117 | 1013 −369 | −2038 −294 | −1963 −249 | 563 |
| 543(N) | −2171 −149 −16 | −2655 −500 −7108 | −1458 233 −8150 | −1748 43 −894 | −3334 −381 −1115 | −2364 399 −701 | −2267 106 −1378 | −3943 −626 * | −2365 210 * | −3936 −466 | −3437 −720 | 4205 275 | −2932 394 | −2205 45 | −2608 96 | −2224 359 | −2439 117 | −3392 −369 | −3253 −294 | −2909 −249 | 564 |
| 544(I) | −1257 −149 −16 | −1007 −500 −7108 | −3424 233 −8150 | −2868 43 −894 | −1397 −381 −1115 | −2811 399 −701 | −1254 106 −1378 | 2188 −626 * | −2500 210 * | 1333 −466 | 382 −720 | −2341 275 | −2749 394 | −1996 45 | −2283 96 | −1922 359 | −1186 117 | −115 −369 | −815 −294 | 2061 −249 | 565 |
| 545(I) | −1831 −149 −16 | −1391 −500 −7108 | −4327 233 −8150 | −3871 43 −894 | −1200 −381 −1115 | −3991 399 −701 | −3265 106 −1378 | 2941 −626 * | −3675 210 * | 1302 −466 | −22 −720 | −3631 275 | −3727 394 | −3275 45 | −3598 96 | −3245 359 | −1791 117 | 1578 −369 | −2650 −294 | −2410 −249 | 566 |
| 546(E) | 999 −149 −16 | −1712 −500 −7108 | 787 233 −8150 | 1203 43 −894 | −1974 −381 −1115 | −1412 399 −701 | −152 106 −1378 | −1661 −626 * | 194 210 * | −1721 −466 | −863 −720 | −101 275 | −1546 394 | 266 45 | −305 96 | 466 359 | −419 117 | 822 −369 | −1983 −294 | −1349 −249 | 567 |
| 547(T) | 590 −149 −16 | −1479 −500 −7108 | 974 233 −8150 | −206 43 −894 | −2293 −381 −1115 | −1346 399 −701 | −555 106 −1378 | −1995 −626 * | −272 210 * | −2077 −466 | −1218 −720 | −407 275 | −1671 394 | −167 45 | −745 96 | 1655 359 | 1771 117 | −1514 −369 | −2333 −294 | −1741 −249 | 568 |
| 548(S) | −897 −149 −16 | −1462 −500 −7108 | −2333 233 −8150 | −2543 43 −894 | −3185 −381 −1115 | −1640 399 −701 | −2474 106 −1378 | −3294 −626 * | −2686 210 * | −3497 −466 | −2780 −720 | −1973 275 | −2360 394 | −2483 45 | −2703 96 | 3465 359 | −1316 117 | −2413 −369 | −3310 −294 | −3025 −249 | 569 |
| 549(T) | −866 −149 −16 | −1511 −500 −7108 | −1211 233 −8150 | −1054 43 −894 | −1813 −381 −1115 | −1680 399 −701 | 2857 106 −1378 | −1969 −626 * | −793 210 * | −2130 −466 | −1455 −720 | −1074 275 | −2117 394 | −914 45 | −1013 96 | −989 359 | 3041 117 | −1609 −369 | −2119 −294 | −1469 −249 | 570 |
| 550(W) | −587 −149 −16 | −608 −500 −7108 | −2405 233 −8150 | −1898 43 −894 | −479 −381 −1115 | −1928 399 −701 | −993 106 −1378 | −42 −626 * | −1552 210 * | −528 −466 | 62 −720 | −1554 275 | −2129 394 | −1332 45 | −1550 96 | 365 359 | −609 117 | 2511 −369 | 3028 −294 | −502 −249 | 571 |
| 551(W) | 947 −149 −16 | −1346 −500 −7108 | −3135 233 −8150 | −2759 43 −894 | 3172 −381 −1115 | −2759 399 −701 | −620 106 −1378 | −882 −626 * | −2412 210 * | −912 −466 | −526 −720 | −2088 275 | −2831 394 | −1938 45 | −2273 96 | −1901 359 | −1498 117 | −870 −369 | 3648 −294 | 929 −249 | 572 |
| 552(Q) | −1772 −149 −16 | −2604 −500 −7108 | −1870 233 −8150 | −1079 43 −894 | −3217 −381 −1115 | −2374 399 −701 | −569 106 −1378 | −2777 −626 * | 660 210 * | −2529 −466 | −1835 −720 | −1110 275 | −2420 394 | 3075 45 | 2723 96 | −1671 359 | −1571 117 | −2504 −369 | −2437 −294 | −2192 −249 | 573 |
| 553(Q) | −2562 −149 −16 | −2904 −500 −7108 | −1886 233 −8150 | −1971 43 −894 | −3251 −381 −1115 | −2661 399 −701 | −2079 106 −1378 | −3690 −626 * | −1565 210 * | −3469 −466 | −3081 −720 | −2107 275 | −3091 394 | 4371 45 | −1665 96 | −2585 359 | −2674 117 | −3411 −369 | −3077 −294 | −2821 −249 | 574 |
| 554(D) | −1791 −149 −16 | −3663 −500 −7108 | 3414 233 −8150 | 1659 43 −894 | −3853 −381 −1115 | −1647 399 −701 | −1043 106 −1378 | −3807 −626 * | −1343 210 * | −3679 −466 | −3054 −720 | −251 275 | −2201 394 | −725 45 | −2227 96 | −1438 359 | −1872 117 | −3282 −369 | −3836 −294 | −2831 −249 | 575 |

TABLE 6-continued

| | | | | | | | | | | | | | | | | | |
|---|---|---|---|---|---|---|---|---|---|---|---|---|---|---|---|---|---|
| 555(H) | −3205 −149 −16 | −3079 −500 −7108 | −2723 233 −8150 | −2890 43 −894 | −2110 −381 −1115 | −3046 399 −701 | 5295 106 −1378 | −4135 −626 * | −2617 210 * | −3813 −466 | −3561 −720 | −2886 275 | −3482 394 | −2833 45 | −2620 96 | −3291 359 | −3356 117 | −3895 −369 | −2397 −294 | −1681 −249 | 576 |
| 556(N) | −2171 −149 −16 | −2655 −500 −7108 | −1458 233 −8150 | −1748 43 −894 | −3334 −381 −1115 | −2364 399 −701 | −2267 106 −1378 | −3943 −626 * | −2365 210 * | −3936 −466 | −3437 −720 | 4205 275 | −2932 394 | −2205 45 | −2608 96 | −2224 359 | −2439 117 | −3392 −369 | −3253 −294 | −2909 −249 | 577 |
| 557(G) | −2594 −149 −16 | −2690 −500 −7108 | −3304 233 −8150 | −3623 43 −894 | −4328 −381 −1115 | 3747 399 −701 | −3462 106 −1378 | −4761 −626 * | −3953 210 * | −4671 −466 | −4212 −720 | −3320 275 | −3352 394 | −3748 45 | −3779 96 | −2839 359 | −2981 117 | −4004 −369 | −3668 −294 | −4222 −249 | 578 |
| 558(Y) | −3620 −149 −16 | −2706 −500 −7108 | −4179 233 −8150 | −4428 43 −894 | 3303 −381 −1115 | −4051 399 −701 | −393 106 −1378 | −2536 −626 * | −4005 210 * | −1939 −466 | −1984 −720 | −2749 275 | −3933 394 | −2855 45 | −3452 96 | −3299 359 | −3498 117 | −2688 −369 | 350 −294 | 3843 −249 | 579 |
| 559(S) | −344 −149 −16 | −978 −500 −7108 | −2187 233 −8150 | −2155 43 −894 | −2953 −381 −1115 | −1227 399 −701 | −2035 106 −1378 | −2643 −626 * | −2108 210 * | −2926 −466 | −2093 −720 | −1523 275 | −1940 394 | −1902 45 | −2216 96 | 2907 359 | 1859 117 | −1800 −369 | −3181 −294 | −2875 −249 | 580 |
| 560(H) | −3205 −149 −16 | −3079 −500 −7108 | −2723 233 −8150 | −2890 43 −894 | −2110 −381 −1115 | −3046 399 −701 | 5295 106 −1378 | −4135 −626 * | −2617 210 * | −3813 −466 | −3561 −720 | −2886 275 | −3482 394 | −2833 45 | −2620 96 | −3291 359 | −3356 117 | −3895 −369 | −2397 −294 | −1681 −249 | 581 |
| 561(Q) | −2562 −149 −16 | −2904 −500 −7108 | −1886 233 −8150 | −1971 43 −894 | −3251 −381 −1115 | −2661 399 −701 | −2079 106 −1378 | −3690 −626 * | −1565 210 * | −3469 −466 | −3081 −720 | −2107 275 | −3091 394 | 4371 45 | −2191 96 | −2585 359 | −2674 117 | −3411 −369 | −3077 −294 | −2821 −249 | 582 |
| 562(D) | −1724 −149 −16 | −3448 −500 −7108 | 3411 233 −8150 | 103 43 −894 | −3726 −381 −1115 | −1642 399 −701 | −1058 106 −1378 | −3734 −626 * | −1342 210 * | −3628 −466 | −2991 −720 | 1884 275 | −2196 394 | −745 45 | −1665 96 | −1408 359 | −1822 117 | −3197 −369 | −3743 −294 | −2768 −249 | 583 |
| 563(P) | −2931 −149 −16 | −2878 −500 −7108 | −3420 233 −8150 | −3706 43 −894 | −4181 −381 −1115 | −2925 399 −701 | −3468 106 −1378 | −4621 −626 * | −3859 210 * | −4490 −466 | −4165 −720 | −3491 275 | −4225 394 | −3781 45 | −3695 96 | −3182 359 | −3279 117 | −4087 −369 | −3594 −294 | −4064 −249 | 584 |
| 564(G) | −468 −149 −16 | −1108 −500 −7108 | −1987 233 −8150 | −2183 43 −894 | −3307 −381 −1115 | 3093 399 −701 | −2261 106 −1378 | −3159 −626 * | −2489 210 * | −3374 −466 | −2507 −720 | −1593 275 | −2035 394 | −2163 45 | −2570 96 | 1410 359 | −895 117 | −2119 −369 | −3471 −294 | −3217 −249 | 585 |
| 565(V) | 371 −149 −16 | −671 −500 −7108 | −3209 233 −8150 | −2618 43 −894 | 1562 −381 −1115 | −2580 399 −701 | −1515 106 −1378 | 1368 −626 * | −2275 210 * | 648 −466 | 269 −720 | −2195 275 | −2574 394 | −1917 45 | −2132 96 | −1689 359 | −852 117 | 2127 −369 | −1337 −294 | −1001 −249 | 586 |
| 566(T) | −1238 −149 −16 | −1032 −500 −7108 | −3270 233 −8150 | −2717 43 −894 | −705 −381 −1115 | −2883 399 −701 | −1871 106 −1378 | 1700 −626 * | −2401 210 * | 1666 −466 | 301 −720 | −2442 275 | −2848 394 | −2072 45 | −2345 96 | −2015 359 | 1957 117 | 452 −369 | −1675 −294 | −1395 −249 | 587 |
| 567(T) | −307 −149 −16 | −965 −500 −7108 | −2051 233 −8150 | −1918 43 −894 | −2899 −381 −1115 | 1272 399 −701 | −1866 106 −1378 | −2617 −626 * | −1903 210 * | −2838 −466 | −1975 −720 | −1405 275 | −1889 394 | −1683 45 | −2089 96 | 1577 359 | 2739 117 | −1773 −369 | −3100 −294 | −2780 −249 | 588 |
| 568(H) | 837 −149 −16 | −578 −500 −7108 | −1703 233 −8150 | −1139 43 −894 | −579 −381 −1115 | −1822 399 −701 | 2864 106 −1378 | −45 −626 * | −902 210 * | −418 −466 | 1836 −720 | −1086 275 | −1915 394 | −740 45 | −1071 96 | −867 359 | −423 117 | 1342 −369 | −1041 −294 | −648 −249 | 589 |
| 569(L) | −2092 −149 −16 | −1719 −500 −7108 | −4323 233 −8150 | −3846 43 −894 | −712 −381 −1115 | −3925 399 −701 | −2989 106 −1378 | 451 −626 * | −3531 210 * | 2641 −466 | 428 −720 | −3624 275 | −3640 394 | −2952 45 | −3339 96 | −3191 359 | −2044 117 | 1542 −369 | −2221 −294 | −2096 −249 | 590 |
| 570(L) | 1056 −149 −16 | −648 −500 −7108 | −2733 233 −8150 | −2160 43 −894 | 1291 −381 −1115 | −2277 399 −701 | −874 106 −1378 | 5 −626 * | −1827 210 * | 1649 −466 | 341 −720 | −1760 275 | −2303 394 | −1464 45 | −1729 96 | −1359 359 | −733 117 | −2 −369 | −647 −294 | 1605 −249 | 591 |
| 571(E) | −994 −149 −16 | −2497 −500 −7108 | 67 233 −8150 | 2352 43 −894 | −2818 −381 −1115 | −1564 399 −701 | −437 106 −1378 | −2572 −626 * | 1391 210 * | −2487 −466 | −1645 −720 | 1818 275 | −1831 394 | −24 45 | −503 96 | −812 359 | −956 117 | −2133 −369 | −2633 −294 | −1933 −249 | 592 |

TABLE 6-continued

| | | | | | | | | | | | | | | | | |
|---|---|---|---|---|---|---|---|---|---|---|---|---|---|---|---|---|
| 572(K) | −1592 −149 −971 | −2196 −500 −7108 | −1883 233 −1051 | −1179 43 −894 | −2203 −381 −1115 | −2360 399 −701 | −733 106 −1378 | −1718 −626 * | 3129 210 | 666 −466 | −1212 −720 | −1218 275 | −2435 394 | −383 45 | 258 96 | −1621 359 | −1460 117 | −1669 −369 | −2199 −294 | −1837 −249 | 593 |
| 573(C) | −39 −149 −360 | 2488 −500 −6167 | −473 233 −2274 | 1144 43 −894 | −1043 −381 −1115 | −1085 399 −1874 | −142 106 −459 | −526 −626 * | 67 210 | −851 −466 | −125 −720 | −185 275 | −1325 394 | 126 45 | −296 96 | −170 359 | 1058 117 | −295 −369 | −1316 −294 | −837 −249 | 594 |
| 574(F) | −1315 −149 −38 | −1110 −500 −5845 | −2234 233 −6888 | −2129 43 −894 | 3522 −381 −1115 | −2099 399 −2039 | −247 106 −402 | −203 −626 * | −1900 210 | 58 −466 | 60 −720 | −1632 275 | −2283 394 | −1510 45 | −1804 96 | −1624 359 | −1357 117 | −396 −369 | 303 −294 | 1334 −249 | 595 |
| 575(H) | −354 −149 −38 | −1360 −500 −5845 | 326 233 −6888 | 436 43 −894 | −1031 −381 −1115 | 2689 399 −1026 | −2716 106 | −1410 −626 * | 436 210 | −1450 −466 | −724 −720 | 1667 275 | −1303 394 | 383 45 | 89 96 | −286 359 | −351 117 | −1096 −369 | −1280 −294 | −501 −249 | 596 |
| 576(K) | −1086 −149 −16 | −2304 −500 −7108 | −1032 233 −8150 | −362 43 −894 | −2797 −381 −1115 | −1910 399 −701 | −283 106 −1378 | −2399 −626 * | 2361 210 | −2235 −466 | −1413 −720 | 1695 275 | −1959 394 | 1479 45 | 1362 96 | −963 359 | −952 117 | −2031 −369 | −2264 −294 | −1826 −249 | 597 |
| 577(P) | −1766 −149 −16 | −2832 −500 −7108 | 2091 233 −8150 | −503 43 −894 | −3634 −381 −1115 | −1897 399 −701 | −1480 106 −1378 | −3629 −626 * | −1677 210 | −3608 −466 | −2962 −720 | −830 275 | 3445 394 | −1206 45 | −2322 96 | −1624 359 | −1926 117 | −3087 −369 | −3516 −294 | −2951 −249 | 598 |
| 578(H) | −480 −149 −16 | −1902 −500 −7108 | 1434 233 −8150 | 926 43 −894 | −2176 −381 −1115 | −1399 399 −701 | 2271 106 −1378 | −1932 −626 * | 300 210 * | −1903 −466 | −1004 −720 | −39 275 | −1521 394 | 347 45 | 782 96 | −362 359 | −423 117 | −1511 −369 | −2083 −294 | 1389 −249 | 599 |
| 579(Y) | 839 −149 −16 | −383 −500 −7108 | −2642 233 −8150 | −2032 43 −894 | 1206 −381 −1115 | −2056 399 −701 | −863 106 −1378 | 223 −626 * | −1678 210 | 569 −466 | 461 −720 | −1617 275 | −2100 394 | −1333 45 | −1555 96 | −1135 359 | −472 117 | 1465 −369 | −747 −294 | 1987 −249 | 600 |
| 580(I) | 865 −149 −16 | −836 −500 −7108 | −3163 233 −8150 | −2646 43 −894 | −1108 −381 −1115 | −2692 399 −701 | −1893 106 −1378 | 2677 −626 * | −2382 210 | −556 −466 | −157 −720 | −2324 275 | −2771 394 | −2135 45 | −2380 96 | −1845 359 | 504 117 | 1519 −369 | −1868 −294 | −1491 −249 | 601 |
| 581(R) | −1066 −149 −16 | −2251 −500 −7108 | −943 233 −8150 | −347 43 −894 | −2740 −381 −1115 | 308 399 −701 | −313 106 −1378 | −2349 −626 * | 1342 210 | −2216 −466 | 1401 −720 | 854 275 | −1954 394 | 119 45 | 2761 96 | −953 359 | −949 117 | −1986 −369 | −2272 −294 | −1823 −249 | 602 |
| 582(E) | −370 −149 −16 | −640 −500 −7108 | −961 233 −8150 | 1875 43 −894 | −770 −381 −1115 | −1558 399 −701 | −279 106 −1378 | 900 −626 * | −284 210 * | −670 −466 | 84 −720 | −547 275 | −1598 394 | −160 45 | −606 96 | −577 359 | −301 117 | 965 −369 | −907 −294 | −668 −249 | 603 |
| 583(Y) | −3618 −149 −16 | −2707 −500 −7108 | −4172 233 −8150 | −4418 43 −894 | 2748 −381 −1115 | −4047 399 −701 | −395 106 −1378 | −2537 −626 * | −3997 210 * | −1940 −466 | −1986 −720 | −2748 275 | −3932 394 | −2853 45 | −3448 96 | −3297 359 | −3496 117 | −2688 −369 | 348 −294 | 4199 −249 | 604 |
| 584(F) | −2597 −149 −16 | −2122 −500 −7108 | −4519 233 −8150 | 4116 43 −894 | 2769 −381 −1115 | −4202 399 −701 | −2114 106 −1378 | −140 −626 * | −3797 210 * | 2428 −466 | 469 −720 | −3639 275 | −3772 394 | −2912 45 | −3436 96 | −3471 359 | −2488 117 | −783 −369 | −1265 −294 | −532 −249 | 605 |
| 585(P) | 1615 −149 −16 | −1136 −500 −7108 | −2222 233 −8150 | −2310 43 −894 | −3082 −381 −1115 | −1373 399 −701 | −2227 106 −1378 | −2731 −626 * | −2358 210 * | −3036 −466 | −2272 −720 | −1689 275 | 3445 394 | −2139 45 | −2424 96 | −761 359 | −938 117 | −1937 −369 | −3279 −294 | −3042 −249 | 606 |
| 586(A) | 2397 −149 −16 | −935 −500 −7108 | −2082 233 −8150 | −1846 43 −894 | −2575 −381 −1115 | −1236 399 −701 | −1722 106 −1378 | −2190 −626 * | −1737 210 * | −2475 −466 | −1666 −720 | −1377 275 | 1554 394 | −1552 45 | −1929 96 | −527 359 | 1772 117 | −1532 −369 | −2826 −294 | −2490 −249 | 607 |
| 587(D) | −2784 −149 −16 | −3432 −500 −7108 | 4016 233 −8150 | −1200 43 −894 | −4140 −381 −1115 | −2466 399 −701 | −2197 106 −1378 | −4505 −626 * | −2621 210 * | −4365 −466 | −3956 −720 | −1551 275 | −3014 394 | −2039 45 | −3232 96 | −2593 359 | −2938 117 | −4046 −369 | −3710 −294 | −3552 −249 | 608 |
| 588(A) | 3098 −149 −16 | −930 −500 −7108 | −2580 233 −8150 | −2583 43 −894 | −2894 −381 −1115 | −1243 399 −701 | −2249 106 −1378 | −2309 −626 * | −2448 210 * | −2781 −466 | −2022 −720 | −1697 275 | −1976 394 | −2194 45 | −2449 96 | −591 359 | 1113 117 | −1602 −369 | −3196 −294 | −2952 −249 | 609 |

TABLE 6-continued

| | | | | | | | | | | | | | | | | | | | | |
|---|---|---|---|---|---|---|---|---|---|---|---|---|---|---|---|---|---|---|---|---|
| 589(N) | −2171 −149 −16 | −2655 −500 −7108 | −1458 233 −8150 | −1748 −894 | −3334 −381 −1115 | −2364 399 −701 | −2267 106 −1378 | −3943 −626 * | −2365 210 | −3936 −466 | −3437 −720 | 4205 275 | −2932 394 | −2205 45 | −2608 96 | −2224 359 | −2439 117 | −3392 −369 | −3253 −294 | −2909 −249 | 610 |
| 590(M) | −387 −149 −16 | −854 −500 −7108 | −1643 233 −8150 | −1199 43 −894 | −1437 −381 −1115 | −1461 399 −701 | −1020 106 −1378 | −962 −626 * | −1012 210 | −1269 −466 | 2610 −720 | −1075 275 | −1857 394 | −895 45 | −1259 96 | 1806 359 | 1865 117 | −709 −369 | −1810 −294 | −1406 −249 | 611 |
| 591(H) | −30 −149 −16 | 439 −500 −7108 | 11 233 −8150 | 363 43 −894 | −394 −381 −1115 | −739 399 −701 | 699 106 −1378 | −414 −626 * | 463 210 | −757 −466 | 501 −720 | 286 275 | −577 394 | 639 45 | 165 96 | −23 359 | 111 117 | −312 −369 | 697 −294 | −25 −249 | 612 |
| 592(L) | −2625 −149 −16 | −2145 −500 −7108 | −4613 233 −8150 | −4174 −894 | 1968 −381 −1115 | −4304 399 −701 | −2386 106 −1378 | −72 −626 * | −3866 210 | 2741 −466 | 551 −720 | −3801 275 | −3814 394 | −2959 45 | −3500 96 | −3585 359 | −2511 117 | −745 −369 | −1483 −294 | −874 −249 | 613 |
| 593(L) | −2193 −149 −16 | −1789 −500 −7108 | −4457 233 −8150 | −3877 −894 | −523 −381 −1115 | −4057 399 −701 | −2894 106 −1378 | 279 −626 * | −3584 210 | 2588 −466 | 2231 −720 | −3689 275 | −3624 394 | −2841 45 | −3310 96 | −3261 359 | −2096 117 | 1093 −369 | −2048 −294 | −2035 −249 | 614 |
| 594(A) | 2970 −149 −16 | −925 −500 −7108 | −2555 233 −8150 | −2528 43 −894 | −2849 −381 −1115 | −1243 399 −701 | −2202 106 −1378 | −2276 −626 * | −2388 210 | −2737 −466 | −1975 −720 | −1675 275 | −1968 394 | −2140 45 | −2406 96 | −585 359 | 1607 117 | −1581 −369 | −3151 −294 | −2898 −249 | 615 |
| 595(V) | −1334 −149 −16 | −1034 −500 −7108 | −3629 233 −8150 | −3155 −894 | −1390 −381 −1115 | −3214 399 −701 | −2516 106 −1378 | 2107 −626 * | −2918 210 | −591 −466 | −331 −720 | −2852 275 | −3211 394 | −2701 45 | −2928 96 | −2407 359 | 1824 117 | 2364 −369 | −2380 −294 | −1985 −249 | 616 |
| 596(M) | 998 −149 −16 | −406 −500 −7108 | −1988 233 −8150 | −1399 43 −894 | 1077 −381 −1115 | −46 399 −701 | −692 106 −1378 | 73 −626 * | −1142 210 | 733 −466 | 1731 −720 | −1227 275 | −1918 394 | −903 45 | −1209 96 | 286 359 | −359 117 | 167 −369 | −855 −294 | −487 −249 | 617 |
| 597(H) | −1095 −149 −16 | −2732 −500 −7108 | 1291 233 −8150 | 2125 43 −894 | −2985 −381 −1115 | −1512 399 −701 | 3032 106 −1378 | −2799 −626 * | −427 210 | −2721 −466 | −1890 −720 | 1256 275 | −1861 394 | −159 45 | −1055 96 | −875 359 | −1088 117 | −2329 −369 | −2902 −294 | −2089 −249 | 618 |
| 598(H) | −971 −149 −16 | −1917 −500 −7108 | −1026 233 −8150 | −424 43 −894 | −2119 −381 −1115 | −1866 399 −701 | 2995 106 −1378 | −1811 −626 * | 2402 210 | −1852 −466 | −1093 −720 | −602 275 | −1947 394 | 34 45 | 266 96 | −932 359 | −871 117 | 294 −369 | −1999 −294 | −1507 −249 | 619 |
| 599(C) | 1836 −149 −16 | 3931 −500 −7108 | −2905 233 −8150 | −2499 −894 | −1252 −381 −1115 | −1823 399 −701 | −1705 106 −1378 | 1152 −626 * | −2189 210 | −888 −466 | −389 −720 | −1893 275 | −2246 394 | −1917 45 | −2150 96 | −1063 359 | −756 117 | 157 −369 | −1855 −294 | −1509 −249 | 620 |
| 600(F) | 528 −149 −16 | −777 −500 −7108 | −2899 233 −8150 | −2354 −894 | 2441 −381 −1115 | −2415 399 −701 | −823 106 −1378 | −127 −626 * | −2008 210 | 1363 −466 | 215 −720 | −1876 275 | −2433 394 | −1604 45 | −1876 96 | −1506 359 | −889 117 | −142 −369 | −490 −294 | 1736 −249 | 621 |
| 601(K) | −1239 −149 −16 | −2390 −500 −7108 | −1266 233 −8150 | −522 43 −894 | −2934 −381 −1115 | −2031 399 −701 | −324 106 −1378 | −2495 −626 * | 2422 210 | −2300 −466 | −1501 −720 | 979 275 | −2062 394 | 1504 45 | 1964 96 | −1116 359 | −1081 117 | −2146 −369 | −2296 −294 | −1915 −249 | 622 |
| 602(S) | 699 −149 −16 | −1151 −500 −7108 | −903 233 −8150 | −440 43 −894 | −1699 −381 −1115 | −1408 399 −701 | −579 106 −1378 | −1323 −626 * | −350 210 | −1526 −466 | 1574 −720 | 974 275 | −1694 394 | −269 45 | −750 96 | 2107 359 | −464 117 | −1002 −369 | −1909 −294 | −1408 −249 | 623 |
| 603(Q) | −873 −149 −16 | −2060 −500 −7108 | −736 233 −8150 | −198 43 −894 | −2478 −381 −1115 | −1732 399 −701 | −282 106 −1378 | −2118 −626 * | 1944 210 | −2060 −466 | −1235 −720 | −426 275 | −1836 394 | 1968 45 | 230 96 | −780 359 | 1853 117 | −1758 −369 | −2189 −294 | −1681 −249 | 624 |
| 604(N) | −1080 −149 −16 | −2639 −500 −7108 | 214 233 −8150 | 1668 43 −894 | −2924 −381 −1115 | −1545 399 −701 | −527 106 −1378 | −2711 −626 * | −282 210 | −2635 −466 | −1807 −720 | 2572 275 | −1867 394 | 2104 45 | −814 96 | −876 359 | −1062 117 | −2261 −369 | −2801 −294 | −2043 −249 | 625 |
| 605(K) | −457 −149 −16 | 1622 −500 −7108 | −593 233 −8150 | −29 43 −894 | −1532 −381 −1115 | −1520 399 −701 | −184 106 −1378 | −1170 −626 * | 1745 210 | −1320 −466 | −528 −720 | −275 275 | −1605 394 | 1259 45 | −206 96 | −467 359 | 609 117 | −916 −369 | −1665 −294 | 1434 −249 | 626 |

TABLE 6-continued

| | | | | | | | | | | | | | | | | | | | |
|---|---|---|---|---|---|---|---|---|---|---|---|---|---|---|---|---|---|---|---|
| 606(I) | −1995 | −1561 | −4353 | −3926 | −1045 | −4065 | −3261 | 3346 | −3652 | 924 | 94 | −3716 | −3783 | −3240 | −3554 | −3362 | −1957 | 705 | −2551 | −2295 | 627 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 607(N | −2171 | −2655 | −1458 | −1748 | −3334 | −2364 | −2267 | −3943 | −2365 | −3936 | −3437 | 4205 | −2932 | −2205 | −2608 | −2224 | −2439 | −3392 | −3253 | −2909 | 628 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 608(Y | 1025 | −487 | −2483 | −1892 | −336 | −2087 | −935 | 224 | −1576 | 1270 | 403 | −1587 | −2140 | −1281 | −1535 | −1165 | −537 | 999 | −908 | 2074 | 629 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 609(M | −797 | −587 | −3073 | −2468 | 1091 | −2423 | −1329 | 2169 | −2112 | −34 | 2364 | −2036 | −2429 | −1745 | −1959 | −1522 | 645 | 1209 | −1165 | −836 | 630 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 610(V | −1573 | −1179 | −4043 | −3576 | 867 | −3627 | −2822 | 2175 | −3353 | −312 | −198 | −3256 | −3486 | −3047 | −3296 | −2841 | −1540 | 2804 | −2430 | −2026 | 631 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 611(A | 2440 | −912 | −2339 | −2201 | −2840 | 1287 | −1997 | −2505 | −2116 | −2780 | −1935 | −1522 | −1901 | −1868 | −2234 | −517 | 1851 | −1699 | −3081 | −2799 | 632 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 612(S) | −437 | −1083 | −2006 | −2144 | −3262 | 1583 | −2197 | −3097 | −2380 | −3307 | −2434 | −1562 | −2008 | −2077 | −2485 | 2965 | −857 | −2074 | −3426 | −3160 | 633 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 613(K | −2620 | −2961 | −2461 | −2046 | −3743 | −2791 | −1570 | −3603 | 3784 | −3387 | −2839 | −2048 | −3039 | −1260 | −465 | −2604 | −2536 | −3331 | −3001 | −2988 | 634 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 614(H | −1501 | −2478 | −747 | −589 | −1969 | −2033 | 3845 | −2617 | −5 | −2483 | −1816 | −796 | −2272 | 2881 | −187 | −1387 | −1442 | −1699 | −2088 | −1345 | 635 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 615(P) | −2931 | −2878 | −3420 | −3706 | −4181 | −2925 | −3468 | −4621 | −3859 | −4490 | −4165 | −3491 | 4225 | −3781 | −3695 | −3182 | −3279 | −4087 | −3594 | −4064 | 636 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 616(R | 1242 | −1347 | −1254 | −731 | −2201 | −1510 | −719 | −1792 | −153 | −1944 | −1159 | −782 | −1844 | −375 | 2580 | −656 | 1294 | −1393 | −2232 | −1788 | 637 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 617(P) | 1448 | −1164 | −798 | −305 | −1387 | −1533 | −406 | −980 | −151 | 81 | −453 | −488 | 1572 | 1113 | −529 | −556 | −448 | −759 | −1638 | −1144 | 638 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 618(Q | −557 | −1175 | −1028 | −563 | −1488 | −1618 | −611 | −820 | −317 | −1222 | −557 | −696 | −1835 | 2724 | −638 | −698 | 1378 | 1031 | −1782 | −1308 | 639 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 619(W | −3603 | −2685 | −4198 | −4439 | 2092 | −4053 | −373 | −2561 | −4004 | −1981 | −2004 | −2736 | −3927 | −2842 | −3443 | −3284 | −3472 | −2688 | −3594 | −4064 | 640 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 620(F) | −1507 | −1226 | −3587 | −3073 | 2681 | −3022 | −1217 | 950 | −2707 | 1659 | 313 | −2490 | −2927 | −2137 | −2464 | −2143 | −1430 | −380 | −687 | 1671 | 641 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 621(S) | −344 | −978 | −2188 | −2158 | −2955 | −1227 | −2038 | −2646 | −2111 | −2929 | −2096 | −1524 | −1940 | −1904 | −2218 | 2919 | 1829 | −1801 | −3183 | −2878 | 642 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |
| 622(I) | −1092 | −874 | −3179 | −2611 | −721 | −2765 | −1721 | 1891 | −2310 | 1192 | 241 | −2311 | 1836 | −1986 | −2249 | −1880 | −1042 | 1298 | −1570 | −1257 | 643 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7108 | −8150 | −894 | −1115 | −701 | −1378 | * | | | | | | | | | | | | | |

TABLE 6-continued

| | | | | | | | | | | | | | | | | |
|---|---|---|---|---|---|---|---|---|---|---|---|---|---|---|---|---|
| 623(D) | -891 | -2456 | 2161 | 1856 | -2735 | -1474 | -410 | -2519 | -186 | -2456 | -1593 | -91 | -1753 | 1291 | -767 | -707 | 782 | -2062 | -2639 | -1876 | 644 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 624(E) | -2641 | -3308 | -896 | 3732 | -3966 | -2458 | -2043 | -4105 | -2128 | -4016 | -3555 | -1531 | -2959 | -1842 | -2560 | -2479 | -2750 | -3722 | -3563 | -3385 | 645 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 625(A) | 3438 | -1472 | -2846 | -3040 | -3287 | -1726 | -2735 | -2840 | -3028 | -3257 | -2662 | -2236 | -2447 | -2798 | -2944 | -1216 | -1387 | -2183 | -3405 | -3320 | 646 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 626(K) | -719 | -2060 | -577 | 1623 | -2444 | -1622 | -164 | -2125 | 1699 | -2035 | -1164 | -266 | -1703 | 282 | 1624 | -601 | 634 | -1722 | -2150 | -1583 | 647 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 627(Q) | 1243 | -1432 | -728 | -405 | -2358 | -1377 | -690 | -2055 | -351 | -2150 | -1310 | -555 | -1744 | 2880 | -751 | 1081 | -618 | -1561 | -2401 | -1849 | 648 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 628(H) | -780 | -1536 | -555 | 1361 | -1393 | -1709 | 2249 | -1189 | -144 | 1529 | -640 | -494 | -1865 | -169 | -489 | -816 | -724 | -1022 | -1690 | -1099 | 649 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 629(C) | 456 | 2634 | -3043 | -2479 | -719 | -2386 | -1463 | 624 | -2148 | 1022 | 146 | -2055 | -2467 | -1831 | -2047 | -1515 | -777 | 2135 | -1370 | -1020 | 650 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 630(D) | 59 | -1947 | 1795 | 1154 | -2254 | -1392 | -111 | -1999 | 273 | -1959 | -1053 | -30 | -1526 | 335 | 1177 | -370 | 709 | -1564 | -2142 | -1456 | 651 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 631(Q) | 1161 | -1938 | -287 | 164 | -2274 | -1471 | -154 | -1990 | 1104 | -1956 | -1072 | 1604 | -1598 | 1906 | -101 | -461 | -513 | -1579 | -2132 | -1496 | 652 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 632(G) | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 653 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 633(L) | 2002 | -1175 | -2785 | -2475 | -1055 | -2185 | -1898 | -221 | -2172 | 2054 | -104 | -2097 | -2542 | -1964 | -2186 | -1458 | -1162 | -325 | -1982 | -1669 | 654 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 634(K) | 943 | -1709 | -403 | 133 | -2096 | 781 | -142 | -1801 | 994 | -1811 | -930 | -144 | -1543 | 292 | 938 | 844 | -405 | -1399 | -2023 | -1402 | 655 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 635(I) | 525 | -452 | -2111 | 23 | -445 | -1963 | -805 | 1776 | -1266 | -283 | 345 | -1346 | -2019 | -1026 | -1323 | -1017 | -436 | 1518 | -942 | 1179 | 656 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 636(W) | -1626 | -1321 | -3570 | -3141 | -381 | -3057 | -937 | 2580 | -2760 | -226 | -54 | -2426 | -2999 | -2185 | -2514 | -2189 | -1555 | -448 | 3586 | 581 | 657 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 637(D) | -1498 | -3029 | 3115 | 17 | -3354 | -1691 | -852 | -3199 | 1912 | -3109 | -2371 | -341 | -2120 | -495 | -1230 | -1252 | -1519 | -2742 | -3208 | -2450 | 658 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 638(W) | -3358 | -2599 | -4116 | -4259 | 2442 | -3892 | -536 | -2247 | -3821 | -1683 | -1712 | -2792 | -3835 | -2843 | -3352 | -3227 | -3271 | -2441 | 5485 | 1363 | 659 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 639(C) | 3004 | 3179 | -3175 | -3184 | -2750 | -1300 | -2459 | -2082 | -2872 | -2641 | -1933 | -1922 | -2041 | -2538 | -2722 | -657 | -796 | -1473 | -3106 | -2895 | 660 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |

TABLE 6-continued

| | | | | | | | | | | | | | | | | | | | | |
|---|---|---|---|---|---|---|---|---|---|---|---|---|---|---|---|---|---|---|---|---|
| 640(S) | -897 -149 -16 | -1462 -500 -7108 | -2333 233 -8150 | -2543 43 -894 | -3185 -381 -1115 | -1640 399 -701 | -2474 106 -1378 | -3294 -626 * | -2686 210 * | -3497 -466 | -2780 -720 | -1973 275 | -2360 394 | -2483 45 | -2703 96 | 3465 359 | -1316 117 | -2413 -369 | -3310 -294 | -3025 -249 | 661 |
| 641(T) | -638 -149 -16 | -1323 -500 -7108 | -1200 233 -8150 | -1263 43 -894 | -2717 -381 -1115 | -1420 399 -701 | -1550 106 -1378 | -2421 -626 * | -1436 210 * | -2697 -466 | -1948 -720 | 1009 275 | -2035 394 | -1340 45 | -1682 96 | -796 359 | 3384 117 | -1817 -369 | -2917 -294 | -2452 -249 | 662 |
| 642(H) | -30 -149 -16 | 439 -500 -7108 | 11 233 -8150 | 363 43 -894 | -394 -381 -1115 | -739 399 -701 | 699 106 -1378 | -414 -626 * | 463 210 * | -757 -466 | 501 -720 | 286 275 | -577 394 | 639 45 | 165 96 | -23 359 | 111 117 | -312 -369 | 697 -294 | -25 -249 | 663 |
| 643(D) | 1256 -149 -16 | -1810 -500 -7108 | 2828 233 -8150 | -193 43 -894 | -2711 -381 -1115 | -1421 399 -701 | -825 106 -1378 | -2377 -626 * | -710 210 * | -2507 -466 | -1697 -720 | -438 275 | -1858 394 | -471 45 | -1243 96 | -735 359 | 787 117 | -1875 -369 | -2779 -294 | -2131 -249 | 664 |
| 644(K) | -1038 -149 -16 | -2259 -500 -7108 | -689 233 -8150 | -253 43 -894 | -2738 -381 -1115 | 777 398 -701 | -360 106 -1378 | -2382 -626 * | 2468 210 * | -2269 -466 | -1451 -721 | -481 276 | -1931 395 | 2027 45 | 226 96 | -921 360 | -949 118 | -2002 -369 | -2343 -294 | -1850 -249 | 665 |
| 645(G) | -535 -149 -16 -1044 -149 -16 | -1708 -500 -7108 -1813 -500 -7108 | -1708 233 -8150 -773 233 -8150 | -140 43 -894 -1023 43 -894 | -3430 -381 -1115 -3345 -381 -1115 | 2987 399 -701 | -1699 106 -1378 | -3331 -626 * | -1775 210 * | -3418 -466 | -2659 -720 | 2131 275 | -2239 394 | -1475 45 | -2156 96 | -1127 359 | -1361 117 | -2539 -369 | -3373 -294 | -2907 -249 | 667 |
| 646(E) | -488 -149 -16 | -1836 -500 -7108 | 1360 233 -8150 | 1439 43 -894 | -2104 -381 -1115 | -1403 399 -701 | -131 106 -1378 | -1820 -626 * | 229 210 * | 87 -466 | -955 -720 | -60 275 | -1537 394 | 301 45 | -280 96 | 469 359 | 631 117 | -1431 -369 | -2061 -294 | -1399 -249 | 668 |
| 647(E) | -1127 -149 -16 | -2366 -500 -7108 | -800 233 -8150 | 2480 43 -894 | -2838 -381 -1115 | -1878 399 -701 | -336 106 -1378 | -2455 -626 * | 1396 210 * | -2301 -466 | -1488 -720 | -522 275 | -1975 394 | 95 45 | 1670 96 | -993 359 | -1007 117 | -2085 -369 | -2343 -294 | -1881 -249 | 669 |
| 648(P) | 955 -149 -16 | -915 -500 -7108 | -2251 233 -8150 | -2048 43 -894 | -2204 -381 -1115 | -1361 399 -701 | -1790 106 -1378 | -1375 -626 * | -1894 210 * | -1974 -466 | -1329 -720 | -1523 275 | 3265 394 | -1711 45 | -2016 96 | -660 359 | -714 117 | 631 -369 | -2606 -294 | -2267 -249 | 670 |
| 649(D) | -1535 -149 -16 | -3339 -500 -7108 | 3248 233 -8150 | 856 43 -894 | -3535 -381 -1115 | -1586 399 -701 | -853 106 -1378 | -3417 -626 * | -967 210 * | -3307 -466 | -2587 -720 | -180 275 | -2074 394 | 1731 45 | -1720 96 | -1229 359 | -1578 117 | -2919 -369 | -3496 -294 | -2555 -249 | 671 |
| 650(V) | -1754 -149 -16 | -1297 -500 -7108 | -4329 233 -8150 | -3968 43 -894 | -1770 -381 -1115 | -4053 399 -701 | -3752 106 -1378 | 2602 -626 * | -3840 210 * | -621 -466 | -545 -720 | -3728 275 | -3878 394 | -3699 45 | -3917 96 | -3370 359 | -1746 117 | 2861 -369 | -3276 -294 | -2829 -249 | 672 |
| 651(V) | -1736 -149 -16 | -1298 -500 -7108 | -4275 233 -8150 | -3915 43 -894 | -1733 -381 -1115 | -3969 399 -701 | -3654 106 -1378 | 1867 -626 * | -3766 210 * | -598 -466 | -525 -720 | -3663 275 | -3828 394 | -3619 45 | -3833 96 | -3283 359 | -1733 117 | 3222 -369 | -3208 -294 | -2763 -249 | 673 |
| 652(M) | -2158 -149 -16 | -1763 -500 -7108 | -4466 233 -8150 | -3857 43 -894 | 2098 -381 -1115 | -3961 399 -701 | -2711 106 -1378 | 1339 -626 * | -3551 210 * | 2194 -466 | 2215 -720 | -3609 275 | -3535 394 | -2747 45 | -3220 96 | -3143 359 | -2048 117 | -438 -369 | -1879 -294 | -1836 -249 | 674 |
| 653(A) | 2500 -149 -16 | -821 -500 -7108 | -2504 233 -8150 | -2171 43 -894 | -1756 -381 -1115 | -1515 399 -701 | -1719 106 -1378 | -589 -626 * | -1953 210 * | -1465 -466 | -872 -720 | -1633 275 | -2062 394 | -1734 45 | -2039 96 | -780 359 | 1073 117 | 1394 -369 | -2251 -294 | -1909 -249 | 675 |
| 654(A) | 2412 -149 -16 | -931 -500 -7108 | -2308 233 -8150 | -2228 43 -894 | -3059 -381 -1115 | 1309 399 -701 | -2079 106 -1378 | -2797 -626 * | -2207 210 * | -3025 -466 | -2139 -720 | -1529 275 | -1901 394 | -1934 45 | -2326 96 | -1229 359 | -691 117 | -1849 -369 | -3263 -294 | -2994 -249 | 676 |
| 655(A) | 2464 -149 -16 | -791 -500 -7108 | -2155 233 -8150 | -1787 43 -894 | -1514 -381 -1115 | -1500 399 -701 | -1408 106 -1378 | 1386 -626 * | -1595 210 * | -1309 -466 | -672 -720 | -1424 275 | -1982 394 | -1405 45 | -1732 96 | 688 359 | -624 117 | -473 -369 | -1963 -294 | -1596 -249 | 677 |
| 656(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -3953 210 * | -4671 -466 | -4212 -720 | -3320 275 | -3352 394 | -3748 45 | -3779 96 | -2839 359 | -2981 117 | -4004 -369 | -3668 -294 | -4222 -249 | 678 |

TABLE 6-continued

| | | | | | | | | | | | | | | | | | | |
|---|---|---|---|---|---|---|---|---|---|---|---|---|---|---|---|---|---|---|
| 657(T) | -457 -149 -16 | -1344 -500 -7108 | 1397 233 -8150 | -166 43 -894 | -1749 -381 -1115 | -1438 399 -701 | -424 106 -1378 | -1324 -626 * | -173 210 * | -1546 -466 | -757 -720 | -384 275 | -1663 394 | -77 45 | -623 96 | 628 359 | 1799 117 | 847 -369 | -1920 -294 | -1372 -249 | 679 |
| 658(E) | -1108 -149 -16 | -1855 -500 -7108 | -497 233 -8150 | 2835 43 -894 | -2161 -381 -1115 | -1834 399 -701 | -982 106 -1378 | -964 -626 * | -783 210 * | -1744 -466 | -1237 -720 | -739 275 | -2163 394 | -677 45 | -1197 96 | -1164 359 | -1148 117 | 1427 -369 | -2502 -294 | -1927 -249 | 680 |
| 659(P) | -853 -149 -16 | -1252 -500 -7108 | -2460 233 -8150 | -2393 43 -894 | -2139 -381 -1115 | -1784 399 -701 | -2109 106 -1378 | -974 -626 * | -2210 210 * | -1748 -466 | -1364 -720 | -1924 275 | 3453 394 | -2108 45 | -2271 96 | -1167 359 | -1152 117 | 1448 -369 | -2678 -294 | -2307 -249 | 681 |
| 660(T) | -495 -149 -16 | -998 -500 -7108 | -1197 233 -8150 | -789 43 -894 | -1334 -381 -1115 | -1567 399 -701 | -751 106 -1378 | -851 -626 * | -618 210 * | -1153 -466 | 2261 -720 | 892 275 | -1849 394 | -564 45 | -910 96 | -695 359 | 2581 117 | -648 -369 | -1684 -294 | -1235 -249 | 682 |
| 661(Q) | -425 -149 -16 | -1001 -500 -7108 | -831 233 -8150 | 629 43 -894 | 1174 -381 -1115 | -1595 399 -701 | -316 106 -1378 | -637 -626 * | -152 210 * | 579 -466 | -150 -720 | -476 275 | -1677 394 | 1648 45 | -532 96 | -563 359 | 735 117 | -470 -369 | -1354 -294 | -875 -249 | 683 |
| 662(E) | -2641 -149 -16 | -3308 -500 -7108 | -896 233 -8150 | 3732 43 -894 | -3966 -381 -1115 | -2458 399 -701 | -2043 106 -1378 | -4105 -626 * | -2128 210 * | -4016 -466 | -3555 -720 | -1531 275 | -2959 394 | -1842 45 | -2560 96 | -2479 359 | -2750 117 | -3722 -369 | -3563 -294 | -3385 -249 | 684 |
| 663(I) | 525 -149 -16 | -535 -500 -7108 | -2111 233 -8150 | -1551 43 -894 | -638 -381 -1115 | -1888 399 -701 | -920 106 -1378 | 1560 -626 * | -1309 210 * | -455 -466 | 170 -720 | -1362 275 | -2031 394 | -1084 45 | -1399 96 | 1061 359 | 708 117 | 1332 -369 | -1134 -294 | -763 -249 | 685 |
| 664(M) | -2362 -149 -16 | -1913 -500 -7108 | -4673 233 -8150 | -4086 43 -894 | -501 -381 -1115 | -4285 399 -701 | -3077 106 -1378 | 1692 -626 * | -3808 210 * | 2336 -466 | 2939 -720 | -3933 275 | -3746 394 | -2955 45 | -3477 96 | -3510 359 | -2250 117 | -300 -369 | -2098 -294 | -2139 -249 | 686 |
| 665(A | 2734 -149 -16 | -1554 -500 -7108 | -1235 233 -8150 | -966 43 -894 | -2607 -381 -1115 | -1620 399 -701 | -1015 106 -1378 | -2163 -626 * | 1487 210 * | -2343 -466 | -1601 -720 | -988 275 | -2045 394 | -691 45 | -583 96 | -903 359 | -969 117 | -1725 -369 | -2578 -294 | -2168 -249 | 687 |
| 666(A | 3438 -149 -16 | -1472 -500 -7108 | -2846 233 -8150 | -3040 43 -894 | -3287 -381 -1115 | -1726 399 -701 | -2735 106 -1378 | -2840 -626 * | -3028 210 * | -3257 -466 | -2662 -720 | -2236 275 | -2447 394 | -2798 45 | -2944 96 | -1216 359 | -1387 117 | -2183 -369 | -3405 -294 | -3320 -249 | 688 |
| 667(I) | 1114 -149 -16 | -756 -500 -7108 | -2253 233 -8150 | -1864 43 -894 | -1305 -381 -1115 | -1646 399 -701 | -1394 106 -1378 | 2517 -626 * | -1656 210 * | -1054 -466 | -461 -720 | -1512 275 | -2066 394 | -1454 45 | -1761 96 | 1262 359 | -650 117 | -138 -369 | -1806 -294 | -1439 -249 | 689 |
| 668(D | 900 -149 -16 | -2457 -500 -7108 | 2570 233 -8150 | 175 43 -894 | -2815 -381 -1115 | -1502 399 -701 | -553 106 -1378 | -2590 -626 * | -386 210 * | -2564 -466 | -1737 -720 | -168 275 | -1841 394 | 2095 45 | -969 96 | -821 359 | -1001 117 | -2141 -369 | -2768 -294 | -2010 -249 | 690 |
| 669(I) | 292 -149 -16 | -707 -500 -7108 | -2167 233 -8150 | -1590 43 -894 | -719 -381 -1115 | -2180 399 -701 | -1027 106 -1378 | 2540 -626 * | 537 210 * | 441 -466 | 146 -720 | -1486 275 | -2230 394 | -1118 45 | -1321 96 | -1247 359 | -668 117 | 405 -369 | -1287 -294 | -917 -249 | 691 |
| 670(L) | -2871 -149 -16 | -2457 -500 -7108 | -4231 233 -8150 | -4103 43 -894 | -1033 -381 -1115 | -3803 399 -701 | -3165 106 -1378 | -541 -626 * | -3734 210 * | 3130 -466 | -31 -720 | -3935 275 | -3797 394 | -3286 45 | -3484 96 | -3713 359 | -2869 117 | -1136 -369 | -3405 -294 | -3320 -249 | 692 |
| 671(H | -1177 -149 -16 | -2326 -500 -7108 | -1134 233 -8150 | -457 43 -894 | -2809 -381 -1115 | -1977 399 -701 | 3593 106 -1378 | -2401 -626 * | 1445 210 * | -2244 -466 | -1443 -720 | 844 275 | -2024 394 | 111 45 | 1735 96 | -1061 359 | -1033 117 | -2058 -369 | -2268 -294 | -1857 -249 | 693 |
| 672(E) | 15 -149 -16 | -2170 -500 -7108 | 1563 233 -8150 | 1959 43 -894 | -2472 -381 -1115 | -1425 399 -701 | -226 106 -1378 | -2237 -626 * | 855 210 * | -2177 -466 | -1280 -720 | -49 275 | -1617 394 | 1268 45 | -431 96 | -502 359 | -609 117 | -1785 -369 | -2349 -294 | -1631 -249 | 694 |
| 673(H | -403 -149 -16 | -1628 -500 -7108 | -358 233 -8150 | 195 43 -894 | -1861 -381 -1115 | -1414 399 -701 | 1618 106 -1378 | -1548 -626 * | 320 210 * | -279 -466 | 1074 -720 | 912 275 | -1503 394 | 1197 45 | 1139 96 | 446 359 | -340 117 | -1203 -369 | -1863 -294 | -1247 -249 | 695 |

TABLE 6-continued

| | | | | | | | | | | | | | | | | | | | | | |
|---|---|---|---|---|---|---|---|---|---|---|---|---|---|---|---|---|---|---|---|---|---|
| 674(C) | -513 | 2550 | -2600 | -2019 | 2246 | 845 | -943 | 1137 | -1680 | -244 | 350 | -1605 | -2090 | -1357 | -1587 | -1083 | -488 | 249 | -881 | -474 | 696 |
| | -149 | -500 | 233 | -894 | -381 | 399 | 106 | -626 | 210 | -466 | -720 | 275 | 394 | 45 | 96 | 359 | 117 | -369 | -294 | -249 | |
| — | -340 | -7108 | -2304 | | -1115 | | -1378 | * | * | | | | | | | | | | | | |
| 675(P) | -2312 | -2374 | -2796 | -3036 | -3591 | -2432 | -2883 | -3881 | -3157 | -3835 | -3473 | -2848 | 4156 | -3101 | -3072 | -2546 | -2648 | -3391 | -3143 | -3459 | 697 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -20 | -6788 | -7830 | -894 | -1115 | -1306 | -747 | * | * | | | | | | | | | | | | |
| 676(E) | -985 | -2607 | 1546 | 2542 | -2883 | -1323 | -441 | -2699 | -378 | -2634 | -1828 | 58 | -1713 | -60 | -1032 | 869 | -997 | -2229 | -2828 | -1997 | 698 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -20 | -6788 | -7830 | -894 | -1115 | -1306 | -747 | * | * | | | | | | | | | | | | |
| 677(L) | -2103 | -1693 | -4449 | -3873 | -568 | -4003 | -2874 | 1606 | -3596 | 2406 | 2166 | -3648 | -3596 | -2862 | -3318 | -3203 | -2010 | 674 | -2059 | -2029 | 699 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -421 | -1984 | * | * | | | | | | | | | | | | |
| 678(K) | -2059 | -2767 | -2575 | -1375 | -3583 | -2596 | -558 | -2947 | 3236 | -2620 | -1947 | -1295 | -2560 | -141 | 2026 | -1942 | -1766 | -2709 | -2469 | -2350 | 700 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 679(I) | -1544 | -1176 | -3965 | -3470 | 1894 | -3502 | -2556 | 2750 | -3215 | -120 | -27 | -3124 | -3366 | -2846 | -3113 | -2694 | -1504 | 1816 | -2142 | -1735 | 701 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 680(R) | -2118 | -2789 | -2710 | -1441 | -3626 | -2635 | -569 | -2972 | 2088 | -2636 | -1971 | -1337 | -2591 | -153 | 3343 | -2003 | -1811 | -2743 | -2476 | -2375 | 702 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 681(Y) | -1738 | -1421 | -3486 | -3138 | 2368 | -3054 | -658 | -643 | -2769 | -827 | -509 | -2313 | -3036 | -2175 | -2527 | -2188 | -1672 | 2239 | -69 | 2812 | 703 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 682(V) | -1754 | -1297 | -4329 | -3968 | -1770 | -4053 | -3752 | 2614 | -3840 | -621 | -545 | -3729 | -3878 | -3699 | -3917 | -3370 | -1746 | 2852 | -3276 | -2830 | 704 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 683(N) | -2171 | -2655 | -1458 | -1748 | -3334 | -2364 | -2267 | -3943 | -2365 | -3936 | -3437 | 4205 | -2932 | -2205 | -2608 | -2224 | -2439 | -3392 | -3253 | -2909 | 705 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 684(V) | -1733 | -1299 | -4267 | -3907 | -1727 | -3955 | -3640 | 1809 | -3755 | -594 | -523 | -3653 | -3820 | -3608 | -3821 | -3270 | -1732 | 3240 | -3198 | -2753 | 706 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 685(V) | 484 | -646 | -2970 | -2395 | -744 | -2499 | -1461 | 1423 | -2091 | 572 | 130 | -2055 | -2521 | -1798 | -2031 | -1603 | 1127 | 2072 | -1395 | -1034 | 707 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 686(D) | -1820 | -3681 | 3540 | 1270 | -3878 | -1659 | -1068 | -3841 | -1383 | -3714 | -3101 | -268 | -2218 | -754 | -2274 | -1465 | -1906 | -3315 | -3861 | -2859 | 708 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 687(L) | -2374 | -1911 | -4667 | -4149 | -624 | -4356 | -3248 | 1959 | -3860 | 2621 | 550 | -4014 | -3844 | -3100 | -3584 | -3637 | -2284 | -16 | -2252 | -2226 | 709 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 688(F) | -2145 | -1754 | -4444 | -3835 | 2481 | -3940 | -2678 | 1114 | -3528 | 2066 | 2253 | -3582 | -3521 | -2731 | -3201 | -3119 | -2036 | 444 | -1859 | -1796 | 710 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 689(K) | -770 | -1778 | -879 | -243 | -2063 | -1733 | -251 | 850 | 2294 | -1721 | -926 | -452 | -1801 | 148 | 1146 | 500 | -677 | -1382 | -1948 | -1464 | 711 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |
| 690(L) | -2871 | -2457 | -4231 | -4103 | -1033 | -3803 | -3165 | -541 | -3734 | 3130 | -31 | -3935 | -3797 | -3286 | -3484 | -3713 | -2869 | -1136 | -2394 | -2220 | 712 |
| | -149 | -500 | 233 | 43 | -381 | 399 | 106 | -626 | 210 | -466 | -720 | 275 | 394 | 45 | 96 | 359 | 117 | -369 | -294 | -249 | |
| — | -16 | -7108 | -8150 | -894 | -1115 | -701 | -1378 | * | * | | | | | | | | | | | | |

TABLE 6-continued

| | | | | | | | | | | | | | | | | | | |
|---|---|---|---|---|---|---|---|---|---|---|---|---|---|---|---|---|---|---|
| 691(Q) | −506 | −1867 | −390 | 1178 | −2181 | −1467 | 1538 | −1890 | 436 | −1856 | 1294 | −116 | −1554 | 1790 | 1511 | −401 | −435 | −1488 | −2030 | −1407 | 713 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 692( ) | −30 | 439 | 11 | 363 | −394 | −739 | 699 | −414 | 463 | −757 | 501 | 286 | −577 | 639 | 165 | −23 | 111 | −312 | 697 | −25 | 714 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 693(N) | 911 | −1243 | −1049 | −908 | −2750 | −1283 | −1224 | −2483 | −1070 | −2619 | −1762 | 2307 | −1836 | −911 | −1451 | 2263 | −707 | −1785 | −2854 | −2361 | 715 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 694(E) | 462 | −1884 | 883 | 1229 | −2200 | −1380 | −99 | −1941 | 284 | −1912 | −1007 | −31 | 1086 | 347 | −229 | 391 | 628 | −1510 | −2102 | −1423 | 716 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 695(K) | 472 | −1945 | 816 | 942 | −2258 | 507 | −83 | −2010 | 1429 | −1957 | −1042 | −12 | −1504 | 1244 | −204 | −340 | −412 | −1564 | −2129 | −1439 | 717 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 696(K) | 725 | −1680 | −306 | 1306 | 355 | −1399 | −79 | −1633 | 1414 | −1671 | −800 | −73 | −1499 | 350 | −177 | 548 | −349 | −1268 | −1917 | −1284 | 718 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 697(H) | −195 | −3069 | −3069 | 320 | −2881 | −1429 | 2588 | −2787 | −470 | −2720 | −1925 | 2549 | −1819 | −164 | −1109 | −872 | −1112 | −2328 | −2864 | −2024 | 719 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 698(P) | −1103 | −2714 | 2043 | −258 | −3351 | −1688 | −1206 | −3299 | −1351 | −3294 | −2623 | −586 | 3242 | −916 | −1988 | −1364 | −1649 | −2782 | −3270 | −2663 | 720 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −18 | −6931 | −7973 | −894 | −1115 | −505 | −922 | * | | | | | | | | | | | | | |
| 699(H) | −601 | −1891 | −436 | 1733 | −2050 | −1535 | 2121 | −1882 | 387 | −1862 | −1003 | −192 | −1631 | 281 | 1501 | −502 | −527 | −1509 | −1978 | 1072 | 721 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −18 | −6931 | −7973 | −894 | −1115 | −701 | −1760 | * | | | | | | | | | | | | | |
| 700(G) | 2344 | −1041 | −2392 | −2527 | −3249 | 2572 | −2371 | −2970 | −2636 | −3255 | −2405 | −1721 | −2031 | −2309 | −2645 | −661 | −858 | −2002 | −3433 | −3246 | 722 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 701(L) | −2642 | −2168 | −4788 | −4235 | −465 | 4513 | −3241 | 96 | −3878 | 2891 | 2122 | −4166 | −3888 | −3023 | −3544 | −3807 | −2521 | −607 | −2140 | −2183 | 723 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 702(S) | −532 | −1511 | −753 | −320 | −2262 | −1447 | −524 | −1930 | 1366 | −2008 | −1173 | −494 | −1732 | −137 | −413 | 1983 | 1524 | −1495 | −2248 | −1710 | 724 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 703(D) | −1718 | −3250 | 3403 | −27 | −3066 | −1736 | 2667 | −3486 | −1211 | −3381 | −2732 | −400 | −2240 | −752 | −1917 | −1439 | −1784 | −3023 | −3204 | −2299 | 725 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 704(E) | 1165 | −2746 | 1435 | 2588 | −3046 | −1525 | −639 | −2845 | −567 | −2796 | −1988 | −154 | −1909 | −258 | −1213 | −943 | −1174 | −2380 | −2996 | −2179 | 726 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 705(E) | 921 | −2774 | 1237 | 2767 | −3077 | −1530 | −662 | −2877 | −603 | −2830 | −2029 | −161 | −1924 | −284 | −1256 | −967 | −1205 | −2412 | −3032 | −2209 | 727 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 706(F) | −3342 | −2776 | −4026 | −4232 | 4354 | −3545 | −1431 | −2315 | −4038 | −1801 | −1900 | −3299 | −3780 | −3350 | −3645 | −3490 | −3420 | −2566 | −739 | 349 | 728 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |
| 707(D) | 1198 | −2653 | 2928 | 116 | −3164 | −1523 | −794 | −2975 | −806 | −2952 | −2173 | 1307 | −1973 | −435 | −1474 | −1014 | −1273 | −2473 | −3161 | −2340 | 729 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7108 | −8150 | −894 | −1115 | −701 | −1378 | * | | | | | | | | | | | | | |

TABLE 6-continued

| | | | | | | | | | | | | | | | | | | |
|---|---|---|---|---|---|---|---|---|---|---|---|---|---|---|---|---|---|---|
| 708(N) | 497 -149 -16 | -2045 -500 -7108 | 1492 233 -8150 | 265 43 -894 | -2357 -381 -1115 | -1412 399 -701 | 1608 106 -1378 | -2108 -626 * | 128 210 | -2074 -466 | -1183 -720 | 1928 275 | -1592 394 | 229 45 | -403 96 | 517 359 | -553 117 | -1673 -369 | -2265 -294 | -1565 -249 | 730 |
| 709(Y) | -1550 -149 -16 | -1282 -500 -7108 | -3519 233 -8150 | -3004 43 -894 | -2 -381 -1115 | -3093 399 -701 | -1385 106 -1378 | 1232 -626 * | -2635 210 | 1579 -466 | 299 -720 | -2537 275 | -2990 394 | -2153 45 | -2464 96 | -2220 359 | -1477 117 | -195 -369 | -891 -294 | 3290 -249 | 731 |
| 710(F) | -3342 -149 -16 | -2776 -500 -7108 | -4026 233 -8150 | -4232 43 -894 | 4354 -381 -1115 | -3545 399 -701 | -1431 106 -1378 | -2315 -626 * | -4038 210 | -1801 -466 | -1900 -720 | -3299 275 | -3780 394 | -3350 45 | -3645 96 | -3490 359 | -3420 117 | -2566 -369 | -739 -294 | 349 -249 | 732 |
| 711(T) | -1213 -149 -16 | -1674 -500 -7108 | -2755 233 -8150 | -2906 43 -894 | -3163 -381 -1115 | -1922 399 -701 | -2659 106 -1378 | -2698 -626 * | -2788 210 | -3105 -466 | -2612 -720 | -2311 275 | -2600 394 | -2708 45 | -2753 96 | -1463 359 | 3819 117 | -2197 -369 | -3286 -294 | -3156 -249 | 733 |
| 712(K) | 921 -149 -16 | -1810 -500 -7108 | -280 233 -8150 | 1204 43 -894 | -2126 -381 -1115 | -1422 399 -701 | -125 106 -1378 | -1835 -626 * | 1451 210 | -1838 -466 | -956 -720 | -97 275 | -1544 394 | 311 45 | -168 96 | -386 359 | 1295 117 | -1438 -369 | -2048 -294 | -1407 -249 | 734 |
| 713(D) | -2784 -149 -16 | -3432 -500 -7108 | 4016 233 -8150 | -1200 43 -894 | -4140 -381 -1115 | -2466 399 -701 | -2197 106 -1378 | -4505 -626 * | -2621 210 | -4365 -466 | -3956 -720 | -1551 275 | -3014 394 | -2039 45 | -3232 96 | -2593 359 | -2938 117 | -4046 -369 | -3710 -294 | -3552 -249 | 735 |
| 714(K) | -1441 -149 -16 | -2413 -500 -7108 | -1657 233 -8150 | -802 43 -894 | -3025 -381 -1115 | -2193 399 -701 | -410 106 -1378 | -2523 -626 * | 2846 210 | -2335 -466 | -1581 -720 | -885 275 | -2213 394 | 14 45 | 1863 96 | -1343 359 | 790 117 | -2218 -369 | -2320 -294 | -2022 -249 | 736 |
| 715(P) | -540 -149 -16 | -1180 -500 -7108 | -1850 233 -8150 | -1974 43 -894 | -3103 -381 -1115 | -1352 399 -701 | -2072 106 -1378 | -2962 -626 * | -2149 210 | -3170 -466 | -2355 -720 | -1527 275 | 3509 394 | -1943 45 | -2279 96 | 1382 359 | -938 117 | -2068 -369 | -3276 -294 | -2949 -249 | 737 |
| 716(V) | -1751 -149 -16 | -1297 -500 -7108 | -4323 233 -8150 | -3962 43 -894 | -1768 -381 -1115 | -4044 399 -701 | -3741 106 -1378 | 2446 -626 * | -3832 210 | -620 -466 | -545 -720 | -3721 275 | -3872 394 | -3691 45 | -3908 96 | -3361 359 | -1744 117 | 2965 -369 | -3270 -294 | -2823 -249 | 738 |
| 717(H) | -792 -149 -16 | -632 -500 -7108 | -2808 233 -8150 | -2210 43 -894 | -439 -381 -1115 | -2360 399 -701 | 2159 106 -1378 | 1209 -626 * | -1870 210 | 1529 -466 | 409 -720 | -1883 275 | -2368 394 | -1554 45 | -1794 96 | -1446 359 | -733 117 | 1579 -369 | -1121 -294 | -776 -249 | 739 |
| 718(F) | -3342 -149 -16 | -2776 -500 -7108 | -4026 233 -8150 | -4232 43 -894 | 4354 -381 -1115 | -3545 399 -701 | -1431 106 -1378 | -2315 -626 * | -4038 210 | -1801 -466 | -1900 -720 | -3299 275 | -3780 394 | -3350 45 | -3645 96 | -3490 359 | -3420 117 | -2566 -369 | -739 -294 | 349 -249 | 740 |
| 719(A) | 2895 -149 -16 | -1250 -500 -7108 | -1253 233 -8150 | -1325 43 -894 | -2863 -381 -1115 | -1348 399 -701 | -1637 106 -1378 | -2577 -626 * | -1616 210 | -2833 -466 | -2042 -720 | 1775 275 | -1991 394 | -1424 45 | -1888 96 | -716 359 | -888 117 | -1873 -369 | -3053 -294 | -2611 -249 | 741 |
| 720(Y) | -3687 -149 -16 | -2724 -500 -7108 | -4232 233 -8150 | -4508 43 -894 | 3154 -381 -1115 | -4089 399 -701 | -368 106 -1378 | -2628 -626 * | -4071 210 | -2023 -466 | -2062 -720 | -2751 275 | -3956 394 | -2869 45 | -3483 96 | -3324 359 | -3551 117 | -2761 -369 | 3099 -294 | 3684 -249 | 742 |
| 721(H) | -3205 -149 -16 | -3079 -500 -7108 | -2723 233 -8150 | -2890 43 -894 | -2110 -381 -1115 | -3046 399 -701 | 5295 106 -1378 | -4135 -626 * | -2617 210 | -3813 -466 | -3561 -720 | -2886 275 | -3482 394 | -2833 45 | -2620 96 | -3291 359 | -3356 117 | -3895 -369 | -2397 -294 | -1681 -249 | 743 |
| 722(G) | -459 -149 -16 | -1100 -500 -7108 | -1991 233 -8150 | -2176 43 -894 | -3299 -381 -1115 | 3009 399 -701 | -2249 106 -1378 | -3146 -626 * | -2470 210 | -3360 -466 | -2491 -720 | -1586 275 | -2028 394 | -2146 45 | -3645 96 | 1630 359 | -885 117 | -2108 -369 | -3464 -294 | -3207 -249 | 744 |
| 723(Y) | -3590 -149 -16 | -2700 -500 -7108 | -4146 233 -8150 | -4380 43 -894 | 2110 -381 -1115 | -4028 399 -701 | -403 106 -1378 | -2517 -626 * | -3963 210 | -1928 -466 | -1973 -720 | -2744 275 | -3921 394 | -2844 45 | -3431 96 | -3284 359 | -3474 117 | -2669 -369 | 338 -294 | 4419 -249 | 745 |
| 724(E) | 930 -149 -16 | -1529 -500 -7108 | -450 233 -8150 | 1712 43 -894 | -1762 -381 -1115 | -1469 399 -701 | -180 106 -1378 | -1376 -626 * | 198 210 | -1516 -466 | -699 -720 | -206 275 | -1582 394 | 213 45 | 806 96 | -430 359 | -409 117 | 672 -369 | -1834 -294 | -1256 -249 | 746 |

TABLE 6-continued

| | | | | | | | | | | | | | | | | |
|---|---|---|---|---|---|---|---|---|---|---|---|---|---|---|---|---|
| 725(D) | -696<br>-149<br>-16 | -2211<br>-500<br>-7108 | 2006<br>233<br>-8150 | 276<br>43<br>-894 | -2503<br>-381<br>-1115 | -1435<br>399<br>-701 | 1781<br>106<br>-1378 | -2271<br>-626<br>* | 47<br>210<br>* | -2216<br>-466 | -1327<br>-720 | 1502<br>275 | 621<br>394 | 1163<br>45 | -498<br>96 | -540<br>359 | -655<br>117 | -1822<br>-369 | -2394<br>-294 | -1669<br>-249 | 747 |
| 726(M) | -522<br>-149<br>-16 | -1463<br>-500<br>-7108 | 1325<br>233<br>-8150 | 1144<br>43<br>-894 | -1558<br>-381<br>-1115 | -1519<br>399<br>-701 | -266<br>106<br>-1378 | -1159<br>-626<br>* | 3<br>210<br>* | 493<br>-466 | 2326<br>-720 | -260<br>275 | -1645<br>394 | 90<br>45 | -458<br>96 | -522<br>359 | -468<br>117 | -941<>-369 | -1762<br>-294 | -1204<br>-249 | 748 |
| 727(I) | -1755<br>-149<br>-16 | -1312<br>-500<br>-7108 | -4289<br>233<br>-8150 | -3853<br>43<br>-894 | -1390<br>-381<br>-1115 | -3961<br>399<br>-701 | -3331<br>106<br>-1378 | 2559<br>-626<br>* | -3677<br>210<br>* | 1028<br>-466 | -208<br>-720 | -3600<br>275 | -3736<br>394 | -3367<br>45 | -3647<br>96 | -3222<br>359 | -1724<br>117 | 2382<br>-369 | -2800<br>-294 | -2488<br>-249 | 749 |
| 728(Q) | -1019<br>-149<br>-16 | -2299<br>-500<br>-7108 | -664<br>233<br>-8150 | 1508<br>43<br>-894 | -2732<br>-381<br>-1115 | -1794<br>399<br>-701 | -307<br>106<br>-1378 | -2378<br>-626<br>* | 502<br>210<br>* | -2248<br>-466 | -1420<br>-720 | -437<br>275 | -1902<br>394 | 2305<br>45 | 2189<br>96 | -887<br>359 | -914<br>117 | -1997<br>-369 | -2316<br>-294 | -1812<br>-249 | 750 |
| 729(G) | 676<br>-149<br>-16 | -1581<br>-500<br>-7108 | 1006<br>233<br>-8150 | -319<br>43<br>-894 | -2686<br>-381<br>-1115 | 1982<br>399<br>-701 | -822<br>106<br>-1378 | -2430<br>-626<br>* | -639<br>210<br>* | -2491<br>-466 | -1630<br>-720 | -507<br>275 | -1785<br>394 | -454<br>45 | -1135<br>96 | 1417<br>359 | -738<br>117 | -1837<br>-369 | -2718<br>-294 | -2108<br>-249 | 751 |
| 730(L) | -2364<br>-149<br>-16 | -1901<br>-500<br>-7108 | -4660<br>233<br>-8150 | -4144<br>43<br>-894 | -630<br>-381<br>-1115 | -4349<br>399<br>-701 | -3246<br>106<br>-1378 | 2015<br>-626<br>* | -3856<br>210<br>* | 2597<br>-466 | 544<br>-720 | -4006<br>275 | -3841<br>394 | -3101<br>45 | -3583<br>96 | -3629<br>359 | -2275<br>117 | 2<br>-369 | -2255<br>-294 | -2227<br>-249 | 752 |
| 731(F) | -2056<br>-149<br>-16 | -1668<br>-500<br>-7108 | -4299<br>233<br>-8150 | -3752<br>43<br>-894 | 3006<br>-381<br>-1115 | -3840<br>399<br>-701 | -2396<br>106<br>-1378 | 1861<br>-626<br>* | -3446<br>210<br>* | 1502<br>-466 | 554<br>-720 | -3415<br>275 | -3499<br>394 | -2733<br>45 | -3168<br>96 | -3023<br>359 | -1964<br>117 | -161<br>-369 | -1660<br>-294 | -1259<br>-249 | 753 |
| 732(F) | -3581<br>-149<br>-16 | -2688<br>-500<br>-7108 | -4165<br>233<br>-8150 | -4401<br>43<br>-894 | 3865<br>-381<br>-1115 | -4034<br>399<br>-701 | -401<br>106<br>-1378 | -2491<br>-626<br>* | -3981<br>210<br>* | -1903<br>-466 | -1944<br>-720 | -2746<br>275 | -3921<br>394 | -2847<br>45 | -3438<br>96 | -3284<br>359 | -3462<br>117 | -2647<br>-369 | 341<br>-294 | 3054<br>-249 | 754 |
| 733(D) | -1066<br>-149<br>-16 | -2664<br>-500<br>-7108 | 2593<br>233<br>-8150 | 230<br>43<br>-894 | -2949<br>-381<br>-1115 | 899<br>399<br>-701 | -545<br>106<br>-1378 | -2751<br>-626<br>* | 996<br>210<br>* | -2680<br>-466 | -1846<br>-720 | 1209<br>275 | -1852<br>394 | -148<br>45 | -1001<br>96 | -857<br>359 | -1060<br>117 | -2284<br>-369 | -2863<br>-294 | -2068<br>-249 | 755 |
| 734(R) | -2957<br>-149<br>-16 | -3022<br>-500<br>-7108 | -3318<br>233<br>-8150 | -2735<br>43<br>-894 | -3796<br>-381<br>-1115 | -2998<br>399<br>-701 | -1968<br>106<br>-1378 | -3912<br>-626<br>* | -846<br>210<br>* | -3631<br>-466 | -3157<br>-720 | -2611<br>275 | -3280<br>394 | -1724<br>45 | 4056<br>96 | -3026<br>359 | -2913<br>117 | -3650<br>-369 | -3096<br>-294 | -3185<br>-249 | 756 |
| 735(H) | 673<br>-149<br>-16 | -1400<br>-500<br>-7108 | -855<br>233<br>-8150 | -643<br>43<br>-894 | -2108<br>-381<br>-1115 | -1470<br>399<br>-701 | 3344<br>106<br>-1378 | -1923<br>-626<br>* | -596<br>210<br>* | -2073<br>-466 | -1302<br>-720 | -744<br>275 | 2404<br>394 | -583<br>45 | -931<br>96 | -699<br>359 | -761<br>117 | -1503<br>-369 | -2291<br>-294 | -1733<br>-249 | 757 |
| 736(N) | -1426<br>-149<br>-16 | -2353<br>-500<br>-7108 | -948<br>233<br>-8150 | -735<br>43<br>-894 | -2920<br>-381<br>-1115 | -1991<br>399<br>-701 | -796<br>106<br>-1378 | -2769<br>-626<br>* | 68<br>210<br>* | -2666<br>-466 | -1942<br>-720 | 3441<br>275 | -2268<br>394 | -432<br>45 | 1742<br>96 | -1361<br>359 | -1415<br>117 | -2383<br>-369 | -2592<br>-294 | -2147<br>-249 | 758 |
| 737(H) | -1168<br>-149<br>-16 | -1729<br>-500<br>-7108 | -1567<br>233<br>-8150 | -889<br>43<br>-894 | -1360<br>-381<br>-1115 | -2118<br>399<br>-701 | 3917<br>106<br>-1378 | -1446<br>-626<br>* | 284<br>210<br>* | 543<br>-466 | -865<br>-720 | -957<br>275 | -2175<br>394 | -247<br>45 | 1258<br>96 | -1239<br>359 | -1055<br>117 | -1304<br>-369 | -1577<br>-294 | -976<br>-249 | 759 |
| 738(D) | -1353<br>-149<br>-16 | -3032<br>-500<br>-7108 | 2615<br>233<br>-8150 | 202<br>43<br>-894 | -3188<br>-381<br>-1115 | -1564<br>399<br>-701 | 2079<br>106<br>-1378 | -3118<br>-626<br>* | -756<br>210<br>* | -3034<br>-466 | -2267<br>-720 | 2486<br>275 | -1998<br>394 | -383<br>45 | -1443<br>96 | -1092<br>359 | -1377<br>117 | -2642<br>-369 | -3178<br>-294 | -2294<br>-249 | 760 |
| 739(N) | -812<br>-149<br>-16 | -1675<br>-500<br>-7108 | -1241<br>233<br>-8150 | -20<br>43<br>-894 | -2103<br>-381<br>-1115 | -1394<br>399<br>-701 | -82<br>106<br>-1378 | -1850<br>-626<br>* | 715<br>210<br>* | -1813<br>-466 | -1049<br>-720 | 2293<br>275 | -1591<br>394 | 303<br>45 | 2121<br>96 | -603<br>359 | -621<br>117 | -1504<br>-369 | -1871<br>-294 | -1383<br>-249 | 761 |
| 740(F) | -667<br>-149<br>-27 | -6323<br>-500<br>-7108 | -7365<br>233<br>-8150 | -2438<br>43<br>-894 | 1835<br>-381<br>-1115 | -292<br>399<br>-701 | -2448<br>106<br>-1378 | 332<br>-626<br>* | -2101<br>210<br>* | 1627<br>-466 | 473<br>-720 | -2059<br>275 | -2472<br>394 | -1719<br>45 | -1973<br>96 | -1574<br>359 | -844<br>117 | 1081<br>-369 | -1167<br>-294 | -839<br>-249 | 762 |
| 741(H) | 835<br>-149<br>-16 | -719<br>-500<br>-7108 | -3036<br>233<br>-8150 | -889<br>43<br>-894 | -2475<br>-381<br>-1115 | -1478<br>399<br>-701 | -1354<br>106<br>-1378 | -1148<br>-626<br>* | 102<br>210<br>* | -1306<br>-466 | -513<br>-720 | 945<br>275 | -1582<br>394 | 159<br>45 | -343<br>96 | -433<br>359 | 1418<br>117 | -890<br>-369 | -1646<br>-294 | 876<br>-249 | 763 |
| | 501<br>-149<br>-16 | -1345<br>-500<br>-7108 | -519<br>233<br>-8150 | 3<br>43<br>-894 | -1474<br>-381<br>-1115 | | 2277<br>106<br>-1378 | | | | | | | | | | | | | | |

TABLE 6-continued

| | | | | | | | | | | | | | | | | | | |
|---|---|---|---|---|---|---|---|---|---|---|---|---|---|---|---|---|---|---|
| 742(V) | −1752 −149 −16 | −1297 −500 −7108 | −4324 233 −8150 | −3962 43 −894 | −1768 −381 −1115 | −4045 399 −701 | −3742 106 −1378 | 2459 −626 * | −3833 210 * | −621 −466 | −545 −720 | −3722 275 | −3873 394 | −3691 45 | −3909 96 | −3362 359 | −1744 117 | 2956 −369 | −3271 −294 | −2823 −249 | 764 |
| 743( ) | −30 −149 −16 | 439 −500 −7108 | 11 233 −8150 | 363 43 −894 | −394 −381 −1115 | −739 399 −701 | 699 106 −1378 | −414 −626 * | 463 210 * | −757 −466 | 501 −720 | 286 275 | −577 394 | 639 45 | 165 96 | −23 359 | 111 117 | −312 −369 | 697 −294 | −25 −249 | 765 |
| 744(H) | −991 −149 −16 | −1830 −500 −7108 | −1052 233 −8150 | −504 43 −894 | −1930 −381 −1115 | −1886 399 −701 | 3890 106 −1378 | −1681 −626 * | 1542 210 * | −1767 −466 | −1038 −720 | −666 275 | −1989 394 | −60 45 | 176 96 | −985 359 | −903 117 | 206 −369 | −1921 −294 | −1408 −249 | 766 |
| 745(G) | −494 −149 −16 | −1130 −500 −7108 | −1974 233 −8150 | −2194 43 −894 | −3326 −381 −1115 | 3228 399 −701 | −2287 106 −1378 | −3191 −626 * | −2529 210 * | −3407 −466 | −2546 −720 | −1609 275 | −2055 394 | −2198 45 | −2601 96 | 938 359 | −923 117 | −2148 −369 | −3486 −294 | −3235 −249 | 767 |
| 746(Y) | −3482 −149 −16 | −2868 −500 −7108 | −3701 233 −8150 | −3919 43 −894 | 238 −381 −1115 | −3552 399 −701 | −1112 106 −1378 | −3000 −626 * | −3638 210 * | −2516 −466 | −2526 −720 | −3027 275 | −3772 394 | −3101 45 | −3341 96 | −3418 359 | −3527 117 | −3071 −369 | −441 −294 | 4711 −249 | 768 |
| 747(R) | −1317 −149 −16 | −2448 −500 −7108 | −1232 233 −8150 | 1501 43 −894 | −3004 −381 −1115 | −2062 399 −701 | −362 106 −1378 | −2555 −626 * | 2088 210 * | −2353 −466 | −1567 −720 | −710 275 | −2107 394 | 70 45 | 2409 96 | −1189 359 | −1156 117 | −2213 −369 | −2342 −294 | −1973 −249 | 769 |
| 748(E) | −2641 −149 −16 | −3308 −500 −7108 | −896 233 −8150 | 3732 43 −894 | −3966 −381 −1115 | −2458 399 −701 | −2043 106 −1378 | −4105 −626 * | −2128 210 * | −4016 −466 | −3555 −720 | −1531 275 | −2959 394 | −1842 45 | −2560 96 | −2479 359 | −2750 117 | −3722 −369 | −3563 −294 | −3385 −249 | 770 |
| 749(E) | −603 −149 −16 | −2088 −500 −7108 | 932 233 −8150 | 1740 43 −894 | −2382 −381 −1115 | −1414 399 −701 | −194 106 −1378 | −2138 −626 * | 145 210 * | −2093 −466 | −1197 −720 | 1660 275 | −1889 394 | 1157 45 | −389 96 | −462 359 | −556 117 | 226 −369 | −2276 −294 | −1569 −249 | 771 |
| 750(G) | −2594 −149 −16 | −2690 −500 −7108 | −3304 233 −8150 | −3623 43 −894 | −4328 −381 −1115 | 3747 399 −701 | −3462 106 −1378 | −4761 −626 * | −3953 210 * | −4671 −466 | −4212 −720 | −3320 275 | −3352 394 | −3748 45 | −3779 96 | −2839 359 | −2981 117 | −4004 −369 | −3668 −294 | −4222 −249 | 772 |
| 751(D) | −1242 −149 −16 | −2482 −500 −7108 | 2856 233 −8150 | −92 43 −894 | −3324 −381 −1115 | −1544 399 −701 | −1056 106 −1378 | −3220 −626 * | −1180 210 * | −3222 −466 | −2479 −720 | −411 275 | −2078 394 | −735 45 | −1856 96 | 2119 359 | −1401 117 | −2625 −369 | −3370 −294 | −2572 −249 | 773 |
| 752(I) | −1125 −149 −16 | −1077 −500 −7108 | −3099 233 −8150 | −2749 43 −894 | −1383 −381 −1115 | −2564 399 −701 | −2209 106 −1378 | 2720 −626 * | −2446 210 * | −620 −466 | −388 −720 | −2395 275 | −2828 394 | −2300 45 | −2481 96 | −1819 359 | 2258 117 | 661 −369 | −2292 −294 | −1909 −249 | 774 |
| 753(T) | −1213 −149 −16 | −1674 −500 −7108 | −2755 233 −8150 | −2906 43 −894 | −3163 −381 −1115 | −1922 399 −701 | −2659 106 −1378 | −2698 −626 * | −2788 210 * | −3105 −466 | −2612 −720 | −2311 275 | −2600 394 | −2708 45 | −2753 96 | −1463 359 | 3819 117 | −2197 −369 | −3286 −294 | −3156 −249 | 775 |
| 754(T) | −1213 −149 −16 | −1674 −500 −7108 | −2755 233 −8150 | −2906 43 −894 | −3163 −381 −1115 | −1922 399 −701 | −2659 106 −1378 | −2698 −626 * | −2788 210 * | −3105 −466 | −2612 −720 | −2311 275 | −2600 394 | −2708 45 | −2753 96 | −1463 359 | 3819 117 | −2197 −369 | −3286 −294 | −3156 −249 | 776 |
| 755(P) | −2931 −149 −16 | −2878 −500 −7108 | −3420 233 −8150 | −3706 43 −894 | −4181 −381 −1115 | −2925 399 −701 | −3468 106 −1378 | −4621 −626 * | −3859 210 * | −4490 −466 | −4165 −720 | −3491 275 | 4225 394 | −3781 45 | −3695 96 | −3182 359 | −3279 117 | −4087 −369 | −3594 −294 | −4064 −249 | 777 |
| 756(F) | −3533 −149 −16 | −2667 −500 −7108 | −4143 233 −8150 | −4362 43 −894 | 4034 −381 −1115 | −4011 399 −701 | −413 106 −1378 | −2435 −626 * | −3947 210 * | −1856 −466 | −1895 −720 | −2743 275 | −3904 394 | −2837 45 | −3418 96 | −3264 359 | −3419 117 | −2596 −369 | 327 −294 | 2564 −249 | 778 |

TABLE 6-continued

| | | | | | | | | | | | | | | | | |
|---|---|---|---|---|---|---|---|---|---|---|---|---|---|---|---|---|
| 757(D) | −2784<br>−149<br>−16 | −3432<br>−500<br>−7108 | 4016<br>233<br>−8150 | −1200<br>43<br>−894 | −4140<br>−381<br>−1115 | −2466<br>399<br>−701 | −2197<br>106<br>−1378 | −4505<br>−626<br>* | −2621<br>210<br>* | −4365<br>−466 | −3956<br>−720 | −1551<br>275 | −3014<br>394 | −2039<br>45 | −3232<br>96 | −2593<br>359 | −2938<br>117 | −4046<br>−369 | −3710<br>−294 | −3552<br>−249 | 779 |
| 758(M) | −1664<br>−149<br>−16 | −1479<br>−500<br>−7108 | −3731<br>233<br>−8150 | −3304<br>43<br>−894 | −822<br>−381<br>−1115 | −3209<br>399<br>−701 | −2514<br>106<br>−1378 | 381<br>−626<br>* | −2903<br>210<br>* | 307<br>−466 | 4447<br>−720 | −2987<br>275 | −3235<br>394 | −2579<br>45 | −2815<br>96 | −2469<br>359 | −1688<br>117 | 1155<br>−369 | −2108<br>−294 | −1854<br>−249 | 780 |
| 759(R) | −841<br>−149<br>−16 | −995<br>−500<br>−7108 | −1971<br>233<br>−8150 | −1321<br>43<br>−894 | −932<br>−381<br>−1115 | −2129<br>399<br>−701 | −856<br>106<br>−1378 | −136<br>−626<br>* | −533<br>210<br>* | −467<br>−466 | 2304<br>−720 | −1291<br>275 | −2194<br>394 | −758<br>45 | 2401<br>96 | −1211<br>359 | −783<br>117 | 1416<br>−369 | −1446<br>−294 | −1079<br>−249 | 781 |
| 760(V) | −954<br>−149<br>−16 | −916<br>−500<br>−7108 | −2489<br>233<br>−8150 | −1863<br>43<br>−894 | −806<br>−381<br>−1115 | −2402<br>399<br>−701 | −1212<br>106<br>−1378 | 292<br>−626<br>* | −1157<br>210<br>* | 906<br>−466 | 98<br>−720 | −1725<br>275 | −2437<br>394 | −1258<br>45 | 1435<br>96 | −1506<br>359 | −901<br>117 | 2327<br>−369 | −1472<br>−294 | −1115<br>−249 | 782 |
| 761(V) | −1831<br>−149<br>−16 | −1468<br>−500<br>−7108 | −4142<br>233<br>−8150 | −3585<br>43<br>−894 | −674<br>−381<br>−1115 | −3694<br>399<br>−701 | −2641<br>106<br>−1378 | 526<br>−626<br>* | −3292<br>210<br>* | 1920<br>−466 | 2093<br>−720 | −3318<br>275 | −3425<br>394 | −2728<br>45 | −3099<br>96 | −2876<br>359 | −1760<br>117 | 2327<br>−369 | −2028<br>−294 | −1893<br>−249 | 783 |
| 762(N) | −2171<br>−149<br>−16 | −2655<br>−500<br>−7108 | −1458<br>233<br>−8150 | −1748<br>43<br>−894 | −3334<br>−381<br>−1115 | −2364<br>399<br>−701 | −2267<br>106<br>−1378 | −3943<br>−626<br>* | −2365<br>210<br>* | −3936<br>−466 | −3437<br>−720 | 4205<br>275 | −2932<br>394 | −2205<br>45 | −2608<br>96 | −2224<br>359 | −2439<br>117 | −3392<br>−369 | −3253<br>−294 | −2909<br>−249 | 784 |
| 763(E) | −447<br>−149<br>−16 | −1916<br>−500<br>−7108 | 638<br>233<br>−8150 | 1762<br>43<br>−894 | −2239<br>−381<br>−1115 | −1385<br>399<br>−701 | 1510<br>106<br>−1378 | −1986<br>−626<br>* | 1083<br>210<br>* | −1928<br>−466 | −1009<br>−720 | −19<br>275 | −1493<br>394 | 1244<br>45 | 466<br>96 | −323<br>359 | −386<br>117 | −1540<br>−369 | −2092<br>−294 | −1413<br>−249 | 785 |
| 764(M) | −1749<br>−149<br>−16 | −1382<br>−500<br>−7108 | −4134<br>233<br>−8150 | −3576<br>43<br>−894 | −706<br>−381<br>−1115 | −3632<br>399<br>−701 | −2595<br>106<br>−1378 | 1821<br>−626<br>* | −3291<br>210<br>* | 1705<br>−466 | 2738<br>−720 | −3271<br>275 | −3384<br>394 | −2732<br>45 | −3086<br>96 | −2809<br>359 | −1680<br>117 | 1590<br>−369 | −2012<br>−294 | −1860<br>−249 | 786 |
| 765(D) | −1369<br>−149<br>−16 | −2674<br>−500<br>−7108 | 3374<br>233<br>−8150 | −58<br>43<br>−894 | −3453<br>−381<br>−1115 | −1571<br>399<br>−701 | −1095<br>106<br>−1378 | −3380<br>−626<br>* | −1289<br>210<br>* | −3368<br>−466 | −2659<br>−720 | −394<br>275 | −2124<br>394 | −784<br>45 | −2016<br>96 | 1149<br>359 | −1529<br>117 | −2785<br>−369 | −3505<br>−294 | −2662<br>−249 | 787 |
| 766(R) | −2957<br>−149<br>−16 | −3022<br>−500<br>−7108 | −3318<br>233<br>−8150 | −2735<br>43<br>−894 | −3796<br>−381<br>−1115 | −2998<br>399<br>−701 | −1968<br>106<br>−1378 | −3912<br>−626<br>* | −846<br>210<br>* | −3631<br>−466 | −3157<br>−720 | −2611<br>275 | −3280<br>394 | −1724<br>45 | 4056<br>96 | −3026<br>359 | −2913<br>117 | −3650<br>−369 | −3096<br>−294 | −3185<br>−249 | 788 |
| 767(Y) | −3616<br>−149<br>−16 | −2704<br>−500<br>−7108 | −4178<br>233<br>−8150 | −4426<br>43<br>−894 | 3471<br>−381<br>−1115 | −4049<br>399<br>−701 | −394<br>106<br>−1378 | −2531<br>−626<br>* | −4004<br>210<br>* | −1934<br>−466 | −1979<br>−720 | −2749<br>275 | −3932<br>394 | −2854<br>45 | −3451<br>96 | −3298<br>359 | −3493<br>117 | −2683<br>−369 | 349<br>−294 | 3677<br>−249 | 789 |
| 768(H) | 274<br>−149<br>−16 | −2294<br>−500<br>−7108 | 1079<br>233<br>−8150 | 1119<br>43<br>−894 | −2578<br>−381<br>−1115 | −1451<br>399<br>−701 | 3282<br>106<br>−1378 | −2348<br>−626<br>* | −50<br>210<br>* | −2296<br>−466 | −1419<br>−720 | 1227<br>275 | −1687<br>394 | 101<br>45 | −610<br>96 | −606<br>359 | −736<br>117 | −1901<br>−369 | −2481<br>−294 | −1745<br>−249 | 790 |
| 769(L) | −2092<br>−149<br>−16 | −1719<br>−500<br>−7108 | −4323<br>233<br>−8150 | −3846<br>43<br>−894 | −712<br>−381<br>−1115 | −3925<br>399<br>−701 | −2989<br>106<br>−1378 | 451<br>−626<br>* | −3531<br>210<br>* | 2641<br>−466 | 428<br>−720 | −3624<br>275 | −3640<br>394 | −2952<br>45 | −3339<br>96 | −3191<br>359 | −2044<br>117 | 1542<br>−369 | −2221<br>−294 | −2096<br>−249 | 791 |
| 770(A) | 2058<br>−149<br>−16 | −944<br>−500<br>−7108 | −1182<br>233<br>−8150 | −683<br>43<br>−894 | −1304<br>−381<br>−1115 | −1522<br>399<br>−701 | −653<br>106<br>−1378 | −783<br>−626<br>* | −528<br>210<br>* | −1127<br>−466 | −414<br>−720 | −754<br>275 | −1773<br>394 | 942<br>45 | −860<br>96 | −602<br>359 | 852<br>117 | 724<br>−369 | −1630<br>−294 | −1185<br>−249 | 792 |
| 771(K) | 1238<br>−149<br>−16 | −1887<br>−500<br>−7108 | −1224<br>233<br>−8150 | −813<br>43<br>−894 | −2786<br>−381<br>−1115 | −1805<br>399<br>−701 | −755<br>106<br>−1378 | −2335<br>−626<br>* | 3008<br>210<br>* | −2384<br>−466 | −1637<br>−720 | −897<br>275 | −2102<br>394 | −378<br>45 | −48<br>96 | −1055<br>359 | −1089<br>117 | −1935<br>−369 | −2512<br>−294 | −2122<br>−249 | 793 |
| 772(A) | 1327<br>−149<br>−169 | −1917<br>−500<br>−7108 | 950<br>233<br>−3273 | 1094<br>43<br>−894 | −2220<br>−381<br>−1115 | −1330<br>399<br>−701 | −74<br>106<br>−964 | −1968<br>−626<br>* | 946<br>210<br>* | −1930<br>−466 | −1028<br>−720 | 32<br>275 | −1480<br>394 | 369<br>45 | −228<br>96 | 547<br>359 | −411<br>117 | −1533<br>−369 | −2115<br>−294 | −1424<br>−249 | 794 |
| | −17 | −6956 | −7998 | | | −1036 | | | | | | | | | | | | | | | |

TABLE 6-continued

| | | | | | | | | | | | | | | | | | |
|---|---|---|---|---|---|---|---|---|---|---|---|---|---|---|---|---|---|
| 773(A | 3386 −149 −17 | −1299 −500 −6956 | −2601 233 −7998 | −2766 43 −894 | −3046 −381 −1115 | −1559 399 −525 | −2499 106 −1714 | −2553 −626 * | −2749 210 * | −2990 −466 | −2405 −720 | −2021 275 | −2272 394 | −2539 45 | −2697 96 | −1037 359 | −1201 117 | −1940 −369 | −3200 −294 | −3073 −249 | 795 |
| 774(I | −1087 −149 −16 | −861 −500 −7108 | −3107 233 −8150 | 161 43 −894 | −882 −381 −1115 | −2803 399 −701 | −1771 106 −1378 | 2342 −626 * | −2281 210 * | 1091 −466 | 78 −720 | −2300 275 | −2777 394 | −2009 45 | −2269 96 | −1916 359 | −1039 117 | 1702 −369 | −1691 −294 | −1345 −249 | 796 |
| 775(Q | 375 −149 −16 | −1755 −500 −7108 | −273 233 −8150 | 815 43 −894 | −2036 −381 −1115 | −1376 399 −701 | −39 106 −1378 | −1756 −626 * | 367 210 * | −1753 −466 | −857 −720 | 1007 275 | −1469 394 | 1244 45 | 843 96 | −290 359 | 959 117 | 12 −369 | −1964 −294 | −1309 −249 | 797 |
| 776(M | 1052 −149 −16 | −610 −500 −7108 | −1546 233 −8150 | −994 43 −894 | −696 −381 −1115 | 582 399 −701 | −640 106 −1378 | −244 −626 * | −804 210 * | 810 −466 | 1789 −720 | −967 275 | −1833 394 | −639 45 | −1021 96 | 395 359 | −384 117 | −113 −369 | −1120 −294 | −726 −249 | 798 |
| 777(I | −416 −149 −16 | −776 −500 −7108 | −1113 233 −8150 | 474 43 −894 | −802 −381 −1115 | 469 399 −701 | −424 106 −1378 | 1231 −626 * | −400 210 * | 255 −466 | 48 −720 | −674 275 | −1747 394 | 951 45 | −718 96 | −659 359 | −357 117 | 665 −369 | −1177 −294 | −745 −249 | 799 |
| 778(D | 1034 −149 −16 | −2035 −500 −7108 | 2294 233 −8150 | −106 43 −894 | −2869 −381 −1115 | −1459 399 −701 | −830 106 −1378 | −2614 −626 * | −751 210 * | −2671 −466 | −1863 −720 | −387 275 | 2260 394 | −474 45 | −1320 96 | −825 359 | −1014 117 | −2092 −369 | −2906 −294 | −2215 −249 | 800 |
| 779(A | 1299 −149 −1040 | −1548 −500 −7108 | −409 233 −981 | 909 43 −894 | −1800 −381 −1115 | 43 399 −701 | −141 106 −1378 | −1467 −626 * | 231 210 * | −1558 −466 | −718 −720 | −156 275 | −1340 394 | 264 45 | 1153 96 | −374 359 | −369 117 | 158 −369 | −1848 −294 | −1253 −249 | 801 |
| 780(F | −585 −149 −424 | −915 −500 −6099 | −883 233 −2060 | −659 43 −894 | 2573 −381 −1115 | −1541 399 −1914 | −52 106 −445 | −591 −626 * | −624 210 * | −695 −466 | −233 −720 | 1803 275 | −1767 394 | −468 45 | −869 96 | −739 359 | −609 117 | −487 −369 | −70 −294 | 917 −249 | 802 |
| 781(N | −313 −149 −41 | −1042 −500 −6788 | 254 233 −6759 | 152 43 −894 | −1409 −381 −1115 | −814 399 −2091 | −286 106 −386 | −1511 −626 * | −122 210 * | −1692 −466 | −1083 −720 | −65 275 | −1287 394 | −82 45 | −434 96 | −340 359 | −474 117 | −1140 −369 | −1574 −294 | −976 −249 | 803 |
| 782(E | −647 −149 −41 | −1563 −500 −5717 | 589 233 −6759 | 2680 43 −894 | −1901 −381 −1115 | −941 399 −2091 | −188 106 −386 | −1630 −626 * | 4 210 * | −1762 −466 | −1176 −720 | 156 275 | −1345 394 | 101 45 | −395 96 | −544 359 | −693 117 | −1348 −369 | −1863 −294 | −1374 −249 | 804 |
| 783(K | −682 −149 −41 | −1365 −500 −5717 | −434 233 −6759 | −118 43 −894 | −1773 −381 −1115 | −1231 399 −612 | −19 106 −1532 | −1449 −626 * | 2744 210 * | −1499 −466 | −893 −720 | −244 275 | −1470 394 | 310 45 | 740 96 | −670 359 | −643 117 | −1208 −369 | −1538 −294 | −1198 −249 | 805 |
| 784(Y | −620 −149 −20 | −433 −500 −6788 | −2763 233 −7830 | −2164 43 −894 | −265 −381 −1115 | −2214 399 −1306 | −1076 106 −747 | 1484 −626 * | −1822 210 * | 144 −466 | 2036 −720 | −1779 275 | −2223 394 | −1475 45 | −1707 96 | −1306 359 | −562 117 | 1635 −369 | −935 −294 | 2216 −249 | 806 |
| 785(K | −540 −149 −20 | −1908 −500 −6788 | −286 233 −7830 | 1554 43 −894 | −2271 −381 −1115 | 235 399 −421 | −21 106 −1984 | −1969 −626 * | 1597 210 * | −1892 −466 | −1016 −720 | −65 275 | −1527 394 | 423 45 | 1275 96 | −418 359 | −461 117 | −1559 −369 | −2023 −294 | −1427 −249 | 807 |
| 786(D | −495 −149 −16 | −1834 −500 −7108 | 1772 233 −7830 | 243 43 −894 | −2095 −381 −1115 | −1409 399 −701 | −135 106 −1378 | −1811 −626 * | 226 210 * | 93 −466 | −952 −720 | 959 275 | −1543 394 | 1255 45 | −279 96 | −392 359 | 713 117 | −1426 −369 | −2056 −294 | −1398 −249 | 808 |
| 787(K | −1474 −149 −16 | −2433 −500 −7108 | −1703 233 −8150 | −833 43 −894 | −3058 −381 −1115 | −2216 399 −701 | −418 106 −1378 | −2547 −626 * | 2890 210 * | −2352 −466 | −1602 −720 | −908 275 | −2233 394 | 6 45 | 1874 96 | −1375 359 | 633 117 | −2246 −369 | −2329 −294 | −2042 −249 | 809 |
| 788(H | −451 −149 −16 | −1596 −500 −7108 | −374 233 −8150 | 131 43 −894 | −1721 −381 −1115 | 4 399 −701 | 2032 106 −1378 | −1490 −626 * | 223 210 * | −1570 −466 | −735 −720 | −150 275 | −1554 394 | 1294 45 | −242 96 | 993 359 | −394 117 | −1170 −369 | −1803 −294 | 1657 −249 | 810 |

TABLE 6-continued

| | | | | | | | | | | | | | | | | | | |
|---|---|---|---|---|---|---|---|---|---|---|---|---|---|---|---|---|---|---|
| 789(A) | 2417 | -1302 | -925 | -642 | -2356 | -1358 | -885 | -2038 | -600 | -2179 | -1358 | -718 | -1792 | 1772 | -969 | 686 | -646 | -1531 | -2461 | -1952 | 811 |
| | -149 | -500 | 233 | -894 | -381 | 399 | 106 | -626 | 210 | -466 | -720 | 275 | 394 | 45 | 96 | 359 | 117 | -369 | -294 | -249 | |
| | -16 | -7108 | -8150 | | -1115 | -701 | -1378 | * | | | | | | | | | | | | | |
| 790(E) | 1699 | -2717 | 1896 | 1966 | -3018 | -1521 | -628 | -2814 | -547 | -2768 | -1958 | -152 | -1900 | -245 | -1190 | -928 | -1153 | -2352 | -2970 | -2159 | 812 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 791(F) | -576 | -843 | -1351 | 18 | 2111 | -1835 | -543 | -341 | 927 | 1121 | 58 | -880 | -1903 | -468 | -730 | -859 | -511 | -255 | -1145 | -680 | 813 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 792C | -1112 | 2697 | -3476 | -2950 | -1103 | -2900 | -2047 | 2026 | -2659 | -523 | -143 | -2556 | -2914 | -2378 | -2583 | -2056 | 623 | 2331 | -1900 | -1524 | 814 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 793Q | 419 | -1959 | 511 | 264 | -2287 | -1397 | -160 | -2033 | 201 | -2001 | -1102 | 892 | -1555 | 2127 | -318 | 1297 | -485 | -1597 | -2190 | -1503 | 815 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 794( ) | -30 | 439 | 11 | 363 | -394 | -739 | 699 | -414 | 463 | -757 | 501 | 286 | -577 | 639 | 165 | -23 | 111 | -312 | 697 | -25 | 816 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 795(E) | -617 | -2049 | -177 | 2132 | -2369 | -1467 | 1606 | -2104 | 1334 | -2049 | -1159 | -104 | -1611 | 267 | -171 | 468 | -558 | -1677 | -2212 | -1550 | 817 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 796(M) | -2288 | -1880 | -4481 | -3899 | 1874 | -4066 | -2635 | 72 | -3594 | 1748 | 3848 | -3656 | -3608 | -2775 | -3272 | -3259 | -2174 | -566 | -1778 | -1555 | 818 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 797(D) | -1194 | -2847 | 2837 | 1238 | -3100 | -1527 | -634 | -2920 | -571 | -2845 | -2036 | 1124 | -1913 | -251 | -1231 | -958 | 827 | -2447 | -3037 | -2200 | 819 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 798(H) | -831 | -2392 | 1999 | 980 | -2678 | -1463 | 2287 | -2459 | 551 | -2391 | -1516 | 1798 | -1718 | 62 | -667 | -653 | -799 | -2000 | -2566 | -1815 | 820 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 799(M) | -496 | -1070 | -899 | -350 | 1464 | -1648 | -334 | -716 | 1384 | -934 | 2286 | 1246 | -1730 | -100 | -455 | -629 | -434 | -548 | -1346 | -826 | 821 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 800(I) | -1200 | -1080 | -2894 | -2252 | -618 | -2712 | -1476 | 2020 | -1547 | 1701 | 361 | -2078 | -2664 | -1554 | 1445 | -1820 | -1129 | 84 | -1503 | -1217 | 822 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 801(Q) | 1195 | -1999 | 1275 | 287 | -2307 | -1399 | -132 | -2058 | 888 | -2010 | -1104 | 1022 | -1544 | 1594 | -271 | -396 | -475 | -1616 | -2187 | -1494 | 823 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 802(E) | -464 | -1834 | -313 | 1601 | -2133 | -1426 | -72 | -1849 | 1475 | -301 | -936 | -76 | -1522 | 1237 | -64 | -359 | 488 | -1446 | -2019 | -1377 | 824 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 803(H) | 1285 | -1168 | -1100 | -753 | -1895 | -1421 | 3671 | -1567 | -616 | -1783 | -1019 | -796 | -1815 | -585 | -942 | -599 | 1325 | -1196 | -2122 | -1628 | 825 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 804(H) | -457 | -1111 | -796 | -240 | 1415 | -1595 | 1499 | -796 | -56 | -1014 | -275 | 1464 | -1677 | -16 | 1113 | -558 | -395 | 539 | -1363 | -816 | 826 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |

TABLE 6-continued

| | | | | | | | | | | | | | | | | | | | |
|---|---|---|---|---|---|---|---|---|---|---|---|---|---|---|---|---|---|---|---|
| 805(Q) | 961 -149 -16 | -1898 -500 -7108 | 742 233 -8150 | 284 43 -894 | -2209 -1115 -381 | -1388 399 -701 | 1553 106 -1378 | -1951 -626 * | 1291 210 * | -1907 -466 | -995 -720 | -26 275 | -1499 394 | 1771 45 | -144 96 | -331 359 | -392 117 | -1516 -369 | -2082 -294 | -1407 -249 | 827 |
| 806(Y) | -3616 -149 -16 | -2706 -500 -7108 | -4170 233 -8150 | -4415 43 -894 | 2670 -1115 -381 | -4045 399 -701 | -396 106 -1378 | -2536 -626 * | -3994 210 * | -1940 -466 | -1985 -720 | -2748 275 | -3931 394 | -2852 45 | -3447 96 | -3296 359 | -3495 117 | -2687 -369 | 347 -294 | 4234 -249 | 828 |
| 807(I) | 1201 -149 -16 | -821 -500 -7108 | -2746 233 -8150 | -2313 43 -894 | -1223 -1115 -381 | -2126 399 -701 | -1705 106 -1378 | 2731 -626 * | -2058 210 * | -749 -466 | -304 -720 | -1944 275 | -2428 394 | -1844 45 | -2105 96 | -1330 359 | 893 117 | 505 -369 | -1890 -294 | -1524 -249 | 829 |
| 808(R) | -841 -149 -16 | -995 -500 -7108 | -1971 233 -8150 | -1321 43 -894 | -932 -1115 -381 | -2129 399 -701 | -856 106 -1378 | -136 -626 * | -533 210 * | -467 -466 | 2304 -720 | -1291 275 | -2194 394 | -758 45 | 2401 96 | -1211 359 | -783 117 | 1416 -369 | -1446 -294 | -1079 -249 | 830 |
| 809(D) | -1157 -149 -16 | -2811 -500 -7108 | 2313 233 -8150 | 1149 43 -894 | -3071 -1115 -381 | -1519 399 -701 | -606 106 -1378 | -2891 -626 * | -523 210 * | -2811 -466 | -1992 -720 | 1715 275 | -1893 394 | -218 45 | -1175 96 | 1334 359 | -1159 117 | -2414 -369 | -2998 -294 | -2166 -249 | 831 |
| 810(N) | 377 -149 -16 | -1890 -500 -7108 | -201 233 -8150 | 941 43 -894 | -2201 -1115 -381 | -1398 399 -701 | -93 106 -1378 | -1936 -626 * | 1328 210 * | -1904 -466 | -1001 -720 | 1972 275 | -1518 394 | 353 45 | -173 96 | -356 359 | 594 117 | -1511 -369 | -2089 -294 | -1420 -249 | 832 |
| 811(G) | -1501 -149 -16 | -2131 -500 -7108 | -1258 233 -8150 | -1392 43 -894 | -2600 -1115 -381 | 3138 399 -701 | 2851 106 -1378 | -3219 -626 * | -1608 210 * | -3233 -466 | -2576 -720 | -1477 275 | -2541 394 | -1589 45 | -1850 96 | -1578 359 | -1737 117 | -2674 -369 | -2756 -294 | -2168 -249 | 833 |
| 812(Y) | 385 -149 -16 | -1523 -500 -7108 | -449 233 -8150 | 96 43 -894 | -1722 -1115 -381 | -1461 399 -701 | -132 106 -1378 | -1384 -626 * | 959 210 * | -1486 -466 | -659 -720 | -175 275 | -1554 394 | 1557 45 | -186 96 | -399 359 | 1250 117 | -1083 -369 | -1786 -294 | 1631 -249 | 834 |
| 813(D) | -2784 -149 -16 | -3432 -500 -7108 | 4016 233 -8150 | -1200 43 -894 | -4140 -1115 -381 | -2466 399 -701 | -2197 106 -1378 | -4505 -626 * | -2621 210 * | -4365 -466 | -3956 -720 | -1551 275 | -3014 394 | -2039 45 | -3232 96 | -2593 359 | -2938 117 | -4046 -369 | -3710 -294 | -3552 -249 | 835 |
| 814(L) | -587 -149 -16 | -625 -500 -7108 | -1931 233 -8150 | -1364 43 -894 | -454 -1115 -381 | -1983 399 -701 | 1655 106 -1378 | 818 -626 * | -1068 210 * | 1666 -466 | 322 -720 | -1268 275 | 955 394 | -903 45 | -1182 96 | -1033 359 | -529 117 | 21 -369 | -1001 -294 | -599 -249 | 836 |
| 815(P) | -1667 -149 -16 | -2676 -500 -7108 | -329 233 -8150 | 1564 43 -894 | -3405 -1115 -381 | -1913 399 -701 | -1351 106 -1378 | -3268 -626 * | -1273 210 * | -3276 -466 | -2612 -720 | -852 275 | 3489 394 | -1057 45 | -1736 96 | -1555 359 | -1787 117 | -2810 -369 | -3275 -294 | -2761 -249 | 837 |
| 816(E) | -1715 -149 -16 | -3562 -500 -7108 | 2447 233 -8150 | 2878 43 -894 | -3759 -1115 -381 | -1632 399 -701 | -991 106 -1378 | -3691 -626 * | -1235 210 * | -3569 -466 | -2910 -720 | -235 275 | -2166 394 | -663 45 | -2079 96 | -1378 359 | -1784 117 | -3173 -369 | -3732 -294 | -2750 -249 | 838 |
| 817(V) | -537 -149 -16 | -374 -500 -7108 | -2717 233 -8150 | -2103 43 -894 | 914 -1115 -381 | -2090 399 -701 | -949 106 -1378 | 1111 -626 * | -1742 210 * | -147 -466 | 443 -720 | -1675 275 | -2132 394 | -1398 45 | -1608 96 | -1173 359 | 1109 117 | 1932 -369 | -845 -294 | 1322 -249 | 839 |
| 818(T) | -442 -149 -16 | -1699 -500 -7108 | -325 233 -8150 | 943 43 -894 | -1942 -1115 -381 | -1425 399 -701 | -95 106 -1378 | -1640 -626 * | 311 210 * | -1680 -466 | -816 -720 | 906 275 | -1525 394 | 330 45 | 784 96 | -363 359 | 1592 117 | -1283 -369 | -1922 -294 | 1369 -249 | 840 |
| 819(D) | -1684 -149 -16 | -3395 -500 -7108 | 2909 233 -8150 | 109 43 -894 | -3677 -1115 -381 | -1635 399 -701 | -1030 106 -1378 | -3669 -626 * | -1283 210 * | -3567 -466 | -2912 -720 | 2851 275 | -2178 394 | -713 45 | -2110 96 | -1377 359 | -1776 117 | -3137 -369 | -3688 -294 | -2726 -249 | 841 |
| 820(W) | -2023 -149 -16 | -1815 -500 -7108 | -3480 233 -8150 | -3119 43 -894 | 26 -1115 -381 | -3133 399 -701 | -1280 106 -1378 | -780 -626 * | -2462 210 * | -329 -466 | 2687 -720 | -2604 275 | -3188 394 | -2264 45 | -2350 96 | -2462 359 | -2001 117 | -1067 -369 | 5349 -294 | 158 -249 | 842 |

TABLE 6-continued

| | | | | | | | | | | | | | | | | | | | |
|---|---|---|---|---|---|---|---|---|---|---|---|---|---|---|---|---|---|---|---|
| 821(Q) | -408 -149 -16 | -1655 -500 -7108 | -342 233 -8150 | 851 43 -894 | -1897 -381 -1115 | -1411 399 -701 | -76 106 -1378 | -1588 -626 * | 323 210 * | -1635 -466 | -770 -720 | -87 275 | 785 394 | 1202 45 | 869 96 | -334 359 | 619 117 | 752 -369 | -1887 -294 | -1265 -249 | 843 |
| 822(W) | -2077 -149 -16 | -1892 -500 -7108 | -3023 233 -8150 | -2742 43 -894 | 805 -381 -1115 | -3065 399 -701 | -450 106 -1378 | -1653 -626 * | -2397 210 * | -1546 -466 | -1211 -720 | -2106 275 | -3118 394 | -1977 45 | -2345 96 | 1002 359 | -2038 117 | -1614 -369 | 4785 -294 | 2862 -249 | 844 |
| 823(K) | -479 -149 -16 | -1638 -500 -7108 | -472 233 -8150 | 91 43 -894 | 1024 -381 -1115 | -1483 399 -701 | -125 106 -1378 | -1548 -626 * | 1811 210 * | -1610 -466 | -769 -720 | -180 275 | 147 394 | 288 45 | 950 96 | 516 359 | -413 117 | -1222 -369 | -1868 -294 | -1282 -249 | 845 |
| 824(G) | -736 -276 | -2137 -500 -7108 | 965 233 -2582 | 180 43 -894 | -2586 -381 -1115 | 1581 399 -701 | -401 106 -1378 | -2350 -626 * | -145 210 * | -2321 -466 | -1448 -720 | 1563 275 | 712 394 | 15 45 | -699 96 | 528 359 | -738 117 | -1882 -369 | -2516 -294 | -1799 -249 | 846 |
| 825(L) | -1714 -149 -19 | -1375 -500 -6850 | -3901 233 -7893 | -3421 43 -894 | -618 -381 -1115 | -3530 399 -1215 | -2616 -813 | 734 -626 * | -3109 210 * | 2342 -466 | 497 -720 | -3185 275 | -3329 394 | -2647 45 | -2982 96 | -2766 359 | -1674 117 | 1950 -369 | -2019 -294 | -1825 -249 | 847 |
| 826(K) | -1321 -149 -1043 | -2321 -500 -6850 | -787 233 -983 | -481 43 -894 | -2892 -381 -1115 | -1879 399 -1215 | -447 106 -813 | -2552 -626 * | 3186 210 * | -2406 -466 | -1676 -720 | 717 275 | -2074 394 | -54 45 | 419 96 | -1212 359 | -1230 117 | -2209 -369 | -2369 -294 | -1979 -249 | 848 |
| 827(V) | 11 -149 -38 | -281 -500 -5845 | -1388 233 -6888 | -1014 43 -894 | -772 -381 -1115 | -1145 399 -2039 | -782 106 -402 | 672 -626 * | -779 210 * | -271 -466 | 145 -720 | -834 275 | -1527 394 | -694 45 | -967 96 | -363 359 | 1648 117 | 1687 -369 | -1388 -294 | -977 -249 | 849 |
| 828(D) | -878 -38 | -1818 -500 -5845 | 3239 233 -6888 | 428 43 -894 | -2222 -381 -1115 | -972 399 -2039 | -438 106 -402 | -2180 -626 * | -575 210 * | -2276 -466 | -1711 -720 | 95 275 | -1458 394 | -189 45 | -1148 96 | -733 359 | -979 117 | -1822 -369 | -2152 -294 | -1652 -249 | 850 |
| 829(K) | -453 -149 -38 | -1667 -500 -5845 | 328 233 -6888 | 1484 43 -894 | -2007 -381 -1115 | -1088 399 -2039 | 173 106 -402 | -1659 -626 * | 1862 210 * | -1641 -466 | -861 -720 | 236 275 | -1304 394 | 570 45 | 510 96 | -325 359 | -390 117 | -1317 -369 | -1793 -294 | -1239 -249 | 851 |
| 830(K) | -207 -149 -38 | -1058 -500 -5845 | -256 233 -6888 | 150 43 -894 | -1533 -381 -1115 | -1073 399 -2039 | 83 106 -402 | -1043 -626 * | 1817 210 * | -1222 -466 | -493 -720 | -14 275 | -1295 394 | 442 45 | 505 96 | -228 359 | 1229 117 | -760 -369 | -1520 -294 | -1048 -249 | 852 |
| 831(G) | 414 -149 -38 | -272 -500 -5845 | -462 233 -6888 | -426 43 -894 | -1782 -381 -1115 | 1704 399 -2039 | -635 106 -402 | -1518 -626 * | -577 210 * | -1737 -466 | -936 -720 | -257 275 | -1039 394 | -416 45 | -850 96 | 1592 359 | 98 117 | -853 -369 | -1974 -294 | -1547 -249 | 853 |
| 832(M) | 1337 -149 -38 | -339 -500 -5845 | -1188 233 -6888 | -761 43 -894 | -497 -381 -1115 | -1179 399 -2039 | -525 106 -402 | 361 -626 * | -511 210 * | 26 -466 | 2356 -720 | -679 275 | -1477 394 | -431 45 | -716 96 | -350 359 | -116 117 | 415 -369 | -1109 -294 | -709 -249 | 854 |
| 833(V) | -753 -149 -38 | -590 -500 -5845 | -2446 233 -6888 | -1973 43 -894 | -226 -381 -1115 | -2358 399 -2039 | -1433 106 -402 | 1299 -626 * | -1657 210 * | 1429 -466 | 779 -720 | -1837 275 | -2356 394 | -1469 45 | -1726 96 | -1538 359 | -740 117 | 2084 -369 | -1336 -294 | -966 -249 | 855 |
| 834(T) | 413 -149 -38 | -229 -500 -5845 | -707 233 -6888 | -500 43 -894 | -1469 -381 -1115 | -500 399 -2039 | -543 106 -402 | -1022 -626 * | -421 210 * | -1349 -466 | -599 -720 | -312 275 | -1063 394 | -330 45 | -674 96 | 1483 359 | 1911 117 | -534 -369 | -1729 -294 | -1303 -249 | 856 |

TABLE 6-continued

| | | | | | | | | | | | | | | | | | | |
|---|---|---|---|---|---|---|---|---|---|---|---|---|---|---|---|---|---|---|
| 835(A | 2597 | −310 | −1033 | −1004 | −1499 | −618 | −950 | −768 | −944 | −1290 | −768 | −669 | −1235 | −852 | −1081 | −19 | −107 | −412 | −1828 | −1482 | 857 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5845 | −6888 | −894 | −1115 | −2039 | −402 | * | * | | | | | | | | | | | | |
| 836(T) | 93 | −414 | −954 | −868 | −1353 | −741 | −817 | −616 | −701 | −1116 | −632 | −643 | −1304 | −696 | −854 | −136 | 2822 | −336 | −1700 | −1317 | 858 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −38 | −5845 | −6888 | −894 | −1115 | −2039 | −402 | * | * | | | | | | | | | | | | |
| 837(A | 2597 | −310 | −1033 | −1004 | −1499 | −618 | −950 | −768 | −944 | −1290 | −768 | −669 | −1235 | −852 | −1081 | −19 | −107 | −412 | −1828 | −1482 | 859 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −38 | −5845 | −6888 | −894 | −1115 | −2039 | −402 | * | * | | | | | | | | | | | | |
| 838(A | 2597 | −310 | −1033 | −1004 | −1499 | −618 | −950 | −768 | −944 | −1290 | −768 | −669 | −1235 | −852 | −1081 | −19 | −107 | −412 | −1828 | −1482 | 860 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −38 | −5845 | −6888 | −894 | −1115 | −2039 | −402 | * | * | | | | | | | | | | | | |
| 839(T) | 93 | −414 | −954 | −868 | −1353 | −741 | −817 | −616 | −701 | −1116 | −632 | −643 | −1304 | −696 | −854 | −136 | 2822 | −336 | −1700 | −1317 | 861 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −38 | −5845 | −6888 | −894 | −1115 | −2039 | −402 | * | * | | | | | | | | | | | | |
| 840(A | 2597 | −310 | −1033 | −1004 | −1499 | −618 | −950 | −768 | −944 | −1290 | −768 | −669 | −1235 | −852 | −1081 | −19 | −107 | −412 | −1828 | −1482 | 862 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −38 | −5845 | −6888 | −894 | −1115 | −2039 | −402 | * | * | | | | | | | | | | | | |
| 841(G | −461 | −838 | −976 | −1119 | −2120 | 3148 | −1219 | −2101 | −1326 | −2273 | −1700 | −986 | −1505 | −1212 | −1430 | −653 | −781 | −1558 | −1923 | −1928 | 863 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −38 | −5845 | −6888 | −894 | −1115 | −2039 | −402 | * | * | | | | | | | | | | | | |
| 842(D | −878 | −1818 | 3239 | 428 | −2222 | −972 | −438 | −2180 | −575 | −2276 | −1711 | 95 | −1458 | −189 | −1148 | −733 | −979 | −1822 | −2152 | −1652 | 864 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −38 | −5845 | −6888 | −894 | −1115 | −2039 | −402 | * | * | | | | | | | | | | | | |
| 843(N | −431 | −1158 | 164 | 47 | −1545 | −910 | −407 | −1680 | −257 | −1848 | −1242 | 3201 | −1391 | −207 | −570 | −456 | −599 | −1296 | −1696 | −1106 | 865 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −38 | −5845 | −6888 | −894 | −1115 | −2039 | −402 | * | * | | | | | | | | | | | | |
| 844(E) | −771 | −1700 | 518 | 2837 | −2056 | −1033 | −298 | −1811 | −123 | −1925 | −1338 | 65 | −1445 | −9 | −532 | −658 | −819 | −1519 | −1994 | −1511 | 866 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −38 | −5845 | −6888 | −894 | −1115 | −2039 | −402 | * | * | | | | | | | | | | | | |
| 845( ) | −30 | 439 | 11 | 363 | −394 | −739 | 699 | −414 | 463 | −757 | 501 | 286 | −577 | 639 | 165 | −23 | 111 | −312 | 697 | −25 | 867 |
| | * | * | * | * | * | * | −2716 | * | 0 | * | * | * | * | * | * | * | * | * | * | * | |
| | | | | | | | 699 | | | | | | | | | | | | | | |

TABLE 7

```
HMMER2.0 [2.3.2]
NAME XFP N
ACC PF09364.1
DESC XFP N-terminal domain
LENG 396
ALPH Amino
RF no
CS no
MAP yes
COM hmmbuild -f -F HMM fs.ann SEED.ann
COM hmmcalibrate —seed 0 HMM fs.ann
NSEQ 6
DATE Thu May 3 17:57:17 2007
CKSUM 7893
GA 15.1 15.1
TC 15.1 15.1
NC 14.6 14.6
XT -8455 -4 -1000 -1000 -8455 -4 -8455 -4
NULT -4 -8455
NULE 595 -1558 85 338 -294 453 -1158 197 249 902 -1085 -142 -21 -313 45 531 201 384 -1998 -644
EVD -10.948357 0.672333
```

| HMM | A<br>m->m | C<br>m->i | D<br>m->d | E<br>i->m | F<br>i->i | G<br>d->m | H<br>d->d | I<br>b->m | K<br>m->e | L | M | N | P | Q | R | S | T | V | W | Y | |
|---|---|---|---|---|---|---|---|---|---|---|---|---|---|---|---|---|---|---|---|---|---|
|  | -193 | * | -3000 |  |  |  |  |  |  |  |  |  |  |  |  |  |  |  |  |  |  |
| 1(K) | -1968 | -2951 | -2155 | -1320 | -3390 | -2747 | -966 | -3007 | 2330 | -2844 | -2086 | -1422 | 2165 | -549 | 1590 | -1872 | -1791 | -2712 | -2821 | 1937 | 1 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -11 | -7944 | -8986 | -894 | -1115 | -701 | -1378 | -1193 | -9626 |  |  |  |  |  |  |  |  |  |  |  |  |
| 2(I) | -1769 | -1476 | -4090 | -3550 | -1526 | -3579 | -2618 | 2387 | -3249 | 1441 | -544 | 1396 | -3532 | -2933 | -3155 | -2723 | -1726 | 1550 | -2406 | -2063 | 2 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -11 | -7944 | -8986 | -894 | -1115 | -701 | -1378 | -9818 | -9624 |  |  |  |  |  |  |  |  |  |  |  |  |
| 3(S) | -1378 | -2318 | 1402 | -1145 | -3726 | -2032 | -1821 | -3503 | -1805 | -3583 | -2748 | -1309 | -2587 | -1497 | -2321 | 2452 | 2280 | -2794 | -3796 | -3178 | 3 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -11 | -7944 | -8986 | -894 | -1115 | -701 | -1378 | -9818 | -9622 |  |  |  |  |  |  |  |  |  |  |  |  |
| 4(D) | -2415 | -4334 | 2560 | 2263 | -4523 | -2295 | -1677 | -4467 | -1966 | -4327 | -3682 | -889 | 2279 | -1352 | -2856 | -2064 | -2494 | -3929 | -4515 | -3478 | 4 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -11 | -7944 | -8986 | -894 | -1115 | -701 | -1378 | -9818 | -9620 |  |  |  |  |  |  |  |  |  |  |  |  |
| 5(E) | 818 | -2294 | -768 | 2387 | -2689 | -1890 | -629 | -2403 | -181 | -2389 | -1504 | -596 | -2035 | -193 | 1173 | -879 | 979 | -1984 | -2580 | -1944 | 5 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -11 | -7944 | -8986 | -894 | -1115 | -701 | -1378 | -9818 | -9618 |  |  |  |  |  |  |  |  |  |  |  |  |
| 6(Y) | 868 | -2568 | -747 | 2575 | -2297 | -2202 | -1201 | -2582 | -1098 | -2680 | -1956 | -1001 | -2523 | -938 | -1573 | -1484 | -1571 | -2270 | -2610 | 2844 | 6 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -11 | -7944 | -8986 | -894 | -1115 | -701 | -1378 | -9818 | -9617 |  |  |  |  |  |  |  |  |  |  |  |  |
| 7(L) | -2772 | -2280 | -5308 | -4845 | -1620 | -5006 | -4218 | 1675 | -4673 | 2505 | -404 | -4676 | -4560 | -4047 | -4494 | -4304 | -2713 | 1658 | -3269 | -3192 | 7 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -11 | -7944 | -8986 | -894 | -1115 | -701 | -1378 | -9818 | -9615 |  |  |  |  |  |  |  |  |  |  |  |  |
| 8(H) | 899 | -2380 | -623 | 1169 | -2703 | -1834 | 2073 | -2447 | 1918 | -2389 | -1478 | 1301 | -1952 | -64 | -563 | -794 | -860 | -2005 | -2553 | -1878 | 8 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -11 | -7944 | -8986 | -894 | -1115 | -701 | -1378 | -9818 | -9613 |  |  |  |  |  |  |  |  |  |  |  |  |

TABLE 7-continued

| | | | | | | | | | | | | | | | | | | |
|---|---|---|---|---|---|---|---|---|---|---|---|---|---|---|---|---|---|---|
| 9(K) | −1161 | −2683 | 1251 | −212 | −2990 | 727 | −723 | −2756 | 1972 | −2690 | −1794 | 1663 | −2115 | 1586 | −911 | −1006 | −1116 | −2301 | −2857 | −2139 | 9 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9611 |  |  |  |  |  |  |  |  |  |  |  |  |
| 10(M) | −2709 | −2269 | −5162 | −4623 | −1349 | −4724 | −3702 | 1512 | −4374 | 1792 | 3396 | −4390 | −4320 | −3675 | −4116 | −3951 | −2630 | 1553 | −2866 | −2812 | 10 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9609 |  |  |  |  |  |  |  |  |  |  |  |  |
| 11(H) | −2820 | −4339 | 3411 | −925 | −4078 | −2615 | 3698 | −4807 | −2416 | −4617 | −4088 | −1308 | −3181 | −1809 | −3221 | −2491 | −2928 | −4293 | −4210 | −3302 | 11 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9607 |  |  |  |  |  |  |  |  |  |  |  |  |
| 12(K) | 1531 | −2609 | −1521 | −881 | −3185 | 677 | −855 | −2809 | 2197 | −2705 | −1875 | −1069 | −2428 | −423 | 1698 | −1376 | −1380 | −2418 | −2783 | −2320 | 12 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9605 |  |  |  |  |  |  |  |  |  |  |  |  |
| 13(Y) | −4639 | −3574 | −5042 | −5388 | 3053 | −4919 | −1116 | −3531 | −4943 | −2851 | −2938 | −3536 | −4775 | −3673 | −4311 | −4166 | −4491 | −3684 | 3607 | 3791 | 13 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9604 |  |  |  |  |  |  |  |  |  |  |  |  |
| 14(W) | −3826 | −3700 | −3776 | −3690 | −1600 | −3954 | −2357 | −4085 | −2609 | −3642 | −3464 | −3450 | −4249 | 2161 | −2584 | −3858 | −3853 | −4045 | 5840 | −1155 | 14 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9602 |  |  |  |  |  |  |  |  |  |  |  |  |
| 15(R) | −4488 | −4181 | −4789 | −4318 | −5193 | −4148 | −3436 | −5568 | −2393 | −5152 | −4748 | −4156 | −4479 | −3286 | 4202 | −4614 | −4467 | −5273 | −4267 | −4649 | 15 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9600 |  |  |  |  |  |  |  |  |  |  |  |  |
| 16(A) | 3208 | −1704 | −3999 | −4070 | −3276 | −2242 | −3400 | −1516 | −3824 | −2767 | −2340 | −2844 | −2960 | −3485 | −3660 | −1604 | −1654 | 1301 | −3916 | −3651 | 16 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9598 |  |  |  |  |  |  |  |  |  |  |  |  |
| 17(C) | 3231 | 3331 | −4290 | −4524 | −4051 | −2061 | −3603 | −3558 | −4177 | −4038 | −3241 | −2842 | −2850 | −3725 | −3864 | −1443 | −1636 | −2656 | −4310 | −4227 | 17 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9596 |  |  |  |  |  |  |  |  |  |  |  |  |
| 18(N) | −2093 | −3624 | 1842 | −565 | −4191 | −2225 | −1624 | −4071 | −1786 | −4008 | −3287 | 3436 | −2749 | −1290 | −2544 | −1859 | 1312 | −3511 | −4199 | −3291 | 18 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9594 |  |  |  |  |  |  |  |  |  |  |  |  |
| 19(Y) | −4605 | −3570 | −5021 | −5357 | 2115 | 4893 | −1140 | −3492 | −4921 | −2816 | −2906 | −3546 | −4765 | −3679 | −4305 | −4160 | −4468 | −3656 | −389 | 4545 | 19 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9592 |  |  |  |  |  |  |  |  |  |  |  |  |
| 20(L) | −3485 | −2916 | −5860 | −5269 | −1134 | −5582 | −4270 | 1416 | −5040 | 2720 | 2646 | −5288 | −4721 | −3890 | −4562 | −4907 | −3336 | −1219 | −2912 | −3094 | 20 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9591 |  |  |  |  |  |  |  |  |  |  |  |  |
| 21(A) | 2093 | −1633 | −3496 | −3406 | −3943 | 1228 | −3043 | −3705 | −3256 | −3935 | −3021 | −2418 | −2652 | −2942 | −3281 | 2007 | 1343 | −2649 | −4148 | −3944 | 21 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9589 |  |  |  |  |  |  |  |  |  |  |  |  |
| 22(I) | 1858 | −1782 | 4736 | −4347 | −2337 | −4240 | −3903 | 2415 | −4179 | −1341 | −1167 | −4002 | −4207 | −4002 | −4206 | −3513 | −2172 | 2258 | −3603 | −3167 | 22 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9587 |  |  |  |  |  |  |  |  |  |  |  |  |
| 23(G) | −1257 | −1874 | −3207 | −3523 | −4341 | 3341 | −3408 | −4248 | −3853 | −4463 | −3557 | −2605 | −2866 | −3402 | −3760 | −1410 | −1718 | −3031 | −4475 | −4358 | 23 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9585 |  |  |  |  |  |  |  |  |  |  |  |  |
| 24(M) | −2521 | −2386 | −3846 | −3279 | −1155 | −3984 | −2657 | −686 | −2594 | 1335 | 3429 | −3250 | −3784 | 3078 | −2603 | −3140 | −2428 | −1237 | −2461 | −2296 | 24 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9583 |  |  |  |  |  |  |  |  |  |  |  |  |
| 25(I) | −2891 | −2390 | −5370 | −4957 | −1628 | −5096 | −4334 | 3554 | −4751 | 1008 | −437 | −4806 | −4650 | −4141 | −4574 | −4462 | −2842 | −63 | −3311 | −3180 | 25 |
|  | −149 | −500 | 233 | 43 | −381 | 399 | 106 | −626 | 210 | −466 | −720 | 275 | 394 | 45 | 96 | 359 | 117 | −369 | −294 | −249 |  |
|  | −11 | −7944 | −8986 | −894 | −1115 | −701 | −1378 | −9818 | −9581 |  |  |  |  |  |  |  |  |  |  |  |  |

TABLE 7-continued

| | | | | | | | | | | | | | | | | | | |
|---|---|---|---|---|---|---|---|---|---|---|---|---|---|---|---|---|---|---|
| 26(Y) | −4614 −149 −11 | −3571 −500 −7944 | −5028 233 −8986 | −5366 43 −894 | 3123 −381 −1115 | −4901 399 −701 | −1136 106 −1378 | −3497 −626 −9818 | −4929 210 −9579 | −2819 −466 | −2909 −720 | −3545 275 | −4768 394 | −3679 45 | −4308 96 | −4163 359 | −4474 117 | −3661 −369 | −384 −294 | 4150 −249 | 26 |
| 27(L) | −4119 −149 | −3542 −500 −7944 | −5389 233 −8986 | −5357 43 −894 | −2027 −381 −1115 | −4767 399 −701 | −4358 106 −1378 | −1609 −626 −9818 | −5118 210 −9577 | 3293 −466 | −979 −720 | −5230 275 | −4771 394 | −4474 45 | −4724 96 | −5069 359 | −4106 117 | −2331 −369 | −3412 −294 | −3400 −249 | 27 |
| 28(R) | −1752 −149 −11 | −2663 −500 −7944 | −1994 233 −8986 | −1206 43 −894 | −3071 −381 −1115 | −2612 399 −701 | −927 106 −1378 | −2620 −626 −9818 | 1567 210 −9576 | 1194 −466 | −1815 −720 | −1326 275 | −2642 394 | −523 45 | 2318 96 | 1048 359 | −1606 117 | −2354 −369 | −2690 −294 | −2328 −249 | 28 |
| 29(D) | −2163 −149 −11 | −3991 −500 −7944 | 2853 233 −8986 | 1466 43 −894 | −4198 −381 −1115 | −2225 399 −701 | −1494 106 −1378 | −4086 −626 −9818 | −1627 210 −9574 | −3968 −466 | −3237 −720 | 1901 275 | −2710 394 | −1142 45 | −2410 96 | 971 359 | −2206 117 | −3573 −369 | −4159 −294 | −3203 −249 | 29 |
| 30(N) | −2100 −149 −11 | −2812 −500 −7944 | −1725 233 −8986 | −2071 43 −894 | −4541 −381 −1115 | 1400 399 −701 | −2845 106 −1378 | −4689 −626 −9818 | −3101 210 −9572 | −4717 −466 | −3995 −720 | 3948 275 | −3237 394 | −2675 45 | −3479 96 | −2189 359 | −2459 117 | −3750 −369 | −4448 −294 | −4114 −249 | 30 |
| 31(P) | −2845 −149 −11 | −2996 −500 −7944 | −4029 233 −8986 | −4118 43 −894 | −2821 −381 −1115 | −3470 399 −701 | −3585 106 −1378 | −2547 −626 −9818 | −3827 210 −9570 | 1069 −466 | −2145 −720 | −3734 275 | 3854 394 | −3778 45 | −3737 96 | −3186 359 | −3115 117 | −2756 −369 | −3564 −294 | −3278 −249 | 31 |
| 32(L) | −3571 −149 −11 | −3027 −500 −7944 | −4990 233 −8986 | −4839 43 −894 | −362 −381 −1115 | −4751 399 −701 | −2053 106 −1378 | −1386 −626 −9818 | −4381 210 −9568 | 2878 −466 | −762 −720 | −3969 275 | −4502 394 | −3586 45 | −4013 96 | −4093 359 | −3476 117 | −1986 −369 | −1288 −294 | 2490 −249 | 32 |
| 33(M) | −2211 −149 −11 | −1924 −500 −7944 | −4481 233 −8986 | −3865 43 −894 | 1786 −381 −1115 | −3872 399 −701 | −2670 106 −1378 | −469 −626 −9818 | −3517 210 −9566 | 2158 −466 | 2560 −720 | −3505 275 | −3670 394 | −2910 45 | −3263 96 | −3004 359 | 1361 117 | −903 −369 | −2139 −294 | −1963 −249 | 33 |
| 34(S) | −1891 87 −149 −34 | −526 −500 −6087 | −885 233 −7129 | −918 43 −894 | −1797 −381 −1115 | −699 399 −701 | −997 106 −1378 | −1679 −626 −9818 | −970 210 −9564 | −1948 −466 | −1267 −720 | −663 275 | −1335 394 | −874 45 | −1147 96 | 2826 359 | −252 117 | −1082 −369 | −2036 −294 | −1577 −249 | 34 |
| 35(V) | −734 −149 −34 | −692 −500 −6087 | −2391 233 −7129 | −2193 43 −894 | −909 −381 −1115 | −2832 399 −701 | −218 106 −1378 | 1094 −626 −9818 | −1922 210 −9562 | −136 −466 | −10 −720 | −1902 275 | −2325 394 | −1852 45 | −1974 96 | −1413 359 | −858 117 | 2960 −369 | −1857 −294 | −1405 −249 | 35 |
| 36(T) | −84 −149 −34 | −586 −500 −6087 | −1220 233 −7129 | −1166 43 −894 | −1618 −381 −1115 | −901 399 −701 | −1090 106 −1378 | −915 −626 −9818 | −1004 210 −9560 | −1405 −466 | −917 −720 | −886 275 | −1488 394 | −990 45 | −1134 96 | −317 359 | 3114 117 | −605 −369 | −1941 −294 | −1587 −249 | 36 |
| 37(R) | −2583 −149 −11 | −3338 −500 −7944 | −2968 233 −8986 | −1938 43 −894 | −4226 −381 −1115 | 2024 399 −701 | −1216 106 −1378 | −3597 −626 −9818 | 1648 210 −9558 | −3282 −466 | −2594 −720 | −1884 275 | −3156 394 | −798 45 | 2920 96 | −2479 359 | −2342 117 | −3324 −369 | −3144 −294 | −3007 −249 | 37 |
| 38(E) | −1678 −149 −11 | −2848 −500 −7944 | −628 233 −8986 | 2969 43 −894 | −3815 −381 −1115 | 1219 399 −701 | −1598 106 −1378 | −3602 −626 −9818 | −1552 210 −9557 | −3614 −466 | −2817 −720 | −1072 275 | −2634 394 | −1251 45 | −2123 96 | −1592 359 | 1327 117 | −3012 −369 | −3808 −294 | −3091 −249 | 38 |
| 39(P) | −3058 −149 −11 | −3915 −500 −7944 | 1871 233 −8986 | −1726 43 −894 | −4973 −381 −1115 | −2986 399 −701 | −2783 106 −1378 | −5207 −626 −9818 | −3189 210 −9555 | −5075 −466 | −4546 −720 | −2051 275 | 3849 394 | −2577 45 | −3857 96 | −2918 359 | −3276 117 | −4561 −369 | −4629 −294 | −4315 −249 | 39 |
| 40(L) | −3389 −149 −11 | −2846 −500 −7944 | −8986 233 −5732 | −5157 43 −894 | 1795 −381 −1115 | −5405 399 −701 | −3964 106 −1378 | 1554 −626 −9818 | −4913 210 −9553 | 2673 −466 | 66 −720 | −5067 275 | −4642 394 | −3819 45 | −4457 96 | −4697 359 | −3249 117 | −1211 −369 | −2753 −294 | −2720 −249 | 40 |
| 41(K) | −1121 −149 −11 | −2502 −500 −7944 | −1004 233 −8986 | 1296 43 −894 | −2888 −381 −1115 | −2042 399 −701 | −588 106 −1378 | −2583 −626 −9818 | 2027 210 −9551 | −2485 −466 | −1598 −720 | −681 275 | −2119 394 | 1586 45 | 1299 96 | −1000 359 | 1054 117 | −2164 −369 | −2595 −294 | −2010 −249 | 41 |
| 42(P) | 784 −149 −11 | −2052 −500 −7944 | −818 233 −8986 | 1262 43 −894 | −2296 −381 −1115 | −1869 399 −701 | −546 106 −1378 | −1970 −626 −9818 | −134 210 −9549 | 107 −466 | −1190 −720 | −567 275 | 1773 394 | −132 45 | 1208 96 | −813 359 | −814 117 | −1637 −369 | −2305 −294 | −1705 −249 | 42 |

TABLE 7-continued

| | | | | | | | | | | | | | | | | | |
|---|---|---|---|---|---|---|---|---|---|---|---|---|---|---|---|---|---|
| 43(E) | -2121 -149 -11 | -3903 -500 -7944 | 1652 233 -8986 | 3001 43 -894 | -4126 -381 -1115 | -2231 399 -701 | -1448 106 -1378 | -3991 -626 -9818 | 1462 210 -9547 | -3872 -466 | -3127 -720 | -825 275 | -2693 394 | -1089 45 | -2171 96 | -1828 359 | -2151 117 | -3493 -369 | -4045 -294 | -3137 -249 | 43 |
| 44(H) | -1900 -149 -11 | -3602 -500 -7944 | 2493 233 -8986 | -392 43 -894 | -3825 -381 -1115 | -2165 399 -701 | 3314 106 -1378 | -3680 -626 -9818 | -1250 210 -9545 | -3583 -466 | -2790 -720 | 1715 275 | -2572 394 | 1675 45 | -1911 96 | -1645 359 | -1910 117 | -3197 -369 | -3754 -294 | -2893 -249 | 44 |
| 45(I) | -2547 -149 -11 | -2059 -500 -7944 | -5152 233 -8986 | -4751 43 -894 | -2029 -381 -1115 | -4889 399 -701 | -4388 106 -1378 | 2502 -626 -9818 | -4626 210 -9543 | 1616 -466 | -797 -720 | -4548 275 | -4567 394 | -4264 45 | -4595 96 | -4202 359 | -2516 117 | 2260 -369 | -3637 -294 | -3383 -249 | 45 |
| 46(K) | -4125 -149 -11 | -4091 -500 -7944 | -4017 233 -8986 | -3615 43 -894 | -5101 -381 -1115 | -3960 399 -701 | -2958 106 -1378 | -5182 -626 -9818 | 3972 210 -9541 | -4825 -466 | -4345 -720 | -3552 275 | -4249 394 | -2709 45 | -1809 96 | -4154 359 | -4044 117 | -4895 -369 | -4132 -294 | -4389 -249 | 46 |
| 47(H) | 826 -149 -11 | -2035 -500 -7944 | -963 233 -8986 | -419 43 -894 | -2397 -381 -1115 | -1898 399 -701 | 3051 106 -1378 | -2073 -626 -9818 | -206 210 -9539 | -2136 -466 | -1290 -720 | -675 275 | 932 394 | -235 45 | 1162 96 | -866 359 | 1249 117 | -1718 -369 | -2394 -294 | -1810 -249 | 47 |
| 48(R) | -2700 -149 -11 | -3449 -500 -7944 | -3065 233 -8986 | -1955 43 -894 | -4296 -381 -1115 | -3222 399 -701 | -1177 106 -1378 | -3628 -626 -9818 | 1592 210 -9537 | -3280 -466 | -2601 -720 | 1619 275 | -3187 394 | -756 45 | 3400 96 | -2568 359 | -2401 117 | -3384 -369 | -3125 -294 | -3003 -249 | 48 |
| 49(L) | -2172 -149 -11 | -1972 -500 -7944 | -4362 233 -8986 | -3884 43 -894 | -1289 -381 -1115 | -3737 399 -701 | -2942 106 -1378 | -312 -626 -9818 | -3536 210 -9535 | 2565 -466 | -217 -720 | -3515 275 | 1361 394 | -3084 45 | -3377 96 | -2952 359 | -2169 117 | 1219 -369 | -2509 -294 | -2319 -249 | 49 |
| 50(V) | -2641 -149 -11 | -2155 -500 -7944 | -5210 233 -8986 | -4776 43 -894 | -1803 -381 -1115 | -4918 399 -701 | -4261 106 -1378 | 1765 -626 -9818 | -4623 210 -9533 | 2179 -466 | -584 -720 | -4583 275 | -4545 394 | -4128 45 | -4515 96 | -4219 359 | -2597 117 | 2215 -369 | -3420 -294 | -3258 -249 | 50 |
| 51(G) | -4088 -149 -11 | -3924 -500 -7944 | -4774 233 -8986 | -5139 43 -894 | -5615 -381 -1115 | 3825 399 -701 | -4753 106 -1378 | -6303 -626 -9818 | -5453 210 -9531 | -6014 -466 | -5662 -720 | -4812 275 | -4539 394 | -5232 45 | -5106 96 | -4370 359 | -4472 117 | -5527 -369 | -4696 -294 | -5561 -249 | 51 |
| 52(H) | -4836 -149 -11 | -4275 -500 -7944 | -4356 233 -8986 | -4629 43 -894 | -3663 -381 -1115 | -4242 399 -701 | 5422 106 -1378 | -5932 -626 -9818 | -4492 210 -9529 | -5436 -466 | -5298 -720 | -4579 275 | -4696 394 | -4620 45 | -4352 96 | -5005 359 | -5030 117 | -5648 -369 | -3750 -294 | -3259 -249 | 52 |
| 53(W) | -5598 -149 -11 | -4432 -500 -7944 | -5385 233 -8986 | -5722 43 -894 | -3380 -381 -1115 | -4524 399 -701 | -4140 106 -1378 | -5941 -626 -9818 | -5643 210 -9527 | -5318 -466 | -5354 -720 | -5427 275 | -4938 394 | -5474 45 | -5178 96 | -5909 359 | -5751 117 | -5890 -369 | 6275 -294 | -2993 -249 | 53 |
| 54(G) | -4088 -149 -11 | -3924 -500 -7944 | -4774 233 -8986 | -5139 43 -894 | -5615 -381 -1115 | 3825 399 -701 | -4753 106 -1378 | -6303 -626 -9818 | -5453 210 -9526 | -6014 -466 | -5662 -720 | -4812 275 | -4539 394 | -5232 45 | -5106 96 | -4370 359 | -4472 117 | -5527 -369 | -4696 -294 | -5561 -249 | 54 |
| 55(T) | -1093 -149 -11 | -1706 -500 -7944 | -3487 233 -8986 | -3693 43 -894 | -4074 -381 -1115 | -1966 399 -701 | -3302 106 -1378 | -3842 -626 -9818 | -3638 210 -9524 | -4134 -466 | -3253 -720 | -2558 275 | -2748 394 | -3296 45 | -3520 96 | 1110 359 | 3646 117 | -2760 -369 | -4304 -294 | -4125 -249 | 55 |
| 56(C) | -1052 -149 -11 | 2901 -500 -7944 | -3250 233 -8986 | -2679 43 -894 | -1060 -381 -1115 | -2526 399 -701 | -1634 106 -1378 | 1315 -626 -9818 | -2341 210 -9522 | -866 -466 | -266 -720 | -2229 275 | -2670 394 | -2018 45 | -2238 96 | 1521 359 | 1154 117 | 1349 -369 | -1596 -294 | -1246 -249 | 56 |
| 57(P) | -1362 -149 -11 | -1972 -500 -7944 | -3107 233 -8986 | -3390 43 -894 | -4250 -381 -1115 | -2166 399 -701 | -3327 106 -1378 | -4213 -626 -9818 | -3641 210 -9520 | -4411 -466 | -3553 -720 | -2613 275 | 3840 394 | -3308 45 | -3600 96 | 1256 359 | -1811 117 | -3082 -369 | -4372 -294 | -4198 -249 | 57 |
| 58(G) | -4088 -149 -11 | -3924 -500 -7944 | -4774 233 -8986 | -5139 43 -894 | -5615 -381 -1115 | 3825 399 -701 | -4753 106 -1378 | -6303 -626 -9818 | -5453 210 -9518 | -6014 -466 | -5662 -720 | -4812 275 | -4539 394 | -5232 45 | -5106 96 | -4370 359 | -4472 117 | -5527 -369 | -4696 -294 | -5561 -249 | 58 |
| 59(Q) | -2629 -149 -11 | -2340 -500 -7944 | -4433 233 -8986 | -3873 43 -894 | -1140 -381 -1115 | -4292 399 -701 | -3047 106 -1378 | 1389 -626 -9818 | -3342 210 -9516 | 2319 -466 | -20 -720 | -3746 275 | -4000 394 | 2559 45 | -3238 96 | -3469 359 | -2536 117 | -946 -369 | -2531 -294 | -2422 -249 | 59 |

TABLE 7-continued

| | | | | | | | | | | | | | | | | | | | | | |
|---|---|---|---|---|---|---|---|---|---|---|---|---|---|---|---|---|---|---|---|---|---|
| 60(S) | -1129 | -1869 | -2034 | -2027 | -3771 | -1956 | -2322 | -3546 | -2277 | -3697 | -2821 | 2528 | -2607 | -2062 | -2583 | 2544 | 1447 | -2665 | -3893 | -3470 | 60 |
| — | -149 | -500 | 233 | -894 | -381 | 399 | 106 | -626 | 210 | -466 | -720 | 275 | 394 | 45 | 96 | 359 | 117 | -369 | -294 | -249 | |
| — | -11 | -7944 | -8986 | | -1115 | -701 | -1378 | -9818 | -9514 | | | | | | | | | | | | |
| 61(F) | -3253 | -2755 | -5063 | -4895 | 3979 | -4679 | -2230 | 1673 | -4579 | -697 | -843 | -4029 | -4483 | -3735 | -4216 | -4008 | -3205 | -1123 | -1463 | -453 | 61 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9512 | | | | | | | | | | | | |
| 62(I) | -2667 | -2178 | -5235 | -4799 | -1779 | -4947 | -4278 | 2326 | -4646 | 2166 | -559 | -4613 | -4558 | -4130 | -4529 | -4251 | -2621 | 1716 | -3410 | -3264 | 62 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9510 | | | | | | | | | | | | |
| 63(Y) | -4030 | -3324 | -4830 | -4953 | 82 | -4664 | -1400 | -2548 | -4444 | 776 | -2024 | -3603 | -4588 | -3589 | -4024 | -4010 | -3953 | -2880 | -668 | 4492 | 63 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9508 | | | | | | | | | | | | |
| 64(A) | 2914 | -1624 | -3741 | -3790 | -3997 | -1911 | -3253 | -3736 | -3609 | -4009 | -3103 | -2541 | -2685 | -3231 | -3506 | 1407 | 1356 | -2665 | -4233 | -4079 | 64 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9506 | | | | | | | | | | | | |
| 65(H) | -4836 | -4275 | -4356 | -4629 | -3663 | -4242 | 5422 | -5932 | -4492 | -5436 | -5298 | -4579 | -4696 | -4620 | -4352 | -5005 | -5030 | -5648 | -3750 | -3259 | 65 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9504 | | | | | | | | | | | | |
| 66(C) | 868 | 2955 | -3843 | -3261 | -1152 | -3113 | -2129 | 1511 | -2905 | 1928 | -237 | -2799 | -3137 | -2521 | -2739 | -2241 | -1449 | -4 | -1921 | -1610 | 66 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9502 | | | | | | | | | | | | |
| 67(N) | -3642 | -3838 | -3004 | -3356 | -4743 | -3612 | -3773 | -5643 | -4099 | -5460 | -5060 | 4378 | -4185 | -3865 | -4225 | -3744 | -3950 | -5002 | -4391 | -4381 | 67 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9500 | | | | | | | | | | | | |
| 68(R) | -4488 | -4181 | -4789 | -4318 | -5193 | -4148 | -3436 | -5568 | -2393 | -5152 | -4748 | -4156 | -4479 | -3286 | 4202 | -4614 | -4467 | -5273 | -4267 | -4649 | 68 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9498 | | | | | | | | | | | | |
| 69(I) | 687 | -1693 | -4550 | -4054 | -1797 | -4053 | -3239 | 2451 | -3802 | 1595 | -714 | -3702 | -3939 | -3479 | -3713 | -3246 | -2027 | 1554 | -2897 | -2565 | 69 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9496 | | | | | | | | | | | | |
| 70(I) | -3202 | -2787 | -5004 | -4996 | -2836 | -4384 | -4440 | 3937 | -4838 | -1815 | -1871 | -4704 | -4600 | -4683 | -4704 | -4353 | -3280 | -603 | -3938 | -3661 | 70 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9494 | | | | | | | | | | | | |
| 71(N) | 777 | -2760 | -1484 | -853 | -3260 | -2383 | -822 | -2877 | 1407 | -2738 | -1911 | 2481 | -2455 | -385 | 2206 | -1436 | -1435 | -2500 | -2791 | -2332 | 71 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9492 | | | | | | | | | | | | |
| 72(K) | -1654 | -2912 | 1393 | -667 | -3173 | -2287 | -1055 | -2863 | 3038 | 286 | -2070 | -954 | -2512 | -658 | -811 | -1519 | -1598 | -2533 | -3029 | -2434 | 72 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9490 | | | | | | | | | | | | |
| 73(Y) | -3965 | -3303 | -4553 | -4498 | 2089 | -4562 | 2685 | -3175 | -3880 | -2696 | -2630 | -3283 | -4469 | -3249 | 1301 | -3756 | -3844 | -3248 | -415 | 3893 | 73 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9488 | | | | | | | | | | | | |
| 74(D) | -2647 | -4396 | 3720 | -698 | -4634 | -2448 | -1896 | -4723 | -2212 | -4559 | -3990 | -1090 | -3022 | 1848 | -3057 | -2298 | -2751 | -4181 | -4595 | -3647 | 74 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9486 | | | | | | | | | | | | |
| 75(Q) | 786 | -1836 | -2085 | -1707 | -1785 | -2491 | -1572 | -1296 | -1287 | 1558 | -860 | -1741 | -2731 | 3104 | -1481 | -1664 | -1471 | -1312 | -2370 | -1975 | 75 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9484 | | | | | | | | | | | | |
| 76(N) | -2189 | -3961 | 2351 | -476 | -4203 | -2257 | -1501 | -4079 | 1323 | -3955 | -3231 | 3154 | -2736 | -1150 | -2219 | -1890 | -2229 | -3577 | -4120 | -3208 | 76 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7944 | -8986 | -894 | -1115 | -701 | -1378 | -9818 | -9482 | | | | | | | | | | | | |

TABLE 7-continued

| | | | | | | | | | | | | | | | | | | | | | |
|---|---|---|---|---|---|---|---|---|---|---|---|---|---|---|---|---|---|---|---|---|---|
| 77(M)<br>— | -1639<br>-149<br>-11 | -1552<br>-500<br>-7944 | -3944<br>233<br>-8986 | -3485<br>43<br>-894 | -1584<br>-381<br>-1115 | -3112<br>399<br>-701 | -2598<br>106<br>-1378 | -102<br>-626<br>-9818 | -3126<br>210<br>-9480 | -813<br>-466 | 4345<br>-720 | -2996<br>275 | -3316<br>394 | -2834<br>45 | -3037<br>96 | -2326<br>359 | 1195<br>117 | 1340<br>-369 | -2475<br>-294 | -2167<br>-249 | 77 |
| 78(I)<br>— | -2541<br>-149<br>-11 | -2130<br>-500<br>-7944 | -4989<br>233<br>-8986 | -4447<br>43<br>-894 | 1768<br>-381<br>-1115 | -4503<br>399<br>-701 | -3473<br>106<br>-1378 | 2245<br>-626<br>-9818 | -4181<br>210<br>-9478 | 1829<br>-466 | -210<br>-720 | -4162<br>275 | -4181<br>394 | -3554<br>45 | -3947<br>96 | -3708<br>359 | -2469<br>117 | 1402<br>-369 | -2759<br>-294 | -2626<br>-249 | 78 |
| 79(Y)<br>— | -4613<br>-149<br>-11 | -3570<br>-500<br>-7944 | -5027<br>233<br>-8986 | -5365<br>43<br>-894 | 3096<br>-381<br>-1115 | -4900<br>399<br>-701 | -1135<br>106<br>-1378 | -3496<br>-626<br>-9818 | -4928<br>210<br>-9476 | -2818<br>-466 | -2908<br>-720 | -3544<br>275 | -4767<br>394 | -3678<br>45 | -4307<br>96 | -4162<br>359 | -4473<br>117 | -3660<br>-369 | -383<br>-294 | 4168<br>-249 | 79 |
| 80(M)<br>— | -2401<br>-149<br>-11 | -1938<br>-500<br>-7944 | -4995<br>233<br>-8986 | -4588<br>43<br>-894 | -2135<br>-381<br>-1115 | -4683<br>399<br>-701 | -4177<br>106<br>-1378 | 2411<br>-626<br>-9818 | -4441<br>210<br>-9474 | -955<br>-466 | 3356<br>-720 | -4340<br>275 | -4447<br>394 | -4169<br>45 | -4437<br>96 | -3971<br>359 | -2375<br>117 | 2371<br>-369 | -3610<br>-294 | -3272<br>-249 | 80 |
| 81(C)<br>— | -924<br>-149<br>-11 | 2595<br>-500<br>-7944 | -3097<br>233<br>-8986 | -2552<br>43<br>-894 | -1083<br>-381<br>-1115 | 823<br>399<br>-701 | -1551<br>106<br>-1378 | -560<br>-626<br>-9818 | -2221<br>210<br>-9472 | -963<br>-466 | 2359<br>-720 | -2072<br>275 | -2516<br>394 | -1903<br>45 | -2136<br>96 | 739<br>359 | -963<br>117 | 2007<br>-369 | -1573<br>-294 | -1229<br>-249 | 81 |
| 82(G)<br>— | -4088<br>-149<br>-11 | -3924<br>-500<br>-7944 | -4774<br>233<br>-8986 | -5139<br>43<br>-894 | -5615<br>-381<br>-1115 | 3825<br>399<br>-701 | -4753<br>106<br>-1378 | -6303<br>-626<br>-9818 | -5453<br>210<br>-9470 | -6014<br>-466 | -5662<br>-720 | -4812<br>275 | -4539<br>394 | -5232<br>45 | -5106<br>96 | -4370<br>359 | -4472<br>117 | -5527<br>-369 | -4696<br>-294 | -5561<br>-249 | 82 |
| 83(P)<br>— | -4497<br>-149<br>-11 | -4117<br>-500<br>-7944 | -4899<br>233<br>-8986 | -5251<br>43<br>-894 | -5560<br>-381<br>-1115 | -4139<br>399<br>-701 | -4798<br>106<br>-1378 | -6328<br>-626<br>-9818 | -5454<br>210<br>-9468 | -5976<br>-466 | -5741<br>-720 | -5026<br>275 | 4302<br>394 | -5328<br>45 | -5104<br>96 | -4798<br>359 | -4844<br>117 | -5739<br>-369 | -4665<br>-294 | -5484<br>-249 | 83 |
| 84(G)<br>— | -4088<br>-149<br>-11 | -3924<br>-500<br>-7944 | -4774<br>233<br>-8986 | -5139<br>43<br>-894 | -5615<br>-381<br>-1115 | 3825<br>399<br>-701 | -4753<br>106<br>-1378 | -6303<br>-626<br>-9818 | -5453<br>210<br>-9466 | -6014<br>-466 | -5662<br>-720 | -4812<br>275 | -4539<br>394 | -5232<br>45 | -5106<br>96 | -4370<br>359 | -4472<br>117 | -5527<br>-369 | -4696<br>-294 | -5561<br>-249 | 84 |
| 85(H)<br>— | -4836<br>-149<br>-11 | -4275<br>-500<br>-7944 | -4356<br>233<br>-8986 | -4629<br>43<br>-894 | -3663<br>-381<br>-1115 | -4242<br>399<br>-701 | 5422<br>106<br>-1378 | -5932<br>-626<br>-9818 | -4492<br>210<br>-9464 | -5436<br>-466 | -5298<br>-720 | -4579<br>275 | -4696<br>394 | -4620<br>45 | -4352<br>96 | -5005<br>359 | -5030<br>117 | -5648<br>-369 | -3750<br>-294 | -3259<br>-249 | 85 |
| 86(G)<br>— | -4088<br>-149<br>-11 | -3924<br>-500<br>-7944 | -4774<br>233<br>-8986 | -5139<br>43<br>-894 | -5615<br>-381<br>-1115 | 3825<br>399<br>-701 | -4753<br>106<br>-1378 | -6303<br>-626<br>-9818 | -5453<br>210<br>-9461 | -6014<br>-466 | -5662<br>-720 | -4812<br>275 | -4539<br>394 | -5232<br>45 | -5106<br>96 | -4370<br>359 | -4472<br>117 | -5527<br>-369 | -4696<br>-294 | -5561<br>-249 | 86 |
| 87(G)<br>— | 2125<br>-149<br>-11 | -1842<br>-500<br>-7944 | -3631<br>233<br>-8986 | -3927<br>43<br>-894 | -4350<br>-381<br>-1115 | 3048<br>399<br>-701 | -3538<br>106<br>-1378 | -4169<br>-626<br>-9818 | -4033<br>210<br>-9459 | -4428<br>-466 | -3528<br>-720 | -2733<br>275 | -2876<br>394 | -3575<br>45 | -3846<br>96 | -1489<br>359 | -1707<br>117 | -2984<br>-369 | -4482<br>-294 | -4443<br>-249 | 87 |
| 88(P)<br>— | -2640<br>-149<br>-11 | -3260<br>-500<br>-7944 | -2127<br>233<br>-8986 | -2297<br>43<br>-894 | -4320<br>-381<br>-1115 | -2987<br>399<br>-701 | -2661<br>106<br>-1378 | -4510<br>-626<br>-9818 | -2216<br>210<br>-9457 | -4379<br>-466 | -3792<br>-720 | -2411<br>275 | 3576<br>394 | 2864<br>45 | -2373<br>96 | -2683<br>359 | -2863<br>117 | -3935<br>-369 | -4069<br>-294 | -3806<br>-249 | 88 |
| 89(A)<br>— | 2982<br>-149<br>-11 | -1594<br>-500<br>-7944 | -3754<br>233<br>-8986 | -3796<br>43<br>-894 | -3529<br>-381<br>-1115 | 1052<br>399<br>-701 | -3162<br>106<br>-1378 | -2818<br>-626<br>-9818 | -3604<br>210<br>-9455 | -3423<br>-466 | -2664<br>-720 | -2573<br>275 | -2719<br>394 | -3219<br>45 | -3468<br>96 | -1317<br>359 | -1463<br>117 | 1086<br>-369 | -3887<br>-294 | -3678<br>-249 | 89 |
| 90(M)<br>— | -1348<br>-149<br>-11 | -1165<br>-500<br>-7944 | -3573<br>233<br>-8986 | -2973<br>43<br>-894 | 1525<br>-381<br>-1115 | 706<br>399<br>-701 | -1766<br>106<br>-1378 | 1561<br>-626<br>-9818 | -2606<br>210<br>-9453 | -377<br>-466 | 3758<br>-720 | -2527<br>275 | -2921<br>394 | -2210<br>45 | -2439<br>96 | -2009<br>359 | -1294<br>117 | -310<br>-369 | -1556<br>-294 | -1184<br>-249 | 90 |
| 91(V)<br>— | -1974<br>-149<br>-11 | -1692<br>-500<br>-7944 | -4373<br>233<br>-8986 | -3885<br>43<br>-894 | -1655<br>-381<br>-1115 | -3760<br>399<br>-701 | -3023<br>106<br>-1378 | 236<br>-626<br>-9818 | -3586<br>210<br>-9451 | 1658<br>-466 | -599<br>-720 | -3493<br>275 | -3751<br>394 | -3250<br>45 | -3485<br>96 | -2959<br>359 | 1156<br>117 | 2628<br>-369 | -2723<br>-294 | -2419<br>-249 | 91 |
| 92(S)<br>— | 1951<br>-149<br>-11 | -1569<br>-500<br>-7944 | -3422<br>233<br>-8986 | -3255<br>43<br>-894 | -3372<br>-381<br>-1115 | 1033<br>399<br>-701 | -2819<br>106<br>-1378 | -2999<br>-626<br>-9818 | -3074<br>210<br>-9449 | -3315<br>-466 | -2500<br>-720 | -2366<br>275 | -2636<br>394 | -2776<br>45 | -3104<br>96 | 2094<br>359 | -1382<br>117 | 1224<br>-369 | -3674<br>-294 | -3414<br>-249 | 92 |
| 93(N)<br>— | 1058<br>-149<br>-11 | -2388<br>-500<br>-7944 | -785<br>233<br>-8986 | -572<br>43<br>-894 | -3066<br>-381<br>-1115 | -1969<br>399<br>-701 | -1036<br>106<br>-1378 | -2804<br>-626<br>-9818 | -709<br>210<br>-9447 | -2811<br>-466 | -1947<br>-720 | 2272<br>275 | 2144<br>394 | 1706<br>45 | -1182<br>96 | -1128<br>359 | -1239<br>117 | -2319<br>-369 | -3013<br>-294 | -2367<br>-249 | 93 |

TABLE 7-continued

| | | | | | | | | | | | | | | | | | |
|---|---|---|---|---|---|---|---|---|---|---|---|---|---|---|---|---|---|
| 94(C) | −968 | 2761 | −3158 | −2743 | −1848 | −2096 | −2020 | −1352 | −2456 | 835 | −1054 | −2166 | −2572 | −2189 | −2458 | 2381 | 1213 | −1124 | −2305 | −1969 | 94 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9445 | | | | | | | | | | | | |
| 95(Y) | −4608 | −3570 | −5023 | −5360 | 2380 | −4895 | −1138 | −3494 | −4924 | −2817 | −2907 | −3545 | −4766 | −3679 | −4306 | −4161 | −4470 | −3658 | −386 | 4475 | 95 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9443 | | | | | | | | | | | | |
| 96(L) | −3428 | −2867 | −5794 | −5267 | −1216 | −5534 | −4333 | 1535 | −5028 | 2951 | −6 | −5264 | −4750 | −3972 | −4604 | −4907 | −3306 | −978 | −2993 | −3105 | 96 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9441 | | | | | | | | | | | | |
| 97(D) | −2629 | −4604 | 3026 | 2782 | −4770 | −2374 | −1828 | −4782 | −2235 | −4614 | −4052 | −973 | −2960 | −1523 | −3217 | −2241 | −2730 | −4225 | −4757 | −3689 | 97 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9439 | | | | | | | | | | | | |
| 98(G) | −2862 | −3768 | 1871 | −1615 | −5004 | 3370 | −2705 | −5181 | −3146 | −5060 | −4493 | −1931 | −3470 | −2488 | −3861 | −2740 | −3106 | −4452 | −4685 | −4318 | 98 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9437 | | | | | | | | | | | | |
| 99(T) | −1078 | −1695 | −3486 | −3659 | −4077 | −1954 | −3276 | −3853 | −3599 | −4130 | −3239 | −2539 | −2733 | −3255 | −3500 | 2681 | 2838 | −2756 | −4301 | −4124 | 99 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9435 | | | | | | | | | | | | |
| 100(Y) | −3992 | −3300 | −4836 | −4941 | 66 | −4664 | −1423 | −2456 | −4436 | 992 | −1925 | −3615 | −4579 | −3584 | −4019 | −4006 | −3913 | −2810 | −690 | 4437 | 100 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9433 | | | | | | | | | | | | |
| 101(S) | −1032 | −1663 | −3422 | −3512 | −4087 | 1390 | −3188 | −3870 | −3492 | −4107 | −3184 | −2468 | −2688 | −3124 | −3454 | 2496 | 2388 | −2740 | −4293 | −4121 | 101 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9430 | | | | | | | | | | | | |
| 102(E) | −1823 | −3131 | −875 | 2933 | −3614 | −2362 | −1174 | −3322 | −553 | −3205 | −2407 | −1048 | 1540 | −771 | 1382 | −1665 | −1779 | −2906 | −3277 | −2712 | 102 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9428 | | | | | | | | | | | | |
| 103(F) | 863 | −914 | −3349 | −2737 | 2502 | −2631 | −1388 | −298 | −2350 | 698 | −39 | −2234 | −2667 | −1962 | −2166 | −1719 | −1033 | 1141 | −1185 | 1869 | 103 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9426 | | | | | | | | | | | | |
| 104(Y) | −4352 | −3468 | 4770 | −5008 | 2112 | −4760 | −1124 | −3396 | −4660 | −2798 | −2831 | 1505 | −4661 | −3557 | −4156 | −4005 | −4236 | −3515 | −387 | 4271 | 104 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9424 | | | | | | | | | | | | |
| 105(P) | 1085 | −2001 | −3515 | −3791 | −4319 | −2231 | −3514 | −4118 | −3884 | −4378 | −3566 | −2802 | 3892 | −3541 | −3758 | −1662 | −1872 | −3068 | −4416 | −4363 | 105 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9422 | | | | | | | | | | | | |
| 106(N) | −1628 | −3254 | 1441 | 2076 | −3527 | −2085 | −1091 | −3331 | −913 | −3246 | −2403 | 2397 | −2414 | −688 | 1516 | −1414 | −1613 | −2859 | −3417 | −2622 | 106 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9420 | | | | | | | | | | | | |
| 107(I) | −1569 | 2626 | −3973 | −3416 | −1377 | −3324 | −2311 | 2751 | −3082 | −941 | −528 | −2965 | −3319 | −2753 | −2944 | −2457 | −1527 | 1473 | −2109 | 2078 | 107 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9418 | | | | | | | | | | | | |
| 108(T) | 908 | −1834 | −1592 | −1168 | −2951 | −1885 | −1379 | −2651 | −1086 | −2760 | −1898 | −1245 | −2295 | 1915 | −1496 | 1739 | 2152 | −2098 | −3019 | −2494 | 108 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9416 | | | | | | | | | | | | |
| 109(M) | −879 | −2216 | −787 | 1054 | 1375 | −1857 | −485 | −2215 | 1265 | −2203 | 1871 | −512 | −1943 | 1655 | 1154 | −781 | −811 | −1824 | −2400 | −1773 | 109 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9414 | | | | | | | | | | | | |
| 110(D) | −2264 | −3415 | 3677 | −1019 | −4473 | −2407 | −2124 | −4366 | −2457 | −4415 | −3784 | −1339 | −3017 | −1850 | −3214 | −2128 | 1551 | −3724 | −4492 | −3732 | 110 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7944 | −8986 | −894 | −1115 | −701 | −1378 | −9818 | −9412 | | | | | | | | | | | | |

TABLE 7-continued

| | | | | | | | | | | | | | | | | |
|---|---|---|---|---|---|---|---|---|---|---|---|---|---|---|---|---|
| 111(E) | −1628 −149 −11 | −2756 −500 −7944 | −1092 233 −8986 | 2433 43 −894 | −3004 −381 −1115 | −2358 399 −701 | −986 106 −1378 | −2615 −626 −9818 | 1561 210 −9409 | 1281 −466 | −1850 −720 | −1034 275 | −2517 394 | −587 45 | −533 96 | −1527 359 | −1543 117 | −2348 −369 | −2851 −294 | −2339 −249 | 111 |
| 112(E) | 800 −149 −11 | −2932 −500 −7944 | 1355 233 −8986 | 2151 43 −894 | −3219 −381 −1115 | −1985 399 −701 | −890 106 −1378 | −3005 −626 −9818 | −643 210 −9407 | −2935 −466 | −2058 −720 | 1450 275 | −2244 394 | 1611 45 | −1220 96 | −1179 359 | −1330 117 | −2541 −369 | −3109 −294 | −2350 −249 | 112 |
| 113(G) | −4088 −149 −11 | −3924 −500 −7944 | −4774 233 −8986 | −5139 43 −894 | −5615 −381 −1115 | 3825 399 −701 | −4753 106 −1378 | −6303 −626 −9818 | −5453 210 −9405 | −6014 −466 | −5662 −720 | −4812 275 | −4539 394 | −5232 45 | −5106 96 | −4370 359 | −4472 117 | −5527 −369 | −4696 −294 | −5561 −249 | 113 |
| 114(M) | −3599 −149 −11 | −3029 −500 −7944 | −5877 233 −8986 | −5316 43 −894 | −1121 −381 −1115 | −5599 399 −701 | −4270 106 −1378 | −608 −626 −9818 | −5016 210 −9403 | 2422 −466 | 4020 −720 | −5344 275 | −4752 394 | −3899 45 | −4542 96 | −4979 359 | −3452 117 | −1416 −369 | −2899 −294 | −3042 −249 | 114 |
| 115(K) | −1165 −149 −11 | −2535 −500 −7944 | −1051 233 −8986 | −455 43 −894 | −2930 −381 −1115 | −2079 399 −701 | −612 106 −1378 | −2618 −626 −9818 | 1972 210 −9401 | −2514 −466 | −1633 −720 | 1596 275 | −2153 394 | 1677 45 | 1320 96 | 873 359 | −1075 117 | −2202 −369 | −2617 −294 | −2045 −249 | 115 |
| 116(K) | −2618 −149 −11 | −3410 −500 −7944 | −2984 233 −8986 | −1883 43 −894 | −4230 −381 −1115 | −3176 399 −701 | −1148 106 −1378 | −3580 −626 −9818 | 2782 210 −9399 | −3243 −466 | −2552 −720 | 1766 275 | −3140 394 | −725 45 | 2514 96 | −2486 359 | −2331 117 | −3326 −369 | −3100 −294 | −2957 −249 | 116 |
| 117(L) | −3686 −149 −11 | −3083 −500 −7944 | −5668 233 −8986 | −5295 43 −894 | −2704 −381 −1115 | −5391 399 −701 | −3131 106 −1378 | −837 −626 −9818 | −5017 210 −9397 | 2713 −466 | −141 −720 | −4846 275 | −4727 394 | −3862 45 | −4511 96 | −4763 359 | −3544 117 | −1624 −369 | −2119 −294 | −1439 −249 | 117 |
| 118(F) | −2097 −149 −11 | 2719 −500 −7944 | −4399 233 −8986 | −3936 43 −894 | 3542 −381 −1115 | −3704 399 −701 | −2285 106 −1378 | 1698 −626 −9818 | −3592 210 −9394 | −670 −466 | −559 −720 | −3345 275 | −3691 394 | −3092 45 | −3380 96 | −2887 359 | −2074 117 | −315 −369 | −1780 −294 | −1028 −249 | 118 |
| 119(K) | −2616 −149 −11 | −3410 −500 −7944 | −2980 233 −8986 | −1881 43 −894 | −4228 −381 −1115 | −3175 399 −701 | −1148 106 −1378 | −3580 −626 −9818 | 2804 210 −9392 | −3243 −466 | −2552 −720 | 1766 275 | −3139 394 | −724 45 | 2483 96 | −2484 359 | −2330 117 | −3325 −369 | −3099 −294 | −2957 −249 | 119 |
| 120(Q) | −1950 −149 −11 | −2899 −500 −7944 | −2068 233 −8986 | −1380 43 −894 | −3575 −381 −1115 | −2688 399 −701 | −1085 106 −1378 | −3122 −626 −9818 | 5 210 −9390 | −2965 −466 | −2212 −720 | −1472 275 | −2788 394 | 3499 45 | 1706 96 | −1878 359 | 1393 117 | −2788 −369 | −2974 −294 | −2647 −249 | 120 |
| 121(F) | −4720 −149 −11 | −3927 −500 −7944 | −5139 233 −8986 | −5454 43 −894 | 4513 −381 −1115 | −4504 399 −701 | −2520 106 −1378 | −3938 −626 −9818 | −5326 210 −9388 | −3307 −466 | −3429 −720 | −4469 275 | −4782 394 | −4575 45 | −4818 96 | −4787 359 | −4810 117 | −4172 −369 | −1812 −294 | −736 −249 | 121 |
| 122(S) | −1944 −149 −11 | −2458 −500 −7944 | −3696 233 −8986 | −4011 43 −894 | −4410 −381 −1115 | −2644 399 −701 | −3753 106 −1378 | −4675 −626 −9818 | −4191 210 −9386 | −4807 −466 | −4070 −720 | −3198 275 | −3384 394 | −3886 45 | −4051 96 | 3656 359 | −2393 117 | −3615 −369 | −4374 −294 | −4307 −249 | 122 |
| 123(F) | −4150 −149 −11 | −3318 −500 −7944 | −4992 233 −8986 | −5163 43 −894 | 3777 −381 −1115 | −4801 399 −701 | −1232 106 −1378 | −2695 −626 −9818 | −4739 210 −9384 | 954 −466 | −2105 −720 | −3556 275 | −4637 394 | −3592 45 | −4183 96 | −4031 359 | −4023 117 | −3011 −369 | −484 −294 | 2534 −249 | 123 |
| 124(P) | −4497 −149 −11 | −4117 −500 −7944 | −4899 233 −8986 | −5251 43 −894 | −5560 −381 −1115 | −4139 399 −701 | −4798 106 −1378 | −6328 −626 −9818 | −5454 210 −9382 | −5976 −466 | −5741 −720 | −5026 275 | −4302 394 | −5328 45 | −5104 96 | −4798 359 | −4844 117 | −5739 −369 | −4665 −294 | −5484 −249 | 124 |
| 125(G) | −4088 −149 −11 | −3924 −500 −7944 | −4774 233 −8986 | −5139 43 −894 | −5615 −381 −1115 | 3825 399 −701 | −4753 106 −1378 | −6303 −626 −9818 | −5453 210 −9379 | −6014 −466 | −5662 −720 | −4812 275 | −4539 394 | −5232 45 | −5106 96 | −4370 359 | −4472 117 | −5527 −369 | −4696 −294 | −5561 −249 | 125 |
| 126(G) | −4088 −149 −11 | −3924 −500 −7944 | −4774 233 −8986 | −5139 43 −894 | −5615 −381 −1115 | 3825 399 −701 | −4753 106 −1378 | −6303 −626 −9818 | −5453 210 −9377 | −6014 −466 | −5662 −720 | −4812 275 | −4539 394 | −5232 45 | −5106 96 | −4370 359 | −4472 117 | −5527 −369 | −4696 −294 | −5561 −249 | 126 |
| 127(I) | −2878 −149 −11 | −2414 −500 −7944 | −5081 233 −8986 | −4778 43 −894 | 2015 −381 −1115 | −4697 399 −701 | −2956 106 −1378 | 3488 −626 −9818 | −4533 210 −9375 | −580 −466 | −695 −720 | −4245 275 | −4462 394 | −3882 45 | −4297 96 | −4026 359 | −2840 117 | −329 −369 | −2190 −294 | −1350 −249 | 127 |

TABLE 7-continued

| | | | | | | | | | | | | | | | | | | |
|---|---|---|---|---|---|---|---|---|---|---|---|---|---|---|---|---|---|---|
| 128(P) | -1112 -149 -11 | -1752 -500 -7944 | -3015 233 -8986 | -3242 43 -894 | -4210 -381 -1115 | 2077 399 -701 | -3186 106 -1378 | -4033 -626 -9818 | -3529 210 -9373 | -4251 -466 | -3331 -720 | -2415 275 | 3138 394 | -3114 45 | -3525 96 | 1101 359 | -1561 117 | -2858 -369 | -4391 -294 | -4208 -249 | 128 |
| 129(S) | -1944 -149 -11 | -2458 -500 -7944 | -3696 233 -8986 | -4011 43 -894 | -4410 -381 -1115 | -2644 399 -701 | -3753 106 -1378 | -4675 -626 -9818 | -4191 210 -9371 | -4807 -466 | -4070 -720 | -3198 275 | -3384 394 | -3886 45 | -4051 96 | 3656 359 | -2393 117 | -3615 -369 | -4374 -294 | -4307 -249 | 129 |
| 130(H) | -4836 -149 -11 | -4275 -500 -7944 | -4356 233 -8986 | -4629 43 -894 | -3663 -381 -1115 | -4242 399 -701 | 5422 106 -1378 | -5932 -626 -9818 | -4492 210 -9369 | -5436 -466 | -5298 -720 | -4579 275 | -4696 394 | -4620 45 | -4352 96 | -5005 359 | -5030 117 | -5648 -369 | -3750 -294 | -3259 -249 | 130 |
| 131(M) | 726 -149 -11 | 2516 -500 -7944 | -3320 233 -8986 | -2699 43 -894 | 1540 -381 -1115 | -2560 399 -701 | -1464 106 -1378 | -135 -626 -9818 | -2311 210 -9366 | -587 -466 | 3158 -720 | -2207 275 | -2612 394 | -1942 45 | -2131 96 | -1653 359 | -952 117 | 1415 -369 | -1331 -294 | -989 -249 | 131 |
| 132(A) | 2437 -149 -11 | -1736 -500 -7944 | -2547 233 -8986 | -2496 43 -894 | -3668 -381 -1115 | -1942 399 -701 | -2557 106 -1378 | -3365 -626 -9818 | -2590 210 -9364 | -3601 -466 | -2745 -720 | 1872 275 | -2625 394 | -2364 45 | -2796 96 | -1269 359 | 2286 117 | -2528 -369 | -3861 -294 | -3523 -249 | 132 |
| 133(P) | 2199 -149 -11 | -1920 -500 -7944 | -3558 233 -8986 | -3810 43 -894 | -4266 -381 -1115 | -2163 399 -701 | -3478 106 -1378 | -4045 -626 -9818 | -3859 210 -9362 | -4314 -466 | -3481 -720 | -2754 275 | 3455 394 | -3500 45 | -3727 96 | -1576 359 | -1785 117 | -2985 -369 | -4394 -294 | -4324 -249 | 133 |
| 134(E) | -2302 -149 -11 | -4193 -500 -7944 | 1609 233 -8986 | 3106 43 -894 | -4369 -381 -1115 | -2263 399 -701 | -1582 106 -1378 | -4283 -626 -9818 | -1777 210 -9360 | -4150 -466 | -3462 -720 | -851 275 | -2781 394 | 1870 45 | -2594 96 | -1969 359 | -2359 117 | -3762 -369 | -4338 -294 | -3341 -249 | 134 |
| 135(T) | -1509 -149 -11 | -1748 -500 -7944 | -4032 233 -8986 | -3964 43 -894 | -2803 -381 -1115 | -2637 399 -701 | -3374 106 -1378 | -581 -626 -9818 | -3680 210 -9358 | -2093 -466 | -1801 -720 | -3053 275 | -3237 394 | -3460 45 | -3596 96 | -1989 359 | 3160 117 | 2274 -369 | -3655 -294 | -3308 -249 | 135 |
| 136(P) | -4497 -149 -11 | -4117 -500 -7944 | -4899 233 -8986 | -5251 43 -894 | -5560 -381 -1115 | -4139 399 -701 | -4798 106 -1378 | -6328 -626 -9818 | -5454 210 -9355 | -5976 -466 | -5741 -720 | -5026 275 | 4302 394 | -5328 45 | -5104 96 | -4798 359 | -4844 117 | -5739 -369 | -4665 -294 | -5484 -249 | 136 |
| 137(G) | -4088 -149 -11 | -3924 -500 -7944 | -4774 233 -8986 | -5139 43 -894 | -5615 -381 -1115 | 3825 399 -701 | -4753 106 -1378 | -6303 -626 -9818 | -5453 210 -9353 | -6014 -466 | -5662 -720 | -4812 275 | -4539 394 | -5232 45 | -5106 96 | -4370 359 | -4472 117 | -5527 -369 | -4696 -294 | -5561 -249 | 137 |
| 138(S) | 1402 -149 -11 | -1678 -500 -7944 | -3661 233 -8986 | -3893 43 -894 | -4185 -381 -1115 | -1940 399 -701 | -3408 106 -1378 | -3979 -626 -9818 | -3851 210 -9351 | -4254 -466 | -3335 -720 | -2598 275 | -2733 394 | -3421 45 | -3678 96 | 3267 359 | -1525 117 | -2799 -369 | -4407 -294 | -4277 -249 | 138 |
| 139(I) | -2917 -149 -11 | -2413 -500 -7944 | -5393 233 -8986 | -4971 43 -894 | -1597 -381 -1115 | -5119 399 -701 | -4331 106 -1378 | 3518 -626 -9818 | -4766 210 -9349 | 1140 -466 | -403 -720 | -4828 275 | -4654 394 | -4126 45 | -4574 96 | -4483 359 | -2863 117 | -105 -369 | -3287 -294 | -3176 -249 | 139 |
| 140(H) | -2691 -149 -11 | -3511 -500 -7944 | -1351 233 -8986 | -1619 43 -894 | -2597 -381 -1115 | -2858 399 -701 | 4977 106 -1378 | -4322 -626 -9818 | -2002 210 -9347 | -4099 -466 | -3606 -720 | 1623 275 | -3363 394 | -2027 45 | -2266 96 | -2576 359 | -2835 117 | -3872 -369 | -2991 -294 | -2056 -249 | 140 |
| 141(E) | -4205 -149 -11 | -4417 -500 -7944 | -2343 233 -8986 | 3901 43 -894 | -5349 -381 -1115 | -3698 399 -701 | -3534 106 -1378 | -5837 -626 -9818 | -3838 210 -9344 | -5561 -466 | -5237 -720 | -3039 275 | -4218 394 | -3453 45 | -4201 96 | -4072 359 | -4352 117 | -5409 -369 | -4640 -294 | -4860 -249 | 141 |
| 142(G) | -4088 -149 -11 | -3924 -500 -7944 | -4774 233 -8986 | -5139 43 -894 | -5615 -381 -1115 | 3825 399 -701 | -4753 106 -1378 | -6303 -626 -9818 | -5453 210 -9342 | -6014 -466 | -5662 -720 | -4812 275 | -4539 394 | -5232 45 | -5106 96 | -4370 359 | -4472 117 | -5527 -369 | -4696 -294 | -5561 -249 | 142 |
| 143(G) | -4088 -149 -11 | -3924 -500 -7944 | -4774 233 -8986 | -5139 43 -894 | -5615 -381 -1115 | 3825 399 -701 | -4753 106 -1378 | -6303 -626 -9818 | -5453 210 -9340 | -6014 -466 | -5662 -720 | -4812 275 | -4539 394 | -5232 45 | -5106 96 | -4370 359 | -4472 117 | -5527 -369 | -4696 -294 | -5561 -249 | 143 |
| 144(E) | -4205 -149 -11 | -4417 -500 -7944 | -2343 233 -8986 | 3901 43 -894 | -5349 -381 -1115 | -3698 399 -701 | -3534 106 -1378 | -5837 -626 -9818 | -3838 210 -9338 | -5561 -466 | -5237 -720 | -3039 275 | -4218 394 | -3453 45 | -4201 96 | -4072 359 | -4352 117 | -5409 -369 | -4640 -294 | -4860 -249 | 144 |

TABLE 7-continued

| | | | | | | | | | | | | | | | | | | | | | |
|---|---|---|---|---|---|---|---|---|---|---|---|---|---|---|---|---|---|---|---|---|---|
| 145(L) <br> — | -4119 <br> -149 <br> -11 | -3542 <br> -500 <br> -7944 | -5389 <br> 233 <br> -8986 | -5357 <br> 43 <br> -894 | -2027 <br> -381 <br> -1115 | -4767 <br> 399 <br> -701 | -4358 <br> 106 <br> -1378 | -1609 <br> -626 <br> -9818 | -5118 <br> 210 <br> -9335 | 3293 <br> -466 | -979 <br> -720 | -5230 <br> 275 | -4771 <br> 394 | -4474 <br> 45 | -4724 <br> 96 | -5069 <br> 359 | -4106 <br> 117 | -2331 <br> -369 | -3412 <br> -294 | -3400 <br> -249 | 145 |
| 146G <br> — | -4088 <br> -149 <br> -11 | -3924 <br> -500 <br> -7944 | -4774 <br> 233 <br> -8986 | -5139 <br> 43 <br> -894 | -5615 <br> -381 <br> -1115 | 3825 <br> 399 <br> -701 | -4753 <br> 106 <br> -1378 | -6303 <br> -626 <br> -9818 | -5453 <br> 210 <br> -9333 | -6014 <br> -466 | -5662 <br> -720 | -4812 <br> 275 | -4539 <br> 394 | -5232 <br> 45 | -5106 <br> 96 | -4370 <br> 359 | -4472 <br> 117 | -5527 <br> -369 | -4696 <br> -294 | -5561 <br> -249 | 146 |
| 147Y <br> — | -4791 <br> -149 <br> -11 | -3935 <br> -500 <br> -7944 | -4914 <br> 233 <br> -8986 | -5231 <br> 43 <br> -894 | -815 <br> -381 <br> -1115 | -4530 <br> 399 <br> -701 | -2178 <br> 106 <br> -1378 | -4357 <br> -626 <br> -9818 | -5024 <br> 210 <br> -9331 | -3745 <br> -466 | -3807 <br> -720 | -4206 <br> 275 | -4772 <br> 394 | -4328 <br> 45 | -4584 <br> 96 | -4677 <br> 359 | -4837 <br> 117 | -4435 <br> -369 | -1477 <br> -294 | 4857 <br> -249 | 147 |
| 148C <br> — | 2078 <br> -149 <br> -11 | 2882 <br> -500 <br> -7944 | -3724 <br> 233 <br> -8986 | -3518 <br> 43 <br> -894 | -2695 <br> -381 <br> -1115 | -2001 <br> 399 <br> -701 | -2704 <br> 106 <br> -1378 | -2106 <br> -626 <br> -9818 | -3218 <br> 210 <br> -9329 | -2589 <br> -466 | -1876 <br> -720 | -2467 <br> 275 | -2661 <br> 394 | -2861 <br> 45 | -3107 <br> 96 | 1882 <br> 359 | -1336 <br> 117 | 1253 <br> -369 | -3116 <br> -294 | -2838 <br> -249 | 148 |
| 149(L) <br> — | -4119 <br> -149 <br> -11 | -3542 <br> -500 <br> -7944 | -5389 <br> 233 <br> -8986 | -5357 <br> 43 <br> -894 | -2027 <br> -381 <br> -1115 | -4767 <br> 399 <br> -701 | -4358 <br> 106 <br> -1378 | -1609 <br> -626 <br> -9818 | -5118 <br> 210 <br> -9326 | 3293 <br> -466 | -979 <br> -720 | -5230 <br> 275 | -4771 <br> 394 | -4474 <br> 45 | -4724 <br> 96 | -5069 <br> 359 | -4106 <br> 117 | -2331 <br> -369 | -3412 <br> -294 | -3400 <br> -249 | 149 |
| 150(S) <br> — | 1113 <br> -149 <br> -11 | -1682 <br> -500 <br> -7944 | -3645 <br> 233 <br> -8986 | -3884 <br> 43 <br> -894 | -4190 <br> -381 <br> -1115 | -1942 <br> 399 <br> -701 | -3410 <br> 106 <br> -1378 | -3986 <br> -626 <br> -9818 | -3853 <br> 210 <br> -9324 | -4261 <br> -466 | -3343 <br> -720 | -2598 <br> 275 | -2736 <br> 394 | -3423 <br> 45 | -3680 <br> 96 | 3340 <br> 359 | -1530 <br> 117 | -2804 <br> -369 | -4411 <br> -294 | -4280 <br> -249 | 150 |
| 151(H) <br> — | -2323 <br> -149 <br> -11 | -2561 <br> -500 <br> -7944 | -3097 <br> 233 <br> -8986 | -3086 <br> 43 <br> -894 | -1647 <br> -381 <br> -1115 | -3098 <br> 399 <br> -701 | 4888 <br> 106 <br> -1378 | -2143 <br> -626 <br> -9818 | -2537 <br> 210 <br> -9322 | -2630 <br> -466 | -2333 <br> -720 | -2801 <br> 275 | -3547 <br> 394 | -2728 <br> 45 | -2559 <br> 96 | -2581 <br> 359 | -2516 <br> 117 | 1445 <br> -369 | -2255 <br> -294 | -1333 <br> -249 | 151 |
| 152A <br> — | 2928 <br> -149 <br> -11 | -1667 <br> -500 <br> -7944 | -3720 <br> 233 <br> -8986 | -3939 <br> 43 <br> -894 | -4168 <br> -381 <br> -1115 | -1934 <br> 399 <br> -701 | -3412 <br> 106 <br> -1378 | -3952 <br> -626 <br> -9818 | -3863 <br> 210 <br> -9320 | -4230 <br> -466 | -3311 <br> -720 | -2605 <br> 275 | -2728 <br> 394 | -3429 <br> 45 | -3681 <br> 96 | 2146 <br> 359 | -1516 <br> 117 | -2782 <br> -369 | -4394 <br> -294 | -4269 <br> -249 | 152 |
| 153Y <br> — | -3656 <br> -149 <br> -11 | -3073 <br> -500 <br> -7944 | -4655 <br> 233 <br> -8986 | -4705 <br> 43 <br> -894 | 2072 <br> -381 <br> -1115 | -4415 <br> 399 <br> -701 | -1160 <br> 106 <br> -1378 | -2834 <br> -626 <br> -9818 | -4311 <br> 210 <br> -9317 | -2480 <br> -466 | -2370 <br> -720 | -3332 <br> 275 | -4386 <br> 394 | -3385 <br> 45 | -3897 <br> 96 | -3630 <br> 359 | 1330 <br> 117 | -2897 <br> -369 | -449 <br> -294 | 4200 <br> -249 | 153 |
| 154G <br> — | -4088 <br> -149 <br> -11 | -3924 <br> -500 <br> -7944 | -4774 <br> 233 <br> -8986 | -5139 <br> 43 <br> -894 | -5615 <br> -381 <br> -1115 | 3825 <br> 399 <br> -701 | -4753 <br> 106 <br> -1378 | -6303 <br> -626 <br> -9818 | -5453 <br> 210 <br> -9315 | -6014 <br> -466 | -5662 <br> -720 | -4812 <br> 275 | -4539 <br> 394 | -5232 <br> 45 | -5106 <br> 96 | -4370 <br> 359 | -4472 <br> 117 | -5527 <br> -369 | -4696 <br> -294 | -5561 <br> -249 | 154 |
| 155A <br> — | 3609 <br> -149 <br> -11 | -2508 <br> -500 <br> -7944 | -4184 <br> 233 <br> -8986 | -4493 <br> 43 <br> -894 | -4592 <br> -381 <br> -1115 | -2737 <br> 399 <br> -701 | -3989 <br> 106 <br> -1378 | -4421 <br> -626 <br> -9818 | -4496 <br> 210 <br> -9313 | -4701 <br> -466 | -4051 <br> -720 | -3440 <br> 275 | -3474 <br> 394 | -4171 <br> 45 | -4253 <br> 96 | -2294 <br> 359 | -2487 <br> 117 | -3536 <br> -369 | -4484 <br> -294 | -4643 <br> -249 | 155 |
| 156(I) <br> — | 1599 <br> -149 <br> -11 | -1799 <br> -500 <br> -7944 | -4782 <br> 233 <br> -8986 | -4398 <br> 43 <br> -894 | -2369 <br> -381 <br> -1115 | -4319 <br> 399 <br> -701 | -3996 <br> 106 <br> -1378 | 2490 <br> -626 <br> -9818 | -4241 <br> 210 <br> -9311 | -1351 <br> -466 | -1186 <br> -720 | -4067 <br> 275 | -4263 <br> 394 | -4075 <br> 45 | -4278 <br> 96 | -3599 <br> 359 | -2201 <br> 117 | 2395 <br> -369 | -3673 <br> -294 | -3229 <br> -249 | 156 |
| 157(F) <br> — | -3470 <br> -149 <br> -11 | -2920 <br> -500 <br> -7944 | -5747 <br> 233 <br> -8986 | -5177 <br> 43 <br> -894 | 3140 <br> -381 <br> -1115 | -5423 <br> 399 <br> -701 | -3794 <br> 106 <br> -1378 | -632 <br> -626 <br> -9818 | -4917 <br> 210 <br> -9308 | 2061 <br> -466 | 2648 <br> -720 | -5046 <br> 275 | -4645 <br> 394 | -3788 <br> 45 | -4437 <br> 96 | -4711 <br> 359 | -3319 <br> 117 | -1432 <br> -369 | -2615 <br> -294 | -2450 <br> -249 | 157 |
| 158(D) <br> — | -4232 <br> -149 <br> -11 | -4465 <br> -500 <br> -7944 | 4158 <br> 233 <br> -8986 | -2649 <br> 43 <br> -894 | -5412 <br> -381 <br> -1115 | -3676 <br> 399 <br> -701 | -3575 <br> 106 <br> -1378 | -6036 <br> -626 <br> -9818 | -4125 <br> 210 <br> -9306 | -5722 <br> -466 | -5419 <br> -720 | -2993 <br> 275 | -4216 <br> 394 | -3512 <br> 45 | -4617 <br> 96 | -4077 <br> 359 | -4401 <br> 117 | -5553 <br> -369 | -4696 <br> -294 | -4914 <br> -249 | 158 |
| 159(N) <br> — | -2152 <br> -149 <br> -11 | -3226 <br> -500 <br> -7944 | -1659 <br> 233 <br> -8986 | -1246 <br> 43 <br> -894 | -3822 <br> -381 <br> -1115 | -2724 <br> 399 <br> -701 | -1126 <br> 106 <br> -1378 | -3401 <br> -626 <br> -9818 | -63 <br> 210 <br> -9304 | -3176 <br> -466 | -2432 <br> -720 | 3327 <br> 275 | -2852 <br> 394 | 1866 <br> 45 | 1828 <br> 96 | -2010 <br> 359 | -2006 <br> 117 | -3064 <br> -369 | -3127 <br> -294 | -2771 <br> -249 | 159 |
| 160(P) <br> — | -4497 <br> -149 <br> -11 | -4117 <br> -500 <br> -7944 | -4899 <br> 233 <br> -8986 | -5251 <br> 43 <br> -894 | -5560 <br> -381 <br> -1115 | -4139 <br> 399 <br> -701 | -4798 <br> 106 <br> -1378 | -6328 <br> -626 <br> -9818 | -5454 <br> 210 <br> -9301 | -5976 <br> -466 | -5741 <br> -720 | -5026 <br> 275 | -4302 <br> 394 | -5328 <br> 45 | -5104 <br> 96 | -4798 <br> 359 | -4844 <br> 117 | -5739 <br> -369 | -4665 <br> -294 | -5484 <br> -249 | 160 |
| 161(D) <br> — | -2185 <br> -149 <br> -11 | -4023 <br> -500 <br> -7944 | 2971 <br> 233 <br> -8986 | 1468 <br> 43 <br> -894 | -4227 <br> -381 <br> -1115 | -2230 <br> 399 <br> -701 | -1509 <br> 106 <br> -1378 | -4119 <br> -626 <br> -9818 | -1656 <br> 210 <br> -9299 | -4000 <br> -466 | -3274 <br> -720 | 1608 <br> 275 | -2722 <br> 394 | -1160 <br> 45 | -2448 <br> 96 | 972 <br> 359 | -2231 <br> 117 | -3604 <br> -369 | -4191 <br> -294 | -3227 <br> -249 | 161 |

TABLE 7-continued

| | | | | | | | | | | | | | | | | | | |
|---|---|---|---|---|---|---|---|---|---|---|---|---|---|---|---|---|---|---|
| 162(L) | −3047 | −2911 | −3749 | −3527 | −1475 | −4117 | −2954 | −1124 | −2671 | 2926 | −473 | −3500 | −4084 | 1801 | −2645 | −3601 | −3002 | −1759 | −2782 | −2505 | 162 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9297 | | | | | | | | | | | | |
| 163(I) | −2388 | −1937 | −4948 | −4533 | 1635 | −4599 | −3887 | 3268 | −4365 | −905 | −875 | −4243 | −4379 | −4047 | −4325 | −3869 | −2360 | 1592 | −3319 | −2869 | 163 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9295 | | | | | | | | | | | | |
| 164(V | 1092 | −1556 | −3968 | −3774 | −2577 | −2468 | −3041 | −599 | −3503 | −2045 | −1609 | −2850 | −3046 | −3196 | −3407 | −1780 | 1216 | 3071 | −3285 | −2961 | 164 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9292 | | | | | | | | | | | | |
| 165(F) | 1547 | −939 | −2765 | −2207 | 1594 | −2286 | −1398 | −514 | −1927 | −906 | −256 | −1896 | 1121 | −1657 | −1937 | −1398 | 1348 | 1100 | −1513 | −1155 | 165 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9290 | | | | | | | | | | | | |
| 166C | 1272 | 5052 | −4189 | −4423 | −4093 | 1091 | −3532 | −3812 | −4117 | −4134 | −3233 | −2716 | −2738 | −3626 | −3808 | −1304 | −1508 | −2711 | −4345 | −4265 | 166 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9288 | | | | | | | | | | | | |
| 167(V | −2483 | −1992 | −5115 | −4742 | −2252 | −4880 | −4534 | 1808 | −4643 | 723 | −1005 | −4536 | −4599 | −4405 | −4684 | −4208 | −2462 | 3131 | −3865 | −3512 | 167 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9285 | | | | | | | | | | | | |
| 168(V | 699 | −1835 | −4861 | −4496 | −2442 | −4434 | −4193 | 1822 | −4360 | −1374 | −1231 | −4183 | −4356 | −4220 | −4421 | −3732 | −2257 | 3136 | −3831 | −3371 | 168 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9283 | | | | | | | | | | | | |
| 169(G | −4088 | −3924 | −4774 | −5139 | −5615 | 3825 | −4753 | −6303 | −5453 | −6014 | −5662 | −4812 | −4539 | −5232 | −5106 | −4370 | −4472 | −5527 | −4696 | −5561 | 169 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9281 | | | | | | | | | | | | |
| 170(D | −4232 | −4465 | 4158 | −2649 | −5412 | −3676 | −3575 | −6036 | −4125 | −5722 | −5419 | −2993 | −4216 | −3512 | −4617 | −4077 | −4401 | −5553 | −4696 | −4914 | 170 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9278 | | | | | | | | | | | | |
| 171(G | −4088 | −3924 | −4774 | −5139 | −5615 | 3825 | −4753 | −6303 | −5453 | −6014 | −5662 | −4812 | −4539 | −5232 | −5106 | −4370 | −4472 | −5527 | −4696 | −5561 | 171 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9276 | | | | | | | | | | | | |
| 172E | −4205 | −4417 | −2343 | 3901 | −5349 | −3698 | −3534 | −5837 | −3838 | −5561 | −5237 | −3039 | −4218 | −3453 | −4201 | −4072 | −4352 | −5409 | −4640 | −4860 | 172 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9274 | | | | | | | | | | | | |
| 173(A | 3289 | −1671 | −3729 | −3971 | −4173 | −1939 | −3433 | −3954 | −3901 | −4239 | −3324 | −2617 | −2734 | −3460 | −3704 | 1119 | −1523 | −2786 | −4402 | −4279 | 173 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9271 | | | | | | | | | | | | |
| 174E | −4205 | −4417 | −2343 | 3901 | −5349 | −3698 | −3534 | −5837 | −3838 | −5561 | −5237 | −3039 | −4218 | −3453 | −4201 | −4072 | −4352 | −5409 | −4640 | −4860 | 174 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9269 | | | | | | | | | | | | |
| 175(T | −2430 | −2823 | −4179 | −4462 | −4591 | −3027 | −4037 | −4454 | −4406 | −4707 | −4191 | −3664 | −3724 | −4237 | −4215 | −2689 | 4010 | −3747 | −4431 | −4588 | 175 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9267 | | | | | | | | | | | | |
| 176G | −4088 | −3924 | −4774 | −5139 | −5615 | 3825 | −4753 | −6303 | −5453 | −6014 | −5662 | −4812 | −4539 | −5232 | −5106 | −4370 | −4472 | −5527 | −4696 | −5561 | 176 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9264 | | | | | | | | | | | | |
| 177(P | −4497 | −4117 | −4899 | −5251 | −5560 | −4139 | −4798 | −6328 | −5454 | −5976 | −5741 | −5026 | 4302 | −5328 | −5104 | −4798 | −4844 | −5739 | −4665 | −5484 | 177 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9262 | | | | | | | | | | | | |
| 178(L) | −2381 | −2370 | −4412 | −4172 | −1521 | −3608 | −3357 | −845 | −3741 | 2871 | −437 | −3695 | −3832 | −3365 | −3575 | −2971 | 1469 | −1264 | −2889 | −2744 | 178 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9260 | | | | | | | | | | | | |

TABLE 7-continued

| | | | | | | | | | | | | | | | | | |
|---|---|---|---|---|---|---|---|---|---|---|---|---|---|---|---|---|---|
| 179(A) | 3191 -149 -11 | -1777 -500 -7944 | -3712 233 -8986 | -3682 43 -894 | -2796 -381 -1115 | -2273 399 -701 | -3050 106 -1378 | -2040 -626 -9818 | -3349 210 -9257 | -2216 -466 | 2634 -720 | -2731 275 | -2945 394 | -3125 45 | -3255 96 | -1630 359 | -1688 117 | -1822 -369 | -3467 -294 | -3179 -249 | 179 |
| 180(T) | 1105 -149 -11 | -1691 -500 -7944 | -3751 233 -8986 | -3950 43 -894 | -4036 -381 -1115 | -1980 399 -701 | -3391 106 -1378 | -3579 -626 -9818 | -3788 210 -9255 | -4004 -466 | -3179 -720 | -2639 275 | -2764 394 | -3418 45 | -3611 96 | -1351 359 | 3649 117 | -2631 -369 | -4299 -294 | -4165 -249 | 180 |
| 181(S) | 1115 -149 -11 | -1654 -500 -7944 | -3622 233 -8986 | -3791 43 -894 | -4192 -381 -1115 | 1188 399 -701 | -3347 106 -1378 | -3991 -626 -9818 | -3762 210 -9253 | -4236 -466 | -3295 -720 | -2550 275 | -2702 394 | -3327 45 | -3634 96 | 3032 359 | -1489 117 | -2786 -369 | -4402 -294 | -4277 -249 | 181 |
| 182( | -5598 -149 -11 | -4432 -500 -7944 | -5385 233 -8986 | -5722 43 -894 | -3380 -381 -1115 | -4524 399 -701 | -4140 106 -1378 | -5941 -626 -9818 | -5643 210 -9250 | -5318 -466 | -5354 -720 | -5427 275 | -4938 394 | -5474 45 | -5178 96 | -5909 359 | -5751 117 | -5890 -369 | 6275 -294 | -2993 -249 | 182 |
| 183(H) | -2817 -149 -11 | -3584 -500 -7944 | -1743 233 -8986 | -1758 43 -894 | -2728 -381 -1115 | -3054 399 -701 | 4625 106 -1378 | -4009 -626 -9818 | -1063 210 -9248 | -3728 -466 | -3189 -720 | -1926 275 | -3378 394 | 2752 45 | -1170 96 | -2680 359 | -2782 117 | -3708 -369 | -2912 -294 | -2121 -249 | 183 |
| 184(S) | 2113 -149 -11 | -1671 -500 -7944 | -3691 233 -8986 | -3909 43 -894 | -4175 -381 -1115 | -1935 399 -701 | -3404 106 -1378 | -3963 -626 -9818 | -3845 210 -9246 | -4238 -466 | -3318 -720 | -2599 275 | -2728 394 | -3415 45 | -3673 96 | 2974 359 | -1518 117 | -2788 -369 | -4398 -294 | -4270 -249 | 184 |
| 185(N) | -1667 -149 -11 | -2295 -500 -7944 | -1303 233 -8986 | -1206 43 -894 | -1708 -381 -1115 | -2454 399 -701 | 2688 106 -1378 | 1228 -626 -9818 | -1127 210 -9243 | -2276 -466 | -1659 -720 | 3307 275 | -2730 394 | -1191 45 | -1399 96 | -1726 359 | -1677 117 | -1853 -369 | -2144 -294 | -1341 -249 | 185 |
| 186(K) | -4125 -149 -11 | -4091 -500 -7944 | -4017 233 -8986 | -3615 43 -894 | -5101 -381 -1115 | -3960 399 -701 | -2958 106 -1378 | -5182 -626 -9818 | 3972 210 -9241 | -4825 -466 | -4345 -720 | -3552 275 | -4249 394 | -2709 45 | -1809 96 | -4154 359 | -4044 117 | -4895 -369 | -4132 -294 | -4389 -249 | 186 |
| 187(F) | -3793 -149 -11 | -3163 -500 -7944 | -5295 233 -8986 | -5191 43 -894 | 4063 -381 -1115 | -5003 399 -701 | -2160 106 -1378 | -1329 -626 -9818 | -4845 210 -9238 | 1075 -466 | -704 -720 | -4205 275 | -4663 394 | -3781 45 | -4356 96 | -4376 359 | -3689 117 | -1985 -369 | -1339 -294 | -323 -249 | 187 |
| 188(I) | -2691 -149 -11 | -2201 -500 -7944 | -5254 233 -8986 | -4813 43 -894 | -1747 -381 -1115 | -4966 399 -701 | -4275 106 -1378 | 2399 -626 -9818 | -4658 210 -9236 | 2193 -466 | -527 -720 | -4632 275 | -4563 394 | -4118 45 | -4528 96 | -4270 359 | -2643 117 | 1553 -369 | -3385 -294 | -3255 -249 | 188 |
| 189(N | -2608 -149 -11 | -4312 -500 -7944 | 1902 233 -8986 | -698 43 -894 | -4665 -381 -1115 | -2423 399 -701 | -1924 106 -1378 | -4776 -626 -9818 | -2319 210 -9234 | -4628 -466 | -4060 -720 | 3855 275 | -3013 394 | -1633 45 | -3242 96 | -2275 359 | -2738 117 | -4189 -369 | -4662 -294 | -3683 -249 | 189 |
| 190(P) | -4497 -149 -11 | -4117 -500 -7944 | -4899 233 -8986 | -5251 43 -894 | -5560 -381 -1115 | -4139 399 -701 | -4798 106 -1378 | -6328 -626 -9818 | -5454 210 -9231 | -5976 -466 | -5741 -720 | -5026 275 | 4302 394 | -5328 45 | -5104 96 | -4798 359 | -4844 117 | -5739 -369 | -4665 -294 | -5484 -249 | 190 |
| 191(A | 1597 -149 -11 | -1385 -500 -7944 | -1621 233 -8986 | -1030 43 -894 | -1453 -381 -1115 | -2189 399 -701 | -892 106 -1378 | 994 -626 -9818 | 1158 210 -9229 | -1265 -466 | -571 -720 | -1153 275 | -2261 394 | -699 45 | 1188 96 | -1186 359 | -908 117 | 900 -369 | -1781 -294 | -1350 -249 | 191 |
| 192(R | -1138 -149 -11 | -2535 -500 -7944 | -738 233 -8986 | 1346 43 -894 | -2893 -381 -1115 | -1985 399 -701 | -675 106 -1378 | -2612 -626 -9818 | -163 210 -9229 | -2551 -466 | -1669 -720 | 1495 275 | -2128 394 | -235 45 | 2008 96 | -1012 359 | 1851 117 | -2189 -369 | -2703 -294 | -2067 -249 | 192 |
| 193(D | -2243 -149 -11 | -3522 -500 -7944 | 3665 233 -8986 | -856 43 -894 | -4525 -381 -1115 | -2330 399 -701 | -2015 106 -1378 | -4560 -626 -9818 | -2391 210 -9226 | -4501 -466 | -3857 -720 | -1194 275 | -2947 394 | -1733 45 | -3224 96 | 1260 359 | -2461 117 | -3845 -369 | -4571 -294 | -3690 -249 | 193 |
| 194(G | -4088 -149 -11 | -3924 -500 -7944 | -4774 233 -8986 | -5139 43 -894 | -5615 -381 -1115 | 3825 399 -701 | -4753 106 -1378 | -6303 -626 -9818 | -5453 210 -9222 | -6014 -466 | -5662 -720 | -4812 275 | -4539 394 | -5232 45 | -5106 96 | -4370 359 | -4472 117 | -5527 -369 | -4696 -294 | -5561 -249 | 194 |
| 195(A | 3150 -149 -11 | -1781 -500 -7944 | -3954 233 -8986 | -3897 43 -894 | -2697 -381 -1115 | -2590 399 -701 | -3290 106 -1378 | 1498 -626 -9818 | -3639 210 -9219 | -1978 -466 | -1734 -720 | -3003 275 | -3197 394 | -3386 45 | -3549 96 | -1945 359 | -1810 117 | -689 -369 | -3544 -294 | -3207 -249 | 195 |

TABLE 7-continued

| | | | | | | | | | | | | | | | | | |
|---|---|---|---|---|---|---|---|---|---|---|---|---|---|---|---|---|---|
| 196(V) | −2448 −149 −11 | −1959 −500 −7944 | −5109 233 −8986 | −4794 43 −894 | −2563 −381 −1115 | −4877 399 −701 | −4851 106 −1378 | 1886 −626 −9818 | −4730 210 −9217 | −1341 −466 | −1284 −720 | −4579 275 | −4666 394 | −4653 45 | −4865 96 | −4248 359 | −2447 117 | 3388 −369 | −4252 −294 | −3753 −249 | 196 |
| 197(L) | −3405 −149 −11 | −2846 −500 −7944 | −5779 233 −8986 | −5255 43 −894 | −1228 −381 −1115 | −5518 399 −701 | −4333 106 −1378 | 1719 −626 −9818 | −5019 210 −9214 | 2902 −466 | −18 −720 | −5245 275 | −4745 394 | −3976 45 | −4603 96 | −4888 359 | −3285 117 | −936 −369 | −3002 −294 | −3110 −249 | 197 |
| 198(P) | −4497 −149 −11 | −4117 −500 −7944 | −4899 233 −8986 | −5251 43 −894 | −5560 −381 −1115 | −4139 399 −701 | −4798 106 −1378 | −6328 −626 −9818 | −5454 210 −9212 | −5976 −466 | −5741 −720 | −5026 275 | 4302 394 | −5328 45 | −5104 96 | −4798 359 | −4844 117 | −5739 −369 | −4665 −294 | −5484 −249 | 198 |
| 199(I) | −2459 −149 −11 | −1963 −500 −7944 | −5126 233 −8986 | −4808 43 −894 | −2568 −381 −1115 | −4914 399 −701 | −4889 106 −1378 | 3247 −626 −9818 | −4751 210 −9209 | −1338 −466 | −1283 −720 | −4603 275 | −4685 394 | −4676 45 | −4891 96 | −4286 359 | −2455 117 | 2426 −369 | −4274 −294 | −3777 −249 | 199 |
| 200(L) | −4119 −149 −11 | −3542 −500 −7944 | −5389 233 −8986 | −5357 43 −894 | −2027 −381 −1115 | −4767 399 −701 | −4358 106 −1378 | −1609 −626 −9818 | −5118 210 −9207 | 3293 −466 | −979 −720 | −5230 275 | −4771 394 | −4474 45 | −4724 96 | −5069 359 | −4106 117 | −2331 −369 | −3412 −294 | −3400 −249 | 200 |
| 201(H) | −2395 −149 −11 | −4306 −500 −7944 | 1759 233 −8986 | 1612 43 −894 | −4428 −381 −1115 | −2292 399 −701 | 4419 106 −1378 | −4404 −626 −9818 | −1894 210 −9205 | −4265 −466 | −3611 −720 | −881 275 | −2831 394 | −1320 45 | −2741 96 | −2046 359 | −2464 117 | −3880 −369 | −4428 −294 | −3405 −249 | 201 |
| 202(L) | −4119 −149 −11 | −3542 −500 −7944 | −5389 233 −8986 | −5357 43 −894 | −2027 −381 −1115 | −4767 399 −701 | −4358 106 −1378 | −1609 −626 −9818 | −5118 210 −9202 | 3293 −466 | −979 −720 | −5230 275 | −4771 394 | −4474 45 | −4724 96 | −5069 359 | −4106 117 | −2331 −369 | −3412 −294 | −3400 −249 | 202 |
| 203(N) | −3642 −149 −11 | −3838 −500 −7944 | −3004 233 −8986 | −3356 43 −894 | −4743 −381 −1115 | −3612 399 −701 | −3773 106 −1378 | −5643 −626 −9818 | −4099 210 −9200 | −5460 −466 | −5060 −720 | 4378 275 | −4185 394 | −3865 45 | −4225 96 | −3744 359 | −3950 117 | −5002 −369 | −4391 −294 | −4381 −249 | 203 |
| 204(G) | −4088 −149 −11 | −3924 −500 −7944 | −4774 233 −8986 | −5139 43 −894 | −5615 −381 −1115 | 3825 399 −701 | −4753 106 −1378 | −6303 −626 −9818 | −5453 210 −9197 | −6014 −466 | −5662 −720 | −4812 275 | −4539 394 | −5232 45 | −5106 96 | −4370 359 | −4472 117 | −5527 −369 | −4696 −294 | −5561 −249 | 204 |
| 205(Y) | −4606 −149 −11 | −3570 −500 −7944 | −5022 233 −8986 | −5359 43 −894 | 2254 −381 −1115 | −4894 399 −701 | −1139 106 −1378 | −3493 −626 −9818 | −4923 210 −9195 | −2816 −466 | −2906 −720 | −3546 275 | −4765 394 | −3679 45 | −4305 96 | −4161 359 | −4469 117 | −3657 −369 | −387 −294 | 4510 −249 | 205 |
| 206(K) | −4125 −149 −11 | −4091 −500 −7944 | −4017 233 −8986 | −3615 43 −894 | −5101 −381 −1115 | −3960 399 −701 | −1858 106 −1378 | −5182 −626 −9818 | 3972 210 −9192 | −4825 −466 | −4345 −720 | −3552 275 | −4249 394 | −2709 45 | −1809 96 | −4154 359 | −4044 117 | −4895 −369 | −4132 −294 | −4389 −249 | 206 |
| 207(I) | −3202 −149 −11 | −2787 −500 −7944 | −5004 233 −8986 | −4996 43 −894 | −2836 −381 −1115 | −4384 399 −701 | −4440 106 −1378 | 3937 −626 −9818 | −4838 210 −9190 | −1815 −466 | −1871 −720 | −4704 275 | −4600 394 | −4683 45 | −4704 96 | −4353 359 | −3280 117 | −603 −369 | −3938 −294 | −3661 −249 | 207 |
| 208(S) | 1943 −149 −11 | −1773 −500 −7944 | −2482 233 −8986 | −2503 43 −894 | −3907 −381 −1115 | −1935 399 −701 | −2647 106 −1378 | −3686 −626 −9818 | −2717 210 −9187 | −3870 −466 | −2975 −720 | 1555 275 | −2640 394 | −2445 45 | −2934 96 | 2632 359 | −1475 117 | −2699 −369 | −4064 −294 | −3728 −249 | 208 |
| 209(N) | −2546 −149 −11 | −4182 −500 −7944 | −358 233 −8986 | 1608 43 −894 | −4553 −381 −1115 | −2427 399 −701 | −1858 106 −1378 | −4587 −626 −9818 | −2065 210 −9185 | −4451 −466 | −3846 −720 | 3842 275 | −2989 394 | −1553 45 | −2799 96 | −2233 359 | −2653 117 | −4040 −369 | −4492 −294 | −3586 −249 | 209 |
| 210(P) | −3075 −149 −11 | −3411 −500 −7944 | −3652 233 −8986 | −3377 43 −894 | −4713 −381 −1115 | −3421 399 −701 | −2871 106 −1378 | −4754 −626 −9818 | −1885 210 −9182 | −4551 −466 | −3970 −720 | −3201 275 | 3874 394 | −2637 45 | 1884 96 | −3201 359 | −3246 117 | −4233 −369 | −4063 −294 | −4155 −249 | 210 |
| 211(T) | −1093 −149 −11 | −1706 −500 −7944 | −3487 233 −8986 | −3693 43 −894 | −4074 −381 −1115 | −1966 399 −701 | −3302 106 −1378 | −3842 −626 −9818 | −3638 210 −9180 | −4134 −466 | −3253 −720 | −2558 275 | −2748 394 | −3296 45 | −3520 96 | 1110 359 | 3646 117 | −2760 −369 | −4304 −294 | −4125 −249 | 211 |
| 212(I) | −2500 −149 −11 | −2007 −500 −7944 | −5132 233 −8986 | −4756 43 −894 | −2220 −381 −1115 | −4898 399 −701 | −4538 106 −1378 | 2959 −626 −9818 | −4657 210 −9177 | 869 −466 | −973 −720 | −4554 275 | −4605 394 | −4399 45 | −4689 96 | −4227 359 | −2477 117 | 2250 −369 | −3844 −294 | −3510 −249 | 212 |

TABLE 7-continued

| | | | | | | | | | | | | | | | |
|---|---|---|---|---|---|---|---|---|---|---|---|---|---|---|---|
| 213(Y) | −3774 | −3094 | −5016 | −5007 | 2147 | −4760 | −1471 | −1948 | 4610 | 2513 | −1319 | −3670 | −4532 | −3545 | −4108 | −3980 | −3652 | −2427 | −717 | 2621 | 213 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9175 | | | | | | | | | | | | |
| 214(A) | 2561 | −1647 | −3667 | −3813 | −4167 | 1400 | −3339 | −3961 | −3748 | −4207 | −3269 | −2554 | −2698 | −3319 | −3621 | 1972 | −1482 | −2770 | −4380 | −4254 | 214 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9172 | | | | | | | | | | | | |
| 215(R) | −2761 | 3372 | −4411 | −3701 | −4318 | −3291 | −2762 | −4186 | −1690 | −4160 | −3592 | −3256 | −3742 | −2538 | 3812 | −2949 | −2961 | −3734 | −3870 | −3866 | 215 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9170 | | | | | | | | | | | | |
| 216(I) | −1976 | −1690 | −4334 | −3831 | −1599 | −3763 | −2958 | 3100 | −3513 | −670 | 2664 | −3459 | −3733 | −3184 | −3413 | −2951 | 1215 | 192 | −2661 | −2363 | 216 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9167 | | | | | | | | | | | | |
| 217(S) | −1740 | −2857 | 1787 | −890 | −4083 | −2148 | −1822 | −3944 | −1950 | −3947 | −3166 | −1164 | 2282 | −1503 | −2599 | 2462 | −1955 | −3236 | −4123 | −3368 | 217 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9165 | | | | | | | | | | | | |
| 218(D) | −1796 | −3465 | 2956 | 1278 | −3721 | −2140 | 2354 | −3541 | 1157 | −3446 | −2631 | −742 | −2513 | −824 | −1706 | −1558 | −1793 | −3064 | −3617 | −2792 | 218 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9162 | | | | | | | | | | | | |
| 219(D) | −1468 | −2962 | 2158 | 2010 | −3256 | −2035 | −1014 | −3010 | −825 | −2993 | −2150 | −673 | −2334 | −612 | −1413 | 1100 | −1455 | 908 | −3204 | −2451 | 219 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9160 | | | | | | | | | | | | |
| 220(E) | −2636 | −4572 | 1783 | 3438 | −4760 | −2391 | −1842 | −4773 | −2236 | −4607 | −4040 | −996 | −2973 | −1538 | −3199 | −2254 | −2736 | −4219 | −4732 | −3692 | 220 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9157 | | | | | | | | | | | | |
| 221(L) | −3421 | −2860 | −5790 | −5264 | −1219 | −5529 | −4333 | 1589 | −5025 | 2937 | −9 | −5258 | −4748 | −3973 | −4603 | −4902 | −3300 | −965 | −2995 | −3106 | 221 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9155 | | | | | | | | | | | | |
| 222(H) | −1434 | −2670 | −1420 | 1033 | −3099 | −2316 | 2338 | −2728 | 1395 | 511 | −1776 | −966 | −2367 | −301 | 2245 | −1323 | −1317 | −2360 | −2690 | −2208 | 222 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9152 | | | | | | | | | | | | |
| 223(K) | 1469 | −2443 | 1279 | −267 | −2862 | −1879 | −707 | −2612 | 1960 | −2574 | −1677 | −575 | −2071 | −271 | −856 | 1040 | −1018 | −2154 | −2755 | −2069 | 223 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9150 | | | | | | | | | | | | |
| 224(F) | −3694 | −3088 | −5579 | −5263 | 3299 | −5296 | −2867 | −919 | −4969 | 2350 | −235 | −4680 | −4707 | −3837 | −4468 | −4661 | −3559 | −1683 | −1918 | −1128 | 224 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9147 | | | | | | | | | | | | |
| 225(F) | −4720 | −3927 | −5139 | −5454 | 4513 | −4504 | −2520 | −3938 | −5326 | −3307 | −3429 | −4469 | −4782 | −4575 | −4818 | −4787 | −4810 | −4172 | −1812 | −736 | 225 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9145 | | | | | | | | | | | | |
| 226(E) | 688 | −2344 | −716 | 2314 | −2761 | −1878 | −641 | −2492 | −210 | −2459 | −1564 | −580 | −2036 | −201 | 1256 | 1020 | −948 | −2051 | −2637 | −1982 | 226 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9142 | | | | | | | | | | | | |
| 227(G) | −4088 | −3924 | −4774 | −5139 | −5615 | 3825 | −4753 | −6303 | −5453 | −6014 | −5662 | −4812 | −4539 | −5232 | −5106 | −4370 | −4472 | −5527 | −4696 | −5561 | 227 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9140 | | | | | | | | | | | | |
| 228(Y) | −1597 | −1396 | −3573 | −3051 | 2007 | −3040 | −1283 | −840 | −2686 | 801 | 2421 | 1263 | −3058 | −2245 | −2516 | −2133 | −1532 | −823 | −882 | 2863 | 228 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9137 | | | | | | | | | | | | |
| 229(G) | −4088 | −3924 | −4774 | −5139 | −5615 | 3825 | −4753 | −6303 | −5453 | −6014 | −5662 | −4812 | −4539 | −5232 | −5106 | −4370 | −4472 | −5527 | −4696 | −5561 | 229 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8986 | −894 | −1115 | −701 | −1378 | −9818 | −9134 | | | | | | | | | | | | |

TABLE 7-continued

| | | | | | | | | | | | | | | | | | | |
|---|---|---|---|---|---|---|---|---|---|---|---|---|---|---|---|---|---|---|
| 230(Y) | −4620 −149 −11 | −3593 −500 −7944 | −5015 233 −8986 | −5337 43 −894 | 280 −381 −1115 | −4863 399 −701 | −1187 106 −1378 | −3570 −626 −9818 | −4864 210 −9132 | −2899 −466 | −2980 −720 | −3577 275 | −4762 394 | −3702 45 | −4279 96 | −4188 359 | −4490 117 | −3719 −369 | 3436 −294 | 4551 −249 | 230 |
| 231(H) | −862 −149 | −2311 −500 −7944 | −632 233 −8986 | 1878 43 −894 | −2629 −381 −1115 | −1803 399 −701 | 2148 106 −1378 | −2371 −626 −9818 | 1173 210 −9129 | −2322 −466 | −1409 −720 | −442 275 | −1911 394 | −24 45 | −537 96 | 854 359 | 933 117 | −1933 −369 | −2493 −294 | −1820 −249 | 231 |
| 232(P) | −1820 −149 −11 | −2216 −500 −7944 | −3792 233 −8986 | −3938 43 −894 | −3452 −381 −1115 | −2669 399 −701 | −3505 106 −1378 | −2107 −626 −9818 | −3787 210 −9127 | −3057 −466 | −2729 −720 | −3136 275 | 3804 394 | −3614 45 | −3691 96 | −2143 359 | −2196 117 | 1506 −369 | −3938 −294 | −3681 −249 | 232 |
| 233(Y) | 996 −149 −11 | −1294 −500 −7944 | −2366 233 −8986 | −1763 43 −894 | −954 −381 −1115 | −2474 399 −701 | −1131 106 −1378 | −841 −626 −9818 | −1179 210 −9124 | 533 −466 | −479 −720 | −1680 275 | −2552 394 | −1243 45 | 1281 96 | −1538 359 | −1120 117 | −749 −369 | −1438 −294 | 3229 −249 | 233 |
| 234(F) | −1969 −149 −11 | −1770 −500 −7944 | −3543 233 −8986 | 966 43 −894 | 3139 −381 −1115 | −3305 399 −701 | −1223 106 −1378 | 1499 −626 −9818 | −2815 210 −9122 | −1359 −466 | −912 −720 | −2576 275 | −3319 394 | −2375 45 | −2708 96 | −2407 359 | −1903 117 | −1180 −369 | −760 −294 | 2316 −249 | 234 |
| 235(V) | −2342 −149 −11 | −1893 −500 −7944 | −4914 233 −8986 | −4505 43 −894 | 1622 −381 −1115 | −4568 399 −701 | −3913 106 −1378 | 1826 −626 −9818 | −4342 210 −9119 | −1030 −466 | −963 −720 | −4213 275 | −4369 394 | −4072 45 | −4326 96 | −3838 359 | −2317 117 | 3076 −369 | −3397 −294 | −2930 −249 | 235 |
| 236(E) | 722 −149 −11 | −2323 −500 −7944 | −653 233 −8986 | 2387 43 −894 | −2684 −381 −1115 | −1948 399 −701 | −848 106 −1378 | −2315 −626 −9818 | −559 210 −9116 | −2434 −466 | −1603 −720 | 1662 275 | −2171 394 | −449 45 | −1065 96 | −1048 359 | −1111 117 | 813 −369 | −2716 −294 | −2073 −249 | 236 |
| 237(G) | 917 −149 −11 | −3198 −500 −7944 | 1792 233 −8986 | −603 43 −894 | −3972 −381 −1115 | 2355 399 −701 | −1545 106 −1378 | −3811 −626 −9818 | −1605 210 −9114 | −3767 −466 | −2983 −720 | 1737 275 | −2642 394 | −1194 45 | −2291 96 | −1663 359 | −1944 117 | −3223 −369 | −3965 −294 | −3136 −249 | 237 |
| 238(D) | −1266 −149 −13 | −2437 −500 −7670 | 2763 233 −8713 | 82 43 −894 | −3208 −381 −1115 | 2150 399 −701 | −912 106 −1378 | −3128 −626 −9818 | −1082 210 −9111 | −3109 −466 | −2410 −720 | −254 275 | −1932 394 | −608 45 | −1769 96 | −1060 359 | −1365 117 | −2572 −369 | −3146 −294 | −2456 −249 | 238 |
| 239(D) | −1223 −149 −649 | −1491 −500 −7744 | 3618 233 −8713 | 1594 43 −894 | −376 −381 −1115 | −2587 399 −345 | −2232 106 −1378 | −4512 −626 −9818 | −1982 210 −9101 | −4352 −466 | −3784 −720 | −740 275 | −2721 394 | −1283 45 | −2949 96 | −1999 359 | −2481 117 | −3960 −369 | −4490 −294 | −2890 −249 | 240 |
| 240(N) | −2102 −149 −11 | −2902 −500 −7944 | −1648 233 −8986 | −157 43 −894 | −3277 −381 −1115 | −1911 399 −701 | −263 106 −1378 | −1662 −626 −9818 | −1068 210 −9098 | −1836 −466 | −1165 −720 | −1350 275 | 2605 394 | −1031 45 | −1373 96 | −1420 359 | 1364 117 | −1468 −369 | −1606 −294 | 2015 −249 | 241 |
| 241(H) | −1293 −149 −11 | −1824 −500 −7944 | 3872 233 −8713 | −571 43 −894 | −3494 −381 −1115 | −2332 399 −701 | 2376 106 −1378 | −3716 −626 −9818 | −1893 210 −9109 | −3662 −466 | −3195 −720 | −920 275 | −2449 394 | −1361 45 | −2516 96 | −1915 359 | −2242 117 | −3285 −369 | −3201 −294 | −1073 −249 | 241 |
| 242(D) | −694 −149 −23 | −999 −500 −6702 | −1141 233 −7744 | −940 43 −894 | −1064 −381 −1115 | −1767 399 −701 | −919 106 −1378 | 2282 −626 −9818 | −849 210 −9109 | −787 −466 | −349 −720 | 2352 275 | −2038 394 | −817 45 | −1093 96 | −1000 359 | −743 117 | 143 −369 | −1624 −294 | −2362 −249 | 242 |
| 243(P) | −1431 −149 −23 | −2871 −500 −6702 | −230 233 −7744 | 2243 43 −894 | −3163 −381 −1115 | −1925 399 −1555 | −1632 106 −600 | −3017 −626 −9818 | −719 210 −9106 | −2971 −466 | −2155 −720 | −593 275 | −2261 394 | −564 45 | −1242 96 | 1041 359 | −1433 117 | −2572 −369 | −3114 −294 | −3437 −249 | 243 |
| 244(M) | −2381 −149 −11 | −4329 −500 −7944 | −1284 233 −8987 | −1248 43 −894 | −4505 −381 −1115 | −2138 399 −345 | −1588 106 −1378 | −4512 −626 −9818 | −1982 210 −9103 | −4352 −466 | −3784 −720 | −740 275 | −2721 394 | −1283 45 | −2949 96 | −1999 359 | −2481 117 | −3960 −369 | −4490 −294 | 2015 −249 | 244 |
| | 683 −149 −11 | −1426 −500 −7944 | 1643 233 −8987 | 43 −894 | −1482 −381 −1115 | −2033 399 −701 | 2376 106 −1378 | −1054 −626 −9818 | −631 210 −9095 | 424 −466 | 2181 −720 | −936 275 | 1207 394 | −541 45 | −1010 96 | −1420 359 | 1364 117 | −1468 −369 | −1606 −294 | −1337 −249 | 245 |
| 245(S) | 861 −149 −11 | −1834 −500 −7944 | 1340 233 −8987 | −516 43 −894 | −2191 −381 −1115 | −1877 399 −701 | −758 106 −1378 | −1838 −626 −9818 | −462 210 −9093 | 203 −466 | −1169 −720 | −752 275 | −2056 394 | −387 45 | −921 96 | 1571 359 | −810 117 | −892 −369 | −1806 −294 | −1756 −249 | 246 |
| 246(M) | −1263 −149 −11 | −1161 −500 −7944 | −3038 233 −8987 | −2448 43 −894 | −745 −381 −1115 | −2739 399 −701 | −1453 106 −1378 | 1314 −626 −9818 | −2054 210 −9090 | −532 −466 | 3663 −720 | −2170 275 | −2762 394 | 1690 45 | −2026 96 | −1815 359 | −1199 117 | −464 −369 | −2319 −294 | 1937 −249 | 247 |

TABLE 7-continued

| | | | | | | | | | | | | | | | | | | |
|---|---|---|---|---|---|---|---|---|---|---|---|---|---|---|---|---|---|---|
| 247(H) | −2671 −149 −11 | −3516 −500 −7944 | −1308 233 −8987 | −1575 43 −894 | −2624 −381 −1115 | −2837 399 −701 | 4896 106 −1378 | −4310 −626 −9818 | −1982 210 −9087 | −4092 −466 | −3590 −720 | 1952 275 | −3342 394 | −1994 45 | −2257 96 | −2551 359 | −2812 117 | −3859 −369 | −3012 −294 | −2078 −249 | 248 |
| 248(R) | −2804 −149 −11 | −3490 −500 −7944 | −3516 233 −8987 | −2098 43 −894 | −4381 −381 −1115 | −3320 399 −701 | −1175 106 −1378 | −3662 −626 −9818 | 2379 210 −9085 | −3289 −466 | −2620 −720 | −1979 275 | −3242 394 | 2620 45 | 2657 96 | −2671 359 | −2465 117 | −3437 −369 | −3117 −294 | −3033 −249 | 249 |
| 249(R) | 732 −149 −11 | −1128 −500 −7944 | −2794 233 −8987 | −2187 43 −894 | −1101 −381 −1115 | −2570 399 −701 | −1459 106 −1378 | −356 −626 −9818 | −1683 210 −9082 | 1417 −466 | −262 −720 | −1988 275 | −2651 394 | −1613 45 | 1995 96 | −1657 359 | −1104 117 | 1378 −369 | −1647 −294 | −1297 −249 | 250 |
| 250(M) | 923 −149 −11 | −1665 −500 −7944 | −3899 233 −8987 | −3427 43 −894 | 1737 −381 −1115 | −3128 399 −701 | −2177 106 −1378 | −660 −626 −9818 | −3081 210 −9079 | −421 −466 | 4324 −720 | −2915 275 | −3268 394 | −2649 45 | −2926 96 | −2316 359 | −1774 117 | −849 −369 | −1851 −294 | −1321 −249 | 251 |
| 251(A) | 3609 −149 −11 | −2508 −500 −7944 | −4184 233 −8987 | −4493 43 −894 | −4592 −381 −1115 | −2737 399 −701 | −3989 106 −1378 | −4421 −626 −9818 | −4496 210 −9077 | −4701 −466 | −4051 −720 | −3440 275 | −3474 394 | −4171 45 | −4253 96 | −2294 359 | −2487 117 | −3536 −369 | −4484 −294 | −4643 −249 | 252 |
| 252(E) | 1863 −149 −11 | −2261 −500 −7944 | −1000 233 −8987 | 2576 43 −894 | −3283 −381 −1115 | −2007 399 −701 | −1447 106 −1378 | −2956 −626 −9818 | −1252 210 −9074 | −3072 −466 | −2244 −720 | −1127 275 | −2442 394 | −1087 45 | −1727 96 | −1275 359 | 1155 117 | −2422 −369 | −3329 −294 | −2724 −249 | 253 |
| 253(T) | −1822 −149 −11 | −1611 −500 −7944 | −4151 233 −8987 | −3676 43 −894 | −1688 −381 −1115 | −3491 399 −701 | −2844 106 −1378 | 186 −626 −9818 | −3366 210 −9071 | 815 −466 | −670 −720 | −3264 275 | −3577 394 | −3075 45 | −3294 96 | −2693 359 | 2637 117 | 2187 −369 | −2655 −294 | −2324 −249 | 254 |
| 254(M) | −3494 −149 −11 | −2937 −500 −7944 | −5788 233 −8987 | −5208 43 −894 | 2737 −381 −1115 | −5472 399 −701 | −3898 106 −1378 | −624 −626 −9818 | −4954 210 −9069 | 2288 −466 | 2851 −720 | −5116 275 | −4665 394 | −3807 45 | −4466 96 | −4768 359 | −3340 117 | −1435 −369 | −2676 −294 | −2586 −249 | 255 |
| 255(D) | −2671 −149 −11 | −4634 −500 −7944 | 3718 233 −8987 | 1448 43 −894 | −4812 −381 −1115 | −2395 399 −701 | −1863 106 −1378 | −4839 −626 −9818 | −2290 210 −9066 | −4667 −466 | −4121 −720 | −999 275 | −2987 394 | −1563 45 | −3285 96 | −2280 359 | −2777 117 | −4278 −369 | −4793 −294 | −3731 −249 | 256 |
| 256( | −807 −149 −11 | −1865 −500 −7944 | 984 233 −8987 | −295 43 −894 | −2038 −381 −1115 | −1850 399 −701 | 2023 106 −1378 | 698 −626 −9818 | 1219 210 −9063 | −1817 −466 | −996 −720 | −567 275 | −1940 394 | −139 45 | −647 96 | −780 359 | 1016 117 | −1409 −369 | 2991 −294 | −1556 −249 | 257 |
| 257(C) | 2301 −149 −11 | 2673 −500 −7944 | −4116 233 −8987 | −3625 43 −894 | −1761 −381 −1115 | −3338 399 −701 | −2704 106 −1378 | 1666 −626 −9818 | −3330 210 −9061 | −1177 −466 | −798 −720 | −3141 275 | −3451 394 | −3036 45 | −3235 96 | −2529 359 | −1663 117 | 1516 −369 | −2564 −294 | −2191 −249 | 258 |
| 258(F) | −1716 −149 −11 | −1417 −500 −7944 | −4136 233 −8987 | −3595 43 −894 | 2444 −381 −1115 | −3534 399 −701 | −2588 106 −1378 | 1707 −626 −9818 | −3287 210 −9058 | −928 −466 | −598 −720 | −3178 275 | −3504 394 | −2965 45 | −3167 96 | −2682 359 | 1032 117 | 2265 −369 | −2368 −294 | −1993 −249 | 259 |
| 259(E | −2313 −149 −11 | −4187 −500 −7944 | 2435 233 −8987 | 2792 43 −894 | −4402 −381 −1115 | −2263 399 −701 | −1610 106 −1378 | −4323 −626 −9818 | −1844 210 −9055 | −4194 −466 | −3514 −720 | −860 275 | −2792 394 | −1276 45 | −2693 96 | 882 359 | −2382 117 | −3790 −369 | −4388 −294 | −3377 −249 | 260 |
| 260(E | −1939 −149 −11 | −3595 −500 −7944 | 1643 233 −8987 | 2581 43 −894 | −3872 −381 −1115 | −2212 399 −701 | −1304 106 −1378 | −3690 −626 −9818 | −1146 210 −9053 | −3580 −466 | −2792 −720 | −818 275 | −2607 394 | −925 45 | 2340 96 | −1689 359 | −1941 117 | −3216 −369 | −3731 −294 | −2921 −249 | 261 |
| 261(I) | −3202 −149 −11 | −2787 −500 −7944 | −5004 233 −8987 | −4996 43 −894 | −2836 −381 −1115 | −4384 399 −701 | 4440 106 −1378 | 3937 −626 −9818 | −4838 210 −9050 | −1815 −466 | −1871 −720 | −4704 275 | −4600 394 | −4683 45 | −4704 96 | −4353 359 | −3280 117 | −603 −369 | −3938 −294 | −3661 −249 | 262 |
| 262(H | −1017 −149 −11 | 2728 −500 −7944 | −2493 233 −8987 | −1992 43 −894 | −1270 −381 −1115 | −2240 399 −701 | 3922 106 −1378 | −987 −626 −9818 | −1659 210 −9047 | 529 −466 | −639 −720 | −1791 275 | −2500 394 | −1540 45 | −1774 96 | 784 359 | −1071 117 | −839 −369 | −1737 −294 | −1261 −249 | 263 |
| 263(Q | 741 −149 −11 | −3277 −500 −7944 | 2434 233 −8987 | −357 43 −894 | −3577 −381 −1115 | −2095 399 −701 | −1155 106 −1378 | −3386 −626 −9818 | −1029 210 −9044 | −3313 −466 | −2481 −720 | 1522 275 | −2449 394 | 2598 45 | −1654 96 | −1458 359 | −1671 117 | −2910 −369 | −3496 −294 | −2688 −249 | 264 |

TABLE 7-continued

| | | | | | | | | | | | | | | | | | | |
|---|---|---|---|---|---|---|---|---|---|---|---|---|---|---|---|---|---|---|
| 264(I) | −3202 | −2787 | −5004 | −4996 | −2836 | −4384 | −4440 | 3937 | −4838 | −1815 | −1871 | −4704 | −4600 | −4683 | −4704 | −4353 | −3280 | −603 | −3938 | −3661 | 265 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8987 | −894 | −1115 | −701 | −1378 | −9818 | −9042 | | | | | | | | | | | | |
| 265(Q | −2715 | −3506 | −2454 | −1838 | −4264 | −3140 | −1326 | −3747 | 2319 | −3422 | −2758 | −1861 | −3215 | 3713 | −73 | −2577 | −2482 | −3480 | −3261 | −3082 | 266 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8987 | −894 | −1115 | −701 | −1378 | −9818 | −9039 | | | | | | | | | | | | |
| 266(H | 766 | −2665 | −1250 | −679 | −3083 | −2257 | 3314 | −2738 | 2115 | −2633 | −1790 | −913 | −2340 | 1628 | −214 | −1286 | −1299 | −2357 | −2720 | −2207 | 267 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7944 | −8987 | −894 | −1115 | −701 | −1378 | −9818 | −9036 | | | | | | | | | | | | |
| 267(A | 1483 | −2544 | 1329 | 1148 | −2853 | −1866 | −632 | −2614 | −278 | −2555 | −1651 | 1353 | −2033 | −189 | 1407 | −900 | −994 | −2162 | −2727 | −2019 | 268 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7945 | −8987 | −894 | −1115 | −701 | −1378 | −9818 | −9033 | | | | | | | | | | | | |
| 268(A | 3609 | −2508 | −4184 | −4493 | −4592 | −2737 | −3989 | −4421 | −4496 | −4701 | −4051 | −3440 | −3474 | −4171 | −4253 | −2294 | −2487 | −3536 | −4484 | −4643 | 269 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −11 | −7945 | −8987 | −894 | −1115 | −701 | −1378 | −9818 | −9031 | | | | | | | | | | | | |
| 269(R | −2965 | −3547 | −3408 | −2282 | −4379 | −3379 | −1388 | −3839 | 12 | −3467 | −2835 | −2157 | −3384 | 1874 | 3734 | −2857 | −2671 | −3611 | −3250 | −3161 | 270 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −1308 | −7945 | −761 | −894 | −1115 | −701 | −1378 | −9818 | −9028 | | | | | | | | | | | | |
| 270(N | −1039 | −2562 | 586 | 2367 | −2858 | −1300 | −470 | −2699 | −385 | −2652 | −1895 | 2515 | −1724 | −111 | −973 | −813 | −1067 | −2247 | −2807 | −2007 | 271 |
| | −149 | −500 | 235 | 43 | −381 | 399 | 106 | −626 | 210 | −466 | −720 | 275 | 394 | 45 | 96 | 359 | 117 | −369 | −294 | −249 | |
| | −714 | −1382 | −7703 | −151 | −3331 | −2609 | −258 | −9818 | −9025 | | | | | | | | | | | | |
| 271(N | −622 | −1477 | −200 | −357 | −2707 | 2061 | −999 | −2606 | −952 | −2696 | −1925 | 2838 | −1767 | −722 | −1374 | −664 | −868 | −1957 | −2760 | −2210 | 273 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −24 | −6661 | −7703 | −894 | −1115 | −156 | −3286 | −9818 | −9022 | | | | | | | | | | | | |
| 272(S) | −828 | −2001 | −805 | 1032 | −2258 | −1836 | −533 | −1931 | −149 | −2007 | −1158 | −547 | −1941 | −119 | 1234 | 1440 | 1026 | 880 | −2282 | −1677 | 274 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −242 | −7945 | −8987 | −894 | −1115 | −701 | −1378 | −9818 | −9020 | | | | | | | | | | | | |
| 273(N | −1190 | −2573 | 1355 | 1126 | −2861 | 654 | −1054 | −2615 | −530 | −2616 | −1754 | 2375 | −2165 | −395 | −1071 | −1062 | 1012 | −2205 | −2829 | 1781 | 275 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −12 | −7945 | −8987 | −894 | −1115 | −701 | −1378 | −9818 | −9017 | | | | | | | | | | | | |
| 274(Q | 645 | −2328 | 1160 | −107 | −2646 | 495 | −476 | −2397 | −72 | −2344 | −1425 | 1283 | −1901 | 1657 | 1361 | −730 | −798 | −1950 | −2514 | −1827 | 276 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −12 | −7945 | −8987 | −894 | −1115 | −701 | −1378 | −9818 | −9014 | | | | | | | | | | | | |
| 275(M | −816 | −2072 | 1026 | 1269 | −2307 | −1806 | −491 | 649 | −121 | −2050 | −1908 | 1387 | −1908 | −67 | −614 | −740 | 927 | −1644 | −2309 | −1678 | 277 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −12 | −7945 | −8987 | −894 | −1115 | −701 | −1378 | −9011 | | | | | | | | | | | | | |
| 276(C | 897 | 2636 | −1616 | 1312 | −2623 | 1770 | −1334 | −2281 | −1102 | −2451 | −1631 | −1244 | −2278 | −1004 | −1507 | −1024 | 1250 | −1839 | −2782 | −2281 | 278 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −242 | −7945 | −8987 | −894 | −1115 | −701 | −1378 | −9818 | −9008 | | | | | | | | | | | | |
| 277(S) | −911 | −1183 | −1682 | 1126 | −1300 | −2191 | −1054 | 1565 | −1062 | −1045 | −424 | −1278 | −2298 | −937 | −1360 | 1632 | −874 | 1229 | −1746 | −1317 | 279 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −12 | −7716 | −8758 | −894 | −1115 | −701 | −1378 | −9818 | −9006 | | | | | | | | | | | | |
| 278(R | −2689 | −3297 | −3482 | −2098 | −4001 | −3278 | −2130 | 1210 | 1825 | −3091 | −2443 | −1979 | −3214 | −777 | 3313 | −2610 | −2385 | −3099 | −3035 | −2916 | 280 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7945 | −8987 | −894 | −1115 | −701 | −1378 | −9818 | −9003 | | | | | | | | | | | | |
| 279(P) | −4497 | −4117 | −4899 | −5251 | −5560 | −4139 | −4798 | −6328 | −5454 | −5976 | −5741 | −5026 | 4302 | −5328 | −5104 | −4798 | −4844 | −5739 | −4665 | −5484 | 281 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −12 | −7945 | −8987 | −894 | −1115 | −701 | −1378 | −9818 | −9000 | | | | | | | | | | | | |
| 280(R | 778 | −2256 | −849 | 1049 | 1188 | −1910 | −526 | −2252 | 1217 | −2239 | −1363 | −569 | −1997 | −87 | 2088 | −847 | −872 | −1870 | −2431 | −1819 | 282 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −12 | −7945 | −8987 | −894 | −1115 | −701 | −1378 | −9818 | −8997 | | | | | | | | | | | | |

TABLE 7-continued

| | | | | | | | | | | | | | | | | | |
|---|---|---|---|---|---|---|---|---|---|---|---|---|---|---|---|---|---|
| 281( — | -4593 -149 -12 | -3601 -500 -7945 | -4995 233 -8987 | -5296 43 -894 | 213 -381 -1115 | -4817 399 -701 | -1247 106 -1378 | -3585 -626 -9818 | -4805 210 -8994 | -2925 -466 | -3000 -720 | -3610 275 | -4749 394 | -3723 45 | -4255 96 | -4202 359 | -4477 117 | -3731 -369 | 5803 -294 | 2567 -249 | 283 |
| 282(P) — | -4497 -149 -12 | -4117 -500 -7945 | -4899 233 -8987 | -5251 43 -894 | -5560 -381 -1115 | -4139 399 -701 | -4798 106 -1378 | -6328 -626 -9818 | -5454 210 -8992 | -5976 -466 | -5741 -720 | -5026 275 | 4302 394 | -5328 45 | -5104 96 | -4798 359 | -4844 117 | -5739 -369 | -4665 -294 | -5484 -249 | 284 |
| 283(M — | -2922 -149 -12 | -2503 -500 -7945 | -5243 233 -8987 | -4802 43 -894 | -1395 -381 -1115 | -4799 399 -701 | -3922 106 -1378 | 1630 -626 -9818 | -4451 210 -8989 | -67 -466 | 4721 -720 | -4580 275 | -4460 394 | -3821 45 | -4212 96 | -4136 359 | -2877 117 | -524 -369 | -2992 -294 | -2887 -249 | 285 |
| 284(I — | -2495 -149 -12 | -2001 -500 -7945 | -5129 233 -8987 | -4756 43 -894 | -2240 -381 -1115 | -4897 399 -701 | -4552 106 -1378 | 2929 -626 -9818 | -4659 210 -8986 | 812 -466 | -991 -720 | -4553 275 | -4608 394 | -4412 45 | -4697 96 | -4228 359 | -2473 117 | 2322 -369 | -3865 -294 | -3522 -249 | 286 |
| 285(I — | -2456 -149 -12 | -1959 -500 -7945 | -5125 233 -8987 | -4808 43 -894 | -2579 -381 -1115 | -4919 399 -701 | -4900 106 -1378 | 3028 -626 -9818 | -4754 210 -8983 | -1349 -466 | -1292 -720 | -4605 275 | -4688 394 | -4684 45 | -4898 96 | -4291 359 | -2452 117 | 2714 -369 | -4288 -294 | -3786 -249 | 287 |
| 286(M — | 848 -149 -12 | -1916 -500 -7945 | -4474 233 -8987 | -3859 43 -894 | 1726 -381 -1115 | -3859 399 -701 | -2665 106 -1378 | -466 -626 -9818 | -3512 210 -8980 | 2254 -466 | 2464 -720 | -3496 275 | -3662 394 | -2906 45 | -3258 96 | -2991 359 | -2116 117 | -895 -369 | -2138 -294 | -1962 -249 | 288 |
| 287(R — | -4488 -149 -12 | -4181 -500 -7945 | -4789 233 -8987 | -4318 43 -894 | -5193 -381 -1115 | -4148 399 -701 | -3436 106 -1378 | -5568 -626 -9818 | -2393 210 -8977 | -5152 -466 | -4748 -720 | -4156 275 | -4479 394 | -3286 45 | 4202 96 | -4614 359 | -4467 117 | -5273 -369 | -4267 -294 | -4649 -249 | 289 |
| 288(T — | -1068 -149 -12 | -1511 -500 -7945 | -3017 233 -8987 | -2766 43 -894 | -2440 -381 -1115 | -2076 399 -701 | -2321 106 -1378 | -1926 -626 -9818 | -2515 210 -8974 | 691 -466 | -1630 -720 | -2213 275 | -2655 394 | -2340 45 | -2580 96 | 984 359 | 3190 117 | -1612 -369 | -2890 -294 | -2538 -249 | 290 |
| 289(P) — | -4497 -149 -12 | -4117 -500 -7945 | -4899 233 -8987 | -5251 43 -894 | -5560 -381 -1115 | -4139 399 -701 | -4798 106 -1378 | -6328 -626 -9818 | -5454 210 -8972 | -5976 -466 | -5741 -720 | -5026 275 | 4302 394 | -5328 45 | -5104 96 | -4798 359 | -4844 117 | -5739 -369 | -4665 -294 | -5484 -249 | 291 |
| 290(K — | -4125 -149 -12 | -4091 -500 -7945 | -4017 233 -8987 | -3615 43 -894 | -5101 -381 -1115 | -3960 399 -701 | -2958 106 -1378 | -5182 -626 -9818 | 3972 210 -8969 | -4825 -466 | -4345 -720 | -3552 275 | -4249 394 | -2709 45 | -1809 96 | -4154 359 | -4044 117 | -4895 -369 | -4132 -294 | -4389 -249 | 292 |
| 291(G — | -4088 -149 -12 | -3924 -500 -7945 | -4774 233 -8987 | -5139 43 -894 | -5615 -381 -1115 | 3825 399 -701 | -4753 106 -1378 | -6303 -626 -9818 | -5453 210 -8966 | -6014 -466 | -5662 -720 | -4812 275 | -4539 394 | -5232 45 | -5106 96 | -4370 359 | -4472 117 | -5527 -369 | -4696 -294 | -5561 -249 | 293 |
| 292( — | -3761 -149 -12 | -3778 -500 -7945 | -4018 233 -8987 | -3442 43 -894 | -2596 -381 -1115 | -3886 399 -701 | -2358 106 -1378 | -4281 -626 -9818 | 1706 210 -8963 | -3948 -466 | -3562 -720 | -3262 275 | -4095 394 | -2403 45 | -1546 96 | -3781 359 | -3651 117 | -4139 -369 | 5825 -294 | -2093 -249 | 294 |
| 293(T — | -1328 -149 -12 | -1922 -500 -7945 | -3470 233 -8987 | -3733 43 -894 | -4307 -381 -1115 | 2277 399 -701 | -3460 106 -1378 | -4117 -626 -9818 | -3841 210 -8960 | -4377 -466 | -3512 -720 | -2726 275 | -2930 394 | -3472 45 | -3723 96 | -1571 359 | 3260 117 | -3014 -369 | -4415 -294 | -4352 -249 | 295 |
| 294(C — | -1973 -149 -12 | 4291 -500 -7945 | -4548 233 -8987 | -4851 43 -894 | -4702 -381 -1115 | 3097 399 -701 | -4084 106 -1378 | -4671 -626 -9818 | -4689 210 -8957 | -4886 -466 | -4115 -720 | -3509 275 | -3445 394 | -4310 45 | -4354 96 | -2238 359 | -2433 117 | -3616 -369 | -4524 -294 | -4782 -249 | 296 |
| 295(P — | -4497 -149 -12 | -4117 -500 -7945 | -4899 233 -8987 | -5251 43 -894 | -5560 -381 -1115 | -4139 399 -701 | -4798 106 -1378 | -6328 -626 -9818 | -5454 210 -8954 | -5976 -466 | -5741 -720 | -5026 275 | 4302 394 | -5328 45 | -5104 96 | -4798 359 | -4844 117 | -5739 -369 | -4665 -294 | -5484 -249 | 297 |
| 296(K — | -2049 -149 -12 | -3206 -500 -7945 | 1214 233 -8987 | -1125 43 -894 | -3777 -381 -1115 | -2660 399 -701 | -1057 106 -1378 | -3338 -626 -9818 | 3118 210 -8951 | -3117 -466 | -2350 -720 | -1305 275 | -2771 394 | -635 45 | 1683 96 | -1896 359 | -1900 117 | -2990 -369 | -3089 -294 | -2711 -249 | 298 |
| 297(Y — | -3980 -149 -1892 | -3319 -500 -7945 | -4251 233 -465 | 999 43 -894 | 2912 -381 -1115 | -4528 399 -701 | -1135 106 -1378 | -3159 -626 -9818 | -4198 210 -8948 | -2674 -466 | -2627 -720 | -3261 275 | -4474 394 | -3325 45 | -3891 96 | -3769 359 | -3878 117 | -3246 -369 | -434 -294 | 3896 -249 | 299 |

TABLE 7-continued

| | | | | | | | | | | | | | | | | | |
|---|---|---|---|---|---|---|---|---|---|---|---|---|---|---|---|---|---|
| 298(N) | −682 −149 −35 | −1389 −500 −6088 | −43 233 −7130 | −192 43 −894 | −1821 −381 −1115 | −1114 399 −2832 | −672 106 −218 | −2026 −626 −9818 | −553 210 −8945 | −2169 −466 | −1573 −720 | 3502 275 | −1613 394 | −485 45 | −863 96 | −706 359 | −866 117 | −1616 −369 | −1943 −294 | −1374 −249 | 300 |
| 299(D) | −1183 −149 −35 | −2113 −500 −6088 | 3476 233 −7130 | 202 43 −894 | −2559 −381 −1115 | −1197 399 −2832 | −709 106 −218 | −2583 −626 −9818 | −900 210 −8943 | −2640 −466 | −2095 −720 | −138 275 | −1700 394 | −471 45 | −1494 96 | −1021 359 | −1294 117 | −2203 −369 | −2437 −294 | −1969 −249 | 301 |
| 300( ) | −2006 −149 −35 | −1640 −500 −6088 | −2485 233 −7130 | −2452 43 −894 | 132 −381 −1115 | −2122 399 −2832 | −859 106 −218 | −1689 −626 −9818 | −1966 210 −8940 | −1425 −466 | −1294 −720 | −2093 275 | −2439 394 | −1935 45 | −1852 96 | −2230 359 | −2075 117 | −1731 −369 | 5734 −294 | 501 −249 | 302 |
| 301(S) | 87 −149 −35 | −526 −500 −6088 | −885 233 −7130 | −918 43 −894 | −1797 −381 −1115 | −699 399 −2832 | −997 106 −218 | −1679 −626 −9818 | −970 210 −8937 | −1948 −466 | −1267 −720 | −663 275 | −1335 394 | −874 45 | −1147 96 | 2826 359 | −252 117 | −1082 −369 | −2036 −294 | −1577 −249 | 303 |
| 302(G) | −822 −149 −35 | −1159 −500 −6088 | −1384 233 −7130 | −1565 43 −894 | −2531 −381 −1115 | 3361 399 −2832 | −1634 106 −218 | −2586 −626 −9818 | −1803 210 −8934 | −2721 −466 | −2161 −720 | −1396 275 | −1832 394 | −1670 45 | −1866 96 | −1023 359 | −1160 117 | −1997 −369 | −2255 −294 | −2352 −249 | 304 |
| 303(P) | −1003 −149 −35 | −1278 −500 −6088 | −1425 233 −7130 | −1532 43 −894 | −2259 −381 −1115 | −1370 399 −2832 | −1531 106 −218 | −2247 −626 −9818 | −1572 210 −8931 | −2349 −466 | −1911 −720 | −1434 275 | 3795 394 | −1555 45 | −1648 96 | −1199 359 | −1287 117 | −1861 −369 | −2108 −294 | −2096 −249 | 305 |
| 304(K) | −1075 −149 −35 | −1727 −500 −6088 | −849 233 −7130 | −488 43 −894 | −2222 −381 −1115 | −1560 399 −2832 | −298 106 −218 | −1928 −626 −9818 | 3141 210 −8928 | −1906 −466 | −1299 −720 | −589 275 | −1788 394 | 39 45 | 576 96 | −1050 359 | −1018 117 | −1673 −369 | −1848 −294 | −1572 −249 | 306 |
| 305(V) | −2351 −149 −12 | −1948 −500 −7945 | −4836 233 −8987 | −4325 43 −894 | 1729 −381 −1115 | −4359 399 −133 | −3437 106 −3510 | 1662 −626 −9818 | −4074 210 −8925 | 1144 −466 | −429 −720 | −4011 275 | −4122 394 | −3586 45 | −3910 96 | −3565 359 | −2297 117 | 2576 −369 | −2861 −294 | −2632 −249 | 307 |
| 306(D) | −2623 −149 −35 | −4424 −500 −6088 | 3671 233 −7130 | −647 43 −894 | −4716 −381 −1115 | −2401 399 −701 | −1896 106 −1378 | −4807 −626 −9818 | −2315 210 −8922 | −4650 −466 | −4093 −720 | 1964 275 | −2996 394 | −1602 45 | −3278 96 | −2267 359 | −2747 117 | −4224 −369 | −4722 −294 | −3696 −249 | 308 |
| 307(G) | −4088 −149 −12 | −3924 −500 −7945 | −4774 233 −8987 | −5139 43 −894 | −5615 −381 −1115 | 3825 399 −701 | −4753 106 −1378 | −6303 −626 −9818 | −5453 210 −8919 | −6014 −466 | −5662 −720 | −4812 275 | −4539 394 | −5232 45 | −5106 96 | −4370 359 | −4472 117 | −5527 −369 | −4696 −294 | −5561 −249 | 309 |
| 308(K) | −1892 −149 −12 | −1727 −500 −7945 | −465 233 −8987 | −488 43 −894 | −2222 −381 −1115 | −1560 399 −701 | −1378 106 −1378 | −1928 −626 −9818 | 3141 210 −8916 | −1906 −466 | −1299 −720 | −589 275 | −1788 394 | 39 45 | 576 96 | −1050 359 | −1018 117 | −1673 −369 | −1848 −294 | −1572 −249 | 310 |
| 309(G) | −822 −149 −35 | −1159 −500 −6088 | −1384 233 −7130 | −1565 43 −894 | −2531 −381 −1115 | 3361 399 −2832 | −1634 106 −218 | −2586 −626 −9818 | −1803 210 −8913 | −2721 −466 | −2161 −720 | −1396 275 | −1832 394 | −1670 45 | −1866 96 | −1023 359 | −1160 117 | −1997 −369 | −2255 −294 | −2352 −249 | 311 |
| 310(M) | −972 −149 −12 | −1126 −500 −7945 | −2062 233 −8987 | −1461 43 −894 | −1092 −381 −1115 | −2307 399 −701 | 2087 106 −3510 | −624 −626 −9818 | 1939 210 −8910 | 525 −466 | 2294 −720 | −1457 275 | −2364 394 | −1036 45 | −1244 96 | −1332 359 | −906 117 | 985 −369 | −1529 −294 | −1141 −249 | 312 |
| 311(K) | −1820 −149 −12 | −2479 −500 −7945 | −2019 233 −8987 | −1558 43 −894 | −1288 −381 −1115 | −2659 399 −701 | −1288 106 −1378 | −2471 −626 −9818 | 2648 210 −8910 | −2477 −466 | −1862 −720 | −1639 275 | 2280 394 | −1101 45 | −838 96 | −1862 359 | −1798 117 | −2256 −369 | −2259 −294 | −1515 −249 | 313 |
| 312(T) | −1151 −149 −12 | −994 −500 −7945 | −3207 233 −8987 | −2614 43 −894 | −1014 −381 −1115 | −2726 399 −701 | −1631 106 −1378 | 1486 −626 −9818 | −2292 210 −8907 | 872 −466 | −195 −720 | 1131 275 | −2765 394 | −1990 45 | −2222 96 | −1813 359 | 1899 117 | 1286 −369 | −1587 −294 | −1232 −249 | 314 |
| 313(E) | −4205 −149 −12 | −4417 −500 −7945 | −2343 233 −8987 | 3901 43 −894 | −5349 −381 −1115 | −3698 399 −701 | −3534 106 −1378 | −5837 −626 −9818 | −3838 210 −8904 | −5561 −466 | −5237 −720 | −3039 275 | −4218 394 | −3453 45 | −4201 96 | −4072 359 | −4352 117 | −5409 −369 | −4640 −294 | −4860 −249 | 315 |
| 314(G) | −2817 −149 −12 | −3261 −500 −7945 | −2719 233 −8987 | −3002 43 −894 | −3965 −381 −1115 | 3464 399 −701 | 2847 106 −1378 | −5005 −626 −9818 | −3386 210 −8901 | −4897 −466 | −4328 −720 | −2988 275 | −3770 394 | −3306 45 | −3516 96 | −2944 359 | −3148 117 | −4263 −369 | −3982 −294 | −3566 −249 | 316 |

TABLE 7-continued

| | | | | | | | | | | | | | | | | |
|---|---|---|---|---|---|---|---|---|---|---|---|---|---|---|---|---|
| 315(F) | -1106 -149 -12 | -1561 -500 -7945 | -3154 233 -8987 | -2946 43 -894 | 2579 -381 -1115 | -2093 399 -701 | -2290 106 -1378 | -2229 -626 -9818 | -2773 210 -8895 | -2503 -466 | -1842 -720 | -2289 275 | -2698 394 | -2501 45 | -2812 96 | 2488 359 | 1579 117 | -1836 -369 | -2597 -294 | -1956 -249 | 317 |
| 316( | -4550 -149 -12 | -3570 -500 -7945 | -5043 233 -8987 | -5348 43 -894 | 3560 -381 -1115 | -4834 399 -701 | -1253 106 -1378 | -3407 -626 -9818 | -4915 210 -8892 | -2729 -466 | -2820 -720 | -3625 275 | -4750 394 | -3739 45 | -4322 96 | -4199 359 | -4435 117 | -3608 -369 | 4998 -294 | 679 -249 | 318 |
| 317(R | -4488 -149 -12 | -4181 -500 -7945 | -4789 233 -8987 | -4318 43 -894 | -5193 -381 -1115 | -4148 399 -701 | -3436 106 -1378 | -5568 -626 -9818 | -2393 210 -8889 | -5152 -466 | -4748 -720 | -4156 275 | -4479 394 | -3286 45 | 4202 96 | -4614 359 | -4467 117 | -5273 -369 | -4267 -294 | -4649 -249 | 319 |
| 318(A | 3015 -149 -12 | -1667 -500 -7945 | -3723 233 -8987 | -3946 43 -894 | -4169 -381 -1115 | -1935 399 -701 | -3415 106 -1378 | -3952 -626 -9818 | -3869 210 -8886 | -4231 -466 | -3312 -720 | -2607 275 | -2729 394 | -3434 45 | -3685 96 | 1976 359 | -1516 117 | -2782 -369 | -4395 -294 | -4270 -249 | 320 |
| 319(H | -4836 -149 -12 | -4275 -500 -7945 | -4356 233 -8987 | -4629 43 -894 | -3663 -381 -1115 | -4242 399 -701 | 5422 106 -1378 | -5932 -626 -9818 | -4492 210 -8883 | -5436 -466 | -5298 -720 | -4579 275 | -4696 394 | -4620 45 | -4352 96 | -5005 359 | -5030 117 | -5648 -369 | -3750 -294 | -3259 -249 | 321 |
| 320(Q | -4207 -149 -12 | -4117 -500 -7945 | -3531 233 -8987 | -3731 43 -894 | -4752 -381 -1115 | -3930 399 -701 | -3721 106 -1378 | -5554 -626 -9818 | -3395 210 -8880 | -5179 -466 | -4897 -720 | -3823 275 | -4399 394 | 4556 45 | -3405 96 | -4301 359 | -4380 117 | -5208 -369 | -4301 -294 | -4384 -249 | 322 |
| 321(V | -2838 -149 -12 | -2616 -500 -7945 | -4834 233 -8987 | -4880 43 -894 | -3213 -381 -1115 | -3955 399 -701 | -4416 106 -1378 | -610 -626 -9818 | -4757 210 -8877 | -2310 -466 | -2253 -720 | -4383 275 | -4345 394 | -4643 45 | -4642 96 | -3732 359 | -3007 117 | 3763 -369 | -4157 -294 | -3886 -249 | 323 |
| 322(P) | -4497 -149 -12 | -4117 -500 -7945 | -4899 233 -8987 | -5251 43 -894 | -5560 -381 -1115 | -4139 399 -701 | -4798 106 -1378 | -6328 -626 -9818 | -5454 210 -8873 | -5976 -466 | -5741 -720 | -5026 275 | 4302 394 | -5328 45 | -5104 96 | -4798 359 | -4844 117 | -5739 -369 | -4665 -294 | -5484 -249 | 324 |
| 323(L) | -3647 -149 -12 | -3060 -500 -7945 | -5937 233 -8987 | -5371 43 -894 | -1118 -381 -1115 | -5682 399 -701 | -4332 106 -1378 | -610 -626 -9818 | -5087 210 -8870 | 2996 -466 | 2562 -720 | -5429 275 | -4784 394 | -3924 45 | -4592 96 | -5073 359 | -3493 117 | -1434 -369 | -2915 -294 | -3081 -249 | 325 |
| 324(A | 1628 -149 -12 | -2000 -500 -7945 | -1147 233 -8987 | -671 43 -894 | -2849 -381 -1115 | 708 399 -701 | -956 106 -1378 | -2576 -626 -9818 | 1413 210 -8867 | -2602 -466 | -1707 -720 | -874 275 | 1246 394 | -539 45 | -1044 96 | 862 359 | -977 117 | -2054 -369 | -2809 -294 | -2207 -249 | 326 |
| 325(G | -994 -149 -12 | -1140 -500 -7945 | -2933 233 -8987 | -2481 43 -894 | -1432 -381 -1115 | 1651 399 -701 | -1741 106 -1378 | -844 -626 -9818 | -2217 210 -8864 | 1593 -466 | -640 -720 | -2068 275 | -2570 394 | -1955 45 | -2226 96 | 912 359 | -1096 117 | 1103 -369 | -1926 -294 | -1575 -249 | 327 |
| 326(M | 1630 -149 -12 | -1391 -500 -7945 | 944 233 -8987 | -805 43 -894 | -1486 -381 -1115 | -2021 399 -701 | -819 106 -1378 | -1063 -626 -9818 | -696 210 -8861 | 342 -466 | 2038 -720 | -972 275 | -2133 394 | -594 45 | -1070 96 | 829 359 | -812 117 | -889 -369 | -1808 -294 | -1343 -249 | 328 |
| 327(R | 741 -149 -12 | -2275 -500 -7945 | -1345 233 -8987 | -792 43 -894 | -2855 -381 -1115 | -2120 399 -701 | 2241 106 -1378 | -2529 -626 -9818 | -225 210 -8858 | -2528 -466 | -1693 -720 | -987 275 | -2298 394 | 476 45 | 2769 96 | 943 359 | -1193 117 | -2130 -369 | -2695 -294 | -2176 -249 | 329 |
| 328(E | -921 -149 -12 | -2389 -500 -7945 | 1203 233 -8987 | 1772 43 -894 | -2695 -381 -1115 | -1817 399 -701 | -532 106 -1378 | -2446 -626 -9818 | 1276 210 -8855 | -2398 -466 | -1488 -720 | 451 275 | -1950 394 | -84 45 | -661 96 | -792 359 | 1210 117 | -2005 -369 | -2575 -294 | 1454 -249 | 330 |
| 329(N | -1665 -149 -12 | -3235 -500 -7945 | -2933 233 -8987 | -369 43 -894 | -3518 -381 -1115 | -2098 399 -701 | 2328 106 -1378 | -3335 -626 -9818 | -1031 210 -8852 | -3275 -466 | -2450 -720 | 2949 275 | -2451 394 | -767 45 | -1649 96 | -1460 359 | 1173 117 | -2871 -369 | -3460 -294 | -2660 -249 | 331 |
| 330(M | -984 -149 -12 | -1840 -500 -7945 | -1021 233 -8987 | 1102 43 -894 | -2105 -381 -1115 | -1976 399 -701 | -854 106 -1378 | -1713 -626 -9818 | -582 210 -8849 | -1892 -466 | 2223 -720 | -850 275 | 1910 394 | -518 45 | -1007 96 | -1020 359 | 1988 117 | -1453 -369 | -2293 -294 | -1758 -249 | 332 |
| 331(A | 2196 -149 -12 | -2790 -500 -7945 | -511 233 -8987 | 1218 43 -894 | -3438 -381 -1115 | 973 399 -701 | -1226 106 -1378 | -3215 -626 -9818 | -1068 210 -8845 | -3198 -466 | -2356 -720 | 1800 275 | -2422 394 | -839 45 | -1642 96 | -1356 359 | -1536 117 | -2702 -369 | -3401 -294 | -2670 -249 | 333 |

TABLE 7-continued

| | | | | | | | | | | | | | | | | | | |
|---|---|---|---|---|---|---|---|---|---|---|---|---|---|---|---|---|---|---|
| 332H | -1254 -149 -12 | -2578 -500 -7945 | -716 233 -8987 | -424 43 -894 | -2897 -381 -1115 | -2040 399 -701 | 3715 106 -1378 | -2651 -626 -9818 | -343 210 -8842 | -2622 -466 | -1770 -720 | 1388 275 | -2228 394 | 1875 45 | -752 96 | -1137 359 | 1164 117 | -2249 -369 | -2782 -294 | -2139 -249 | 334 |
| 333(L) | -2624 -149 -12 | -2340 -500 -7945 | -4474 233 -8987 | -3875 43 -894 | 1811 -381 -1115 | -4126 399 -701 | -2401 106 -1378 | -789 -626 -9818 | -3050 210 | 2542 -466 | -178 -720 | -3525 275 | -3908 394 | -2863 45 | 1521 96 | -3305 359 | -2528 117 | -1300 -369 | -1886 -294 | -1260 -249 | 335 |
| 334(N) | -994 -149 -12 | -2499 -500 -7945 | 1168 233 -8987 | 1208 43 -894 | -2810 -381 -1115 | -1843 399 -701 | -590 106 -1378 | -2571 -626 -9818 | 1159 210 -8839 | -2510 -466 | -1599 -720 | 1604 275 | 1101 394 | 1558 45 | -751 96 | -854 359 | -943 117 | -2117 -369 | -2678 -294 | -1972 -249 | 336 |
| 335Q | -1074 -149 -12 | -1608 -500 -7945 | -1378 233 -8987 | 1055 43 -894 | -1583 -381 -1115 | -2212 399 -701 | -948 106 -1378 | -1034 -626 -9818 | -735 210 -8836 | 1334 -466 | -653 -720 | -1095 275 | -2304 394 | 2285 45 | -1076 96 | -1227 359 | -1014 117 | 962 -369 | -1974 -294 | -1519 -249 | 337 |
| 336(L) | -3687 -149 -12 | -3085 -500 -7945 | -5735 233 -8987 | -5323 43 -894 | 1918 -381 -1115 | -5462 399 -701 | -3361 106 -1378 | -783 -626 -9818 | -5056 210 -8833 | 2956 -466 | -82 -720 | -4983 275 | -4746 394 | -3886 45 | -4547 96 | -4848 359 | -3542 117 | -1585 -369 | -2287 -294 | -1717 -249 | 338 |
| 337(E | -1470 -149 -12 | -2699 -500 -7945 | -964 233 -8987 | 2371 43 -894 | -3064 -381 -1115 | -2232 399 -701 | -901 106 -1378 | -2597 -626 -9818 | 2215 210 -8830 | -2668 -466 | -1868 -720 | -905 275 | -2396 394 | -486 45 | -559 96 | -1359 359 | -1400 117 | 909 -369 | -2856 -294 | -2297 -249 | 339 |
| 338(E | 690 -149 -12 | -2696 -500 -7945 | 1523 233 -8987 | 1869 43 -894 | -2999 -381 -1115 | 734 399 -701 | -738 106 -1378 | -2770 -626 -9818 | 1285 210 -8827 | -2707 -466 | -1812 -720 | -539 275 | -2120 394 | -303 45 | -973 96 | -1012 359 | -1128 117 | -2313 -369 | -2880 -294 | -2153 -249 | 340 |
| 339( | -5598 -149 -12 | -4432 -500 -7945 | -5385 233 -8987 | -5722 43 -894 | -3380 -381 -1115 | -4524 399 -701 | -4140 106 -1378 | -5941 -626 -9818 | -5643 210 -8823 | -5318 -466 | -5354 -720 | -5427 275 | -4938 394 | -5474 45 | -5178 96 | -5909 359 | -5751 117 | -5890 -369 | 6275 -294 | -2993 -249 | 341 |
| 340(M | -3596 -149 -12 | -3028 -500 -7945 | -5873 233 -8987 | -5313 43 -894 | -1121 -381 -1115 | -5593 399 -701 | -4267 106 -1378 | -607 -626 -9818 | -5011 210 -8820 | 2392 -466 | 4057 -720 | -5338 275 | -4750 394 | -3897 45 | -4538 96 | -4973 359 | -3450 117 | -1415 -369 | -2899 -294 | -3039 -249 | 342 |
| 341(K | -991 -149 -12 | -2413 -500 -7945 | -818 233 -8987 | 1144 43 -894 | -2767 -381 -1115 | -1924 399 -701 | -530 106 -1378 | -2487 -626 -9818 | 1895 210 -8817 | -2410 -466 | -1508 -720 | 1562 275 | -2015 394 | -77 45 | 1221 96 | -869 359 | 1088 117 | -2056 -369 | -2547 -294 | -1918 -249 | 343 |
| 342(S) | -1944 -149 -12 | -2458 -500 -7945 | -3696 233 -8987 | -4011 43 -894 | -4410 -381 -1115 | -2644 399 -701 | -3753 106 -1378 | -4675 -626 -9818 | -4191 210 -8814 | -4807 -466 | -4070 -720 | -3198 275 | -3384 394 | -3886 45 | -4051 96 | 3656 359 | -2393 117 | -3615 -369 | -4374 -294 | -4307 -249 | 344 |
| 343Y | -4791 -149 -12 | -3935 -500 -7945 | -4914 233 -8987 | -5231 43 -894 | -815 -381 -1115 | -4530 399 -701 | -2178 106 -1378 | -4357 -626 -9818 | -5024 210 -8811 | -3745 -466 | -3807 -720 | -4206 275 | -4772 394 | -4328 45 | -4584 96 | -4677 359 | -4837 117 | -4435 -369 | -1477 -294 | 4857 -249 | 345 |
| 344K | -2113 -149 -12 | -3150 -500 -7945 | -2249 233 -8987 | -1388 43 -894 | -3797 -381 -1115 | -2829 399 -701 | -992 106 -1378 | -3281 -626 -9818 | 2710 210 -8807 | -3026 -466 | -2265 -720 | 1725 275 | -2831 394 | 1860 45 | 1625 96 | -1985 359 | -1911 117 | -2964 -369 | -2962 -294 | -2675 -249 | 346 |
| 345(P) | -2272 -149 -12 | 3432 -500 -7945 | -4625 233 -8987 | -4892 43 -894 | -4644 -381 -1115 | -2928 399 -701 | -4139 106 -1378 | -4609 -626 -9818 | -4669 210 -8804 | -4819 -466 | -4180 -720 | -3725 275 | 3909 394 | -4404 45 | -4368 96 | -2543 359 | -2718 117 | -3748 -369 | -4454 -294 | -4686 -249 | 347 |
| 346E | -2460 -149 -12 | -4036 -500 -7945 | -460 233 -8987 | 3371 43 -894 | -4348 -381 -1115 | -2457 399 -701 | -1702 106 -1378 | -4275 -626 -9818 | -1584 210 -8801 | -4118 -466 | -3462 -720 | -3198 275 | -2946 394 | 2051 45 | -2090 96 | -2167 359 | -2503 117 | -3804 -369 | -4163 -294 | -3385 -249 | 348 |
| 347(E | -2181 -149 -12 | -3963 -500 -7945 | 1851 233 -8987 | 3002 43 -894 | -4213 -381 -1115 | -2236 399 -701 | -1529 106 -1378 | -4092 -626 -9818 | -1674 210 -8798 | -3990 -466 | -3269 -720 | -843 275 | -2732 394 | -1182 45 | -2455 96 | -1882 359 | 1292 117 | -3581 -369 | -4185 -294 | -3235 -249 | 349 |
| 348(L) | -3686 -149 -12 | -3084 -500 -7945 | -5725 233 -8987 | -5318 43 -894 | 2066 -381 -1115 | -5451 399 -701 | -3323 106 -1378 | -791 -626 -9818 | -5050 210 -8794 | 2922 -466 | -90 -720 | -4961 275 | -4743 394 | -3882 45 | -4541 96 | -4834 359 | -3541 117 | -1590 -369 | -2260 -294 | -1671 -249 | 350 |

TABLE 7-continued

| | | | | | | | | | | | | | | | | | | |
|---|---|---|---|---|---|---|---|---|---|---|---|---|---|---|---|---|---|---|
| 349(F) | −3772 −149 −12 | −3147 −500 −7945 | −5332 233 −8987 | −5198 −894 | 4004 −381 −1115 | −5042 399 −701 | −2246 106 −1378 | −1256 −626 −9818 | −4859 210 −8788 | 1259 −466 | −621 −720 | −4264 275 | −4667 394 | −3786 45 | −4369 96 | −4411 359 | −3663 117 | −1931 −369 | −1412 −294 | −419 −249 | 351 |
| 350(D) | −2611 −149 −12 | −4416 −500 −7945 | 3402 233 −8987 | −640 43 −894 | −4705 −381 −1115 | −2395 399 −701 | −1885 106 −1378 | −4789 −626 −9818 | −2297 210 −8785 | −4633 −466 | −4071 −720 | 2681 275 | −2988 394 | −1589 45 | −3255 96 | −2256 359 | −2733 117 | −4207 −369 | −4711 −294 | −3684 −249 | 352 |
| 351(E) | 2436 −149 −12 | −2868 −500 −7945 | −924 233 −8987 | 2744 43 −894 | −4080 −381 −1115 | −2309 399 −701 | −2015 106 −1378 | −3815 −626 −9818 | −2053 210 −8781 | −3929 −466 | −3209 −720 | −1413 275 | −2875 394 | −1718 45 | −2576 96 | −1853 359 | −2106 117 | −3206 −369 | −4090 −294 | −3471 −249 | 353 |
| 352(H) | 692 −149 −12 | −2743 −500 −7945 | 2175 233 −8987 | −223 43 −894 | −3038 −381 −1115 | −1936 399 −701 | 2515 106 −1378 | −2810 −626 −9818 | −480 210 −8778 | −2751 −466 | −1863 −720 | 1409 275 | −2154 394 | 1594 45 | −1031 96 | −1057 359 | −1179 117 | −2357 −369 | −2927 −294 | −2196 −249 | 354 |
| 353(G) | −2929 −149 −12 | −3168 −500 −7945 | −3518 233 −8987 | −3782 43 −894 | −1975 −381 −1115 | 3489 399 −701 | −2803 106 −1378 | −4394 −626 −9818 | −4019 210 −8775 | −4184 −466 | −3856 −720 | −3400 275 | −3940 394 | −3733 45 | −3967 96 | −3094 359 | −3258 117 | −3950 −369 | −2519 −294 | 2220 −249 | 355 |
| 354(S) | 743 −149 −12 | −1505 −500 −7945 | −1390 233 −8987 | −843 43 −894 | −1747 −381 −1115 | −1981 399 −701 | −884 106 −1378 | −1345 −626 −9818 | −674 210 −8771 | 588 −466 | −830 −720 | −999 275 | −2148 394 | −615 45 | 1093 96 | 1645 359 | 1025 117 | −1123 −369 | −2016 −294 | −1540 −249 | 356 |
| 355(P) | −2511 −149 −12 | −2204 −500 −7945 | −4688 233 −8987 | −4170 43 −894 | −1213 −381 −1115 | −4215 399 −701 | −3207 106 −1378 | 1516 −626 −9818 | −3824 210 −8768 | 2221 −466 | −98 −720 | −3895 275 | 2348 394 | −3271 45 | −3624 96 | −3424 359 | −2456 117 | −677 −369 | −2586 −294 | −2462 −249 | 357 |
| 356(K) | −1302 −149 −12 | −1414 −500 −7945 | −2419 233 −8987 | −1840 43 −894 | −1577 −381 −1115 | −2693 399 −701 | −1530 106 −1378 | 1325 −626 −9818 | 2435 210 −8765 | −1189 −466 | −660 −720 | −1855 275 | −2761 394 | −1446 45 | −1616 96 | −1749 359 | 1313 117 | 1240 −369 | −2101 −294 | −1697 −249 | 358 |
| 357(E) | 687 −149 −12 | −2542 −500 −7945 | −623 233 −8987 | 1957 43 −894 | −2905 −381 −1115 | −1944 399 −701 | −710 106 −1378 | −2641 −626 −9818 | 1433 210 −8762 | −2592 −466 | −1707 −720 | −604 275 | 1914 394 | −274 45 | −748 96 | −998 359 | −1082 117 | −2205 −369 | −2761 −294 | −2094 −249 | 359 |
| 358(E) | −2040 −149 −12 | −3771 −500 −7945 | 1647 233 −8987 | 2163 43 −894 | −4056 −381 −1115 | 1964 399 −701 | −1435 106 −1378 | −3921 −626 −9818 | −1508 210 −8758 | −3821 −466 | −3060 −720 | −809 275 | −2658 394 | −1075 45 | −2248 96 | 864 359 | −2081 117 | −3410 −369 | −4011 −294 | −3098 −249 | 360 |
| 359(I) | −2526 −149 −12 | −2113 −500 −7945 | −4983 233 −8987 | −4447 43 −894 | 1598 −381 −1115 | −4503 399 −701 | −3494 106 −1378 | 2404 −626 −9818 | −4186 210 −8755 | 1749 −466 | −242 −720 | −4162 275 | −4188 394 | −3576 45 | −3962 96 | −3711 359 | −2456 117 | 1420 −369 | −2790 −294 | −2649 −249 | 361 |
| 360(R) | −1519 −149 −12 | −2765 −500 −7945 | −1433 233 −8987 | 1043 43 −894 | −3230 −381 −1115 | −2362 399 −701 | −786 106 −1378 | −2853 −626 −9818 | 1407 210 −8752 | −2712 −466 | −1878 −720 | −1010 275 | −2424 394 | −346 45 | 2271 96 | −1399 359 | 2090 117 | −2477 −369 | −2766 −294 | −2295 −249 | 362 |
| 361(A) | 2266 −149 −12 | −3817 −500 −7945 | 1712 233 −8987 | 2253 43 −894 | −4133 −381 −1115 | −2221 399 −701 | −1507 106 −1378 | −3996 −626 −9818 | −1626 210 −8748 | −3910 −466 | −3174 −720 | −845 275 | −2706 394 | −1158 45 | −2386 96 | −1834 359 | −2166 117 | −3485 −369 | −4107 −294 | −3184 −249 | 363 |
| 362(F) | −1042 −149 −12 | −885 −500 −7945 | −3196 233 −8987 | −2582 43 −894 | 2439 −381 −1115 | −2571 399 −701 | 2436 106 −1378 | 1238 −626 −9818 | −2213 210 −8745 | 706 −466 | 10 −720 | −2148 275 | −2609 394 | −1856 45 | −2072 96 | −1653 359 | 1024 117 | −245 −369 | −1243 −294 | −832 −249 | 364 |
| 363(M) | 2115 −149 −12 | −1084 −500 −7945 | −3069 233 −8987 | −2501 43 −894 | −1009 −381 −1115 | −2553 399 −701 | −1611 106 −1378 | 411 −626 −9818 | −2186 210 −8741 | 950 −466 | 2374 −720 | −2167 275 | −2680 394 | −1891 45 | −2150 96 | −1666 359 | 1057 117 | −397 −369 | −1620 −294 | −1292 −249 | 365 |
| 364(P) | −4497 −149 −12 | −4117 −500 −7945 | −4899 233 −8987 | −5251 43 −894 | −5560 −381 −1115 | −4139 399 −701 | −4798 106 −1378 | −6328 −626 −9818 | −5454 210 −8738 | −5976 −466 | −5741 −720 | −5026 275 | 4302 394 | −5328 45 | −5104 96 | −4798 359 | −4844 117 | −5739 −369 | −4665 −294 | −5484 −249 | 366 |
| 365(K) | −1362 −149 −12 | −2752 −500 −7945 | −891 233 −8987 | 1110 43 −894 | −3142 −381 −1115 | −2149 399 −701 | −769 106 −1378 | −2837 −626 −9818 | 2560 210 −8735 | −2727 −466 | −1865 −720 | −782 275 | 1373 394 | 1618 45 | −441 96 | −1221 359 | −1281 117 | −2420 −369 | −2829 −294 | −2241 −249 | 367 |

TABLE 7-continued

| | | | | | | | | | | | | | | | | | | |
|---|---|---|---|---|---|---|---|---|---|---|---|---|---|---|---|---|---|---|
| 366(G) | 1022 -149 -12 | -1909 -500 -7945 | -2732 233 -8987 | -2555 -894 43 | -3858 -381 -1115 | 2953 399 -701 | -2403 106 -1378 | -3572 -626 -9818 | -1903 210 -8731 | -3702 -466 | -2863 -720 | -2142 275 | -2736 394 | -2152 45 | 1711 96 | -1431 359 | -1592 117 | -2728 -369 | -3841 -294 | -3572 -249 | 368 |
| 367(E) | -1926 -149 -12 | -3649 -500 -7945 | 1536 233 -8987 | 2753 43 -894 | -3890 -381 -1115 | -2165 399 -701 | -1327 106 -1378 | -3735 -626 -9818 | -1325 210 -8728 | -3640 -466 | -2851 -720 | 1567 275 | -2586 394 | -953 45 | -2024 96 | -1665 359 | 1092 117 | -3244 -369 | -3826 -294 | -2947 -249 | 369 |
| 368(K) | -2153 -149 -12 | -2373 -500 -7945 | -3052 233 -8987 | -2232 43 -894 | -1767 -381 -1115 | -3262 399 -701 | -1649 106 -1378 | -1215 -626 -9818 | 3030 210 -8725 | 859 -466 | 2514 -720 | -2219 275 | -3217 394 | -1370 45 | -831 96 | -2425 359 | -2024 117 | -1487 -369 | -2493 -294 | -2241 -249 | 370 |
| 369(R) | -4488 -149 -12 | -4181 -500 -7945 | -4789 233 -8987 | -4318 43 -894 | -5193 -381 -1115 | -4148 399 -701 | -3436 106 -1378 | -5568 -626 -9818 | -2393 210 -8721 | -5152 -466 | -4748 -720 | -4156 275 | -4479 394 | -3286 45 | 4202 96 | -4614 359 | -4467 117 | -5273 -369 | -4267 -294 | -4649 -249 | 371 |
| 370(M) | -3269 -149 -12 | -2747 -500 -7945 | -5652 233 -8987 | -5079 43 -894 | -1177 -381 -1115 | -5325 399 -701 | -4102 106 -1378 | 1525 -626 -9818 | -4829 210 -8718 | 1255 -466 | 4460 -720 | -5012 275 | -4616 394 | -3829 45 | -4428 96 | -4616 359 | -3145 117 | -974 -369 | -2895 -294 | -3004 -249 | 372 |
| 371(G) | 2030 -149 -12 | -1651 -500 -7945 | -3665 233 -8987 | -3855 43 -894 | -4195 -381 -1115 | 2704 399 -701 | -3377 106 -1378 | -3993 -626 -9818 | -3822 210 -8714 | -4242 -466 | -3302 -720 | -2568 275 | -2705 394 | -3371 45 | -3670 96 | 1117 359 | -1491 117 | -2786 -369 | -4410 -294 | -4294 -249 | 373 |
| 372(A) | 2364 -149 -12 | -1861 -500 -7945 | -1953 233 -8987 | -1763 43 -894 | -3466 -381 -1115 | -1952 399 -701 | -1976 106 -1378 | -3199 -626 -9818 | -1760 210 -8711 | -3331 -466 | -2471 -720 | -1666 275 | -2522 394 | 1987 45 | -2080 96 | 1936 359 | -1374 117 | -2468 -369 | -3555 -294 | -3102 -249 | 374 |
| 373(N) | -1618 -149 -12 | -2562 -500 -7945 | -1583 233 -8987 | -1250 43 -894 | -3475 -381 -1115 | -2356 399 -701 | -1296 106 -1378 | -3134 -626 -9818 | -474 210 -8707 | -3082 -466 | -2296 -720 | 3378 275 | -2657 394 | -908 45 | 1726 96 | -1605 359 | 1129 117 | -2676 -369 | -3159 -294 | -2725 -249 | 375 |
| 374(P) | -1913 -149 -12 | -2274 -500 -7945 | -2279 233 -8987 | -2086 43 -894 | -1517 -381 -1115 | -2783 399 -701 | 2782 106 -1378 | -2081 -626 -9818 | -1589 210 -8704 | 560 -466 | -1612 -720 | -2058 275 | 3317 394 | -1785 45 | -1716 96 | -2097 359 | -1976 117 | -2000 -369 | -2063 -294 | -1260 -249 | 376 |
| 375(H) | -929 -149 -12 | -2010 -500 -7945 | -791 233 -8987 | 1272 43 -894 | -2044 -381 -1115 | -1913 399 -701 | 2963 106 -1378 | -1853 -626 -9818 | -298 210 -8700 | -1959 -466 | -1145 -720 | 1363 275 | -2029 394 | -239 45 | -766 96 | -888 359 | -872 117 | 799 -369 | -2186 -294 | 1512 -249 | 377 |
| 376(A) | 2877 -149 -12 | -1669 -500 -7945 | -3800 233 -8987 | -3976 43 -894 | -4022 -381 -1115 | -1962 399 -701 | -3382 106 -1378 | -3596 -626 -9818 | -3795 210 -8700 | -3999 -466 | -3156 -720 | -2631 275 | -2746 394 | -3409 45 | -3616 96 | -1328 359 | 2512 117 | -2627 -369 | -4284 -294 | -4151 -249 | 378 |
| 377(N) | -3122 -149 -12 | -3352 -500 -7945 | -2328 233 -8987 | -2577 43 -894 | -596 -381 -1115 | -3446 399 -701 | -1619 106 -1378 | -3701 -626 -9818 | -2981 210 -8693 | -3309 -466 | -3133 -720 | 3888 275 | -3831 394 | -2693 45 | -3130 96 | -3026 359 | -3247 117 | -3561 -369 | -1270 -294 | 2585 -249 | 379 |
| 378(G) | -2018 -149 -12 | -2692 -500 -7945 | -1922 233 -8987 | -2271 43 -894 | -4544 -381 -1115 | 3363 399 -701 | -2969 106 -1378 | -4678 -626 -9818 | -3249 210 -8690 | -4731 -466 | -3990 -720 | 1984 275 | -3232 394 | -2825 45 | -3564 96 | -2140 359 | -2400 117 | -3690 -369 | -4460 -294 | -4184 -249 | 380 |
| 379(G) | -1257 -149 -12 | -1874 -500 -7945 | -3207 233 -8987 | -3523 43 -894 | -4341 -381 -1115 | 3341 399 -701 | -3408 106 -1378 | -4248 -626 -9818 | -3853 210 -8687 | -4463 -466 | -3557 -720 | -2605 275 | -2866 394 | -3402 45 | -3760 96 | 1410 359 | -1718 117 | -3031 -369 | -4475 -294 | -4358 -249 | 381 |
| 380(Y) | -1236 -149 -12 | -1100 -500 -7945 | -3220 233 -8987 | -2594 43 -894 | -757 -381 -1115 | -2737 399 -701 | -1473 106 -1378 | -388 -626 -9818 | -2061 210 -8683 | 1865 -466 | -99 -720 | -2233 275 | -2760 394 | -1870 45 | 1132 96 | -1823 359 | -1172 117 | 1244 -369 | -1376 -294 | 2076 -249 | 382 |
| 381(L) | -2379 -149 -12 | -2141 -500 -7945 | 1254 233 -8987 | -3407 43 -894 | -1292 -381 -1115 | -3975 399 -701 | -2923 106 -1378 | 1518 -626 -9818 | -3405 210 -8679 | 2543 -466 | -203 -720 | -3359 275 | -3842 394 | -2943 45 | -3392 96 | -3194 359 | -2319 117 | -538 -369 | -2579 -294 | -2378 -249 | 383 |
| 382(R) | -1224 -149 -12 -288 | -1996 -500 -7945 | -1644 233 -2519 | -1058 43 -894 | -2408 -381 -1115 | -2207 399 -701 | -1005 106 -1378 | -2022 -626 -9818 | -378 210 -8676 | 315 -466 | -1393 -720 | -1189 275 | 1416 394 | -662 45 | 2668 96 | 937 359 | -1215 117 | -1747 -369 | -2459 -294 | -2006 -249 | 384 |

TABLE 7-continued

| | | | | | | | | | | | | | | | | |
|---|---|---|---|---|---|---|---|---|---|---|---|---|---|---|---|---|
| 383(R | -1347 -149 -14 | -2594 -500 -7671 | -872 233 -8713 | 1389 43 -894 | -3097 -381 -1115 | -2078 399 -1555 | -754 106 -600 | -2768 -626 -9818 | -37 210 -8672 | -2671 -466 | -1846 -720 | -784 275 | -2259 394 | -333 45 | 2876 96 | 1137 359 | -1287 117 | -2364 -369 | -2765 -294 | -2230 -249 | 385 |
| 384(N | -1422 -149 -14 | -3052 -500 -7671 | 1734 233 -8714 | 1461 43 -894 | -3326 -381 -1115 | 980 399 -345 | -901 106 -2232 | -3136 -626 -9818 | -759 210 -8669 | -3056 -466 | -2213 -720 | 1864 275 | -2210 394 | -500 45 | -1385 96 | 1028 359 | -1413 117 | -2660 -369 | -3236 -294 | -2429 -249 | 386 |
| 385(L) | -4119 -149 -12 | -3542 -500 -7945 | -5389 233 -8987 | -5357 -894 | -2027 -381 -1115 | -4767 399 -701 | -4358 106 -1378 | -1609 -626 -9818 | -5118 210 -8665 | 3293 -466 | -979 -720 | -5230 275 | -4771 394 | -4474 45 | -4724 96 | -5069 359 | -4106 117 | -2331 -369 | -3412 -294 | -3400 -249 | 387 |
| 386(K | -1622 -149 -12 | -2790 -500 -7945 | -1624 233 -8987 | 1030 43 -894 | -3260 -381 -1115 | -2461 399 -701 | -828 106 -1378 | -2846 -626 -9818 | 2708 210 -8662 | -2716 -466 | -1905 -720 | -1116 275 | -2506 394 | -393 45 | 1496 96 | -1511 359 | -1487 117 | 892 -369 | -2768 -294 | -2339 -249 | 388 |
| 387(M | -1888 -149 -12 | -1623 -500 -7945 | -4198 233 -8987 | -3600 43 -894 | -1092 -381 -1115 | -3572 399 -701 | -2482 106 -1378 | -158 -626 -9818 | -3255 210 -8658 | 2140 -466 | 2397 -720 | -3210 275 | -3470 394 | -2776 45 | -3059 96 | -2699 359 | 1034 117 | 1479 -369 | -2114 -294 | -1890 -249 | 389 |
| 388(P | -4497 -149 -12 | -4117 -500 -7945 | -4899 233 -8987 | -5251 43 -894 | -5560 -381 -1115 | -4139 399 -701 | -4798 106 -1378 | -6328 -626 -9818 | -5454 210 -8655 | -5976 -466 | -5741 -720 | -5026 275 | 4302 394 | -5328 45 | -5104 96 | -4798 359 | -4844 117 | -5739 -369 | -4665 -294 | -5484 -249 | 390 |
| 389(D | -2522 -149 -12 | -4504 -500 -7945 | 3422 233 -8987 | 1446 43 -894 | -4683 -381 -1115 | 938 399 -701 | -1750 106 -1378 | -4661 -626 -9818 | -2127 210 -8651 | -4504 -466 | -3910 -720 | -909 275 | -2894 394 | -1438 45 | -3092 96 | -2147 359 | -2619 117 | -4102 -369 | -4695 -294 | -3603 -249 | 391 |
| 390( | -3715 -149 -12 | -3061 -500 -7945 | -5054 233 -8987 | -5000 43 -894 | 2784 -381 -1115 | -4779 399 -701 | -1574 106 -1378 | -1778 -626 -9818 | -4602 210 -8647 | 1668 -466 | -1132 -720 | -3738 275 | -4524 394 | -3553 45 | -4110 96 | -4005 359 | -3593 117 | -2304 -369 | 4571 -294 | 289 -249 | 392 |
| 391(H | -1137 -149 -12 | -2529 -500 -7945 | 1169 233 -8987 | 405 43 -894 | -2911 -381 -1115 | -2042 399 -701 | 2148 106 -1378 | -2611 -626 -9818 | 1514 210 -8644 | -2512 -466 | -1626 -720 | -678 275 | -2128 394 | 1722 45 | 2034 96 | -1013 359 | -1053 117 | -2189 -369 | -2623 -294 | -2031 -249 | 393 |
| 392(Q | -1523 -149 -12 | -3117 -500 -7945 | 2166 233 -8987 | 1365 43 -894 | -3403 -381 -1115 | -2057 399 -701 | -1004 106 -1378 | -3194 -626 -9818 | 1438 210 -8640 | -3110 -466 | -2253 -720 | -667 275 | -2351 394 | 2526 45 | -1325 96 | -1325 359 | -1499 117 | -2728 -369 | -3276 -294 | -2509 -249 | 394 |
| 393(Y | -4598 -149 -12 | -3559 -500 -7945 | -5006 233 -8987 | -5329 -894 | 2257 -381 -1115 | -4898 399 -701 | 2594 106 -1378 | -3515 -626 -9818 | -4887 210 -8637 | -2848 -466 | -2926 -720 | -3523 275 | -4759 394 | -3654 45 | -4280 96 | -4143 359 | -4453 117 | -3662 -369 | -366 -294 | 4237 -249 | 395 |
| 394(A | 2380 -149 -12 | -2381 -500 -7945 | -1061 233 -8988 | 1282 43 -894 | -3846 -381 -1115 | 2045 399 -701 | -1941 106 -1378 | -3614 -626 -9818 | -1958 210 -8633 | -3704 -466 | -2890 -720 | -1385 275 | -2665 394 | -1636 45 | -2457 96 | -1509 359 | -1729 117 | -2895 -369 | -3915 -294 | -3319 -249 | 396 |
| 395(V | -2097 -149 -12 | -1741 -500 -7945 | -4406 233 -8988 | -4026 -894 | -2222 -381 -1115 | -4103 399 -701 | -3555 106 -1378 | 2399 -626 -9818 | -3840 210 -8629 | -1319 -466 | -1108 -720 | 1444 275 | -4071 394 | -3681 45 | -3882 96 | -3349 359 | -2094 117 | 2762 -369 | -3366 -294 | -2920 -249 | 397 |
| 396(D | -928 -12 | -2371 * | 1886 * | -165 * | -2715 * | -1822 * | -563 * | -2464 * | 1387 0 | -2421 * | -1512 * | -478 * | 1080 * | -116 * | -692 * | 750 * | 1043 * | -2018 * | -2599 * | -1913 * | 398 |
| | * | * | * | * | * | * | * | -9818 | | | | | | | | | | | | | |

TABLE 8

```
HMMER2.0 [2.3.2]
NAME  XFP
ACC   PF03894.6
DESC  D-xylulose 5-phosphate/D-fructose 6-phosphate phosphoketolase
LENG  187
ALPH  Amino
RF    no
CS    no
MAP   yes
COM   hmmbuild -f -F HMM fs.ann SEED.ann
COM   hmmcalibrate --seed 0 HMM fs.ann
NSEQ  6
CKSUM 8559
GA    15.5 15.5
TC    18.2 15.7
NC    13.6 14.2
XT    -8455 -4 -1000 -1000 -8455 -4 -8455 -4
NULT  -4 -8455
NULE  595 -1558 85 338 -294 453 -1158 197 249 902 -1085 -142 -21 -313 45 531 201 384 -1998 -644
EVD   -10.339054 0.664450
```

| HMM | A m->m | C m->i | D m->d | E i->m | F i->i | G d->m | H d->d | I b->m | K m->e | L | M | N | P | Q | R | S | T | V | W | X | Y |
|---|---|---|---|---|---|---|---|---|---|---|---|---|---|---|---|---|---|---|---|---|---|
| 1(M) | -222 | * | -2807 | -2222 | -1930 | -1975 | -1841 | -1394 | -1946 | -1641 | 3218 | -1876 | 1316 | -1826 | -2064 | -1219 | 2730 | -1183 | -2403 | -2047 | 1 |
|  | -919 | -1308 | -2565 | 43 | -381 | 399 | 106 | -626 | 210 | -466 | -720 | 275 | 394 | 45 | 96 | 359 | 117 | -369 | -294 | -249 |  |
|  | -149 | -500 | 233 | -894 | -1115 | -701 | -1378 | -1222 | -8539 |  |  |  |  |  |  |  |  |  |  |  |  |
|  | -14 | -7717 | -8760 |  |  |  |  |  |  |  |  |  |  |  |  |  |  |  |  |  |  |
| 2(R) | 691 | -1720 | -837 | -294 | -1975 | -1756 | -501 | 673 | -144 | -1751 | -937 | 1196 | -1878 | -121 | 1881 | 951 | -681 | -1325 | -2078 | -1516 | 2 |
|  | -149 | -500 | 233 | -894 | -381 | 399 | 106 | -626 | -210 | -466 | -720 | 275 | 394 | 45 | 96 | 359 | 117 | -369 | -294 | -249 |  |
|  | -14 | -7717 | -8760 | -1115 | -701 | -1378 | -626 | -8535 |  |  |  |  |  |  |  |  |  |  |  |  |  |
| 3(V) | -885 | -1621 | -999 | 990 | -1982 | -1862 | -915 | -1514 | -733 | -1796 | -1048 | -873 | 1044 | -622 | -1147 | 858 | -916 | 2279 | -2227 | -1717 | 3 |
|  | -149 | -500 | 233 | -894 | -381 | 399 | 106 | -626 | 210 | -466 | -720 | 275 | 394 | 45 | 96 | 359 | 117 | -369 | -294 | -249 |  |
|  | -14 | -7717 | -8760 | -1115 | -701 | -1378 | -8762 | -8531 |  |  |  |  |  |  |  |  |  |  |  |  |  |
| 4(L) | -2842 | -2379 | -5209 | -4634 | -994 | -4802 | -3633 | -174 | -4364 | 2574 | 2538 | -4478 | -4252 | -3491 | -4019 | -4045 | -2735 | 1455 | -2614 | -2661 | 4 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -14 | -7717 | -8760 | -894 | -1115 | -701 | -1378 | -8762 | -8527 |  |  |  |  |  |  |  |  |  |  |  |  |
| 5(G) | -1046 | -1667 | -2864 | -3162 | -4077 | 3372 | -3114 | -3979 | -3511 | -4193 | -3299 | -2337 | -2643 | -3089 | -3461 | 1104 | -1501 | -2797 | -4216 | -4066 | 5 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -14 | -7717 | -8760 | -894 | -1115 | -701 | -1378 | -8762 | -8524 |  |  |  |  |  |  |  |  |  |  |  |  |
| 6(K) | 696 | -1959 | -661 | -115 | -2242 | -1707 | -387 | -1932 | 1754 | -1971 | -1104 | -400 | -1809 | 1727 | -429 | 726 | -657 | 544 | -2214 | -1595 | 6 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -14 | -7717 | -8760 | -894 | -1115 | -701 | -1378 | -8762 | -8520 |  |  |  |  |  |  |  |  |  |  |  |  |
| 7(Y) | -4363 | -3343 | -4802 | -5127 | 2939 | -4674 | -927 | -3251 | -4692 | -2586 | -2669 | -3329 | -4545 | -3458 | -4081 | -3935 | -4227 | -3413 | -177 | 4223 | 7 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -14 | -7717 | -8760 | -894 | -1115 | -701 | -1378 | -8762 | -8516 |  |  |  |  |  |  |  |  |  |  |  |  |
| 8(C) | -1627 | 2687 | -3970 | -3367 | 1521 | -3283 | -2148 | -37 | -3007 | 2149 | 118 | -2930 | -3201 | -2520 | -2790 | -2405 | -1562 | 1206 | -1785 | -1498 | 8 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -14 | -7718 | -8760 | -894 | -1115 | -701 | -1378 | -8762 | -8512 |  |  |  |  |  |  |  |  |  |  |  |  |

TABLE 8-continued

| | | | | | | | | | | | | | | | | | | |
|---|---|---|---|---|---|---|---|---|---|---|---|---|---|---|---|---|---|---|
| 9(R) | 737 | -2550 | 1594 | -497 | -3149 | -1980 | -968 | -2870 | -526 | -2846 | -2019 | -774 | -2281 | -570 | 3052 | -1221 | -1340 | -2417 | -3004 | -2383 | 9 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8508 | | | | | | | | | | | | |
| 10(D) | -2399 | -4358 | 3324 | 2308 | -4527 | -2166 | -1608 | -4527 | -1994 | -4367 | -3790 | -765 | -2746 | -1301 | -2656 | -2018 | -2496 | -3976 | -4515 | -3456 | 10 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8504 | | | | | | | | | | | | |
| 11(V) | -2284 | -1804 | -4895 | -4504 | -1990 | -4629 | -4189 | 2412 | -4382 | 1011 | -761 | -4283 | -4358 | -4111 | -4394 | -3938 | -2259 | 2686 | -3549 | -3219 | 11 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8500 | | | | | | | | | | | | |
| 12(M) | -2278 | -1867 | -4746 | -4224 | -1303 | -4284 | -3343 | 1656 | -3973 | 1240 | 3304 | -3939 | -3999 | -3423 | -3784 | -3494 | -2217 | 2073 | -2691 | -2538 | 12 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8496 | | | | | | | | | | | | |
| 13(K) | 693 | -2202 | -1423 | -749 | -2553 | -2182 | -674 | -2107 | 2480 | -2170 | -1388 | -928 | -2252 | -275 | 1432 | -1210 | -1146 | 1012 | -2378 | -1932 | 13 |
| | -149 | -500 | 233 | 43 | -381 | 399 | 106 | -626 | 210 | -466 | -720 | 275 | 394 | 45 | 96 | 359 | 369 | -369 | -294 | -249 | |
| | -14 | -7718 | -8760 | -894 | -1115 | -701 | -1378 | -8762 | -8492 | | | | | | | | | | | | |
| 14(N) | -1049 | -1434 | -1773 | -1500 | -1636 | -2109 | -1397 | -1127 | -1366 | 1815 | -824 | 2287 | -2427 | -1298 | -1590 | -1307 | 1405 | -1004 | -2112 | -1674 | 14 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8488 | | | | | | | | | | | | |
| 15(N) | -3232 | -3514 | -2565 | -2905 | -4358 | -3267 | -3364 | -5192 | -3627 | -5059 | -4632 | 4348 | -3843 | -3410 | -3792 | -3319 | -3533 | -4568 | -4087 | -3976 | 15 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -867 | -7718 | -1171 | -894 | -1115 | -701 | -1378 | -8762 | -8484 | | | | | | | | | | | | |
| 16(E) | -1220 | -2441 | 99 | 2757 | -2966 | -1568 | -808 | -2774 | -675 | -2772 | -2036 | -363 | 2075 | -466 | -1190 | -1070 | -1278 | -2337 | -2879 | -2244 | 16 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -22 | -6873 | -7915 | -894 | -1115 | -701 | -1378 | -8762 | -8480 | | | | | | | | | | | | |
| 17(D) | -1004 | -1749 | 2891 | -305 | -2104 | -1632 | -363 | -886 | -981 | -1762 | -1266 | -575 | -2040 | -692 | -1495 | -1057 | -1089 | 1706 | -2499 | -1874 | 17 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -460 | -6873 | -1933 | -894 | -1115 | -701 | -1378 | -8762 | -8476 | | | | | | | | | | | | |
| 18(M) | 823 | -1578 | 1383 | -173 | -1837 | -216 | -2846 | -1480 | -107 | -1624 | 2041 | -425 | 938 | -38 | -569 | -595 | 1047 | -1187 | -1968 | -1402 | 18 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7493 | -8536 | -894 | -1115 | -701 | -1378 | -8762 | -8472 | | | | | | | | | | | | |
| 19(T) | -897 | -2121 | -888 | -291 | -2541 | -1355 | -715 | -2206 | 1465 | -2164 | -1310 | -532 | -1923 | 20 | 1428 | 1124 | 1894 | -1823 | -2313 | -1770 | 19 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7493 | -8536 | -894 | -1115 | -701 | -1378 | -8762 | -8468 | | | | | | | | | | | | |
| 20(N) | -867 | -2024 | -881 | -423 | -2654 | -1825 | -413 | -2361 | -230 | -2371 | -1499 | -2664 | -2000 | -273 | 1178 | 870 | 1294 | -1909 | -2569 | -1974 | 20 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8464 | | | | | | | | | | | | |
| 21(F) | -3465 | -2876 | -5057 | -4893 | 3938 | -4762 | -2035 | -1021 | -4547 | 1305 | -409 | -4001 | -4411 | -3532 | -4090 | -4106 | -3362 | -1663 | -1215 | -228 | 21 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8459 | | | | | | | | | | | | |
| 22(R) | -4070 | -3868 | -4406 | -3890 | -4820 | -3837 | -3026 | -5122 | -1946 | -4739 | -4314 | -3731 | -4155 | -2844 | 4177 | -4178 | -4041 | -4836 | -3949 | -4248 | 22 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8455 | | | | | | | | | | | | |
| 23(I) | -2379 | -1901 | -4955 | -4531 | -1728 | -4662 | -4059 | 2900 | -4381 | 1570 | -512 | -4321 | -4336 | -3965 | -4313 | -3959 | -2342 | 1650 | -3306 | -3087 | 23 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8451 | | | | | | | | | | | | |
| 24(F) | -2676 | -2354 | -4538 | -4394 | 3992 | -3956 | -1878 | -728 | -4074 | -869 | -959 | -3497 | -4006 | -3383 | -3780 | -3277 | -2708 | 1235 | -1189 | -154 | 24 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8447 | | | | | | | | | | | | |
| 25(G) | -1031 | -1653 | -2874 | -3165 | -4069 | 3287 | -3106 | -3964 | -3500 | -4180 | -3282 | -2329 | -2632 | -3078 | -3451 | 1430 | -1486 | -2782 | -4212 | -4060 | 25 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8443 | | | | | | | | | | | | |

TABLE 8-continued

| | | | | | | | | | | | | | | | | |
|---|---|---|---|---|---|---|---|---|---|---|---|---|---|---|---|---|
| 26(P) | -4077 | -3791 | -4518 | -4858 | -5206 | -3818 | -4460 | -5898 | -5053 | -5602 | -5343 | -4628 | 4289 | -4938 | -4749 | -4364 | -4429 | -5313 | -4385 | -5119 | 26 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8439 | | | | | | | | | | | | |
| 27(D) | -3832 | -4189 | 4132 | -2236 | -5073 | -3341 | -3194 | -5633 | -3716 | -5365 | -5035 | -2584 | -3886 | -3102 | -4252 | -3662 | -4000 | -5151 | -4434 | -4544 | 27 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8435 | | | | | | | | | | | | |
| 28(E) | -3777 | -4125 | -1925 | 3871 | -4984 | -3355 | -3125 | -5379 | -3371 | -5156 | -4796 | -2611 | -3875 | -3007 | -3762 | -3630 | -3916 | -4960 | -4357 | -4463 | 28 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8430 | | | | | | | | | | | | |
| 29(T) | -1009 | -1466 | -1761 | -1492 | -1840 | -2028 | -1429 | -1343 | -1350 | 766 | -1045 | 1393 | -2396 | -1299 | -1587 | -1239 | 2910 | -1154 | -2256 | -1801 | 29 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8426 | | | | | | | | | | | | |
| 30(M) | 1499 | -1643 | -917 | 1243 | -1962 | -1786 | -691 | -1586 | -425 | -1763 | 2853 | -693 | -1975 | -349 | -862 | 779 | -773 | -1304 | -2139 | -1601 | 30 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8422 | | | | | | | | | | | | |
| 31(S) | -1644 | -2173 | -3321 | -3615 | -4077 | -2357 | -3411 | -4307 | -3792 | -4459 | -3725 | -2859 | -3095 | -3512 | -3692 | 3619 | -2088 | -3285 | -4091 | -3959 | 31 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8418 | | | | | | | | | | | | |
| 32(N) | -3232 | -3514 | -2565 | -2905 | -4358 | -3267 | -3364 | -5192 | -3627 | -5059 | -4632 | 4348 | -3843 | -3410 | -3792 | -3319 | -3533 | -4568 | -4087 | -3976 | 32 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8414 | | | | | | | | | | | | |
| 33(R) | -2793 | -3369 | -3662 | -2108 | -4312 | -3237 | -1071 | -3580 | 2493 | -3189 | -2545 | -1934 | -3162 | -654 | 3328 | -2667 | -2432 | -3373 | -2988 | -2947 | 33 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7718 | -8760 | -894 | -1115 | -701 | -1378 | -8762 | -8409 | | | | | | | | | | | | |
| 34(L) | -3410 | -2836 | -5464 | -5039 | 1728 | -5176 | -3154 | -570 | -4762 | 2953 | 115 | -4708 | -4504 | -3649 | -4284 | -4539 | -3272 | -1347 | -2103 | -1550 | 34 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7719 | -8761 | -894 | -1115 | -701 | -1378 | -8762 | -8406 | | | | | | | | | | | | |
| 35(W) | -901 | -2337 | 1407 | -65 | -2541 | -1747 | 2100 | -2368 | -133 | -2334 | -1447 | 1385 | -1904 | 1561 | -644 | -770 | -849 | -1946 | 3634 | -1773 | 35 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8401 | | | | | | | | | | | | |
| 36(A) | 2155 | -3109 | 1523 | 1273 | -3479 | 1112 | -1076 | -3288 | -1004 | -3231 | -2417 | -592 | -2329 | -693 | -1651 | -1350 | -1580 | -2804 | -3429 | -2615 | 36 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -145 | -7718 | -8760 | -894 | -1115 | -701 | -1378 | -8762 | -8397 | | | | | | | | | | | | |
| 37(V) | 1023 | -958 | -3146 | -2600 | -1103 | -2513 | -1686 | 63 | -2290 | -801 | 2200 | -2204 | -2668 | -2000 | -2237 | -1650 | 1119 | 2408 | -1689 | -1335 | 37 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8392 | | | | | | | | | | | | |
| 38(F) | -3852 | -3057 | -4741 | -4884 | 3335 | -4537 | -1011 | -2489 | -4461 | 957 | -1921 | -3313 | -4388 | -3349 | -3926 | -3759 | -3730 | -2762 | -269 | 3290 | 38 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8388 | | | | | | | | | | | | |
| 39(E) | -2083 | -3395 | -722 | 2943 | -3878 | -2383 | -1214 | -3575 | 2285 | -3395 | -2666 | -1041 | -2696 | -830 | -750 | -1870 | -2023 | -3182 | -3392 | -2873 | 39 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8384 | | | | | | | | | | | | |
| 40(V) | -1086 | -1419 | -2113 | -1929 | -1724 | 796 | 2671 | -1274 | -1766 | -1761 | -1123 | -1760 | -2533 | -1690 | -1904 | -1385 | -1234 | 2825 | -2172 | -1669 | 40 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8379 | | | | | | | | | | | | |
| 41(T) | -869 | -1487 | -3137 | -3257 | -3760 | -1746 | -2945 | -3506 | -3200 | -3791 | -2920 | -2268 | -2512 | -2898 | -3156 | -2152 | 3197 | -2486 | -3990 | -3777 | 41 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8375 | | | | | | | | | | | | |
| 42(K) | -1040 | -2442 | -581 | 1137 | -2735 | -1868 | -548 | -2490 | 2386 | -2427 | -1554 | 1311 | -2012 | -114 | -440 | -908 | -975 | -2076 | -2562 | 1837 | 42 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8371 | | | | | | | | | | | | |

TABLE 8-continued

| | | | | | | | | | | | | | | | | |
|---|---|---|---|---|---|---|---|---|---|---|---|---|---|---|---|---|
| 43(R) | −2795 −149 −291 | −3370 −500 −7718 | −3663 233 −2514 | −2111 −894 | −4313 −381 −1115 | −3239 399 −701 | −1074 106 −1378 | −3582 −626 −8762 | 2384 210 | −3191 −466 | −2548 −720 | −1936 275 | −3164 394 | −657 45 | 3395 96 | −2670 359 | −2434 117 | −3375 −369 | −2990 −294 | −2949 −249 | 43 |
| 44(Q) | −1085 −149 −17 | −1755 −500 −7443 | −1145 233 −8484 | −887 43 −894 | 1733 −381 −1115 | 985 399 −1459 | −888 106 −652 | −1755 −626 −8762 | −8366 −814 210 −8362 | −1851 −466 | −1208 −720 | −1026 275 | −2253 394 | 3209 45 | −1142 96 | −1159 359 | −1127 117 | −1521 −369 | −1673 −294 | −859 −249 | 44 |
| 45(W) | −4735 −149 −17 | −3754 −500 −7443 | −4703 233 −8486 | −4993 −894 | −2377 −381 −1115 | −3915 399 −372 | −3273 106 −2136 | −4870 −626 −8762 | −4782 210 −8358 | −4319 −466 | −4338 −720 | −4620 275 | −4317 394 | −4639 45 | −4390 96 | −4998 359 | −4881 117 | −4870 −369 | −6237 −294 | −1984 −249 | 45 |
| 46(M) | −914 −149 −15 | −874 −500 −7718 | 871 233 −8760 | −1922 −894 | −783 −381 −1115 | −2384 399 −701 | −1220 106 −1378 | 1249 −626 −8762 | −1670 210 −8353 | 662 −466 | 3001 −720 | −1756 275 | −2427 394 | −1420 45 | −1731 96 | −1438 359 | 1257 117 | −98 −369 | −1343 −294 | −990 −249 | 46 |
| 47(M) | 641 −149 −15 | −2071 −500 −7718 | −521 233 −8760 | 1084 43 −894 | −2362 −381 −1115 | −1649 399 −701 | −321 106 −1378 | −2091 −626 −8762 | 82 210 −8349 | −2076 −466 | 2071 −720 | 1285 275 | −1749 394 | 1468 45 | −420 96 | 684 359 | −616 117 | −1678 −369 | −2276 −294 | −1612 −249 | 47 |
| 48(Q) | −757 −149 −15 | −2178 −500 −7718 | −529 233 −8760 | 1705 43 −894 | −2487 −381 −1115 | 519 399 −701 | −368 106 −1378 | −2219 −626 −8762 | 1195 210 −8344 | −2182 −466 | −1278 −720 | −340 275 | −1806 394 | 1749 45 | −411 96 | −642 359 | −696 117 | 453 −369 | −2362 −294 | −1699 −249 | 48 |
| 49(Y) | −1288 −149 −15 | −1144 −500 −7718 | −3267 233 −8760 | −2757 43 −894 | −710 −381 −1115 | −2784 399 −701 | −1561 106 −1378 | 2546 −626 −8762 | −2393 210 −8340 | −763 −466 | −315 −720 | −2345 275 | −2866 394 | −2105 45 | −2314 96 | −1913 359 | 1335 117 | −38 −369 | −1365 −294 | 2756 −249 | 49 |
| 50(K) | −1352 −149 −15 | −2460 −500 −7718 | 1542 233 −8760 | −473 43 −894 | −2590 −381 −1115 | −2065 399 −701 | −876 106 −1378 | −2234 −626 −8762 | 1932 210 −8335 | 1737 −466 | −1566 −720 | −761 275 | −2285 394 | −505 45 | −815 96 | −1266 359 | −1304 117 | −1990 −369 | −2658 −294 | −2071 −249 | 50 |
| 51(P) | −1299 −149 −291 | −2774 −500 −7718 | −236 233 −8760 | 1949 43 −894 | −3178 −381 −1115 | −1870 399 −701 | −886 106 −1378 | −2961 −626 −8762 | −678 210 −8331 | −2912 −466 | −2058 −720 | 1447 275 | 2218 394 | −481 45 | −1251 96 | 890 359 | −1302 117 | −2487 −369 | −3099 −294 | −2347 −249 | 51 |
| 52(P) | 1084 −149 −17 | −2190 −500 −7443 | −341 233 −2514 | 2185 −894 | −2933 −381 −1115 | −1688 399 −701 | −929 106 −1378 | −2655 −626 −8762 | −732 210 −8313 | −2706 −466 | −1884 −720 | −590 275 | 2271 394 | −556 45 | −1245 96 | −978 359 | −1128 117 | −2169 −369 | −2938 −294 | −2278 −249 | 52 |
| 53(N) | −1418 −149 −17 | −2809 −500 −7443 | 2479 233 −8486 | −106 43 −894 | −2949 −381 −1115 | −1799 399 −701 | −652 106 −1459 | −2766 −626 −8762 | −883 210 −8326 | 578 −466 | −2068 −720 | 2542 275 | −2188 394 | −576 45 | −1502 96 | −1234 359 | −1435 117 | −2399 −369 | −3048 −294 | −2264 −249 | 53 |
| 54(D) | −283 −149 −15 | −2124 −500 −7443 | −2563 233 | 66 43 −894 | −2357 −381 −1115 | −1565 399 −1459 | −509 106 −652 | −1956 −626 −8762 | −285 210 −8322 | −2113 −466 | −1336 −720 | −255 275 | −1834 394 | 1955 45 | −808 96 | −781 359 | −871 117 | 1155 −369 | −2428 −294 | −1753 −249 | 54 |
| 55(D) | −888 −149 −19 | −3680 −500 −7180 | 2400 233 −8222 | 2554 −894 | −3868 −381 −1115 | −1865 399 −1865 | −463 106 −1066 | −3813 −626 −8762 | −8317 −1341 210 −8313 | −3684 −466 | −3041 −720 | −289 275 | −2233 394 | −743 45 | −2210 96 | −1458 359 | −1880 117 | −3289 −369 | −3847 −294 | −2846 −249 | 55 |
| 56(G) | −1805 −149 −1334 | −3680 −500 −7180 | 2903 233 −753 | 2554 43 −894 | −3868 −381 | −1689 399 | −1066 106 −463 | −3813 −626 −8762 | −1341 210 −8313 | −2342 −466 | −1770 −720 | −1048 275 | −1555 394 | −1281 45 | −1496 96 | −708 359 | −838 117 | −1625 −369 | −1974 −294 | −1993 −249 | 56 |
| 57(G) | −515 −149 −41 | −887 −500 −5887 | −1038 233 −6930 | −1187 43 −894 | −2183 −381 −1115 | 3187 399 −2652 | −1282 106 −250 | −2175 −626 −8762 | −1398 210 −8308 | −2342 −466 | −1770 −720 | −1048 275 | −1555 394 | −1281 45 | −1496 96 | −708 359 | −838 117 | −1625 −369 | −1974 −294 | −1993 −249 | 57 |
| 58(E) | −515 −149 −41 | −887 −500 −5887 | −1038 233 −6930 | −1187 43 −894 | −2183 −381 −1115 | 3187 399 −151 | −1282 106 −3329 | −2175 −626 −8762 | −1398 210 −8304 | −1038 −466 | −631 −720 | −1602 275 | −2663 394 | −1361 45 | −1800 96 | −1658 359 | −1319 117 | 1113 −369 | −1614 −294 | −909 −249 | 58 |
| 59(H) | −1346 −149 −15 | −1562 −500 −7718 | −1816 233 −8760 | 2436 43 −894 | 2337 −381 −1115 | −2525 399 −701 | −1279 106 −1378 | −603 −626 −8762 | −1533 210 −8299 | −1038 −466 | −631 −720 | −1602 275 | −2663 394 | −1361 45 | −1800 96 | −1658 359 | −1319 117 | 1113 −369 | −1614 −294 | −909 −249 | 59 |
| | −933 −149 −15 | −961 −500 −7718 | −2242 233 −8760 | −1707 43 −894 | −764 −381 −1115 | −2320 399 −701 | 2094 106 −1378 | 1132 −626 −8762 | 1839 210 −8295 | 1839 −466 | −65 −720 | 1195 275 | −2382 394 | −1248 45 | −1495 96 | −1381 359 | −874 117 | −319 −369 | −1292 −294 | −847 −249 | |

TABLE 8-continued

| | | | | | | | | | | | | | | | | |
|---|---|---|---|---|---|---|---|---|---|---|---|---|---|---|---|---|
| 60(M) | -1293 -149 -15 | -1342 -500 -7718 | -2996 233 -8760 | -2500 -894 | -1038 -381 -1115 | -2617 399 -701 | -1796 106 -1378 | -510 -626 -8762 | -2162 210 -8290 | -890 -466 | -3410 -720 | -2240 275 | -2790 394 | -1938 45 | -2186 96 | 2108 359 | -1323 117 | -630 -369 | -1840 -294 | -1502 -249 | 60 |
| 61(P) | 2028 -149 -15 | -1663 -500 -7718 | -1726 -233 -8760 | -1624 43 -894 | -3398 -381 -1115 | 998 399 -701 | -1915 106 -1378 | -3145 -626 -8762 | -1828 210 -8285 | -3283 -466 | -2409 -720 | 1487 275 | 2266 394 | -1625 45 | -2185 96 | -1038 359 | -1207 117 | -2349 -369 | -3511 -294 | -3060 -249 | 61 |
| 62(D) | -752 -149 -15 | -2203 -500 -7718 | 1771 233 -8760 | 1070 43 -894 | -2520 -381 -1115 | -1688 399 -701 | 106 -1378 | -2261 -626 -8762 | 1383 210 -8281 | -2210 -466 | -1298 -720 | -324 275 | -1796 394 | 94 45 | 1124 96 | -630 359 | -691 117 | 543 -369 | -2379 -294 | -1707 -249 | 62 |
| 63(R) | -796 -149 -231 | -2105 -500 -7504 | -2838 233 -8546 | 1238 43 -894 | -2496 -381 -1115 | 1498 399 -701 | -359 106 -1378 | -2206 -626 -8762 | 49 210 -8276 | -2188 -466 | -1314 -720 | -382 275 | -1834 394 | 11 45 | 1567 96 | -698 359 | 1155 117 | -1794 -369 | -2375 -294 | -1748 -249 | 63 |
| 64(G) | -2419 -149 -17 | -2885 -500 -7718 | -3067 233 -8760 | -2886 43 -894 | -4406 -381 -1115 | 3143 399 -701 | -421 106 -2011 | -4353 -626 -8762 | -1679 210 -8271 | -4234 -466 | -3572 -720 | -2708 275 | -3407 394 | -2316 45 | 2444 96 | -2556 359 | 2650 117 | -3716 -369 | -3837 -294 | -3878 -249 | 64 |
| 65(R) | -1920 -149 -15 | -2516 -500 -7718 | -2433 233 -8760 | -1527 43 -894 | -2802 -381 -1115 | -2746 399 -701 | -961 106 -1378 | 1879 -626 -8762 | 176 210 -8267 | -2261 -466 | -1647 -720 | -1532 275 | -2759 394 | 1746 45 | 2935 96 | -1945 359 | -1744 117 | -2067 -369 | -2537 -294 | -2247 -249 | 65 |
| 66(V) | -2252 -149 -15 | -1773 -500 -7718 | 4891 233 -8760 | -4567 43 -894 | -2335 -381 -1115 | -4633 399 -701 | -4538 106 -1378 | 1812 -626 -8762 | -4482 210 -8262 | -1132 -466 | -1073 -720 | -4339 275 | -4440 394 | -4385 45 | -4597 96 | -3992 359 | -2250 117 | 3374 -369 | -3973 -294 | -3489 -249 | 66 |
| 67(M) | -849 -149 -15 | -923 -500 -7718 | 1670 233 -8760 | -1529 43 -894 | -893 -381 -1115 | -2248 399 -701 | -1067 106 -1378 | -233 -626 -8762 | -1327 210 -8257 | 600 -466 | 2147 -720 | -1485 275 | -2308 394 | -1135 45 | -1498 96 | -1282 359 | 1243 117 | 1140 -369 | -1394 -294 | -1015 -249 | 67 |
| 68(E) | -1776 -149 -15 | -3015 -500 -7718 | -373 233 -8760 | 3097 43 -894 | -3872 -381 -1115 | -2071 399 -701 | -1546 106 -1378 | -3755 -626 -8762 | -1570 210 -8253 | -3731 -466 | -2992 -720 | -934 275 | -2595 394 | -1219 45 | -2164 96 | 1764 359 | -1926 117 | -3163 -369 | -3855 -294 | -3091 -249 | 68 |
| 69(M) | -1335 -149 -15 | -1165 -500 -7718 | -3272 233 -8760 | -2688 43 -894 | -1002 -381 -1115 | -2941 399 -701 | -1834 106 -1378 | 1451 -626 -8762 | -2360 210 -8248 | -376 -466 | 3121 -720 | -2427 275 | -2930 394 | 2286 45 | -2331 96 | -2034 359 | -1279 117 | 1529 -369 | -1766 -294 | -1445 -249 | 69 |
| 70(L) | -3777 -149 -15 | -3243 -500 -7718 | -5089 233 -8760 | -5032 43 -894 | -1735 -381 -1115 | -4514 399 -701 | -4040 106 -1378 | -1299 -626 -8762 | -4754 210 -8243 | -3261 -466 | 696 -720 | -4891 275 | -4508 394 | -4152 45 | -4395 96 | -4705 359 | -3767 117 | -1993 -369 | -3125 -294 | -3069 -249 | 70 |
| 71(S) | -1644 -149 -15 | -2173 -500 -7718 | -3321 233 -8760 | -3615 43 -894 | -4077 -381 -1115 | -2357 399 -701 | -3411 106 -1378 | -4307 -626 -8762 | -3792 210 -8238 | -4459 -466 | -3725 -720 | -2859 275 | -3095 394 | -3512 45 | -3692 96 | 3619 359 | -2088 117 | -3285 -369 | -4091 -294 | -3959 -249 | 71 |
| 72(E) | -3777 -149 -15 | -4125 -500 -7718 | -1925 233 -8760 | 3871 43 -894 | -4984 -381 -1115 | -3355 399 -701 | -3125 106 -1378 | -5379 -626 -8762 | -3371 210 -8234 | -5156 -466 | -4796 -720 | -2611 275 | -3875 394 | -3007 45 | -3762 96 | -3630 359 | -3916 117 | -4960 -369 | -4357 -294 | -4463 -249 | 72 |
| 73(H) | -4406 -149 -15 | -3961 -500 -7718 | -3921 233 -8760 | -4171 43 -894 | -3231 -381 -1115 | -3926 399 -701 | 5401 106 -1378 | -5468 -626 -8762 | -3992 210 -8229 | -5013 -466 | -4849 -720 | -4130 275 | -4378 394 | -4151 45 | -3893 96 | -4548 359 | -4592 117 | -5195 -369 | -3383 -294 | -2818 -249 | 73 |
| 74(Q) | -1172 -149 -15 | -1561 -500 -7718 | -1803 233 -8760 | -1343 43 -894 | -1477 -381 -1115 | -2292 399 -701 | -1190 106 -1378 | -991 -626 -8762 | -908 210 -8224 | 1463 -466 | -565 -720 | -1415 275 | -2454 394 | 2378 45 | -1119 96 | -1403 359 | 1904 117 | -979 -369 | -1998 -294 | -1592 -249 | 74 |
| 75(C) | 943 -149 -15 | 4854 -500 -7718 | -3669 233 -8760 | -3391 43 -894 | -1886 -381 -1115 | -2164 399 -701 | -2449 106 -1378 | -922 -626 -8762 | -3000 210 -8219 | 676 -466 | -1025 -720 | -2492 275 | -2705 394 | -2686 45 | -2861 96 | -1458 359 | -1303 117 | -805 -369 | -2559 -294 | -2242 -249 | 75 |
| 76(E) | -2096 -149 -15 | -3637 -500 -7718 | -282 233 -8761 | 2979 43 -894 | -3947 -381 -1115 | -2215 399 -701 | -1377 106 -1378 | -3824 -626 -8762 | -1173 210 -8214 | -3688 -466 | -2987 -720 | -859 275 | -2659 394 | 2792 45 | -1646 96 | -1832 359 | -2117 117 | -3370 -369 | -3761 -294 | -3011 -249 | 76 |

TABLE 8-continued

| | | | | | | | | | | | | | | | | | | | |
|---|---|---|---|---|---|---|---|---|---|---|---|---|---|---|---|---|---|---|---|
| 77(G) | −3681 −149 −15 | −3593 −500 −7718 | −4389 233 −8761 | −4747 −894 | −5281 −381 −1115 | 3812 399 −701 | −4419 106 −1378 | −5908 −626 −8762 | −5071 210 −8209 | −5671 −466 | −5288 −720 | −4417 275 | −4223 394 | −4850 45 | −4766 96 | −3952 359 | −4069 117 | −5125 −369 | −4424 −294 | −5214 −249 | 77 |
| 78(W) | −4254 −149 −15 | −3318 −500 −7718 | −4804 233 −8761 | −5081 43 −894 | 3098 −381 −1115 | −4588 399 −701 | −1050 106 −1378 | −3111 −626 −8762 | −4645 210 −8205 | −2453 −466 | −2534 −720 | −3403 275 | −4509 394 | −3506 45 | −4073 96 | −3950 359 | −4146 117 | −3314 −369 | 5352 −294 | 877 −249 | 78 |
| 79(L) | −3375 −149 −15 | −2814 −500 −7718 | −5645 233 −8761 | −5079 43 −894 | −928 −381 −1115 | −5372 399 −701 | −4042 106 −1378 | −409 −626 −8762 | −4777 210 −8200 | 2894 −466 | 2856 −720 | −5098 275 | −4540 394 | −3683 45 | −4317 96 | −4734 359 | −3229 117 | −1208 −369 | −2698 −294 | −2837 −249 | 79 |
| 80(E) | −2150 −149 −15 | −3708 −500 −7718 | −263 233 −8761 | 3290 43 −894 | −4011 −381 −1115 | −2224 399 −701 | −1421 106 −1378 | −3906 −626 −8762 | −1260 210 −8195 | −3766 −466 | −3081 −720 | −868 275 | −2687 394 | 2032 45 | −1753 96 | −1875 359 | −2180 117 | −3447 −369 | −3837 −294 | −3070 −249 | 80 |
| 81(G) | 2022 −149 −15 | −1618 −500 −7718 | −3291 233 −8761 | −3557 43 −894 | −4069 −381 −1115 | 3053 399 −701 | −3239 106 −1378 | −3867 −626 −8762 | −3682 210 −8190 | −4133 −466 | −3245 −720 | −2462 275 | −2643 394 | −3254 45 | −3542 96 | −1260 359 | −1474 117 | −2727 −369 | −4214 −294 | −4140 −249 | 81 |
| 82(Y) | −4444 −149 −15 | −3646 −500 −7718 | −4593 233 −8761 | −4892 43 −894 | −509 −381 −1115 | −4268 399 −701 | −1873 106 −1378 | −3993 −626 −8762 | −4663 210 −8185 | −3407 −466 | −3460 −720 | −3884 275 | −4503 394 | −3998 45 | −4255 96 | −4336 359 | −4491 117 | −4072 −369 | −1177 −294 | 4829 −249 | 82 |
| 83(L) | −1931 −149 −15 | −1973 −500 −7719 | −3870 233 −8761 | −3595 43 −894 | −1374 −381 −1115 | −3144 399 −701 | −2842 106 −1378 | −646 −626 −8762 | −3171 210 −8180 | 2519 −466 | −338 −720 | −3150 275 | −3415 394 | −2899 45 | −3072 96 | −2469 359 | 2215 117 | −950 −369 | −2583 −294 | −2364 −249 | 83 |
| 84(L) | −3777 −149 −15 | −3243 −500 −7719 | −5089 233 −8761 | −5032 43 −894 | −1735 −381 −1115 | −4514 399 −701 | −4040 106 −1378 | −1299 −626 −8762 | −4754 210 −8175 | 3261 −466 | −696 −720 | −4891 275 | −4508 394 | −4152 45 | −4395 96 | −4705 359 | −3767 117 | −1993 −369 | −3125 −294 | −3069 −249 | 84 |
| 85(T) | −2081 −149 −15 | −2497 −500 −7719 | −3792 233 −8761 | −4048 43 −894 | −4206 −381 −1115 | −2712 399 −701 | −3671 106 −1378 | −3972 −626 −8762 | −3974 210 −8170 | −4274 −466 | −3765 −720 | −3291 275 | −3408 394 | −3829 45 | −3824 96 | −2338 359 | 3976 117 | −3321 −369 | −4129 −294 | −4203 −249 | 85 |
| 86(G) | −3681 −149 −15 | −3593 −500 −7719 | −4389 233 −8761 | −4747 43 −894 | −5281 −381 −1115 | 3812 399 −701 | −4419 106 −1378 | −5908 −626 −8762 | −5071 210 −8165 | −5671 −466 | −5288 −720 | −4417 275 | −4223 394 | −4850 45 | −4766 96 | −3952 359 | −4069 117 | −5125 −369 | −4424 −294 | −5214 −249 | 86 |
| 87(R) | −4070 −149 −15 | −3868 −500 −7719 | −4406 233 −8761 | −3890 43 −894 | −4820 −381 −1115 | −3837 399 −701 | −3026 106 −1378 | −5122 −626 −8762 | −1946 210 −8160 | −4739 −466 | −4314 −720 | −3731 275 | −4155 394 | −2844 45 | 4177 96 | −4178 359 | −4041 117 | −4836 −369 | −3949 −294 | −4248 −249 | 87 |
| 88(H) | −1602 −149 −15 | −2202 −500 −7719 | −2033 233 −8761 | −2051 43 −894 | −2524 −381 −1115 | −2310 399 −701 | 4500 106 −1378 | −3130 −626 −8762 | −1754 210 −8155 | −3221 −466 | −2593 −720 | −1952 275 | −2860 394 | −1941 45 | −1889 96 | −1744 359 | 2351 117 | −2641 −369 | −2857 −294 | −2142 −249 | 88 |
| 89(G) | 1424 −149 −15 | −1648 −500 −7719 | −3257 233 −8761 | −3538 43 −894 | −4097 −381 −1115 | 3299 399 −701 | −3253 106 −1378 | −3902 −626 −8762 | −3697 210 −8150 | −4166 −466 | −3283 −720 | −2476 275 | −2666 394 | −3269 45 | −3560 96 | −1290 359 | −1506 117 | −2760 −369 | −4228 −294 | −4161 −249 | 89 |
| 90(F) | 653 −149 −15 | −1307 −500 −7719 | −3869 233 −8761 | −3274 43 −894 | 2383 −381 −1115 | −3222 399 −701 | −2101 106 −1378 | 2307 −626 −8762 | −2923 210 −8145 | 979 −466 | 54 −720 | −2851 275 | −3158 394 | −2477 45 | −2735 96 | −2341 359 | −1496 117 | −62 −369 | −1785 −294 | −1478 −249 | 90 |
| 91(F) | −4268 −149 −15 | −3318 −500 −7719 | −4807 233 −8761 | −5092 43 −894 | 4134 −381 −1115 | −4606 399 −701 | −1026 106 −1378 | −3118 −626 −8762 | −4656 210 −8140 | −2457 −466 | −2538 −720 | −3389 275 | −4515 394 | −3495 45 | −4075 96 | −3946 359 | −4154 117 | −3320 −369 | 3520 −294 | 904 −249 | 91 |
| 92(A) | 2436 −149 −15 | −1450 −500 −7719 | −3080 233 −8761 | −3062 43 −894 | −3722 −381 −1115 | −1707 399 −701 | −2801 106 −1378 | −3478 −626 −8762 | −3005 210 −8134 | −3713 −466 | −2813 −720 | −2174 275 | 1760 394 | −2697 45 | −3044 96 | 2014 359 | −1242 117 | −2447 −369 | −3930 −294 | −3709 −249 | 92 |
| 93(S) | −797 −149 −15 | 2971 −500 −7719 | −3664 233 −8761 | −3672 43 −894 | −3546 −381 −1115 | −1712 399 −701 | −2998 106 −1378 | −3220 −626 −8762 | −3388 210 −8139 | −3539 −466 | −2685 −720 | −2356 275 | −2477 394 | −3023 45 | −3254 96 | −2975 359 | −1394 117 | −2305 −369 | −3830 −294 | −3649 −249 | 93 |

TABLE 8-continued

| | | | | | | | | | | | | | | | | | | |
|---|---|---|---|---|---|---|---|---|---|---|---|---|---|---|---|---|---|---|
| 94(Y) | −4444 | −3646 | −4593 | −4892 | −509 | −4268 | −1873 | −3993 | −4663 | −3407 | −3460 | −3884 | −4503 | −3998 | −4255 | −4336 | −4491 | −4072 | −1177 | 4829 | 94 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −15 | −7719 | −8761 | −894 | −1115 | −701 | −1378 | −8762 | −8124 | | | | | | | | | | | | |
| 95(E) | −3777 | −4125 | −1925 | 3871 | −4984 | −3355 | −3125 | −5379 | −3371 | −5156 | −4796 | −2611 | −3875 | −3007 | −3762 | −3930 | −3916 | −4960 | −4357 | −4463 | 95 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −15 | −7719 | −8761 | −894 | −1115 | −701 | −1378 | −8762 | −8119 | | | | | | | | | | | | |
| 96(A) | 2588 | −1457 | −3368 | −3530 | −3881 | −1722 | −3095 | −3647 | −3472 | −3926 | −3021 | −2338 | −2505 | −3081 | −3355 | 2536 | −1295 | −2531 | −4108 | −3950 | 96 |
| | −149 | −500 | 233 | −894 | −381 | 399 | 106 | −626 | 210 | −466 | −720 | 275 | 394 | 45 | 96 | 359 | 117 | −369 | −294 | −249 | |
| | −15 | −7719 | −8761 | | −1115 | −701 | −1378 | −8762 | −8114 | | | | | | | | | | | | |
| 97(F) | −4350 | −3618 | −4843 | −5137 | −4483 | −4245 | −2206 | −3493 | −4990 | −2887 | −3007 | −4147 | −4512 | −4243 | −4506 | −4433 | −4439 | −3737 | −1500 | −417 | 97 |
| | −149 | −500 | 233 | −894 | −381 | 399 | 106 | −626 | 210 | −466 | −720 | 275 | 394 | 45 | 96 | 359 | 117 | −369 | −294 | −249 | |
| | −15 | −7719 | −8761 | | −1115 | −701 | −1378 | −8762 | −8109 | | | | | | | | | | | | |
| 98(M) | 706 | −1201 | −3821 | −3231 | −1007 | −3165 | −2103 | 1510 | −2884 | 1469 | 2600 | −2801 | −3121 | −2481 | −2711 | −2285 | −1405 | −3737 | −1846 | −1550 | 98 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −15 | −7719 | −8761 | −894 | −1115 | −701 | −1378 | −8762 | −8103 | | | | | | | | | | | | |
| 99(H) | −1732 | −2580 | −1961 | −1265 | −3039 | −2507 | 3869 | −2740 | 117 | −2656 | −1919 | −1338 | −2617 | −548 | 2281 | −1696 | 1373 | −2439 | −2662 | −2280 | 99 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7719 | −8761 | −894 | −1115 | −701 | −1378 | −8762 | −8098 | | | | | | | | | | | | |
| 100(I) | −2262 | −1772 | −4916 | −4590 | −2360 | −4692 | −4608 | 2948 | −4520 | −1146 | −1086 | −4377 | −4472 | −4432 | −4647 | −4052 | −2257 | 2744 | −4024 | −3536 | 100 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7719 | −8761 | −894 | −1115 | −701 | −1378 | −8762 | −8093 | | | | | | | | | | | | |
| 101(V) | −2259 | −1770 | −4911 | −4585 | −2361 | −4682 | −4599 | 2472 | −4513 | −1151 | −1088 | −4370 | −4467 | −4427 | −4640 | −4043 | −2254 | 3105 | −4021 | −3531 | 101 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7719 | −8761 | −894 | −1115 | −701 | −1378 | −8762 | −8087 | | | | | | | | | | | | |
| 102(D) | −1281 | −2033 | 3087 | −908 | −2698 | −2028 | −1475 | −1596 | −1454 | −2381 | −1758 | −1118 | −2459 | −1191 | −1938 | −1365 | 1158 | 1286 | −3025 | −2452 | 102 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7719 | −8761 | −894 | −1115 | −701 | −1378 | −8762 | −8082 | | | | | | | | | | | | |
| 103(S) | −1644 | −2173 | −3321 | −3615 | −4077 | −2357 | −3411 | −4307 | −3792 | −4459 | −3725 | −2859 | −3095 | −3512 | −3692 | 3619 | −2088 | −3285 | −4091 | −3959 | 103 |
| | −149 | −500 | 233 | −894 | −381 | 399 | 106 | −626 | 210 | −466 | −720 | 275 | 394 | 45 | 96 | 359 | 117 | −369 | −294 | −249 | |
| | −16 | −7719 | −8761 | | −1115 | −701 | −1378 | −8762 | −8077 | | | | | | | | | | | | |
| 104(M) | −3457 | −3250 | −4578 | −4682 | −2595 | −3839 | −3833 | −2264 | −4294 | −1708 | 5248 | −4331 | −4225 | −4184 | −4072 | −3938 | −3655 | −2653 | −3435 | −3236 | 104 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7719 | −8761 | −894 | −1115 | −701 | −1378 | −8762 | −8071 | | | | | | | | | | | | |
| 105(L) | −2433 | −2031 | −4839 | −4270 | 1637 | −4331 | −3217 | 1476 | −3985 | 2288 | 96 | −3990 | −3978 | −3290 | −3710 | −3525 | −2348 | 1287 | −2465 | −2367 | 105 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7719 | −8761 | −894 | −1115 | −701 | −1378 | −8762 | −8066 | | | | | | | | | | | | |
| 106(N) | −952 | −1482 | −1959 | −1737 | −2360 | −1930 | −1748 | −1480 | −1701 | −2148 | −1486 | −2935 | −2420 | −1580 | −1960 | −1182 | 2024 | 1339 | −2731 | −2304 | 106 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7719 | −8761 | −894 | −1115 | −701 | −1378 | −8762 | −8061 | | | | | | | | | | | | |
| 107(Q) | −3758 | −3792 | −3072 | −3245 | −3586 | −3586 | −3274 | −5053 | −2880 | −4719 | −4410 | −3349 | −4049 | 4526 | −3692 | −3829 | −3917 | −4726 | −3973 | −3953 | 107 |
| | −149 | −500 | 233 | −894 | −381 | 399 | 106 | −626 | 210 | −466 | −720 | 275 | 394 | 45 | 96 | 359 | 117 | −369 | −294 | −249 | |
| | −16 | −7719 | −8761 | | −1115 | −701 | −1378 | −8762 | −8055 | | | | | | | | | | | | |
| 108(H) | −3941 | −3303 | −3939 | −4079 | 336 | −4266 | 4844 | −3317 | −3580 | −2730 | −2734 | −3097 | −4295 | −3109 | −3362 | −3663 | −3868 | −3403 | −373 | 2757 | 108 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7719 | −8761 | −894 | −1115 | −701 | −1378 | −8762 | −8050 | | | | | | | | | | | | |
| 109(A) | 2381 | −1319 | −2661 | −2353 | 1521 | 924 | −2061 | −2159 | −2216 | −2443 | −1684 | −1875 | −2365 | −1993 | −2375 | 1314 | −1085 | −1685 | −2841 | −2472 | 109 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7719 | −8761 | −894 | −1115 | −701 | −1378 | −8762 | −8044 | | | | | | | | | | | | |
| 110(K) | −3709 | −3782 | −3592 | −3179 | −4734 | −3639 | −2561 | −4748 | 3938 | −4426 | −3926 | −3130 | −3916 | −2292 | −1410 | −3723 | −3624 | −4465 | −3818 | −3998 | 110 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −16 | −7719 | −8761 | −894 | −1115 | −701 | −1378 | −8762 | −8039 | | | | | | | | | | | | |

TABLE 8-continued

| | | | | | | | | | | | | | | | | | |
|---|---|---|---|---|---|---|---|---|---|---|---|---|---|---|---|---|---|
| 111(W) | -4239 -149 -16 | -3322 -500 -7719 | -4800 233 -8761 | -5070 43 -894 | 2397 -381 -1115 | -4565 399 -701 | -1086 106 -1378 | -3101 -626 -8762 | -4634 210 -8033 | -2445 -466 | -2527 -720 | -3425 275 | -4503 394 | -3523 45 | -4074 96 | -3959 359 | -4140 117 | -3310 -369 | 5693 -294 | 837 -249 | 111 |
| 112(L) | -3174 -149 -16 | -2633 -500 -7719 | -5520 233 -8761 | -4994 43 -894 | -1029 -381 -1115 | -5242 399 -701 | -4053 106 -1378 | 1453 -626 -8762 | -4737 210 -8028 | 2932 -466 | 174 -720 | -4959 275 | -4514 394 | -3738 45 | -4340 96 | -4596 359 | -3057 117 | -761 -369 | -2778 -294 | -2863 -249 | 112 |
| 113(K) | -1073 -149 -16 | -2547 -500 -7719 | 1983 233 -8761 | 1205 43 -894 | -2885 -381 -1115 | -1851 399 -701 | -580 106 -1378 | -2624 -626 -8762 | -2040 210 -8022 | -2541 -466 | -1656 -720 | -477 275 | -2021 394 | -141 45 | 1183 96 | -924 359 | -1014 117 | -2183 -369 | -2682 -294 | -2014 -249 | 113 |
| 114(M) | 1488 -149 -16 | -784 -500 -7719 | -2685 233 -8761 | -2089 43 -894 | -758 -381 -1115 | -2378 399 -701 | -1239 106 -1378 | 1284 -626 -8762 | -1794 210 -8017 | -540 -466 | 2454 -720 | -1834 275 | -2427 394 | 1221 45 | -1791 96 | -1444 359 | -817 117 | 1168 -369 | -1289 -294 | -933 -249 | 114 |
| 115(C) | 1116 -149 -16 | 3924 -500 -7719 | -3654 233 -8761 | -3615 43 -894 | -3360 -381 -1115 | 1383 399 -701 | -2916 106 -1378 | -3025 -626 -8762 | -3341 210 -8011 | -3335 -466 | -2502 -720 | -2336 275 | -2465 394 | -2960 45 | -3214 96 | -1051 359 | 2263 117 | -2200 -369 | -3668 -294 | -3472 -249 | 115 |
| 116(V) | -1842 -149 -16 -588 -149 -42 | -579 -500 -7719 | -489 -8761 -2160 -8761 | -894 -1946 43 -894 | -759 -381 -1115 | -1834 399 -701 | -1555 106 -1378 | 1143 -626 -8762 | -1670 210 -8006 | -9 -466 | 123 -720 | -1684 275 | -2156 394 | -1608 45 | -1741 96 | -1222 359 | -711 117 | 2811 -369 | -1682 -294 | -1223 -249 | 116 |
| 117(R) | 740 -149 -16 | -1533 -500 -7719 | -1479 233 -8761 | -915 43 -894 | -1874 -381 -1115 | -1953 399 -701 | -873 106 -1378 | -1460 -626 -8762 | -464 210 -8006 -8000 | 601 -466 | -933 -720 | -1028 275 | -2151 394 | -588 45 | 2555 96 | 747 359 | -902 117 | -1223 -369 | -2081 -294 | -1631 -249 | 117 |
| 118(E) | -1519 -149 -16 | -3167 -500 -7719 | 1458 233 -8761 | 2619 43 -894 | -3424 -381 -1115 | -1929 399 -701 | 2323 106 -1378 | -3240 -626 -8762 | -838 210 -7994 | -3155 -466 | -2323 -720 | -534 275 | -2279 394 | 1614 45 | -1462 96 | -1295 359 | -1511 117 | -2766 -369 | -3331 -294 | -2516 -249 | 118 |
| 119(I) | -1108 -149 -16 | -1022 -500 -7719 | -2831 233 -8761 | -2246 43 -894 | -840 -381 -1115 | -2607 399 -701 | -1460 106 -1378 | 2037 -626 -8762 | -1908 210 -7972 | 1407 -466 | 36 -720 | -2034 275 | -2633 394 | 1279 45 | -1920 96 | -1682 359 | 1280 117 | -126 -369 | -1499 -294 | -1169 -249 | 119 |
| 120(P) | -1226 -149 -16 | -2486 -500 -7719 | -584 233 -8761 | -427 43 -894 | -3101 -381 -1115 | 1037 399 -701 | -903 106 -1378 | -2834 -626 -8762 | -1189 210 -7989 -7966 | -2796 -466 | -1949 -720 | 1466 275 | 2619 394 | -497 45 | -899 96 | -1126 359 | -1246 117 | -2362 -369 | -2960 -294 | -2322 -249 | 120 |
| 121(W) | -5218 -149 -16 | -4132 -500 -7719 | -5085 233 -8761 | -5404 43 -894 | -2925 -381 -1115 | -4252 399 -701 | -3753 106 -1378 | -5470 -626 -8762 | -5268 210 -7983 | -4877 -466 | -4907 -720 | -5071 275 | -4661 394 | -5108 45 | -4833 96 | -5506 359 | -5369 117 | -5443 -369 | -6261 -294 | -2535 -249 | 121 |
| 122(R) | -2786 -149 -16 | -3324 -500 -7719 | -3159 233 -8761 | -2158 43 -894 | -3444 -381 -1115 | -3203 399 -701 | 2835 106 -1378 | -3646 -626 -8762 | 19 210 -7977 | -3307 -466 | -2690 -720 | -2048 275 | -3245 394 | -942 45 | 3648 96 | -2697 359 | -2534 117 | -3415 -369 | -2888 -294 | -2551 -249 | 122 |
| 123(H) | 661 -149 -16 | -2311 -500 -7719 | -894 233 -8761 | -302 43 -894 | -2686 -381 -1115 | 811 399 -701 | 2065 106 -1378 | -2371 -626 -8762 | 1951 210 -7966 | -2300 -466 | -1425 -720 | -565 275 | -1991 394 | -22 45 | 1309 96 | -873 359 | -899 117 | -1971 -369 | -2431 -294 | -1856 -249 | 123 |
| 124(D) | -1783 -149 -16 | -3362 -500 -7719 | 2774 233 -8761 | -330 43 -894 | -3711 -381 -1115 | -2050 399 -701 | -1197 106 -1378 | -3534 -626 -8762 | 1468 210 -7960 | -3445 -466 | -2669 -720 | -689 275 | 2225 394 | -827 45 | -1652 96 | -1548 359 | -1805 117 | -3056 -369 | -3598 -294 | -2798 -249 | 124 |
| 125(I) | -2784 -149 -16 | -2321 -500 -7719 | -4408 233 -8761 | -4214 43 -894 | 2256 -381 -1115 | -4011 399 -701 | 1193 106 -1378 | 3098 -626 -8762 | -3823 210 -7948 | -1290 -466 | -1179 -720 | -3131 275 | -3919 394 | -3037 45 | -1652 96 | -3182 359 | -2704 117 | -1420 -369 | -513 -294 | 2319 -249 | 125 |
| 126(S) | 1918 -149 -16 | -1460 -500 -7719 | -2882 233 -8762 | -2748 43 -894 | -3664 -381 -1115 | 1367 399 -701 | -2596 106 -1378 | -3426 -626 -8762 | -2688 210 -7948 | -3630 -466 | -2719 -720 | -2048 275 | 1372 394 | -2426 45 | -3465 96 | 1999 359 | -1206 117 | -2419 -369 | -3840 -294 | -3573 -249 | 126 |
| 127(S) | -1644 -149 -16 | -2173 -500 -7719 | -3321 233 -8762 | -3615 43 -894 | -4077 -381 -1115 | -2357 399 -701 | -3411 106 -1378 | -4307 -626 -8762 | -3792 210 -7943 | -4459 -466 | -3725 -720 | -2859 275 | -3095 394 | -3512 45 | -3692 96 | 3619 359 | -2088 117 | -3285 -369 | -4091 -294 | -3959 -249 | 127 |

TABLE 8-continued

| | | | | | | | | | | | | | | | | |
|---|---|---|---|---|---|---|---|---|---|---|---|---|---|---|---|---|
| 128(I) | −2843 −149 −16 | −2399 −500 −7719 | −5187 233 −8762 | −4720 −894 | −1139 −381 −1115 | −4765 399 −701 | −3832 106 −1378 | −83 −626 −8762 | 4437 210 −7937 | −2876 −466 | −38 −720 | −4542 275 | −4330 394 | −3660 45 | −4145 96 | −4094 359 | −2781 117 | 1324 −369 | −2793 −294 | −2769 −249 | 128 |
| 129(N) | −3232 −149 −16 | −3514 −500 −7719 | −2565 233 −8762 | −2905 43 −894 | −4358 −381 −1115 | −3267 399 −701 | −3364 106 −1378 | −5192 −626 −8762 | −3627 210 −7931 | −5059 −466 | −4632 −720 | 4348 275 | −3843 394 | −3410 45 | −3792 96 | −3319 359 | −3533 117 | −4568 −369 | −4087 −294 | −3976 −249 | 129 |
| 130(Y) | −1616 −149 −16 | −1344 −500 −7719 | −3951 233 −8762 | −3366 43 −894 | −912 −381 −1115 | −3313 399 −701 | −2164 106 −1378 | 1486 −626 −8762 | −3018 210 −7925 | 1578 −466 | −20 −720 | −2936 275 | −3238 394 | −2574 45 | −2829 96 | −2438 359 | −1554 117 | 1298 −369 | −1825 −294 | 2867 −249 | 130 |
| 131(I) | −2438 −149 −16 | −1963 −500 −7719 | −4986 233 −8762 | −4538 43 −894 | −1573 −381 −1115 | −4670 399 −701 | −3957 106 −1378 | −2309 −626 −8762 | −4367 210 −7919 | 2112 −466 | −365 −720 | −4331 275 | −4311 394 | −3863 45 | −4246 96 | −3955 359 | −2391 117 | 1749 −369 | −3152 −294 | −2992 −249 | 131 |
| 132(M) | 694 −149 −16 | −667 −500 −7720 | −2636 233 −8762 | −2033 43 −894 | −642 −381 −1115 | −2235 399 −701 | −1106 106 −1378 | −145 −626 −8762 | −1725 210 −7913 | 645 −466 | 2178 −720 | −1733 275 | −2301 394 | −1435 45 | −1691 96 | 561 359 | 1254 117 | 1172 −369 | −1134 −294 | −779 −249 | 132 |
| 133(T) | −866 −149 −16 | −1487 −500 −7720 | −3132 233 −8762 | −3246 43 −894 | −3768 −381 −1115 | −1744 399 −701 | −2940 106 −1378 | −3519 −626 −8762 | −3190 210 −7907 | −3799 −466 | −2925 −720 | −2263 275 | −2509 394 | −2888 45 | −3152 96 | 2652 359 | 2778 117 | −2491 −369 | −3995 −294 | −3782 −249 | 133 |
| 134(S) | −1644 −149 −16 | −2173 −500 −7720 | −3321 233 −8762 | −3615 43 −894 | −4077 −381 −1115 | −2357 399 −701 | −3411 106 −1378 | −4307 −626 −8762 | −3792 210 −7901 | −4459 −466 | −3725 −720 | −2859 275 | −3095 394 | −3512 45 | −3692 96 | 3619 359 | −2088 117 | −3285 −369 | −4091 −294 | −3959 −249 | 134 |
| 135(H) | −1254 −149 −16 | −2216 −500 −7720 | −843 233 −8762 | −755 43 −894 | −2687 −381 −1115 | −1970 399 −701 | 3314 106 −1378 | −2636 −626 −8762 | −839 210 −7895 | −2710 −466 | −1932 −720 | 1437 275 | −2343 394 | −837 45 | −1206 96 | −1244 359 | 2636 117 | −2214 −369 | −2810 −294 | −2158 −249 | 135 |
| 136(W) | −2217 −149 −16 | −1998 −500 −7720 | 4211 233 −8762 | −3930 43 −894 | −1050 −381 −1115 | −3517 399 −701 | −2291 106 −1378 | −446 −626 −8762 | −3456 210 −7889 | −1314 −466 | −1150 −720 | −3322 275 | −3697 394 | −3202 45 | −3309 96 | −2906 359 | −2265 117 | 3288 −369 | 3612 −294 | −961 −249 | 136 |
| 137(W) | 1105 −149 −16 | −2160 −500 −7720 | −3956 233 −8762 | −3730 43 −894 | 1959 −381 −1115 | −3434 399 −701 | 1130 106 −1378 | −1795 −626 −8762 | −3348 210 −7883 | −1692 −466 | −1411 −720 | −2810 275 | −3571 394 | −2764 45 | −3122 96 | −2642 359 | −2381 117 | −1804 −369 | 5259 −294 | 566 −249 | 137 |
| 138(R) | −2269 −149 −16 | −3123 −500 −7720 | −2497 233 −8762 | −1540 43 −894 | −3728 −381 −1115 | −2880 399 −701 | 2414 106 −1378 | −3259 −626 −8762 | 347 210 −7877 | −2971 −466 | −2265 −720 | −1547 275 | −2868 394 | 2539 45 | 3022 96 | −2145 359 | −2019 117 | −2993 −369 | −2838 −294 | −2604 −249 | 138 |
| 139(Q) | −3758 −149 −16 | −3792 −500 −7720 | −3072 233 −8762 | −3245 43 −894 | −4342 −381 −1115 | −3586 399 −701 | −3274 106 −1378 | −5053 −626 −8762 | −2880 210 −7870 | −4719 −466 | −4410 −720 | −3349 275 | −4049 394 | 4526 45 | −2916 96 | −3829 359 | −3917 117 | −4726 −369 | −3973 −294 | −3953 −249 | 139 |
| 140(D) | −2399 −149 −16 | −4357 −500 −7720 | 3309 233 −8762 | 2333 43 −894 | −4526 −381 −1115 | −2166 399 −701 | −1607 106 −1378 | −4526 −626 −8762 | −1993 210 −7864 | −4365 −466 | −3789 −720 | −765 275 | −2745 394 | −1300 45 | −2954 96 | −2017 359 | −2495 117 | −3974 −369 | −4514 −294 | −3455 −249 | 140 |
| 141(H) | −4406 −149 −16 | −3961 −500 −7720 | −3921 233 −8762 | −4171 43 −894 | −3231 −381 −1115 | −3926 399 −701 | 5401 106 −1378 | −5468 −626 −8762 | −3992 210 −7858 | −5013 −466 | −4849 −720 | −4130 275 | −4378 394 | −4151 45 | −3893 96 | −4548 359 | −4592 117 | −5195 −369 | −3383 −294 | −2818 −249 | 141 |
| 142(N) | −3232 −149 −16 | −3514 −500 −7720 | −2565 233 −8762 | −2905 43 −894 | −4358 −381 −1115 | −3267 399 −701 | −3364 106 −1378 | −5192 −626 −8762 | −3627 210 −7852 | −5059 −466 | −4632 −720 | 4348 275 | −3843 394 | −3410 45 | −3792 96 | −3319 359 | −3533 117 | −4568 −369 | −4087 −294 | −3976 −249 | 142 |
| 143(G) | −3681 −149 −17 | −3593 −500 −7720 | −4389 233 −8762 | −4747 43 −894 | −5281 −381 −1115 | 3812 399 −701 | −4419 106 −1378 | −5908 −626 −8762 | −5071 210 −7845 | −5671 −466 | −5288 −720 | −4417 275 | −4223 394 | −4850 45 | −4766 96 | −3952 359 | −4069 117 | −5125 −369 | −4424 −294 | −5214 −249 | 143 |
| 144(F) | −4352 −149 −17 | −3337 −500 −7720 | −4799 233 −8762 | −5121 43 −894 | 3888 −381 −1115 | −4670 399 −701 | −928 106 −1378 | −3235 −626 −8762 | −4686 210 −7839 | −2571 −466 | −2654 −720 | −3328 275 | −4541 394 | −3456 45 | −4078 96 | −3931 359 | −4217 117 | −3400 −369 | −178 −294 | −3260 −249 | 144 |

TABLE 8-continued

| | | | | | | | | | | | | | | | | | | |
|---|---|---|---|---|---|---|---|---|---|---|---|---|---|---|---|---|---|---|
| 145(T) | −866 | −1487 | −3132 | −3246 | −3768 | −1744 | −2940 | −3519 | −3190 | −3799 | −2625 | −2263 | −2509 | −2888 | −3152 | 2652 | 2778 | −2491 | −3995 | −3782 | 145 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7833 | | | | | | | | | | | | |
| 146(H) | −4406 | −3961 | −3921 | −4171 | −3231 | −3926 | 5401 | −5468 | −3992 | −5013 | −4849 | −4130 | −4378 | −4151 | −3893 | −4548 | −4592 | −5195 | −3383 | −2818 | 146 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7827 | | | | | | | | | | | | |
| 147(Q) | −3758 | −3792 | −3072 | −3245 | −4342 | −3586 | −3274 | −5053 | −2880 | −4719 | −4410 | −3349 | −4049 | 4526 | −2916 | −3829 | −3917 | −4726 | −3973 | −3953 | 147 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7820 | | | | | | | | | | | | |
| 148(D) | −2001 | −3292 | 3601 | −626 | −4238 | −2111 | −1759 | −4246 | −2092 | −4199 | −3539 | −963 | −2715 | −1470 | −2900 | 1255 | −2206 | −3561 | −4288 | −3412 | 148 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7814 | | | | | | | | | | | | |
| 149(P) | −4077 | −3791 | −4518 | −4858 | −5206 | −3818 | −4460 | −5898 | −5053 | −5602 | −5343 | −4628 | 4289 | −4938 | −4749 | −4364 | −4429 | −5313 | −4385 | −5119 | 149 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7807 | | | | | | | | | | | | |
| 150(G) | −2415 | −2868 | −3074 | −2972 | −4434 | 3359 | −2704 | −4428 | −1915 | −4330 | −3670 | −2780 | −3430 | −2492 | −1875 | −2564 | −2676 | −3754 | −3904 | −3964 | 150 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7801 | | | | | | | | | | | | |
| 151(F) | −2339 | −1986 | −4665 | −4064 | 3176 | −4095 | −2859 | −229 | −3739 | 1224 | 2452 | −3737 | −3789 | −3040 | −3446 | −3256 | −2245 | 1216 | −2175 | −2011 | 151 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7794 | | | | | | | | | | | | |
| 152(I) | −2056 | −1731 | −4386 | −3851 | −1203 | −3873 | −2916 | −2392 | −3540 | 2065 | −105 | −3529 | −3714 | −3075 | −3381 | −3054 | 1098 | 51 | −2437 | −2237 | 152 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7788 | | | | | | | | | | | | |
| 153(D) | −1118 | −2211 | 2195 | −621 | −3243 | 803 | −1223 | −3009 | −1065 | −3036 | −2177 | −857 | −2246 | −848 | −1597 | 985 | 2152 | −2413 | −3246 | −2588 | 153 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7781 | | | | | | | | | | | | |
| 154(H) | −1003 | −1199 | −2356 | −1954 | −1388 | −2206 | 3132 | −636 | −1619 | −1264 | 667 | −1770 | −2496 | −1555 | −1734 | −1385 | 1395 | 2407 | −1879 | −1430 | 154 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7775 | | | | | | | | | | | | |
| 155(M) | 695 | −1534 | −4131 | −3535 | −944 | −3528 | −2430 | 2154 | −3199 | 1674 | 2687 | −3161 | −3396 | −2699 | −2998 | −2660 | −1749 | −182 | −2022 | −1814 | 155 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7768 | | | | | | | | | | | | |
| 156(L) | 682 | −1592 | −4101 | −3606 | −1242 | −3407 | −2684 | 95 | −3291 | 2495 | −186 | −3196 | −3443 | −2879 | −3157 | −2606 | −1799 | 1329 | −2351 | −2114 | 156 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7762 | | | | | | | | | | | | |
| 157(N) | −1782 | −3518 | 1546 | 1312 | −3758 | −1994 | −1175 | −3610 | −1194 | −3512 | −2730 | 2977 | −2426 | −804 | −1905 | 1148 | −1804 | −3115 | −3698 | −2808 | 157 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7755 | | | | | | | | | | | | |
| 158(K) | −2459 | −2938 | −2880 | −2055 | −2893 | −3094 | −1378 | −2442 | 3407 | 840 | −1882 | −2005 | −3159 | −1028 | −200 | −2490 | −2293 | −2474 | −2837 | −2553 | 158 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7748 | | | | | | | | | | | | |
| 159(K) | −1148 | −2117 | −1407 | −950 | −3066 | −1999 | −1021 | −2720 | 2980 | −2713 | −1884 | −1076 | −2995 | −623 | −548 | −886 | 1179 | −2234 | −2851 | −2379 | 159 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7741 | | | | | | | | | | | | |
| 160(P) | 1034 | −1295 | −2486 | −2150 | 1616 | −1809 | −1863 | −1877 | −2017 | −2165 | −1435 | −1781 | 2897 | −1813 | −2195 | 966 | −1055 | −1493 | −2567 | −2152 | 160 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −17 | −7720 | −8762 | −894 | −1115 | −701 | −1378 | −8762 | −7735 | | | | | | | | | | | | |
| 161(D) | −2104 | −3998 | 2881 | 1352 | −4180 | 1216 | −1393 | −4095 | −1610 | −3965 | −3275 | 1701 | −2586 | −1055 | −2452 | −1771 | −2164 | −3570 | −4160 | −3154 | 161 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −1843 | −7720 | −490 | −894 | −1115 | −701 | −1378 | −8762 | −7728 | | | | | | | | | | | | |

TABLE 8-continued

| | | | | | | | | | | | | | | | | | |
|---|---|---|---|---|---|---|---|---|---|---|---|---|---|---|---|---|---|
| 162(N) | -498 -149 -43 | -1221 -500 -5920 | 110 233 -6962 | -15 43 -894 | -1620 -381 -1115 | -964 399 -2643 | -477 106 -252 | -1773 -626 -8762 | -335 210 -7721 | -1934 -466 | -1330 -720 | 3292 275 | -1450 394 | -280 45 | -647 96 | -522 359 | -670 117 | -1383 -369 | -1763 -294 | -1178 -249 | 162 |
| 163(D) | -961 -149 -43 | -1901 -500 -5920 | 3312 233 -6962 | 369 43 -894 | -2315 -381 -1115 | -1032 399 -2643 | -511 106 -252 | -2292 -626 -8762 | -663 210 -7714 | -2377 -466 | -1817 -720 | 34 275 | -1523 394 | -264 45 | -1242 96 | -811 359 | -1065 117 | -1927 -369 | -2232 -294 | -1739 -249 | 163 |
| 164(H) | -997 -149 -43 | -1393 -500 -5920 | -635 233 -6962 | -583 43 -894 | -386 -381 -1115 | -1411 399 -2643 | 4407 106 -3320 | -1664 -626 -8762 | -259 210 -7707 | -1594 -466 | -1144 -720 | -676 275 | -1756 394 | -466 45 | -415 96 | -1034 359 | -1055 117 | -1464 -369 | -790 -294 | 42 -249 | 164 |
| 165(V) | -2121 -149 -17 | -1684 -500 -7720 | -4679 233 -8763 | -4254 -894 | 1449 -381 -1115 | -4310 399 -152 | -3633 106 | 2372 -626 -8762 | -4076 210 -7700 | -839 -466 | -756 -720 | -3954 275 | -4126 394 | -3800 45 | -4049 96 | -3566 359 | -2094 117 | 2791 -369 | -3155 -294 | -2717 -249 | 165 |
| 166(V) | -1172 -149 -17 | -1063 -500 -7721 | -3285 233 -8763 | -2755 43 -894 | -1280 -381 -1115 | -2703 399 -701 | -1906 106 -1378 | 1464 -626 -8762 | -2465 210 -7693 | -907 -466 | -407 -720 | -2383 275 | -2845 394 | -2193 45 | -2434 96 | 949 359 | 1115 117 | 2471 -369 | -1913 -294 | -1547 -249 | 166 |
| 167(R) | -2428 -149 -17 | -3127 -500 -7721 | -2310 233 -8763 | -1828 43 -894 | -3921 -381 -1115 | -2880 399 -701 | -1372 106 -1378 | -3657 -626 -8762 | -155 210 -7687 | -3392 -466 | -2732 -720 | 1602 275 | -3079 394 | -997 45 | 3685 96 | -2367 359 | -2329 117 | -3316 -369 | -3168 -294 | -2942 -249 | 167 |
| 168(I) | 673 -149 -17 | -1102 -500 -7721 | -3159 233 -8763 | -2611 43 -894 | -1247 -381 -1115 | -2870 399 -701 | -1866 106 -1378 | 2195 -626 -8762 | -2325 210 -7679 | -820 -466 | -354 -720 | -2364 275 | -2914 394 | 1287 45 | -2345 96 | -1977 359 | -1221 117 | 2181 -369 | -1906 -294 | -1534 -249 | 168 |
| 169(Y) | -4444 -149 -17 | -3646 -500 -7721 | -4593 233 -8763 | -4892 43 -894 | -509 -381 -1115 | -4268 399 -701 | -1873 106 -1378 | -3993 -626 -8762 | -4663 210 -7672 | -3407 -466 | -3460 -720 | -3884 275 | -4503 394 | -3998 45 | -4255 96 | -4336 359 | -4491 117 | -4072 -369 | -1177 -294 | 4829 -249 | 169 |
| 170(F) | -3400 -149 -17 | -2827 -500 -7721 | -5361 233 -8763 | -4990 43 -894 | 2846 -381 -1115 | -5067 399 -701 | -2816 106 -1378 | -651 -626 -8762 | -4697 210 -7665 | 2592 -466 | 25 -720 | -4506 275 | -4471 394 | -3608 45 | -4224 96 | -4409 359 | -3268 117 | -1403 -369 | -1851 -294 | -1138 -249 | 170 |
| 171(P) | 1191 -149 -17 | -1755 -500 -7721 | -3163 233 -8763 | -3402 43 -894 | -3998 -381 -1115 | -1985 399 -701 | -3182 106 -1378 | -3756 -626 -8762 | -3492 210 -7658 | -4031 -466 | -3233 -720 | -2502 275 | 3818 394 | -3181 45 | -3412 96 | -1407 359 | -1613 117 | -2766 -369 | -4124 -294 | -4023 -249 | 171 |
| 172(P) | 1902 -149 -17 | -1437 -500 -7721 | -3147 233 -8763 | -3131 43 -894 | -3577 -381 -1115 | -1724 399 -701 | -2798 106 -1378 | -3245 -626 -8762 | -3019 210 -7651 | -3540 -466 | -2684 -720 | -2204 275 | 3083 394 | -2726 45 | -3028 96 | -1065 359 | 1432 117 | -2336 -369 | -3823 -294 | -3602 -249 | 172 |
| 173(D) | -3832 -149 -17 | -4189 -500 -7721 | 4132 233 -8763 | -2236 43 -894 | -5073 -381 -1115 | -3341 399 -701 | -3194 106 -1378 | -5633 -626 -8762 | -3716 210 -7644 | -5365 -466 | -5035 -720 | -2584 275 | -3886 394 | -3102 45 | -4252 96 | -3662 359 | -4000 117 | -5151 -369 | -4434 -294 | -4544 -249 | 173 |
| 174(A) | 2913 -149 -18 | -1375 -500 -7722 | -3689 233 -8764 | -3354 43 -894 | -3146 -381 -1115 | 1014 399 -701 | -2798 106 -1378 | -2432 -626 -8762 | -3176 210 -7638 | -3025 -466 | -2284 -720 | -2297 275 | -2499 394 | -2833 45 | -3104 96 | -1111 359 | -1235 117 | 1120 -369 | -3514 -294 | -3272 -249 | 174 |
| 175(N) | -3232 -149 -18 | -3514 -500 -7721 | -2565 233 -8764 | -2905 43 -894 | -4358 -381 -1115 | -3267 399 -701 | -3364 106 -1378 | -5192 -626 -8762 | -3627 210 -7629 | -5059 -466 | -4632 -720 | 4348 275 | -3843 394 | -3410 45 | -3792 96 | -3319 359 | -3533 117 | -4568 -369 | -4087 -294 | -3976 -249 | 175 |
| 176(C) | -775 -149 -18 | 3036 -500 -7721 | -2850 233 -8763 | -2408 43 -894 | -1588 -381 -1115 | -1919 399 -701 | -1731 106 -1378 | -1110 -626 -8762 | -2133 210 -7622 | -1469 -466 | 2376 -720 | -1909 275 | -2363 394 | -1881 45 | -2164 96 | 925 359 | 2536 117 | -890 -369 | -2035 -294 | -1692 -249 | 176 |

TABLE 8-continued

| | | | | | | | | | | | | | | | | | | | |
|---|---|---|---|---|---|---|---|---|---|---|---|---|---|---|---|---|---|---|---|
| 177(L) | −3406 | −2832 | −5440 | −5026 | 2063 | −5151 | −3069 | −587 | −4746 | 2880 | 97 | −4659 | −4495 | −3638 | −4269 | −4506 | −3269 | −1359 | −2041 | −1444 | 177 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −18 | −7721 | −8763 | −894 | −1115 | −701 | −1378 | −8762 | −7615 | | | | | | | | | | | | |
| 178(L) | −3777 | −3243 | −5089 | −5032 | −1735 | −4514 | −4040 | −1299 | −4754 | 3261 | −696 | −4891 | −4508 | −4152 | −4395 | −4705 | −3767 | −1993 | −3125 | −3069 | 178 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −18 | −7721 | −8763 | −894 | −1115 | −701 | −1378 | −8762 | −7607 | | | | | | | | | | | | |
| 179(C) | 2942 | 2982 | −3827 | −3914 | −3641 | −1706 | −3124 | −3330 | −3613 | −3649 | −2779 | −2414 | −2485 | −3185 | −3403 | 1168 | −1242 | −2356 | −3925 | −3779 | 179 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −18 | −7721 | −8763 | −894 | −1115 | −701 | −1378 | −8762 | −7600 | | | | | | | | | | | | |
| 180(V) | −2004 | −1608 | −4544 | −4142 | −2135 | −4125 | −3700 | 1840 | −3967 | −1140 | −967 | −3830 | −4052 | −3798 | −4000 | −3390 | 1338 | 2999 | −3399 | −2963 | 180 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −18 | −7721 | −8763 | −894 | −1115 | −701 | −1378 | −8762 | −7592 | | | | | | | | | | | | |
| 181(F) | 1588 | −850 | −2996 | −2447 | 2261 | −2299 | −1475 | −182 | −2129 | −756 | −166 | −2019 | −2485 | −1821 | −2060 | −1435 | 1085 | 1429 | −1479 | −1117 | 181 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −18 | −7721 | −8763 | −894 | −1115 | −701 | −1378 | −8762 | −7585 | | | | | | | | | | | | |
| 182(D) | 1088 | −3814 | 3226 | 1427 | −4086 | −2058 | −1384 | −3970 | −1570 | −3872 | −3169 | −670 | −2570 | −1045 | −2378 | −1733 | −2102 | −3453 | −4076 | −3107 | 182 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −18 | −7721 | −8763 | −894 | −1115 | −701 | −1378 | −8762 | −7577 | | | | | | | | | | | | |
| 183(H) | −2540 | −3259 | −3155 | −1838 | −4078 | −3083 | 3373 | −3420 | 2334 | −3069 | −2392 | −1745 | −3017 | −555 | 2597 | −2412 | −2222 | −3187 | −2907 | −2791 | 183 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −18 | −7721 | −8763 | −894 | −1115 | −701 | −1378 | −8762 | −7570 | | | | | | | | | | | | |
| 184(C) | 998 | 4910 | −3920 | −3803 | −2550 | −2066 | −2898 | −917 | −3459 | −2125 | −1635 | −2602 | −2717 | −3092 | −3274 | −1392 | −1333 | 1279 | −3175 | −2885 | 184 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −18 | −7721 | −8763 | −894 | −1115 | −701 | −1378 | −8762 | −7562 | | | | | | | | | | | | |
| 185(M) | −3195 | −2670 | −5480 | −4897 | 2597 | −5129 | −3599 | −426 | −4630 | 2310 | 2844 | −4767 | −4399 | −3550 | −4175 | −4399 | −3050 | −1206 | −2449 | −2343 | 185 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −18 | −7721 | −8763 | −894 | −1115 | −701 | −1378 | −8762 | −7555 | | | | | | | | | | | | |
| 186(Q) | −1978 | −3010 | −1873 | −1184 | −3573 | −2640 | 2315 | −3132 | 2388 | −2890 | −2142 | −1292 | −2679 | 3064 | 193 | −1845 | −1787 | −2819 | −2820 | −2501 | 186 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −18 | −7721 | −8763 | −894 | −1115 | −701 | −1378 | −8762 | −7547 | | | | | | | | | | | | |
| 187(S) | −1150 | −2122 | 1356 | −858 | −3376 | −1832 | −1484 | −3135 | −1404 | −3212 | −2374 | −1042 | −2342 | −1143 | −1916 | 2458 | 2054 | −2488 | −3434 | −2812 | 187 |
| | * | * | * | * | * | * | * | * | 0 | * | * | * | * | * | * | * | * | * | * | * | * |
| | | | | | | | | −8762 | | | | | | | | | | | | | |

TABLE 9

```
HMMER2.0 [2.3.2]
NAME XFP C
ACC PF09363.1
DESC XFP C-terminal domain
LENG 212
ALPH Amino
RF no
CS no
MAP yes
COM hmmbuild -f -F HMM_fs.ann SEED.ann
COM hmmcalibrate-seed 0 HMM_fs.ann
NSEQ 6
DATE Thu May 3 17:57:02 2007
CKSUM 5491
GA 25.0 25.0
TC 47.0 29.4
NC 15.7 15.7
XT -8455 -4 -1000 -1000 -8455 -4 -8455 -4
NULT -4 -8455
NULE 595 -1558 85 338 -294 453 -1158 197 249 902 -1085 -142 -21 -313 45 531 201 384 -1998 -644
EVD -10.483098 0.640397
```

| HMM | A<br>m→m | C<br>m→i | D<br>m→d | E<br>i→m | F<br>i→i | G<br>d→m | H<br>d→d | I<br>b→m | K<br>m→e | L | M | N | P | Q | R | S | T | V | W | Y | |
|---|---|---|---|---|---|---|---|---|---|---|---|---|---|---|---|---|---|---|---|---|---|
| | -193 | * | -2999 | | | | | | | | | | | | | | | | | | |
| 1(K) | -4125 | -4091 | -4017 | -3615 | -5101 | -3960 | -2958 | -5182 | 3972 | -4825 | -4345 | -3552 | -4249 | -2709 | -1809 | -4154 | -4044 | -4895 | -4132 | -4389 | 1 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -1193 | -8721 | | | | | | | | | | | | |
| 2(Q) | -1392 | -2802 | -618 | -424 | -3105 | -2084 | 2223 | -2893 | -446 | -2828 | -1977 | 1616 | 1057 | 3114 | -866 | -1245 | -1350 | -2468 | -2957 | -2283 | 2 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -8914 | -8718 | | | | | | | | | | | | |
| 3(P) | 1097 | -2000 | -3515 | -3791 | -4319 | -2230 | -3513 | -4117 | -3884 | -4378 | -3565 | -2801 | 3889 | -3540 | -3757 | -1661 | -1871 | -3066 | -4416 | -4363 | 3 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -8914 | -8714 | | | | | | | | | | | | |
| 4(H) | 829 | -2314 | -845 | -285 | -2656 | -1910 | 2103 | -2366 | 0 | -2324 | -1434 | -569 | -2003 | 1714 | 2028 | 709 | -889 | -1956 | -2490 | -1870 | 4 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -8914 | -8711 | | | | | | | | | | | | |
| 5(W) | 872 | -1301 | -1524 | -969 | -1324 | -2103 | -863 | -924 | -771 | 407 | -486 | -1096 | 1119 | 2314 | -1087 | -1098 | -833 | -778 | 2741 | -1233 | 5 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -8914 | -8707 | | | | | | | | | | | | |
| 6(Q) | 1139 | -1910 | -1850 | -1613 | -3267 | -2003 | -1790 | -2923 | -1462 | -3080 | -2266 | -1578 | -2518 | 3569 | -1755 | -1258 | 1437 | -2329 | -3351 | -2895 | 6 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -8914 | -8704 | | | | | | | | | | | | |
| 7(W) | -4606 | -3595 | -5007 | -5318 | 253 | -4844 | -1211 | -3574 | -4838 | -2908 | -2986 | -3590 | -4756 | -3710 | -4268 | -4192 | -4482 | -3721 | 5473 | 3368 | 7 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -8914 | -8700 | | | | | | | | | | | | |
| 8(L) | -2343 | -2040 | -4542 | -3937 | 1831 | -4019 | -2749 | 1548 | -3592 | 2218 | 65 | -3613 | -3780 | 1482 | -3353 | -3156 | -2252 | -936 | -2180 | -1956 | 8 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -8914 | -8697 | | | | | | | | | | | | |

TABLE 9-continued

| | | | | | | | | | | | | | | | | | | | | | |
|---|---|---|---|---|---|---|---|---|---|---|---|---|---|---|---|---|---|---|---|---|---|
| 9(T) | -1385<br>-149<br>-12 | -2322<br>-500<br>-7945 | 1417<br>233<br>-8987 | -1149<br>43<br>-894 | -3726<br>-381<br>-1115 | -2036<br>399<br>-701 | -1831<br>106<br>-1378 | -3500<br>-626<br>-8914 | -1823<br>210<br>-8693 | -3585<br>-466 | -2754<br>-720 | -1314<br>275 | -2593<br>394 | -1510<br>45 | -2340<br>96 | 1921<br>359 | 2800<br>117 | -2796<br>-369 | -3801<br>-294 | -3184<br>-249 | 9 |
| 10(M) | -1554<br>-149<br>-12 | -1399<br>-500<br>-7945 | -3470<br>233<br>-8987 | -2849<br>43<br>-894 | -1043<br>-381<br>-1115 | -3109<br>399<br>-701 | -1939<br>106<br>-1378 | -255<br>-626<br>-8914 | 1071<br>210<br>-8690 | 1028<br>-466 | 3713<br>-720 | -2584<br>275 | -3080<br>394 | -2156<br>45 | -2304<br>96 | -2204<br>359 | -1488<br>117 | 1337<br>-369 | -1856<br>-294 | -1572<br>-249 | 10 |
| 11(D) | -2255<br>-149<br>-12 | -4080<br>-500<br>-7945 | 2935<br>233<br>-8987 | 2308<br>43<br>-894 | -4312<br>-381<br>-1115 | -2253<br>399<br>-701 | -1576<br>106<br>-1378 | -4208<br>-626<br>-8914 | -1768<br>210<br>-8687 | -4097<br>-466 | -3398<br>-720 | -854<br>275 | -2767<br>394 | -1236<br>45 | -2584<br>96 | -1939<br>359 | 1141<br>117 | -3689<br>-369 | -4293<br>-294 | -3313<br>-249 | 11 |
| 12(E) | -1169<br>-149<br>-12 | -2634<br>-500<br>-7945 | -621<br>233<br>-8987 | 2512<br>43<br>-894 | -2971<br>-381<br>-1115 | -1972<br>399<br>-701 | -696<br>106<br>-1378 | -2711<br>-626<br>-8914 | 1193<br>210<br>-8683 | -2634<br>-466 | -1746<br>-720 | -602<br>275 | -2134<br>394 | 1564<br>45 | -675<br>96 | 777<br>359 | -1111<br>117 | -2271<br>-369 | -2782<br>-294 | -2114<br>-249 | 12 |
| 13(A) | 3176<br>-149<br>-12 | -1703<br>-500<br>-7945 | -4006<br>233<br>-8987 | -4070<br>43<br>-894 | -3246<br>-381<br>-1115 | -2260<br>399<br>-701 | -3401<br>106<br>-1378 | -1441<br>-626<br>-8914 | -3823<br>210<br>-8679 | -2722<br>-466 | -2304<br>-720 | -2855<br>275 | -2973<br>394 | -3487<br>45 | -3663<br>96 | -1620<br>359 | -1659<br>117 | 1420<br>-369 | -3901<br>-294 | -3631<br>-249 | 13 |
| 14(I) | -1158<br>-149<br>-12 | -1549<br>-500<br>-7945 | -1727<br>233<br>-8987 | 1889<br>43<br>-894 | -1669<br>-381<br>-1115 | -2385<br>399<br>-701 | -1107<br>106<br>-1378 | 1890<br>-626<br>-8914 | -836<br>210<br>-8676 | -1344<br>-466 | -736<br>-720 | -1323<br>275 | -2456<br>394 | -885<br>45 | 1317<br>96 | -1399<br>359 | -1097<br>117 | 1018<br>-369 | -2055<br>-294 | -1611<br>-249 | 14 |
| 15(H) | 848<br>-149<br>-12 | -2322<br>-500<br>-7945 | -1179<br>233<br>-8987 | -560<br>43<br>-894 | -2630<br>-381<br>-1115 | -2119<br>399<br>-701 | 2363<br>106<br>-1378 | -2275<br>-626<br>-8914 | 2038<br>210<br>-8672 | -2278<br>-466 | -1446<br>-720 | -801<br>275 | -2188<br>394 | -233<br>45 | 1325<br>96 | -1089<br>359 | -1073<br>117 | 627<br>-369 | -2469<br>-294 | -1939<br>-249 | 15 |
| 16(H) | -1354<br>-149<br>-12 | -2628<br>-500<br>-7945 | -576<br>233<br>-8987 | 1333<br>43<br>-894 | -2749<br>-381<br>-1115 | -2068<br>399<br>-701 | 3770<br>106<br>-1378 | -2560<br>-626<br>-8914 | -570<br>210<br>-8669 | 422<br>-466 | -1777<br>-720 | 1432<br>275 | -2292<br>394 | -513<br>45 | -1032<br>96 | -1235<br>359 | -1312<br>117 | -2213<br>-369 | -2778<br>-294 | -2099<br>-249 | 16 |
| 17(C) | 947<br>-149<br>-12 | 4245<br>-500<br>-7945 | -3771<br>233<br>-8987 | -3246<br>43<br>-894 | -1380<br>-381<br>-1115 | -2866<br>399<br>-701 | -2176<br>106<br>-1378 | -26<br>-626<br>-8914 | -2899<br>210<br>-8665 | 843<br>-466 | -500<br>-720 | -2705<br>275 | -3040<br>394 | -2556<br>45 | -2758<br>96 | -2038<br>359 | -1382<br>117 | 1326<br>-369 | -2062<br>-294 | -1723<br>-249 | 17 |
| 18(T) | -1296<br>-149<br>-12 | -2623<br>-500<br>-7945 | -1140<br>233<br>-8987 | 1900<br>43<br>-894 | -3034<br>-381<br>-1115 | -2174<br>399<br>-701 | -690<br>106<br>-1378 | -2702<br>-626<br>-8914 | 1486<br>210<br>-8662 | -2593<br>-466 | -1730<br>-720 | -817<br>275 | -2254<br>394 | -245<br>45 | 1344<br>96 | -1174<br>359 | 1932<br>117 | -2302<br>-369 | -2686<br>-294 | -2143<br>-249 | 18 |
| 19(A) | 2122<br>-149<br>-12 | -2640<br>-500<br>-7945 | 1402<br>233<br>-8987 | -254<br>43<br>-894 | -2963<br>-381<br>-1115 | -1940<br>399<br>-701 | -736<br>106<br>-1378 | -2715<br>-626<br>-8914 | 1187<br>210<br>-8658 | -2660<br>-466 | -1774<br>-720 | -577<br>275 | -2132<br>394 | 1562<br>45 | -869<br>96 | -1024<br>359 | -1125<br>117 | -2273<br>-369 | -2833<br>-294 | -2136<br>-249 | 19 |
| 20(G) | -4088<br>-149<br>-12 | -3924<br>-500<br>-7945 | -4774<br>233<br>-8987 | -5139<br>43<br>-894 | -5615<br>-381<br>-1115 | 3825<br>399<br>-701 | -4753<br>106<br>-1378 | -6303<br>-626<br>-8914 | -5453<br>210<br>-8655 | -6014<br>-466 | -5662<br>-720 | -4812<br>275 | -4539<br>394 | -5232<br>45 | -5106<br>96 | -4370<br>359 | -4472<br>117 | -5527<br>-369 | -4696<br>-294 | -5561<br>-249 | 20 |
| 21(I) | 1832<br>-149<br>-12 | -1779<br>-500<br>-7945 | -4707<br>233<br>-8987 | -4321<br>43<br>-894 | -2320<br>-381<br>-1115 | -4169<br>399<br>-701 | -3857<br>106<br>-1378 | 2857<br>-626<br>-8914 | -4145<br>210<br>-8651 | -1329<br>-466 | -1156<br>-720 | -3958<br>275 | -4165<br>394 | -3960<br>45 | -4165<br>96 | -3443<br>359 | -2157<br>117 | 1658<br>-369 | -3571<br>-294 | -3143<br>-249 | 21 |
| 22(A) | 1979<br>-149<br>-12 | -2132<br>-500<br>-7945 | 1358<br>233<br>-8987 | -1230<br>43<br>-894 | -3624<br>-381<br>-1115 | 895<br>399<br>-701 | -1764<br>106<br>-1378 | -3399<br>-626<br>-8914 | -1659<br>210<br>-8647 | -3464<br>-466 | -2589<br>-720 | -1343<br>275 | -2501<br>394 | -1420<br>45 | -2138<br>96 | 1914<br>359 | -1456<br>117 | -2656<br>-369 | -3665<br>-294 | -3086<br>-249 | 22 |
| 23(I) | -1613<br>-149<br>-12 | -1432<br>-500<br>-7945 | -3370<br>233<br>-8987 | 991<br>43<br>-894 | -1684<br>-381<br>-1115 | -3301<br>399<br>-701 | -2327<br>106<br>-1378 | 2219<br>-626<br>-8914 | -2660<br>210<br>-8644 | -1128<br>-466 | -723<br>-720 | -2715<br>275 | -3318<br>394 | -2464<br>45 | -2756<br>96 | -2418<br>359 | 1220<br>117 | 2185<br>-369 | -2433<br>-294 | -2038<br>-249 | 23 |
| 24(W) | -3333<br>-149<br>-12 | -2943<br>-500<br>-7945 | -4821<br>233<br>-8987 | -4705<br>43<br>-894 | -865<br>-381<br>-1115 | -4258<br>399<br>-701 | -2319<br>106<br>-1378 | 1550<br>-626<br>-8914 | -4105<br>210<br>-8640 | -1483<br>-466 | -1550<br>-720 | -3928<br>275 | -4360<br>394 | -3731<br>45 | -3856<br>96 | -3853<br>359 | -3350<br>117 | -1751<br>-369 | 5765<br>-294 | -662<br>-249 | 24 |
| 25(D) | -2155<br>-149<br>-12 | -3941<br>-500<br>-7945 | 2895<br>233<br>-8988 | 1331<br>43<br>-894 | -4165<br>-381<br>-1115 | -2244<br>399<br>-701 | -1467<br>106<br>-1378 | -4031<br>-626<br>-8914 | 2266<br>210<br>-8637 | -3906<br>-466 | -3170<br>-720 | -838<br>275 | -2712<br>394 | -1110<br>45 | -2170<br>96 | -1857<br>359 | -2186<br>117 | -3532<br>-369 | -4076<br>-294 | -3168<br>-249 | 25 |

TABLE 9-continued

| | | | | | | | | | | | | | | | | | |
|---|---|---|---|---|---|---|---|---|---|---|---|---|---|---|---|---|---|
| 26(W) | −4535 | −3580 | −5043 | −5339 | 2264 | −4800 | −1315 | −3404 | −4909 | −2727 | −2820 | −3667 | −4744 | −3774 | −4331 | −4221 | −4434 | −3613 | 5781 | 611 | 26 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7945 | −8988 | −894 | −1115 | −701 | −1378 | −8914 | −8633 | | | | | | | | | | | | |
| 27(A) | 3609 | −2508 | −4184 | −4493 | −4592 | −2737 | −3989 | −4421 | −4496 | −4701 | −4051 | −3440 | −3474 | −4171 | −4253 | −2294 | −2487 | −3536 | −4484 | −4643 | 27 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7945 | −8988 | −894 | −1115 | −701 | −1378 | −8914 | −8629 | | | | | | | | | | | | |
| 28(S) | −1944 | −2458 | −3696 | −4011 | −4410 | −2644 | −3753 | −4675 | −4191 | −4807 | −4070 | −3198 | −3384 | −3886 | −4051 | 3656 | −2393 | −3615 | −4374 | −4307 | 28 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7945 | −8988 | −894 | −1115 | −701 | −1378 | −8914 | −8626 | | | | | | | | | | | | |
| 29(N) | −1462 | −2164 | −1894 | −2122 | −3935 | −2171 | −2578 | −3801 | −2603 | −4009 | −3230 | 3172 | −2856 | −2392 | −2846 | −1616 | 2907 | −2960 | −4077 | −3633 | 29 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7945 | −8988 | −894 | −1115 | −701 | −1378 | −8914 | −8622 | | | | | | | | | | | | |
| 30(D) | 2036 | −3092 | 3356 | −1144 | −4437 | −2344 | −2201 | −4300 | −2537 | −4380 | −3702 | −1420 | −2974 | −1935 | −3248 | −2004 | −2335 | −3577 | −4473 | −3774 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7945 | −8988 | −894 | −1115 | −701 | −1378 | −8914 | −8618 | | | | | | | | | | | | |
| 31(K) | 719 | −2804 | 1286 | −282 | −3133 | −1980 | −846 | −2900 | 2557 | −2836 | −1958 | 1613 | −2216 | −421 | −1059 | −1135 | −1263 | −2444 | −3007 | −2283 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7945 | −8988 | −894 | −1115 | −701 | −1378 | −8914 | −8615 | | | | | | | | | | | | |
| 32(G) | −1795 | −2851 | 1703 | −1000 | −4330 | −2898 | −2022 | −4220 | −2294 | −4229 | −3471 | −1259 | −2791 | −1732 | −2991 | 1182 | −2066 | −3405 | −4399 | −3633 | 32 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1206 | −7945 | −837 | −894 | −1115 | −701 | −1378 | −8914 | −8611 | | | | | | | | | | | | |
| 33(N) | −713 | −1555 | −300 | −476 | −2841 | 2208 | −1131 | −2756 | −1105 | −2843 | −2074 | 2836 | −1863 | −861 | −1525 | −760 | −971 | −2081 | −2888 | −2349 | 33 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −24 | −6764 | −7806 | −894 | −1115 | −162 | −3231 | −8914 | −8607 | | | | | | | | | | | | |
| 34(E) | 652 | −2550 | 1383 | 2004 | −2857 | −1868 | −643 | −2618 | −298 | −2563 | −1660 | −497 | −2040 | 1542 | −832 | −908 | 985 | −2168 | −2738 | −2028 | 34 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7945 | −8988 | −894 | −1115 | −701 | −1378 | −8914 | −8604 | | | | | | | | | | | | |
| 35(E) | 978 | −3351 | −336 | 2983 | −3871 | −2170 | −1425 | −3692 | −1401 | −3640 | −2859 | 1765 | −2619 | −1063 | −2043 | −1667 | −1932 | −3175 | −3830 | −3006 | 35 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7945 | −8988 | −894 | −1115 | −701 | −1378 | −8914 | −8600 | | | | | | | | | | | | |
| 36(P) | −1823 | −2153 | −3843 | −3947 | −3271 | −2734 | −3495 | −1581 | −3785 | −2766 | −2465 | −3169 | 3446 | −3607 | −3696 | −2195 | −2168 | 2328 | −3859 | −3579 | 36 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7945 | −8988 | −894 | −1115 | −701 | −1378 | −8914 | −8596 | | | | | | | | | | | | |
| 37(D) | −2642 | −4390 | 3693 | −696 | −4628 | −2447 | −1891 | −4714 | −2203 | −4552 | −3980 | −1088 | −3019 | 1971 | −3045 | −2293 | −2745 | −4173 | −4588 | −3642 | 37 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7945 | −8988 | −894 | −1115 | −701 | −1378 | −8914 | −8592 | | | | | | | | | | | | |
| 38(V) | −2557 | −2122 | −5071 | −4711 | −1962 | −4673 | −4220 | 320 | −4512 | 984 | −791 | −4445 | −4483 | −4165 | −4454 | −4020 | −2550 | 3348 | −3513 | −3210 | 38 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7945 | −8988 | −894 | −1115 | −701 | −1378 | −8914 | −8589 | | | | | | | | | | | | |
| 39(V) | −2838 | −2616 | 4834 | −4880 | −3213 | −3955 | −4416 | −610 | −4757 | −2310 | −2253 | −4383 | −4345 | −4643 | −4642 | −3732 | −3007 | 3763 | −4157 | −3886 | 39 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7946 | −8988 | −894 | −1115 | −701 | −1378 | −8914 | −8585 | | | | | | | | | | | | |
| 40(M) | −3038 | −2583 | −5400 | −4796 | 1866 | −4936 | −3671 | 2288 | −4513 | 1389 | 3379 | −4610 | 4379 | −3590 | −4127 | −4157 | −2917 | −1104 | −2668 | −2694 | 40 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −13 | −7946 | −8988 | −894 | −1115 | −701 | −1378 | −8914 | −8581 | | | | | | | | | | | | |
| 41(A) | 3609 | −2508 | −4184 | −4493 | −4592 | −2737 | −3989 | −4421 | −4496 | −4701 | −4051 | −3440 | −3474 | −4171 | −4253 | −2294 | −2487 | −3536 | −4484 | −4643 | 41 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −13 | −7946 | −8988 | −894 | −1115 | −701 | −1378 | −8914 | −8577 | | | | | | | | | | | | |
| 42(C) | 2065 | 2925 | −3988 | −4043 | −3973 | 1287 | −3331 | −3726 | −3772 | −3993 | −3088 | −2601 | −2687 | −3352 | −3601 | 2060 | −1451 | −2653 | −4224 | −4091 | 42 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −13 | −7946 | −8988 | −894 | −1115 | −701 | −1378 | −8914 | −8574 | | | | | | | | | | | | |

TABLE 9-continued

| | | | | | | | | | | | | | | | | | | |
|---|---|---|---|---|---|---|---|---|---|---|---|---|---|---|---|---|---|---|
| 43(A) | 2866 −149 −13 | 2846 −500 −7946 | −4109 233 −8988 | −4001 −894 | −2791 −381 −1115 | −2206 399 −701 | −3077 106 −1378 | −1268 −626 −8914 | −3662 210 −8570 | −2419 −466 | −1888 −720 | −2761 275 | −2871 394 | −3275 45 | −3465 96 | −1533 359 | −1500 117 | 1398 −369 | −3377 −294 | −3097 −249 | 43 |
| 44(G) | −4088 −149 −13 | −3924 −500 −7946 | −4774 233 −8988 | −5139 43 −894 | −5615 −381 −1115 | 3825 399 −701 | −4753 106 −1378 | −6303 −626 −8914 | −5453 210 | −6014 −466 | −5662 −720 | −4812 275 | −4539 394 | −5232 45 | −5106 96 | −4370 359 | −4472 117 | −5527 −369 | −4696 −294 | −5561 −249 | 44 |
| 45(D) | 1008 −149 −13 | −3741 −500 −7946 | 3309 233 −8988 | −578 43 −894 | −4350 −381 −1115 | −2242 399 −701 | −1698 106 −1378 | −4254 −626 −8914 | −1941 210 −8566 | −4177 −466 | −3484 −720 | 1820 275 | −2795 394 | −1375 45 | −2757 96 | −1930 359 | −2306 117 | −3665 −369 | −4371 −294 | −3418 −249 | 45 |
| 46(V) | −1488 −149 −13 | −1444 −500 −7946 | −2805 233 −8988 | 1912 43 −894 | −1672 −381 −1115 | −3036 399 −701 | −1995 106 −1378 | 1499 −626 −8914 | −2149 210 −8562 | −1163 −466 | −719 −720 | −2290 275 | −3083 394 | −1996 45 | −2352 96 | −2120 359 | 998 117 | 2130 −369 | −2347 −294 | −1936 −249 | 46 |
| 47(P) | −2288 −149 −13 | −2497 −500 −7946 | −3856 233 −8988 | −3931 43 −894 | −2960 −381 −1115 | −3134 399 −701 | −3483 106 −1378 | 1588 −626 −8914 | −3705 210 −8558 | −2343 −466 | −2229 −720 | −3416 275 | 3829 394 | −3629 45 | −3645 96 | −2690 359 | −2575 117 | −1605 −369 | −3649 −294 | −3323 −249 | 47 |
| 48(T) | −1494 −149 −13 | −1874 −500 −7946 | −3613 233 −8988 | −3499 43 −894 | −2448 −381 −1115 | −2472 399 −701 | −2890 106 −1378 | −1675 −626 −8914 | −3034 210 −8555 | −1763 −466 | 2674 −720 | −2770 275 | −3069 394 | −2947 45 | −2983 96 | −1828 359 | 3524 117 | −1602 −369 | −3212 −294 | −2888 −249 | 48 |
| 49(F) | −1077 −149 −13 | −1060 −500 −7946 | −2607 233 −8988 | −2006 43 −894 | 1617 −381 −1115 | −2517 399 −701 | −1308 106 −1378 | 1338 −626 −8914 | 853 210 −8551 | 1327 −466 | −74 −720 | −1856 275 | −2554 394 | 1561 45 | −1724 96 | −1568 359 | −1013 117 | −416 −369 | −1457 −294 | −1095 −249 | 49 |
| 50(E) | −4205 −149 −13 | −4417 −500 −7946 | −2343 233 −8988 | 3901 43 −894 | −5349 −381 −1115 | −3698 399 −701 | −3534 106 −1378 | −5837 −626 −8914 | −3838 210 −8547 | −5561 −466 | −5237 −720 | −3039 275 | −4218 394 | −3453 45 | −4201 96 | −4072 359 | −4352 117 | −5409 −369 | −4640 −294 | −4860 −249 | 50 |
| 51(T) | 1578 −149 −13 | −1365 −500 −7946 | −3818 233 −8988 | −3310 43 −894 | −1660 −381 −1115 | −3164 399 −701 | −2456 106 −1378 | 1709 −626 −8914 | −3026 210 −8543 | −1148 −466 | −726 −720 | −2898 275 | −3288 394 | −2750 45 | −2975 96 | −2334 359 | 2031 117 | 1609 −369 | −2396 −294 | −2024 −249 | 51 |
| 52(M) | −3164 −149 −13 | −2670 −500 −7946 | −5546 233 −8988 | −4970 43 −894 | −1172 −381 −1115 | −5167 399 −701 | −3972 106 −1378 | −395 −626 −8914 | −4712 210 −8539 | 2611 −466 | 2735 −720 | −4857 275 | −4533 394 | −3759 45 | −4329 96 | −4434 359 | −3047 117 | 1340 −369 | −2847 −294 | −2936 −249 | 52 |
| 53(A) | 3164 −149 −13 | −2290 −500 −7946 | −2449 233 −8988 | −2301 43 −894 | −3900 −381 −1115 | −2380 399 −701 | −2191 106 −1378 | −3516 −626 −8914 | 1483 210 −8535 | −3644 −466 | −2906 −720 | −2112 275 | −2939 394 | −1904 45 | −1531 96 | −1776 359 | −1904 117 | −2880 −369 | −3730 −294 | −3462 −249 | 53 |
| 54(A) | 3609 −149 −13 | −2508 −500 −7946 | −4184 233 −8988 | −4493 43 −894 | −4592 −381 −1115 | −2737 399 −701 | −3989 106 −1378 | −4421 −626 −8914 | −4496 210 −8531 | −4701 −466 | −4051 −720 | −3440 275 | −3474 394 | −4171 45 | −4253 96 | −2294 359 | −2487 117 | −3536 −369 | −4484 −294 | −4643 −249 | 54 |
| 55(V) | 950 −149 −13 | −941 −500 −7946 | −2811 233 −8988 | −2248 43 −894 | −1031 −381 −1115 | −2327 399 −701 | −1422 106 −1378 | −440 −626 −8914 | −1962 210 −8527 | 740 −466 | −250 −720 | −1933 275 | −2494 394 | −1690 45 | −1964 96 | 896 359 | 1079 117 | 1807 −369 | −1521 −294 | −1165 −249 | 55 |
| 56(H) | 659 −149 −13 | −2340 −500 −7946 | 1265 233 −8988 | 1241 43 −894 | −2654 −381 −1115 | −1788 399 −701 | 2240 106 −1378 | −2406 −626 −8914 | −89 210 −8524 | −2353 −466 | −1435 −720 | −421 275 | −1907 394 | 1509 45 | −604 96 | −738 359 | 910 117 | −1959 −369 | −2525 −294 | −1836 −249 | 56 |
| 57(M) | 905 −149 −13 | −1698 −500 −7946 | −4314 233 −8988 | −3724 43 −894 | −1143 −381 −1115 | −3706 399 −701 | −2623 106 −1378 | 2145 −626 −8914 | −3388 210 −8520 | 1126 −466 | 3388 −720 | −3345 275 | −3578 394 | −2895 45 | −3189 96 | −2841 359 | −1918 117 | −295 −369 | −2218 −294 | −2005 −249 | 57 |
| 58(L) | −3094 −149 −13 | −2629 −500 −7946 | −5472 233 −8988 | −5009 43 −894 | −1335 −381 −1115 | −5054 399 −701 | −4133 106 −1378 | −266 −626 −8914 | −4744 210 −8516 | 2900 −466 | −148 −720 | −4850 275 | −4577 394 | −3917 45 | −4430 96 | −4403 359 | −3029 117 | 1404 −369 | −3024 −294 | −3024 −249 | 58 |
| 59(N) | −1718 −149 −13 | −2924 −500 −7946 | −1536 233 −8988 | −943 43 −894 | −3401 −381 −1115 | −2491 399 −701 | 2272 106 −1378 | −3022 −626 −8914 | 67 210 −8508 | −2851 −466 | −2042 −720 | 2480 275 | −2560 394 | 1853 45 | 2240 96 | −1589 359 | −1584 117 | −2659 −369 | −2864 −294 | −2426 −249 | 59 |

TABLE 9-continued

| | | | | | | | | | | | | | | | | | | | | |
|---|---|---|---|---|---|---|---|---|---|---|---|---|---|---|---|---|---|---|---|---|
| 60(Q) | −1303 | −2782 | −604 | 1957 | −3121 | −2037 | −786 | −2861 | 1397 | −2771 | −1895 | 1587 | −2225 | 2403 | −741 | −1147 | −1246 | −2420 | −2908 | −2240 | 60 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8504 | | | | | | | | | | | | |
| 61(M) | −836 | −1314 | 1097 | −815 | 1234 | −2045 | 2007 | −937 | −682 | −1198 | 2233 | −976 | −2124 | 1369 | −1042 | −1018 | −776 | 996 | −1675 | −1208 | 61 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8500 | | | | | | | | | | | | |
| 62(F) | −1264 | −1055 | −3592 | −2980 | 2448 | 801 | −1770 | 1523 | −2606 | 732 | −96 | −2510 | −2888 | −2223 | −2426 | −1975 | −1207 | 1242 | −1588 | −1251 | 62 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −267 | −7946 | −8988 | −894 | −1115 | −701 | −1378 | −8914 | −8496 | | | | | | | | | | | | |
| 63(P) | −4031 | −3755 | −2622 | −4814 | −5166 | −3783 | −4422 | −5849 | −5008 | −5560 | −5299 | −4583 | 4287 | −4894 | −4709 | −4316 | −4383 | −5266 | −4354 | −5078 | 63 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −14 | −7693 | −8735 | −894 | −1115 | −1509 | −1378 | −8914 | −8492 | | | | | | | | | | | | |
| 64(E) | −1699 | −3425 | 1700 | 2340 | −3660 | −1960 | −1101 | −3504 | −1077 | −3405 | −2608 | 1773 | −2370 | 2059 | −1764 | −1441 | −1711 | −3013 | −3587 | −2715 | 64 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −14 | −7693 | −8735 | −894 | −1115 | −358 | −1378 | −8914 | −8488 | | | | | | | | | | | | |
| 65(L) | 891 | −2044 | −4713 | −4184 | −1318 | −4146 | −2187 | 1658 | −3880 | 2504 | −198 | −3858 | −3970 | −3332 | −3681 | −3346 | −2320 | −337 | −2643 | −2499 | 65 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8484 | | | | | | | | | | | | |
| 66(R) | −3030 | −3584 | −3982 | −2344 | −4551 | −3458 | −1269 | −3800 | 2924 | −3397 | −2757 | −2153 | −3376 | −852 | 3034 | −2903 | −2656 | −3598 | −3188 | −3160 | 66 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8480 | | | | | | | | | | | | |
| 67(F) | −2326 | −1891 | −4869 | −4440 | 2685 | −4485 | −3701 | 2340 | −4251 | −921 | −863 | −4124 | −4292 | −3931 | −4198 | −3737 | −2296 | 2290 | −3181 | −2708 | 67 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8476 | | | | | | | | | | | | |
| 68(R) | −3054 | −3592 | −3980 | −2373 | −4560 | −3469 | −1297 | −3823 | 1781 | −3421 | −2785 | −2179 | −3395 | −881 | 3702 | −2930 | −2684 | −3621 | −3206 | −3181 | 68 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8472 | | | | | | | | | | | | |
| 69(F) | −3145 | −2644 | −4628 | −4516 | 2787 | −4252 | −4113 | −1824 | −4116 | −1928 | −1754 | −3303 | −4186 | −3281 | −3729 | −3432 | −3069 | 2671 | −580 | 2537 | 69 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8468 | | | | | | | | | | | | |
| 70(V) | −2243 | −1824 | −4833 | −4454 | −2402 | −4433 | −1269 | 1762 | −4305 | −1350 | −1201 | −4152 | −4338 | −4160 | −4358 | −3722 | −1258 | 3104 | −3760 | −3307 | 70 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8455 | | | | | | | | | | | | |
| | −2450 | −1960 | −8988 | −4795 | −2565 | −4880 | −4855 | 1914 | −4732 | −1343 | −1286 | −4581 | −4668 | −4656 | −4868 | −4252 | −2448 | 3379 | −4256 | −3756 | |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −5111 | −894 | −1115 | −701 | −1378 | −8914 | −8451 | | | | | | | | | | | | |
| 71(N) | −1525 | −2287 | −1522 | −1828 | −4053 | −2153 | −2507 | −4149 | −2667 | −4251 | −3455 | 3942 | −2849 | −2311 | −3012 | 1045 | −1898 | −3178 | −4209 | −3651 | 71 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8459 | | | | | | | | | | | | |
| 72(V) | −2838 | −2616 | −4834 | −4880 | −3213 | −3955 | −4416 | −610 | −4757 | −2310 | −2253 | −4383 | −4345 | −4643 | −4642 | −3732 | −3007 | 3763 | −4157 | −3886 | 72 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8455 | | | | | | | | | | | | |
| 73(V) | −2243 | −1824 | −4833 | −4454 | −2402 | −4433 | −4113 | −1824 | −4305 | −1350 | −1201 | −4152 | −4338 | −4160 | −4358 | −3722 | −1258 | 3104 | −3760 | −3307 | 73 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8451 | | | | | | | | | | | | |
| 74(D) | −2668 | −4634 | 3697 | 1529 | −4809 | −2393 | −1860 | −4835 | −2286 | −4663 | −4116 | −996 | −2985 | −1560 | −3281 | −2276 | −2774 | −4274 | −4791 | −3728 | 74 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8447 | | | | | | | | | | | | |
| 75(L) | −3647 | −3060 | −5937 | −5371 | −1118 | −5682 | −4333 | −610 | −5087 | 3001 | 2533 | −5429 | −4784 | −3925 | −4592 | −5073 | −3493 | −1435 | −2916 | −3081 | 75 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8443 | | | | | | | | | | | | |
| 76(M) | −1722 | −1497 | −3954 | −3355 | −1014 | 848 | −2243 | 1549 | −2997 | 978 | 3830 | −2966 | −3285 | −2560 | −2824 | −2460 | −1661 | −398 | −1947 | −1696 | 76 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −13 | −7946 | −8988 | −894 | −1115 | −701 | −1378 | −8914 | −8439 | | | | | | | | | | | | |

TABLE 9-continued

| | | | | | | | | | | | | | | | | |
|---|---|---|---|---|---|---|---|---|---|---|---|---|---|---|---|---|
| 77(K) | −1675 −149 −13 | −2604 −500 −7946 | −1914 233 −8988 | −1147 43 −894 | −3023 −381 −1115 | −2553 399 −701 | −912 106 −1378 | −2542 −626 −8914 | 2655 210 −8435 | −2539 −466 | −1775 −720 | −1279 275 | −2595 394 | −506 45 | 1666 96 | −1628 359 | 1008 117 | 985 −369 | −2674 −294 | −2295 −249 | 77 |
| 78(L) | −4119 −149 −13 | −3542 −500 −7946 | −5389 233 −8988 | −5357 43 −894 | −2027 −381 −1115 | −4767 399 −701 | −4358 106 −1378 | −1609 −626 −8914 | −5118 210 −8430 | 3293 −466 | −979 −720 | −5230 275 | −4771 394 | −4474 45 | −4724 96 | −5069 359 | −4106 117 | −2331 −369 | −3412 −294 | −3400 −249 | 78 |
| 79(Q) | −1357 −149 −13 | −2106 −500 −7946 | −1510 233 −8988 | −1196 43 −894 | −2392 −381 −1115 | −2243 399 −701 | −1288 106 −1378 | −2153 −626 −8914 | −824 210 −8426 | 371 −466 | −1573 −720 | −1327 275 | −2535 394 | 3535 45 | −1081 96 | 1033 359 | −1413 117 | −1913 −369 | −2627 −294 | −2087 −249 | 79 |
| 80(P) | −1393 −149 −13 | −2284 −500 −7946 | −1577 233 −8988 | −1362 43 −894 | −3557 −381 −1115 | −2164 399 −701 | −1558 106 −1378 | −3266 −626 −8914 | 1432 210 −8422 | −3269 −466 | −2444 −720 | −1443 275 | 2774 394 | −1192 45 | −1186 96 | 2003 359 | −1560 117 | −2662 −369 | −3389 −294 | −2924 −249 | 80 |
| 81(K) | −1010 −149 −13 | −2349 −500 −7946 | −767 233 −8988 | 1764 43 −894 | −2657 −381 −1115 | −1927 399 −701 | −589 106 −1378 | −2362 −626 −8914 | 1961 210 −8418 | 301 −466 | −1468 −720 | −584 275 | −2042 394 | −153 45 | −523 96 | 917 359 | −946 117 | −1969 −369 | −2533 −294 | −1906 −249 | 81 |
| 82(H) | −956 −149 −13 | −2424 −500 −7946 | −615 233 −8988 | 1087 43 −894 | −2749 −381 −1115 | −1853 399 −701 | 2292 106 −1378 | −2494 −626 −8914 | 2040 210 −8414 | −2432 −466 | −1522 −720 | 1288 275 | −1978 394 | −92 45 | −585 96 | 753 359 | −897 117 | −2050 −369 | −2592 −294 | −1916 −249 | 82 |
| 83(G) | −1873 −149 −13 | −1186 −500 −7946 | −474 233 −8988 | −1603 43 −894 | −2565 −381 −1115 | 3376 399 −701 | −1668 106 −1378 | −2627 −626 −8914 | −1844 210 −8409 | −2759 −466 | −2200 −720 | −1431 275 | −1859 394 | −1709 45 | −1902 96 | −1054 359 | −1192 117 | −2034 −369 | −2282 −294 | −2387 −249 | 83 |
| 84(A) | 2862 −149 −36 | −488 −500 −6109 | −1346 233 −7151 | −1349 43 −894 | −1807 −381 −1115 | −785 399 −701 | −1257 106 −1378 | −1119 −626 −8914 | −1298 210 −8405 | −1627 −466 | −1088 −720 | −934 275 | −1428 394 | −1183 45 | −1403 96 | −201 359 | −309 117 | −714 −369 | −2107 −294 | −1798 −249 | 84 |
| 85(L) | −1446 −149 −36 | −1261 −500 −6109 | −2639 233 −7151 | −2396 43 −894 | −166 −381 −1115 | −2529 399 −701 | −1687 106 −1378 | 443 −626 −8914 | −1969 210 −8401 | 2652 −466 | 716 −720 | −2264 275 | −2607 394 | −1810 45 | −1925 96 | −2083 359 | −1460 117 | 71 −369 | −1338 −294 | −963 −249 | 85 |
| 86(E) | −1620 −149 −15 | −3077 −500 −7696 | −205 233 −7151 | 2781 43 −894 | −2713 −381 −1115 | −2016 399 −701 | −1952 106 −1378 | −3107 −626 −8914 | −935 210 −8397 | −3054 −466 | −2295 −720 | 1905 275 | −2376 394 | −703 45 | −1502 96 | −1416 359 | −1618 117 | −2704 −369 | −2909 −294 | 1972 −249 | 86 |
| 87(H) | −1687 −149 −15 | −3020 −500 −7696 | −524 233 −8738 | −508 43 −894 | −3027 −381 −1115 | −1502 399 −701 | −1027 106 −1378 | −3137 −626 −8914 | −478 210 −8392 | −3027 −466 | −2263 −720 | 1907 275 | −2446 394 | 2055 45 | −794 96 | −1508 359 | −1649 117 | −2742 −369 | −2951 −294 | −2237 −249 | 87 |
| 88(P) | −2450 −149 −15 | −4345 −500 −7696 | 1816 233 −8738 | 1516 43 −894 | −4562 −381 −1115 | −2311 399 −701 | 4043 106 −1378 | −4514 −626 −8914 | −2022 210 −8379 | −4375 −466 | −3745 −720 | −914 275 | 3318 394 | −1394 45 | −2920 96 | −2098 359 | −2536 117 | −3971 −369 | −4556 −294 | −3521 −249 | 88 |
| 89(H) | −2178 −149 −13 | −3297 −500 −7946 | −1451 233 −8988 | 1311 43 −894 | −3729 −381 −1115 | −2695 399 −701 | 4349 106 −1378 | −3419 −626 −8914 | −165 210 −8384 | −3210 −466 | −2472 −720 | −1349 275 | −2852 394 | −755 45 | 1705 96 | −2018 359 | −2038 117 | −3087 −369 | −3149 −294 | −2733 −249 | 89 |
| 90(G) | 1135 −149 −13 | −2508 −500 −7946 | −960 233 −8988 | 1390 43 −894 | −3988 −381 −1115 | 2880 399 −701 | −1982 106 −1378 | −3774 −626 −8914 | −2052 210 −8375 | −3851 −466 | −3054 −720 | −1368 275 | −2715 394 | −1683 45 | −2580 96 | −1591 359 | −1835 117 | −3036 −369 | −4050 −294 | −3424 −249 | 90 |
| 91(M) | −3620 −149 −13 | −3042 −500 −7946 | −5906 233 −8988 | −5341 43 −894 | −1118 −381 −1115 | −5639 399 −701 | −4298 106 −1378 | −608 −626 −8914 | −5051 210 −8379 | 2656 −466 | 3645 −720 | −5383 275 | −4766 394 | −3909 45 | −4566 96 | −5021 359 | −3469 117 | −1425 −369 | −2906 −294 | −3062 −249 | 91 |
| 92(S) | −1385 −149 −13 | −2104 −500 −7946 | −1840 233 −8988 | −2115 43 −894 | −4039 −381 −1115 | −2094 399 −701 | −2642 106 −1378 | −4072 −626 −8914 | −2802 210 −8371 | −4207 −466 | −3375 −720 | 1808 275 | −2809 394 | −2466 45 | −3073 96 | 3255 359 | −1780 117 | −3055 −369 | −4205 −294 | −3726 −249 | 92 |
| 93(D) | −2954 −149 −13 | −4081 −500 −7946 | 3777 233 −8988 | −1338 43 −894 | −4930 −381 −1115 | −2812 399 −701 | −2481 106 −1378 | −5106 −626 −8914 | −2896 210 −8366 | −4959 −466 | −4423 −720 | −1697 275 | 1695 394 | −2236 45 | −3689 96 | −2728 359 | −3134 117 | −4489 −369 | −4667 −294 | −4137 −249 | 93 |

TABLE 9-continued

| | | | | | | | | | | | | | | | | | | |
|---|---|---|---|---|---|---|---|---|---|---|---|---|---|---|---|---|---|---|
| 94(R) | 847 -149 -13 | -2632 -500 -7946 | -1132 233 -8988 | 2003 43 -894 | -3046 -381 -1115 | -2175 399 -701 | -695 106 -1378 | -2716 -626 -8914 | 1321 210 -8362 | -2604 -466 | -1741 -720 | -819 275 | -2258 394 | -250 45 | 2101 96 | -1179 359 | -1206 117 | -2313 -369 | -2696 -294 | -2152 -249 | 94 |
| 95(D) | -2629 -149 -13 | -4604 -500 -7946 | 3009 233 -8988 | 2799 43 -894 | -4770 -381 -1115 | -2374 399 -701 | -1828 106 -1378 | -4782 -626 -8914 | -2234 210 -8358 | -4614 -466 | -4051 -720 | -973 275 | -2960 394 | -1523 45 | -3216 96 | -2241 359 | -2730 117 | -4224 -369 | -4757 -294 | -3689 -249 | 95 |
| 96(F) | -4587 -149 -13 | -3562 -500 -7946 | -5019 233 -8988 | -5350 43 -894 | 4191 -381 -1115 | -4887 399 -701 | -1144 106 -1378 | -3464 -626 -8914 | -4916 210 -8353 | -2789 -466 | -2878 -720 | -3547 275 | -4760 394 | -3678 45 | -4301 96 | -4156 359 | -4453 117 | -3634 -369 | -393 -294 | 2478 -249 | 96 |
| 97(D) | 988 -149 -13 | -3875 -500 -7946 | 2907 233 -8988 | 1483 43 -894 | -4100 -381 -1115 | -2208 399 -701 | -1447 106 -1378 | -3972 -626 -8914 | -1539 210 -8349 | -3865 -466 | -3114 -720 | 1567 275 | -2675 394 | -1089 45 | -2294 96 | -1800 359 | -2126 117 | -3467 -369 | -4055 -294 | -3126 -249 | 97 |
| 98(S) | 1458 -149 -13 | -2457 -500 -7946 | 1399 233 -8988 | -292 43 -894 | -2897 -381 -1115 | -1890 399 -701 | -750 106 -1378 | -2648 -626 -8914 | 1311 210 -8344 | -2615 -466 | -1722 -720 | -599 275 | -2098 394 | -317 45 | -922 96 | 1668 359 | -1053 117 | -2187 -369 | -2800 -294 | -2113 -249 | 98 |
| 99(L) | -3562 -149 -13 | -3022 -500 -7946 | -4998 233 -8988 | -4839 43 -894 | -384 -381 -1115 | -4758 399 -701 | -2089 106 -1378 | -1358 -626 -8914 | -4382 210 -8340 | 2908 -466 | -731 -720 | -3989 275 | -4502 394 | -3590 45 | -4015 96 | -4103 359 | -3467 117 | -1964 -369 | -1321 -294 | 2369 -249 | 99 |
| 100(F) | -4720 -149 -13 | -3927 -500 -7946 | -5139 233 -8988 | -5454 43 -894 | 4513 -381 -1115 | -4504 399 -701 | -2520 106 -1378 | -3938 -626 -8914 | -5326 210 -8335 | -3307 -466 | -3429 -720 | -4469 275 | -4782 394 | -4575 45 | -4818 96 | -4787 359 | -4810 117 | -4172 -369 | -1812 -294 | -736 -249 | 100 |
| 101(T) | -1345 -149 -13 | -1936 -500 -7946 | -3485 233 -8988 | -3748 43 -894 | -4307 -381 -1115 | 1297 399 -701 | -3469 106 -1378 | -4115 -626 -8914 | -3845 210 -8331 | -4377 -466 | -3519 -720 | -2741 275 | -2943 394 | -3484 45 | -3725 96 | -1588 359 | 3638 117 | -3022 -369 | -4411 -294 | -4351 -249 | 101 |
| 102(P) | 1040 -149 -13 | -1933 -500 -7946 | -1444 233 -8988 | -985 43 -894 | -2825 -381 -1115 | -1942 399 -701 | -1172 106 -1378 | -2498 -626 -8914 | 1349 210 -8326 | -2593 -466 | -1749 -720 | -1119 275 | 2171 394 | -794 45 | -1131 96 | -1051 359 | 1955 117 | -2025 -369 | -2847 -294 | -2320 -249 | 102 |
| 103(D | -2253 -149 -13 | -3538 -500 -7946 | 3694 233 -8988 | -855 43 -894 | -4532 -381 -1115 | -2334 399 -701 | -2017 106 -1378 | -4570 -626 -8914 | -2397 210 -8322 | -4510 -466 | -3869 -720 | -1194 275 | -2951 394 | -1736 45 | -3233 96 | 1140 359 | -2471 117 | -3857 -369 | -4578 -294 | -3695 -249 | 103 |
| 104G | -1873 -149 -13 | -1186 -500 -7946 | -1419 233 -474 | -1603 43 -894 | -2565 -381 -1115 | 3376 399 -701 | -1668 106 -1378 | -2627 -626 -8914 | -1844 210 -8317 | -2759 -466 | -2200 -720 | -1431 275 | -1859 394 | -1709 45 | -1902 96 | -1054 359 | -1192 117 | -2034 -369 | -2282 -294 | -2387 -249 | 104 |
| 105(K | -853 -149 -13 | -6109 -500 -7946 | -7151 233 -8988 | -894 | -1115 | -133 -701 | -3504 106 -1378 | -3484 -626 -8914 | 3142 210 -8313 | -3184 -466 | -2485 -720 | -1825 275 | -3101 394 | -717 45 | 1860 96 | -2405 359 | 1288 117 | -3220 -369 | -3066 -294 | -2911 -249 | 105 |
| 106(P) | -36 -149 -13 | -3301 -500 -7946 | -3024 233 -8988 | -1871 43 -894 | -4114 -381 -1115 | -3126 399 -701 | -1139 106 -1378 | -4916 -626 -8914 | -3129 210 -8308 | -4732 -466 | -4256 -720 | -3117 275 | 3925 394 | -3250 45 | -3218 96 | -3230 359 | -3395 117 | -4360 -369 | -3686 -294 | -3131 -249 | 106 |
| 107V | -2513 -149 -13 | -3472 -500 -7946 | -2885 233 -8988 | -3107 43 -894 | -3559 -381 -1115 | -3370 399 -701 | 2901 106 -1378 | -4726 -626 -8914 | -3042 210 -8304 | -1338 -466 | -1282 -720 | -4575 275 | -4662 394 | -4648 45 | -4859 96 | -4241 359 | -2447 117 | 3416 -369 | -4245 -294 | -3747 -249 | 107 |
| 108(I) | -3125 -149 -13 | -1784 -500 -7946 | -4073 233 -8988 | -3538 43 -894 | -1026 -381 -1115 | -3659 399 -701 | -4842 106 -1378 | 1787 -626 -8914 | -4726 210 -8299 | 1092 -466 | -254 -720 | -3185 275 | -3570 394 | -2750 45 | -2918 96 | -2809 359 | -1976 117 | 421 -369 | -2001 -294 | -1514 -249 | 108 |
| 109(F) | -2038 -149 -13 | -3927 -500 -7946 | -5139 233 -8988 | -5454 43 -894 | 4513 -381 -1115 | -4504 399 -701 | -2520 106 -1378 | -3938 -626 -8914 | -5326 210 -8295 | -3307 -466 | -3429 -720 | -4469 275 | -4782 394 | -4575 45 | -4818 96 | -4787 359 | -4810 117 | -4172 -369 | -1812 -294 | -736 -249 | 109 |
| 110(N | 2479 -149 -13 | -1867 -500 -7946 | -2193 233 -8988 | -2351 43 -894 | -4027 -381 -1115 | 1237 399 -701 | -2680 106 -1378 | -3819 -626 -8914 | -2833 210 -8290 | -4000 -466 | -3118 -720 | 2632 275 | -2690 394 | -2487 45 | -3076 96 | -1354 359 | -1567 117 | -2811 -369 | -4182 -294 | -3832 -249 | 110 |

TABLE 9-continued

| | | | | | | | | | | | | | | | | | |
|---|---|---|---|---|---|---|---|---|---|---|---|---|---|---|---|---|---|
| 111(Y) | −4612 −149 −13 | −3570 −500 −7946 | −5027 233 −8988 | −5365 43 −894 | 3457 −381 −1115 | −4900 399 −701 | −1135 106 −1378 | −3495 −626 −8914 | −4928 210 −8285 | −2816 −466 | −2906 −720 | −3544 275 | −4767 394 | −3678 45 | −4307 96 | −4162 359 | −4473 117 | −3659 −369 | −383 −294 | 3895 −249 | 111 |
| 112(H) | −4836 −149 −13 | −4275 −500 −7946 | −4356 233 −8989 | −4629 43 −894 | −3663 −381 −1115 | −4242 399 −701 | 5422 106 −1378 | −5932 −626 −8914 | −4492 210 −8281 | −5436 −466 | −5298 −720 | −4579 275 | −4696 394 | −4620 45 | −4352 96 | −5005 359 | −5030 117 | −5648 −369 | −3750 −294 | −3259 −249 | 112 |
| 113(G) | 1132 −149 −7946 | −1656 −500 −7946 | −3630 233 −8989 | −3843 43 −894 | −4215 −381 −1115 | 3045 399 −701 | −3388 106 −1378 | −4017 −626 −8914 | −3845 210 −8281 | −4265 −466 | −3324 −720 | −2567 275 | −2709 394 | −3385 45 | −3688 96 | 1328 359 | −1497 117 | −2799 −369 | −4429 −294 | −4315 −249 | 113 |
| 114(Y) | −4604 −149 −13 | −3569 −500 −7946 | −5020 233 −8989 | −5357 43 −894 | 2093 −381 −1115 | −4892 399 −701 | −1140 106 −1378 | −3492 −626 −8914 | −4921 210 −8276 | −2815 −466 | −2905 −720 | −3546 275 | −4764 394 | −3679 45 | −4305 96 | −4160 359 | −4468 117 | −3656 −369 | −389 −294 | 4550 −249 | 114 |
| 115(P) | 1686 −149 −13 | −1775 −500 −7946 | −1257 233 −8989 | 1192 43 −894 | −2259 −381 −1115 | −1996 399 −701 | −1137 106 −1378 | −1747 −626 −8914 | −939 210 −8271 | −2059 −466 | −1306 −720 | −1082 275 | 2013 394 | −833 45 | −1354 96 | −1109 359 | −1078 117 | 1053 −369 | −2490 −294 | −1979 −249 | 115 |
| 116(W) | −911 −149 −13 | −1979 −500 −7946 | 1204 233 −8989 | −354 43 −894 | −1971 −381 −1115 | −1917 399 −701 | 2044 106 −1378 | −1821 −626 −8914 | −260 210 −8267 | −1921 −466 | 2147 −720 | −627 275 | −2020 394 | 1682 45 | −714 96 | −875 359 | −851 117 | −1531 −369 | 3682 −294 | −1476 −249 | 116 |
| 117(D) | −1595 −149 −13 | −2205 −500 −7946 | 2386 233 −8989 | −1132 43 −894 | −2251 −381 −1115 | −2360 399 −701 | −1616 106 −1378 | −1668 −626 −8914 | −1672 210 −8262 | 1961 −466 | −1361 −720 | −1358 275 | −2717 394 | −1399 45 | −2106 96 | −1703 359 | 1087 117 | −1603 −369 | −2785 −294 | −2280 −249 | 117 |
| 118(I) | −2533 −149 −13 | −2040 −500 −7946 | −5154 233 −8989 | −4770 43 −894 | −2133 −381 −1115 | −4913 399 −701 | −4501 106 −1378 | 3201 −626 −8914 | −4662 210 −8257 | 936 −466 | −891 −720 | −4572 275 | −4602 394 | −4354 45 | −4667 96 | −4240 359 | −2507 117 | 1754 −369 | −3764 −294 | −3470 −249 | 118 |
| 119(H) | −1221 −149 −13 | −2591 −500 −7947 | −1040 233 −8989 | 1217 43 −894 | −2989 −381 −1115 | −2108 399 −701 | 3064 106 −1378 | −2676 −626 −8914 | 1463 210 −8253 | −2566 −466 | −1690 −720 | 1307 275 | −2192 394 | −200 45 | 1508 96 | −1095 359 | −1130 117 | −2261 −369 | −2664 −294 | −2094 −249 | 119 |
| 120(R) | 862 −149 −14 | −2187 −500 −7946 | −859 233 −8989 | −332 43 −894 | −2662 −381 −1115 | 770 399 −701 | −616 106 −1378 | −2382 −626 −8914 | −160 210 −8248 | −2365 −466 | −1469 −720 | −604 275 | −1998 394 | 1525 45 | 1934 96 | 922 359 | −871 117 | −1941 −369 | −2551 −294 | −1920 −249 | 120 |
| 121(L) | −3417 −149 −14 | −2857 −500 −7948 | −5787 233 −8990 | −5262 43 −894 | −1221 −381 −1115 | −5526 399 −701 | −4333 106 −1378 | 1616 −626 −8914 | −5024 210 −8244 | 2930 −466 | −11 −720 | −5255 275 | −4747 394 | −3973 45 | −4603 96 | −4899 359 | −3296 117 | −959 −369 | −2997 −294 | −3107 −249 | 121 |
| 122(T) | −1746 −149 −14 | −1500 −500 −7947 | −4034 233 −8989 | −3432 43 −894 | 1750 −381 −1115 | −3391 399 −701 | −2252 106 −1378 | 1561 −626 −8914 | −3078 210 −8238 | 1096 −466 | −52 −720 | −3017 275 | −3319 394 | −2616 45 | −2884 96 | −2508 359 | 2450 117 | −353 −369 | −1923 −294 | −1630 −249 | 122 |
| 123(Y) | −4607 −149 −14 | −3570 −500 −7947 | −5022 233 −8989 | −5359 43 −894 | 2289 −381 −1115 | −4894 399 −701 | −1139 106 −1378 | −3493 −626 −8914 | −4923 210 −8234 | −2816 −466 | −2907 −720 | −3546 275 | −4765 394 | −3679 45 | −4305 96 | −4161 359 | −4470 117 | −3658 −369 | −387 −294 | 4501 −249 | 123 |
| 124(D) | −1348 −149 −14 | −2787 −500 −7947 | 2242 233 −8989 | −415 43 −894 | −3129 −381 −1115 | −2090 399 −701 | 2199 106 −1378 | −2863 −626 −8914 | −263 210 −8229 | −2769 −466 | −1903 −720 | −717 275 | −2264 394 | 1787 45 | 2067 96 | −1197 359 | −1284 117 | −2435 −369 | −2889 −294 | −2250 −249 | 124 |
| 125(R) | −4488 −149 −14 | −4181 −500 −7947 | −4789 233 −8989 | −4318 43 −894 | −5193 −381 −1115 | −4148 399 −701 | −3436 106 −1378 | −5568 −626 −8914 | −2393 210 −8224 | −5152 −466 | −4748 −720 | −4156 275 | −4479 394 | −3286 45 | 4202 96 | −4614 359 | −4467 117 | −5273 −369 | −4267 −294 | −4649 −249 | 125 |
| 126(T) | −900 −149 −510 | −1750 −500 −7947 | −1012 233 −1783 | 977 43 −894 | −1985 −381 −1115 | 754 399 −701 | −770 106 −1378 | 1034 −626 −8914 | −516 210 −8214 | −1791 −466 | −1012 −720 | −790 275 | 1172 394 | −435 45 | −956 96 | −941 359 | 1779 117 | −1338 −369 | −2179 −294 | −1644 −249 | 126 |
| 127(N) | −1735 −149 −17 | −2957 −500 −7453 | −337 233 −8496 | −503 43 −894 | −3341 −381 −1115 | −2022 399 −258 | −1191 106 −2612 | −3403 −626 −8914 | −833 210 −8209 | −3305 −466 | −2603 −720 | 3506 275 | −2459 394 | 2336 45 | −1181 96 | −1571 359 | −1796 117 | −2939 −369 | −3255 −294 | −2559 −249 | 127 |

TABLE 9-continued

| | | | | | | | | | | | | | | | | | | | |
|---|---|---|---|---|---|---|---|---|---|---|---|---|---|---|---|---|---|---|---|
| 128(H) | −1956 −149 −14 | −3025 −500 −7947 | −776 233 −8989 | −1013 43 −894 | −3561 −381 −1115 | 1155 399 −701 | 4532 106 −1378 | −3890 −626 −8914 | −1721 210 −8205 | −3852 −466 | −3139 −720 | 1561 275 | −2848 394 | −1522 45 | −2169 96 | −1872 359 | −2130 117 | −3302 −369 | −3700 −294 | −2914 −249 | 128 |
| 129(D) | −1326 −149 −14 | −2680 −500 −7947 | 2762 233 −8989 | −433 43 −894 | −3190 −381 −1115 | 751 399 −701 | −1003 106 −1378 | −2946 −626 −8914 | −718 210 −8200 | −2918 −466 | −2057 −720 | −743 275 | −2295 394 | −594 45 | 1178 96 | −1205 359 | 1254 117 | −2474 −369 | −3108 −294 | −2410 −249 | 129 |
| 130(N) | −1803 −149 −14 | −2774 −500 −7947 | −1319 233 −8989 | −1257 43 −894 | −3841 −381 −1115 | 1092 399 −701 | −1554 106 −1378 | −3580 −626 −8914 | −862 210 −8195 | −3494 −466 | −2719 −720 | 3434 275 | −2788 394 | −1187 45 | 1621 96 | −1770 359 | −1905 117 | −3037 −369 | −3520 −294 | −3054 −249 | 130 |
| 131(L) | −2659 −149 −14 | −2243 −500 −7947 | −5081 233 −8989 | −4521 43 −894 | 1845 −381 −1115 | −4592 399 −701 | −3494 106 −1378 | 1459 −626 −8914 | −4246 210 −8190 | 2227 −466 | −106 −720 | −4254 275 | −4217 394 | −3540 45 | −3970 96 | −3797 359 | −2575 117 | 1425 −369 | −2707 −294 | −2618 −249 | 131 |
| 132(H) | −1265 −149 −14 | −1465 −500 −7947 | −2433 233 −8989 | −2035 43 −894 | −1445 −381 −1115 | −2449 399 −701 | 3775 106 −1378 | 1372 −626 −8914 | −1614 210 −8185 | −1394 −466 | −839 −720 | −1901 275 | −2701 394 | −1628 45 | −1732 96 | −1623 359 | 2191 117 | −807 −369 | −1952 −294 | −1432 −249 | 132 |
| 133(V) | −2378 −149 −14 | −2013 −500 −7947 | −4879 233 −8989 | −4522 43 −894 | −2020 −381 −1115 | −4336 399 −701 | −3971 106 −1378 | 321 −626 −8914 | −4271 210 −8180 | −861 −466 | 2587 −720 | −4174 275 | −4288 394 | −3996 45 | −4221 96 | −3659 359 | −2396 117 | 3344 −369 | −3447 −294 | −3110 −249 | 133 |
| 134(H) | −1298 −149 −14 | −2431 −500 −7947 | −1191 233 −8989 | 1210 43 −894 | −2723 −381 −1115 | −2201 399 −701 | 3201 106 −1378 | −2373 −626 −8914 | −8180 | −2378 −466 | −1563 −720 | −884 275 | −2290 394 | −333 45 | 2092 96 | −1222 359 | −1207 117 | 912 −369 | −2555 −294 | −2032 −249 | 134 |
| 135(G) | −4088 −149 −14 | −3924 −500 −7947 | −4774 233 −8989 | −5139 43 −894 | −5615 −381 −1115 | 3825 399 −701 | −4753 106 −1378 | −6303 −626 −8914 | −5453 210 −8175 | −6014 −466 | −5662 −720 | −4812 275 | −4539 394 | −5232 45 | −5106 96 | −4370 359 | −4472 117 | −5527 −369 | −4696 −294 | −5561 −249 | 135 |
| 136(Y) | −4791 −149 −14 | −3935 −500 −7947 | −4914 233 −8989 | −5231 43 −894 | −815 −381 −1115 | −4530 399 −701 | −2178 106 −1378 | −4357 −626 −8914 | −5024 210 −8170 | −3745 −466 | −3807 −720 | −4206 275 | −4772 394 | −4328 45 | −4584 96 | −4677 359 | −4837 117 | −4435 −369 | −1477 −294 | 4857 −249 | 136 |
| 137(R) | −2010 −149 −14 | −3025 −500 −7947 | −2206 233 −8989 | −1337 43 −894 | −3603 −381 −1115 | −2773 399 −701 | −965 106 −1378 | −3110 −626 −8914 | 2304 210 −8165 | −2910 −466 | 2165 −720 | 1370 275 | −2777 394 | −536 45 | 2519 96 | −1900 359 | −1822 117 | −2804 −369 | −2890 −294 | −2581 −249 | 137 |
| 138(E) | −4205 −149 −14 | −4417 −500 −7947 | −2343 233 −8989 | 3901 43 −894 | −5349 −381 −1115 | −3698 399 −701 | −3534 106 −1378 | −5837 −626 −8914 | −3838 210 −8160 | −5561 −466 | −5237 −720 | −3039 275 | −4218 394 | −3453 45 | −4201 96 | −4072 359 | −4352 117 | −5409 −369 | −4640 −294 | −4860 −249 | 138 |
| 139(E) | −1541 −149 −14 | −3143 −500 −7947 | 1571 233 −8989 | 2510 43 −894 | −3425 −381 −1115 | −2060 399 −701 | −1020 106 −1378 | −3219 −626 −8914 | 1175 210 −8155 | −3136 −466 | −2281 −720 | −669 275 | −2361 394 | 1840 45 | −1368 96 | −1340 359 | −1518 117 | −2751 −369 | −3304 −294 | −2529 −249 | 139 |
| 140(G) | −4088 −149 −14 | −3924 −500 −7947 | −4774 233 −8989 | −5139 43 −894 | −5615 −381 −1115 | 3825 399 −701 | −4753 106 −1378 | −6303 −626 −8914 | −5453 210 −8150 | −6014 −466 | −5662 −720 | −4812 275 | −4539 394 | −5232 45 | −5106 96 | −4370 359 | −4472 117 | −5527 −369 | −4696 −294 | −5561 −249 | 140 |
| 141(T) | −1448 −149 −14 | −2786 −500 −7947 | 1566 233 −8989 | 494 43 −894 | −3406 −381 −1115 | −2031 399 −701 | −1186 106 −1378 | −3187 −626 −8914 | −1023 210 −8145 | −3164 −466 | −2316 −720 | 1513 275 | −2396 394 | −794 45 | −1603 96 | 1061 359 | 2567 117 | −2675 −369 | −3364 −294 | −2628 −249 | 141 |
| 142(I) | −1880 −149 −14 | −1845 −500 −7947 | −4196 233 −8989 | −3993 43 −894 | −2337 −381 −1115 | −3273 399 −701 | −3434 106 −1378 | 2845 −626 −8914 | −3687 210 −8140 | −1437 −466 | −1287 −720 | −3407 275 | −3652 394 | −3527 45 | −3649 96 | −2612 359 | 2766 117 | 19 −369 | −3410 −294 | −3029 −249 | 142 |
| 143(T) | −1427 −149 −14 | −2097 −500 −7947 | −2121 233 −8989 | −2355 43 −894 | −3933 −381 −1115 | −2165 399 −701 | −2713 106 −1378 | −3790 −626 −8914 | −2759 210 −8134 | −4026 −466 | −3246 −720 | 1603 275 | −2869 394 | −2560 45 | −2943 96 | −1604 359 | 3622 117 | −2931 −369 | −4094 −294 | −3692 −249 | 143 |
| 144(T) | −2430 −149 −14 | −2823 −500 −7947 | −4179 233 −8989 | −4462 43 −894 | −4591 −381 −1115 | −3027 399 −701 | −4037 106 −1378 | −4454 −626 −8914 | −4406 210 −8124 | −4707 −466 | −4191 −720 | −3664 275 | −3724 394 | −4237 45 | −4215 96 | −2689 359 | 4010 117 | −3747 −369 | −4431 −294 | −4588 −249 | 144 |

TABLE 9-continued

| | | | | | | | | | | | | | | | | | | |
|---|---|---|---|---|---|---|---|---|---|---|---|---|---|---|---|---|---|---|
| 145(P) | -1505 -149 -14 | -2080 -500 -7947 | -3392 233 -8989 | -3633 43 -894 | -4254 -381 -1115 | -2301 399 -701 | -3425 106 -1378 | -4043 -626 -8914 | -3658 210 -8119 | -4296 -466 | -3530 -720 | -2794 275 | 3850 394 | -3427 45 | -3585 96 | -1744 359 | 1558 117 | -3083 -369 | -4340 -294 | -4254 -249 | 145 |
| 146(F) | -3994 -149 -14 | -3227 -500 -7947 | -4915 233 -8989 | -5043 43 -894 | 3832 -381 -1115 | -4698 399 -701 | -1205 106 -1378 | -2713 -626 -8914 | -4616 210 -8114 | -2132 -466 | 2459 -720 | -3492 275 | -4563 394 | -3530 45 | -4094 96 | -3916 359 | -3878 117 | -2950 -369 | -467 -294 | 2613 -249 | 146 |
| 147(D) | -2625 -149 -14 | -4424 -500 -7947 | 3697 233 -8989 | -649 43 -894 | -4717 -381 -1115 | -2403 399 -701 | -1898 106 -1378 | -4810 -626 -8914 | -2318 210 -8109 | -4653 -466 | -4097 -720 | 1859 275 | -2997 394 | -1605 45 | -3282 96 | -2269 359 | -2750 117 | -4226 -369 | -4723 -294 | -3698 -249 | 147 |
| 148(M) | -3455 -149 -14 | -2954 -500 -7947 | -5636 233 -8989 | -5138 43 -894 | -1157 -381 -1115 | -5278 399 -701 | -4061 106 -1378 | -621 -626 -8914 | -4736 210 -8103 | 1276 -466 | 4790 -720 | -5054 275 | -4653 394 | -3832 45 | -4350 96 | -4674 359 | -3346 117 | -1354 -369 | -2859 -294 | -2873 -249 | 148 |
| 149(M) | 737 -149 -14 | -1039 -500 -7947 | -2128 233 -8989 | -1551 43 -894 | -1071 -381 -1115 | -2251 399 -701 | -1108 106 -1378 | -553 -626 -8914 | -1284 210 -8098 | -925 -466 | 2340 -720 | -1505 275 | -2347 394 | -1148 45 | 1957 96 | -1292 359 | 992 117 | 1190 -369 | -1511 -294 | -1125 -249 | 149 |
| 150(V) | -1589 -149 -14 | -1340 -500 -7947 | -3842 233 -8989 | -3261 43 -894 | -1369 -381 -1115 | -3310 399 -701 | -2277 106 -1378 | 1533 -626 -8914 | -2856 210 -8093 | -783 -466 | 2491 -720 | -2892 275 | -3292 394 | -2604 45 | 1266 96 | -2434 359 | -1540 117 | 2552 -369 | -2138 -294 | -1796 -249 | 150 |
| 151(C) | -948 -149 -14 | 2699 -500 -7947 | -2923 233 -8989 | -2314 43 -894 | -734 -381 -1115 | -2453 399 -701 | -1287 106 -1378 | -272 -626 -8914 | -1969 210 -8087 | 629 -466 | -6 -720 | -1970 275 | -2503 394 | 2182 45 | -1898 96 | -1524 359 | -890 117 | 1281 -369 | -1253 -294 | 1875 -249 | 151 |
| 152(N) | -1513 -149 -14 | -2274 -500 -7947 | -1534 233 -8989 | -1835 43 -894 | -4051 -381 -1115 | -2147 399 -701 | -2506 106 -1378 | -4137 -626 -8914 | -2664 210 -8082 | -4241 -466 | -3442 -720 | 3900 275 | -2843 394 | -2309 45 | -3007 96 | 1223 359 | -1886 117 | -3166 -369 | -4207 -294 | -3653 -249 | 152 |
| 153(Q) | -1078 -149 -14 | -2597 -500 -7947 | 1398 233 -8989 | 1298 43 -894 | -2904 -381 -1115 | 570 399 -701 | -660 106 -1378 | -2670 -626 -8914 | 1137 210 -8077 | -2607 -466 | -1702 -720 | 1544 275 | -2056 394 | 1583 45 | -856 96 | -929 359 | -1031 117 | -2214 -369 | -2776 -294 | -2059 -249 | 153 |
| 154(M) | -2272 -149 -14 | -1957 -500 -7947 | -4590 233 -8989 | -3986 43 -894 | -1077 -381 -1115 | -4004 399 -701 | -2865 106 -1378 | 1417 -626 -8914 | -3652 210 -8071 | 2191 -466 | 2665 -720 | -3646 275 | -3782 394 | -3053 45 | -3407 96 | -3149 359 | 1251 117 | -644 -369 | -2313 -294 | -2179 -249 | 154 |
| 155(D) | -2253 -149 -14 | -3537 -500 -7947 | 3692 233 -8989 | -855 43 -894 | -4532 -381 -1115 | -2333 399 -701 | -2017 106 -1378 | -4569 -626 -8914 | -2396 210 -8066 | -4510 -466 | -3868 -720 | -1194 275 | -2951 394 | -1735 45 | -3232 96 | 1151 359 | -2470 117 | -3856 -369 | -4577 -294 | -3695 -249 | 155 |
| 156(R) | -4488 -149 -14 | -4181 -500 -7947 | -4789 233 -8989 | -4318 43 -894 | -5193 -381 -1115 | -4148 399 -701 | -3436 106 -1378 | -5568 -626 -8914 | -2393 210 -8061 | -5152 -466 | -4748 -720 | -4156 275 | -4479 394 | -3286 45 | 4202 96 | -4614 359 | -4467 117 | -5273 -369 | -4267 -294 | -4649 -249 | 156 |
| 157(F) | -4608 -149 -14 | -3568 -500 -7947 | -5026 233 -8989 | -5363 43 -894 | 3806 -381 -1115 | -4898 399 -701 | -1136 106 -1378 | -3489 -626 -8914 | -4926 210 -8055 | -2811 -466 | -2901 -720 | -3545 275 | -4766 394 | -3678 45 | -4306 96 | -4161 359 | -4469 117 | -3654 -369 | -384 -294 | 3465 -249 | 157 |
| 158(H) | 1044 -149 -14 | -2139 -500 -7947 | -1080 233 -8989 | -861 43 -894 | -3017 -381 -1115 | -1958 399 -701 | 3956 106 -1378 | -2774 -626 -8914 | -984 210 -8050 | -2841 -466 | -1992 -720 | 1421 275 | -2333 394 | -887 45 | -1434 96 | 909 359 | -1252 117 | -2260 -369 | -3059 -294 | -2457 -249 | 158 |
| 159(L) | -1995 -149 -14 | -1713 -500 -7947 | -4228 233 -8989 | -3647 43 -894 | -1208 -381 -1115 | -3730 399 -701 | -2645 106 -1378 | 1439 -626 -8914 | -3309 210 -8050 | 2122 -466 | -164 -720 | -3321 275 | -3602 394 | 1641 45 | -3161 96 | -2864 359 | -1930 117 | 1443 -369 | -2284 -294 | -2058 -249 | 159 |
| 160(A) | 2383 -149 14 | -1556 -500 -7947 | -2401 233 -8989 | -2072 43 -894 | -2208 -381 -1115 | -2210 399 -701 | -1881 106 -1378 | -1266 -626 -8914 | -1832 210 -8039 | -1939 -466 | -1334 -720 | -1898 275 | -2639 394 | 1793 45 | -2020 96 | -1435 359 | -1318 117 | 1882 -369 | -2638 -294 | -2245 -249 | 160 |
| 161(I) | 855 -149 -14 | -2283 -500 -7947 | -1296 233 -8989 | -661 43 -894 | -2565 -381 -1115 | -2186 399 -701 | -701 106 -1378 | 1827 -626 -8914 | 1284 210 -8033 | -2220 -466 | -1411 -720 | -884 275 | -2249 394 | 1555 45 | 1499 96 | -1169 359 | -1126 117 | -1886 -369 | -2436 -294 | -1937 -249 | 161 |

TABLE 9-continued

| | | | | | | | | | | | | | | | | |
|---|---|---|---|---|---|---|---|---|---|---|---|---|---|---|---|---|
| 162(D) — — | -1082 -149 -14 | -2449 -500 -7947 | 2531 233 -8989 | -267 43 -894 | -2754 -381 -1115 | -1915 399 -701 | -698 106 -1378 | -2479 -626 -8914 | 1332 210 -8028 | -2474 -466 | 2209 -720 | -579 275 | -2090 394 | -271 45 | -827 96 | 743 359 | -1039 117 | -2075 -369 | -2684 -294 | -2016 -249 | 162 |
| 163(V — — | 2572 -149 -14 | -1717 -500 -7947 | -4125 233 -8989 | -4110 43 -894 | -2971 -381 -1115 | -2517 399 -701 | -3473 106 -1378 | -716 -626 -8914 | -3875 210 -8022 | -2280 -466 | -1954 -720 | -3032 275 | -3163 394 | -3569 45 | -3746 96 | -1871 359 | -1754 117 | 2604 -369 | -3798 -294 | -3481 -249 | 163 |
| 164(M — — | -2861 -149 -14 | -2402 -500 -7947 | -5299 233 -8989 | -4748 43 -894 | -1283 -381 -1115 | -4880 399 -701 | -3804 106 -1378 | 1499 -626 -8914 | -4501 210 -8017 | 2317 -466 | 2674 -720 | -4552 275 | -4398 394 | -3712 45 | -4200 96 | -4119 359 | -2770 117 | 1228 -369 | -2863 -294 | -2864 -249 | 164 |
| 165(Q — — | -2277 -149 -14 | -4157 -500 -7947 | 2369 233 -8989 | 2212 43 -894 | -4337 -381 -1115 | -2257 399 -701 | -1565 106 -1378 | -4246 -626 -8914 | -1745 210 -8011 | -4116 -466 | -3418 -720 | -845 275 | -2768 394 | 2820 45 | -2553 96 | -1949 359 | -2331 117 | -3727 -369 | -4303 -294 | -3315 -249 | 165 |
| 166(W — — | -895 -149 -14 | -1130 -500 -7947 | -1817 233 -8989 | -1235 43 -894 | -1105 -381 -1115 | -2196 399 -701 | 2271 106 -1378 | -700 -626 -8914 | -958 210 -8006 | 627 -466 | -314 -720 | 1121 275 | -2263 394 | -882 45 | 1030 96 | -1203 359 | -832 117 | 1095 -369 | 2753 -294 | -1082 -249 | 166 |
| 167(L) — — | 894 -149 -14 | -1665 -500 -7947 | -4454 233 -8989 | -3932 43 -894 | -1615 -381 -1115 | -3916 399 -701 | -3023 106 -1378 | 1762 -626 -8914 | -3653 210 -8000 | 2037 -466 | -555 -720 | -3565 275 | -3811 394 | -3286 45 | -3532 96 | -3090 359 | -1967 117 | 1475 -369 | -2679 -294 | -2377 -249 | 167 |
| 168(P) — — | -1358 -149 -14 | -1915 -500 -7947 | 1378 233 -8990 | -983 43 -894 | -1290 -381 -1115 | -2313 399 -701 | -1059 106 -1378 | -1560 -626 -8914 | -1164 210 -7994 | 599 -466 | -1093 -720 | -1181 275 | 2573 394 | -988 45 | -1557 96 | -1458 359 | -1325 117 | -1413 -369 | -1772 -294 | 2001 -249 | 168 |
| 169(H — — | 835 -149 -14 | -2044 -500 -7947 | -983 233 -8990 | -412 43 -894 | -2272 -381 -1115 | -1961 399 -701 | 2288 106 -1378 | -1925 -626 -8914 | -107 210 -7989 | -2006 -466 | -1181 -720 | -671 275 | -2047 394 | 2276 45 | 1159 96 | -910 359 | -883 117 | 818 -369 | -2280 -294 | -1718 -249 | 169 |
| 170(N — — | -2018 -149 -14 | -3288 -500 -7947 | 1710 233 -8990 | -611 43 -894 | -3318 -381 -1115 | -2277 399 -701 | -1523 106 -1378 | -3152 -626 -8914 | -1621 210 -7983 | 1866 -466 | -2576 -720 | 2651 275 | -2730 394 | -1220 45 | -2271 96 | -1839 359 | -2066 117 | -2863 -369 | -3553 -294 | -2765 -249 | 170 |
| 171(R — — | -1939 -149 -14 | -2994 -500 -7947 | -2042 233 -8990 | -1272 43 -894 | -3636 -381 -1115 | 697 399 -701 | -982 106 -1378 | -3164 -626 -8914 | 2274 210 -7977 | -2958 -466 | -2181 -720 | -1388 275 | 1383 394 | -551 45 | 2420 96 | -1831 359 | -1784 117 | -2823 -369 | -2935 -294 | -2603 -249 | 171 |
| 172(Y — — | -813 -149 -14 | -1780 -500 -7947 | -908 233 -8990 | -364 43 -894 | -1941 -381 -1115 | 446 399 -701 | -570 106 -1378 | -1583 -626 -8914 | 1228 210 -7972 | -1731 -466 | -928 -720 | 1199 275 | -1968 394 | -200 45 | -701 96 | -813 359 | 1109 117 | 664 -369 | -2082 -294 | 1675 -249 | 172 |
| 173(V — — | 1834 -149 -14 | -1515 -500 -7947 | -2997 233 -8990 | -2525 43 -894 | -2124 -381 -1115 | -2365 399 -701 | -2002 106 -1378 | -972 -626 -8914 | -1828 210 -7966 | -1816 -466 | -1242 -720 | -2181 275 | -2772 394 | -1966 45 | 1207 96 | -1599 359 | -1390 117 | 2598 -369 | -2580 -294 | -2228 -249 | 173 |
| 174(N — — | 2098 -149 -26 | -1102 -500 -6760 | -662 233 -7802 | -657 43 -894 | -2411 -381 -1115 | -1122 399 -701 | -1037 106 -1378 | -2101 -626 -8914 | -916 210 -7960 | -2331 -466 | -1548 -720 | 2678 275 | -1684 394 | -766 45 | -1264 96 | -457 359 | -604 117 | -1513 -369 | -2576 -294 | -2066 -249 | 174 |
| 175(Q — — | -711 -149 -26 | -1121 -500 -6760 | -1177 233 -7802 | -831 43 -894 | -1223 -381 -1115 | -1760 399 -701 | -770 106 -1378 | -238 -626 -8914 | -424 210 -7954 | -821 -466 | -384 -720 | -912 275 | -1989 394 | 2576 45 | -639 96 | -946 359 | -736 117 | 2065 -369 | -1698 -294 | -1211 -249 | 175 |
| 176(N — — | -707 -149 -26 | -1550 -500 -6760 | -295 233 -7802 | -469 43 -894 | -2833 -381 -1115 | 2212 399 -701 | -1124 106 -1378 | -2747 -626 -8914 | -1097 210 -7948 | -2834 -466 | -2065 -720 | 2825 275 | -1857 394 | -854 45 | -1516 96 | -754 359 | -965 117 | -2073 -369 | -2881 -294 | -2341 -249 | 176 |
| 177(L) — — | -1446 -149 -686 | -1261 -500 -6760 | -2639 233 -1453 | -2396 43 -894 | -166 -381 -1115 | -2529 399 -2557 | -1687 106 -269 | 443 -626 -8914 | -1969 210 -7943 | 2652 -466 | 716 -720 | -2264 275 | -2607 394 | -1810 45 | -1925 96 | -2083 359 | -1460 117 | 71 -369 | -1338 -294 | -963 -249 | 177 |
| 178(C — — | 1406 -149 -37 | 3275 -500 -6111 | -7153 233 -7153 | -2171 43 -894 | -2790 -381 -1115 | 2067 399 -435 | -1941 106 -1965 | -2431 -626 -8914 | -1828 210 -7937 | -2675 -466 | -1880 -720 | -1777 275 | -2338 394 | -1781 45 | 1478 96 | -1008 359 | -1091 117 | -1870 -369 | -3029 -294 | -2681 -249 | 178 |

TABLE 9-continued

| | | | | | | | | | | | | | | | | | | | | | |
|---|---|---|---|---|---|---|---|---|---|---|---|---|---|---|---|---|---|---|---|---|---|
| 179(N) | 1616 | -1783 | -884 | -388 | -2121 | -1793 | -600 | -1720 | 1446 | -1882 | -1075 | 1636 | -1951 | -220 | -618 | -795 | -775 | 841 | -2206 | -1651 | 179 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7695 | -8737 | -894 | -1115 | -701 | -1378 | -8914 | -7931 | | | | | | | | | | | | |
| 180(H) | 826 | -2030 | 1249 | -286 | -2281 | -1850 | -2187 | -1963 | -256 | -2046 | 2137 | -570 | -1980 | -190 | -741 | 713 | -829 | -1630 | -2333 | -1721 | 180 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7925 | | | | | | | | | | | | |
| 181(L) | -1888 | -1658 | -4011 | -3398 | 1778 | -3497 | -2279 | 1355 | 1112 | 2128 | -19 | -3057 | -3387 | -2573 | -2834 | -2608 | -1812 | -657 | -1938 | -1655 | 181 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7919 | | | | | | | | | | | | |
| 182(C) | -1582 | 2847 | -3677 | -3112 | -1572 | -3286 | -2308 | 2397 | 1781 | -1057 | -639 | -2820 | -3303 | -2550 | -2691 | -2415 | -1546 | 1459 | -2297 | -1922 | 182 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7913 | | | | | | | | | | | | |
| 183(Q) | 889 | -2895 | 1501 | 1223 | -3185 | -1975 | -867 | -2968 | -610 | -2899 | -2019 | 1640 | -2225 | 2395 | -1182 | -1154 | -1298 | -2505 | -3073 | -2320 | 183 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7907 | | | | | | | | | | | | |
| 184(M) | 624 | -2075 | -807 | 1189 | -2318 | -1853 | -499 | -2000 | 1304 | 56 | 1892 | -530 | -1940 | -75 | 1281 | -778 | -783 | -1655 | -2297 | -1689 | 184 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7901 | | | | | | | | | | | | |
| 185(M) | -2863 | -2466 | -4981 | -4452 | -787 | -4528 | -2772 | -688 | -4077 | 1881 | 3969 | -4038 | -4163 | -3323 | -3759 | -3712 | -2755 | -1286 | -2008 | 2156 | 185 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7895 | | | | | | | | | | | | |
| 186(N) | 889 | -2816 | 1294 | -278 | -3142 | -1979 | -855 | -2912 | 2030 | -2849 | -1972 | 2349 | -2220 | -431 | -1093 | -1140 | -1272 | -2455 | -3022 | -2293 | 186 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7889 | | | | | | | | | | | | |
| 187(W) | -912 | -2365 | 1857 | 1258 | -2669 | -1819 | -525 | -2416 | -128 | -2373 | -1466 | -456 | -1946 | -77 | 1280 | 718 | -855 | -1981 | 2923 | -1868 | 187 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7883 | | | | | | | | | | | | |
| 188(K) | -1038 | -1343 | -1852 | -1266 | 1554 | -2283 | -1007 | -874 | 2350 | -1087 | 2145 | -1336 | -2361 | -894 | -1097 | -1304 | 1178 | -773 | -1689 | -1243 | 188 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7877 | | | | | | | | | | | | |
| 189(L) | -2298 | -2730 | -2950 | -2003 | -2607 | -3127 | -1308 | -2182 | -152 | 2394 | -1514 | -1955 | -3117 | 1691 | 1757 | -2379 | -2109 | -2248 | -2689 | -2425 | 189 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7870 | | | | | | | | | | | | |
| 190(V) | -1079 | -1178 | -2219 | 953 | -1217 | -2479 | -1279 | 1243 | 1083 | 512 | -362 | -1650 | -2531 | -1279 | -1608 | -1507 | -1021 | 1902 | -1713 | -1318 | 190 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7864 | | | | | | | | | | | | |
| 191(E) | -1354 | -2910 | 1356 | 2455 | -3203 | -1991 | -882 | -2982 | 1322 | -2913 | -2038 | -608 | -2244 | -460 | -1170 | -1178 | 1230 | -2523 | -3086 | -2339 | 191 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7858 | | | | | | | | | | | | |
| 192(H) | 995 | 2611 | -2882 | -2350 | -1156 | -2330 | 3755 | 1388 | -2017 | -1028 | -400 | -2003 | -2551 | -1787 | -2019 | -1469 | -1023 | -451 | -1652 | -1275 | 192 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7852 | | | | | | | | | | | | |
| 193(F) | -873 | -2098 | -751 | 1196 | 2231 | -1853 | -534 | -2026 | -137 | -2078 | -1223 | 1242 | -1958 | -115 | 1091 | -800 | 953 | -1680 | -2329 | -1708 | 193 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7845 | | | | | | | | | | | | |
| 194(Q) | 684 | -2845 | -419 | 1349 | -3160 | -1991 | -875 | -2930 | -582 | -2870 | -1997 | 2370 | -2238 | 2528 | -1121 | -1166 | -1300 | -2477 | -3045 | -2315 | 194 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7839 | | | | | | | | | | | | |
| 195(Y) | -3797 | -3103 | -4834 | -4924 | 2259 | -4579 | -1182 | -2596 | -4505 | -2328 | -2267 | -3426 | -4481 | -3479 | -4016 | -3789 | -3700 | 1231 | 456 | 4130 | 195 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8990 | -894 | -1115 | -701 | -1378 | -8914 | -7833 | | | | | | | | | | | | |

TABLE 9-continued

| | | | | | | | | | | | | | | | | | | | |
|---|---|---|---|---|---|---|---|---|---|---|---|---|---|---|---|---|---|---|---|
| 196(I) | 1842 | −1480 | −3746 | −3421 | −2131 | −2613 | −2685 | 2759 | −3142 | −1622 | −1194 | −2759 | −3062 | −2873 | −3093 | −1882 | 1362 | −243 | −2830 | −2485 | 196 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8990 | −894 | −1115 | −701 | −1378 | −8914 | −7827 | | | | | | | | | | | |
| 197(C | −917 | 2447 | −2927 | −2307 | −742 | −2421 | −1266 | −267 | −1915 | −627 | 2390 | −1950 | −2475 | −1643 | 1928 | −1495 | −858 | 1278 | −1243 | 1688 | 197 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8990 | −894 | −1115 | −701 | −1378 | −8914 | −7820 | | | | | | | | | | | |
| 198(E) | −2062 | −3846 | 1749 | 2650 | −4068 | −2200 | −1423 | −3938 | −1496 | −3829 | −3070 | 1774 | −2658 | −1061 | −2241 | 835 | −2093 | −3434 | −4016 | −3094 | 198 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8990 | −894 | −1115 | −701 | −1378 | −8914 | −7814 | | | | | | | | | | | |
| 199(H | −1285 | −2612 | −523 | 1316 | −2833 | −2011 | 3126 | −2579 | −558 | −2606 | −1772 | 2447 | −2236 | −462 | −1057 | −1160 | −1248 | 676 | −2824 | −2144 | 199 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8990 | −894 | −1115 | −701 | −1378 | −8914 | −7807 | | | | | | | | | | | |
| 200(G | −2654 | −3212 | −2507 | −2588 | −4732 | 3403 | −2707 | −4668 | 1545 | −4548 | −3892 | −2604 | −3567 | −2456 | −2072 | −2733 | −2883 | −4011 | −4170 | −4141 | 200 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8990 | −894 | −1115 | −701 | −1378 | −8914 | −7801 | | | | | | | | | | | |
| 201(Y | −818 | −1798 | 1165 | 976 | −1948 | −1871 | −567 | 748 | −261 | −1738 | −935 | −608 | −1966 | 1445 | −722 | −813 | −758 | 820 | −2091 | 1672 | 201 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8990 | −894 | −1115 | −701 | −1378 | −8914 | −7794 | | | | | | | | | | | |
| 202(D | −4232 | −4465 | 4158 | −2649 | −5412 | −3676 | −3575 | −6036 | −4125 | −5722 | −5419 | −2993 | −4216 | −3512 | −4617 | −4077 | −4401 | −5553 | −4696 | −4914 | 202 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8990 | −894 | −1115 | −701 | −1378 | −8914 | −7788 | | | | | | | | | | | |
| 203(M | −2141 | −1848 | −4423 | −3825 | −1086 | −3850 | −2726 | 2359 | −3484 | 1059 | 3290 | −3479 | 1362 | −2946 | −3270 | −2988 | −2066 | −538 | −2251 | −2080 | 203 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8990 | −894 | −1115 | −701 | −1378 | −8914 | −7781 | | | | | | | | | | | |
| 204(P | −4497 | −4117 | −4899 | −5251 | −5560 | −4139 | −4798 | −6328 | −5454 | −5976 | −5741 | −5026 | 4302 | −5328 | −5104 | −4798 | −4844 | −5739 | −4665 | −5484 | 204 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8990 | −894 | −1115 | −701 | −1378 | −8914 | −7775 | | | | | | | | | | | |
| 205(E) | −2636 | −4572 | 1810 | 3431 | −4760 | −2390 | −1841 | −4772 | −2235 | −4607 | −4040 | −995 | −2973 | −1537 | −3199 | −2253 | −2735 | −4218 | −4733 | −3691 | 205 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8990 | −894 | −1115 | −701 | −1378 | −8914 | −7768 | | | | | | | | | | | |
| 206(I | −2944 | −2476 | −5069 | −4784 | 2837 | −4680 | −2731 | 3180 | −4519 | −584 | −703 | −4172 | −4449 | −3817 | −4249 | −3998 | −2901 | −494 | −1967 | −1074 | 206 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8990 | −894 | −1115 | −701 | −1378 | −8914 | −7762 | | | | | | | | | | | |
| 207(T) | −1149 | −1001 | −3245 | −2651 | −830 | −2680 | −1537 | −200 | −2295 | 678 | −115 | −2252 | −2729 | −1967 | −2187 | −1772 | 2521 | 1202 | −1425 | 1941 | 207 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8991 | −894 | −1115 | −701 | −1378 | −8914 | −7755 | | | | | | | | | | | |
| 208(N | 968 | −3781 | 2422 | 1475 | −4014 | −2190 | −1399 | −3875 | −1453 | −3773 | −3006 | 2431 | −2639 | −1035 | −2184 | −1745 | −2052 | −3376 | −3962 | −3054 | 208 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8991 | −894 | −1115 | −701 | −1378 | −8914 | −7748 | | | | | | | | | | | |
| 209(W | 1214 | −2627 | −4165 | −4274 | −2248 | −2999 | −2977 | −3589 | −3845 | −3575 | −3208 | −3402 | −3626 | −3726 | −3688 | −2549 | −2659 | −3197 | 5855 | −1919 | 209 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8991 | −894 | −1115 | −701 | −1378 | −8914 | −7741 | | | | | | | | | | | |
| 210(V | −1358 | −2495 | −1397 | −737 | −2853 | −2276 | −735 | −2472 | 1340 | −2436 | −1616 | −951 | 1242 | 1587 | 1414 | −1276 | −1250 | 1808 | −2580 | −2097 | 210 |
| | −149 | −500 | 233 | 43 | −381 | 399 | 106 | −626 | 210 | −466 | −720 | 275 | 394 | 45 | 96 | 359 | 117 | −369 | −294 | −249 |
| | −15 | −7948 | −8991 | −894 | −1115 | −701 | −1378 | −8914 | −7735 | | | | | | | | | | | |
| 211(W | −3498 | −2927 | −4676 | −4658 | 236 | 4377 | −1183 | −2501 | −4186 | −2296 | −2147 | −3324 | −4322 | −3336 | −3785 | −3580 | −3418 | 1241 | 5352 | 2614 | 211 |
| | −149 | −500 | 233 | 43 | −381 | 399 | 106 | −626 | 210 | −466 | −720 | 275 | 394 | 45 | 96 | 359 | 117 | −369 | −294 | −249 |
| | −16 | −7949 | −8991 | −894 | −1115 | −701 | −1378 | −8914 | −7728 | | | | | | | | | | | |
| 212(H | −955 | −1646 | −1373 | −926 | 1547 | 635 | 2162 | −1632 | −859 | −1839 | −1087 | −1075 | 2103 | −763 | −1254 | 967 | −989 | −1372 | −2122 | −1543 | 212 |
| | * | * | * | * | * | * | * | * | 0 | * | * | * | * | * | * | * | * | * | * | * |
| | * | * | * | * | * | * | * | −8914 | | | | | | | | | | | | |

TABLE 14

```
HMMER2.0 [2.2g]
NAME PTA_PTB_exp_seqs
LENG 355
ALPH Amino
RF no
CS no
MAP yes
COM /app/public/hmmer/current/bin/hmmbuild PTA_exp_hmm PTA_PTB_exp_seqs.aln
COM /app/public/hmmer/current/bin/hmmcalibrate PTA_exp_hmm
NSEQ 10
DATE Mon Nov 30 18:53:24 2009
CKSUM 2317
XT  -8455  -4  -1000  -1000  -8455  -4  -8455  -4
NULT  -4  -8455
NULE  595  -1558  85  338  -294  453  -1158  197  249  902  -1085  -142  -21  -313  45  531  201  384  -1998  -644
EVD  -321.869965  0.133020
```

| HMM | A m->m | C m->i | D m->d | E i->m | F i->i | G d->m | H d->d | I b->m | K m->e | L | M | N | P | Q | R | S | T | V | W | Y | |
|---|---|---|---|---|---|---|---|---|---|---|---|---|---|---|---|---|---|---|---|---|---|
|  | -438 |  | -1933 |  |  |  |  |  |  |  |  |  |  |  |  |  |  |  |  |  |  |
| 1(M) | -1511 | -1258 | -3275 | -2807 | 2269 | -2995 | -1346 | 266 | -2474 | 800 | 3792 | -2446 | -2858 | -1968 | -2335 | -2172 | -1449 | -138 | -793 | -87 | 26 |
|  | -149 | -500 | 233 | 43 | -381 | 399 | 106 | -626 | 210 | -466 | -720 | 275 | 394 | 45 | 96 | 359 | 117 | -369 | -294 | -249 | |
|  | -23 | -6577 | -7619 | -894 | -1115 | -701 | -1378 | -438 | * | | | | | | | | | | | | |
| 2(M) | 426 | -1446 | -3780 | -3363 | -1521 | -2856 | -2514 | -90 | -3024 | -729 | 4481 | -2828 | -3133 | -2721 | -2939 | -2091 | -1564 | 1100 | -2424 | -2124 | 27 |
|  | -149 | -500 | 233 | 43 | -381 | 399 | 106 | -626 | 210 | -466 | -720 | 275 | 394 | 45 | 96 | 359 | 117 | -369 | -294 | -249 | |
|  | -10 | -7762 | -8804 | -894 | -1115 | -701 | -1378 | * | * | | | | | | | | | | | | |
| 3(D) | -898 | -2223 | 2613 | -202 | -2512 | -1832 | -557 | -2225 | 779 | -2241 | 1722 | -504 | -1962 | -125 | -678 | 389 | 566 | -1836 | -2468 | -1816 | 28 |
|  | -149 | -500 | 233 | 43 | -381 | 399 | 106 | -626 | 210 | -466 | -720 | 275 | 394 | 45 | 96 | 359 | 117 | -369 | -294 | -249 | |
|  | -9 | -7942 | -8984 | -894 | -1115 | -701 | -1378 | * | * | | | | | | | | | | | | |
| 4(L) | -3343 | -2811 | -5687 | -5115 | 2061 | -5345 | -3911 | 1769 | -4867 | 2527 | 56 | -5003 | -4615 | -3800 | -4424 | -4629 | -3207 | -1173 | -2733 | -2675 | 29 |
|  | -149 | -500 | 233 | 43 | -381 | 399 | 106 | -626 | 210 | -466 | -720 | 275 | 394 | 45 | 96 | 359 | 117 | -369 | -294 | -249 | |
|  | -9 | -7942 | -8984 | -894 | -1115 | -701 | -1378 | * | * | | | | | | | | | | | | |
| 5(F) | -3039 | -2583 | -5400 | -4800 | 2731 | -4939 | -3665 | 2351 | -4517 | 1482 | 1999 | -4610 | -4383 | -3595 | -4132 | -4161 | -2919 | -1092 | -2663 | -2673 | 30 |
|  | -149 | -500 | 233 | 43 | -381 | 399 | 106 | -626 | 210 | -466 | -720 | 275 | 394 | 45 | 96 | 359 | 117 | -369 | -294 | -249 | |
|  | -9 | -7942 | -8984 | -894 | -1115 | -701 | -1378 | * | * | | | | | | | | | | | | |
| 6(E) | -1913 | -3483 | -329 | 3240 | -3847 | -2201 | -1343 | -3669 | -1205 | -3580 | -2799 | -844 | -2614 | 1375 | -1770 | 328 | -1937 | -3187 | -3742 | -2936 | 31 |
|  | -149 | -500 | 233 | 43 | -381 | 399 | 106 | -626 | 210 | -466 | -720 | 275 | 394 | 45 | 96 | 359 | 117 | -369 | -294 | -249 | |
|  | -9 | -7942 | -8984 | -894 | -1115 | -701 | -1378 | * | * | | | | | | | | | | | | |
| 7(K) | -892 | -2327 | -754 | -192 | -2667 | -1850 | -472 | -2397 | 1835 | -2332 | -1421 | 831 | -1938 | 1186 | 1037 | 1297 | 497 | -1961 | -2483 | -1835 | 32 |
|  | -149 | -500 | 233 | 43 | -381 | 399 | 106 | -626 | 210 | -466 | -720 | 275 | 394 | 45 | 96 | 359 | 117 | -369 | -294 | -249 | |
|  | -9 | -7942 | -8984 | -894 | -1115 | -701 | -1378 | * | * | | | | | | | | | | | | |
| 8(I) | 514 | -1727 | -4577 | -4078 | -1745 | -4080 | -3252 | 2588 | -3824 | 1712 | -655 | -3731 | -3953 | -3476 | -3724 | -3273 | -2060 | 1203 | -2879 | -2568 | 33 |
|  | -149 | -500 | 233 | 43 | -381 | 399 | 106 | -626 | 210 | -466 | -720 | 275 | 394 | 45 | 96 | 359 | 117 | -369 | -294 | -249 | |
|  | -9 | -7942 | -8984 | -894 | -1115 | -701 | -1378 | * | * | | | | | | | | | | | | |
| 9(W) | 681 | -1696 | -954 | -400 | 531 | -1888 | -578 | 324 | 1375 | -1628 | -839 | -651 | -1974 | 1030 | 909 | 344 | -741 | -1214 | 2014 | -1462 | 34 |
|  | -149 | -500 | 233 | 43 | -381 | 399 | 106 | -626 | 210 | -466 | -720 | 275 | 394 | 45 | 96 | 359 | 117 | -369 | -294 | -249 | |
|  | -9 | -7942 | -8984 | -894 | -1115 | -701 | -1378 | * | * | | | | | | | | | | | | |
| 10(E) | -1665 | -3313 | 1727 | 2676 | -3578 | 225 | -1130 | -3392 | -1004 | -3309 | -2472 | -694 | -2435 | 928 | -1638 | 306 | -1659 | -2915 | -3488 | -2672 | 35 |
|  | -149 | -500 | 233 | 43 | -381 | 399 | 106 | -626 | 210 | -466 | -720 | 275 | 394 | 45 | 96 | 359 | 117 | -369 | -294 | -249 | |
|  | -9 | -7942 | -8984 | -894 | -1115 | -701 | -1378 | * | * | | | | | | | | | | | | |

TABLE 14-continued

| | | | | | | | | | | | | | | | | | | | | | |
|---|---|---|---|---|---|---|---|---|---|---|---|---|---|---|---|---|---|---|---|---|---|
| 11(K) | -1580 | 1884 | -1764 | -1020 | -2907 | -2481 | -845 | -2479 | 1956 | 772 | -1679 | -1179 | -2514 | 1923 | 1777 | -1525 | -1447 | -2203 | -2604 | -2197 | 36 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 12(A) | 2315 | -1624 | -4424 | -3936 | -1894 | -3936 | -3165 | 1771 | -3688 | 61 | -834 | -3585 | -3870 | -3418 | -3634 | -3127 | -1946 | 1865 | -2913 | -2538 | 37 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 13(K) | 240 | -2148 | -1205 | -600 | -2451 | -2088 | -695 | -2066 | 2741 | -2143 | -1331 | -829 | -2179 | -293 | 688 | -1066 | 326 | 519 | -2394 | -1872 | 38 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 14(Q) | 251 | -2245 | 585 | -74 | -2564 | 1048 | -408 | -2314 | 875 | -2260 | -1335 | -384 | 515 | 1120 | 955 | 394 | -715 | -1866 | -2429 | -1747 | 39 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 15(D) | 511 | -2241 | 1741 | -132 | -2549 | -1792 | -445 | -2281 | 1286 | 455 | -1337 | -435 | -1886 | 971 | 685 | -711 | -760 | -1857 | -2426 | -1765 | 40 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 16(K) | -884 | -2341 | 1633 | -125 | -2653 | 223 | -507 | -2400 | 1752 | -2356 | -1445 | 919 | 707 | -57 | -629 | -761 | -829 | 80 | -2535 | -1850 | 41 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 17(K) | 535 | -1741 | -1193 | -620 | -1889 | -2043 | -709 | 327 | 2612 | -1654 | -903 | -840 | -2126 | 854 | -679 | -1007 | -888 | 295 | -2069 | -1566 | 42 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 18(K) | -2416 | -3238 | -2867 | -1785 | -4015 | -3059 | -1120 | -3414 | 2580 | -3139 | -2429 | -1764 | -3047 | -698 | 2089 | -2312 | 2234 | -3140 | -3041 | -2859 | 43 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 19(I) | -2521 | -2024 | -5153 | -4783 | -2223 | -4929 | -4595 | 3447 | -4687 | 294 | -972 | -4589 | -4629 | -4430 | -4724 | -4267 | -2498 | 1528 | -3873 | -3540 | 44 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 20(V) | 213 | -1847 | -4873 | -4520 | -2465 | -4420 | -4247 | 1419 | -4388 | -1381 | -1247 | -4198 | -4362 | -4252 | -4452 | -3727 | -2270 | 3336 | -3880 | -3419 | 45 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 21(F) | -3693 | -3087 | -5586 | -5265 | 3261 | -5504 | -2888 | -912 | -4973 | 2381 | -226 | -4694 | -4708 | -3838 | -4472 | -4669 | -3558 | -1678 | -1934 | -1153 | 46 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 22(P) | 1357 | -1977 | -3526 | -3796 | -4305 | -2211 | -3504 | -4098 | -3878 | -4361 | -3542 | -2788 | 3823 | -3529 | -3749 | -1636 | -1847 | -3043 | -4411 | -4353 | 47 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 23(E) | -2645 | -4564 | 1495 | 3508 | -4762 | -2401 | -1853 | -4778 | -2245 | -4613 | -4046 | -1009 | -2982 | -1550 | -3202 | -2265 | -2745 | -4225 | -4728 | -3699 | 48 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 24(G) | 828 | -1562 | -2312 | -1921 | -2620 | 2562 | -1856 | -2263 | -1813 | -2508 | -1731 | -1730 | -2452 | -1660 | -2098 | 554 | 782 | -1818 | -2902 | 1503 | 49 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 25(E) | -1027 | -2214 | -837 | 2256 | -2461 | -1966 | -641 | -2117 | 974 | 634 | -1343 | -652 | -2082 | -229 | -588 | -955 | 1152 | -1790 | -2438 | -1847 | 50 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 26(W) | -150 | 757 | 49 | 299 | -277 | -651 | 839 | -485 | 392 | -910 | 599 | 300 | -401 | 623 | 162 | -99 | 38 | -448 | 1107 | 126 | 51 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |
| 27(D) | -2650 | -4626 | 3535 | 2005 | -4794 | -2383 | -1844 | -4814 | -2264 | -4643 | -4090 | -983 | -2972 | -1542 | -3255 | -2259 | -2754 | -4254 | -4780 | -3711 | 52 |
|  | -149 | -500 | 233 | 43 | -381 | 399 | 106 | -626 | 210 | -466 | -720 | 275 | 394 | 45 | 96 | 359 | 117 | -369 | -294 | -249 |  |
|  | -9 | -7942 | -8984 | -894 | -1115 | -701 | -1378 | * |  |  |  |  |  |  |  |  |  |  |  |  |  |

TABLE 14-continued

| | | | | | | | | | | | | | | | | | | | |
|---|---|---|---|---|---|---|---|---|---|---|---|---|---|---|---|---|---|---|---|
| 28(E) | −884 | −1962 | −861 | 2360 | −2149 | −1901 | −576 | 272 | 764 | −268 | −1086 | −611 | 909 | −182 | −632 | −849 | −822 | −1489 | −2226 | −1648 | 53 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 29(R) | −4488 | −4181 | −4789 | −4318 | −5193 | −4148 | −3436 | −5568 | −2393 | −5152 | −4748 | −4156 | −4479 | −3286 | 4202 | −4614 | −4467 | −5273 | −4267 | −4649 | 54 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 30(V) | −1615 | −1406 | −3692 | −3190 | −1680 | −3315 | −2460 | 2105 | −2933 | −1136 | −730 | 1527 | −3366 | −2700 | −2939 | −2463 | 576 | 2489 | −2439 | −2054 | 55 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 31(L) | −2893 | −2389 | −5409 | −4931 | −1519 | −5116 | −4253 | 2238 | −4753 | 2516 | −300 | −4794 | −4601 | −4030 | −4524 | −4423 | −2823 | 819 | −3207 | −3187 | 56 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 32(K) | −810 | −2256 | −666 | 736 | −2577 | 491 | −428 | 19 | 1965 | −2266 | −1348 | −419 | −1872 | 1176 | 702 | 323 | −747 | −1879 | −2434 | −1767 | 57 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 33(A) | 3609 | −2508 | −4184 | −4493 | −4592 | −2737 | −3989 | −4421 | −4496 | −4701 | −4051 | −3440 | −3474 | −4171 | −4253 | −2294 | −2487 | −3536 | −4484 | −4643 | 58 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 34(A) | 2937 | −1528 | −3502 | −3308 | −3125 | −1952 | −2769 | −2630 | −3081 | −3039 | −2271 | −2390 | −2643 | −2779 | −3078 | 549 | 1011 | 493 | −3475 | −3206 | 59 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 35(H) | 804 | −2234 | 624 | 1374 | −2527 | −1779 | 1863 | −180 | −65 | −2239 | −1335 | −424 | −1886 | −14 | −572 | 1383 | −764 | −1842 | −2435 | −1765 | 60 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 36(K) | −927 | −1951 | −1003 | 613 | −2143 | −1960 | −589 | 446 | 1801 | −1893 | 1449 | −680 | −2039 | −201 | 1687 | −903 | −856 | −1504 | −2198 | 1303 | 61 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 37(I) | −3179 | −2647 | −5611 | −5124 | −1356 | −5341 | −4317 | 2901 | −4907 | 2264 | −148 | −5052 | −4698 | −4019 | −4582 | −4697 | −3088 | −546 | −3099 | −3137 | 62 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 38(I) | 1305 | −916 | −2346 | −1758 | −894 | −2325 | −1140 | 1372 | 98 | 911 | −104 | −1638 | −2383 | 1135 | −1607 | −1364 | −839 | 747 | −1366 | −994 | 63 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 39(K) | 103 | −2280 | −655 | 781 | −2607 | −33 | −431 | −2352 | 2090 | −2292 | −1371 | 817 | −1875 | 1393 | 703 | −697 | −754 | −1906 | −2454 | −1782 | 64 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 40(D) | −876 | −2355 | 1990 | 1398 | −2673 | −1797 | −489 | −2425 | 861 | −2368 | −1450 | 862 | −1916 | −35 | 739 | −749 | −818 | −1976 | −2535 | 1245 | 65 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 41(G) | −1910 | −3521 | 1036 | −459 | −3833 | 2939 | −1305 | −3641 | 669 | −3546 | −2760 | −819 | −2598 | 922 | −1710 | −1672 | −1918 | −3170 | −3710 | −2907 | 66 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 42(L) | −2752 | −2316 | −5181 | −4626 | 1316 | −4723 | −3629 | 2215 | −4364 | 2228 | −104 | −4388 | −4302 | −3622 | −4077 | −3942 | −2665 | 822 | −2775 | −2716 | 67 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 43(A) | 2595 | −1592 | −4065 | −3655 | −1874 | −3190 | −2875 | 69 | −3364 | 237 | −870 | −3140 | −3438 | −3084 | −3305 | −2430 | −1771 | 2003 | −2788 | −2442 | 68 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 44(K) | −781 | −2248 | 1290 | 1182 | −2566 | −1751 | −412 | −18 | 1303 | −2262 | −1338 | 836 | −1846 | 47 | 956 | −662 | 674 | −1869 | −2432 | −1751 | 69 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |

TABLE 14-continued

| | | | | | | | | | | | | | | | | | | |
|---|---|---|---|---|---|---|---|---|---|---|---|---|---|---|---|---|---|---|
| 45(P) | −1999 −149 −9 | −1685 −500 −7942 | −4334 233 −8984 | −3818 43 −894 | −1612 −381 −1115 | −3852 399 −701 | −2976 106 −1378 | 1828 −626 * | −3535 210 * | 394 −466 | −557 −720 | −3486 275 | 3050 394 | −3199 45 | −3450 96 | −3026 359 | −1964 117 | 1176 −369 | −2676 −294 | −2369 −249 | 70 |
| 46(V) | −2452 −149 −9 | −1958 −500 −7942 | −5119 233 −8984 | −4802 43 −894 | −2578 −381 −1115 | −4903 399 −701 | −4884 106 −1378 | 2288 −626 * | −4745 210 * | −1352 −466 | −1293 −720 | −4595 275 | −4680 394 | −4675 45 | −4887 96 | −4275 359 | −2449 117 | 3237 −369 | −4279 −294 | −3776 −249 | 71 |
| 47(L) | −2998 −149 −9 | −2538 −500 −7942 | −5403 233 −8984 | −4947 43 −894 | −1395 −381 −1115 | −4989 399 −701 | −4115 106 −1378 | −173 −626 * | −4693 210 * | 2765 −466 | −209 −720 | −4769 275 | −4551 394 | −3928 45 | −4414 96 | −4328 359 | −2940 117 | 1827 −369 | −3062 −294 | −3033 −249 | 72 |
| 48(V) | −2510 −149 −9 | −2021 −500 −7942 | −5126 233 −8984 | −4737 43 −894 | −2130 −381 −1115 | −4872 399 −701 | −4437 106 −1378 | 1947 −626 * | −4622 210 * | 1286 −466 | −893 −720 | −4529 275 | −4574 394 | −4319 45 | −4624 96 | −4190 359 | −2483 117 | 2866 −369 | −3732 −294 | −3431 −249 | 73 |
| 49(G) | 931 −149 −9 | −1908 −500 −7942 | −3564 233 −8984 | −3879 43 −894 | −4400 −381 −1115 | 3463 399 −701 | −3561 106 −1378 | −4237 −626 * | −4052 210 * | −4490 −466 | −3601 −720 | −2764 275 | −2927 394 | −3600 45 | −3877 96 | −1557 359 | −1777 117 | −3055 −369 | −4501 −294 | −4478 −249 | 74 |
| 50(N) | 91 −149 −9 | −2861 −500 −7942 | 975 233 −8984 | −587 43 −894 | −3637 −381 −1115 | −2069 399 −701 | −1361 106 −1378 | −3439 −626 * | −1272 210 * | −3412 −466 | −2579 −720 | 2972 275 | −2496 394 | −985 45 | −1877 96 | 1896 359 | −1654 117 | −2876 −369 | −3606 −294 | −2851 −249 | 75 |
| 51(E) | −1387 −149 −9 | −2840 −500 −7942 | −463 233 −8984 | 2722 43 −894 | −3195 −381 −1115 | −2028 399 −701 | −944 106 −1378 | −2952 −626 * | −645 210 * | −2907 −466 | −2050 −720 | −684 275 | 1763 394 | 936 45 | −1162 96 | −1231 359 | 313 117 | −2508 −369 | −3091 −294 | −2377 −249 | 76 |
| 52(N) | 1378 −149 −9 | −2248 −500 −7942 | 457 233 −8984 | 624 43 −894 | 806 −381 −1115 | −1762 399 −701 | −434 106 −1378 | −2299 −626 * | 865 210 * | −2258 −466 | −1342 −720 | 1494 275 | −1863 394 | 20 45 | −534 96 | 341 359 | −740 117 | −1863 −369 | −2438 −294 | −1760 −249 | 77 |
| 53(E) | 975 −149 −9 | −2349 −500 −7942 | 734 233 −8984 | 2085 43 −894 | −2655 −381 −1115 | −1807 399 −701 | −516 106 −1378 | −2399 −626 * | 1272 210 * | −2359 −466 | −1451 −720 | −445 275 | −1934 394 | −67 45 | −640 96 | −772 359 | −840 117 | 10 −369 | −2541 −294 | −1856 −249 | 78 |
| 54(I) | −2526 −149 −9 | −2030 −500 −7942 | −5153 233 −8984 | −4776 43 −894 | −2181 −381 −1115 | −4921 399 −701 | −4549 106 −1378 | 3338 −626 * | −4675 210 * | 616 −466 | −934 −720 | −4580 275 | −4616 394 | −4394 45 | −4697 96 | −4253 359 | −2501 117 | 1644 −369 | −3821 −294 | −3507 −249 | 79 |
| 55(K) | 398 −149 −9 | −2606 −500 −7942 | −1173 233 −8984 | 479 43 −894 | −3022 −381 −1115 | −2165 399 −701 | −660 106 −1378 | −2692 −626 * | 2540 210 * | −2573 −466 | −1705 −720 | −805 275 | −2232 394 | 1750 45 | 1236 96 | −1146 359 | −1168 117 | −2286 −369 | −2659 −294 | −2117 −249 | 80 |
| 56(E) | 1257 −149 −9 | −2318 −500 −7942 | −622 233 −8984 | 1753 43 −894 | −2641 −381 −1115 | −1799 399 −701 | −475 106 −1378 | −2386 −626 * | 1275 210 * | −2333 −466 | −1417 −720 | −437 275 | −1908 394 | 1398 45 | −542 96 | 391 359 | −801 117 | −1943 −369 | −2501 −294 | −1824 −249 | 81 |
| 57(F) | 471 −149 −9 | −982 −500 −7942 | −1994 233 −8984 | −1417 43 −894 | 1160 −381 −1115 | −2213 399 −701 | −1003 106 −1378 | −523 −626 * | 1101 210 * | 784 −466 | −172 −720 | 584 275 | −2279 394 | −1043 45 | −1416 96 | −1230 359 | 532 117 | 1019 −369 | −1408 −294 | −1017 −249 | 82 |
| 58(A) | 3609 −149 −9 | −2508 −500 −7942 | −4184 233 −8984 | −4493 43 −894 | −4592 −381 −1115 | −2737 399 −701 | −3989 106 −1378 | −4421 −626 * | −4496 210 * | −4701 −466 | −4051 −720 | −3440 275 | −3474 394 | −4171 45 | −4253 96 | −2294 359 | −2487 117 | −3536 −369 | −4484 −294 | −4643 −249 | 83 |
| 59(K) | 252 −149 −9 | −2225 −500 −7942 | 594 233 −8984 | −101 43 −894 | −2531 −381 −1115 | 1206 399 −701 | −438 106 −1378 | −2270 −626 * | 1451 210 * | −150 −466 | −1326 −720 | 673 275 | −1865 394 | 14 45 | −536 96 | 340 359 | −739 117 | −1841 −369 | −2425 −294 | −1752 −249 | 84 |
| 60(E) | 1167 −149 −9 | −2286 −500 −7942 | 732 233 −8984 | 1831 43 −894 | −2598 −381 −1115 | −1667 399 −701 | −407 106 −1378 | −2354 −626 * | 951 210 * | −2301 −466 | −1391 −720 | −300 275 | −1816 394 | 40 45 | −560 96 | 783 359 | −749 117 | −1906 −369 | −2475 −294 | −1775 −249 | 85 |
| 61(H) | −815 −149 −11 | −727 −500 −7654 | −2621 233 −8696 | −2031 43 −894 | 1145 −381 −1115 | −2289 399 −1585 −337 | −585 106 −2262 | −200 −626 * | −1722 210 * | 1681 −466 | 107 −720 | 494 275 | −2340 394 | −1435 45 | −1697 96 | −1354 359 | −755 117 | 1054 −369 | −1030 −294 | −564 −249 | 86 |
| | −299 −149 | −2449 −500 | | | | | | | | | | | | | | | | | | | |

TABLE 14-continued

| | | | | | | | | | | | | | | | | | |
|---|---|---|---|---|---|---|---|---|---|---|---|---|---|---|---|---|---|
| 62(N) | −1704 | −3281 | 1777 | −397 | −3622 | 1646 | −1188 | −3429 | −1036 | −3352 | −2526 | 2598 | −2480 | −796 | 1047 | −1495 | −1710 | −2949 | −3526 | −2731 | 87 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 63(M) | 20 | −1214 | −3805 | −3190 | 774 | −3078 | −1973 | 1042 | −2815 | 1458 | 2157 | −2723 | −3056 | −2395 | −2615 | −2183 | −1382 | 1944 | −1731 | −1436 | 88 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 64(D) | 605 | −2467 | 2563 | −401 | −3040 | −1918 | −912 | −2798 | −624 | −2777 | −1892 | 929 | −2187 | −492 | −1157 | 1186 | 553 | −2307 | −2970 | −2279 | 89 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 65(L) | −3447 | −2885 | −5829 | −5243 | −1145 | −5544 | −4253 | 1795 | −5014 | 2666 | 2377 | −5248 | −4707 | −3887 | −4549 | −4864 | −3303 | −1162 | −2916 | −3088 | 90 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 66(D) | 250 | −2410 | 1559 | 1458 | −2748 | 39 | −576 | −2502 | −207 | −2454 | −1544 | −475 | −1976 | −130 | −729 | 1014 | 986 | −2052 | −2631 | −1936 | 91 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 67(G) | −2653 | −3216 | −2503 | −2570 | −4722 | 3367 | −2672 | −4647 | 1672 | −4521 | −3864 | −2587 | −3560 | −2414 | −2013 | −2728 | −2874 | −3999 | −4152 | −4117 | 92 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 68(V) | 1628 | −1694 | 4600 | −4141 | −2065 | −4161 | −3476 | 2051 | −3925 | 24 | −959 | −3809 | −4058 | −3687 | −3896 | −3377 | −2060 | 2431 | −3181 | −2784 | 93 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 69(Q) | −1107 | −2491 | −869 | 2104 | −2843 | −2005 | −610 | −2548 | 1501 | −2474 | 1449 | −645 | −2106 | 2280 | −390 | −986 | −1031 | −2135 | −2613 | −2004 | 94 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 70(I) | −2462 | −1971 | −5120 | −4803 | −2532 | −4890 | −4848 | 3484 | −4737 | −1301 | −1256 | −4591 | −4671 | −4645 | −4865 | −4262 | −2459 | 1950 | −4227 | −3745 | 95 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 71(V) | −1021 | −845 | −3291 | 115 | −783 | −2586 | −1463 | 1772 | −2289 | 711 | 1731 | −2204 | −2623 | −1926 | −2122 | −1672 | −963 | 1810 | −1336 | 1149 | 96 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 72(D) | −4232 | −4465 | 4158 | −2649 | −5412 | −3676 | −3575 | −6036 | −4125 | −5722 | −5419 | −2993 | −4216 | −3512 | −4617 | −4077 | −4401 | −5553 | −4696 | −4914 | 97 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 73(P) | −1143 | −1675 | −3005 | −2989 | −3065 | −2064 | −2700 | 565 | −2869 | −2950 | −2300 | −2338 | 3698 | −2683 | −2908 | 587 | −1504 | −2001 | −3467 | −3104 | 98 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 74(H) | 1253 | −2202 | −717 | 1654 | −2478 | −1838 | 2550 | −2187 | 868 | −372 | −1310 | −496 | −1938 | −63 | −532 | −776 | −809 | −1802 | −2405 | −1767 | 99 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 75(T) | −1143 | −1868 | −2054 | −2081 | −3765 | −1965 | −2374 | −3533 | −2354 | −3699 | −2834 | 2518 | −2626 | −2132 | −2643 | 882 | 2968 | −2663 | −3905 | −3493 | 100 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 76(Y) | −1148 | −1566 | −1831 | −1449 | −1231 | −2241 | −1207 | −1418 | −1361 | −1676 | −1002 | 1156 | −2489 | −1227 | −1649 | 1580 | −1191 | 429 | −1711 | 3317 | 101 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 77(W) | −150 | 757 | 49 | 299 | −277 | −651 | 839 | −485 | 392 | −910 | 599 | 300 | −401 | 623 | 162 | −99 | 38 | −448 | 1107 | 126 | 102 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |
| 78(E) | −1130 | −2548 | 993 | 1837 | −2823 | −1914 | −731 | −2562 | −425 | 645 | −1679 | −557 | 1649 | −306 | −961 | 330 | −1088 | −2151 | −2765 | −2070 | 103 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | | | | | | | | | | | | | |

TABLE 14-continued

| | | | | | | | | | | | | | | | | | | |
|---|---|---|---|---|---|---|---|---|---|---|---|---|---|---|---|---|---|---|
| 79(K) | 705 | -2293 | -914 | -357 | -2734 | 819 | -598 | -2445 | 2189 | | -1507 | -628 | -2037 | -153 | 975 | 617 | -923 | -2013 | -2558 | -1945 | 104 |
| — | -149 | -500 | 233 | 43 | -381 | 399 | 106 | -626 | 210 | | -720 | 275 | 394 | 45 | 96 | 359 | 117 | -369 | -294 | -249 | |
| — | -1567 | -7942 | -603 | -894 | -1115 | -701 | -1378 | * | * | | | | | | | | | | | |
| 80(E) | -1455 | -2350 | 50 | 3362 | -2809 | -1547 | -927 | -2700 | -845 | | -2178 | -487 | -2000 | -660 | -1278 | -1311 | -1525 | -2365 | -2625 | -2220 | 105 |
| — | -149 | -500 | 233 | 43 | -381 | 399 | 106 | -626 | 210 | | -720 | 275 | 394 | 45 | 96 | 359 | 117 | -369 | -294 | -249 | |
| — | -26 | -6400 | -7442 | -894 | -1115 | -1808 | -485 | * | * | | | | | | | | | | | |
| 81(M) | -551 | -928 | 1713 | -589 | -942 | -1741 | -615 | 5 | -559 | | 2643 | -741 | -1867 | -429 | -905 | -804 | -519 | 1266 | -1450 | -997 | 106 |
| — | -149 | -500 | 233 | 43 | -381 | 399 | 106 | -626 | 210 | | -720 | 275 | 394 | 45 | 96 | 359 | 117 | -369 | -294 | -249 | |
| — | -19 | -6823 | -7865 | -894 | -1115 | -167 | -3194 | * | * | | | | | | | | | | | |
| 82(K) | -936 | -1587 | -1304 | -718 | -1678 | -2068 | -727 | -1273 | 1622 | | 1465 | -909 | -2141 | -440 | 1553 | -1037 | 1209 | -1083 | -1910 | 1220 | 107 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 83(Q) | 216 | -3288 | 1080 | 1963 | -3557 | -2088 | -1124 | -3366 | -985 | | -2450 | -697 | -2432 | 3156 | -1608 | -1439 | -1648 | -2893 | -3467 | -2658 | 108 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 84(E) | 661 | -2268 | 1307 | 1400 | -2586 | -40 | -425 | -2337 | -12 | | -1359 | -392 | -1857 | 1107 | 956 | -675 | 492 | -1889 | -2452 | -1768 | 109 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 85(M) | -2903 | -2473 | -4675 | -4372 | 1750 | -4229 | -1624 | -1350 | -3989 | | 3626 | -3447 | -4067 | -3192 | -3628 | -3390 | -2808 | -1716 | -937 | 3375 | 110 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 86(A) | 1901 | -908 | -3172 | -2568 | -899 | -2621 | 1244 | 994 | -2224 | | -105 | -2185 | -2665 | -1906 | -2124 | -1705 | -1008 | 1900 | -1447 | -1095 | 111 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 87(Q) | -1463 | -3014 | 2011 | -328 | -3316 | -2053 | -949 | -3092 | -641 | | -2150 | -769 | -2319 | 2525 | 696 | -1279 | -1430 | -2636 | -3169 | -2433 | 112 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 88(A) | 2248 | -2123 | 670 | -520 | -2701 | -1892 | -856 | -2400 | -496 | | -1589 | -392 | -2126 | -446 | 1017 | -948 | 1463 | -1971 | -2692 | -2080 | 113 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 89(F) | -2727 | -2338 | -4825 | -4352 | 3286 | -4296 | -2265 | 816 | -3996 | | -226 | -3736 | -4033 | -3222 | -3652 | -3458 | -2628 | -1306 | 3005 | -774 | 114 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 90(Y) | -2126 | -1823 | -4287 | -3802 | -723 | -3742 | -2094 | -327 | -3430 | | -480 | -3251 | -3663 | -2945 | -3227 | -2891 | -2068 | 2283 | -1586 | 3201 | 115 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 91(E) | 703 | -3188 | -772 | 3501 | -4265 | -2379 | -2017 | -4040 | -2108 | | -3438 | -1356 | -2948 | -1721 | -2684 | -2006 | -2303 | -3449 | -4241 | -3565 | 116 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 92(R) | -2413 | -2234 | -4171 | -3369 | -1308 | -3884 | -2460 | 877 | -2018 | | -224 | -3190 | -3714 | -2356 | 2764 | -3076 | -2310 | -961 | -2462 | -2283 | 117 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 93(R) | 738 | -2612 | -3347 | -2738 | -4144 | -2736 | -2052 | -3768 | -900 | | -3029 | -2409 | -3189 | -1725 | 3817 | -2171 | -2228 | -3209 | -3627 | -3498 | 118 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 94(K) | 503 | -2445 | -1015 | -703 | -3184 | 562 | -1018 | -2893 | 2978 | | -1992 | 704 | -2331 | -602 | -835 | -1206 | -1297 | -2406 | -2999 | -2416 | 119 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |
| 95(H) | -928 | -2405 | -563 | 997 | -2720 | 1543 | 2401 | -2472 | 959 | | -1504 | 868 | -1955 | -84 | -643 | 392 | -872 | -2026 | -2586 | -1897 | 120 |
| — | -149 | -500 | 233 | 43 | -381 | 399 | 106 | -626 | 210 | | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | |

TABLE 14-continued

| | | | | | | | | | | | | | | | | | | | |
|---|---|---|---|---|---|---|---|---|---|---|---|---|---|---|---|---|---|---|---|
| 96(K) | −4125 −149 −809 | −4091 −500 −7942 | −4017 233 −1234 | −3615 −894 | −5101 −381 −1115 | −3960 399 −701 | −2958 106 −1378 | −5182 −626 * | 3972 210 * | −4825 −466 | −4345 −720 | −3552 275 | −4249 394 | −2709 45 | −1809 96 | −4154 359 | −4044 117 | −4895 −369 | −4132 −294 | −4389 −249 | 121 |
| 97(G) | −2666 −149 −15 | −2751 −500 −7148 | −3377 233 −8190 | −3700 −894 | −4393 −381 −1115 | 3753 399 −541 | −3528 106 −1677 | −4841 −626 * | −4031 210 * | −4741 −466 | −4286 −720 | −3394 275 | −3411 394 | −3824 45 | −3848 96 | −2912 359 | −3053 117 | −4080 −369 | −3719 −294 | −4290 −249 | 122 |
| 98(M) | 412 −149 −10 | −754 −500 −7762 | −2560 233 −8804 | −1966 −894 | −741 −381 −1115 | −2291 399 −413 | −1150 106 −2007 | 981 −626 * | −1684 210 * | −598 −466 | 3179 −720 | 1245 275 | −2352 394 | −1421 45 | −1700 96 | −1351 359 | 649 117 | 877 −369 | −1235 −294 | −874 −249 | 123 |
| 99(T) | −2430 −149 −9 | −2823 −500 −7942 | −4179 233 −8984 | −4462 −894 | −4591 −381 −1115 | −3027 399 −701 | −4037 106 −1378 | −4454 −626 * | −4406 210 * | −4707 −466 | −4191 −720 | −3664 275 | −3724 394 | −4237 45 | −4215 96 | −2689 359 | 4010 117 | −3747 −369 | −4431 −294 | −4588 −249 | 124 |
| 100(P) | 270 −149 −9 | −1065 −500 −7942 | −2103 233 −8984 | 243 −894 | −1059 −381 −1115 | −2317 399 −701 | −1151 106 −1378 | 1403 −626 * | −1372 210 * | 790 −466 | −240 −720 | −1539 275 | 2257 394 | −1198 45 | −1557 96 | −1358 359 | −904 117 | −375 −369 | −1531 −294 | −1145 −249 | 125 |
| 101(E) | −2392 −149 −9 | −4275 −500 −7942 | 1163 233 −8984 | 3312 −894 | −4486 −381 −1115 | −2295 399 −701 | −1667 106 −1378 | −4423 −626 * | −1934 210 * | −4288 −466 | −3633 −720 | −894 275 | 1125 394 | −1341 45 | −2802 96 | −2049 359 | −2468 117 | −3888 −369 | −4470 −294 | −3454 −249 | 126 |
| 102(Q) | 297 −149 −9 | −2471 −500 −7942 | 1012 233 −8984 | −160 −894 | −2788 −381 −1115 | −1849 399 −701 | −577 106 −1378 | −2543 −626 * | 1870 210 * | −2482 −466 | −1573 −720 | 944 275 | −1994 394 | 2462 45 | −693 96 | −848 359 | −930 117 | −2093 −369 | −2649 −294 | −1955 −249 | 127 |
| 103(A | 3227 −149 −9 | −1594 −500 −7942 | −3807 233 −8984 | −3849 −894 | −3646 −381 −1115 | −1945 399 −701 | −3198 106 −1378 | −3067 −626 * | −3621 210 * | −3576 −466 | −2783 −720 | −2572 275 | −2704 394 | −3241 45 | −3481 96 | 576 359 | −1455 117 | 241 −369 | −3977 −294 | −3779 −249 | 128 |
| 104(D | 1261 −149 −9 | −2267 −500 −7942 | 1791 233 −8984 | 738 −894 | −2557 −381 −1115 | −1813 399 −701 | −517 106 −1378 | −2280 −626 * | −130 210 * | −2273 −466 | −1380 −720 | −464 275 | −1934 394 | −76 45 | 1383 96 | −771 359 | −825 117 | 386 −369 | −2479 −294 | −1813 −249 | 129 |
| 105(K | 415 −149 −9 | −2546 −500 −7942 | −735 233 −8984 | 1917 −894 | −2896 −381 −1115 | −1973 399 −701 | −635 106 −1378 | −2621 −626 * | 2122 210 * | −2543 −466 | −1653 −720 | −608 275 | −2101 394 | 1705 45 | −517 96 | −981 359 | −1047 117 | −2189 −369 | −2683 −294 | −2042 −249 | 130 |
| 106(M | 308 −149 −9 | −827 −500 −7942 | −2563 233 −8984 | −1964 −894 | −795 −381 −1115 | −2335 399 −701 | −1167 106 −1378 | 1419 −626 * | 607 210 * | −677 −466 | 2765 −720 | −1747 275 | −2393 394 | −1425 45 | −1700 96 | −1388 359 | 1409 117 | −241 −369 | 2166 −294 | −912 −249 | 131 |
| 107(M | −2838 −149 −9 | −2385 −500 −7942 | −5273 233 −8984 | −4720 −894 | −1280 −381 −1115 | −4846 399 −701 | −3769 106 −1378 | 1119 −626 * | −4469 210 * | 2241 −466 | 2938 −720 | −4517 275 | −4377 394 | −3690 45 | −4172 96 | −4080 359 | −2748 117 | 1487 −369 | −2847 −294 | −2840 −249 | 132 |
| 108(K | −1031 −149 −169 | −2407 −500 −3204 | −918 233 −8984 | 1080 −894 | −2761 −381 −1115 | −1972 400 −701 | −550 106 −1378 | −2464 −626 * | 1949 210 * | −434 −466 | −1505 −720 | −616 275 | −2053 394 | −100 45 | 1475 96 | 1180 359 | −952 117 | −2050 −369 | −2533 −294 | −1929 −249 | 133 |
| 109(D | −4232 −149 −9 | −4465 −500 −7942 | 4158 233 −8984 | −2649 −894 | −2913 −381 −1115 | −3676 399 −701 | −3575 106 −1378 | −6036 −626 * | −4125 210 * | −5722 −466 | −5419 −720 | −2993 275 | −4216 394 | −3512 45 | −4617 96 | −4077 359 | −4401 117 | −5553 −369 | −4696 −294 | −4914 −249 | 135 |
| 110(P) | −893 −149 −9 | 2081 −500 −7942 | −1781 233 −8984 | 940 −894 | −1121 −381 −1115 | −2183 399 −701 | −978 106 −1378 | 444 −626 * | −1070 210 * | −1013 −466 | −334 −720 | −1295 275 | 2567 394 | −933 45 | −1326 96 | −1202 359 | −842 117 | −568 −369 | −1538 −294 | 1138 −249 | 136 |
| 111(N | −1006 −149 −9 | −916 −500 −7942 | −2854 233 −8984 | −2266 −894 | −891 −381 −1115 | −2503 399 −701 | −1385 106 −1378 | 865 −626 * | −1966 210 * | 1747 −466 | −97 −720 | 1859 275 | −2563 394 | −1688 45 | −1947 96 | −70 359 | −954 117 | 854 −369 | −1419 −294 | −1063 −249 | 137 |
| 112(Y | −4083 −149 −9 | −3282 −500 −7942 | −4926 233 −8984 | −5082 −894 | 1832 −381 −1115 | −4728 399 −701 | −1188 106 −1378 | −2828 −626 * | −4652 210 * | −2243 −466 | 2245 −720 | −3495 275 | −4595 394 | −3549 45 | −4122 96 | −3951 359 | −3965 117 | −3052 −369 | −449 −294 | 4351 −249 | 138 |

TABLE 14-continued

| | | | | | | | | | | | | | | | | | | | |
|---|---|---|---|---|---|---|---|---|---|---|---|---|---|---|---|---|---|---|---|
| 113(F) | -4576 | -3559 | -5015 | -5343 | 4263 | -4881 | -1152 | -3449 | -4910 | -2776 | -2865 | -3550 | -4757 | -3679 | -4300 | -4154 | -4444 | -3622 | -401 | 2124 | 139 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 114(G | 2612 | -1827 | -3654 | -3943 | -4336 | 2661 | -3533 | -4149 | -4027 | -4411 | -3508 | -2727 | -2864 | -3570 | -3838 | -1474 | -1691 | -2967 | -4475 | -4432 | 140 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 115(T) | 1598 | -1522 | -3726 | -3555 | -2787 | -2149 | -2868 | -1443 | -3288 | -2470 | -1892 | -2585 | -2799 | -2974 | -3213 | -1463 | 2927 | 1522 | -3313 | -3022 | 141 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 116(M | 845 | -1514 | -3507 | -3305 | -2427 | -2152 | -2615 | -1675 | -2968 | -2025 | 4655 | -2481 | -2760 | -2728 | -2908 | -1457 | 695 | -1444 | -2989 | -2699 | 142 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 117(M | 103 | -2295 | -4810 | -4261 | -1123 | -4222 | -3233 | -505 | -3905 | 1982 | 4088 | -3963 | -4004 | -3263 | -3656 | -3428 | -2527 | -1018 | -2542 | -2485 | 143 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 118(V | 249 | -1764 | -4559 | -4171 | -2124 | -3892 | -3557 | 400 | -3936 | 216 | -1010 | -3749 | -3970 | -3700 | -3906 | -3157 | -2087 | 3302 | -3297 | -2917 | 144 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 119(Y | -1748 | -2787 | -1867 | -1117 | -3134 | -2580 | -896 | -2823 | 2430 | -2708 | -1928 | -1262 | -2616 | -482 | 1298 | 588 | -1603 | -2513 | -2720 | 2852 | 145 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 120(M | 543 | -1502 | 454 | -655 | -1569 | -2005 | -725 | -1152 | 1280 | 1097 | 2617 | -860 | -2092 | -451 | -910 | -972 | -801 | -975 | -1856 | -1371 | 146 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 121(G | -2913 | -3668 | 945 | -1911 | -5049 | 3566 | -2931 | -5265 | -3381 | -5155 | -4587 | -2191 | -3583 | -2748 | -4001 | -2853 | -3188 | -4499 | -4671 | -4461 | 147 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 122(E) | 418 | -2234 | 1260 | 1822 | -2533 | -1769 | -443 | -2271 | 1177 | -485 | -1330 | -412 | -1871 | 9 | -542 | -693 | -747 | -1845 | -2428 | 811 | 148 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 123(V | 2475 | -1721 | -4141 | -4120 | -2951 | -2548 | -3488 | -657 | -3886 | -2245 | -1927 | -3055 | -3187 | -3584 | -3760 | -1902 | -1766 | 2703 | -3796 | -3475 | 149 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 124(D | -4232 | -4465 | 4158 | -2649 | -5412 | -3676 | -3575 | -6036 | -4125 | -5722 | -5419 | -2993 | -4216 | -3512 | -4617 | -4077 | -4401 | -5553 | -4696 | -4914 | 150 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 125(G | -1595 | -2107 | -3720 | -3963 | -3970 | 3471 | -3570 | -3119 | -3981 | -3886 | -3293 | -2985 | -3155 | -3665 | -3837 | -1865 | -2027 | 946 | -4215 | -4068 | 151 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 126(M | -2025 | 2478 | -4388 | -3797 | -1130 | -3739 | -2667 | -158 | -3453 | 1208 | 4105 | -3402 | -3608 | -2937 | -3236 | -2881 | -1961 | 880 | -2231 | -2028 | 152 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 127(W | -150 | 757 | 49 | 299 | -277 | -651 | 839 | -485 | 392 | -910 | 599 | 300 | -401 | 623 | 162 | -99 | 38 | -448 | 1107 | 126 | 153 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 128(V | -2447 | -1962 | -5103 | -4789 | -2553 | -4857 | -4827 | 1666 | -4719 | -1334 | -1279 | -4568 | -4656 | -4638 | -4849 | -4228 | -2447 | 3448 | -4233 | -3737 | 154 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |
| 129(S) | 2131 | -1670 | -3692 | -3910 | -4174 | -1935 | -3404 | -3963 | -3845 | -4238 | -3317 | -2599 | -2728 | -3415 | -3673 | 2964 | -1517 | -2788 | -4397 | -4269 | 155 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | | | | | | | | | | | | | | |

TABLE 14-continued

| | | | | | | | | | | | | | | | | | | |
|---|---|---|---|---|---|---|---|---|---|---|---|---|---|---|---|---|---|---|
| 130(G) | −4088 −149 −9 | −3924 −500 −7942 | −4774 233 −8984 | −5139 43 −894 | −5615 −381 −1115 | 3825 399 −701 | −4753 106 −1378 | −6303 −626 * | −5453 210 * | −6014 −466 | −5662 −720 | −4812 275 | −4539 394 | −5232 45 | −5106 96 | −4370 359 | −4472 117 | −5527 −369 | −4696 −294 | −5561 −249 | 156 |
| 131(A) | 3075 −149 −9 | −1760 −500 −7942 | −2603 233 −8984 | −2695 43 −894 | −3957 −381 −1115 | −1941 399 −701 | −2800 106 −1378 | −3736 −626 * | −2952 210 * | −3942 −466 | −3051 −720 | 1370 275 | −2670 394 | −2640 45 | −3110 96 | 792 359 | −1502 117 | −2723 −369 | −4139 −294 | −3839 −249 | 157 |
| 132(V) | 1970 −149 −9 | −1618 −500 −7942 | −4439 233 −8984 | −3946 43 −894 | −1865 −381 −1115 | −3942 399 −701 | −3147 106 −1378 | 1777 −626 * | −3693 210 * | 528 −466 | −807 −720 | −3588 275 | −3866 394 | −3412 45 | −3626 96 | −3130 359 | −1942 117 | 2096 −369 | −2880 −294 | −2511 −249 | 158 |
| 133(H) | −1102 −149 −9 | 2379 −500 −7942 | −1738 233 −8984 | −1466 43 −894 | −2663 −381 −1115 | −2010 399 −701 | 4358 106 −1378 | −2506 −626 * | −1383 210 * | −2678 −466 | −1892 −720 | 969 275 | −2465 394 | −1337 45 | −1706 96 | 783 359 | −1293 117 | −2046 −369 | −2891 −294 | −2346 −249 | 159 |
| 134(S) | 419 −149 −9 | −1643 −500 −7942 | −3250 233 −8984 | −3104 43 −894 | −3814 −381 −1115 | −1905 399 −701 | −2857 106 −1378 | −3555 −626 * | −2981 210 * | −3781 −466 | −2885 −720 | −2311 275 | 2298 394 | −2716 45 | −3080 96 | 2397 359 | 1614 117 | −2583 −369 | −4014 −294 | −3764 −249 | 160 |
| 135(T) | −1102 −149 −9 | −1714 −500 −7942 | −3480 233 −8984 | −3700 43 −894 | −4076 −381 −1115 | −1973 399 −701 | −3311 106 −1378 | −3843 −626 * | −3648 210 * | −4140 −466 | −3265 −720 | −2565 275 | −2755 394 | −3310 45 | −3525 96 | 656 359 | 3729 117 | −2765 −369 | −4307 −294 | −4127 −249 | 161 |
| 136(G) | 2443 −149 −9 | −1650 −500 −7942 | −3680 233 −8984 | −3879 43 −894 | −4195 −381 −1115 | 2494 399 −701 | −3389 106 −1378 | −3992 −626 * | −3844 210 * | −4243 −466 | −3304 −720 | −2574 275 | −2707 394 | −3388 45 | −3682 96 | 672 359 | −1492 117 | −2786 −369 | −4412 −294 | −4299 −249 | 162 |
| 137(D) | −2610 −149 −9 | −4414 −500 −7942 | 3375 233 −8984 | −640 43 −894 | −4704 −381 −1115 | −2395 399 −701 | −1885 106 −1378 | −4787 −626 * | −2296 210 * | −4632 −466 | −4069 −720 | 2731 275 | −2988 394 | −1589 45 | −3253 96 | −2255 359 | −2733 117 | −4206 −369 | −4710 −294 | −3683 −249 | 163 |
| 138(T) | −1802 −149 −9 | −1610 −500 −7942 | −4107 233 −8984 | −3628 43 −894 | −1625 −381 −1115 | −3434 399 −701 | −2777 106 −1378 | 121 −626 * | −3310 210 * | 979 −466 | −612 −720 | −3213 275 | −3529 394 | −3008 45 | −3231 96 | −2634 359 | 2771 117 | 1888 −369 | −2588 −294 | −2269 −249 | 164 |
| 139(L) | −2900 −149 −9 | −2445 −500 −7942 | −5330 233 −8984 | −4886 43 −894 | −1470 −381 −1115 | −4921 399 −701 | −4106 106 −1378 | −73 −626 * | −4643 210 * | 2578 −466 | −286 −720 | −4689 275 | −4527 394 | −3948 45 | −4403 96 | −4253 359 | −2850 117 | 2224 −369 | −3114 −294 | −3047 −249 | 165 |
| 140(R) | −4488 −149 −9 | −4181 −500 −7942 | −4789 233 −8984 | −4318 43 −894 | −5193 −381 −1115 | −4148 399 −701 | −3436 106 −1378 | −5568 −626 * | −2393 210 * | −5152 −466 | −4748 −720 | −4156 275 | −4479 394 | −3286 45 | 4202 96 | −4614 359 | −4467 117 | −5273 −369 | −4267 −294 | −4649 −249 | 166 |
| 141(P) | 1695 −149 −9 | −1951 −500 −7942 | −3539 233 −8984 | −3802 43 −894 | −4288 −381 −1115 | −2189 399 −701 | −3492 106 −1378 | −4075 −626 * | −3870 210 * | −4341 −466 | −3515 −720 | −2772 275 | 3709 394 | −3517 45 | −3739 96 | −1609 359 | −1819 117 | −3017 −369 | −4404 −294 | −4341 −249 | 167 |
| 142(A) | 2997 −149 −9 | −1820 −500 −7942 | −3672 233 −8984 | −3957 43 −894 | −4327 −381 −1115 | 2092 399 −701 | −3531 106 −1378 | −4137 −626 * | −4026 210 * | −4400 −466 | −3498 −720 | −2726 275 | −2859 394 | −3569 45 | −3834 96 | −1467 359 | −1684 117 | −2957 −369 | −4469 −294 | −2269 −249 | 168 |
| 143(L) | −3221 −149 −9 | −2748 −500 −7942 | −5558 233 −8984 | −5092 43 −894 | −1274 −381 −1115 | −5134 399 −701 | −4164 106 −1378 | −386 −626 * | −4812 210 * | 3030 −466 | −86 −720 | −4956 275 | −4613 394 | −3913 45 | −4456 96 | −4503 359 | −3148 117 | 772 −369 | −2987 −294 | −3018 −249 | 169 |
| 144(Q) | −2871 −149 −9 | −3512 −500 −7942 | −2899 233 −8984 | −2161 43 −894 | −4235 −381 −1115 | −3278 399 −701 | −1502 106 −1378 | −3869 −626 * | −191 210 * | −3535 −466 | −2901 −720 | −2118 275 | −3368 394 | 4099 45 | 1519 96 | −2774 359 | −2657 117 | −3608 −369 | −3317 −294 | −3159 −249 | 170 |
| 145(I) | −2460 −149 −9 | −1967 −500 −7942 | −5122 233 −8984 | −4804 43 −894 | −2546 −381 −1115 | −4899 399 −701 | −4864 106 −1378 | 3420 −626 * | −4742 210 * | −1315 −466 | −1266 −720 | −4595 275 | −4676 394 | −4657 45 | −4875 96 | −4271 359 | −2457 117 | 2106 −369 | −4245 −294 | −3757 −249 | 171 |
| 146(I) | −2482 −149 −9 | −1984 −500 −7942 | −5127 233 −8984 | −4768 43 −894 | −2335 −381 −1115 | −4912 399 −701 | −4643 106 −1378 | 3097 −626 * | −4684 210 * | 313 −466 | −1075 −720 | −4568 275 | −4633 394 | −4487 45 | −4753 96 | −4252 359 | −2463 117 | 2302 −369 | −3978 −294 | −3593 −249 | 172 |

TABLE 14-continued

| | | | | | | | | | | | | | | | | | | | |
|---|---|---|---|---|---|---|---|---|---|---|---|---|---|---|---|---|---|---|---|
| 147(K) | −2698 −149 −9 | −3306 −500 −7942 | −2555 233 −8984 | −2385 43 −894 | −4613 −381 −1115 | 1689 399 −701 | −2226 106 −1378 | −4379 −626 * | 3466 210 * | −4176 −466 | −3510 −720 | −2406 275 | −3487 394 | −1898 45 | −1272 96 | −2718 359 | −2789 117 | −3870 −369 | −3879 −294 | −3804 −249 | 173 |
| 148(T) | −1775 −149 −9 | −2078 −500 −7942 | −3737 233 −8984 | −3648 43 −894 | −2269 −381 −1115 | −2758 399 −701 | −3026 106 −1378 | −1461 −626 * | −3198 210 * | 577 −466 | −1417 −720 | −3004 275 | −3304 394 | −3108 45 | −3140 96 | −2144 359 | 3610 117 | −1504 −369 | −3171 −294 | −2809 −249 | 174 |
| 149(K) | 1442 −149 −9 | −2243 −500 −7942 | −1132 233 −8984 | −565 43 −894 | −2592 −381 −1115 | −2073 399 −701 | −704 106 −1378 | −2218 −626 * | 2425 210 * | −2266 −466 | −1439 −720 | −805 275 | −2179 394 | 1424 45 | −419 96 | −1063 359 | −1056 117 | 139 −369 | −2490 −294 | −1948 −249 | 175 |
| 150(P) | −2229 −149 −9 | −3531 −500 −7942 | −751 233 −8984 | 745 43 −894 | −4074 −381 −1115 | −2482 399 −701 | −1471 106 −1378 | −3788 −626 * | 860 210 * | −3650 −466 | −2934 −720 | −1174 275 | 3599 394 | −1104 45 | −1174 96 | −2025 359 | −2220 117 | −3370 −369 | −3701 −294 | −3125 −249 | 176 |
| 151(G) | −4088 −149 −9 | −3924 −500 −7942 | −4774 233 −8984 | −5139 43 −894 | −5615 −381 −1115 | 3825 399 −701 | −4753 106 −1378 | −6303 −626 * | −5453 210 * | −6014 −466 | −5662 −720 | −4812 275 | −4539 394 | −5232 45 | −5106 96 | −4370 359 | −4472 117 | −5527 −369 | −4696 −294 | −5561 −249 | 177 |
| 152(C) | 1031 −149 −9 | 2336 −500 −7942 | −3000 233 −8984 | −2410 43 −894 | −865 −381 −1115 | −2361 399 −701 | −1377 106 −1378 | −341 −626 * | −2075 210 * | 407 −466 | −99 −720 | −2001 275 | −2486 394 | −1756 45 | −1986 96 | 688 359 | 649 117 | 1750 −369 | −1361 −294 | −1013 −249 | 178 |
| 153(K) | 299 −149 −9 | −2345 −500 −7942 | −751 233 −8984 | −248 43 −894 | −2698 −381 −1115 | −1882 399 −701 | 2125 106 −1378 | −2424 −626 * | 2532 210 * | −2376 −466 | −1479 −720 | 830 275 | −1996 394 | −103 45 | −500 96 | 327 359 | −894 117 | −1997 −369 | −2541 −294 | −1898 −249 | 179 |
| 154(T) | −908 −149 −9 | −953 −500 −7942 | −2280 233 −8984 | −1684 43 −894 | −935 −381 −1115 | −2313 399 −701 | −1108 106 −1378 | 722 −626 * | 344 210 * | 1215 −466 | −140 −720 | −1590 275 | −2372 394 | −1223 45 | 1008 96 | −1350 359 | 1552 117 | 668 −369 | −1392 −294 | −1018 −249 | 180 |
| 155(V) | 248 −149 −9 | −1426 −500 −7942 | −4165 233 −8984 | −3634 43 −894 | −1671 −381 −1115 | −3597 399 −701 | −2693 106 −1378 | 2073 −626 * | −3341 210 * | 492 −466 | −700 −720 | −3234 275 | −3564 394 | −3048 45 | −3243 96 | −2750 359 | 488 117 | 2467 −369 | −2499 −294 | −2124 −249 | 181 |
| 156(S) | −1944 −149 −9 | −2458 −500 −7942 | −3696 233 −8984 | −4011 43 −894 | −4410 −381 −1115 | −2644 399 −701 | −3753 106 −1378 | −4675 −626 * | −4191 210 * | −4807 −466 | −4070 −720 | −3198 275 | −3384 394 | −3886 45 | −4051 96 | 3656 359 | −2393 117 | −3615 −369 | −4374 −294 | −4307 −249 | 182 |
| 157(G) | 693 −149 −9 | −1658 −500 −7942 | −3600 233 −8984 | −3793 43 −894 | −4209 −381 −1115 | 2495 399 −701 | −3362 106 −1378 | −4011 −626 * | −3794 210 * | −4256 −466 | −3314 −720 | −2553 275 | −2706 394 | −3347 45 | −3658 96 | 2479 359 | −1495 117 | −2797 −369 | −4419 −294 | −4298 −249 | 183 |
| 158(F) | 757 −149 −9 | −848 −500 −7942 | −3195 233 −8984 | −2588 43 −894 | 2258 −381 −1115 | −2533 399 −701 | −1456 106 −1378 | 1163 −626 * | −2229 210 * | −678 −466 | −69 −720 | −2151 275 | −2599 394 | −1889 45 | −2097 96 | 1006 359 | −949 117 | 1406 −369 | −1371 −294 | −1020 −249 | 184 |
| 159(F) | −3561 −149 −9 | −3044 −500 −7942 | −5093 233 −8984 | −4992 43 −894 | 4144 −381 −1115 | −4702 399 −701 | −2042 106 −1378 | −1417 −626 * | −4612 210 * | −651 −466 | 2173 −720 | −3997 275 | −4516 394 | −3679 45 | −4183 96 | −4055 359 | −3507 117 | −1990 −369 | −1263 −294 | −230 −249 | 185 |
| 160(I) | −2399 −149 −9 | −1985 −500 −7942 | −4894 233 −8984 | −4389 43 −894 | 1240 −381 −1115 | −4436 399 −701 | −3536 106 −1378 | 2456 −626 * | −4148 210 * | 1300 −466 | −435 −720 | −4090 275 | −4179 394 | −3651 45 | −3986 96 | −3652 359 | −2345 117 | 2073 −369 | −2927 −294 | −2716 −249 | 186 |
| 161(M) | −2968 −149 −9 | −2569 −500 −7942 | −5237 233 −8984 | −4809 43 −894 | −1359 −381 −1115 | −4763 399 −701 | −3886 106 −1378 | 1091 −626 * | −4419 210 * | −34 −466 | 4848 −720 | −4576 275 | −4450 394 | −3792 45 | −4170 96 | −4116 359 | −2930 117 | −673 −369 | −2953 −294 | −2839 −249 | 187 |
| 162(Q) | 309 −149 −9 | −798 −500 −7942 | −2699 233 −8984 | −2096 43 −894 | 1118 −381 −1115 | −2361 399 −701 | −1203 106 −1378 | 789 −626 * | −1796 210 * | 499 −466 | 6 −720 | −1823 275 | −2416 394 | 1904 45 | −1779 96 | 902 359 | −818 117 | 786 −369 | −1249 −294 | −892 −249 | 188 |
| 163(V) | −884 −149 −9 | −1453 −500 −7942 | −1331 233 −8984 | −759 43 −894 | −1529 −381 −1115 | −2054 399 −701 | −754 106 −1378 | 426 −626 * | 1538 210 * | −1352 −466 | −623 −720 | −938 275 | 708 394 | −503 45 | 609 96 | −1024 359 | 716 117 | 1556 −369 | −1814 −294 | −1348 −249 | 189 |

TABLE 14-continued

| | | | | | | | | | | | | | | | | | | | | |
|---|---|---|---|---|---|---|---|---|---|---|---|---|---|---|---|---|---|---|---|---|
| 164(P) | -1205 -149 -9 | -2096 -500 -7942 | -1371 233 -8984 | -1294 43 -894 | -3530 -381 -1115 | 1986 399 -701 | -1732 106 -1378 | -3286 -626 * | -1522 210 * | -3357 -466 | -2495 -720 | -1382 275 | 2600 394 | 1480 45 | -1930 96 | 689 359 | -1438 117 | -2587 -369 | -3557 -294 | -3013 -249 | 190 |
| 165(I) | -1308 -149 -9 | -2864 -500 -7942 | 2377 233 -8984 | 1708 43 -894 | -3151 -381 -1115 | -1969 399 -701 | -847 106 -1378 | -2932 -626 * | 908 210 * | -2865 -466 | -1984 -720 | 1026 275 | -2212 394 | -422 45 | -1139 96 | -1136 359 | -1274 117 | -2473 -369 | -3039 -294 | 1438 -249 | 191 |
| 166(C) | 544 -149 -9 | 3117 -500 -7942 | -563 233 -8984 | 1527 43 -894 | -2011 -381 -1115 | -1598 399 -701 | -229 106 -1378 | -1884 -626 * | 984 210 * | -1975 -466 | -920 -720 | -317 275 | -1617 394 | 1132 45 | -431 96 | -599 359 | -614 117 | -1564 -369 | -1347 -294 | -1372 -249 | 192 |
| 167(E) | -1135 -149 -9 | -2652 -500 -7942 | 805 233 -8984 | 2212 43 -894 | -2960 -381 -1115 | 449 399 -701 | -701 106 -1378 | -2724 -626 * | -352 210 * | -2658 -466 | -1760 -720 | -534 275 | -2098 394 | 1133 45 | 1725 96 | -983 359 | -1089 117 | -2270 -369 | -2825 -294 | -2111 -249 | 193 |
| 168(Y) | -3596 -149 -809 | -3426 -500 -7942 | -4011 233 -1234 | -4236 43 -894 | -756 -381 -1115 | -3926 399 -701 | -2017 106 -1378 | -3923 -626 * | -4119 210 * | -3489 -466 | -3396 -720 | -3558 275 | 1274 394 | -3712 45 | -3935 96 | -3640 359 | -3783 117 | -3834 -369 | -1423 -294 | 4617 -249 | 194 |
| 169(G) | -2666 -149 -15 | -2751 -500 -7148 | -3377 233 -8190 | -3700 43 -894 | -4393 -381 -1115 | 3753 399 -701 | -3528 106 -334 | -4841 -626 * | -4031 210 * | -4741 -466 | -4286 -720 | -3394 275 | -3411 394 | -3824 45 | -3848 96 | -2912 359 | -3053 117 | -4080 -369 | -3719 -294 | -4290 -249 | 195 |
| 170(H) | -909 -149 -15 | -2472 -500 -7148 | 1648 233 -8190 | 1963 43 -894 | -2749 -381 -1115 | -1496 399 -701 | 2279 106 -334 | -2536 -626 * | -207 210 * | -2473 -466 | -1609 -720 | -112 275 | -1774 394 | -16 45 | -789 96 | 911 359 | -884 117 | -2079 -369 | -2655 -294 | -1892 -249 | 196 |
| 171(D) | -1659 -149 -15 | -3544 -500 -7148 | 3062 233 -8190 | 1534 43 -894 | -3720 -381 -1115 | -1620 399 -701 | -946 106 -334 | -3633 -626 * | -1158 210 * | -3508 -466 | -2820 -720 | 1807 275 | -2140 394 | -608 45 | -1992 96 | -1327 359 | -1718 117 | -3114 -369 | -3702 -294 | -2701 -249 | 197 |
| 172(G) | -2666 -149 -15 | -2751 -500 -7148 | -3377 233 -8190 | -3700 43 -894 | -4393 -381 -1115 | 3753 399 -701 | -3528 106 -334 | -4841 -626 * | -4031 210 * | -4741 -466 | -4286 -720 | -3394 275 | -3411 394 | -3824 45 | -3848 96 | -2912 359 | -3053 117 | -4080 -369 | -3719 -294 | -4290 -249 | 198 |
| 173(M) | 896 -149 -13 | -558 -500 -7148 | -2670 233 -8190 | -2060 43 -894 | 1251 -381 -1115 | -1358 399 -701 | -713 106 -334 | 43 -626 * | -1731 210 * | 665 -466 | 2262 -720 | -1717 275 | -2232 394 | -1411 45 | -1654 96 | -1259 359 | 1662 117 | 83 -369 | -1007 -294 | -665 -249 | 199 |
| 174(L) | -3012 -149 -13 | -2483 -500 -7414 | -8456 | -4588 43 -894 | 2563 -381 -1115 | -2185 399 -701 | -1048 106 -421 | -365 -626 * | -4286 210 * | 2641 -466 | 286 -720 | -4144 275 | -4140 394 | -3283 45 | -3862 96 | -3990 359 | -2889 117 | -1078 -369 | -1633 -294 | -952 -249 | 200 |
| | -13 | -7414 | -8456 | | | -1982 399 -701 | | | | | | | | | | | | | | | |
| 175(V) | -1666 -149 -9 | -1535 -500 -7942 | -3931 233 -8984 | -3496 43 -894 | -1547 -381 -1115 | 517 399 -701 | -2567 106 -1378 | -46 -626 * | -3176 210 * | 1766 -466 | -593 -720 | -3023 275 | -3348 394 | -2859 45 | -3069 96 | -2394 359 | -1705 117 | 2567 -369 | -2418 -294 | -2089 -249 | 201 |
| | | | | | | -249 -701 | -2575 106 -1378 | | | | | | | | | | | | | | |
| 176(F) | -4576 -149 -9 | -3559 -500 -7942 | -5015 233 -8984 | -5343 43 -894 | 4263 -381 -1115 | -4881 399 -701 | -1152 106 -1378 | -3449 -626 * | -4910 210 * | -2776 -466 | -2865 -720 | -3550 275 | -4757 394 | -3679 45 | -4300 96 | -4154 359 | -4444 117 | -3622 -369 | -401 -294 | 2124 -249 | 202 |
| 177(A) | 3345 -149 -9 | -1674 -500 -7942 | -3727 233 -8984 | -3977 43 -894 | -4175 -381 -1115 | -1941 399 -701 | -3439 106 -1378 | -3955 -626 * | -3910 210 * | -4243 -466 | -3329 -720 | -2621 275 | -2737 394 | -3468 45 | -3709 96 | 825 359 | -1527 117 | -2788 -369 | -4405 -294 | -4282 -249 | 203 |
| 178(W) | -150 -149 -9 | 757 -500 -7942 | 49 233 -8984 | 299 43 -894 | -277 -381 -1115 | -651 399 -701 | 839 106 -1378 | -485 -626 * | 392 210 * | -910 -466 | 599 -720 | 300 275 | -401 394 | 623 45 | 162 96 | -99 359 | 38 117 | -448 -369 | 1107 -294 | 126 -249 | 204 |
| 179(D) | -4232 -149 -9 | -4465 -500 -7942 | 4158 233 -8984 | -2649 43 -894 | -5412 -381 -1115 | -3676 399 -701 | -3575 106 -1378 | -6036 -626 * | -4125 210 * | -5722 -466 | -5419 -720 | -2993 275 | -4216 394 | -3512 45 | -4617 96 | -4077 359 | -4401 117 | -5553 -369 | -4696 -294 | -4914 -249 | 205 |
| 180(C) | -1236 -149 -9 | 5496 -500 -7942 | -4197 233 -8984 | -4463 43 -894 | -4068 -381 -1115 | -2103 399 -701 | -3603 106 -1378 | -3911 -626 * | -4139 210 * | -4251 -466 | -3414 -720 | -2867 275 | -2893 394 | -3739 45 | -3846 96 | 647 359 | -1702 117 | -2864 -369 | -4296 -294 | -4138 -249 | 206 |

TABLE 14-continued

| | | | | | | | | | | | | | | | | | |
|---|---|---|---|---|---|---|---|---|---|---|---|---|---|---|---|---|---|
| 181(A | 2681 -149 -9 | -1648 -500 -7942 | -3686 233 -8984 | -3867 43 -894 | -4184 -381 -1115 | 2067 399 -701 | -3375 106 -1378 | -3979 -626 * | -3817 210 * | -4229 -466 | -3291 -720 | -2570 275 | -2704 394 | -3369 45 | -3665 96 | 954 359 | -1488 117 | -2779 -369 | -4401 -294 | -4284 -249 | 207 |
| 182(V | -2422 -149 -9 | -1967 -500 -7942 | -4993 233 -8984 | -4556 43 -894 | -1946 -381 -1115 | -4647 399 -701 | -4007 106 -1378 | 2482 -626 * | -4386 210 * | 447 -466 | 1863 -720 | -4301 275 | -4388 394 | -4024 45 | -4325 96 | -3914 359 | -2387 117 | 2602 -369 | -3399 -294 | -3128 -249 | 208 |
| 183(N | -1642 -149 -9 | -1630 -500 -7942 | -3011 233 -8984 | -2702 43 -894 | -1675 -381 -1115 | -3027 399 -701 | -2261 106 -1378 | -141 -626 * | -2480 210 * | 399 -466 | -827 -720 | 3044 275 | -3220 394 | -2357 45 | -2577 96 | -2236 359 | -1678 117 | 2152 -369 | -2448 -294 | -1987 -249 | 209 |
| 184(I | -1310 -149 -9 | -1421 -500 -7942 | -2217 233 -8984 | 1185 43 -894 | -1569 -381 -1115 | -2673 399 -701 | -1609 106 -1378 | 2204 -626 * | -1689 210 * | -1167 -466 | -660 -720 | -1843 275 | -2154 394 | -1552 45 | -1934 96 | -1762 359 | -1280 117 | 885 -369 | -2135 -294 | -1720 -249 | 210 |
| 185(N | 257 -149 -9 | 1558 -500 -7942 | 440 233 -8984 | 612 43 -894 | -2481 -381 -1115 | -1765 399 -701 | -435 106 -1378 | -2211 -626 * | -31 210 * | -2194 -466 | 1330 -720 | 2360 275 | -1863 394 | 1379 45 | -534 96 | -683 359 | -729 117 | -1796 -369 | -2393 -294 | -1727 -249 | 211 |
| 186(P | -2875 -149 -9 | -3093 -500 -7942 | -3978 233 -8984 | -4134 43 -894 | -3333 -381 -1115 | -3398 399 -701 | -3665 106 -1378 | -3255 -626 * | -3879 210 * | -167 -466 | -2945 -720 | -3727 275 | 4087 394 | -3894 45 | -3795 96 | -3160 359 | -3199 117 | -3243 -369 | -3784 -294 | -3483 -249 | 212 |
| 187(T | -1617 -149 -9 | -2991 -500 -7942 | 2432 233 -8984 | -518 43 -894 | -3614 -381 -1115 | -2086 399 -701 | -1314 106 -1378 | -3413 -626 * | -1230 210 * | -3383 -466 | -2559 -720 | 996 275 | -2497 394 | -937 45 | -1848 96 | 429 359 | 2498 117 | -2889 -369 | -3583 -294 | -2811 -249 | 213 |
| 188(A | 2241 -149 -9 | -1737 -500 -7942 | -1506 233 -8984 | 513 43 -894 | -2489 -381 -1115 | -1943 399 -701 | -1317 106 -1378 | -2071 -626 * | -1119 210 * | -2312 -466 | -1526 -720 | -1230 275 | -2307 394 | -1010 45 | -1520 96 | 1714 359 | -1101 117 | 416 -369 | -2692 -294 | -2195 -249 | 214 |
| 189(E | 525 -149 -9 | -2429 -500 -7942 | 1776 233 -8984 | 1822 43 -894 | -2741 -381 -1115 | -1821 399 -701 | -551 106 -1378 | -2497 -626 * | -176 210 * | -2443 -466 | -1530 -720 | -453 275 | 124 394 | 1127 45 | -700 96 | -809 359 | 481 117 | -2048 -369 | -2615 -294 | -1917 -249 | 215 |
| 190(Q | -1567 -149 -9 | -3175 -500 -7942 | 1704 233 -8984 | 1474 43 -894 | -3449 -381 -1115 | -2060 399 -701 | -1054 106 -1378 | -3249 -626 * | -877 210 * | -3174 -466 | -2325 -720 | -671 275 | -2377 394 | 2979 45 | -1481 96 | -1362 359 | 1084 117 | -2781 -369 | -3353 -294 | -2563 -249 | 216 |
| 191(L | -3337 -149 -9 | -2808 -500 -7942 | -5707 233 -8984 | -5127 43 -894 | -1152 -381 -1115 | -5377 399 -701 | -4133 106 -1378 | -460 -626 * | -4878 210 * | 2928 -466 | 1801 -720 | -5079 275 | -4636 394 | -3831 45 | -4452 96 | -4675 359 | -3207 117 | 697 -369 | -2886 -294 | -3022 -249 | 217 |
| 192(A | 3213 -149 -9 | -1669 -500 -7942 | -3729 233 -8984 | -3963 43 -894 | -4171 -381 -1115 | -1937 399 -701 | -3427 106 -1378 | -3953 -626 * | -3889 210 * | -4236 -466 | -3319 -720 | -2614 275 | -2732 394 | -3450 45 | -3697 96 | 1430 359 | -1520 117 | -2784 -369 | -4399 -294 | -4276 -249 | 218 |
| 193(E | -2200 -149 -9 | -4049 -500 -7942 | 2514 233 -8984 | 2580 43 -894 | -4247 -381 -1115 | -2234 399 -701 | -1519 106 -1378 | -4143 -626 * | -1674 210 * | -4022 -466 | -3301 -720 | 1158 275 | -2729 394 | -1171 45 | -2473 96 | 318 359 | -2248 117 | -3627 -369 | -4213 -294 | -3243 -249 | 219 |
| 194(I | -2474 -149 -9 | -2002 -500 -7942 | -5104 233 -8984 | -4792 43 -894 | -2432 -381 -1115 | -4811 399 -701 | -4734 106 -1378 | 3681 -626 * | -4697 210 * | -1199 -466 | -1182 -720 | -4556 275 | -4627 394 | -4560 45 | -4788 96 | -4186 359 | -2477 117 | 1241 -369 | -4098 -294 | -3650 -249 | 220 |
| 195(A | 3609 -149 -9 | -2508 -500 -7942 | -4184 233 -8984 | -4493 43 -894 | -4592 -381 -1115 | -2737 399 -701 | -3989 106 -1378 | -4421 -626 * | -4496 210 * | -4701 -466 | -4051 -720 | -3440 275 | -3474 394 | -4171 45 | -4253 96 | -2294 359 | -2487 117 | -3536 -369 | -4484 -294 | -4643 -249 | 221 |
| 196(I | -1091 -149 -9 | -1076 -500 -7942 | -2583 233 -8984 | 413 43 -894 | -1145 -381 -1115 | -2551 399 -701 | -1453 106 -1378 | 2635 -626 * | -1815 210 * | -911 -466 | -317 -720 | -1908 275 | -2625 394 | -1603 45 | -1923 96 | -64 359 | 352 117 | 1441 -369 | -1667 -294 | -1289 -249 | 222 |
| 197(Q | 518 -149 -9 | -2071 -500 -7942 | -706 233 -8984 | 1236 43 -894 | -2329 -381 -1115 | -1787 399 -701 | -464 106 -1378 | 158 -626 * | -79 210 * | -2066 -466 | -1190 -720 | -460 275 | -1883 394 | 1523 45 | -571 96 | 1071 359 | 1153 117 | -1661 -369 | -2309 -294 | -1673 -249 | 223 |

TABLE 14-continued

| | | | | | | | | | | | | | | | | | | | |
|---|---|---|---|---|---|---|---|---|---|---|---|---|---|---|---|---|---|---|---|
| 198(S) | 690 -149 -9 | -1632 -500 -7942 | -3665 233 -8984 | -3707 43 -894 | -4013 -381 -1115 | -1911 399 -701 | -3224 106 -1378 | -3755 -626 * | -3549 210 * | -4023 -466 | -3114 -720 | -2519 275 | -2683 394 | -3185 45 | -3470 96 | 2818 359 | 2263 117 | -2676 -369 | -4240 -294 | -4079 -249 | 224 |
| 199(A) | 2957 -149 -9 | -1575 -500 -7942 | -3607 233 -8984 | -3525 43 -894 | -3508 -381 -1115 | 456 399 -701 | -2992 106 -1378 | -3142 -626 * | -3331 210 * | -3468 -466 | -2642 -720 | -2460 275 | -2661 394 | -2989 45 | -3286 96 | 646 359 | -1410 117 | 731 -369 | -3811 -294 | -3585 -249 | 225 |
| 200(E) | 56 -149 -9 | -2745 -500 -7942 | 1143 233 -8984 | 2154 43 -894 | -3045 -381 -1115 | -1930 399 -701 | -765 106 -1378 | -2818 -626 * | 1875 210 * | -2752 -466 | -1859 -720 | 945 275 | -2144 394 | -332 45 | -1009 96 | -1045 359 | -1166 117 | -2359 -369 | -2923 -294 | -2190 -249 | 226 |
| 201(T) | -1256 -149 -9 | -2015 -500 -7942 | -1982 233 -8984 | -1726 43 -894 | -3420 -381 -1115 | -2098 399 -701 | -1785 106 -1378 | -3082 -626 * | 927 210 * | -3191 -466 | -2379 -720 | -1663 275 | -2604 394 | -1463 45 | -1433 96 | 524 359 | 3369 117 | -2475 -369 | -3390 -294 | -2984 -249 | 227 |
| 202(W) | 2769 -149 -9 | -2207 -500 -7942 | -4068 233 -8984 | -3807 43 -894 | 2256 -381 -1115 | -3458 399 -701 | -1352 106 -1378 | -1888 -626 * | -3438 210 * | -1847 -466 | -1513 -720 | -2925 275 | -3632 394 | -2881 45 | -3227 96 | -2665 359 | -2391 117 | -1867 -369 | 3112 -294 | 296 -249 | 228 |
| 203(R) | -2470 -149 -540 | -3357 -500 -7942 | -2623 233 -8984 | 1389 43 -894 | -4114 -381 -1115 | -3061 399 -701 | -1112 106 -1378 | -3509 -626 * | 2409 210 * | -3196 -466 | -2485 -720 | -1713 275 | -3049 394 | -686 45 | 2844 96 | -2333 359 | -2214 117 | -3234 -369 | -3079 -294 | -2887 -249 | 229 |
| 204(M) | 816 -149 -9 | -1388 -500 -7942 | -1697 233 -8984 | -782 43 -894 | -226 -381 -1115 | -1511 399 -701 | -358 106 -1378 | -1120 -626 * | 1679 210 * | 119 -466 | 1761 -720 | 1028 275 | -1755 394 | -26 45 | -458 96 | -619 359 | -511 117 | -896 -369 | -1709 -294 | -1189 -249 | 230 |
| 205(L) | -2837 -149 -13 | -2376 -500 -7414 | -8456 233 -8984 | -4745 43 -894 | -1320 -381 -1115 | -4877 399 -249 | -3831 106 -2660 | 1365 -626 * | -4505 210 * | 2429 -466 | 1943 -720 | -4548 275 | 4406 394 | -3738 45 | -4219 96 | -4120 359 | -2750 117 | 1537 -369 | -2900 -294 | -2889 -249 | 231 |
| 206(C) | -1191 -149 -9 | 2897 -500 -7942 | -3560 233 -8984 | -2991 43 -894 | 2519 -381 -1115 | -2720 399 -701 | -1807 106 -1378 | -69 -626 * | -2623 210 * | -837 -466 | -305 -720 | -2465 275 | -2840 394 | -2267 45 | -2460 96 | -1855 359 | 899 117 | 2022 -369 | -1675 -294 | -1297 -249 | 232 |
| 207(G) | -1539 -149 -9 | -3140 -500 -7942 | 2028 233 -8984 | -312 43 -894 | -3421 -381 -1115 | 2111 399 -701 | -1027 106 -1378 | -3216 -626 * | 685 210 * | -3138 -466 | -2285 -720 | 998 275 | -2361 394 | 1202 45 | -1409 96 | -1339 359 | -1520 117 | -2749 -369 | -3312 -294 | -2532 -249 | 233 |
| 208(I) | 334 -149 -9 | -1130 -500 -7942 | 401 233 -8984 | 620 43 -894 | -1157 -381 -1115 | -2255 399 -701 | -1040 106 -1378 | 2289 -626 * | -1141 210 * | -979 -466 | 1812 -720 | -1358 275 | -2323 394 | -992 45 | -1401 96 | -1264 359 | -866 117 | 644 -369 | -1591 -294 | -1181 -249 | 234 |
| 209(E) | 425 -149 -9 | -2447 -500 -7942 | 1685 235 -8984 | 2151 43 -894 | -2749 -381 -1115 | -1843 399 -701 | -586 106 -1378 | -2497 -626 * | 831 210 * | -2456 -466 | -1553 -720 | -477 275 | -1993 394 | -142 45 | -743 96 | -847 359 | -928 117 | 108 -369 | -2639 -294 | -1943 -249 | 235 |
| 210(P) | -4497 -149 -169 | -4117 -500 -3204 | -4899 233 -8984 | -5251 43 -206 | -5560 -381 -2913 | -4139 399 -701 | -4798 106 -1378 | -6328 -626 * | -5454 210 * | -5976 -466 | -5741 -720 | -5026 275 | 4302 394 | -5328 45 | -5104 96 | -4798 359 | -4844 117 | -5739 -369 | -4665 -294 | -5484 -249 | 237 |
| 211(R) | -2896 -149 -9 | -3530 -500 -7942 | -3730 233 -8984 | -2192 43 -894 | -4456 -381 -1115 | -3379 399 -701 | -1195 106 -1378 | -3707 -626 * | 2481 210 * | -3319 -466 | -2662 -720 | -2040 275 | -3291 394 | 1300 45 | 3145 96 | -2762 359 | -2535 117 | -3495 -369 | -3134 -294 | -3075 -249 | 238 |
| 212(V) | -2838 -149 -9 | -2616 -500 -7942 | -4834 233 -8984 | -4880 43 -894 | -3213 -381 -1115 | -3955 399 -701 | -4416 106 -1378 | -610 -626 * | -4757 210 * | -2310 -466 | -2253 -720 | -4383 275 | -4345 394 | -4643 45 | -4642 96 | -3732 359 | -3007 117 | 3763 -369 | -4157 -294 | -3886 -249 | 239 |
| 213(A) | 3345 -149 -9 | -1674 -500 -7942 | -3727 233 -8984 | -3977 43 -894 | -4175 -381 -1115 | -1941 399 -701 | -3439 106 -1378 | -3955 -626 * | -3910 210 * | -4243 -466 | -3329 -720 | -2621 275 | -2737 394 | -3468 45 | -3709 96 | 825 359 | -1527 117 | -2788 -369 | -4405 -294 | -4282 -249 | 240 |
| 214(M) | -3386 -149 -9 | -2926 -500 -7942 | -5503 233 -8984 | -5047 43 -894 | -1187 -381 -1115 | -5101 399 -701 | -3953 106 -1378 | -644 -626 * | -4586 210 * | 916 -466 | 4893 -720 | -4906 275 | -4599 394 | -3801 45 | -4244 96 | -4517 359 | -3301 117 | -1338 -369 | -2841 -294 | -2779 -249 | 241 |

TABLE 14-continued

| | | | | | | | | | | | | | | | | | | | | |
|---|---|---|---|---|---|---|---|---|---|---|---|---|---|---|---|---|---|---|---|---|
| 215(L) | −4119 | −3542 | −5389 | −5357 | −2027 | −4767 | −4359 | −1609 | −5118 | 3293 | −979 | −5230 | −4771 | −4474 | −4724 | −5069 | −4106 | −2331 | −3412 | −3400 | 242 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 216(S) | −1944 | −2458 | −3696 | −4011 | −4410 | −2644 | −3753 | −4675 | −4191 | −4807 | −4070 | −3198 | −3384 | −3886 | −4051 | 3656 | −2393 | −3615 | −4374 | −4307 | 243 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 217(F) | −4596 | −3564 | −5022 | −5356 | 4100 | −4892 | −1140 | −3474 | −4920 | −2799 | −2888 | −3546 | −4763 | −3678 | −4303 | −4158 | −4459 | −3642 | −389 | 2808 | 244 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 218(S) | −1944 | −2458 | −3696 | −4011 | −4410 | −2644 | −3753 | −4675 | −4191 | −4807 | −4070 | −3198 | −3384 | −3886 | −4051 | 3656 | −2393 | −3615 | −4374 | −4307 | 245 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 219(T) | −1086 | −1700 | −3489 | −3680 | −4071 | −1960 | −3290 | −3842 | −3622 | −4127 | −3243 | −2550 | −2741 | −3278 | −3511 | 1633 | 3501 | −2755 | −4299 | −4122 | 246 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 220(K | −1211 | −2188 | −1252 | −684 | −2201 | −2183 | −735 | −2041 | 2458 | −2110 | 2342 | 1770 | −2264 | −372 | −433 | −1182 | −1128 | −1772 | −2263 | 1110 | 247 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 221(G | −4088 | −3924 | −4774 | −5139 | −5615 | 3825 | −4753 | −6303 | −5453 | −6014 | −5662 | −4812 | −4539 | −5232 | −5106 | −4370 | −4472 | −5527 | −4696 | −5561 | 248 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 222(S) | −1944 | −2458 | −3696 | −4011 | −4410 | −2644 | −3753 | −4675 | −4191 | −4807 | −4070 | −3198 | −3384 | −3886 | −4051 | 3656 | −2393 | −3615 | −4374 | −4307 | 249 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 223(A | 3609 | −2508 | −4184 | −4493 | −4592 | −2737 | −3989 | −4421 | −4496 | −4701 | −4051 | −3440 | −3474 | −4171 | −4253 | −2294 | −2487 | −3536 | −4484 | −4643 | 250 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 224(K | −2345 | −3215 | −2680 | −1702 | −4004 | −2994 | −1114 | −3430 | 3145 | −3150 | −2429 | −1707 | −3005 | −690 | 1537 | 1210 | −2130 | −3134 | −3052 | −2847 | 251 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 225(H | −1041 | −1842 | −1795 | −1535 | −3225 | 1554 | 2940 | −2958 | −1555 | −3088 | −2233 | −1512 | −2445 | −1442 | −1925 | 2143 | 928 | −2312 | −3333 | −2843 | 252 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 226(P) | −1812 | −3493 | 1638 | 2272 | −3746 | −2139 | −1234 | −3572 | 714 | −3480 | −2668 | −741 | 2320 | −848 | −1793 | −1570 | −1815 | −3091 | −3658 | −2819 | 253 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 227(M | −1063 | −1672 | −1185 | 1731 | −1647 | −2144 | −910 | −1218 | −725 | 1142 | 2726 | 1099 | −2261 | −651 | −1101 | −1179 | −1008 | −1100 | −2011 | −1532 | 254 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 228(W | −150 | 757 | 49 | 299 | −277 | −651 | 839 | −485 | 392 | −910 | 599 | 300 | −401 | 623 | 162 | −99 | 38 | −448 | 1107 | 126 | 255 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 229(V | −1683 | −1779 | −4225 | −4114 | −2704 | −2952 | −3573 | −161 | −3855 | −1868 | −1633 | −3296 | −3474 | −3653 | −3791 | −2302 | 2073 | 3159 | −3712 | −3334 | 256 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 230(E) | 576 | −3124 | 2215 | 2294 | −3448 | −2061 | −1092 | −3240 | −936 | −3183 | −2340 | −696 | −2393 | −692 | −1547 | −1375 | 1093 | −2772 | −3374 | −2589 | 257 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |
| 231(K | 315 | −2794 | −1360 | −1079 | −3606 | −2397 | −1201 | −3242 | 3269 | −3135 | −2344 | 1290 | −2657 | −798 | −553 | −1655 | −1723 | −2800 | −3186 | −2733 | 258 |
| | −149 | −500 | 233 | 43 | −381 | 399 | 106 | −626 | 210 | −466 | −720 | 275 | 394 | 45 | 96 | 359 | 117 | −369 | −294 | −249 | |
| | −9 | −7942 | −8984 | −894 | −1115 | −701 | −1378 | * | | | | | | | | | | | | | |

TABLE 14-continued

| | | | | | | | | | | | | | | | | | | |
|---|---|---|---|---|---|---|---|---|---|---|---|---|---|---|---|---|---|---|
| 232(V) | -1806 -149 -9 | -1830 -500 -7942 | -4356 233 -8984 | -4254 -894 | -2729 -381 -1115 | -3152 399 -701 | -3789 106 -1378 | -6 -626 * | -4016 210 * | -1803 -466 | -1616 -720 | -3476 275 | -3637 394 | -3839 45 | -3966 96 | -2513 359 | 660 117 | 3495 -369 | -3859 -294 | -3459 -249 | 259 |
| 233(Q) | 793 -149 -9 | -1527 -500 -7942 | -1108 233 -8984 | -552 43 -894 | -1618 -381 -1115 | -1947 399 -701 | 1457 106 -1378 | 1157 -626 * | 637 210 * | -1440 -466 | -683 -720 | -772 275 | -2030 394 | 1773 45 | -839 96 | -896 359 | 518 117 | 491 -369 | -1868 -294 | -1365 -249 | 260 |
| 234(E) | 300 -149 -9 | -2398 -500 -7942 | 695 233 -8984 | 1659 43 -894 | -2713 -381 -1115 | -1806 399 -701 | -518 106 -1378 | -2470 -626 * | 1395 210 * | -2411 -466 | -1494 -720 | 1531 275 | -1936 394 | 1405 45 | -648 96 | -775 359 | -852 117 | -2018 -369 | -2579 -294 | -1883 -249 | 261 |
| 235(A) | 3370 -149 -9 | -1675 -500 -7942 | -3725 233 -8984 | -3979 43 -894 | -4176 -381 -1115 | -1943 399 -701 | -3442 106 -1378 | -3956 -626 * | -3915 210 * | -4245 -466 | -3332 -720 | -2623 275 | -2739 394 | -3473 45 | -3712 96 | 667 359 | -1529 117 | -2789 -369 | -4406 -294 | -4283 -249 | 262 |
| 236(T) | -1487 -149 -9 | -1747 -500 -7942 | -4009 233 -8984 | -3951 43 -894 | -2829 -381 -1115 | -2596 399 -701 | -3358 106 -1378 | -658 -626 * | -3663 210 * | -2137 -466 | -1837 -720 | -3024 275 | -3208 394 | -3442 45 | -3576 96 | -1949 359 | 3247 117 | 2128 -369 | -3661 -294 | -3318 -249 | 263 |
| 237(K) | 78 -149 -9 | -2444 -500 -7942 | -636 233 -8984 | 1476 43 -894 | -2774 -381 -1115 | -1872 399 -701 | -554 106 -1378 | -2516 -626 * | 2347 210 * | -2450 -466 | -1542 -720 | 1061 275 | -1996 394 | 1188 45 | -567 96 | -849 359 | -918 117 | -2073 -369 | -2605 -294 | -1935 -249 | 264 |
| 238(L) | -2340 -149 -9 | -2043 -500 -7942 | -4429 233 -8984 | -3825 43 -894 | -1249 -381 -1115 | -4051 399 -701 | -2880 106 -1378 | 2209 -626 * | 47 210 * | 2445 -466 | -154 -720 | -3576 275 | -3849 394 | -2947 45 | -3012 96 | -3227 359 | -2264 117 | -489 -369 | -2490 -294 | -2321 -249 | 265 |
| 239(A) | 3066 -149 -9 | -1532 -500 -7942 | -3416 233 -8984 | -3204 43 -894 | -2546 -381 -1115 | -2126 399 -701 | -2613 106 -1378 | -1745 -626 * | -2919 210 * | 251 -466 | -1678 -720 | -2434 275 | -2743 394 | -2680 45 | -2903 96 | -1429 359 | 721 117 | -1481 -369 | -3078 -294 | -2775 -249 | 266 |
| 240(K) | -2775 -149 -9 | -3478 -500 -7942 | -3431 233 -8984 | -2065 43 -894 | -4356 -381 -1115 | -3299 399 -701 | -1170 106 -1378 | -3648 -626 * | 3068 210 * | -3281 -466 | -2609 -720 | -1958 275 | -3227 394 | 2481 45 | 1606 96 | -2643 359 | -2444 117 | -3419 -369 | -3113 -294 | -3021 -249 | 267 |
| 241(E) | 5 -149 -9 | -3248 -500 -7942 | -527 233 -8984 | 3274 43 -894 | -3691 -381 -1115 | -2238 399 -701 | -1242 106 -1378 | -3429 -626 * | 736 210 * | -3351 -466 | -2559 -720 | -905 275 | -2586 394 | -855 45 | -1282 96 | -1630 359 | -1816 117 | -2982 -369 | -3491 -294 | -2801 -249 | 268 |
| 242(R) | 1203 -149 -9 | -1274 -500 -7942 | -1535 233 -8984 | -960 43 -894 | 714 -381 -1115 | -2112 399 -701 | -836 106 -1378 | -874 -626 * | 1242 210 * | 45 -466 | 1502 -720 | -1087 275 | -2184 394 | -670 45 | 1607 96 | -1097 359 | -814 117 | -732 -369 | -1655 -294 | -1220 -249 | 269 |
| 243(A) | 1867 -149 -9 | -2550 -500 -7942 | 755 233 -8984 | 648 43 -894 | -2859 -381 -1115 | -1875 399 -701 | -646 106 -1378 | -2618 -626 * | -291 210 * | -2563 -466 | -1661 -720 | 1632 275 | -2046 394 | -205 45 | 1386 96 | -915 359 | -1009 117 | -2170 -369 | -2737 -294 | -2031 -249 | 270 |
| 244(P) | -1833 -149 -9 | -2267 -500 -7942 | -3769 233 -8984 | -3944 43 -894 | -3591 -381 -1115 | -2645 399 -701 | -3527 106 -1378 | -2530 -626 * | -3805 210 * | -3285 -466 | -2936 -720 | -3132 275 | -3954 394 | -3636 45 | -3703 96 | -2130 359 | -2228 117 | 835 -369 | -4002 -294 | -3761 -249 | 271 |
| 245(D) | 206 -149 -9 | -2972 -500 -7942 | 2710 233 -8984 | 1351 43 -894 | -3255 -381 -1115 | -2000 399 -701 | 1755 106 -1378 | -3042 -626 * | -683 210 * | -2972 -466 | -2100 -720 | -614 275 | -2269 394 | 1462 45 | -1262 96 | -1213 359 | -1369 117 | -2579 -369 | -3148 -294 | -2386 -249 | 272 |
| 246(L) | -3414 -149 -9 | -2874 -500 -7942 | -5769 233 -8984 | -5161 43 -894 | 1383 -381 -1115 | -5422 399 -701 | -4072 106 -1378 | 994 -626 * | -4912 210 * | 2728 -466 | 2007 -720 | -5118 275 | -4630 394 | -3791 45 | -4438 96 | -4708 359 | -3264 117 | -1344 -369 | -2810 -294 | -2947 -249 | 273 |
| 247(A) | 1831 -149 -9 | -2029 -500 -7942 | 575 233 -8984 | -204 43 -894 | -2274 -381 -1115 | -1806 399 -701 | -494 106 -1378 | -1962 -626 * | 927 210 * | -82 -466 | -1160 -720 | -494 275 | 270 394 | -72 45 | -607 96 | -735 359 | 508 117 | -1613 -369 | -2285 -294 | -1663 -249 | 274 |
| 248(I) | -2431 -149 -9 | -2000 -500 -7942 | -4947 233 -8984 | -4466 43 -894 | 1231 -381 -1115 | -4532 399 -701 | -3688 106 -1378 | 3189 -626 * | -4249 210 * | 517 -466 | -529 -720 | -4183 275 | -4266 394 | -3781 45 | -4114 96 | -3766 359 | -2383 117 | 1363 -369 | -3060 -294 | -2816 -249 | 275 |

TABLE 14-continued

| | | | | | | | | | | | | | | | | | | | | | |
|---|---|---|---|---|---|---|---|---|---|---|---|---|---|---|---|---|---|---|---|---|---|
| 249(D) | -4232 | -4465 | 4158 | -2649 | -5412 | -3676 | -3575 | -6036 | -4125 | -5722 | -5419 | -2993 | -4216 | -3512 | -4617 | -4077 | -4401 | -5553 | -4696 | -4914 | 276 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 250(G) | -4088 | -3924 | -4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 277 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 251(E) | -4205 | -4417 | -2343 | 3901 | -5349 | -3698 | -3534 | -5837 | -3838 | -5561 | -5237 | -3039 | -4218 | -3453 | -4201 | -4072 | -4352 | -5409 | -4640 | -4860 | 278 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 252(L) | -3602 | -3015 | -5919 | -5328 | 1158 | -5654 | -4138 | -616 | -5093 | 2938 | 2013 | -5330 | -4744 | -3877 | -4575 | -4984 | -3438 | -1455 | -2794 | -2838 | 279 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 253(Q) | -4207 | -4117 | -3531 | -3731 | -4752 | -3930 | -3721 | -5554 | -3395 | -5179 | -4897 | -3823 | -4399 | 4556 | -3405 | -4301 | -4380 | -5208 | -4301 | -4384 | 280 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 254(F) | -2863 | -2433 | -5172 | -4640 | 3169 | -4702 | -3234 | -392 | -4348 | 1785 | -84 | -4307 | -4290 | -3544 | -4021 | -3916 | -2769 | 1504 | -2393 | -2005 | 281 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 255(D) | -4232 | -4465 | 4158 | -2649 | -5412 | -3676 | -3575 | -6036 | -4125 | -5722 | -5419 | -2993 | -4216 | -3512 | -4617 | -4077 | -4401 | -5553 | -4696 | -4914 | 282 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 256(A) | 3609 | -2508 | -4184 | -4493 | -4592 | -2737 | -3989 | -4421 | -4496 | -4701 | -4051 | -3440 | -3474 | -4171 | -4253 | -2294 | -2487 | -3536 | -4484 | -4643 | 283 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 257(A) | 3186 | -1669 | -3728 | -3961 | -4171 | -1936 | -3425 | -3953 | -3886 | -4235 | -3318 | -2613 | -2731 | -3447 | -3695 | 1524 | -1520 | -2783 | -4398 | -4275 | 284 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 258(F) | -3002 | -2525 | -5316 | -4818 | 3177 | -4924 | -3350 | 2613 | -4551 | 818 | -147 | -4496 | -4441 | -3703 | -4215 | -4169 | -2905 | -737 | -2444 | -1989 | 285 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 259(V) | -2294 | -2438 | 724 | -2485 | -3071 | -3156 | -3064 | -720 | -3372 | -2390 | -2164 | -2598 | -3629 | -2975 | -3716 | -2757 | -2460 | 3538 | -3861 | -3370 | 286 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 260(P) | -1594 | -2934 | -619 | 588 | -3418 | -2163 | -1118 | -3148 | 755 | -3092 | -2272 | -870 | 3320 | -720 | -1108 | 321 | -1590 | -2706 | -3251 | -2595 | 287 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 261(E) | 232 | -2432 | -633 | 1887 | -2799 | -1880 | -622 | -2541 | 1768 | -2491 | -1591 | -543 | -2032 | -178 | -679 | 1460 | -962 | -2096 | -2660 | -1989 | 288 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 262(V) | -2838 | -2616 | 4834 | -4880 | -3213 | -3955 | -4416 | -610 | -4757 | -2310 | -2253 | -4383 | -4345 | -4643 | -4642 | -3732 | -3007 | 3763 | -4157 | -3886 | 289 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |

TABLE 14-continued

| | | | | | | | | | | | | | | | | | | |
|---|---|---|---|---|---|---|---|---|---|---|---|---|---|---|---|---|---|---|
| 263(A) | 3303<br>-149<br>-9 | -1827<br>-500<br>-7942 | -3692<br>233<br>-8984 | -3978<br>43<br>-894 | -4328<br>-381<br>-1115 | 1129<br>399<br>-701 | -3541<br>106<br>-1378 | -4137<br>-626<br>* | -4037<br>210<br>* | -4403<br>-466 | -3503<br>-720 | -2739<br>275 | -2867<br>394 | -3583<br>45 | -3840<br>96 | -1477<br>359 | -1693<br>117 | -2962<br>-369 | -4468<br>-294 | -4428<br>-249 | 290 |
| 266(K) | -4125<br>-149<br>-9 | -4091<br>-500<br>-7942 | -4017<br>233<br>-8984 | -3615<br>43<br>-894 | -5101<br>-381<br>-1115 | -3960<br>399<br>-701 | -2958<br>106<br>-1378 | -5182<br>-626<br>* | 3972<br>210<br>* | -4825<br>-466 | -4345<br>-720 | -3552<br>275 | -4249<br>394 | -2709<br>45 | -1809<br>96 | -4154<br>359 | -4044<br>117 | -4895<br>-369 | -4132<br>-294 | -4389<br>-249 | 293 |
| 267(A) | 3348<br>-149<br>-9 | -2109<br>-500<br>-7942 | -3336<br>233<br>-8984 | -3412<br>43<br>-894 | -1764<br>-381<br>-1115 | -2509<br>399<br>-701 | -2437<br>106<br>-1378 | -2956<br>-626<br>* | -3286<br>210<br>* | -3118<br>-466 | -2630<br>-720 | -2708<br>275 | -3150<br>394 | -3050<br>45 | -3249<br>96 | -1903<br>359 | -2016<br>117 | -2533<br>-369 | -2364<br>-294 | 1487<br>-249 | 294 |
| 268(P) | -1528<br>-149<br>-9 | -2315<br>-500<br>-7942 | -1720<br>233<br>-8984 | -1687<br>43<br>-894 | -3833<br>-381<br>-1115 | -2233<br>399<br>-701 | -1895<br>106<br>-1378 | -3559<br>-626<br>* | 797<br>210<br>* | -3582<br>-466 | -2793<br>-720 | -1690<br>275 | 3653<br>394 | -1574<br>45 | -1445<br>96 | 406<br>359 | -1768<br>117 | -2881<br>-369 | -3673<br>-294 | -3270<br>-249 | 295 |
| 269(G) | -1935<br>-149<br>-9 | -3089<br>-500<br>-7942 | 2442<br>233<br>-8984 | -885<br>43<br>-894 | -4418<br>-381<br>-1115 | 2762<br>399<br>-701 | -1974<br>106<br>-1378 | -4330<br>-626<br>* | -2285<br>210<br>* | -4310<br>-466 | -3586<br>-720 | -1182<br>275 | -2821<br>394 | -1681<br>45 | -3048<br>96 | 394<br>359 | -2183<br>117 | -3549<br>-369 | -4481<br>-294 | -3646<br>-249 | 296 |
| 270(S) | -1944<br>-149<br>-9 | -2458<br>-500<br>-7942 | -3696<br>233<br>-8984 | -4011<br>43<br>-894 | -4410<br>-381<br>-1115 | -2644<br>399<br>-701 | -3753<br>106<br>-1378 | -4675<br>-626<br>* | -4191<br>210<br>* | -4807<br>-466 | -4070<br>-720 | -3198<br>275 | -3384<br>394 | -3886<br>45 | -4051<br>96 | 3656<br>359 | -2393<br>117 | -3615<br>-369 | -4374<br>-294 | -4307<br>-249 | 297 |
| 271(K) | -986<br>-149<br>-9 | -2487<br>-500<br>-7942 | 579<br>233<br>-8984 | 781<br>43<br>-894 | -2798<br>-381<br>-1115 | -1840<br>399<br>-701 | -584<br>106<br>-1378 | -2559<br>-626<br>* | 1709<br>210<br>* | -2499<br>-466 | -1588<br>-720 | 1699<br>275 | 1485<br>394 | -137<br>45 | -743<br>96 | 394<br>359 | -935<br>117 | -2105<br>-369 | -2668<br>-294 | -1964<br>-249 | 298 |
| 272(V) | -2488<br>-149<br>-9 | -1997<br>-500<br>-7942 | -5115<br>233<br>-8984 | -4741<br>43<br>-894 | -2236<br>-381<br>-1115 | -4876<br>399<br>-701 | -4521<br>106<br>-1378 | 1399<br>-626<br>* | -4638<br>210<br>* | 586<br>-466 | -992<br>-720 | -4534<br>275 | -4596<br>394 | -4394<br>45 | -4675<br>96 | -4204<br>359 | -2466<br>117 | 3282<br>-369 | -3849<br>-294 | -3500<br>-249 | 299 |
| 273(A) | 2860<br>-149<br>-9 | -2613<br>-500<br>-7942 | -1445<br>233<br>-8984 | -1105<br>43<br>-894 | -3345<br>-381<br>-1115 | -2365<br>399<br>-701 | -1181<br>106<br>-1378 | -2968<br>-626<br>* | 911<br>210<br>* | -2930<br>-466 | -2150<br>-720 | -1269<br>275 | -2615<br>394 | 1502<br>45 | -562<br>96 | -1587<br>359 | -1627<br>117 | -2570<br>-369 | -3048<br>-294 | -2602<br>-249 | 300 |
| 274(G) | -4088<br>-149<br>-9 | -3924<br>-500<br>-7942 | -4774<br>233<br>-8984 | -5139<br>43<br>-894 | -5615<br>-381<br>-1115 | 3825<br>399<br>-701 | -4753<br>106<br>-1378 | -6303<br>-626<br>* | -5453<br>210<br>* | -6014<br>-466 | -5662<br>-720 | -4812<br>275 | -4539<br>394 | -5232<br>45 | -5106<br>96 | -4370<br>359 | -4472<br>117 | -5527<br>-369 | -4696<br>-294 | -5561<br>-249 | 301 |
| 275(H) | -1098<br>-149<br>-9 | -2519<br>-500<br>-7942 | 644<br>233<br>-8984 | -333<br>43<br>-894 | -2880<br>-381<br>-1115 | -1987<br>399<br>-701 | 2767<br>106<br>-1378 | -2597<br>-626<br>* | 2281<br>210<br>* | -2509<br>-466 | -1617<br>-720 | 857<br>275 | -2093<br>394 | -153<br>45 | 1114<br>96 | -970<br>359 | -1024<br>117 | -2167<br>-369 | -2636<br>-294 | -2015<br>-249 | 302 |
| 276(A) | 3609<br>-149<br>-9 | -2508<br>-500<br>-7942 | -4184<br>233<br>-8984 | -4493<br>43<br>-894 | -4592<br>-381<br>-1115 | -2737<br>399<br>-701 | -3989<br>106<br>-1378 | -4421<br>-626<br>* | -4496<br>210<br>* | -4701<br>-466 | -4051<br>-720 | -3440<br>275 | -3474<br>394 | -4171<br>45 | -4253<br>96 | -2294<br>359 | -2487<br>117 | -3536<br>-369 | -4484<br>-294 | -4643<br>-249 | 303 |
| 277(N) | -1586<br>-149<br>-9 | -2305<br>-500<br>-7942 | -1738<br>233<br>-8984 | -2020<br>43<br>-894 | -4028<br>-381<br>-1115 | -2232<br>399<br>-701 | -2587<br>106<br>-1378 | -3973<br>-626<br>* | -2635<br>210<br>* | -4158<br>-466 | -3406<br>-720 | 4054<br>275 | -2920<br>394 | -2402<br>45 | -2900<br>96 | -1720<br>359 | 681<br>117 | -3116<br>-369 | -4157<br>-294 | -3676<br>-249 | 304 |
| 278(V) | -2446<br>-149<br>-9 | -1963<br>-500<br>-7942 | -5100<br>233<br>-8984 | -4786<br>43<br>-894 | -2548<br>-381<br>-1115 | -4847<br>399<br>-701 | -4816<br>106<br>-1378 | 1583<br>-626<br>* | -4714<br>210<br>* | -1330<br>-466 | -1276<br>-720 | -4562<br>275 | -4651<br>394 | -4631<br>45 | -4841<br>96 | -4218<br>359 | -2447<br>117 | 3468<br>-369 | -4224<br>-294 | -3729<br>-249 | 305 |
| 279(W) | -150<br>-149<br>-9 | 757<br>-500<br>-7942 | 49<br>233<br>-8984 | 299<br>43<br>-894 | -277<br>-381<br>-1115 | -651<br>399<br>-701 | 839<br>106<br>-1378 | -485<br>-626<br>* | 392<br>210<br>* | -910<br>-466 | 599<br>-720 | 300<br>275 | -401<br>394 | 623<br>45 | 162<br>96 | -99<br>359 | 38<br>117 | -448<br>-369 | 1107<br>-294 | 126<br>-249 | 306 |

TABLE 14-continued

| | | | | | | | | | | | | | | | | | | |
|---|---|---|---|---|---|---|---|---|---|---|---|---|---|---|---|---|---|---|
| 280(F) | −3486 −149 −9 | −2932 −500 −7942 | −5765 233 −8984 | −5195 43 −894 | 3114 −381 −1115 | −5447 399 −701 | −3820 106 −1378 | −632 −626 * | −4937 210 * | 2173 −466 | 2384 −720 | −5073 275 | −4656 394 | −3798 45 | −4452 96 | −4740 359 | −3334 117 | −1436 −369 | −2628 −294 | −2474 −249 | 307 |
| 281(I) | −2458 −149 −9 | −1961 −500 −7942 | −5125 233 −8984 | −4807 43 −894 | −2569 −381 −1115 | −4914 399 −701 | −4890 106 −1378 | 3219 −626 * | −4751 210 * | −1339 −466 | −1284 −720 | −4603 275 | −4685 394 | −4676 45 | −4892 96 | −4286 359 | −2453 117 | 2471 −369 | −4276 −294 | −3778 −249 | 308 |
| 282(F) | −4720 −149 −9 | −3927 −500 −7942 | −5139 233 −8984 | −5454 43 −894 | 4513 −381 −1115 | −4504 399 −701 | −2520 106 −1378 | −3938 −626 * | −5326 210 * | −3307 −466 | −3429 −720 | −4469 275 | −4782 394 | −4575 45 | −4818 96 | −4787 359 | −4810 117 | −4172 −369 | −1812 −294 | −736 −249 | 309 |
| 283(P) | −4497 −149 −9 | −4117 −500 −7942 | −4899 233 −8984 | −5251 43 −894 | −5560 −381 −1115 | −4139 399 −701 | −4798 106 −1378 | −6328 −626 * | −5454 210 * | −5976 −466 | −5741 −720 | −5026 275 | 4302 394 | −5328 45 | −5104 96 | −4798 359 | −4844 117 | −5739 −369 | −4665 −294 | −5484 −249 | 310 |
| 284(D) | −2322 −149 −9 | −4185 −500 −7942 | 3035 233 −8984 | 1469 43 −894 | −4418 −381 −1115 | −2266 399 −701 | −1625 106 −1378 | −4341 −626 * | −1869 210 * | −4214 −466 | −3539 −720 | −867 275 | −2800 394 | −1293 45 | −2724 96 | 1786 359 | −2396 117 | −3805 −369 | −4409 −294 | −3395 −249 | 311 |
| 285(L) | −3492 −149 −9 | −2925 −500 −7942 | −5831 233 −8984 | −5302 43 −894 | −1190 −381 −1115 | −5571 399 −701 | −4334 106 −1378 | 974 −626 * | −5050 210 * | 3059 −466 | 17 −720 | −5312 275 | −4763 394 | −3965 45 | −4606 96 | −4957 359 | −3364 117 | −1095 −369 | −2972 −294 | −3089 −249 | 312 |
| 286(Q) | −2004 −149 −9 | −3769 −500 −7942 | 1173 233 −8984 | 2079 43 −894 | −3991 −381 −1115 | −2187 399 −701 | −1375 106 −1378 | −3849 −626 * | −1403 210 * | −3743 −466 | −2969 −720 | 1136 275 | −2626 394 | 3177 45 | −2117 96 | −1727 359 | −2027 117 | −3352 −369 | −3926 −294 | −3026 −249 | 313 |
| 287(A) | 2861 −149 −9 | 2401 −500 −7942 | −3941 233 −8984 | −3933 43 −894 | −3713 −381 −1115 | −1915 399 −701 | −3209 106 −1378 | −3405 −626 * | −3647 210 * | −3703 −466 | −2846 −720 | −2573 275 | −2679 394 | −3249 45 | −3498 96 | 1246 359 | 795 117 | −2497 −369 | −4004 −294 | −3830 −249 | 314 |
| 288(G) | 804 −149 −9 | −1917 −500 −7942 | −3555 233 −8984 | −3872 43 −894 | −4406 −381 −1115 | 3488 399 −701 | −3564 106 −1378 | −4245 −626 * | −4053 210 * | −4497 −466 | −3611 −720 | −2768 275 | −2934 394 | −3603 45 | −3880 96 | −1567 359 | −1787 117 | −3064 −369 | −4502 −294 | −4481 −249 | 315 |
| 289(N) | −3642 −149 −9 | −3838 −500 −7942 | −3004 233 −8984 | −3356 43 −894 | −4743 −381 −1115 | −3612 399 −701 | −3773 106 −1378 | −5643 −626 * | −4099 210 * | −5460 −466 | −5060 −720 | 4378 275 | −4185 394 | −3865 45 | −4225 96 | −3744 359 | −3950 117 | −5002 −369 | −4391 −294 | −4381 −249 | 316 |
| 290(I) | −3202 −149 −9 | −2787 −500 −7942 | −5004 233 −8984 | −4996 43 −894 | −2836 −381 −1115 | −4384 399 −701 | −4440 106 −1378 | 3937 −626 * | −4838 210 * | −1815 −466 | −1871 −720 | −4704 275 | −4600 394 | −4683 45 | −4704 96 | −4353 359 | −3280 117 | −603 −369 | −3938 −294 | −3661 −249 | 317 |
| 291(G) | 1452 −149 −9 | −1874 −500 −7942 | −3596 233 −8984 | −3903 43 −894 | −4376 −381 −1115 | 3335 399 −701 | −3550 106 −1378 | −4203 −626 * | −4044 210 * | −4459 −466 | −3565 −720 | −2747 275 | −2900 394 | −3588 45 | −3862 96 | −1522 359 | −1740 117 | −3018 −369 | −4492 −294 | −4461 −249 | 318 |
| 292(Y) | −4791 −149 −9 | −3935 −500 −7942 | −4914 233 −8984 | −5231 43 −894 | −815 −381 −1115 | −4530 399 −701 | −2178 106 −1378 | −4357 −626 * | −5024 210 * | −3745 −466 | −3807 −720 | −4206 275 | −4772 394 | −4328 45 | −4584 96 | −4677 359 | −4837 117 | −4435 −369 | −1477 −294 | 4857 −249 | 319 |
| 293(K) | −4125 −149 −9 | −4091 −500 −7942 | −4017 233 −8984 | −3615 43 −894 | −5101 −381 −1115 | −3960 399 −701 | −2958 106 −1378 | −5182 −626 * | 3972 210 * | −4825 −466 | −4345 −720 | −3552 275 | −4249 394 | −2709 45 | −1809 96 | −4154 359 | −4044 117 | −4895 −369 | −4132 −294 | −4389 −249 | 320 |
| 294(I) | −3130 −149 −9 | −2603 −500 −7942 | −5572 233 −8984 | −5096 43 −894 | −1392 −381 −1115 | −5301 399 −701 | −4317 106 −1378 | 3061 −626 * | −4881 210 * | 2084 −466 | −185 −720 | −5010 275 | −4688 394 | −4034 45 | −4578 96 | −4656 359 | −3046 117 | −463 −369 | −3127 −294 | −3143 −249 | 321 |
| 295(A) | 2675 −149 −9 | −1535 −500 −7942 | −3836 233 −8984 | −3683 43 −894 | −2774 −381 −1115 | −2214 399 −701 | −2959 106 −1378 | −1215 −626 * | −3410 210 * | −2393 −466 | −1857 −720 | −2670 275 | −2859 394 | −3085 45 | −3310 96 | −1533 359 | 792 117 | 2057 −369 | −3350 −294 | −3057 −249 | 322 |

TABLE 14-continued

| | | | | | | | | | | | | | | | | | | | |
|---|---|---|---|---|---|---|---|---|---|---|---|---|---|---|---|---|---|---|---|
| 296(Q) | -4207 | -4117 | -3531 | -3731 | -4752 | -3930 | -3721 | -5554 | -3395 | -5179 | -4897 | -3823 | -4399 | 4556 | -3405 | -4301 | -4380 | -5208 | -4301 | -4384 | 323 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 297(R) | -4488 | -4181 | -4789 | -4318 | -5193 | -4148 | -3436 | -5568 | -2393 | -5152 | -4748 | -4156 | -4479 | -3286 | 4202 | -4614 | -4467 | -5273 | -4267 | -4649 | 324 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 298(F) | -3500 | -2941 | -5773 | -5206 | 3166 | -5461 | -3812 | -635 | -4949 | 2227 | 2003 | -5083 | -4665 | -3805 | -4462 | -4757 | -3346 | -1441 | -2619 | -2449 | 325 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 299(G) | 2279 | -1650 | -3675 | -3870 | -4196 | 2606 | -3385 | -3993 | -3836 | -4243 | -3303 | -2572 | -2706 | -3382 | -3678 | 828 | -1491 | -2786 | -4412 | -4298 | 326 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 300(K) | -1571 | -2888 | -927 | -655 | -3321 | 2063 | 1468 | -3019 | 2355 | -2910 | -2082 | 920 | -2447 | -523 | -551 | -1431 | -1504 | -2612 | -2998 | -2431 | 327 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 301(F) | 2448 | -2615 | -4303 | -4172 | 2956 | -3922 | -1214 | -2324 | -3828 | -2183 | -1926 | -3107 | -3996 | -3105 | -3543 | -3119 | -2926 | -2325 | -560 | 2239 | 328 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 302(E) | -1402 | -2920 | 1061 | 2832 | -3242 | -2054 | -879 | -2998 | 774 | -2910 | -2042 | -672 | -2284 | -454 | 1073 | -1230 | -1357 | -2549 | -3055 | -2355 | 329 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 303(A) | 3609 | -2508 | -4184 | -4493 | -4592 | -2737 | -3989 | -4421 | -4496 | -4701 | -4051 | -3440 | -3474 | -4171 | -4253 | -2294 | -2487 | -3536 | -4484 | -4643 | 330 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 304(I) | -1878 | -1552 | -4312 | -3775 | -1491 | -3734 | -2739 | 2447 | -3471 | 521 | -541 | -3367 | -3656 | -3110 | -3335 | -2889 | -1832 | 2126 | -2430 | 2171 | 331 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 305(G) | -4088 | -3924 | -4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 332 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 306(P) | -4497 | -4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 333 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 307(I) | -2574 | -2082 | -5179 | -4778 | -2009 | -4923 | -4424 | 3104 | -4656 | 1327 | -776 | -4584 | -4587 | -4278 | -4620 | -4242 | -2542 | 1595 | -3640 | -3399 | 334 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 308(C) | -1490 | 2918 | -3842 | -3258 | -1170 | -3142 | -2133 | 1934 | -2902 | 1595 | -258 | -2806 | -3152 | -2528 | -2741 | -2266 | 1394 | 65 | -1929 | -1611 | 335 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 309(Q) | -4207 | -4117 | -3531 | -3731 | -4752 | -3930 | -3721 | -5554 | -3395 | -5179 | -4897 | -3823 | -4399 | 4556 | -3405 | -4301 | -4380 | -5208 | -4301 | -4384 | 336 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 310(G) | -4088 | -3924 | -4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 337 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 311(L) | -3686 | -3084 | -5727 | -5319 | 2036 | -5453 | -3331 | -789 | -5052 | 2929 | -88 | -4966 | -4743 | -3883 | -4542 | -4837 | -3542 | -1589 | -2266 | -1680 | 338 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |

TABLE 14-continued

| | | | | | | | | | | | | | | | | | | | | | |
|---|---|---|---|---|---|---|---|---|---|---|---|---|---|---|---|---|---|---|---|---|---|
| 312(A) | 2898 -149 -9 | -1987 -500 -7942 | -2240 233 -8984 | -2485 43 -894 | -4049 -381 -1115 | -2085 399 -701 | -2826 106 -1378 | -3885 -626 * | -3004 210 * | -4117 -466 | -3288 -720 | 2707 275 | -2813 394 | -2683 45 | -3186 96 | -1506 359 | -1726 117 | -2917 -369 | -4217 -294 | -3861 -249 | 339 |
| 313(K) | 1066 -149 -9 | -2626 -500 -7942 | -1795 233 -8984 | -1052 43 -894 | -3050 -381 -1115 | -2498 399 -701 | -872 106 -1378 | -2618 -626 * | 2866 210 * | -2563 -466 | 1526 -720 | -1206 275 | -2543 394 | -458 45 | 1142 96 | -1556 359 | -1494 117 | -2321 -369 | -2682 -294 | -2281 -249 | 340 |
| 314(P) | -4497 -149 -9 | -4117 -500 -7942 | -4899 233 -8984 | -5251 43 -894 | -5560 -381 -1115 | -4139 399 -701 | -4798 106 -1378 | -6328 -626 * | -5454 210 * | -5976 -466 | -5741 -720 | -5026 275 | 4302 394 | -5328 45 | -5104 96 | -4798 359 | -4844 117 | -5739 -369 | -4665 -294 | -5484 -249 | 341 |
| 315(V) | -2475 -149 -9 | -1980 -500 -7942 | -5117 233 -8984 | -4752 43 -894 | -2317 -381 -1115 | -4893 399 -701 | -4598 106 -1378 | 2349 -626 * | -4663 210 * | 557 -466 | -1062 -720 | -4548 275 | -4617 394 | -4458 45 | -4725 96 | -4228 359 | -2455 117 | 2932 -369 | -3943 -294 | -3564 -249 | 342 |
| 316(H) | 173 -149 -9 | -2262 -500 -7942 | -944 233 -8984 | -767 43 -894 | -3091 -381 -1115 | -1973 399 -701 | 2974 106 -1378 | -2865 -626 * | -947 210 * | -2905 -466 | -2052 -720 | 2949 275 | -2338 394 | -840 45 | -1414 96 | 1020 359 | -1292 117 | -2346 -369 | -3104 -294 | -2474 -249 | 343 |
| 317(D) | -4232 -149 -9 | -4465 -500 -7942 | 4158 233 -8984 | -2649 43 -894 | -5412 -381 -1115 | -3676 399 -701 | -3575 106 -1378 | -6036 -626 * | -4125 210 * | -5722 -466 | -5419 -720 | -2993 275 | -4216 394 | -3512 45 | -4617 96 | -4077 359 | -4401 117 | -5553 -369 | -4696 -294 | -4914 -249 | 344 |
| 318(L) | -4119 -149 -9 | -3542 -500 -7942 | -5389 233 -8984 | -5357 43 -894 | -2027 -381 -1115 | -4767 399 -701 | -4359 106 -1378 | -1609 -626 * | -5118 210 * | 3293 -466 | -979 -720 | -5230 275 | -4771 394 | -4474 45 | -4724 96 | -5069 359 | -4106 117 | -2331 -369 | -3412 -294 | -3400 -249 | 345 |
| 319(S) | -1944 -149 -9 | -2458 -500 -7942 | -3696 233 -8984 | -4011 43 -894 | -4410 -381 -1115 | -2644 399 -701 | -3753 106 -1378 | -4675 -626 * | -4191 210 * | -4807 -466 | -4070 -720 | -3198 275 | -3384 394 | -3886 45 | -4051 96 | 3656 359 | -2393 117 | -3615 -369 | -4374 -294 | -4307 -249 | 346 |
| 320(R) | -4488 -149 -9 | -4181 -500 -7942 | -4789 233 -8984 | -4318 43 -894 | -5193 -381 -1115 | -4148 399 -701 | -3436 106 -1378 | -5568 -626 * | -2393 210 * | -5152 -466 | -4748 -720 | -4156 275 | -4479 394 | -3286 45 | 4202 96 | -4614 359 | -4467 117 | -5273 -369 | -4267 -294 | -4649 -249 | 347 |
| 321(G) | -4088 -149 -9 | -3924 -500 -7942 | -4774 233 -8984 | -5139 43 -894 | -5615 -381 -1115 | 3825 399 -701 | -4753 106 -1378 | -6303 -626 * | -5453 210 * | -6014 -466 | -5662 -720 | -4812 275 | -4539 394 | -5232 45 | -5106 96 | -4370 359 | -4472 117 | -5527 -369 | -4696 -294 | -5561 -249 | 348 |
| 322(C) | -1383 -149 -9 | 5545 -500 -7942 | 4327 233 -8984 | -4558 43 -894 | -4019 -381 -1115 | -2243 399 -701 | -3671 106 -1378 | -3414 -626 * | -4157 210 * | -3975 -466 | -3301 -720 | -3006 275 | -3016 394 | -3818 45 | -3871 96 | -1656 359 | 540 117 | -2675 -369 | -4269 -294 | -4170 -249 | 349 |
| 323(S) | -1998 -149 -9 | -3389 -500 -7942 | 920 233 -8984 | -646 43 -894 | -4194 -381 -1115 | -2202 399 -701 | -1688 106 -1378 | -4095 -626 * | -1857 210 * | -4037 -466 | -3301 -720 | 1873 275 | -2745 394 | -1360 45 | -2596 96 | 2972 359 | -2145 117 | -3473 -369 | -4215 -294 | -3333 -249 | 350 |
| 324(A) | 1796 -149 -9 | -2218 -500 -7942 | 759 233 -8984 | 1121 43 -894 | -2509 -381 -1115 | -1874 399 -701 | -667 106 -1378 | -2198 -626 * | -343 210 * | -2259 -466 | -1405 -720 | -578 275 | -2039 394 | -254 45 | -849 96 | 333 359 | -937 117 | 1127 -369 | -2521 -294 | -1880 -249 | 351 |
| 325(E) | -2264 -149 -9 | -4130 -500 -7942 | 1161 233 -8984 | 3061 43 -894 | -4316 -381 -1115 | -2257 399 -701 | -1556 106 -1378 | -4221 -626 * | -1720 210 * | -4092 -466 | -3390 -720 | -846 275 | -2763 394 | 2340 45 | -2512 96 | -1940 359 | -2316 117 | -3705 -369 | -4277 -294 | -3299 -249 | 352 |
| 326(D) | -33 -149 -9 | -4335 -500 -7942 | 3607 233 -8984 | 1205 43 -894 | -4570 -381 -1115 | -2294 399 -701 | -1708 106 -1378 | -4511 -626 * | -2035 210 * | -4382 -466 | -3756 -720 | -897 275 | -2858 394 | -1390 45 | -2952 96 | -2084 359 | -2528 117 | -3963 -369 | -4583 -294 | -3525 -249 | 353 |
| 327(I) | -2456 -149 -9 | -1959 -500 -7942 | -5125 233 -8984 | -4808 43 -894 | -2580 -381 -1115 | -4919 399 -701 | -4900 106 -1378 | 3012 -626 * | -4754 210 * | -1350 -466 | -1292 -720 | -4605 275 | -4688 394 | -4684 45 | -4898 96 | -4291 359 | -2452 117 | 2731 -369 | -4288 -294 | -3786 -249 | 354 |

TABLE 14-continued

| | | | | | | | | | | | | | | | | | | |
|---|---|---|---|---|---|---|---|---|---|---|---|---|---|---|---|---|---|---|
| 328(Y) | −2065 −149 | −1703 −500 −7942 | −4458 233 −8984 | −4000 −894 | −1497 −381 −1115 | −3978 399 −701 | −2824 106 −1378 | 1512 −626 * | −3720 210 * | −1096 −466 | −877 −720 | −3567 275 | −3903 394 | −3404 45 | −3627 96 | −3169 359 | −2033 117 | 2744 −369 | −2424 −294 | 2949 −249 | 355 |
| 329(K) | 9 −149 | −1420 −3005 −500 −7942 | 1129 233 −8984 | 1097 43 −894 | −3290 −381 −1115 | 1087 399 −701 | −935 106 −1378 | −3080 −626 * | 2093 210 * | −3005 −466 | −2135 −720 | 1724 275 | −2283 394 | −517 45 | −1280 96 | −1233 359 | −1393 117 | −2613 −369 | −3178 −294 | −2412 −249 | 356 |
| 330(W) | −150 −149 | 757 −500 −7942 | 49 233 −8984 | 299 43 −894 | −277 −381 −1115 | −651 399 −701 | 839 106 −1378 | −485 −626 * | 392 210 * | −910 −466 | 599 −720 | 300 275 | −401 394 | 623 45 | 162 96 | −99 359 | 38 117 | −448 −369 | 1107 −294 | 126 −249 | 357 |
| 331(V) | 242 −149 | −1739 −500 −7942 | −4505 233 −8984 | −4069 −894 | −1901 −381 −1115 | −3865 399 −701 | −3328 106 −1378 | 339 −626 * | −3811 210 * | 1145 −466 | −812 −720 | −3662 275 | −3892 394 | −3515 45 | −3741 96 | −3100 359 | −2045 117 | 3053 −369 | −3031 −294 | −2693 −249 | 358 |
| 332(A) | 2785 −149 | −1548 −500 −7942 | −3757 233 −8984 | −3706 43 −894 | −3183 −381 −1115 | −2010 399 −701 | −3016 106 −1378 | −2274 −626 * | −3464 210 * | −3018 −466 | −2323 −720 | −2559 275 | −2725 394 | −3105 45 | −3346 96 | 519 359 | −1436 117 | 1956 −369 | −3604 −294 | −3353 −249 | 359 |
| 333(A) | 2301 −149 | −1785 −500 −7942 | −4329 233 −8984 | −3814 −894 | −1389 −381 −1115 | −3715 399 −701 | −2881 106 −1378 | 1608 −626 * | −3501 210 * | 1601 −466 | −328 −720 | −3440 275 | −3685 394 | −3079 45 | −3364 96 | −2901 359 | −2013 117 | −142 −369 | −2516 −294 | −2281 −249 | 360 |
| 334(I) | −2461 −149 | −1969 −500 −7942 | −5121 233 −8984 | −4803 43 −894 | −2539 −381 −1115 | −4894 399 −701 | −4855 106 −1378 | 3457 −626 * | −4740 210 * | −1307 −466 | −1260 −720 | −4593 275 | −4673 394 | −4650 45 | −4870 96 | −4267 359 | −2458 117 | 2020 −369 | −4235 −294 | −3750 −249 | 361 |
| 335(T) | 1694 −149 | −1679 −500 −7942 | −3770 233 −8984 | −3955 43 −894 | −4023 −381 −1115 | −1971 399 −701 | −3381 106 −1378 | −3579 −626 * | −3783 210 * | −3994 −466 | −3161 −720 | −2633 275 | −2754 394 | −3407 45 | −3608 96 | −1339 359 | 3474 117 | −2625 −369 | −4286 −294 | −4150 −249 | 362 |
| 336(A) | 3145 −149 | 2363 −500 −7942 | −4124 233 −8984 | −4092 43 −894 | −3068 −381 −1115 | −2102 399 −701 | −3176 106 −1378 | −1748 −626 * | −3745 210 * | −2761 −466 | −2179 −720 | −2727 275 | −2812 394 | −3341 45 | −3530 96 | −1439 359 | −1489 117 | 622 −369 | −3594 −294 | −3345 −249 | 363 |
| 337(V) | 1549 −149 | −1561 −500 −7942 | −3980 233 −8984 | −3800 43 −894 | −2617 −381 −1115 | −2450 399 −701 | −3066 106 −1378 | −638 −626 * | −3529 210 * | −2084 −466 | −1647 −720 | −2851 275 | −3038 394 | −3217 45 | −3427 96 | −1764 359 | 645 117 | 3033 −369 | −3323 −294 | −3003 −249 | 364 |
| 338(Q) | −1998 −149 | −3480 −500 −7942 | −470 233 −8984 | 1001 −894 | −3872 −381 −1115 | −2292 399 −701 | −1373 106 −1378 | −3668 −626 * | −1085 210 * | −3566 −466 | −2804 −720 | −947 275 | 1060 394 | 3783 45 | −1533 96 | −1779 359 | −2007 117 | −3214 −369 | −3690 −294 | −2964 −249 | 365 |
| 339(A) | 2845 −149 | −1741 −500 −7942 | −2441 233 −8984 | −2116 43 −894 | −3476 −381 −1115 | 181 399 −701 | −2133 106 −1378 | −3194 −626 * | −1899 210 * | −3346 −466 | −2475 −720 | −1852 275 | −2527 394 | −1850 45 | 1122 96 | 752 359 | −1333 117 | −2425 −369 | −3579 −294 | −3191 −249 | 366 |
| 340(Q) | 288 −149 −444 | −1371 −500 −7942 | −2820 233 −8984 | −2256 43 −894 | −1089 −381 −1115 | −2819 399 −701 | −1668 106 −1378 | 1024 −626 * | −1933 210 * | 1596 −466 | −165 −720 | −2151 275 | −2848 394 | 2772 45 | −2022 96 | −1891 359 | −1329 117 | −469 −369 | −1817 −294 | −1496 −249 | 367 |
| 341(A) | 2553 −149 | −1499 −500 −7942 | −1940 233 −8984 | −1106 43 −894 | −1437 −381 −1115 | −1994 399 −701 | −884 106 −1378 | −1437 −626 * | −516 210 * | −1637 −466 | −947 −720 | −1150 275 | −2220 394 | −717 45 | 1070 96 | −1116 359 | −989 117 | −1219 −369 | −1772 −294 | 1598 −249 | 368 |
| 342(Q) | −840 −149 −154 | −7510 −500 −7942 | −1618 233 −8984 | −3381 43 −894 | −2487 −381 −1115 | −1844 399 478 | −471 106 −1378 | −2205 −626 * | −189 210 * | −2230 −466 | −1379 −720 | −273 275 | −1821 394 | 2234 45 | −719 96 | −721 359 | −813 117 | 565 −369 | −2466 −294 | −1782 −249 | 369 |
| 343(K) | −542 −149 −435 | −2183 −500 −7942 | 2051 233 −8984 | 46 43 −894 | −1686 −381 −1115 | −2041 399 −701 | −294 106 −402 | 542 −626 * | 1621 210 * | −1463 −466 | −666 −720 | −332 275 | −1689 394 | 78 45 | −434 96 | −539 359 | −484 117 | 817 −369 | −1827 −294 | −1263 −249 | 370 |
| 344(K) | 842 −149 −1110 | −1833 −500 −7368 | 903 233 −1975 | −68 43 −894 | −2188 −381 −1115 | −1329 399 −2041 | −107 106 −402 | −1924 −626 * | 1349 210 * | −1907 −466 | −1015 −720 | −8 275 | −1492 394 | 329 45 | −247 96 | 1153 359 | −413 117 | −1495 −369 | −2105 −294 | −1431 −249 | 371 |
| | −1110 | −6951 | −919 | | | −2432 | −296 | | | | | | | | | | | | | | |

TABLE 14-continued

| | | | | | | | | | | | | | | | | | |
|---|---|---|---|---|---|---|---|---|---|---|---|---|---|---|---|---|---|
| 345(R) | -956 | -1423 | -1186 | -681 | -1830 | -1454 | -276 | -1686 | 690 | -1640 | -1095 | -694 | -1696 | 14 | 3253 | -1003 | -929 | -1464 | -1574 | -1319 | 372 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -37 | -5878 | -6920 | -894 | -1115 | -2888 | -209 | * | * | | | | | | | | | | | | |
| 346(E) | -804 | -1735 | 497 | 2874 | -2096 | -1058 | -327 | -1858 | -157 | -1967 | -1380 | 40 | -1471 | -39 | -568 | -688 | -853 | -1562 | -2027 | -1547 | 373 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -37 | -5878 | -6920 | -894 | -1115 | -2888 | -209 | * | * | | | | | | | | | | | | |
| 347(R) | -956 | -1423 | -1186 | -681 | -1830 | -1454 | -276 | -1686 | 690 | -1640 | -1095 | -694 | -1696 | 14 | 3253 | -1003 | -929 | -1464 | -1574 | -1319 | 374 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -37 | -5878 | -6920 | -894 | -1115 | -2888 | -209 | * | * | | | | | | | | | | | | |
| 348(S) | 227 | -390 | -660 | -668 | -1564 | -565 | -762 | -1409 | -705 | -1690 | -1020 | -460 | -1182 | -625 | -900 | 2604 | -94 | -861 | -1818 | -1338 | 375 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -37 | -5878 | -6920 | -894 | -1115 | -2888 | -209 | * | * | | | | | | | | | | | | |
| 349(L) | -1162 | -1035 | -2273 | -2015 | -35 | -2243 | -1374 | 599 | -1587 | 2466 | 801 | -1903 | -2350 | -1486 | -1587 | -1745 | -1181 | 283 | -1141 | -718 | 376 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -37 | -5878 | -6920 | -894 | -1115 | -2888 | -209 | * | * | | | | | | | | | | | | |
| 350(H) | -948 | -1353 | -590 | -533 | -353 | -1374 | 4354 | -1609 | -210 | -1544 | -1090 | -628 | -1716 | -415 | -369 | -985 | -1004 | -1409 | -758 | 74 | 377 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -37 | -5878 | -6920 | -894 | -1115 | -2888 | -209 | * | * | | | | | | | | | | | | |
| 351(T) | 71 | -435 | -987 | -905 | -1386 | -761 | -851 | -654 | -738 | -1152 | -667 | -673 | -1327 | -733 | -889 | -159 | 2865 | -370 | -1730 | -1351 | 378 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -37 | -5878 | -6920 | -894 | -1115 | -2888 | -209 | * | * | | | | | | | | | | | | |
| 352(L) | -1162 | -1035 | -2273 | -2015 | -35 | -2243 | -1374 | 599 | -1587 | 2466 | 801 | -1903 | -2350 | -1486 | -1587 | -1745 | -1181 | 283 | -1141 | -718 | 379 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -37 | -5878 | -6920 | -894 | -1115 | -2888 | -209 | * | * | | | | | | | | | | | | |
| 353(V) | -558 | -557 | -2112 | -1895 | -730 | -1799 | -1509 | 1150 | -1619 | 15 | 149 | -1639 | -2121 | -1558 | -1693 | -1183 | -681 | 2778 | -1647 | -1187 | 380 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -37 | -5878 | -6920 | -894 | -1115 | -2888 | -209 | * | * | | | | | | | | | | | | |
| 354(E) | -804 | -1735 | 497 | 2874 | -2096 | -1058 | -327 | -1858 | -157 | -1967 | -1380 | 40 | -1471 | -39 | -568 | -688 | -853 | -1562 | -2027 | -1547 | 381 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -37 | -5878 | -6920 | -894 | -1115 | -2888 | -209 | * | * | | | | | | | | | | | | |
| 355(W) | -150 | 757 | 49 | 299 | -277 | -127 | -3565 | -485 | 392 | -910 | 599 | 300 | -401 | 623 | 162 | -99 | 38 | -448 | 1107 | 126 | 382 |
| | * | * | * | * | * | -651 | 839 | * | 0 | * | * | * | * | * | * | * | * | * | * | * | |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09550999B2). An electronic copy of the "Sequence Listing" will also be available from the USPTO upon request and payment of the fee set forth in 37 CFR 1.19(b)(3).

What is claimed:

1. A recombinant host cell comprising:
   (i) at least one genetic modification in an endogenous gene encoding a polypeptide having pyruvate decarboxylase activity, wherein the at least one genetic modification reduces or eliminates pyruvate decarboxylase activity; and
   (ii) a heterologous polynucleotide encoding a polypeptide having phosphoketolase activity.

2. The recombinant host cell of claim 1, wherein said host cell further comprises:
   (iii) a heterologous polynucleotide encoding a polypeptide having phosphotransacetylase activity.

3. The recombinant host cell of claim 1, wherein said host cell has a reduced requirement for an exogenous two-carbon substrate for its growth in culture compared to a recombinant eukaryotic host cell comprising (i) and not (ii).

4. The recombinant host cell of claim 1, wherein said host cell has improved growth as compared to a host cell comprising (i) and not (ii) in culture media that is not supplemented with an exogenous two-carbon carbon substrate.

5. The recombinant host cell of claim 4, wherein said exogenous to-carbon substrate is ethanol or acetate.

6. The recombinant host cell of claim 1, wherein said endogenous gene encoding a polypeptide having pyruvate decarboxylase activity is PDC1, PDC5, PDC6, or combinations thereof and said host cell is *S. cerevisiae*.

7. The recombinant host cell of claim 1, wherein said heterologous polynucleotide encoding a polypeptide having phosphoketolase activity is xpk1 from *Lactobacillus plantarum*, xpkA from *Lactobacillus pentosus* MD363 or 6-phosphate phosphoketolase from *B. lactis*.

8. The recombinant host cell of claim 1 wherein said polypeptide having phosphoketolase activity comprises at least 85% identity to SEQ ID NO 481 or an active fragment thereof.

9. The recombinant host cell of claim 2, wherein said heterologous polynucleotide encoding a polypeptide having phosphotransacetylase activity is EutD from *Lactobacillus plantarum* or phosphotransacetylase from *Bacillus subtilis*.

10. The recombinant host cell of claim 2, wherein said, polypeptide having phosphotransacetylase activity comprises at least 85% identity to SEQ ID NO: 1472 or an active fragment thereof.

11. The recombinant host cell of claim 1, wherein said host cell is a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizosaccharomyces, Kluyveromyces, Yarrowia, Pichia, Candida, Hansenula*, or *Saccharomyces*.

12. The recombinant host cell of claim 1 wherein said host, cell is *Saccharomyces cerevisiae*.

13. The recombinant host cell of claim 1 further comprising a pyruvate-utilizing biosynthetic pathway, wherein said pyruvate-utilizing biosynthetic pathway forms a product selected from the group consisting of: 2,3-butanediol, 2-butanol, 2-butanone, valine, leucine, lactic acid, malate, and isoamyl alcohol.

14. The recombinant host cell of claim 1, further comprising a pyruvate-utilizing biosynthetic pathway herein said pyruvate-utilizing biosynthetic pathway is an isobutanol biosynthetic pathway comprising the substrate to product conversions:
   (i) pyruvate to acetolactate;
   (ii) acetolactate to 2,3-dihydroxyisovalerate;
   (iii) 2,3-dihydroxyisovalerate to 2-ketoisovalerate;
   (iv) 2-ketoisovalerate to isobutyraldehyde;
   (v) isobutyraldehyde to isobutanol; and
   wherein said recombinant host cell produces isobutanol.

15. The recombinant host cell of claim 13, wherein said pyruvate-utilizing biosynthetic pathway is a 2-butanone biosynthetic pathway comprising the substrate to product conversions:
   (i) pyruvate to acetolactate;
   (ii) acetolactate to acetoin;
   (iii) acetoin to 2,3-butanediol;
   (iv) 2,3-butanediol to 2-butanone;
   wherein said recombinant host cell produces 2-butanone.

16. The recombinant host cell of claim 13, wherein said pyruvate-utilizing biosynthetic pathway is a 2-butanol biosynthetic pathway comprising the substrate to product conversions:
   (i) pyruvate to acetolactate;
   (ii) acetolactate to acetoin;
   (iii) acetoin to 2,3-butanediol;
   (iv) 2,3-butanediol to 2-butanone;
   (v) 2-butanone to 2-butanol;
   wherein said recombinant host cell produces 2-butanol.

17. The recombinant host cell of claim 1 wherein the phosphoketolase matches the Profile HMM given in Table 6 with an E value of less than 7.5E-242.

18. The recombinant host cell of claim 1 wherein the phosphoketolase matches the Profile HMMs given in Tables 6, 7, 8, and 9 with E values of less than 7.5E-242, 1.1E-124, 2.1E-49, 7.8E-37, respectively.

19. The recombinant host cell of claim 1 further comprising a phosphotransacetylase which matches the Profile HMM given in Table 14 with an E value of less than 5E-34.

20. The recombinant host cell of claim 13, wherein said pyruvate-utilizing biosynthetic pathway is a 2,3-butanediol biosynthetic pathway comprising the substrate to product conversations:

(i) pyruvate to acetolactate;
(ii) acetolactate to acetoin;
(iii) acetoin 2,3-butanediol; and
wherein said recombinant host cell produces 2,3 butanediol.

21. A method for the production of 2,3-butanediol, 2-butanol, 2-butanone, valine, leucine, lactic acid, malic acid, alanine, fumaric acid, succinic acid or isoamyl alcohol comprising growing the recombinant host cell of claim 13 under conditions wherein the product is produced and optionally recovering the product.

22. A method for the production of isobutanol comprising growing the recombinant host cell of claim 14 under conditions wherein the product is produced and optionally recovering the product.

* * * * *